United States Patent
Haaber et al.

(10) Patent No.: US 12,076,375 B2
(45) Date of Patent: Sep. 3, 2024

(54) TREATING AND PREVENTING E COLI INFECTIONS

(71) Applicant: SNIPR Biome ApS, Copenhagen (DK)

(72) Inventors: Jakob Krause Haaber, Copenhagen (DK); Szabolcs Semsey, Copenhagen (DK); Mette Grove, Copenhagen (DK); Birgitte Damholt, Copenhagen (DK); Dziuginta Jasinskyte, Copenhagen (DK); Yilmaz Emre Gençay, Copenhagen (DK)

(73) Assignee: SNIPR BIOME APS, Copenhagen (DK)

( * ) Notice: Subject to any disclaimer, the term of this patent is extended or adjusted under 35 U.S.C. 154(b) by 0 days.

(21) Appl. No.: 17/812,359

(22) Filed: Jul. 13, 2022

(65) Prior Publication Data

US 2022/0387559 A1 Dec. 8, 2022

(30) Foreign Application Priority Data

Jun. 29, 2022 (GB) .................................. 2209518

(51) Int. Cl.
| | | |
|---|---|---|
| A61K 38/46 | (2006.01) | |
| A61K 35/76 | (2015.01) | |
| A61P 31/04 | (2006.01) | |
| C12N 15/113 | (2010.01) | |

(52) U.S. Cl.
CPC ............ *A61K 38/465* (2013.01); *A61K 35/76* (2013.01); *A61P 31/04* (2018.01); *C12N 15/113* (2013.01); *C12N 2310/20* (2017.05)

(58) Field of Classification Search
CPC ....... A61K 38/465; A61K 35/76; A61P 31/04; C12N 15/113; C12N 2310/20
See application file for complete search history.

(56) References Cited

U.S. PATENT DOCUMENTS

| | | | |
|---|---|---|---|
| 4,626,504 A | 12/1986 | Puhler | |
| 4,870,287 A | 9/1989 | Cole | |
| 5,633,154 A | 5/1997 | Schaefer | |
| 5,760,395 A | 6/1998 | Johnstone | |
| 5,844,905 A | 12/1998 | Mckay | |
| 5,885,796 A | 3/1999 | Linsley | |
| 6,207,156 B1 | 3/2001 | Kuchroo | |
| 7,459,272 B2 | 12/2008 | Morris | |
| 8,003,323 B2 | 8/2011 | Morris | |
| 8,008,449 B2 | 8/2011 | Korman | |
| 8,017,114 B2 | 9/2011 | Korman | |
| 8,119,129 B2 | 2/2012 | Jure-kunkel | |
| 8,241,498 B2 | 8/2012 | Summer | |
| 8,252,576 B2 | 8/2012 | Campbell | |
| 8,329,867 B2 | 12/2012 | Lazar | |
| 8,354,509 B2 | 1/2013 | Carven | |
| 8,735,553 B1 | 5/2014 | Li | |
| 8,906,682 B2 | 12/2014 | June | |
| 8,911,993 B2 | 12/2014 | June | |
| 8,916,381 B1 | 12/2014 | June | |
| 8,975,071 B1 | 3/2015 | June | |
| 9,101,584 B2 | 8/2015 | June | |
| 9,102,760 B2 | 8/2015 | June | |
| 9,102,761 B2 | 8/2015 | June | |
| 9,113,616 B2 | 8/2015 | Stevens | |
| 9,328,156 B2 | 5/2016 | June | |
| 9,464,140 B2 | 10/2016 | June | |
| 9,481,728 B2 | 11/2016 | June | |
| 9,499,629 B2 | 11/2016 | June | |
| 9,518,123 B2 | 12/2016 | June | |
| 9,540,445 B2 | 1/2017 | June | |
| 9,593,339 B1 | 3/2017 | Bermudes | |
| 9,701,964 B2 | 7/2017 | Clube | |
| 9,758,583 B2 | 9/2017 | Wang | |
| 9,822,372 B2 | 11/2017 | Zhang | |
| 9,879,269 B2 | 1/2018 | Barrangou | |
| 9,889,164 B2 | 2/2018 | Falb et al. | |
| 10,066,233 B2 | 9/2018 | Barrangou | |
| 10,136,639 B2 | 11/2018 | Wuest | |
| 10,136,649 B2 | 11/2018 | Barrangou | |
| 10,195,273 B2 | 2/2019 | Clube | |
| 10,300,138 B2 | 5/2019 | Clube | |
| 10,300,139 B2 | 5/2019 | Clube | |
| 10,303,379 B2 | 5/2019 | Bab-dinitz et al. | |
| 10,363,308 B2 | 7/2019 | Clube | |
| 10,463,049 B2 | 11/2019 | Clube | |
| 10,506,812 B2 | 12/2019 | Clube | |

(Continued)

FOREIGN PATENT DOCUMENTS

| | | |
|---|---|---|
| CA | 3010891 A1 | 7/2017 |
| EP | 2320940 B1 | 5/2011 |

(Continued)

OTHER PUBLICATIONS

Fagen JR et al. Advancing the design and delivery of CRISPR antimicrobials. 2017. Current Opinion in Biomedical Engineering. 4: 57-64. (Year: 2017).*
Flament-Simon SC et al. Clonal Structure, Virulence Factor-encoding Genes and Antibiotic Resistance of *Escherichia coli*, Causing Urinary Tract Infections and other Extraintestinal Infections in Humans in Spain and France during 2016. 2020. Antibiotics. 9, 161. p. 1-17 (Year: 2020).*
Rousset F et al. Genome-wide CRISPR-dCas9 screens in *E. coli* identify essential genes and phage host factors. 2018. PLoS Genetics. p. 1-28. (Year: 2018).*
Silva JB et al. Host receptors for bacteriophage adsorption. 2016. FEMS Microbiology Letters. 363. p. 1-11 (Year: 2016).*
Abedon, S.T. et al. (Dec. 2003). "Experimental Examination of Bacteriophage Latent-Period Evolution as a Response to Bacterial Availability," Applied and Environmental Microbiology 69(12):7499-7506.

(Continued)

*Primary Examiner* — Paul J Holland
(74) *Attorney, Agent, or Firm* — MORRISON & FOERSTER LLP

(57) ABSTRACT

The invention relates to methods and compositions for treating or preventing an infection by *E coli* cells in human or animal subjects. The method comprises administering to the subject a plurality of transduction particles that encode a nuclease for targeting the genomes of B2 phylogroup *E coli* cells.

31 Claims, 2 Drawing Sheets

Specification includes a Sequence Listing.

(56) References Cited

U.S. PATENT DOCUMENTS

| | | |
|---|---|---|
| 10,524,477 B2 | 1/2020 | Clube |
| 10,561,148 B2 | 2/2020 | Clube |
| 10,582,712 B2 | 3/2020 | Clube |
| 10,596,255 B2 | 3/2020 | Clube |
| 10,603,379 B2 | 3/2020 | Clube |
| 10,624,349 B2 | 4/2020 | Clube |
| 10,660,943 B2 | 5/2020 | Bikard et al. |
| 10,751,427 B2 | 8/2020 | Clube |
| 10,760,065 B2 | 9/2020 | Lu et al. |
| 10,760,075 B2 | 9/2020 | Sommer et al. |
| 10,765,740 B2 | 9/2020 | Clube et al. |
| 10,920,222 B2 | 2/2021 | Sommer et al. |
| 10,953,090 B2 | 3/2021 | Clube et al. |
| 11,141,481 B2 | 10/2021 | Clube |
| 11,147,830 B2 | 10/2021 | Clube |
| 11,166,994 B2 | 11/2021 | Lichtenstein et al. |
| 11,274,317 B2 | 3/2022 | Fricke et al. |
| 11,291,693 B2 | 4/2022 | Falb et al. |
| 11,291,723 B2 | 4/2022 | Clube |
| 11,351,252 B2 | 6/2022 | Clube |
| 11,400,110 B2 | 8/2022 | Clube |
| 11,421,227 B2 | 8/2022 | Sommer et al. |
| 11,471,530 B2 | 10/2022 | Clube |
| 11,471,531 B2 | 10/2022 | Clube et al. |
| 11,485,973 B2 | 11/2022 | Sommer et al. |
| 11,517,582 B2 | 12/2022 | Clube et al. |
| 11,547,716 B2 | 1/2023 | Clube |
| 11,578,333 B2 | 2/2023 | Martinez et al. |
| 11,612,617 B2 | 3/2023 | Clube |
| 11,629,350 B2 | 4/2023 | Martinez et al. |
| 11,642,363 B2 | 5/2023 | Clube |
| 11,643,653 B2 | 5/2023 | Sommer et al. |
| 11,788,085 B2 | 10/2023 | Sommer et al. |
| 2002/0001590 A1 | 1/2002 | Kelly et al. |
| 2002/0044922 A1 | 4/2002 | Mardh |
| 2002/0058027 A1 | 5/2002 | Nelson et al. |
| 2003/0049841 A1 | 3/2003 | Short |
| 2004/0096974 A1 | 5/2004 | Herron |
| 2005/0118719 A1 | 6/2005 | Schmidt |
| 2009/0155768 A1 | 6/2009 | Scholl |
| 2010/0076057 A1 | 3/2010 | Sontheimer |
| 2010/0093617 A1 | 4/2010 | Barrangou |
| 2010/0172874 A1 | 7/2010 | Turnbaugh |
| 2011/0002889 A1 | 1/2011 | Barrangou |
| 2011/0008369 A1 | 1/2011 | Finnefrock |
| 2011/0136688 A1 | 6/2011 | Scholl |
| 2011/0143997 A1 | 6/2011 | Henry et al. |
| 2012/0177645 A1 | 7/2012 | Langermann |
| 2012/0269859 A1 | 10/2012 | Minato |
| 2012/0294796 A1 | 11/2012 | Johnson |
| 2013/0011828 A1 | 1/2013 | Barrangou |
| 2013/0109053 A1 | 5/2013 | Macdonald |
| 2013/0121968 A1 | 5/2013 | Quay |
| 2013/0287748 A1 | 10/2013 | June |
| 2013/0288368 A1 | 10/2013 | June |
| 2013/0309258 A1 | 11/2013 | June |
| 2014/0022021 A1 | 1/2014 | Kusachi |
| 2014/0068797 A1 | 3/2014 | Doudna |
| 2014/0105912 A1 | 4/2014 | Noelle |
| 2014/0106449 A1 | 4/2014 | June |
| 2014/0107092 A1 | 4/2014 | Meyerson |
| 2014/0179726 A1 | 6/2014 | Bajaj |
| 2014/0199767 A1 | 7/2014 | Barrangou |
| 2014/0234972 A1 | 8/2014 | Zhang |
| 2014/0294898 A1 | 10/2014 | Miller |
| 2014/0341920 A1 | 11/2014 | Noelle |
| 2014/0349400 A1 | 11/2014 | Jakimo et al. |
| 2014/0370017 A1 | 12/2014 | June |
| 2015/0004705 A1 | 1/2015 | Lu et al. |
| 2015/0031134 A1 | 1/2015 | Zhang |
| 2015/0032263 A1 | 1/2015 | Keyl et al. |
| 2015/0044772 A1 | 2/2015 | Zhao |
| 2015/0050699 A1 | 2/2015 | Siksnys |
| 2015/0050729 A1 | 2/2015 | June |
| 2015/0064138 A1 | 3/2015 | Lu |
| 2015/0093822 A1 | 4/2015 | June |
| 2015/0099299 A1 | 4/2015 | June |
| 2015/0118202 A1 | 4/2015 | June |
| 2015/0125463 A1 | 5/2015 | Cogswell |
| 2015/0132263 A1 | 5/2015 | Liu et al. |
| 2015/0132419 A1 | 5/2015 | Arvik |
| 2015/0139943 A1 | 5/2015 | Campana |
| 2015/0140001 A1 | 5/2015 | Lee |
| 2015/0184139 A1 | 7/2015 | Zhang |
| 2015/0225730 A1 | 8/2015 | Minshull et al. |
| 2015/0232881 A1 | 8/2015 | Glucksmann |
| 2015/0290244 A1 | 10/2015 | June |
| 2015/0353905 A1 | 12/2015 | Weiss |
| 2016/0009805 A1 | 1/2016 | Kowanetz |
| 2016/0009813 A1 | 1/2016 | Themeli |
| 2016/0024510 A1 | 1/2016 | Bikard |
| 2016/0040215 A1 | 2/2016 | Henn et al. |
| 2016/0081314 A1 | 3/2016 | Thurston |
| 2016/0115488 A1 | 4/2016 | Zhang |
| 2016/0115489 A1 | 4/2016 | Zhang |
| 2016/0130355 A1 | 5/2016 | June |
| 2016/0159905 A1 | 6/2016 | Abdiche |
| 2016/0159907 A1 | 6/2016 | June |
| 2016/0160186 A1 | 6/2016 | Parsley |
| 2016/0194404 A1 | 7/2016 | June |
| 2016/0208012 A1 | 7/2016 | June |
| 2016/0237455 A1 | 8/2016 | Glucksmann |
| 2016/0244784 A1 | 8/2016 | Jacobson et al. |
| 2016/0281053 A1 | 9/2016 | Sorek |
| 2016/0324938 A1 | 11/2016 | Bikard |
| 2016/0333348 A1 | 11/2016 | Clube |
| 2016/0339064 A1 | 11/2016 | Kovarik et al. |
| 2016/0345578 A1 | 12/2016 | Barrangou |
| 2016/0347836 A1 | 12/2016 | Grosso |
| 2016/0354416 A1 | 12/2016 | Gajewski |
| 2017/0022499 A1 | 1/2017 | Lu |
| 2017/0037416 A1 | 2/2017 | Barrangou |
| 2017/0106025 A1 | 4/2017 | Kovarik |
| 2017/0106026 A1 | 4/2017 | Kovarik |
| 2017/0114351 A1 | 4/2017 | Mahfouz |
| 2017/0143772 A1 | 5/2017 | Mulder |
| 2017/0173085 A1 | 6/2017 | Kovarik |
| 2017/0173086 A1 | 6/2017 | Boyle et al. |
| 2017/0174713 A1 | 6/2017 | Du |
| 2017/0175142 A1 | 6/2017 | Zhang |
| 2017/0196225 A1 | 7/2017 | Clube |
| 2017/0216370 A1 | 8/2017 | Falb et al. |
| 2017/0246221 A1 | 8/2017 | Clube |
| 2017/0247690 A1 | 8/2017 | Quake |
| 2017/0304443 A1 | 10/2017 | Lebwohl |
| 2017/0314015 A1 | 11/2017 | Friedland et al. |
| 2017/0327582 A1 | 11/2017 | Bissonnette |
| 2017/0340733 A1 | 11/2017 | Cao |
| 2018/0015131 A1 | 1/2018 | Gajewski |
| 2018/0055852 A1 | 3/2018 | Kutok |
| 2018/0064114 A1 | 3/2018 | Clube |
| 2018/0064115 A1 | 3/2018 | Clube |
| 2018/0070594 A1 | 3/2018 | Clube |
| 2018/0084785 A1 | 3/2018 | Clube |
| 2018/0084786 A1 | 3/2018 | Clube |
| 2018/0140698 A1 | 5/2018 | Clube |
| 2018/0146681 A1 | 5/2018 | Clube |
| 2018/0147221 A1 | 5/2018 | Von Maltzahn et al. |
| 2018/0155721 A1 | 6/2018 | Lu |
| 2018/0155729 A1 | 6/2018 | Beisel |
| 2018/0161368 A1 | 6/2018 | Odegard |
| 2018/0179547 A1 | 6/2018 | Zhang |
| 2018/0200342 A1 | 7/2018 | Bikard |
| 2018/0273937 A1 | 9/2018 | Beisel et al. |
| 2018/0273940 A1 | 9/2018 | Sommer |
| 2018/0303934 A1 | 10/2018 | Clube |
| 2018/0326057 A1 | 11/2018 | Clube |
| 2018/0326093 A1 | 11/2018 | Clube |
| 2018/0355378 A1 | 12/2018 | Krom et al. |
| 2018/0371405 A1 | 12/2018 | Barrangou |
| 2019/0010506 A1 | 1/2019 | Falb et al. |
| 2019/0015441 A1 | 1/2019 | Shachar |
| 2019/0021343 A1 | 1/2019 | Barrangou |
| 2019/0070233 A1 | 3/2019 | Yeung |

(56) References Cited

U.S. PATENT DOCUMENTS

| | | |
|---|---|---|
| 2019/0117709 A1 | 4/2019 | Kovarik |
| 2019/0133135 A1 | 5/2019 | Clube |
| 2019/0134194 A1 | 5/2019 | Clube |
| 2019/0136230 A1 | 5/2019 | Sather |
| 2019/0142881 A1 | 5/2019 | Turner et al. |
| 2019/0160120 A1 | 5/2019 | Haaber |
| 2019/0230936 A1 | 8/2019 | Clube |
| 2019/0240325 A1 | 8/2019 | Clube |
| 2019/0240326 A1 | 8/2019 | Clube |
| 2019/0255084 A1 | 8/2019 | Schentag |
| 2019/0256900 A1 | 8/2019 | Zhang |
| 2019/0282628 A1 | 9/2019 | Falb et al. |
| 2019/0298779 A1 | 10/2019 | Falb |
| 2019/0321468 A1 | 10/2019 | Clube et al. |
| 2019/0321469 A1 | 10/2019 | Clube et al. |
| 2019/0321470 A1 | 10/2019 | Clube |
| 2019/0359933 A1 | 11/2019 | Swee |
| 2020/0030444 A1 | 1/2020 | Clube |
| 2020/0046773 A1 | 2/2020 | Borody |
| 2020/0068901 A1 | 3/2020 | Clube |
| 2020/0077663 A1 | 3/2020 | Clube |
| 2020/0085066 A1 | 3/2020 | Clube |
| 2020/0087660 A1 | 3/2020 | Sommer |
| 2020/0102551 A1 | 4/2020 | Barrangou |
| 2020/0115716 A1 | 4/2020 | Martinez |
| 2020/0121787 A1 | 4/2020 | Clube |
| 2020/0128832 A1 | 4/2020 | Clube |
| 2020/0157237 A1 | 5/2020 | Regev |
| 2020/0164070 A1 | 5/2020 | Clube |
| 2020/0179460 A1 | 6/2020 | Kovarik |
| 2020/0199570 A1 | 6/2020 | Novick |
| 2020/0205416 A1 | 7/2020 | Clube |
| 2020/0254035 A1 | 8/2020 | Haaber |
| 2020/0267992 A1 | 8/2020 | Clube |
| 2020/0282027 A1 | 9/2020 | Bikard et al. |
| 2020/0337313 A1 | 10/2020 | Clube |
| 2020/0354690 A1 | 11/2020 | Garofolo |
| 2020/0390886 A1 | 12/2020 | Clube |
| 2021/0009996 A1 | 1/2021 | Sommer |
| 2021/0060180 A1 | 3/2021 | Clube |
| 2021/0113689 A1 | 4/2021 | Clube |
| 2021/0145006 A1 | 5/2021 | Clube |
| 2021/0147827 A1 | 5/2021 | Clube |
| 2021/0147857 A1 | 5/2021 | Clube |
| 2021/0163960 A1 | 6/2021 | Martinez et al. |
| 2021/0169942 A1 | 6/2021 | Falb et al. |
| 2021/0189406 A1 | 6/2021 | Martinez et al. |
| 2021/0198665 A1 | 7/2021 | Sommer et al. |
| 2021/0230559 A1 | 7/2021 | Clube |
| 2021/0238167 A1 | 8/2021 | Glimcher et al. |
| 2021/0283167 A1 | 9/2021 | Clube |
| 2021/0290654 A1 | 9/2021 | Clube |
| 2021/0386773 A1 | 12/2021 | Clube |
| 2022/0056457 A1 | 2/2022 | Edgell et al. |
| 2022/0162270 A1 | 5/2022 | Szabolcs |
| 2022/0233575 A1 | 7/2022 | Clube et al. |
| 2022/0241318 A1 | 8/2022 | Clube et al. |
| 2022/0259588 A1 | 8/2022 | Sommer et al. |
| 2022/0273696 A1 | 9/2022 | Clube |
| 2022/0275380 A1 | 9/2022 | Porse |
| 2022/0282245 A1 | 9/2022 | Sommer et al. |
| 2022/0290133 A1 | 9/2022 | Sommer et al. |
| 2022/0362280 A1 | 11/2022 | Clube |
| 2023/0193241 A1 | 6/2023 | Clube et al. |
| 2023/0248822 A1 | 8/2023 | Clube |
| 2023/0330167 A1 | 10/2023 | Haaber |
| 2023/0364268 A1 | 11/2023 | Clube |

FOREIGN PATENT DOCUMENTS

| | | |
|---|---|---|
| EP | 2325332 A1 | 5/2011 |
| EP | 2840140 A1 | 2/2015 |
| EP | 3291679 A1 | 3/2018 |
| EP | 3461337 A1 | 4/2019 |
| EP | 3132035 B8 | 4/2020 |
| EP | 3132036 B8 | 4/2020 |
| EP | 3630975 A1 | 4/2020 |
| EP | 3633032 A2 | 4/2020 |
| EP | 3634442 A1 | 4/2020 |
| EP | 3634473 A1 | 4/2020 |
| JP | 2010285425 A | 12/2010 |
| RU | 2531343 C2 | 10/2014 |
| WO | 198702702 A1 | 5/1987 |
| WO | 1995001994 A1 | 1/1995 |
| WO | 1998042752 A1 | 10/1998 |
| WO | 2000037504 A2 | 6/2000 |
| WO | 2000037504 A3 | 6/2000 |
| WO | 200069269 A1 | 11/2000 |
| WO | 2001014424 A2 | 3/2001 |
| WO | 2001014424 A3 | 3/2001 |
| WO | 200193904 A1 | 12/2001 |
| WO | 200207742 A2 | 1/2002 |
| WO | 200207742 A3 | 8/2002 |
| WO | 2005003168 A2 | 1/2005 |
| WO | 2005009465 A1 | 2/2005 |
| WO | 2005003168 A3 | 5/2005 |
| WO | 2005046579 A2 | 5/2005 |
| WO | 2005046579 A3 | 8/2005 |
| WO | 2006003179 A2 | 1/2006 |
| WO | 2006003179 A3 | 5/2006 |
| WO | 2006072625 A2 | 7/2006 |
| WO | 2006072626 A1 | 7/2006 |
| WO | 2006121168 A1 | 11/2006 |
| WO | 2006072625 A3 | 12/2006 |
| WO | 2007025097 A2 | 3/2007 |
| WO | 2007042573 A2 | 4/2007 |
| WO | 2007025097 A3 | 7/2007 |
| WO | 2007042573 A3 | 7/2007 |
| WO | 2008084106 A1 | 7/2008 |
| WO | 2008108989 A2 | 9/2008 |
| WO | 2008132601 A1 | 11/2008 |
| WO | 2008108989 A3 | 3/2009 |
| WO | 2009044273 A2 | 4/2009 |
| WO | 2009101611 A1 | 8/2009 |
| WO | 2008084106 A9 | 9/2009 |
| WO | 2009044273 A3 | 9/2009 |
| WO | 2009114335 A2 | 9/2009 |
| WO | 2010011961 A2 | 1/2010 |
| WO | 2010027827 A2 | 3/2010 |
| WO | 2010027827 A3 | 5/2010 |
| WO | 2009114335 A3 | 6/2010 |
| WO | 2010011961 A1 | 6/2010 |
| WO | 2010065939 A1 | 6/2010 |
| WO | 2010075424 A2 | 7/2010 |
| WO | 2010075424 A3 | 9/2010 |
| WO | 2011014438 A1 | 2/2011 |
| WO | 2011066342 A2 | 6/2011 |
| WO | 2011066342 A3 | 7/2011 |
| WO | 2012054726 A1 | 4/2012 |
| WO | 2012071411 A2 | 5/2012 |
| WO | 2012079000 A1 | 6/2012 |
| WO | 2012071411 A3 | 8/2012 |
| WO | 2012079000 A4 | 8/2012 |
| WO | 2012160448 A2 | 11/2012 |
| WO | 2012164565 A1 | 12/2012 |
| WO | 2013006490 A2 | 1/2013 |
| WO | 2013025779 A1 | 2/2013 |
| WO | 2012160448 A3 | 5/2013 |
| WO | 2013063361 A1 | 5/2013 |
| WO | 2013067492 A1 | 5/2013 |
| WO | 2013176772 A1 | 11/2013 |
| WO | 2014012001 A2 | 1/2014 |
| WO | 2014015252 A1 | 1/2014 |
| WO | 2014018423 A2 | 1/2014 |
| WO | 2014018423 A3 | 1/2014 |
| WO | 2014040962 A1 | 3/2014 |
| WO | 2014043432 A1 | 3/2014 |
| WO | 2013006490 A3 | 5/2014 |
| WO | 2014093595 A1 | 6/2014 |
| WO | 2014093661 A2 | 6/2014 |
| WO | 2014093661 A3 | 8/2014 |
| WO | 2014124226 A1 | 8/2014 |
| WO | 2014150624 A1 | 9/2014 |
| WO | 2014093661 A9 | 10/2014 |

(56) References Cited

FOREIGN PATENT DOCUMENTS

| | | |
|---|---|---|
| WO | 2014204725 A1 | 12/2014 |
| WO | 2015016718 A1 | 2/2015 |
| WO | 2015034872 A2 | 3/2015 |
| WO | 2014012001 A3 | 4/2015 |
| WO | 2015034872 A3 | 4/2015 |
| WO | 2015058018 A1 | 4/2015 |
| WO | 2015069682 A2 | 5/2015 |
| WO | 2015070083 A1 | 5/2015 |
| WO | 2015070193 A1 | 5/2015 |
| WO | 2015071474 A2 | 5/2015 |
| WO | 2015075688 A1 | 5/2015 |
| WO | 2015088643 A1 | 6/2015 |
| WO | 2015089351 A1 | 6/2015 |
| WO | 2015089419 A2 | 6/2015 |
| WO | 2015069682 A3 | 7/2015 |
| WO | 2015071474 A3 | 8/2015 |
| WO | 2015089419 A3 | 9/2015 |
| WO | 2015136541 A2 | 9/2015 |
| WO | 2015148680 A1 | 10/2015 |
| WO | 2015153940 A1 | 10/2015 |
| WO | 2015155686 A2 | 10/2015 |
| WO | 2015159068 A1 | 10/2015 |
| WO | 2015159086 A1 | 10/2015 |
| WO | 2015159087 A1 | 10/2015 |
| WO | 2015136541 A3 | 11/2015 |
| WO | 2015155686 A3 | 12/2015 |
| WO | 2016044745 A1 | 3/2016 |
| WO | 2016063263 A2 | 4/2016 |
| WO | 2016063263 A3 | 6/2016 |
| WO | 2016084088 A1 | 6/2016 |
| WO | 2016141108 A1 | 9/2016 |
| WO | 2016177682 A1 | 11/2016 |
| WO | 2016183532 A1 | 11/2016 |
| WO | 2016196361 A1 | 12/2016 |
| WO | 2016196605 A1 | 12/2016 |
| WO | 2016205276 A1 | 12/2016 |
| WO | 2017009399 A1 | 1/2017 |
| WO | 2017042347 A1 | 3/2017 |
| WO | 2017058751 A1 | 4/2017 |
| WO | 2017074566 A1 | 5/2017 |
| WO | 2017112620 A1 | 6/2017 |
| WO | 2017118598 A1 | 7/2017 |
| WO | 2017123418 A1 | 7/2017 |
| WO | 2017136795 A1 | 8/2017 |
| WO | 2017211753 A1 | 12/2017 |
| WO | 2018064165 A2 | 4/2018 |
| WO | 2018081502 A1 | 5/2018 |
| WO | 2018112194 A1 | 6/2018 |
| WO | 2018115519 A1 | 6/2018 |
| WO | 2018217351 A1 | 11/2018 |
| WO | 2018217981 A1 | 11/2018 |
| WO | 2018222969 A1 | 12/2018 |
| WO | 2018226853 A1 | 12/2018 |
| WO | 2019002218 A2 | 1/2019 |
| WO | 2019002218 A3 | 2/2019 |
| WO | 2018064165 A3 | 6/2019 |
| WO | 2019243307 A1 | 12/2019 |
| WO | 2019243373 A1 | 12/2019 |
| WO | 2020072248 A1 | 4/2020 |
| WO | 2020072250 A1 | 4/2020 |
| WO | 2020072253 A1 | 4/2020 |
| WO | 2020072254 A1 | 4/2020 |
| WO | 2020118435 A1 | 6/2020 |
| WO | 2020152369 A1 | 7/2020 |
| WO | 2021092254 A1 | 5/2021 |
| WO | 2021097118 A1 | 5/2021 |
| WO | 2022003209 A1 | 1/2022 |
| WO | 2022063986 A2 | 3/2022 |

OTHER PUBLICATIONS

Abernethy, J. K. et al, (Mar. 2015, e-pub. Jan. 14, 2015). "Thirty Day All-Cause Mortality in Patients With *Escherichia coli* Bacteraemia in England," Clin. Microbial. Infect. 21:251.e1-251.e8.

Advisory Action, dated Dec. 9, 2021 for U.S. Appl. No. 90/014,705, filed Mar. 23, 2021, 9 pages.

Aklujkar et al. (2010) "Interference With Histidyl-tRNA Synthetase by a CRISPR Spacer Sequence as a Factor in the Evolution of Pelobacter Carbinolicus," BMC Evolutionary Biology 10:203, 15 pages.

American Lung Association (2019). "Preventing COPD," retrieved from https://www.lung.org/lung-health-and-diseases/lung-disease-lookup/copd/symptoms-causes-risk-factors/preventing-copd.html, last visited Aug. 5, 2019, 1 page.

Anatoliotaki, M. et al. (2004). "Bloodstream Infections in Patients with Solid Tumors: Associated Factors, Microbial Spectrum and Outcome," Infection 2004, 32(2):65-71.

Ang, Y.L.E. et al. (2015). "Best Practice in the Treatment of Advanced Squamous Cell Lung Cancer," Ther. Adv. Respir. Dis. 9(5):224-235.

Anonymous (Apr. 2016). "Checkpoint Inhibition: A Promising Immunotherapeutic Approach for Colorectal Cancer," Oncology, 5(3): 1-5, retrieved from http//www.personalizedmedonc.com/publications/pro/april-2016-vol-5-no-3/checkpoint-inhibition-a-promising-irmunotherapeutic-approach-for-colorectal cancer-2/, last visited Aug. 27, 2019, 5 pages.

Arnold, I.C. et al. (Apr. 8, 2015, e-pub. Mar. 4, 2015). "Helicobacter Hepaticus Infection in BALB/c Mice Abolishes Subunit-Vaccine-Induced Protection Against M. Tuberculosis," Vaccine 33(15):1808-1814.

Arslan, Z. et al. (May 7, 2013). "RcsB-BglJ-Mediated Activation of Cascade Operon Does Not Induce the Maturation of CRISPR RNAs in *E. coli* K12," RNA Biology 10(5):708-715.

Arumugam et al. (May 12, 2011). "Enterotypes of the human gut microbiome," Nature 473(7346):174-180, 16 pages.

Bae, T. et al. (2006). "Prophages of *Staphylococcus aureus* Newman and Their Contribution to Virulence," Molecular Microbiology pp. 1-13.

Barrangou, R. et al. (Mar. 2007). "CRISPR Provides Acquired Resistance Against Viruses in Prokaryotes," Science, 315:1709-1712.

Beghain, J. et al. (Jul. 2018, e-pub. Jun. 19, 2018), "ClermonTyping: An Easy-To-Use and Accurate in Silico Method for Escherichia Genus Strain Phylotyping," Microbial Genomics 4:1-8.

Beisel, C.L. et al. (2014). "A CRISPR Design for Next-Generation Antimicrobials," Genome Biology 15:516, 4 pages.

Belizario, J.E. et al. (Oct. 6, 2015). "Human Microbiomes and Their Roles in Dysbiosis, Common Diseases, and Novel Therapeutic Approaches," Frontiers in Microbiology 6(1050):1-16.

Bellanger, X. et al. (Jul. 1, 2014, e-pub. Jan. 27, 2014). "Conjugative and Mobilizable Genomic Islands in Bacteria: Evolution and Diversity," FEMS Microbiology Reviews 38(20144):720-760.

Bikard, D. et al. (2013, e-pub. Jun. 12, 2013). "Programmable Repression and Activation of Bacterial Gene Expression Using an Engineered CRISPR-Cas System," Nucleic Acids Research 41(15):7429-7437.

Bikard, D. et al. (2017, e-pub. Sep. 6, 2017). "Using CRISPR-Cas Systems as Antimicrobials," Current Opinion in Microbiology 37:155-160.

Bikard, D. et al. (Aug. 16, 2012). "CRISPR Interference Can Prevent Natural Transformation and Virulence Acquisition during In Vivo Bacterial Infection," Cell Host & Microbe 12(2):177-186.

Bikard, D. et al. (Nov. 2014). "Development of Sequence-Specific Antimicrobials Based on Programmable CRISPR-Cas Nucleases," Nature Biotechnology 32(11):1146-1151, 16 pages.

Broaders, E. et al. (Jul./Aug. 2013). "Mobile Genetic Elements of the Human Gastrointestinal Tract," Gut Microbes 4(4):271-280.

Brouns, S.J.J. et al. (Aug. 15, 2008). Supplemental Material for "Small CRISPR RNAs Guide Antiviral Defense in Prokaryotes," Science 321:960-964.

Brouns, S.J.J. et al. (Aug. 15, 2008). "Small CRISPR RNAs Guide Antiviral Defense in Prokaryotes," Science 321:960-964.

Bryksin, A.V. et al. (Oct. 8, 2010). "Rational Design of a Plasmic, Origin That Replicates Efficiently in Both Gram-Positive and Gram-Negative Bacteria," PloS One 5(10):e13244, 9 pages.

Bugrysheva, J.V. et al. (Jul. 2011, E-Pub. Apr. 29, 2011). "The Histone-Like Protein Hlp Is Essential for Growth of *Streptococcus*

(56) References Cited

OTHER PUBLICATIONS

*pyogenes*: Comparison of Genetic Approaches to Study Essential Genes," Appl. Environ. Microbiol. 77(13):4422-4428.
Bullman, S. et al. (Nov. 23, 2017). "Analysis of Fusobacterium Persistence and Antibiotic Response in Colorectal Cancer," Science pp. 1443-1448, 10 pages.
Burns, M.B. et al. (2015). "Virulence Genes Are a Signature of the Microbiome in the Colorectal Tumor Microenvironment," Genome Medicine 7:55, 12 pages.
Catalao, M.J. et al. (Jul. 2013, e-pub. Nov. 8, 2012). "Diversity in Bacterial Lysis Systems: Bacteriophages Show the Way," FEMS Microbiology Reviews 37(4):554-571.
Chan, B.K. et al. (2013). "Phage Cocktails and the Future of Phage Therapy," Future Microbiol. 8(6):769-783.
Chan, C.T.Y. et al. (Dec. 2015). "'Deadman' and 'Passcode' Microbial Kill Switches for Bacterial Containment," Nat. Chem. Biol. 12(2):82-86.
Cheadle, E.J. et al. (2012). "Chimeric Antigen Receptors for T-Cell Based Therapy," Methods Mol. Biol. 907:645-666, 36 pages.
Chen, S. et al. (Sep. 1, 2018). "Fastp: An Ultra-Fast All-In-One FASTQ Preprocessor," Bioinformatics 34(17):i884-i890.
Chen, Z. et al. (Aug. 7, 2020). "Akkermansia muciniphila Enhances the Antitumor Effect of Cisplatin in Lewis Lung Cancer Mice," Journal of Immunology Research 2020(2969287):1-13.
Citorik, R.J. et al. (Nov. 2014, e-pub Sep. 21, 2014). "Sequence-Specific Antimicrobials Using Efficiently Delivered RNA-Guided Nucleases," Nat. Biotechnol. 32(11):1141-1145, 18 pages.
Cobb, R.E. et al. (2015). "High-Efficiency Multiplex Genome Editing of Streptomyces Species Using an Engineered CRISPR/Cas System," ACS Synth. Biol. 4:723-728.
Cochrane, K. et al. (2016, e-pub. Nov. 3, 2015). "Complete Genome Sequences and Analysis of the Fusobacterium nucleatum Subspecies Animalis 7-1 Bacteripophage Φfunu1 and Φfunu2," Anaerobe 38:125-129. Abstract Only.
Cong, L. et al. (Feb. 15, 2013, e-pub. Oct. 11, 2013). "Multiplex Genome Engineering Using CRISPR/Cas Systems," Science 339(6121):819-823, 9 pages.
Consumer Updates (2019). "Combating Antibiotic Resistance," retrieved from https://www.fda.gov/ForConsumers/ConsumerUpdates/ucm092810.htm, last visited Jan. 28, 2019.
Coyne, M.J. et al. (2014). "Evidence of Extensive DNA Transfer between Bacteroidales Species Within the Human Gut," mBio 5(3):e01305-14, 12 pages.
Cronan, J.E. (Jan. 2013). "Improved Plasmid-Based System for Fully Regulated Off-To-On Gene Expression in *Escherichia coli*: Application to Production of Toxic Proteins," Plasmid 69(1):81-89, 17 pages.
Cui, L. et al. (2016, e-pub. Apr. 8, 2016). "Consequences of Cas9 Cleavage in the Chromosome of *Escherichia coli*," Nucleic Acids Research 44(9):4243-4251.
Daillere, R. et al. (Oct. 18, 2016). "Enterococcus hirae and Barnesiella intestinihominis Facilitate Cyclophosphamide-Induced Therapeutic Immunomodulatory Effects," Immunity 95:931-943.
Datsenko, K.A. et al. (Jul. 10, 2012). "Molecular Memory of Prior Infections Activates the CRISPR/Cas Adaptive Bacterial Immunity System," Nature Communication 3:945, 7 pages.
De Filippo, C. et al. (Aug. 33 2010). "Impact of Diet in Shaping Gut Microbiota Revealed by a Comparative Study in Children From Europe and Rural Africa," Proc. Natl. Acad. Sci. USA 107(33):14691-14696, 6 pages.
De Paepe, M. et al. (Mar. 28, 2014). "Bacteriophages: An Underestimated Role in Human and Animal Health?" Frontiers in Cellular and Infection Microbiology 4(39):1-11.
Deeks, E.D. (2014, e-pub. Jul. 15, 2014). "Nivolumab: A Review of Its Use in Patients With Malignant Melanoma," Drugs 74:1233-1239.
Deghorain, M. et al. (Nov. 23, 2012). "The Staphylococci Phages Family: An Overview," Viruses 4:3316-3335.
Del Castillo, M. et al. (Dec. 1, 2016). The Spectrum of Serious Infections Among Patients Receiving Immune Checkpoint Blockade for the Treatment of Melanoma Clin. Infect. Dis. 63:1490-1493.
Denham, J.D. et al. (2018). "Case Report: Treatment of Enteropathogenic *Escherichia coli* Diarrhea in Cancer Patients: A Series of Three Cases," Case Reports in Infectious Diseases Article ID 8438701:1-3.
Derosa, L. et al. (2018, e-pub. Mar. 30, 2018). "Negative Association of Antibiotics on Clinical Activity of Immune Checkpoint Inhibitors in Patients With Advanced Renal Cell and Non-Small-Cell Lung Cancer," Annals of Oncology. 2 pages.
Dhar, A.D. (Jul. 20, 2018). "Overview of Bacterial Skin Infections," Merck Manual retrieved from https://www.merckmanuals.com/home/skin-disorders/bacterial-skin-infections/overview-of-bacterial-skin-infections, last visited Jul. 20, 2018, 3 pages.
Dickson, R.P. et al. (Jan./Feb. 2017). "Bacterial Topography of the Healthy Human Lower Respiratory Tract," American Society for Microbiology 8(1):e02287-6, 12 pages.
Diez-Villasenor, C. et al. (May 2013). "CRISPR-Spacer Integration Reporter Plasmids Reveal Distinct Genuine Acquisition Specificities Among CROSPR-Cas 1-E Variants of *Escherichia coli*," RNA Biology 10(5):792-802.
Dutilh, B.E. et al. (Jul. 24, 2014). "A Highly Abundant Bacteriophage Discovered in the Unknown Sequences of Human Faecal Metagenomes," Nature Communications 5(4498):1-10.
Ebrahimizadeh, W. et al. (Mar. 18, 2014). "Bacteriophage Vehicles for Phage Display: Biology, Mechanism, and Application," Current Microbiology 69(2):109-120.
Edgar et al. (Dec. 2010). "The *Escherichia coli* CRISPR System Protects From λ Lysogenization, Lysogens, and Prophage Induction," Journal of Bacteriology 192(23):6291-6294, Supplemental Material, 2 pages.
Edgar et al. (Dec. 2010). "The *Escherichia coli* CRISPR System Protects From λ Lysogenization, Lysogens, and Prophage Induction," Journal of Bacteriology 192(23):6291-6294.
Ericsson, A.C. et al. (Sep. 10, 2015). "Differential Susceptibility to Colorectal Cancer Due to Naturally Occurring Gut Microbiota," Oncotarget 6(32):33689-33704.
Esvelt, K.M. et al. (Nov. 2013). "Orthogonal Cas9 Proteins for RNA-Guided Gene Regulation and Editing," Nature Methods 10(11):1116-1123.
European Office Action, dated Jun. 29, 2021, for European Patent Application No. 16719873.8, 24 pages.
European Search Report, dated Oct. 4, 2021, for European Patent Application No. 21170379.8, 6 pages.
European Search Report, dated Oct. 8, 2021, for European Patent Application No. 21170380.6, 7 pages.
Ex Parte Re-Exam Communication Transmittal Form, dated Jun. 30, 2021, for U.S. Appl. No. 90/014,705, for Reexamination U.S. Pat. No. 10,953,090, 26 pages.
Ex Parte Re-Exam Communication Transmittal Form, dated May 25, 2022, for Control No. 90/014,705, for Reexamination U.S. Pat. No. 10,953,090, 19 pages.
Ex Parte Re-Exam, mailed Apr. 21, 2021, for U.S. Appl. No. 90/014,705, filed Mar. 26, 2021, for Reexamination U.S. Pat. No. 10,953,090, 15 pages.
Ex Parte Re-Exam, mailed Apr. 30, 2021, for U.S. Appl. No. 90/014,681, filed Feb. 16, 2021, for Reexamination U.S. Pat. No. 10,920,222, 25 pages.
Ex Parte Re-Exam, mailed Dec. 10, 2018, for U.S. Appl. No. 90/014,184, filed Aug. 10, 2018, for Reexamination U.S. Pat. No. 9,701,964 102 pages.
Ex Parte Re-Exam, mailed Dec. 16, 2021, for U.S. Appl. No. 90/014,877, filed Oct. 6, 2021, for Reexamination U.S. Pat. No. 10,953,090, 12 pages.
Ex Parte Re-Exam, mailed Feb. 22, 2021, for U.S. Appl. No. 16/700,856, filed Dec. 2, 2019, for Reexamination U.S. Pat. No. 10,920,222, 459 pages.
Ex Parte Re-Exam, mailed Mar. 23, 2021, for U.S. Appl. No. 16/453,604, filed Jun. 26, 2019, for Reexamination U.S. Pat. No. 10,953,090, 235 pages.

(56) References Cited

OTHER PUBLICATIONS

Ex Parte Re-Exam, mailed Mar. 24, 2021, for U.S. Appl. No. 90/014,681, filed Mar. 24, 2021, for Reexamination U.S. Pat. No. 10,920,222, 18 pages.
Ex Parte Re-Exam, mailed Nov. 15, 2021, for U.S. Appl. No. 90/014,877, 12 pages.
Ex Parte Re-Exam, mailed Sep. 27, 2021, for U.S. Appl. No. 90/014,705, filed Mar. 23, 2021, for Reexamination U.S. Pat. No. 10,953,090, 16 pages.
Extended European Search Report, dated Jul. 27, 2020, for European Patent Application No. 20155001.9, 9 pages.
Extended European Search Report, dated Sep. 24, 2020, for European Patent Application No. 20154858.3, 12 bages.
Fact Sheet (Oct. 2010). "Antimicrobial Resistance," National Institutes of Health, 1-2.
Foca, A. et al. (2015, e-pub. Apr. 7, 2015). Gut Inflammation and Immunity: What Is the Role of the Human Gut Virome? Mediators of Inflammation 2015(326032):1-7.
Fujita, K. et al. (2017). "Emerging Concern of Infectious Diseases in Lung Cancer Patients Receiving Immune Checkpoint Inhibitor Therapy," Eur. Resp. J. 50, OA1478. (Abstract Only).
Galperin, M.Y. (Dec. 2013). "Genome Diversity of Spore-Forming Firmicutes," Microbiology Spectrum 1(2): TBS-0015-2012, 27 pages.
Garneau, J. E. et al. (Nov. 4, 2010). "The CRISPR/Cas Bacterial Immune System Cleaves Phage and Plasmid DNA," Nature 468(7320):67-71, 28 pages.
Garon, E.B. et al. (Oct. 2015). "Current Perspectives In Immunotherapy for Non-Small Cell Lung Cancer," Seminars In Oncology 42(5 Supp. 2):S11-S18.
Garrett W.S. et al. (Oct. 5, 2007). "Communicable Ulcerative Colitis Induced by T-Bet Deficiency in the Innate Immune System," Cell 131(1):33-45, 23 pages.
Gauer, R.L. et al. (Jul. 1, 2013). "Early Recognition and Management of Sepsis in Adults: The First Six Hours," American Family Physician 88(1):44-53.
Geller, L.T. et al. (Sep. 15, 2017). "Potential Role of Intratumor Bacteria in Mediating Tumor Resistance to the Chemotherapeutic Drug Gemcitabine," Cancer, 1156-1160, 6 pages.
Goldwater, P.N. et al. (2012). "Treatment of Enterohemorrhagic *Escherichia coli* (EHEC) Infection and Hemolytic Uremic Syndrome (HUS)," BMC Medicine 10:12, 8 pages.
Golubovskaya, V. et al. (Mar. 15, 2016). "Different Subsets of T Cells, Memory, Effector Functions, and CAR-T Immunotherapy," Cancers 8(36), 12 pages.
Gomaa et al. (Jan. 28, 2014). "Programmable Removal of Bacterial Strains by Use of Genome-Targeting CRISPR-Cas Systems," mBio 5(1):e000928-13.
Gomaa, A.A. (2016). "Sequence Specific CRISPR-Based Antimicrobials From Treating Multidrug-Resistant Infections," Dissertation to the Graduate Faculty of North Carolina State University, 188 pages.
Gomaa, A.A. et al. (Jan./Feb. 2014). Supplemental Material to "Programmable Removal of Bacterial Strains by Use of GenomeTargeting CRISPR-Cas Systems," American Society for Microbiology 5(1):1-9.
Goodall, E.C.A. et al. (Feb. 20, 2018). "The Essential Genome of *Escherichia coli* K-12," Am. Society for Microbiology—mBio 9(1):e02096-17, 18 pages.
Gopalakrishnan, V. et al. (Jan. 5, 2018). "Gut Microbiome Modulates Response to Anti-PD-1 Immunotherapy in Melanoma Patients," Science 359:97-103, 20 pages.
Green, J. (Jul. 20, 2018). Colgate https://www.colgate.com/en-us/oral-health/conditions/mouth-sores-and-infections/eight-common-oral-infections-0615, last visited Jul. 20, 2018, 4 pages.
Gudbergsdottir, S. et al. (2011, e-pub. Nov. 18, 2010). "Dynamic Properties of the Sulfolobus CRISPR/ Cas and CRISPR/Cmr Systems When Challenged With Vector-Borne Viral and Plasmid Genes and Protospacers," Molecular Microbiology 79(1):35-49.
Gudiol, C. et al. (2016). "Bloodstream Infections in Patients With Solid Tumors," Virulence 7(3):298-308.

Guedan, S. et al. (Aug. 14, 2014). "ICOS-Based Chimeric Antigen Receptors Program Bipolar TH17/TH1 Cells," Blood 124(7):1070-1080.
Guglielmi, G. (2020). "How Gut Bacteria Boost Cancer Immunotherapy," retrieved from the Internet https://microbiomepost.com/how--gut-bacteria-boost-cancer-immunotherapy/, last visited Jul. 25, 2021, 2 pages.
Gupta, R. et al. (2011). "P-27/HP Endolysin as Antibacterial Agent for Antibiotic Resistant *Staphylococcus aureus* of Human Infections," Curr. Microbiol. 63:39-45.
Gur, C. et al. (Feb. 17, 2015). "Binding of the Fap2 Protein of Fusobacterium nucleatum to Human Inhibitory Receptor TIGIT Protects Tumors from Immune Cell Attack," Immunity 42(2):344-355.
Gutierrez, B. et al. (Apr. 30, 2018). "Genome-Wide CRISPR-Cas9 Screen in *E. coli* Identifies Design Rules for Efficient Targeting," 22 pages.
Ha, Y.E. et al. (2013). "Epidemiology and Clinical Outcomes of Bloodstream Infections Caused by Extended-Spectrum β-Lactamase-Producing *Escherichia coli* in Patients With Cancer," Int. J. Antimicr. Agen. 42(5):403-409.
Hamanishi, J. et al. (2016, e-pub. Feb. 22, 2016). "PD-1/PD-L1 Blockade In Cancer Treatment: Perspectives and Issues," International Journal of Clinical Oncology 21:462-473.
Hansen, J.J. et al. (Mar. 2015). "Therapeutic Manipulation of the Microbiome in IBD: Current Results and Future Approaches," Curr. T. Options Gastroentrol. 13(1):1-18.
Hargreaves, K.R. et al. (Aug. 26, 2014). "Abundant and Diverse Clustered Regularly Interspaced Short Palindromic Repeat Spacers in Clostridium difficile Strains and Prophages Target Multiple Phage Types within This Pathogen," mBio 5(5):e01045-13.
Harrington, L.E. (Nov. 2005, e-pub. Oct. 2, 2005). "Interleukin 17-producing CD4+ Effector T Cells Develop via a Lineage Distinct From the T Helper Type 1 and 2 Lineages," Nat. Immunol. 6(11):1123-1132.
Hartland, E.L. et al. (Apr. 30, 2013). "Enteropathogenic and Enterohemorrhagic *E. coli*: Ecology, Pathogenesis, and Evolution," Frontiers in Cellular and Infection Microbiology 3(15):1-3.
Hase, K. (Nov. 2014). "Intestinal Microbiota and Immunity," Infectious Disease (in Japanese). 44(6):193-200 22 pages. English Translation.
Hatoum-Aslan, A. (Jun. 19, 2018). "Phage Genetic Engineering Using CRISPR-Cas Systems," Viruses 10:335, 11 pages.
Healthline (2019). "Cystic Fibrosis," retrieved from https://www.healthline.conn/health/cystic-fibrosis#prevention, last visited Aug. 5, 2019, 14 pages.
Hooper, L.V. et al. (Jun. 8, 2012). "Interactions Between the Microbiota and the Immune System," Science 336 (6086):1268-1273, 16 pages.
Horvath, P. et al. (2008, e-pub. Dec. 7, 2007). "Diversity, Activity, and Evolution of CRISPR Loci in *Streptococcus thermophiles*," Journal of Bacteriology 190(4):1401-1412.
Hotta, K. et al. (2011, e-pub. Sep. 20, 2011). "Prognostic Significance of CD45RO+ Memory T Cells in Renal Cell Carcinoma," British Journal of Cancer 105:1191-1196.
Huddleston, J.R. (Jun. 20, 2014). "Horizontal Gene Transfer in the Human Gastrointestinal Tract: Potential Spread of Antibiotic Resistance Genes," Infection and Drug Resistance 7:167-176.
Huo, Y. et al. (Sep. 2014). "Structures of CRISPR Cas3 Offer Mechanistic Insights Into Cascade-Activated DNA Unwinding and Degradations," Nat. Struct. Mol. Biol. 21(9):771-777, 21 pages.
Hurwitz, A.A. et al. (Aug. 1998). "CTLA-4 Blockade Synergizes With Tumor-Derived Granulocyte-Macrophage Colony-Stimulating Factor for Treatment of an Experimental Mammary Carcinoma," Proc. Natl. Acad. Sci. USA 95:10067-10071.
Ichikawa, M. et al. (Dec. 2019). "The Relationship Between Gut Microbiome, Immune System, and Cancer," Jpn. J. Cancer Chemother 16(12):1807-1813. English Abstract.
International Search Report and The Written Opinion of the International Searching Authority for PCT/EP2018/066954, dated Oct. 23, 2018, filed Jun. 25, 2018, 14 pages.

(56) References Cited

OTHER PUBLICATIONS

International Search Report and The Written Opinion of the International Searching Authority for PCT/EP2019/057453, dated Aug. 16, 2019, filed Mar. 25, 2019, 21 pages.
International Search Report and Written Opinion, dated May 12, 2022, for PCT Application No. PCT/EP2021/076360, 23 pages.
International Search Report for PCT/EP2016/059803, dated Jun. 30, 2016, filed May 3, 2016, 6 pages.
International Search Report for PCT/EP2018/082053, dated Mar. 14, 2019, filed Nov. 21, 2018, 9 pages.
Invitation to Pay Additional Fees, dated Feb. 4, 2022, for PCT Application No. PCT/EP2021/076360, filed Sep. 24, 2021, 13 pages.
Ivanov, I.I. et al. (May 2010). "Segmented Filamentous Bacteria Take the Stage," Muscosal Immunol. 3(3):209-212, 7 pages.
Jiang, W. et al. (Jan. 29, 2013). "RNA-Guided Editing of Bacterial Genomes Using CRISPR-Cas Systems," Nat. Biotechnology 31:233-241.
Jiang, W. et al. (Mar. 2013, e-pub. Sep. 1, 2013). "CRISPR-Assisted Editing of Bacterial Genomes," Nat. Biotechnol. 31(3):233-239.
Jiang, W. et al. (Nov. 2013). "Demonstration of CRISPR/Cas9/sgRNA-Mediated Targeted Gene Modification in *Arabidopsis*, Tobacco, Sorghum and Rice," Nucleic Acids Research 41(20):e188, 12 pages.
Jin, Y. et al. (2019, e-pub. Apr. 23, 2019). "The Diversity of Gut Microbiome is Associated With Favorable Responses to Anti-Programmed Death 1 Immunotherapy in Chinese Patients With NSCLC," Journal of Thoracic Oncology 14 (8):1378-1389.
Jinek et al. (Aug. 17, 2012). "A Programmable Dual-RNA-Guided DNA Endonuclease In Adaptive Bacterial Immunity," Science 337(6096):816-821.
Johnson, C. M. et al. (Nov. 23, 2015). "Integrative and Conjugative Elements (ICEs): What They Do and How They Work," Annual Review of Genetics 49(1):577-601, 33 pages.
Jones, R.B. et al. (2008). "Tim-3 Expression Defines a Novel Population of Dysfunctional T Cells With Highly Elevated Frequencies in Progressive HIV-1 Infection," J. Exp. Med. 205(12):2763-2779.
Kaiser, J. (Nov. 2, 2017). "Your Gut Bacteria Could Determine How You Respond to Cutting-Edge Cancer Drugs," Science retrieved from Internet https://www.sciencemag.org/news/2017/11/your-gut-bacteria-could-dtermine-how-you-respond-cutting-edge-cancer-drugs, last visited Jul. 25, 2021, 4 pages.
Karch, H. et al. (Jul. 1999). "Epidemiology and diagnosis of Shiga toxin-producing *Escherichia coli* infections," Diagnostic Microbiology and Infectious Disease (34(3):229-243.
Kaulich, M. et al. (2015, e-pub. Jan. 13, 2015). "Efficient CRISPR-rAAV Engineering of Endogenous Genes to Study Protein Function by Allele-Specific RNAi," Nucleic Acids Research 43(7):e45, 8 pages.
Keskin, H. et al. (Nov. 20, 2014). "Transcript-RNA-Templated DNA Recombination and Repair," Nature 515:436-439.
Khoja, L. et al. (2015). "Pembrolizumab," Journal for Immuno Therapy of Cancer 3(36):1-13.
Kochenderfer, J.N. et al. (Sep. 2009). "Construction and Pre-clinical Evaluation of An Anti-CD19 Chimeric Antigen Receptor," J. Immunother. 32(7):689-702, 26 pages.
Koonin, E.V. et al. (2017, e-pub. Jun. 9, 2017). "Diversity, Classification and Evolution of CRISPR-Cas Systems," Current Opinion in Microbiology 37:67-78.
Kosiewicz, M.M. et al. (2014, e-pub. Mar. 26, 2014). "Relationship Between Gut Microbiota and Development of T Cell Associated Disease," FEBS Lett. 588:4195-4206.
Kostic, A.D. et al. (Aug. 14, 2013). "Fusobacterium nucleatum Potentiates Intestinal Tumorigenesis and Modulates the Tumor-Immune Microenvironment," Cell Host Microbe. 14(2):207-215, 18 pages.
Krom, R.J. et al. (Jul. 5, 2015). "Engineered Phagemids for Nonlytic, Targeted Antibacterial Therapies," Nano Letters 15(7):4808-4813.
Kugelberg, E. et al. (Aug. 2005). "Establishment of a Superficial Skin Infection Model in Mice by Using *Staphylococcus aureus* and *Streptococcus pyogenes*," Antimicrob Agents Chemother. 49(8):3435-3441.
Kutter, E. et al. (Jul. 21, 2018). "From Host to Phage Metabolism: Hot Tales of Phage T4's Takeover of *E. coli*," Viruses 10:387, 17 pages.
La Scola, B. et al. (Sep. 4, 2008). "The Virophage as a Unique Parasite of the Giant Mimivirus," Nature Letters 455:100-104.
Leshem, A. et al. (Sep. 29, 2020). "The Gut Microbiome and Individual-Specific Responses to Diet," mSystems 5(5):e00665-20, 12 pages.
Letunic, I. et al. (2021, e-pub. Apr. 22, 2021). "Interactive Tree of Life (iTOL) v5: An Online Tool for Phylogenetic Tree Display and Annotation," Nucleic Acids Research 49:W293-W296.
Lopez-Sanchez, M.-J. et al. (2012, e-pub. Jul. 27, 2012). "The Highly Dynamic CRISPR1 System of *Streptococcus agalactiae* Controls the Diversity of its Mobilome," Molecular Microbiology 85(6):1057-1071.
Lu, T.K. et al. (Jul. 3, 2007). "Dispersing Biofilms With Engineered Enzymatic Bacteriophage," PNAS 104 (27): 11197-11202.
Ludwig, W. et al. (1985). "The Phylogenetic Position of *Streptococcus* and Enterococcus," Journal of General Microbiology 131:543-551.
Luo, M.L. et al. (2015, e-pub. Oct. 17, 2014). "Repurposing Endogenous Type I CRISPR-Cas Systems for Programmable Gene Repression," Nucleic Acids Research 43(1):674-681.
López, P. et al. (Apr. 5, 2016). "Th17 Responses and Natural IgM Antibodies Are Related to Gut Microbiota Composition in Systemic Lupus Erythematosus Patients," Sci. Rep. 6:24072, 12 pages.
Macon, B.L. et al. (Jan. 2, 2018). "Acute Nephrities," retrieved from healthline, https://www.healthline.com/health/acute-nephritic-syndrome##types, last visited Jul. 20, 2018, 13 pages.
Magee, M.S. et al. (Nov. 2014). "Challenges to Chimeric Antigen Receptor (CAR)-T Cell Therapy for Cancer," Discov. Med. 18(100):265-271, 6 pages.
Mahoney, K.M. et al. (2015). "The Next Immune-Checkpoint Inhibitors: PD-1/PD-L1 Blockade in Melanoma," Clinical Therapeutics 37(4):764-782.
Makarova, K.S. et al. (Jun. 2011). "Evolution and Classification of the CRISPR-Cas Systems," Nat. Rev. Microbiol. 9(6):467-477, 23 pages.
Mali, P. et al. (Oct. 2013, e-pub. Sep. 27, 2013). "Cas9 as a Versatile Tool for Engineering Biology," Nature Methods 10(10):957-963, 16 pages.
Mancha-Agresti, P. et al. (Mar. 2017). "A New Broad Range Plasmid for DNA Delivery in Eukaryotic Cells Using Lactic Acid Bacteria: In Vitro and In Vivo Assays," Molecular Therapy: Methods & Clinical Development 4:83-91.
Manica, A. et al. (2011, e-pub. Mar. 8, 2011). "In vivo Activity of CRISPR-Mediated Virus Defence in a Hyperthermophilic Archaeon," Molecular Microbiology 80(2):481-491.
Manson, J.M. et al. (2008). "Chapter 2: The Commensal Microbiology of the Gastrointestinal Tract," in GL Mictrobiota and the Regulation of the Immune System, Advances in Experimental Medicine and Biology vol. 635, pp. 15-28.
Marin, M. et al. (May 2014). "Bloodstream Infections in Patients With Solid Tumors Epidemiology, Antibiotic Therapy, and Outcomes in 528 Episodes in a Single Cancer Center," Medicine 93:143-149.
Marraffini, L.A. et al. (Dec. 19, 2008). "CRISPR Interference Limits Horizontal Gene Transfer in Staphylococci by Targeting DNA," Science 322(5909):1843-1845, 12 pages.
Martel, B. et al. (2014, e-pub. Jul. 24, 2014). "CRISPR-Cas: AN Efficient Tool For Genome Engineering of Virulent Bacteriophages," Nucleic Acids Research 42(14):9504-9513.
Martinez, R.M. et al. (Aug. 12, 2016). "Bloodstream Infections," Microbial Spectrum 4(4):DMIH2-0031-2016, 34 pages.
Matson, V. et al. (Jan. 5, 2018). "The Commensal Microbiome Is Associated With Anti-PD-1 Efficacy in Metastatic Melanoma Patients," Science 359(6371):104-108.

(56) References Cited

OTHER PUBLICATIONS

Matsushiro, A. et al. (Apr. 1999). "Induction of Prophages of Enterohemorrhagic *Escherichia coli* O157:H7 With Norfloxacin," J. Bacteriology 181(7):2257-2260.

Mayo Clinic (2019). "Pulmonary Embolism," retrieved from https://www.nnayoclinic.org/diseases-conditions/pulnnonary-ennbolisnn/synnptonns-causes/syc-20354647, last visited Aug. 5, 2019, 8 pages.

Mayo Clinic (2020). "Infectious Diseases," retrieved from https://www.nnayoclinic.org/diseases-conditions/infectious-diseases/diagnosis-treatnnent/drc-20351179, last visited Jan. 17, 2020, 5 pages.

Mayo Clinic (2020). "Malaria," retrieved from https://www.nnayoclinic.org/diseases-conditions/nnalaria/diagnosis-treatnnent/drc-20351190, last visited Jan. 17, 2020, 3 pages.

Mayo Clinic (2020). "Sexually Transmitted Diseases (STDs)," retrieved from https://www.nnayoclinic.org/diseases-conditions/sexually-transnnitted-diseases-stds/diagnosis-treatnnent/drc-20351246, last visited Jan. 17, 2020, 5 pages.

Mayo Clinic (Jul. 20, 2018). "Bacterial Vaginosis," retrieved from https://www.mayoclinic.org/diseases-conditions/bacterial-vaginosis/symptoms-causes/syc-20352279, last visited Jul. 20, 2018, 3 pages.

Mayo Clinic (Jul. 20, 2018). "Cystitis," retrieved from https://www.mayoclinic.org/diseases-conditions/cystitis/ symptoms-causes/syc-20371306, last visited Jul. 20, 2018, 10 pages.

Mayo Clinic (Jul. 20, 2018). "Meningitis," retrieved from https://www.mayoclinic.org/diseases-conditions/meningitis/symptoms-causes/syc-20350508, last visited Jul. 20, 2018, 6 pages.

Mayo Clinic (Jul. 20, 2018). "Pneumonia," retrieved from https://www.mayoclinic.org/diseases-conditions/pneumonia/symptoms-causes/syc-20354204, last visited Jul. 20, 2018, 5 pages.

Mayo Clinic (Mar. 29, 2020). "Liver Disease," retrieved from https://www.mayoclinic.org/diseases-conditions/liver-problems/diagnosis-treatment/drc-20374507, last visited Mar. 29, 2020, 8 pages.

Medina-Aparicio, L. et al. (May 2011, e-pub. Mar. 11, 2011). "The CRISPR/Cas Immune System Is an Operon Regulated by LeuO, H-NS, and Leucine-Responsive Regulatory Protein in *Salmonella enterica* Serovar Typhi," Journal of Bacteriology 193(10):2396-2407.

Mei, J.-M et al. (1997). "Identification of *Staphylococcus aureus* Virulence Genes in a Murine Model of Bacteraemia Using Signature-Tagged Mutagenesis," Molecular Microbiology 26(2):399-407.

Mercenier, A. (1990). "Molecular Genetics of *Streptococcus Thermophiles*," FEMS Microbiology Letters 87 (1-2):61-77.

Mick, E. et al. (May 2013). "Holding a Grudge: Persisting Anti-Phage CRISPR Immunity in Multiple Human Gut Microbiomes," RNA Biology 10(5):900-906.

Miller, E.S. et al. (Sep. 2003). "Complete Genome Sequence of the Broad-Host-Range Vibriophage KVP40: Comparative Genomics of a T4-Related Bacteriophage," Journal of Bacteriology 185(17):5220-5233.

Mills, S. et al. (Jan./Feb. 2013). "Movers and Shakers: Influence of Bacteriophages in Shaping the Mammalian Gut Microbiota," Gut Microbes 4(1):4-16.

Mima, K. et al. (Aug. 1, 2015, e-pub. Jun. 4, 2014). "Fusobacterium nucleatum and T-Cells in Colorectal Carcinoma," JAMA Oncol. 1(5):653-661.

Mitsuhashi, K. et al. (Mar. 13, 2015). "Association of Fusobacterium Species in Pancreatic Cancer Tissues With Molecular Features and Prognosis," Oncotarget 6(9):7209-7220.

Nakamura, S. et al. (Nov. 2008). "Metagenomic Diagnosis of Bacterial Infections," Emerging Infectious Diseases 14(11):1784-1786.

Nale, J.Y. et al. (2012). "Diverse Temperate Bacteriophage Carriage in Clostridium Difficile 027 Strains," PloS One 7 (5):e37263, 9 pages.

Navarre, L. et al. (2007). "Silencing of Xenogeneic DNA by H-NS—Facilitation of Lateral Gene Transfer in Bacteria by a Defense System That Recognizes Foreign DNA," Genes & Development 21:1456-1471.

Nelson, M.H. et al. (2015). "Harnessing the Microbiome to Enhance Cancer Immunotherapy," Journal of Immunology Research 2015:Article 368736, 12 pages.

News (May 22, 2018). "UK Government and Bill & Melinda Gates Foundation Join Carb-X Partnership in Fight Against Superbugs: Millions Earmarked to Boost Research Into New Life-Saving Products to Address the Global Rise of Drug-Resistant Bacteria," Combating Antibiotic Resistant Bacteria, 7 pages.

Noonan, K.A. et al. (May 20, 2015). "Adoptive Transfer of Activated Marrow-Infiltrating Lymphocytes Induces Measurable Antiumor Immunity in the Bone Marrow in Multiple Myeloma," Science Translational Medicine 7 (228):288ra78, 14 pages.

Norris, J.S. et al. (2000). "Prokaryotic Gene Therapy to Combat Multidrug Resistant Bacterial Infection," Gene Therapy 7:723-725.

Notice of Intent to Issue Ex Parte Reexamination Certificate, mailed Aug. 12, 2019, for U.S. Pat. No. 90/014,184, filed Aug. 10, 2018, 26 pages.

Novosiadly, R. et al. (2016, e-pub. Mar. 30, 2016). "High-Content Molecular Profiling of T-Cell Therapy in Oncology," Molecular Therapy—Oncolytics 3:16009, 6 pages.

Nowak, P. et al. (Nov. 28, 2015). "Gut Microbiota Diversity Predicts Immune Status In HIV-1 Infection," AIDS 29 (18):2409-2418.

Office Action, dated Nov. 4, 2021 for U.S. Appl. No. 90/014,705, filed Mar. 23, 2021, 7 pages.

Okazaki, T. et al. (2007). "PD-1 and PD-1 Ligands: From Discovery to Clinical Application," Intern. Immun. 19 (7):813-824.

Ondov, B.D. et al. (2016). "Mash: Fast Genome and Metagenome Distance Estimation Using MinHash," Genome Biol. 17:132, 14 pages.

O'Reilly, D. et al. (2019, e-pub. Dec. 4, 2018). "Extensive CRISPR RNA Modification Reveals Chemical Compatibility and Structure-Activity Relationships for Cas9 Biochemical Activity," Nucleic Acid Research 47 (2):546-558.

Pardoll, D.M. (Apr. 2012). "The Blockade of Immune Checkpoints in Cancer Immunotherapy," Nat. Rev. Cancer 12 (4): 252-264.

Park, A. (Oct. 18, 2011). "A Surprising Link Between Bacteria and Colon Cancer," Cancer retrieved from http://healthlande.time.com/2011/10/18/a-surprising-link-between-bacteria-and-colon-cancer/, last visited Aug. 27, 2019, 3 pages.

Park, H. et al. (2005). "A Distinct Lineage of CD4 T Cells Regulates Tissue Inflammation by Producing Interleukin 17," Nat. Immunol. 6(11):1133-1141, 24 pages.

Pastagia, N. et al. (Feb. 2011). "A Novel Chimeric Lysin Shows Superiority to Mupirocin for Skin Decolonization of Methicillin-Resistant and -Sensitive *Staphylococcus aureus* Strains," Antimicrobial Agents and Chemotherapy 55 (2):738-744.

Patterson, A.G. et al. (2017, e-pub. Mar. 27, 2017). "Regulation of CRISPR-Cas Adaptive Immune Systems," Current Opinion in Microbiology 37:1-7.

Patterson, A.G. et al. (Dec. 15, 2016). "Quorum Sensing Controls Adaptive Immunity Through the Regulation of Multiple CRISPR-Cas Systems," Mol. Cell 64(6):1102-1108.

Pawluk, A. et al. (Apr. 15, 2014). "A New Group of Phage Anti-CRISPR Genes Inhibits the Type I-E CRISPR-Cas System of Pseudomonas aeruginosa," mBio. 5(2):e00896.

Perez-Chanona, E. et al. (2016, e-pub. Jan. 26, 2016). "The Role of Microbiota in Cancer Therapy," Current Opinion in Immunology 39:75-81.

Pires, D.P. et al. (Sep. 2016, e-pub. Jun. 1, 2016). "Genetically Engineered Phages: A Review of Advances Over the Last Decade," Microbiology and Molecular Biology Reviews 80(3):523-543.

Pul, Ü. et al. (2010, e-pub. Feb. 17, 2010). "Identification and Characterization of *E. coli* CRISPR-cas Promoters and Their Silencing by H-NS," Molecular Microbiology 75(6):1495-1512.

Purdy, D. et al. (2002). "Conjugative Transfer of Clostridial Shuttle Vectors From *Escherichia coli* to Clostridium difficile Through Circumvention of the Restriction Barrier," Molec. Microbiology 46(2):439-452.

Ramalingam, S.S. et al. (2014). "LB2-Metastatic Non-Small Cell Lung Cancer: Phase II Study of Nivolumab (Anti-PD-1, BMS-936558, ONO-4538) In Patients With Advanced, Refractory Squamous Non-Small Cell Lung Cancer," International Journal of Radiation Oncology Biology Physics Late Breaking Abstract (LB2).

(56) References Cited

OTHER PUBLICATIONS

Ran, F.A. et al. (Apr. 9, 2015). "In vivo Genome Editing Using *Staphylococcus aureus* Cas9," Nature 520 (7546):186-191, 28 pages.
Rashid, T. et al. (2013). "The Role of Klebsiella in Crohn's Disease With a Potential for the Use of Antimicrobial Measures," International Journal of Rheumatology 2013(Article ID 610393):1-9.
Ray, K. (Jan. 2020). "Manipulating the Gut Microbiota to Combat Alcoholic Hepatitis," Nature Reviews Gastroenterology & Hepatology 17:3, 1 page.
Rea, K. et al. (2020, e-pub. Nov. 14, 2019). "Gut Microbiota: A Perspective for Psychiatrists," Neuropsychobiology 79:50-62.
Request for Ex Parte Re-Exam Under 35 U.S.C. § 302 and 37 C.F.R. § 1.510 dated Jun. 7, 2022, for U.S. Pat. No. 11,291,723, 328 pages.
Request for Ex Parte Re-Exam Under 35 U.S.C. § 302 and 37 C.F.R. § 1.510 dated Jun. 7, 2022, for U.S. Pat. No. 11,351,252, 219 pages.
Request for Ex Parte Reexamination mailed Aug. 10, 2018, for U.S. Appl. No. 15/160,405, now U.S. Pat. No. 9,701,964, 42 pages.
Request for Ex Parte Reexamination mailed Nov. 1, 2018, for U.S. Appl. No. 15/160,405, now U.S. Pat. No. 9,701,964, 35 pages.
Request for Ex Parte Reexamination under 35 U.S. C. § 302 and 37 C.F.R. § 1.510, dated Feb. 16, 2021, 72 pages.
Richter, C. et al. (2012, e-pub. Oct. 19, 2012). "Function and Regulation of Clustered Regularly Interspaced Short Palindromic Repeats (CRISPR) / CRISPR Associated (Cas) Systems," Viruses 4(12):2291-2311.
Ridaura, V.K. et al. (Sep. 6, 2013). "Cultured Gut Microbiota From Twins Discordant for Obesity Modulate Adiposity and Metabolic Phenotypes in Mice," Science 341(6150):1241214, 22 pages.
Roberts, A.P. et al. (Dec. 1, 2003). "Development of an Integrative Vector for the Expression of Antisense RNA in Clostridium difficile," Journal of Microbiological Methods 55(3):617-624.
Roberts, A.P. et al. (Jun. 2009, e-pub. May 20, 2009). "A Modular Master on the Move: The Tn916 Family of Mobile Genetic Elements," Trends Microbiol. 17(6):251-258. Abstract Only.
Rogers, L. et al. (2016). "Escherichia coli and Other Enterobacteriaceae: Occurrence and Detection," Encyclopedia of Food and Health pp. 545-551.
Rong, Z. et al. (Mar. 14, 2014). "Homologous Recombination in Human Embryonic Stem Cells Using CRISPR/Cas9 Nickase and a Long DNA Donor Template," Protein & Cell 5(4):258-260.
Routy, B. et al. (Jan. 5, 2018, e-pub. Nov. 2, 2017). "Gut Microbiome Influences Efficacy of PD-1-Based Immunotherapy Against Epithelial Tumors," Science 359(6371):91-97.
Roy, S. et al. (May 2017, e-pub. Mar. 17, 2017). "Microbiota: A Key Orchestrator of Cancer Therapy," Nat. Rev. Cancer 17(5):271-285.
Ryan, R.P. et al. (2008). "Diffusible Signals and Interspecies Communication in Bacteria," Microbiology 154:1845-1858.
Safdar, N. et al. (Jun. 4, 2002). "The Commonality of Risk Factors For Nosocomial Colonization and infection With Antimicrobial-Resistant *Staphylococcus Aureus*, Enterococcus, Gram-Negative Bacilli, Clostridium difficile, and Candida," Ann. Intern. Med. 136(11):834-844.
Saito, H. et al. (Jun. 15, 2016, e-pub. Apr. 12, 2016). "Adoptive Transfer of CD8+ T Cells Generated From Inducted Pluripotent Stem Cells Triggers Regressions of Large Tumors Along With Immunological Memory," Cancer Research 76(12):3473-3483.
Samaržija, D. et al. (2001). "Taxonomy, Physiology and Growth of Lactococcus Lactis: A Review," Mljekarstvo 51 (1):35-48.
Samonis, G. et al. (Sep. 2013, e-pub. Apr. 27, 2013). "A Prospective Study of Characteristics and Outcomes of Bacteremia in Patients With Solid Organ or Hematologic Malignancies," Support Care Cancer 21(9):2521-2526.
Sapranauskas, R. et al. (Nov. 1, 2011, e-pub. Aug. 3, 2011). "The *Streptococcus thermophilus* CRISPR/Cas System Provides Immunity in *Escherichia coli*," Nucleic Acids Research 39(21):9275-9282.
Satlin, J.J. et al. (Dec. 1, 2018, e-pub. Nov. 13, 2018). "Colonization With Levofloxacin-Resistant Extended-Spectrum B Lactamase-producing Enterobacteriaceae and Risk of Bacteremia in Hematopoietic Stem Cell Transplant Recipients," Clin. Infect. Dis. 67(11):1720-1728.
Satlin, M.J. et al. (Oct. 1, 2021, e-pub. May 6, 2021). "Colonization with Fluoroquinolone-Resistant Enterobacterales Decreases the Effectiveness of Fluoroquinolone Prophylaxis in Hematopoietic Cell Transplant Recipients," Clin Infect Dis. 73(7):1257-1265.
Schnabi, B.G. (2020), "The Role of Enterococcus Faecalis in Alcoholic Liver Disease," retrieved from https://grantome.com/grant/NIH/O01-BX004594-01A2, last visited Oct. 20, 2020, 2 pages.
Seed, K.D. et al. (Feb. 27, 2013). "A Bacteriophage Encodes Its Own CRISPR/Cas Adaptive Response to Evade Host Innate Immunity," Nature 494(7438):489-491.
Selle, K. et al. (Apr. 1, 2015). "Harnessing CRISPR-Cas Systems for Bacterial Genome Editing," Trends in Microbiology 23(4):225-232.
Sepsis Alliance. (Dec. 14, 2017). "What Are Vaccines," Retrieved from https://www.sepsis.org/sepsisand/prevention-vaccinations/; last visited Jul. 8, 2019, 3 pages.
Sepsis Alliance. (Jul. 8, 2019). "Prevention," Retrieved from https://www.sepsis.org/sepsisand/prevention/; accessed last visited Jul. 8, 2019, 5 pages.
Shank, E.A. et al. (Apr. 2009). "New Developments in Microbial Interspecies Signaling," Curr. Opin. Microbiol. 12 (2):205-214.
Sharan, S.K. et al. (2009). "Recombineering: A Homologous Recombination-Based Method of Genetic Engineering," Nat. Protoc. 4(2):206-223, 37 pages.
Shoemaker, N.B. et al. (Feb. 2001). "Evidence for Extensive Resistance Gene Transfer Among Bacteroides spp. and Among Bacteroides and Other Genera in the Human Colon," Appl. Environ. Microbiol. 67(2):561-68.
Simonsen, M. et al. (Oct. 2008). "Rapid Neighbour-Joining,". Proceedings of the 8th Workshop in Algorithms in Bioinformatics (WABI), pp. 113-122.
Sivan, A. et al. (Nov. 27, 2015, e-pub Nov. 5, 2015). "Commensal Bifidobacterium Promotes Antitumor Immunity and Facilitates Anti-PD-L1 Efficacy," Science 350(6264):1084-1089, 13 pages.
Sivan, A. et al. (Nov. 6, 2014). "Evidence Implicating the Commensal Microbiota in Shaping Anti-Tumor Immunity in Melanoma," Journal for Immuno Therapy of Cancer 2(Suppl. 3):011, 1 page.
Skennerton, C.T. et al. (May 2011). "Phage Encoded H-NS: A Potential Achilles Heel in the Bacterial Defence System," Plos One 6(5):e20095.
Slutsker, L. et al. (Apr. 1998). "A Nationwide Case-Control Study of *Escherichia coli* O157:H7 Infection in the United States," J. Infect. Dis. 177(4):962-966.
Somkuti, G. A. et al. (Apr. 1988). "Genetic Transformation of *Streptococcus thermophilus* by Electroporation," Biochimie 70(4):579-585. Abstract Only.
Sorek, R. et al. (2013, e-pub. Mar. 11, 2013). "CRISPR-Mediated Adaptive Immune Systems in Bacteria and Archaea," Annual Review of Biochemistry 82:237-266.
Sorg, R.A. et al. (Mar. 20, 2014, e-pub. Jun. 4, 2014). "Gene Expression Platform for Synthetic Biology in the Human Pathogen *Streptococcus pneumonia*," ACS Synthetic Biology 4(3):228-239, 38 pages.
Soutourina, O.A. et al. (May 9, 2013). "Genome-Wide Identification of Regulatory RNAs in the Human Pathogen Clostridium difficile," PLos Genet. 9(5):e1003493, 20 pages.
Souvorov, A. et al. (2018). "SKESA: Strategic K-Mer Extension for Scrupulous Assemblies," Genome Biology 19:153, 13 pages.
Stern, A. et al. (2012). "CRISPR Targeting Reveals a Reservoir of Common Phages Associated With the Human Gut Microbiome," Genome Research 22(10):1985-1994.
Stern, A. et al. (Aug. 2010), Self-Targeting By CRISPR: Gene Regulation or Autoimmunity? Trends Genet. 26 (8):335-340, 10 pages.
Stiefel, U. et al. (Aug. 2014, e-pub. May 27, 2014). "Gastrointestinal Colonization With a Cephalosporinase-Producing Bacteroides Species Preserves Colonization Resistance Against Vancomycin-Resistant Enterococcus and Clostridium Difficile in Cephalosporin-Treated Mice," Antimicrob. Agents Chemother. 58(8):4535-4542.

(56) References Cited

OTHER PUBLICATIONS

Stoebel, D.M. et al. (2008). "Anti-Silencing: Overcoming H-NS-Mediated Repression of Transcription in Gramnegative Enteric Bacteria," Microbiology 154:2533-2545.
Suvorov, A. (1988). "Transformation of Group a Streptococci by Electroporation," FEMS Microbiology Letters 56 (1):95-100.
Svenningsen, S.L. et al. (Mar. 22, 2005). "On the Role of Cro in λ Prophage Induction," PNAS 102(12):4465-4469.
Takaishi, H. et al. (2008). "Imbalance In Intestinal Microflora Constitution Could Be Involved in the Pathogenesis of Inflammatory Bowel Disease," Int. J. Med. Microbiol.298:463-472.
Takeda, T. et al. (2011). "Distribution of Genes Encoding Nucleoid-Associated Protein Homologs in Plasmids," International Journal of Evolutionary Biology 2001:685015, 31 pages.
Tan, J. (Dec. 17, 2015). "Immunotherapy Meets Microbiota," Cell 163:1561.
Tao, P. et al. (2019, e-pub. Jul. 6, 2018). "Bacteriophage T4 Nanoparticles for Vaccine Delivery Against Infectious Diseases," Advance Drug Delivery Reviews 145:57-72.
Tarr, P.I. et al. (Mar. 19-25, 2005). "Shiga-Toxin-Producing *Escherichia coli* and Haemolytic Uraemic Syndrome," Lancet 365(9464):1073-1086.
Tlaskalová-Hogenová, H. et al. (2011, e-pub. Jan. 31, 2011). "The Role of Gut Microbiota (Commensal Bacteria) and the Mucosal Barrier in the Pathogenesis of Inflammatory and Autoimmune Diseases and Cancer: Contribution of Germ-Free and Gnotobiotic Animal Models of Human Diseases," Cellular & Molecular Immunology 8:110-120.
Todar, K. (2012). "The Normal Bacterial Flora of Humans," Todar's Online Textbook of Bacteriology, 8 pages.
Topalian, S.L. et al. (Jun. 28, 2012). "Safety, Activity, and Immune Correlates of Anti-PD-1 Antibody in Cancer," N. Engl. J. Med. 366(26):2443-2454, 19 pages.
Turnbaugh, P.J. et al. (Dec. 2006). "An Obesity-Associated Gut Microbiome With Increased Capacity for Energy Harvest," Nature 444:1027-1131.
U.S. Appl. No. 16/626,035, filed Dec. 23, 2019, for Clube et al. (Copy not submitted herewith pursuant to the waiver of 37 C.F.R. 1.98(a)(2)(iii) issued by the Office on Sep. 21, 2004).
U.S. Appl. No. 17/392,827, filed Aug. 3, 2021, for Clube et al. (Copy not submitted herewith pursuant to the waiver of 37 C.F.R. 1.98(a)(2)(iii) issued by the Office on Sep. 21, 2004).
U.S. Appl. No. 17/637,414, filed Feb. 22, 2022, for Porse et al. (Copy not submitted herewith pursuant to the waiver of 37 C.F.R. 1.98(a)(2)(iii) issued by the Office on Sep. 21, 2004).
U.S. Appl. No. 17/671,455, filed Feb. 14, 2022, for Clube et al. (Copy not submitted herewith pursuant to the waiver of 37 C.F.R. 1.98(a)(2)(iii) issued by the Office on Sep. 21, 2004).
U.S. Appl. No. 17/728,793, filed Apr. 25, 2022, for Sommer et al. (Copy not submitted herewith pursuant to the waiver of 37 C.F.R. 1.98(a)(2)(iii) issued by the Office on Sep. 21, 2004).
U.S. Appl. No. 17/748,875, filed May 19, 2022, for Sommer et al. (Copy not submitted herewith pursuant to the waiver of 37 C.F.R. 1.98(a)(2)(iii) issued by the Office on Sep. 21, 2004).
U.S. Appl. No. 17/750,083, filed May 20, 2022, for Sommer et al. (Copy not submitted herewith pursuant to the waiver of 37 C.F.R. 1.98(a)(2)(iii) issued by the Office on Sep. 21, 2004).
U.S. Appl. No. 17/750,101, filed May 20, 2022, for Clube et al. (Copy not submitted herewith pursuant to the waiver of 37 C.F.R. 1.98(a)(2)(iii) issued by the Office on Sep. 21, 2004).
U.S. Appl. No. 17/750,116, filed May 20, 2022, for Clube et al. (Copy not submitted herewith pursuant to the waiver of 37 C.F.R. 1.98(a)(2)(iii) issued by the Office on Sep. 21, 2004).
U.S. Appl. No. 62/168,355, filed May 29, 2015, Barrangou, R. et al. (Copy not submitted herewith pursuant to the waiver of 37 C.F.R. 1.98(a)(2)(iii) issued by the Office on Sep. 21, 2004).
U.S. Appl. No. 62/296,853, filed Feb. 18, 2016, Barrangou, R. et al.(Copy not submitted herewith pursuant to the waiver of 37 C.F.R. 1.98(a)(2)(iii) issued by the Office on Sep. 21, 2004).
Uchiyama, J. et al. (2013, e-pub. Mar. 8, 2013). "Characterization of Helicobacter pylori Bacteriophage KHP30," Applied and Environmental Microbiology 79(10):3176-3184.
USPTO (2021). Engineered Phagmids, information for U.S. Appl. No. 15/780,668, 1 page.
USPTO Interference 106, 123—Declaration to Declare Interference Jun. 11, 2020, 11 pages.
USPTO Interference 106, 123—Junior Party Annotated Claims Jul. 9, 2020, 31 pages.
USPTO Interference 106, 123—Junior Party List of Motions Jul. 16, 2020, 6 pages.
USPTO Interference 106, 123—Redeclaration Jul. 21, 2020, 6 pages.
USPTO Interference 106, 123—Rockefeller Clean Claims Jun. 25, 2020, 7 pages.
USPTO Interference 106, 123—Rockefeller Motion 2 (Indefiniteness), Oct. 16, 2020, 24 pages.
USPTO Interference 106, 123—Rockefeller Notice of Lead and Backup Counsel Jun. 25, 2020, 3 pages.
USPTO Interference 106, 123—Rockefeller Notice of Real Party in Interest Jun. 25, 2020, 3 pages.
USPTO Interference 106, 123—Rockefeller Notice of Related Proceedings Jun. 25, 2020, 3 pages.
USPTO Interference 106, 123—Rockefeller Power of Attorney Jun. 25, 2020, 3 pages.
USPTO Interference 106, 123—Rockefeller Request for File Copies Jun. 25, 2020, 10 pages.
USPTO Interference 106, 123—Rockefeller Revised List of Proposed Motions Aug. 13, 2020, 4 pages.
USPTO Interference 106, 123—Senior Party List of Proposed Motions Jul. 16, 2020, 5 pages.
USPTO Interference 106, 123—SNIPR Clean Claims Jun. 25, 2020, 27 pages.
USPTO Interference 106, 123—SNIPR Motion 2 (Lack of Enablement and Written Description), Oct. 16, 2020, 32 pages.
USPTO Interference 106, 123—SNIPR Motion 4 (Deny Benefit to Count 1), Oct. 16, 2020, 16 pages.
USPTO Interference 106, 123—SNIPR Motion 5 (Substitute Count), Oct. 16, 2020, 41 pages.
USPTO Interference 106, 123—SNIPR Motion 6 (Motion to Designate Claims as Not Corresponding to Count 1 or Proposed Count 2), Oct. 16, 2020, 24 pages.
USPTO Interference 106, 123—SNIPR Notice of Lead and Backup Counsel Jun. 25, 2020, 4 pages.
USPTO Interference 106, 123—SNIPR Notice of Related Proceedings Jun. 25, 2020, 4 pages.
USPTO Interference 106, 123—SNIPR Real Party in Interest Jun. 25, 2020, 3 pages.
USPTO Interference 106, 123—SNIPR Request for File Copies Jun. 25, 2020, 10 pages.
USPTO Interference 106, 123—Standing Order Jun. 11, 2020, 81 pages.
USPTO Interference 106, 123—Decision on Motions, Sep. 7, 2020, 18 pages.
USPTO Interference 106, 123—Joint Stipulated Extension of Time, Sep. 4, 2020, 4 pages.
USPTO Interference 106, 123—Judgement, Nov. 19, 2021, 3 pages.
USPTO Interference 106, 123—Junior Party Revised List of Motions Aug. 13, 2020, 6 pages.
USPTO Interference 106, 123—Memorandum, Jan. 19, 2021, 6 pages.
USPTO Interference 106, 123—Notice of Cross Examination—van der Oost, Dec. 1, 2020, 3 pages.
USPTO Interference 106, 123—Order Additional Applications 37 C.F.R. § 41.104(a), Sep. 3, 2020, 6 pages.
USPTO Interference 106, 123—Order Authorizing Motions and Setting Times 37 C.F.R. 11.104(c) and 121 Aug. 24, 2020, 10 pages.
USPTO Interference 106, 123—Order—Additional Applications, Jan. 13, 2021, 6 pages.
USPTO Interference 106, 123—Order—Bd.R. 109(b)—Authorizing Office Records Jul. 21, 2020, 3 pages.
USPTO Interference 106, 123—Order-Video Dispositions 37 C.F.R. § 41.104(a), Sep. 25, 2020, 3 pages.

(56) References Cited

OTHER PUBLICATIONS

USPTO Interference 106, 123—Rockefeller List of Exhibits, Oct. 16, 2020, 4 pages.
USPTO Interference 106, 123—Rockefeller List of Exhibits, Nov. 13, 2020, 4 pages.
USPTO Interference 106, 123—Rockefeller List of Exhibits, Feb. 19, 2021, 5 pages.
USPTO Interference 106, 123—Rockefeller Motion 1 (Lack of Written Description), Oct. 16, 2020, 30 pages.
USPTO Interference 106, 123—Rockefeller Motion 3 (To Add a Claim), Nov. 13, 2020, 36 pages.
USPTO Interference 106, 123—Rockefeller Notice of Settlement Discussions, Oct. 21, 2020, 3 pages.
USPTO Interference 106, 123—Rockefeller Order—Responsive Motion 37 C.F.R. § 41.121(a)(2), Nov. 2, 2020, 2 pages.
USPTO Interference 106, 123—Rockefeller Reply 1, Feb. 19, 2021, 51 pages.
USPTO Interference 106, 123—Rockefeller Reply 2, Feb. 19, 2021, 37 pages.
USPTO Interference 106, 123—Rockefeller Reply 3, Feb. 19, 2021, 48 pages.
USPTO Interference 106, 123—Rockefeller Updated Notice of Related Proceedings, Nov. 13, 2020, 3 pages.
USPTO Interference 106, 123—SNIPR Exhibit List, Oct. 16, 2020, 7 pages.
JSPTO Interference 106, 123—SNIPR Exhibit List, Feb. 19, 2021, 8 pages.
USPTO Interference 106, 123—SNIPR Motion 1 (Terminate Interference as Contrary to AIA), Oct. 16, 2020, 20 pages.
USPTO Interference 106, 123—SNIPR Notice of Appeal, Dec. 14, 2021, 28 pages.
USPTO Interference 106, 123—SNIPR Request for Oral Argument, Mar. 12, 2021, 4 pages.
USPTO Interference 106, 123—Order—Show Cause, Aug. 19, 2021, 4 pages.
USPTO Interference 106, 123—Rockefeller Notice, Aug. 13, 2021, 3 pages.
USPTO Interference 106, 123—Rockefeller Request for Oral Argument, Mar. 12, 2021, 3 pages.
USPTO Interference 106, 123—Rockefeller Response to Show Cause, Sep. 7, 2021, 7 pages.
USPTO Interference 106, 123—Rockefeller Updated Notice of Related Proceedings, Jul. 15, 2021, 3 pages.
USPTO Interference 106, 123—SNIPR Reply 1, Feb. 19, 2021, 19 pages.
USPTO Interference 106, 123—SNIPR Reply 2, Feb. 19, 2021, 42 pages.
JSPTO Interference 106, 123—SNIPR Reply 4, Feb. 19, 2021, 28 pages.
USPTO Interference 106, 123—SNIPR Reply 5, Feb. 19, 2021, 44 pages.
JSPTO Interference 106, 123—SNIPR Reply 6, Feb. 19, 2021, 27 pages.
Vaisman, A. et al. (2013). "Prevalence and Incidence of Antimicrobial-Resistant Organisms Among Hospitalized Inflammatory Bowel Disease Patients," Can. J. Infect. Dis. Med. Microbiol. 24(4):e117-e121.
Veeranagouda, Y. et al. (Jun. 4, 2014). "Identification of Genes Required for the Survival of B. fragilis Using Massive Parallel Sequencing of a Saturated Transposon Mutant Library," BMC Genomics 15:429, 11 pages.
Vega, N.M. et al. (Oct. 2014). "Collective Antibiotic Resistence: Mechanisms and Implications," Curr. Opin. Microbiol. 21:28-34, 14 pages.
Velasco, E. et al. (2006). "Comparative Study of Clinical Characteristics of Neutropenic and Non-Neutropenic Adult Cancer Patients With Bloodstream Infections," Eur. J. Clin. Microbiol. Infect. Dis. 25:1-7.
Vercoe, R.B. et al. (Apr. 18, 2013). "Cytotoxic Chromosomal Targeting by CRISPR/Cas Systems Can Reshape Bacterial Genomes and Expel or Remodel Pathogenicity Islands," PLOS Genetics 9(4):e1003454, 13 pages.
Villarino, N.F. et al. (Feb. 23, 2016, e-pub. Feb. 8, 2016). "Composition of the Gut Microbiota Modulates the Severity of Malaria," Proc. Natl. Acad. Sci. USA 113(8):2235-2240.
Vétizou, M. et al. (Nov. 27, 2015, e-pub Nov. 5, 2015). "Anticancer Immunotherapy by CTLA-4 Blockade Relies on the Gut Microbiota," Science 350(6264):1079-1084, 13 pages.
Wagner, P.L. (2002). "Bacteriophage Control of Shiga Toxin 1 Production and Release by *Escherichia coli*," Molecular Microbiology 44(4):957-970.
Walters, W.A. et al. (Nov. 17, 2014). "Meta-Analyses of Human Gut Microbes Associated With Obesity and IBD," FEBS Letters 588(22):4223-4233, 34 pages.
Wang, I.-N. et al. (2000). "HOLINS: The Protein Clocks of Bacteriophage Infections," Annu. Rev. Microbiol. 54:799-825.
Wang, J. et al. (2019). "Core Gut Microbiota Analysis of Feces in Healthy Mouse Model," Supplementary Information, 12 pages.
Wang, J. et al. (Apr. 24, 2019). "Core Gut Bacteria Analysis of Healthy Mice," Frontiers in Microbiology 10(887): 1-14.
Waters, J. L. et al. (Nov./Dec. 2013). "Regulation of CTnDOT Conjugative Transfer is a Complex and Highly Coordinated Series of Events," MBIO 4(6):e00569-13, 8 pages.
Wegmann, U. et al. (Apr. 2007). "Complete Genome Sequence of the Prototype Lactic Acid Bacterium Lactococcus actis Subsp. Cremoris MG1363," Journal of Bacteriology 189(8):3256-3270.
Wei, Y. et al. (2015, e-pub. Jan. 14, 2015). "Sequences Spanning the Leader-Repeat Junction Mediate CRISPR Adaptation to Phage in *Streptococcus thermophiles*," Nucleic Acids Research 43(3):1749-1758.
Weir, T.L. et al. (Aug. 6, 2013). "Stool Microbiome and Metabolome Differences Between Colorectal Cancer Patients and Healthy Adults," Plos One 8(8):e70803, 10 pages.
West, N.R. et al. (Dec. 14, 2015). "Immunotherapy Not Working? Check Your Microbiota," Cancer cell 28:687-689.
Westra, E.R. et al. (Jun. 8, 2012). "CRISPR Immunity Relies on the Consecutive Binding and Degradation of Negatively Supercoiled Invader DNA by Cascade and Cas3," Molecular Cell 46:595-605.
Westra, E.R. et al. (Sep. 1, 2010, e-pub. Aug. 18, 2010). "H-NS-Mediated Repression of CRISPR-Based Immunity in *Escherichia coli* K12 Can Be Relieved by the Transcription Activator LeuO," Molecular Microbiology 77 (6):1380-1393.
Westwater, C. et al. (2002). "Development of a P1 Phagemid System for the Delivery of DNA Into Gram-Negative Bacteria," Microbiology 148:943-950.
Westwater, C. et al. (Apr. 2003). "Use of Genetically Engineered Phage to Deliver Antimicrobial Agents to Bacteria: An Alternative Therapy for Treatment of Bacterial Infections," Antimicrobial Agents and Chemotherapy 47 (4):1301-1307.
Wexler, H.M. (Oct. 2007). "Bacteroides: the Good, the Bad, and the Nitty-Gritty," Clinical Microbiology Reviews 20(4):593-621.
Wong, C.S. et al. (Jun. 29, 2000). "The Risk of the Hemolytic-Uremic Syndrome After Antibiotic Treatment of *Escherichia coli* O157:H7 Infections," N. Engl. J. Med. 342(26):1930-1936, 13 pages.
Written Opinion for PCT Application No. PCT/EP2016/059803, dated Jun. 30, 2016, filed May 3, 2016, 6 pages.
Written Opinion for PCT/EP2018/082053, dated Mar. 14, 2019, filed Nov. 21, 2018, 6 pages.
Wu, J. et al. (Jun. 2019). "Fusobacterium nucleatum Contributes to the Carcinogenesis of Colorectal Cancer by Inducting Inflammation and Suppressing Host Immunity," Translational Oncology 12(6):846-851.
Xie, Z. et al. (2013, e-pub. Aug. 9, 2013). "Development of a Tunable Wide-Range Gene Induction System Useful for the Study of Streptococcal Toxin-Antitoxin Systems," Applied and Environmental Microbiology 79(20):6375-6384.
Xu, K. et al. (2015, e-pub. Jul. 20, 2014). "Efficient Genome Engineering in Eukaryotes Using Cas9 From *Streptococcus thermophiles*," Cell Mol. Life Sci. 72:383-399.

(56) References Cited

OTHER PUBLICATIONS

Xu, T. et al. (Jul. 2015). "Efficient Genome Editing in Clostridium cellulolyticum via CRISPR-Cas9 Nickase," Applied and Environmental Microbiology 81(13):4423-4431.
Yang, Y. et al. (Jun. 5, 2014, e-pub. Apr. 13, 2014). "Focused Specificity of Intestinal Th17 Cells Towards Commensal Bacterial Antigens," Nature 510(7503):152-156, 29 pages.
Yao, J. et al. (2016, e-pub. May 9, 2016). "A Pathogen-Selective Antibiotic Minimizes Disturbance to the Microbiome," Antimicrob. Agents Chemother., 24 pages.
Yosef, I. et al. (2011). "High-Temperature Protein G Is Essential for Activity of the *Escherichia coli* Clustered Regularly Interspaced Palindromic Repeats (CRISPR)/Cas System," Proc. Natl. Acad. Sci. USA 108(50):20136-20141.
Yosef, I. et al. (Jun. 9, 2015). "Temperate and Lytic Bacteriophages Programmed to Sensitize and Kill Antibiotic- Resistant Bacteria," Proc. Natl. Acad. Sci. USA 112(23):7267-7272.
Young, R. et al. (1995). "Holins: Form and Function in Bacteriophage Lysis," FEMS Microbiology Reviews 17:191-205.
YourGenome: CRISPR/CAS9, retrieved from https://www.yourgenonne.org/facts/what-is-crispr-cas9, last visited Jan. 6, 2020, 8 pages.
Yu, Z. et al. (Mar. 21, 2014). "Various Applications of TALEN- and CRISPR/Cas9-Mediated Homologous Recombination to Modify the Drosophila Genome," Biology Open 3(4):271-280.
Zembower, T.R. (2004). "Epidemiology of Infections in Cancer Patients," in Infectious Complications in Cancer Patients, Springer International Publishing Switzerland, 48 pages.
Zhang, R. et al. (2009, e-pub. Oct. 30, 2008). "DEG 5.0, A Database of Essential Genes in Both Prokaryotes and Eukaryotes," Nucleic Acids Research 37:D455-D458.
Zhang, T. et al. (Sep. 24, 2016). "The Efficacy and Safety of Anti-PD-1/PD-L1 Antibodies for Treatment of Advanced or Refractory Cancers: A Meta-Analysis," Oncotarget 7(45):73068-73079.
Zhang, X.Z. (2011). "Simple, Fast and High-Efficiency Transformation System for Directed Evolution of Cellulase in Bacillus Subtilis," Microbial Biotechnology 4(1):98-105.
Zimmerhackl, L.B. (Jun. 29, 2000). "*E. coli*, Antibiotics, and The Hemolytic-Uremic Syndrome," N. Engl. J. Med. 342(26):1990-1991.
Zitvogel, L. et al. (Jan. 2015), "Cancer and the Gut Microbiota: An Unexpected Link," Sci. Transl. Med. 7 (271):271ps1, 10 pages.
Zitvogel, L. et al. (Mar. 2018). "The Microbiome in Cancer Immunotherapy: Diagnostic Tools and Therapeutic Strategies," Science 359(6382):1366-1370.
Allaker, R.P. (2019). "Chapter 36—Non-Sporing Anaerobes: Wound Infection; Periodontal Disease; Abscess; Normal Flora," in Bacterial Pathogens and Associated Diseases, pp. 359-364.
Bashir, A. et al. (2016, E-PUB. Dec. 30, 2014). "Fusobacterium nucleatum, Inflammation, and Immunity: The Fire Within Human Gut," Tumor Biol. 37:2805-2810.
Bikard, D. et al. (Nov. 2014, e-pub. Oct. 5, 2014). "Exploiting CRISPR-Cas Nucleases to Produce Sequence-Specific Antimicrobials," Nature Biotechnology 32(11):1146-1150, 6 pages.
Cash, H.L. et al. (Aug. 25, 2006, e-pub. Jul. 28, 2009). "Symbiotic Bacteria Direct Expression of an Intestinal Bactericidal Lectin," Science 313(5790):1126-1130, 13 pages.
Elmore, J.R. et al. (May 2013, e-pub. Mar. 27, 2013). "Programmable Plasmid Interference by the CRISPR-Cas System in Thermococcus kodakarensis," RNA Biology 10(5):828-840.
Ex Parte Re-Exam Communication Transmittal Form, dated Aug. 8, 2022, for Control No. 90/015,047, for Reexamination U.S. Pat. No. 11,351,252, 13 pages.
Ex Parte Re-Exam Communication Transmittal Form, dated Dec. 29, 2022, for Control No. 90/015,047, for Reexamination U.S. Pat. No. 11,351,252, 19 pages.
Ex Parte Re-Exam Communication Transmittal Form, dated Feb. 1, 2023, for Control No. 90/015,048, for Reexamination U.S. Pat. No. 11,291,723, 30 pages.

Ex Parte Re-Exam Communication Transmittal Form, dated Sep. 2, 2022, for Control No. 90/015,048, for Reexamination U.S. Pat. No. 11,291,723, 17 pages.
Extended European Search Report, dated Aug. 12, 2022, for European Patent Application No. 22166966.6, 12 pages.
Extended European Search Report, dated Oct. 10, 2022, for European Patent Application No. 22171899.2, 13 bages.
Fox, G.E. et al. (Jan. 1992). "How Close is Close: 16S rRNA Sequence Identity May Not Be Sufficient to Guarantee Species Identify," International Journal of Systematic Bacteriology 42(1):166-170.
Garcia-Carretero, R. et al. (2017). "Clinical Features and Outcomes of Fusobacterium Species Infections in a Ten-Year Follow-Up," The Journal of Critical Care Medicine 3(4):141-147.
Grice, E.A. et al. (2008). "A Diversity Profile of the Human Skin Microbiota," Genome Research 18:1043-1050.
Ishii, T. et al. (1992). "The Establishment of Human T-Cell Lines Reactive With Specific Periodontal Bacteria," Oral Microbiol. Immunol. 7:225-229.
Kamada, N. et al. (May 1, 2013). "Role of the Gut Microbiota in Immunity and Inflammatory Disease," The Journal of Immunology 13(5):321-335.
Kim, H. et al. (2014, e-pub. Apr. 2, 2014). "A Guide to Genome Engineering with Programmable Nucleases," Nature Reviews Genetics 15(5):321-334.
Li, K. et al. (Jun. 13, 2012). "Analyses of the Microbial Diversity Across the Human Microbiome," PloS One 7(6): e32118, 18 pages.
Lutz, R. et al. (1997). "Independent and Tight Regulation of Transcriptional Units in *Escherichia coli* via the LacRIO, The TetR/O and AraC/11-12 Regulatory Elements," Nucleic Acids Research 25(6):1203-1210.
Mazmanian, S.K. et al. (May 29, 2008). "A Microbial Symbiosis Factor Prevents Intestinal Inflammatory Disease," Nature 453:620-625.
Moubareck, C. et al. (2005, e-pub. Dec. 1, 2004). "Antimicrobial Susceptibility of Bifidobacteria," Journal of Antimicrobial Chemotherapy 55:38-44.
Pongnarisorn, N.J. et al. (2007). "Inflammation Associated With Implants With Different Surface Types," Clinical Oral Impl. Res. 18:114-125.
Qin, J. et al. (Mar. 4, 2010). "A Human Gut Microbial Gene Catalogue Established by Metagenomic Sequencing," Nature 464:59-65, 9 pages.
Rajilić-Stojanović, M. et al. (2014, e-pub Jun. 27, 2014). "The First 1000 Cultured Species of the Human Gastrointestinal Microbiota," FEMS Microbiol. Rev 38(5):996-1047.
Round, J.L et al. (May 1, 2009, e-pub. Jul. 14, 2014). "The Gut Microbiome Shapes Intestinal Immune Responses During Health and Disease," The Journal of Immunology 9(5):313-323, 25 pages.
Sears, C.L. et al. (Oct. 2014). "Bacteroides fragilis Subverts Mucosal Bilogy: From Symbiont to Colon Carcinogenesis," The Journal of Clinical Investigation 124(10):4166-4172.
Sharma, P. et al. (Apr. 3, 2015). "The Future of Immune Checkpoint Therapy," Science 348(6230):56-61.
Sinkunas, T. et al. (2011, e-pub. Feb. 22, 2011). "Cas3 is a Single-Stranded DNA Nuclease and ATP-Dependent Helicase in the CRISPR/Cas Immune System," The EMBO Journal 30(7):1335-1342.
Stanford, E.H.S. (2022). Retrieved from the Internet =https://ehs.stanford.edu/manual/biosafety-manual/decontamination" target=https://ehs.stanford.edu/manual/biosafety-manual/decontamination/a, last visited Nov. 29, 2022, 2 pages.
Takahashi, K. et al. (Apr. 2001). "Heterogeneity of Host Immunological Risk Factors in Patients With Aggressive Periodontitis," J. Periodontol 72(4):425-437, 17 pages.
The Human Microbiome Project Consortium (Jun. 14, 2012). "Structure, Function and Diversity of the Healthy Human Microbiome," Nature 486:207-214.
Van Erp, P.B.G. et al. (Jun. 1, 2015, e-pub. Apr. 26, 2015). "The History and Market Impact of CRISPR RNA-Guided Nucleases," Current Opinion in Virology 12:85-90.

(56) References Cited

OTHER PUBLICATIONS

Waegeman, H. et al. (2011, e-pub. Sep. 8, 2011). "Increasing Recombinant Protein Production in *Escherichia coli* Through Metabolic and Genetic Engineering," J. Ind. Microbiol. Biotechnol. 38:1891-1910.

Wang, F. et al. (Jan. 2, 2018). "Bifidobacterium Can Mitigate Intestinal Immunopathology in the Context of CTLA-4 Blockade," PNAS 115(1):157-161.

Allonsius, C.N. et al. (2019). "The Microbiome of the Invertebrate Model Host Galleria mellonella is Dominated by Enterococcus," Animal Microbiome 1:7, 7 pages.

Evans, D.R. et al. (Apr. 14, 2020). "Systematic Detection of Horizontal Gene Transfer Across Genera Among Multidrug-Resistant Bacteria in a Single Hospital," eLife 9:e53886, 20 pages.

Fitzgerald, S. et al. (2020, e-pub. Sep. 7, 2020). "Redefining the H-NS Protein Family: A Diversity of Specialized Core and Accessory Forms Exhibit Hierarchical Transcriptional Network Integration," Nucl. Acids Res. 48 (18):10184-10198.

Galmbacher, K. et al. (Mar. 8, 2010). "Shigella Mediated Depletion of Macrophages in a Murine Breast Cancer Model is Associated with Tumor Regression," PLoS One 5(3):e9572, 11 pages.

Gao, X. et al. (2010, e-pub. Sep. 19, 2010). "Engineered Polyketide Biosynthesis and Biocatalysis in *Escherichia coli*," Appl. Microbiol. Biotechnol. 88:1233-1242.

González Barrios, A.F. et al. (Jan. 2006). "Autoinducer 2 Controls Biofilm Formation in *Escherichia coli* Through a novel Motility Quorum-Sensing Regulator (MqsR, B3022)," J. Bacteriol 188(1):305-316.

Lombardo, A. et al. (Nov. 2007, e-pub. Oct. 28, 2007). "Gene Editing in Human Steam Cells Using Zinc Finger Nucleases and Integrase-Defective Lentiviral Vector Delivery," Nature Biotechnology 25(11):1298-1306.

Makarova, K.S. et al. (Nov. 2015, e-pub.May 11, 2017). "An Updated Evolutionary Classification of CRISPR-Cas Systems," Nature Rev. Microbiol. 13(11):722-736, 31 pages.

Shalem, O. et al. (May 2015, e-pub. Apr. 9, 2015). "High-Throughput Functional Genomics Using CRISPR-Cas9," Nature Reviews Genetics 16:299-311.

Soucy, S.M. et al. (Aug. 2015). "Horizontal Gene Transfer: Building the Web of Life," Nature Reviews Genetics 16:472-482.

Stackebrandt, E. (2014). "Chapter 15—The Family Lachnospiraceae," in The Prokaryotes—Firmicutes and Tenericutes, 5 pages.

Tiscornia, G. et al. (2006, e-pub. Jun. 27, 2006). "Production and Purification of Lentiviral Vectors," Nature Protocols 1(1):241-245.

U.S. Appl. No. 17/931,876, filed Sep. 13, 2022, for Clube et al. (Copy not submitted herewith pursuant to the waiver of 37 C.F.R. 1.98(a)(2)(iii) issued by the Office on Sep. 21, 2004).

U.S. Appl. No. 18/314,755, filed May 9, 2023, for Haaber et al. (Copy not submitted herewith pursuant to the waiver of 37 C.F.R. 1.98(a)(2)(iii) issued by the Office on Sep. 21, 2004).

U.S. Appl. No. 90/014,047, filed Jun. 7, 2022, for Clube et al.(Copy not submitted herewith pursuant to the waiver of 37 C.F.R. 1.98(a)(2)(iii) issued by the Office on Sep. 21, 2004).

U.S. Appl. No. 90/014,048, filed Jun. 7, 2022, for Clube et al. (Copy not submitted herewith pursuant to the waiver of 37 C.F.R. 1.98(a)(2)(iii) issued by the Office on Sep. 21, 2004).

U.S. Appl. No. 90/014,230, filed Dec. 3, 2018, for Clube et al. (Copy not submitted herewith pursuant to the waiver of 37 C.F.R. 1.98(a)(2)(iii) issued by the Office on Sep. 21, 2004).

U.S. Appl. No. 90/014,681, filed Feb. 16, 2021, for Sommer et al. (Copy not submitted herewith pursuant to the waiver of 37 C.F.R. 1.98(a)(2)(iii) issued by the Office on Sep. 21, 2004).

U.S. Appl. No. 90/014,705, filed Mar. 23, 2021, for Clube et al. (Copy not submitted herewith pursuant to the waiver of 37 C.F.R. 1.98(a)(2)(iii) issued by the Office on Sep. 21, 2004).

Wikipedia (2023). "Mobile Genetic Elements," retrieved from the Internet: https://en.wikipedia.org/wiki/Mobile_genetic_elements, last visited Feb. 27, 2023, 9 pages.

Zhang, Y. et al. (2017). "LsrB-Based and Temperature-Dependent Identification of Bacterial Al-2 Receptor," AMB Expr. 7:188, 10 pages.

Aguilar, C. et al. (2010, e-pub. Dec. 16, 2009). "Chapter 2: Cell-Cell Communication in Biofilms of Gram-Negative Bacteria," Bacterial Signaling pp. 23-40.

Almeida, A. et al. (Jan. 2021, e-pub. Jul. 20, 2020). "A Unified Catalog of 204,938 Reference Genomes from the Human Gut Microbilome," Nat. Biotechnol. 39(1):105-114.

Andrea, A. et al. (Mar. 19, 2019). "Methods and Challenges of Using the Greater Wax Moth (Galleria mellonella) as a Model Organism in Antimicrobial Compound Discovery," Microorganisms 7:85, 9 pages.

Chasteen, L. et al. (2006, e-pub. Nov. 6, 2006). "Eliminating Helper Phage from Phage Display," Nucleic Acids Research 34(21):e145, 11 pages.

Dantas, G. et al. (Oct. 2012, e-pub. Sep. 3, 2012). "Context Matters—The Complex Interplay Between Resitome Genotypes and Resistance Phenotypes," Curr. Opin. Microbiol 15(5):577-582.

Desbois, A.P. et al. (2012). "Chapter 2—Utility of Greater Wax Moth Larva (Galleria mellonella) for Evaluating the Toxicity and Efficacy of New Antimicrobial Agents," in Advances in Applied Microbiology vol. 78, 29 pages.

Dillion, S.C. et al. (2010, e-pub. Apr. 29, 2010). "Genome-Wide Analysis of the H-NS and Sfh Regulatory Networks in *Salmonella typhimurium* Identifies a Plasmid-Encoded Transcription Silencing Mechanism," Molecular Microbiology 76(5):1250-1265.

Dorman, C.J. (2009). "Chapter 2 Nucleoid-Associated Proteins and Bacterial Physiology," Advances in Applied Microbiology 67:47-64.

Doyle, M. et al. (Jan. 12, 2007). "An H-NS-Like Stealth Protein Aids Horizontal DNA Transmission in Bacteria," Science 315:251-252.

Elias, S. et al. (Sep. 2012, e-pub. Feb. 2, 2012). "Multi-Species Biofilms: Living with Friendly Neighbors," FEMS Microbiol. Rev. 36(5):990-1004.

European Opposition, dated Jul. 5, 2023, for European Patent Application No. 3291679, 17 pages.

European Third Party Observation, dated Aug. 3, 2023, for European Patent Application No. 20720177.3, 35 pages.

Ex Parte Re-Exam Communication Transmittal Form, dated Mar. 15, 2023, for Control No. 90/015,047, for Reexamination U.S. Pat. No. 11,351,252, 11 pages.

Federle, M.J. et al. (Nov. 2003). "Interspecies Communication in Bacteria," J. Clin. Invest. 112(9):1291-1299.

Fineran, P.C. et al. (2009). "Transduction: Host DNA Transfer by Bacteriophages," Genetics, Genomics pp. 666-679.

Gao, R. et al. (Dec. 2015, e-pub. Sep. 11, 2015). "Genome-Wide RNA Sequencing Analysis of Quorum Sensing-Controlled Regulons in the Plant-Associated Burkholderia glumae PG1 Strain," Applied and Environmental Microbiology 81(23):7993-8007.

Gohil, N. et al. (Apr. 4, 2018). " Book Review: Quorum Sensing vs. Ouorum Quenching: A Battle With no End in Sight," Frontiers in Cellular and Infection Microbiology 8(106):1-3.

Grøndahl, C. (Apr. 20, 2022). "Snipr Biome Initiates First-In-Human Clinical Trial with SNIPR001," Snipr Biome ApS, 4 pages.

Hagen, S.J. (2015). "Chapter 1—Introduction the Physical Basis of Bacterial Quorum Communication," Biological and Medical Physics, Biomedical Engineering, 5 pages.

Høyland-Kroghsbo, N. et al. (Feb. 19, 2013). "A Quorum-Sensing-Induced Bacteriophage Defense Mechanism," mBio 4(1):e00362-12, 8 pages.

Kalia, V.C. (2015). Quorum Sensing vs Quorum Quenching: A Battle with No End in Sight, Springer Publisher, 383 pages.

Khare, A. et al. (Dec. 8, 2015). "Multifactorial Competition and Resistance in a Two-Species Bacterial System," PLOS Genetics 11(12):e1005715, 21 pages.

Lucchini, S. et al. (Aug. 2006). "H-NS Mediates the Silencing of Laterally Acquire Genes in Bacteria," PLOS Pathogens 2(8):e81, 7 pages.

Meredith, H.R. et al. (Mar. 2015, e-pub. Feb. 17, 2015). "Collective Antibiotic Tolerance: Mechanisms, Dynamics, and Intervention," Nat. Chem. Biol. 11(3):182-188, 20 pages.

(56) References Cited

OTHER PUBLICATIONS

Michelsen, C.F. et al. (Nov. 2014, e-pub. Sep. 2, 2014). "*Staphylococcus aureus* Alters Growth Activity, Autolysis, and Antibiotic Tolerance in a Human Host-Adapted Pseudomonas aeruginosa Lineage," Journal of Bacteriology 196(22):3903-3911.
Mitri, S. et al. (2013, e-pub. Aug. 30, 2013). "The Genotypic View of Social Interactions in Microbial Communites," Annu. Rev. Genet. 47:247-273.
Moons, P. et al. (2009, e-pub. Mar. 20, 2009). "Bacterial Interactions in Biofilms," Crit. Rev. Microbiol. 35 (3):157-168.
Ochoa, S. et al. (2021). "Virulence Assessment of Enterohepatic Helicobacter Species Carried by Dogs Using the Wax Moth Larvae Galleria mellonella as Infection Model," Helicobacter 26:e12808, 8 pages.
Regulating with RNA in Bacteria and Archaea Conference (Dec. 5-8, 2015), 185 pages.
Rinninella, E. et al. (Jan. 10, 2019). "What is the Healty Gut Microbiota Composition? A Changing Ecosystem Across Age, Environment, Diet, and Diseases," Microorganisms 7(1):14, 22 pages.
Roselló-Mora, R. et al. (Jan. 2001). "The Species Concept for Prokaryotes," FEMS Microbiol. Rev. 25(1):39-67.
Rutherford, S.T. et al. (Nov. 1, 2012). "Bacterial Quorum Sensing: Its Role in Virulence and Possibilities for its Control," Cold Spring Harb. Perspect Med. 2(11):a012427, 25 pages.
Srivastava, S. (2013). "Genetics of Bacteria," Springer, India, 207 pages.
Stecher, B. et al. (2011). "Gut Inflammation Can Boost Horizontal Gene Transfer Between Pathogenic and Commensal Enterobacteriaceae," PNAS pp. 1-6, 17 pages.
Xavier, K.B. et al. (Sep. 29, 2005). "Interference With AI-2-Mediated Bacterial Cell-Cell Communication," Nature 437(7059):750-753, 10 pages.
Fukushima, M. et al. (Aug. 2002). "Phylogenetic Analysis of Salmonella, Shigella, and *Escherichia coli* Strains on the Basis of the gyrB Gene Sequence," Journal of Clinical Microbiology 40(8):2779-2785.
Gencay, Y.E. et al. (2023, e-pub. May 4, 2023). "Engineered Phage with Antibacterial CRISPR-Cas Selectively Reduce *E. coli* Burden in Mice," Nature Biotechnology, 23 pages.
Gibb, B. et al. (Jun. 30, 2021). "The Many Applications of Engineered Bacteriophages-An Overview," Pharmaceuticals 14(7):634, 19 pages.
International Search Report and Written Opinion, mailed Oct. 20, 2023, for PCT Application No. PCT/EP2023/067906, filed Jun. 29, 2023, 22 pages.
Nath, A et al. (May 17, 2022). "Phage Delivered CRISPR-Cas System to Combat Multidrug-Resistant Pathogens in Gut Microbiome," Biomedicine & Pharmacotherapy 151:113122, 13 pages.
Perez-Rodriguaz, R. et al. (2010, e-pub. Dec. 13, 2010). "Envelope Stress is a Trigger of Crispr RNA-Mediated DNA Silencing in *Escherichia coli*," Molecular Microbiology 79:584-599.
SNIPRBiome (May 31, 2023). SNIPR Biome Reports Positive Clinical Interim Results for Groundbreaking, First-In-Human, CRISPR-Based Microbial Gene Therapy, 2 pages.
U.S. Appl. No. 17/777,983, filed May 18, 2022, for Haaber et al. (Copy not submitted herewith pursuant to the waiver of 37 C.F.R. 1.98(a)(2)(iii) issued by the Office on Sep. 21, 2004).
U.S. Appl. No. 18/027,847, filed Mar. 22, 2022, for Haaber et al. (Copy not submitted herewith pursuant to the waiver of 37 C.F.R. 1.98(a)(2)(iii) issued by the Office on Sep. 21, 2004).
U.S. Appl. No. 18/501,825, filed Nov. 3, 2023, for Clube et al. (Copy not submitted herewith pursuant to the waiver of 37 C.F.R. 1.98(a)(2)(ill) issued by the Office on Sep. 21, 2004).
U.S. Appl. No. 18/504,952, filed Nov. 8, 2023, for Martinez et al. (Copy not submitted herewith pursuant to the waiver of 37 C.F.R. 1.98(a)(2)(iii) issued by the Office on Sep. 21, 2004).
U.S. Appl. No. 90/019,229, filed Jul. 19, 2023, for Clube et al. not submitted herewith pursuant to the waiver of 37 C.F.R. 1.98(a)(2)(iii) issued by the Office on Sep. 21, 2004).

\* cited by examiner

SEQUENCE LISTING

```
Sequence total quantity: 10
SEQ ID NO: 1              moltype = AA  length = 446
FEATURE                   Location/Qualifiers
source                    1..446
                          mol_type = protein
                          organism = Escherichia coli
SEQUENCE: 1
MMITLRKLPL AVAVAAGVMS AQAMAVDFHG YARSGIGWTG SGGEQQCFQT TGAQSKYRLG    60
NECETYAELK LGQEVWKEGD KSFYFDTNVA YSVAQQNDWE ATDPAFREAN VQGKNLIEWL   120
PGSTIWAGKR FYQRHDVHMI DFYYWDISGP GAGLENIDVG FGKLSLAATR SSEAGGSSSF   180
ASNNIYDYTN ETANDVFDVR LAQMEINPGG TLELGVDYGR ANLRDNYRLV DGASKDGWLF   240
TAEHTQSVLK GFNKFVVQYA TDSMTSQGKG LSQGSGVAFD NEKFAYNINN NGHMLRILDH   300
GAISMGDNWD MMYVGMYQDI NWDNDNGTKW WTVGIRPMYK WTPIMSTVME IGYDNVESQR   360
TGDKNNQYKI TLAQQWQAGD SIWSRPAIRV FATYAKWDEK WGYDYNGDSK VNPNYGKAVP   420
ADFNGGSFGR GDSDEWTFGA QMEIWW                                       446

SEQ ID NO: 2              moltype = AA  length = 294
FEATURE                   Location/Qualifiers
source                    1..294
                          mol_type = protein
                          organism = Escherichia coli
SEQUENCE: 2
MKKTLLAAGA VLALSSSFTV NAAENDKPQY LSDWWHQSVN VVGSYHTRFG PQIRNDTYLE    60
YEAFAKKDWF DFYGYADAPV FFGGNSDAKG IWNHGSPLFM EIEPRFSIDK LTNTDLSFGP   120
FKEWYFANNY IYDMGRNKDG RQSTWYMGLG TDIDTGLPMS LSMNVYAKYQ WQNYGAANEN   180
EWDGYRFKIK YFVPITDLWG GQLSYIGFTN FDWGSDLGDD SGNAINGIKT RTNNSIASSH   240
ILALNYDHWH YSVVARYWHD GGQWNDDAEL NFGNGNFNVR STGWGGYLVV GYNF         294

SEQ ID NO: 3              moltype = DNA  length = 1341
FEATURE                   Location/Qualifiers
source                    1..1341
                          mol_type = other DNA
                          organism = synthetic construct
```

```
SEQUENCE: 3
atgatgatta ctctgcgcaa acttcctctg gcggttgccg tcgcagcggg cgtaatgtct    60
gctcaggcaa tggctgttga tttccacggc tatgcacgtt ccggtattgg ctggacaggt   120
agcggcggtg aacaacagtg tttccagact accggtgctc aaagtaaata ccgtcttggc   180
aacgaatgtg aaacttatgc tgaattaaaa ttgggtcagg aagtgtggaa agagggcgat   240
aagagcttct atttcgacac taacgtggcc tattccgtcg cgcaacagaa tgactgggaa   300
gctaccgatc cggccttccg tgaagcaaac gtgcagggta aaaacctgat cgaatggctg   360
ccaggttcca ccatctgggc aggtaagcgc ttctaccaac gtcatgacgt tcatatgatc   420
gacttctact actgggatat ttctggtcct ggtgccggtc tggaaaacat cgatgttggc   480
ttcggtaaac tctctctggc agcaacccgc tcctctgaag ctggtggttc ttcctcttt    540
gccagcaaca atatttatga ctataccaac gaaaccgcga acgacgtttt cgatgtgcgt   600
ttagcgcaga tggaaatcaa cccgggcggc acattagaac tgggtgtcga ctacggtcgt   660
gccaacctgc gtgataacta tcgtctggtt gatggcgcat cgaaagacgg ctggttattc   720
actgctgaac atactcagag tgtcctgaag ggctttaaca agtttgttgt tcagtacgct   780
actgactcga tgacctcgca gggtaaaggt ctgtcgcagg ttctggcgt cgcgtttgat   840
aacgaaaaat ttgcctacaa tatcaacaac aacggtcaca tgctgcgtat cctcgaccac   900
ggtgcgatct ccatgggcga caactgggac atgatgtacg tgggtatgta ccaggatatc   960
aactgggata acgacaacgg caccaagtgg tggaccgttg gtattcgccc gatgtacaag  1020
tggacgccaa tcatgagcac cgtgatggaa atcggctacg acaacgtcga atcccagcgc  1080
accggcgaca gaacaatca gtacaaaatt ccctcgcac aacaatggca ggctggcgac  1140
agcatctggt cacgcccggc tattcgtgtc ttcgcaacct acgccaagtg ggatgagaaa  1200
tggggtttatg actacaacgg cgatagcaag gttaacccga actacggcaa agccgttcct  1260
gctgatttca acggcggcag cttcggtcgt ggcgacagcg acgagtggac cttcggtgcc  1320
cagatggaaa tctggtggta a                                            1341

SEQ ID NO: 4         moltype = DNA   length = 885
FEATURE              Location/Qualifiers
source               1..885
                     mol_type = other DNA
                     organism = synthetic construct
SEQUENCE: 4
atgaaaaaaa cattactggc agccggtgcg gtactggcgc tctcttcgtc ttttactgtc    60
aacgcagctg aaaacgacaa accgcagtat ctttccgact ggtggcacca gagcgttaac   120
gttgtcggaa gctatcacac ccgtttcgga ccgcagatcc gcaacgatac ctaccttgag   180
tacgaagcat tcgctaaaaa agactggttc gacttctatg gttatgcgga tgcgccgata   240
ttcttcggcg gtaactccga tgcaaaaggt atctggaacc acggttctcc gctgtttatg   300
gaaatcgaac cacgtttctc catcgacaag ctgaccaata ctgaccttag cttcggtccg   360
ttcaaagagt ggtacttcgc gaacaactac atttacgaca tgggtcgtaa taaagatggt   420
cgccagagca cctggtacat gggtctgggt accgatatcg acactggcct gccgatgacg   480
ctgtccatga acgtctatgc gaaataccag tggcagaact atggcgcagc gaacgaaaac   540
gagtgggacg ttaccgtttt caaaattaaa tactttgtgc cgattaccga tctgtgggc    600
ggtcagctga gctacatcgg cttcaccaac ttcgactggg gttccgattt aggggatgac   660
agcggtaacg caatcaacgg tattaagacc cgtactaata actctatcgc ttccagccat   720
attctggctc tgaactacga tcactggcac tactctgtcg tagctcgtta ctggcacgac   780
ggtggtcagt ggaacgacga tgcagaactg aacttcggca acggcaactt caacgttcgc   840
tctaccggct ggggtggtta cctggtagta ggttacaact tctga                   885

SEQ ID NO: 5         moltype = DNA   length = 168903
FEATURE              Location/Qualifiers
source               1..168903
                     mol_type = genomic DNA
                     organism = T4 phage
SEQUENCE: 5
aatttctcctt attaggccgc aagggcctcc atagtttag cgatttggga aacttcatca    60
tcacttaaag agttgcgata accgatgaag tcggaaacaa tacggaattt cttggtaaac   120
tcagcaacca tttatcact gtttttgaa gcattatttg ataatacatc aaaaagatta   180
gttactgtcc aaatgtcatg accgatggta tcttttccac cattaaaata tacaccctgt   240
aatgaactaa ccatattagc gagtcgtgta tattcttcag aaacttcatc tatactgaag   300
tacttcatca taaaatctaa ctcaggatac ttgataattt tatcaatata tcgttttagct  360
gaacttgaat aacctacata cttatcataa tctacatcat caaaagcatc tacatataaa   420
tcacgcaaag cttcaaaaat acattggcac tgaccgagtt ctttttacctt tttctgtaaa   480
agcggacgaa taacataaaa ttcattaatg ccaataagat tagccatacg aatcaaaata   540
ttcatagatg gatgacaaag agatgtagta ccatccatag agaaaatatc agaacgatgc   600
atatacgcta cataaccagt aatttcatct gcttctgatg tgaggcgtaa ataattcctc   660
ttttcccagc gcccgtcttt aatttcaaac ttaaacgctg tagcagcttt aggacgagga   720
gctttacttt taactacctt tggaatataa cttttacta aagcttcaat ttctgacaaa   780
taatgaatgt aacttcatc actttcaaac atcgccataa tatcaggaag caaatcaatc   840
tgcgattcta cttctggatt aataaacaga agacgttcgt tatgatgaat attcaaagtg   900
ttattaaatt cactatcatc taacgcacgt gctaatccac gacaatatt aacacgtttt   960
ttaatattat caataacgat attaattttt gttgtattaa taccaaacag acgataactt  1020
gatgcaacgg ctgaagtttc atgacttttgc ttaatgcgct tcagtcgagg gtcaagattt  1080
acttcataca caactcccgc gttgcataac ttactgtcag gttcaaacat gctctgcatc  1140
ttttatatg acagattttt agtcgtgaat ttgactgaat tactaatcat ataatctcga  1200
gcagaatacc ccatctcat caattcacga tatgtcgatg gaggagatgt agattcttta  1260
aatcgttta catcttcatt aaatgctttc tcactgagtt ctttaactcg ttcaataata  1320
ttttttacgag tgcgatcatc cagtgaaaga gcctcgcgag atggagcaat atcaagtgaa  1380
cccattggaa acttaatgta attcacttca ttgcgaatgc ttagccagtt acggtctcta  1440
ataacaccat cgataggata aacaatacca ccgtagatag catataatcc accacgatca  1500
ggccagtatc tttctggatt tacaccgtaa tagtcatcaa aatccggaaa ataatcaatt  1560
```

```
tcgcggtcaa gaccattaat gatagccaaa tctttgaacg gtcgcatgat ataagaaact   1620
tcataagcaa agtttctaaa gtcttttttct tcaactggaa ctacgatttc aataccagtt   1680
ttatcatctg gacccatttc ttttacgaat gtaggtttaa tctgtggacc atcaccatcc   1740
atgtaagcta cataaccacg aatttcacct ttatgatacg aagtaatact aaacgtatca   1800
gtataactaa acggagattt agaacctaaa ccaaatccgc caataaagtc attagattca   1860
gctttagatg aactgaagta tgaattatac aacccaggag aattatcatc accttgaata   1920
tcaaaatcac tcatacccgg accaaaatct cgacaaacaa atcgtgggtc taaacgtcca   1980
ggaacttgta tgataaattt ttcaggattt ccattaagtg catgagcatc aatcatgtta   2040
gtaatcaatt cacggactac tgcgcgaatc ttgtttgtat acaaatcaga tgacagaatt   2100
ttaaatactt taggagatgc tgtgatgcta aatgctttg atttagaacc attaccaaga   2160
attgttctt tttcagtggt gataatcata atttcctcat taattcatat tacgcttaat   2220
aacttcagca acttctagta gttcatcttt agttgcggtg tcggattgaa ttttatctct   2280
aatatcttta aagcgggttt taaattcttc ggcttctccc atatcgaaaa agcgttgaat   2340
gattctatat tctcgatgaa ctgctttatc aaaaagttct aaatttactt tatatgattt   2400
catttcaata tcctcatttg cccaattaat tataccacat ccttgtggta aagtaaacta   2460
ctggctcatc cattctttac gaaggtcagc attatctccc atgagcattt caaaaagctc   2520
tttccagttc tcaggaagtt taacaacatc atatactggg ttttgaatca tctcacgata   2580
ttcagatttt tccaaagagc caagtcccct aatataacgg atgctatgtt taggtagagc   2640
atctttggca ctctcatatt cagcgactgt ataaaaccat tcttgttttt taccgacctg   2700
agcgatgatt acaggagttt tgacaaagcg aattcgtcct tgctcaaaca attctggcca   2760
attactaaaa aatccgagca gagaaggata aatagaacct aatccaataa tctcttaatt   2820
atgaggtatt tctatagata gcccgaaggc tatccatcgt gatctgcgtc tgtcataata   2880
gcgacattcg catagttcat tgaagaggat ttaatagaac gacgaacatt gttctgcaat   2940
ttatatttt tcatatcaac gctagaagaa tcaattttta caaattttcat tatacacctc   3000
atagaacttt tcatcaggaa tccaaccgcg tttaaattca ttaaatgctc ggccgaataa   3060
tttgaattc acagttatat tattaactga tttccattta gcaactcccg ttcgtttata   3120
atgatcgggg tcatatttcg tgacgtacca ttcatataaa tttggtatta atttacagc   3180
ctctggattt gtcgctgatt tattataca tggtttcgct tttttcaagtt cagctgcttt   3240
tgcagtagca gcaacagtat ttccaacacc aactaatttt tcagtttttaa tgcgtggatc   3300
attaacatga agacgaaaaa cttcgccctt ttcatttta aagcatgtca tgcctttaat   3360
tccaggaagc ttaacacctt tattaacacc gcatcattcc tttggggttaa atgatccttt   3420
aattaataag gcgcatttac ccgatttaac tacttctcat tcaacaactt tatctttcat   3480
aacgttttt gaccattcag atactgctct ttgatggcta aattctagca atttcactat   3540
aatttgcact agaacgtaaa ctattttca gtgtttcaac attctattca tcgcatatgc   3600
catttcacga ttacgatgaa ttttatatag tagaaaatag tgctaaaaag tgttcacgaa   3660
aagtcatgtt tcaccaaatt ttcgttatca tcagaacctc ccattgatct tggaaggata   3720
tgatgaattt caccccttaaa tttagaaacg cgggttttac cccgcactat taagtcatta   3780
tagattttt cgtaattcac ctactgttat ccatttacca ttaatctgta cttcatcatt   3840
ttcatttacg ataattgtat cgccatttag ctcgaaagta aaccactcgc catcttcttt   3900
ttcttcaaac gcttttcac cgagaactag accagtgatt gcgcaaatat caaatagttc   3960
tttgttttta agcatatctg cataagacat accccaactg ttgagaactt taccacgcaa   4020
tggataacca ccgtgaagtt cttttatcacg aacatcaata agatatccga tagccgaatc   4080
accctcagtc aagaaaagag tagtatcagc atctttaccg caaagattcg ctttgatatg   4140
tttatgaacc ttagctttag aagcctttt agctgtcctta gtttctgctg cttttcctgc   4200
cgccaattta cgagccaaag cagcttcaat aatcggcatt agaattgctt cattatttag   4260
aatatcacgt gaaatctttt tagcatcaag ttgaatatga ctacgaattt cgccaaatgg   4320
agaagtcaaa cgctctttag tttgacgaat caatcgcatg ttttcatat cacgaacaaa   4380
cataacgata gtcaaacatt ctttgacacg tgctttagtc acatcaattt tgaacttacg   4440
tttgatttgt ggataaggt cttcacaaat atcatccata gcgcagtcaa tgtgatggcc   4500
accattctta gtatgaatgt tattgacgta tgttaattga cgaaaaccat ccggtgaacg   4560
accaaccgca ataqaacaat tttcttgctc ttgaacaata gcatgttcat cactactgccg   4620
tgcatatttc ttaaaattgc cctgaacctt tttaccatta aaggtaaatt gaatatcagg   4680
ataaactaca gcaagtgtct ggagacgatc cagtgtaatg tcaagataaa cttgggacag   4740
ctcattagtt tcaaatgaca taaaatcagg aatgaaagta acacgagttc ctttccattt   4800
tccaggaata tcttcccatg atttattttc catgccattt gaacaacgaa ctacaatatt   4860
attttgaccg tcgccagttt caccgacaaa catcacagaa aaaatgtttg tcaaactaga   4920
accaacaccg ttcataccgc cggtgacgcg ttctttatca tcaccaaagt taccacctgc   4980
ttttggaata gtccatgcgg caacaggacc aggaatttct tcaccggtag gtgttttaac   5040
catcgcttgt ggaataccgc gaccgttatc ttcaactgtt acttgattgt ttttaatagt   5100
aacattaatt ttattcgcga atttaaactt agtacgaata ccttcatcta ctgagttatc   5160
gataatttca tcaataagct taacaagacc aggtacatac tgaacacttt cccatttacc   5220
aaacataaag cgctcatgcg tttcattagc agaagagcca atgtacatgc cactacgctt   5280
tttgatatgt tcaaatatcgc tcagaatttt aatttcattc ttaatcatca cttatcctcg   5340
tttggtttcg ggaatattat actccggtaa tcataaagct aaaggcccga aggccttta   5400
tttaaaacga atagttgaat cctttaaagaa cagcccagaa catactgttc cttctacttt   5460
ctgcccggta ggtccaatag cacgaaatcc agtatgctgg aaatcatttt cagagcaacc   5520
gaaccaatta tatccagtga tttcaatatt agtaaaacca cttgaagaca aaactttggt   5580
tgcattaatc agcatcagta ctattaatta aagcactgc taatactaat gctgcaattg   5640
aacgactaat atatcata actaccctt aagcaagtcg taaatccat tattcccatg   5700
cttaggaagc ggaaactaac cgaacagcca gccgatgaca atcaggacat acaccagtat   5760
ctcttcaga aattttcttg attttttcgt attctttgc acagtctttg gattgacatt   5820
tataatcata aagcggcata attattcctt aaagtaagct ttcaacatct gatataaaga   5880
ccacgcctga tcattttttt caatagtaac tttcatgact gggaattctg tgaaatcttc   5940
tatttgttct tgctctttct cttcctgctc ttgccttca accgcctgat atggattttc   6000
cacttcatca aagaacccag cttcgttagt agagagccag ataaagtttt cgtcaaggat   6060
atcaccgccg gcacaacgtt tgagtacacc tatggatgtc ataatttag taggacgccc   6120
aagataatca gcatctaaaa tttttaaagg ctccatacct aaacgtcgtg catagattcc   6180
gttatcagta tggtctttaa taaattttc ttgagcttgt ttatttttaa attgataccca   6240
tttattaact tcaaatttaa tagccattaa taaattcct tccagtaagt tgtgccgtct   6300
```

```
tcagtaattt cacgaaatac accataaatt ggctgtttat caccgacttt ctcatacaca   6360
taaacagaag tcaagtgagt aaacttgcta gtatgttcct tttgaactac taccaaattt   6420
ggatcaaata atacatcttc aaattcatca ttagtgcaat tctgaacaat tttacgtttc   6480
attacaattt cctcattaat tgaacagtgg agcgatacgt ttcagaagag tatcaacacc   6540
tttagcgaat tttccatttt attctccaag ttgttttctg tatcagtagt tgatattgat   6600
atagtaccat aatcaactac tgatgtatat agttttatga aaaatttaaa ctttatgcat   6660
agagagcatt gctatagtgt ttaatccaac tttcaggaat gactttgtat gttcctaaaa   6720
ataccacgtt gtacaactta acaccatctt ctacccattg atcggtaatg tatccacaca   6780
tagcgcgagt ataaacaacc cttccatcat ctttaataaa gttaaattca caaggagcaa   6840
tgaacttgat agcctgaccg agtttccact taaagtctac acctacatgc gaagtatcaa   6900
tcgtttcaat tcctttagca ggaacagctt ttaaaaacgc agactcaaga aatttcgcac   6960
gaacatagcc aaactggggt ttagactttc catctttagg aatgatacgc acttttactt   7020
cagaatcttc atctttaaca ccatgcttaa gctgaatgct tacaacttcg accaattttc   7080
ctgctgcttt agaacgggat ttatcagata cacgagctaa ttcaccaata ttaataatca   7140
tagttatctc tcacttgtta aaaagatttt atactccacg ggaccattat actctggtcc   7200
caagagtttg taaactatta attcaaaata gctaccactg cactcgagg aactacggag   7260
tactctccag catgaactac gttcagaagt tcaacgccat cttccaatcc attggtcagt   7320
tacccaacca ccaatcggat tcgcaaatgg acgacgaatg taaactgcct tacacaacaa   7380
atcagtcggg tcttcaggtt tttcaatttc tgtcaataga ttaaaatctt cttcatagat   7440
gatgaatgat gataccctt cataatagtt tctaatttcc atgtacactg taccaatgag   7500
aattccacta ttaacactaa tgacagtaaa aggatatccg ccagttgtac caagaagttc   7560
ccaaaatttg ctatcagtcg tattcgacat tgtctgaaaa tcaatttgat atggttttt    7620
catttgatac gcagtattaa ttttaatcat aattttctct ttagtttaag gtaataaagc   7680
cttttagttc ggcataggat ttacggaaca ttacttgatg cccgccaatg ataacttggt   7740
catctggtac ttcgtataca gcaagataaa atcctttcga agctaattct tcacgctctt   7800
ctcgtgtgaa ccatttcatc atatcatatt cgctagcaaa agcaaaatga taagagcta   7860
caaaccatcc gggaatatga tattctactc caacataatc tttcttgaac ttagtattaa   7920
ttacgatatt agcattttta actaatagtt tgtcttcgtg cggcacagga attctttat    7980
tatcattact atgatgcata aaattaggtc tgtcataacc tacatgtaat aaccactctt   8040
cactccatga atctattata cttctatacg gcgttatttg aacacaaaga tctcggcgta   8100
ttgttatagc gtcttcataa ttaagaatac taaacgatga ttcaacacga taaatttca    8160
ttttattatc ctcagtagct atggtgttat agtaccacaa ctaaccgagg aagtaaacaa   8220
cttttttatcg ttttgttgga agagatagag gatcgcattc ttcctctgat ggagcatctt   8280
caagacccat agcatatcgc aaagcatact tcatcatcga gatgtctttc gcacagtcat   8340
gaatgaatc atgtgcaacg aatccatcta aagttccctt tggaagagga cacgttgtca   8400
tatcacgaac aagcagaagt gcttcaattc tagtacgaat atcacgctga ttccaaaatt   8460
tacaaggttc taacttaaat gtatcaagct cattctcgga aacgccgtta agacgttgaa   8520
tatcgcgaat aagatcgact aaaattggaa aatcaaacga cattccacgg caccagcctt   8580
gagatttcca aggatcgata ttatgtgcat tgatgtaatt attaaatttt gcaataccgt   8640
cgatagtgct tacatcttca tcggatggtg caatatttt tcgagcttca gggagattgat   8700
tcttccacca ttcgatagta cttttagtaa aaagacggtg tccttttttgg cttttttaaat   8760
caaatttgat tttaatgcca cgtgaaacta attcatcgaa tgttttcaact acttctggat   8820
tagggtcaaa agcaattaca gccaaatcaa taaccgctgc ttttcacca cttcccattg   8880
tttcaaaatc tataataaaa tcaaacatta aattttcctc gctaaatcac gaatttgacc   8940
tacagtatag tcttgaatat aaactttatt aataggctca tcaataaatt ttgccataga   9000
ttcaatatct ttttgtattt cttcaagact gtatactatc tttgaagctt tttcgcgaat   9060
agtgatattt tcaggacccg gattttcttg aatgacaact ttaacatttg tcataagaga   9120
tttaaactgg taccaactta attcaatcat taataatcgc ctcataaaga tagctaattt   9180
cgcctaaaac ataatcattg attgtaacag ttttaacttc accgcaaaag aattctaacg   9240
caattaaatc tcgttcaatt tcttctaatt gaagcatcaa cttactagat tcaatttta    9300
cagtttcacg atttttgcta taagctattt cataaatttc gcttacttta tcttgaagaa   9360
gataaaactg atctttagtt atttccacga atagcttcct caaatttaat catacataaa   9420
acacatcata acgaccacgg gtgacaccaa cataaagaag ttgttgagct aattcaacat   9480
ctgcataatg aatacaaggc gtataaatga aagcacggtc tacagacata ccctgcgctt   9540
tatggaatgt tgatgcagga agtgctttca ctttactaaa ctgtgattta gcatcccaaa   9600
aatcactcca cggagctttt ccgcctttgt tccaatttt ataagttct gctgttttag    9660
ctaaaaatag gttaaactta acaattctt cgtcagatga aattatttta atcttttcac    9720
gataatattc atcatcgcca taagtttcta ctgttaaatc ccaatgacga attagatatt   9780
ctccaggaac accacgggct ttaacaaacg ttgatgtata ctctgcttct ataatacgaa   9840
ctaattgtcc gttattaaaa ataatttctg acacaggctt tccatcaatt ttatatgttt   9900
taaataatgg ttcctgcatt acaataattt caccgacaat aaaatcttta tcagtttcaa   9960
aaatcttttt acgaataatg ctatttaact tgtcaacaga tttattcgta aatgccatta  10020
cgcgattttc aaacaaatca tctagtgatt tgacgattga aaaataattt accataaaat  10080
cgcgtaaagc ggtatccatg gtaaatccac gtactccatg cccgtcaaca acttatcat   10140
aattccactt accgttgcga acgtcagtag ctacatcaat aataggagca ttactgcgtt  10200
taacttcagt gagttcacac tgataaaaat ctttatgtgt aaagaatgga ctgatataag  10260
cagtattttc tcctggttca acaggtctga tttgcttatt atcccctatt ccaattatag  10320
tacaccaagg tggaaatagt gaaagcagaa ttttaaatag cttctatca tacattgaca   10380
cttcgtcgca gattaatact ctgcattgt ctaaatcagg tacttctttt tgttcaaaaa   10440
gaacatttc ttcatatgtt actgggttaa ttttaagaat actatgaata gtactcgctt    10500
ctttccctga tagtttgaa agaatctttt tagctgcatg tgtaggagct gctaaaataa    10560
taccagttcc acccgtagat attaaagctt caatgatgaa cttagtaaga gtagtcttac  10620
cggtaccagc aggtccatta atagttacat gatgtttctt ttctttaata gccttcataa  10680
aatgttaaa ggcatttttc tggccttcgg tcaaatcatc aaatgtcatc gtaaatttccc   10740
tgcaattggt atactaacaa tacgcccagt atctaaaatt cgctgatata atctttgcgt  10800
gtctacgtca ggcttaacat gtttaactc tattttatta aaccaaaatt tacgtggagt   10860
ctcaactaat cttggaattc ccttacctaa agctaatcga tactgctctt taagagtggt  10920
aaatacttta tcagcaatct tccattcaaa aaatacagca ggacgatgtt catcaagcgg  10980
aactggcgct gtaaatccgt ctttgtctcg gtaaactatc gcatatacat aaaccatatt  11040
```

```
atcctcggat aagtttaaaa attgaacaat ttagcggata tcctcttttc agtttaagtt   11100
tatcaataaa agacaaattt tgataccgct ctacaccttg aataatttta tcacacatat   11160
catattgcat ttctgcttct gacaactttt tcacaatttt ccaatccgag cctttaagaa   11220
gaacgttcaa tttaacaact tcagcgcctt ctgctatgcg agaaccatca atacgtgctt   11280
taagtgctat aattctcagc ttaatgtcag aggtctgttt tgatttagaa agctgagaaa   11340
tgtgttcaat tcgatttttca cgttttttct gtatagcttt aatttgatta taagtctttt   11400
tgattttagc ccatttcttt tcatctaaat ttagtttatg aacttttttc gcagatgaac   11460
gaccaattcg caaagcaaat aaatcacgct tttcaatcaa ctcttctaaa gtataatcag   11520
aacgaaatgt attatacttt ttctttactg caataacatt cccttaatg tatccaacgt   11580
tattatcaaa acgttctaat gataatttct ctccttcaat acgattatca aaaggttctc   11640
ccgagtaagc acaaacttt tgatctaaaa tgttcttaat gtaattgaag tctaagttaa   11700
aatctttaga acgtcttttt gcagatgcct gagtatgctc taaacgacgt ttaattttac   11760
gaatttggtt attagacagc ttcatatttt tctcacatct tacggacggt taactactta   11820
tactataaca tttttacttt aacttgtaaa caacttttga aaaaatgctt taaaacttc    11880
atggtataat gaatctaagt ccttccatta tagattaaat ccttcaaaat caagagtata   11940
gatagtgtat gttgaacact ttttatactc atatctatct gcaattctaa atacacttcc   12000
agctggtatc attacttctt gttcatctga aactaattcc atattacgat aacgatgact   12060
atccggaaac ttaaagtttg gattgtattc tttacagcgt agagctttta tagcatactc   12120
ctggaaattg aataccatag gagctttgaa ttcaaaaata acttgtgtgt tatactctaa   12180
accagaagca aaatgtagag ctatatttt atcatatgaa gctgatacga ctttatcaaa   12240
tgtaataata tcaattcctt gatttaatac ttgtttagtc tcagctggaa caccctctcca  12300
aagaggttta tcgtttggaa ccaaacgaga tttgattatt tcatttaacc aagaatggtc   12360
atctggttta ttagtaatac aatgaattaa aagttcaatt tcagataaat taaacccttc   12420
agaaagtaat tcttcacgaa tagaagcacg caccgatgca tccattgatt ttatttaaa    12480
atcttttagt tgcattactg agtatttcat tcaactacct caatatcata aactttaaat   12540
gttccaaatg aatcgtgtaa ttttctttt gaaatagaag ttattttata ctttccaatt    12600
ggaatcatcc attcttgttc acgcacaatc atcattaagt tatcagtacg ctctgaatct   12660
aatccatcag tatcttcata cgtgtactta aactcagtat taggagaaga agtataata    12720
tcgctgatat ggtcagaata attaaaagct ttatcagttt ttaaacgaag tattgtttca   12780
gtgaaatatt cagcataaga aaaagaacac gctgtatgca aactagtagt aaatgaatct   12840
accctgttcg ttgaaaacac ttctccaact tgtaaatctt taatgagttc ttttgtcgat   12900
tttgatatac cacgatataa ttgataaggc gatttagtta aatgcttttt aatgatttca   12960
tttaaatgct tatgaagagc ttcattcttt ttggcttcca tacattgcca agaacagac    13020
tgctcaaagt cagtaaattt ttcacagacc ttttataca ttatcatattg aaaatcaacg    13080
ctttcagctt ttatagataa ctgttcaaca tctgcaagat taataatcat gatagcctcc   13140
gtatacttca gaagctatca tatcatcgtt agaaaggaaa gtaaacaact ttttgaatta   13200
ttttgcccag ggagcccaag gcggagggtc aagatggtat gaagctagtt cttctagaag   13260
agcatctggg gcttcaattc cataattctg taatactata cggtactctt tcttataatc   13320
actagaatca ttctggttat tcgtagaatg attatcttct aacatctcaa ataaatccat   13380
attaattcct agcgataaaa accaaattta cgattagttt caatgatctt tctttcttct   13440
tcggacattc tccagcgtag tccaacatca aaatgagccc agaccatcct aacaaatgca   13500
tttatatctt taatatcttc aataatgaat gttttacttt tagaaggttg actcgctaat   13560
ttaactttat cgtcttcaaa catgtcaaaa agaccatatt catgagctct tttatagcct   13620
ttaatagtta aagcttcaga agaagaaaat ggtgaatctg tattctgcaa aatatcttca   13680
gtatgcttta taattagaat aatatttct ggatatttc tttcttttat atctttaatt     13740
aaaaaatccg gattttctgc taaaggaata attaatgagc aattttatc aagtgtatt     13800
actgatttac cttctttaga cataaattct attgaatata attttgctac ttcaatcatg   13860
tgatttcctt ttgcctacta atggaccgtc aggaattttta tttcctgga tatatttctc    13920
attttcttcc atcatttttac tgccaatttt aagaagcaaa tccattgctt catttgcttt   13980
tgctttagct tcttctaacg tcatatcttt gttcatgatt tatcaccata gatgtctctc   14040
atcaatttaa gcgctgagcg ttctatttc ttttcttct cagcactaat cattgatttc     14100
atccattctt ctgattcatt ctgcatttct ttatttgctt gttcaaccca accgtcatca   14160
atatacattg agtttggtct attgaaccat tcaagcatct tcttcagaac tttcattcgt   14220
tttacctaaa acaatagtag gagcatcgtc aaatttatga attttagca aatttggatt    14280
taaattattc cataaagagg taataaaata tgatagcgca ctttcgtccg taattataaa   14340
tttatttcct ttatctattt tccaatcata tattgaatca tatgaatagaa aggataacgg  14400
tttattatta taatatgctt cagcaacatc aatatagtta gatttagtaa atgcttgaat   14460
tgccataaat ggagaatttt gtacagtttc aataattccg atctttttaa gttttatttc   14520
aacatcttct ggaattggca ttgaaataaa atcttctact agatacatat tattgtcata   14580
tcttttatca atcattactg ctacagtaat tggaacatcc ttgacaaacg ccatactaat   14640
actattgata gacatttcaa acaaaattgc ttccataatt ttcctcaatc acaagatgta   14700
gatgaacaac tagaatcaca agaacttcca catgaatcac ctgccatac atgaacagga    14760
acattagtat catatgaatc agaactagac tgtgtattc gtgtgttaga tgatgagta    14820
ggtgttgacc agcgccaagg atttttataa tattcttggg cttcttcata agtcatagta   14880
actgcttcta ctgttccatc tcccatataa acatattcaa ctacagttaa aggaaggtag   14940
tcatttgaaa taggaactac accttcccca ggagttgtag agaaaaaatc cgtaaagaaa   15000
cttttaaacc aattaaagat aaacattaca aaaagcctct tttgaattcg acttgcttct   15060
caccataatc atatcagatc tctacattaa attcgacaga accatcgcg tacatcataa    15120
atgaatgcac aacaacttct gtagaccatg gttcagttc atattcttc attacatgtc   15180
gtgaaatgat aatatctaaa tcttcatttg gtttaatcca acgatttaac atagtactct   15240
cctctataag ataattctat tataccatac tcattttgga aagtaaacca tttaaatgaa   15300
aaaaggactc ccgaaggagt ccttgagtta ttaaccagtt actttccaca aatcttcatt   15360
tgcagcaatc cattcagtac gttgatttc ttcatatact gtagaatatg ctgcttttc     15420
tgaagggaat gtctggtaat gagcgccaga agtcagaat aaagaggaa                 15480
agctacagaa atttcctttc cttcaatttt cttatttcca tctaatttct gtcaaatgt    15540
tttgatatta acataaccgc gagtactagc catgtaattc tcctttattt aaattacatg   15600
attatttata catcttcttt tctgaataag taaattaaat tcttaagagc cgaacttgtt   15660
acatcatatt ttccttaag cgcctttaca accgggcctg ttgctggttt acctaaagaa    15720
acccataact cgtgtatttc gcttttaagt ggttcatgcc aatgcggtgc ttttcttgc    15780
```

```
gcccttgaag ttccttctga aatcttttta tttccgccat tcgaataaaa cttttcatt   15840
acttcagatt gccgagcttt tctttctgcc ctattttggg ctatacgttg tgaattcttc   15900
atccgagttt ttgtttcagg attgtttaat ctaagtttat gttctaatcg ttgttgctca   15960
gtccattttc ttccttctcc accctgacca ccaggagaaa tattaatgca agtatctggg   16020
tgtttacgtt ttaatgcaga tattagctca cgttcaactt catatgattt ttctctagaa   16080
ccatggcatt ttgaccatcg tatttataa ttaaatccat acttacgata tatgttccat    16140
agtattttac ctgaacccgg atatttatca ttatatggat ttacaataaa tgattcatgt   16200
ttcccagcgt accaaaagac gcctttcggc gtcctaactt ttactatata tgttctataa   16260
aattttgtt taatatccat tatcttgacg ttcaaaatta tgtttgttct tcagataata    16320
aagtttaaag atttcttccg cattcattcc aaggccaaca aacatattta atacgaaatg   16380
aaatatatcc acaagctcaa atttaattc gagctggtct tcgggggaca tttcatcaat    16440
gcgtttttct tgcgcttcaa tataacgtgc tttccatttt ttccatacag cagaagcttc   16500
tttttcacca cgtgacattt caccaagaga agtcagaagt tcgcggaatt catcatcaat   16560
acagtctttt tgttcacgca tccaagaaac aacatcaccg gcagttttcta atttatctgg   16620
atgatagcag tattcgcgga cattagccaa acgaatctgt aaaaccgct gcatatcaag    16680
cataacttgc agcggatctt tttcatcacc gagaatatcc cagtattcat tttgagcttt   16740
atcaacacct tcgatcaaat gagcacattc attaaagtga gccattagtt ttcctttcaa   16800
ttcattaata agttaaataa ttatatcatt tgagtatgta agcaattaat taaaaatata   16860
tacttcatca gttccattct tttctttgga atgatatatg ttaaagacgt atttttatt    16920
aagatgcttt acattatatt ttttagacca ttctttaaga agagtgtttt cctttccgtg   16980
gtgttctaaa acattcgact gcccaaattt tattcctcta tcatttaaag aatctaaaag   17040
attttaaaag tcttttttctt catcttctga ccaaaattta ttataatcag caactgttat   17100
gagatacgga ggatctacat atacaaaatc gccgtctaaa attttaacat ctttaaaatg   17160
caatgaacta aagattattt tatcacaatt ttgtttaaag tgattatatt gttttcact    17220
attttttgtt atagttcttt ttccaaacgg agtagtaaaa tttcctttat cgtttatacg   17280
aatcatatta ctaaatccgt gaaaatgaag aacataaaat aaaagaggat ctctagtttt   17340
attataatct tcacgtaatt tcaaaaactc ttcttttgat gtttttgata gtttgtattg   17400
ctttattact tttaaaacgt catcccatga tacattaata agacgcttat acatttcaat   17460
aattggttct tgaatatcat tggccaatac agggccatta acattcaaag acactgataa   17520
acctccacaa aataaatcca cgaatctgtt atatttggga aagtagatt tgagttcagg    17580
taataatgat tgtttattac ctgtatacgc gatagctcct agcattatat tctctcattt   17640
attgcagcaa aaatgaatta tacaattctt catcatatgt atttgatagt aatactaaca   17700
cgttttgcga taaatattaa ttaaaggag gatatatatg gtacaaaaat taatggcact   17760
tgttaatgcc ataaaggta ataagaaacg tatgctttt actattcta ctatggtagg      17820
aattttactc tggaactttta ttttatcacc tgttgcaatt gcacatggtg ttaatattcc   17880
agtagttact cttgatacat tcgtagattt agcatttgct ttagttgggt taatttaaat   17940
cttagcatat ttagatagcc gcattttagc cattaacccc tgggcaatat tatttttcat   18000
atattccata atttgttcag gggttgcacc ttccttttcta atcatatcat taacatcttt   18060
tgatttccag ggagattttat cccaaaacat aacccttct cctgcatcaa ctaatttagt   18120
cattcgttta atagtgtcag ggtgacgagg ttcattattct aagacccaca cacgtctatc   18180
tttaaatgga acaacttcta ggtctaattg accgccgta atagctatac cattttcaat    18240
aaaaagtgaa tctataggtc cttctagaac atatacatca ccatctttaa ctcgttcgac   18300
tccatagatt tttgttgcct caggataagc ttcgatggtg atatatttt gaggagcatc    18360
tttctttaat gcacgtcctt gaaaagactc agcttttcca ttagcattat aaattggaat   18420
aacaagacga ggctcagaaa tttccttttt gtatgttccc ggtgctatgc tattaactaa   18480
tttaggccat tcggttgtaa accaaagata tttccattta tccttttggaa tacaacgagc   18540
ttttacgtat tttataattg gatggtcttc cgccagttta tctaatctaa cacatgacgg   18600
aagagattta attatttctct ctcgggttg tttaggaagt tcttttaggtt tttctattgg   18660
acgactttta cctttttctt ttcttatttc aaagatatac tcacgatata aatcgggttc   18720
aaaactccttt aaatatatttc cgattggtgc atgatagtta cagttataac aatgaatatt   18780
tccttcatta ttatccaccat aataccatcc acgggcttta ttctggtcgg ttttttgaatc   18840
tccacaaaca gggcatctaa accgtaattt aaaagttgaa ctattattta cttgtgtgaa   18900
tttaggtaaa tgagctaatg cacggtatgc aaactcatta tcaatccaag gtattgatga   18960
catttttact cttcttttc tttagattcc tctttttct ttttaggaat ctgttcagga    19020
cctttattta ctacagcgcc tgatgttgtt ccaatagaga tattttcagg attaccacct   19080
gaatctccag cgaccatatc ttcttttgata aattcttttaa atgttttcat attaacctct   19140
attcataaaa gcattaaaaa tttggtcatc aatagaaaca tttactttag gctgttttttc   19200
agatggcaat tcatatccac atattacaat tttatgatca atatcaaaat acacagaagc   19260
aatatgatta atgatatttt cagtaaagtc taaatcaaca tcaatatctt tttgaccaaa   19320
gcccaaggga taaataatgc gagtaattcg attatctttta acaaagattc caccgacata   19380
ctctgtgctg cgtttaaagt ctacacgccg acgaaatgaa aaatattcag gctctttatg   19440
agctcggctc ataggacaca acgaataact agaataagag atgtcaaatc ctacgccttc   19500
aatatgaact aaattgtcat gattaaacca attataatca tatgccaagt ccattagatt   19560
gtcatatgtg aaaagcaccg gattaacatc attggtcaca agcatataat tagcaactgc   19620
tataatttca ttattttaa cgaatacaaa ccgtgattga tgcgaatggc ctggacctga   19680
gttttcacga ttaatgatat aacactgggc accttttata ttgtacgtgt ctttacactt   19740
gtgcatttga taaagcatta ttcacctacc acttcagcga tgatttttt gttattaaag   19800
ttttatcgc aatacagaac ataattatac tgcattacac caccagactt aagctgtttt    19860
tgcacttcag ctttcatttc aggacgatca cgcttaacga tattcataat atctgcttca   19920
atttgagttt caacctcagt ctgatccgca gtcatagacc attcgcacaa atctttatca   19980
taacctgcca tagcaggctg agcagcacaa gaagctaaag caaaaattgt agcaaagatg   20040
aatttttttca tgataatctc ctcagtagtt tatgttata tagtatctca atttccaaca    20100
aaagtaaaca gttatttttaa aatttctgcg taatcacatg ttacaaactg tttctctaac   20160
ttgacgattt tacgaaagta tcttttgcat tggcatgtga gcctcttcgt agggcgaaca   20220
gcaaacttaa taaattccac tcgaccaaat ggagggcttt cttctgctgg aatatctaac   20280
accaattccc acgtatctgc aataagtgct tgaattgcg tattttttcct gacgtctatac   20340
ggagtaggtt taaataaaac aatatgcata ttatcctcgg caatccactt cacatacttt   20400
cttgtcatca atgaaagctt taactaatgc tttattaact tcagcatatt gagtagtagc   20460
ccattgaacg tcatctttca tcattgtgat ttctttagta aacatgcttt cattcttaaa   20520
```

```
ccacccata aaaactacct ttaccaattc cataacaatc tcctcattta accgacaaga    20580
ctactatacc atagtcttgt cagcttgtaa actaaaattt taattcattc gccaaagcat    20640
ctaactgagc tcgagtcgat tcatttcttt gatagcgatt ctgctcagcc tgaatctgtt    20700
gtgaacctgc tacttcgttc acttcagttg gagtagaatc ttgttcaatt tctacccatt    20760
tttgatttcc tttttgaaca cccatcaaaa acttattcca cttattctta tcaccatatc    20820
gtgatttgat ttgcttaatg agttgttgtt cagcagctgc tagctcctcg tttcaatga     20880
ccgcaagcat aaaatcggct gttgctggaa gaccggcaga ttctgcaata tcgctcatgt    20940
taacatcgga gagtcccaa gcttgtttac caacctgtgc tgcagtccaa agaacagttt     21000
cggtttcaac agccagagca cgtaattcct ctgcaatgac tttaacagtt gtgtaactat    21060
tttctgaata aactctaatg cggcaagatt tacaaatacc tagatagtcg acaataatga    21120
ttgttggaac aaaattcttc ttgagcttca attcgtttaa aagtgatcga aatgtattag    21180
cgtctgctcc accagtagga tactgtttaa cgattaaacg accaagagta gatttctcac    21240
gccatttttc cattttttcct ttatactcag cgtaagaaat atgcccatca tcaatgtcat    21300
caagagaaac atcaagcata ttagcgtcaa tacgttagc acagacttct tctgccattt     21360
ccatggaaat gtaaagaaca ttatgtccga gctgtaaata atctgccgct aatgaacaca    21420
atcctaatga tttaccaacg ttaacgccag ccattaaaac gttcagtgtt ccagtttcag    21480
ctccgccttt cgtaatttg ttcagaattc tgagtttaaa tggaaccta cgagctttat      21540
tcatataaga tagccaacgt gcttcgtagt catccatcca atcatgacca acgtaactat    21600
caaatgaaat tgataatgcc tggcgcatga tgtcaggaat agcaccaaca tccggcattt    21660
tcttatttcg ttttccgga ggaagctcag cattagtttg aatttcgatt attttagacg     21720
tagcattaaa catcgcccctt tgctgaacat attttctgt ttcttttact aaccagctgt     21780
ggtcttccgg agaatcagcc agttttgaaa taagtgttt tacaccagaa tattctgttt     21840
cagtaaatga actatttct aatgcaacat ttaacgcatt aatgatgga acgctatggt      21900
actcattaac atgagattta attaatttga atgtatttt agctggacca ctttcaaaat     21960
attctgaatc catatatggc caaacttttg aaaaataagc ttgatcaaat atgagatgag    22020
aaagaataat ttctaccaca cttactcctt aaaagaattt aaattttc tttgacctt       22080
tattaaatgc atcttgcagt tgcattgtaa tacattttc tacatgagga gctaactcag     22140
cttttctttc ttggtcaaga acagcaaagt ccattacaac cttctccatca acccaatcca   22200
gtttagttac atacactata tgcgtagaac catcttctag tttaatgaca atctcctgga    22260
taacatttc catagcagat ttaatatatct taagagactc attaaaaaga cgttcttttc    22320
tttcttcttc ccctccgaa gaggggatt catcgataat ttctagatct aaatctaaat      22380
catcttatt cattaaattc ttccatatca cttagctgtt cgaggtcagt ttctaaatca     22440
gcagctgatt tactttact ttctggagat ttaaatttt caacctttga gttaatcaat      22500
tcatcaactt cagcttcaac aatttcatta ctatcaatag cacctaactg ataagcacgt    22560
ttaatagcat ctcggaatgg ttgatgctta aataaaggac cccagaatgt agtgcagttg    22620
gtatcttttg cacgccaaga ttttcttcg cgaatcatct cgccagtttc ttcgtcaaga     22680
aattcacgag cataccagcc atttttaggt tttaccacga atcctaattc tagagccata    22740
tctaacaatc cagaataagg atcgatacca ccgtcaaatt taacatcaat aaagaattta    22800
cttttttctt taacggtacg agattttct acatttgaaa caaattgata cccctgaaga    22860
tcagaaccat ctttaatctg gcgtttaccg ataatgaata cggtatcagc cgaatacatc    22920
ggtccagtac cacctcccat aactgtttta ctaaacattt cttgtgttc gtatgtatgg     22980
ttaatagcaa tacatggaat attttttagta ctaaaatagg gagttacgat acgaaataag   23040
cttttcattg ttttagctct agtcatatca ctaacaactt tttcatttaa agcatcttca    23100
gtttctttct tagaagctaa gttaccaagt gaatcgataa aaacgactac cttttcgccg    23160
cgttcaattg catccaattg attaaccatg tcaatacgta attgctcaag tgattgaacc    23220
ggagtatgaa ttactcgttc tggatcgact cccatagacc gcaaataagc aggagtaata    23280
ccaaattgac tatcataaaa caaacatact gcatcaggat attgacgcat gtaagatgac    23340
accattgtta atccaaagtt tgattaaaa gattttgatg gacctgccaa aattaacaga    23400
ccagattgca taccaccagt aatttcacca gaaagtgcaa tattcatcat aggaattttt    23460
gttcgaacta catcttttc attaaagaat ttagatgctg ttaattctgc agtcaattta    23520
gaagtagaag cttaatcaa acgagatttt aaatcagaca tataacct tatagtagtg      23580
ttcttgttcc acgaaatact tcgagcattc ttgcataaga tttatttgga aatccagctt    23640
caattgctaa tttttaagc ttaatagcac cggattttcc agagttttcc catatttctt     23700
taatcttttc aatgttatcc cacattattg ggtcacgttt atgtgatggt ttatttctat    23760
tataaccata tggattatta agcaaagctt cttttcgtt tgcttagtt tcttctgact       23820
gcttttgcc tagctgggct ttccggcaaa catcactaaa tccaagatgt tttggtttc       23880
ctttttgagc ttttgaaatt ttttctttgg ttctgatga aactctataa ccaattcttc     23940
taccacccte tccaccaatt tttaaattat aagtcatagg atcatttacc acatctattg    24000
ttactaattc tcttcagca tcacgggctg atttaaaatc tttataaac ccaagaatgc      24060
ttaaattaaa attttctta ccatacttttt tcttggcttg tgctaataaa gttcctgatc    24120
ccatataacc atcatttaaa tcatcggttg aatgagttcc atagtaaatt ttattattaa    24180
ctaaattagt tataacataa gtaattat atttctttc tttatgtctt ttcatgtcat       24240
taatcaactg ctattcgatg aacttctctc ttttctaatc aatataacaa aagaagtccc    24300
aaaaagcaaa cagacctaaa ccgataataa gcaataaagg tcctaacatt tattccaccg    24360
gttaaagata aataacttc taataatagt tcataatttt tataaatcaa tagcttttt      24420
gaacgcatct tgccattcgg ctttctttgc acgggttta tttaaaatat catgttgaat     24480
agaaagcatc tctttacgca aaacatcact gtgttttaac tcattgactc tatcaatgag    24540
ttcagcacga ttatttacat aaaaacgagc atcattaata attcgatgtt tggtatcaaa    24600
ttcttccgtca attagcatca ctgcatcaga tgccattgtt tcccagacgc gtaaggtaat   24660
aaagttgtca ttataattct tgtcaccaat aattaatgca gcaatagctt gactattctt    24720
ttcagatacc atgttcatag gaattttccc agtgaacacc ggagctttgg tccaaggata    24780
tttaggattt taaactgtt tttctcgtgc attgccaaaa aactcaatat ttaaaccggt     24840
gtcaaataag aattctacca tcttggattc gcgttgaccg gaccgaaatg aaccgccata    24900
aataacgcaa aaagttttct tggtaggctt agataattca tatgaatttt                 24960
atattgttca ataggaaat attcaaattc aataacatta tcaactttct tatgcgcagc     25020
cttagcaatg tctaaattta taccttggga aatcactta attggtgatt taattaatag    25080
ctcttcttca gtgtacaaat atgcccatgg tctattttta acatttggcc aagactgcga   25140
aaacggcaaa cgtatatctg taaataaaata ataaattta cttttgtatt ttgccataaa   25200
ttttgtgcgca gataaaaattg ctaaattagg tttaccgcca aaaagttaa tagaagaatt   25260
```

```
aacaactatc aaacggtcat aatcattaac atctacttca tcaaaagatt tagtgtaaac   25320
accattttta agagaaataa tgtcgacatt aagacccatt tcagaaataa ctttaaaaag   25380
ataaatagtt tcagaagatg gaacagtttt aaaattaata acattattac ccatattaat   25440
tatagcaatt ttcatattat tcctttatg ttaaacgatt aagcgtattt tcctacataa   25500
tcttttttcg aaatatgtgt ttcgccagtt tccaccaat gatcaaccaa ataaaaatga   25560
cgagaataca catgtaggct tccaacattc catataatgg aacctgcttt atactggcga   25620
gttgaatcac ctgcattcaa atcagatact aatttatcta atacgtattt ttgccatgca   25680
taatcattac ggaatccgaa gaccacgtca tttgagcgca tgttaacaac cgcattgatt   25740
ttcttgtcac gaatcaggta ttgtactgta ttcgtgcaca tgaaatctga cataccatct   25800
ttattatagt caaactgcat agatggacga gtataaatca tgataccacg tcgagaatca   25860
ggattttgac caagttcagc taaacacatg tcatactgag catagttatc ttctgaccag   25920
atagcccaac cataattcga gttaatttca cctttagaag atgctacttg ttgccaaatc   25980
ttcggtgttt caccccggaat atctttaacg aacaagcttt tagatttata ccattcaagt   26040
tcacgctgaa tgtattcatc attaagagcg ccaaaaataa acggttcatc tgctacaaat   26100
gatgcgccaa taatttcaat agtttttaaca cctgttttat caactacgaa atctttttct   26160
tttaatgcaa gccccaaatg aagacggatt tcttcaactg tcatagagtc actaatcatt   26220
taaacctcaa ttgatacatt catatttaac ttgtaacagt aataaactcc aacctaaaat   26280
aatagttgga atcataagag gaaccgttac actatagtat atacttatta taatcatcaa   26340
gattaaaagc aatgctgcta taattttgct tttcattcct tctctctgat gataattacc   26400
tgatttggct gcgcagactt tttagtttca cctgcaattg accaaataaa tgtaataaac   26460
caaccaataa ttgaccagtt aaacagtaaa gatgcgaaaa agattcctac tgtcgatttt   26520
gacccacgca tcaaggcgat aaaccatgga agcatgtata taataatagc caacacgcct   26580
gaaactaaaa ccataaaaat tgaacctgct actaaagttt ccatgttttc ctcacttagg   26640
tcaaatttt tacacatgaa ttataagaat tcactacata ctccatcgga gcgttttac   26700
ctgtacgcca ctggtaatta ttagcccaat ttgcccaaag ctcagcgcag tagttttcaa   26760
tttttcttc gcgtgtaatt acatctgaat tacgatatgc ttgagcagat tcatctggac   26820
gaatagcttc gtcaaaattc gcctgcattt gttctactgt ctgttttgga gcttctttat   26880
aacacttgac attaggatta taaaatttgc ttgaacagtt tacaattttt cctacatcag   26940
actgatttac taccggtcct tgagctacac aaccagcaag acctaatgca ataaccaaaa   27000
tagcgattt catttcattc tccaaatccg tatcagtagt tgatagttgt atagtaccat   27060
ggaagaacag tcttgtaaac agttttgtga aaaaattttt agggaatcca aagggtccga   27120
aatcatctct ttttcataag tatagattta tattacttgt atgaaaaagg gacctggagg   27180
tcctagattt attctatcag ccaaacagga agtctaacga agcttttct tcatagtcca   27240
tgccagccga ttcacacata cccgcaagcg gtttaacaaa cgattttgg aacaaagttg   27300
agtggtcaat ccaagatagc acatcagaac gaatttcttt tggaagttct gtacccgatg   27360
gccaagcaat gcacttgtca ccaaatggat ttccttcacg taatggaaga accattactt   27420
tatttccatc caaaattgga gctacaccta aaccgctaac agctcgacga taagttagca   27480
caccacgaat atggaacggg catttaaatc ctggccaacc tttatcatca tatttcgcta   27540
tatcgttcgc agttttact tcagcaataa ctttatagtc aagttgacga tattctttct   27600
cgaagttctt gtagtattct tggacagact cttcaccttc ctgaagaata cgacgaatac   27660
tttcttcgag agcttcttgc actgcttttg gtgttgaact ctgctgagtt tccatacccca   27720
tgattttag atgcggttca gcaaatcgct tatcttccat atcataaacg ttcagagcat   27780
aacgctttt cgcttttccaa aatccaccaa cgccctttga accaagcgga gggcaagaaa   27840
tagcttcacg gtccatatgc atcagatgct cgcggttatt catataatca cataactcac   27900
gatatgcaac atcaatcata ggttccatct ttttcttacc gaactgattc atgaattcaa   27960
ccaaatcgtt ctgctctttg aatcggtcaa gaccaacttt tcaataact ttatctacgc   28020
aaacatatac cgaatcagta tcacctgctg caatgaaata ttcatcatta gttccgcata   28080
ctttattcag atattcatta attttacgag caatccactg aataccgact ggccgaaaa   28140
ttgtgatagc agtagcattt cgcaaatcat agtaacggaa atgaatatta ccaagagcac   28200
cataaagact gttaatgaga attttacggt tcagctgatt tgtattagca agtgtagctg   28260
ctttttcaca ttcttcaatc agactattga gaacagattc ggtgtaattc gatagttcat   28320
ttaagaaatc atcactgaac ttaacatatc gttcaacttc tggtttagtt gaacaagacc   28380
ctgcgccttt cataataatc ttttttaatag cttcggcatt catttcttca gcgaacattt   28440
tcttttttcca gtctttacgc tggaaaaata ctttagcgat ttccttttgga atgataccctt   28500
cttgatgttt atcatacatc catccattcg gagaacaaga atattcatca ctcggtttag   28560
gagctgttcc tgcgtatat tcatgaattg gatgaacttt aaactgacca cgaatagttt   28620
caggactaat gttaacctgg cgaataatgc tcggatacag agacgtcaag tcaaaactca   28680
taatgtatcg acgtgcaatt ggtttaggtt caaacacaaa tgcacccgga aaactctgtt   28740
taacgtgcga accttgttga ggaataacct tatgttcacc tttcaatgag ttaaaaataa   28800
tagcatccca agttttaata ggactcatta caccagaaaa aggcatttta gcgtaataag   28860
acatacttaa aactagatcg ataaacccac gaattttatc gattgcttga actgattcta   28920
cgtcaatgat gttataacta atgtatcgtt gatgattagt ctcacgaagt ttattaatag   28980
gaccgtcgta tggtaattta cctttttgg tttcatgttg agcaactgat tccaaagaga   29040
atgacggcaa attagtaaaa gcgaatttct tgtacaaatc taaataatca agaatagata   29100
cgccatcaat agaataaatt tctttgctac cgtacatatt ttgaattagt ttagatttta   29160
cccgaccgat tggagagaaa cgtttcatac tacgttcacc cagaatcatt ttaacacgat   29220
tcatgatata cggaacgtca aacccctcaa tattccaacc agtaaaaata gcaggtcgtt   29280
tctgttccca aagattgata tattccatga gcatatcacg ctcattatcg aatggcatat   29340
aaattactcg gtcaagaatt tcttgaggaa cttcatcacc acctttcacag tcaagcttag   29400
cagctaactt tgcatcccat tttgatactg aaccgtacat tgaattcaaa aggtcgaaaa   29460
cataaaaacg atcgtcaatt gaatcgtaat gagtgatagc atcaattttca tattctgctt   29520
tcattgggtc aggaaattta tcaccagtaa cctcaatgtc acagttagct acacgaacaa   29580
atttttcggtc ataacaatt tctgaaccat atgtatcact tatataagcg agtttaaaat   29640
tccagaggaa gagagcttcg agaccgatgt cttccatccaa tctcgagcat   29700
ctttcattga tggaaattt tgaggagcgc agttttacc atagatgtct ttgtatttg   29760
actcttcctt acaatgccta aacatagttg gaagatattc tacttcacgg gtacgttcct   29820
ttccattttc atcaatataa cgttcaacaa tgttatttcc gactgtttca atagagatat   29880
aaaattcttt catagatatt ccttagttta tagcccgagt tattaggctc ttgatatatt   29940
atactccaaa taaggggccg aagccccttg cttaattacc aatcgtatat ttaggaacga   30000
```

```
gcttccattc atgttttttgt ttaaaagaaa taactcggaa gttattagtt aaatctttca   30060
taaaagttct ttgaccagga acgatttcaa ttagtcccca atcttctaat agccatgcaa   30120
tcgaatcacg acgaacttca tcttcttctg tcatttcaac ttgacgacca tccatacgaa   30180
gcatttcttt aaaatgaacg atatagtata gtccttttt ctgaagaata tgacaggact   30240
gatatagaac tttatcttta ttattagcaa ttcccatacg agtcaaagtt tcttttactt   30300
tcagaaaatc ttcaggtttt ttaagagtaa tttcaatcat tttaccattc caatgctagt   30360
tttttgagtt gtttctgttc ttttacgttc ttagtcactt ctttcaaaaa atcatccgtg   30420
actaaaccttt ttagttcttt taatactaaa ggaagttttc cattttttagt aagaattgat   30480
ttatagttaa ttgcatcatt tgtattaact tgataccgct tagcaagtaa cttaataatc   30540
aatacttcgg tggaatcttc aaccagtttt gcccatttac catatctttt accacgagga   30600
actgcagcca ttagataatt aaaatgagct tcatcactta agcctgatcc aattaaattc   30660
atagcatata cagctggcat acactctgga aattgtgata atgcattttc aaccatgaat   30720
tttgaataat cttttttgagc aatagagcat ttagttttat tattaatagc tccaattatt   30780
tcaaaaaatt catttttctgc ttttttcttta aaagaatcag cagcggattg gacagctgtc   30840
caatcttttg aataccaagc aacttgatgc tcgtttaatt gaatatcatc tttaaataag   30900
ctcatatcac ttccactgca tttcgcatgc taattgaatg aaaagataag ctaaatgcaa   30960
ttcagtatta gctgcaatac catgactg attatttttcg ccgacaattt cgtacatacg   31020
aataatatctt tgtggagtta cacgtgaata gatttcttcg gcaagtttac ccacgaacca   31080
cgaataatca gccgcatatt ttggtgctaa agctctgagt tgtttaacat ctttattttt   31140
gagagactca agaacatcat caatagcacc acgatcgtta gtaaccagtg ataaaatacc   31200
agcatccaaa acacctttag acgaataact atcgagctcg ccaatagttt tacgaaaatc   31260
aggaaaattc tttttaacca aagctgctac aactttcata tcagctatag caattccttc   31320
atgcttgcag atttcagtca atcgacgaat catctgcttc atcatttcaa ttttatcttc   31380
atcagttggt tgaccgaatg taataactcg gcagcgtgac tgaagcggtt taataatacc   31440
atcaatatta ttagcagtaa taataatact acagtttgaa ctataagctt ccataaagga   31500
acgaagatgt cgctgagact ctgctaaccc tgaacgtgca aattcatcaa taacgattac   31560
tttttgacga ccatcaaatg aagcggcgct ggcaaaatta gtcaaaggac cacgaacgaa   31620
atcaatttta caatctgacc cattcacaaa catcatatca gcatttacat catgacataa   31680
tgcttttgct acagttgttt tacctgttcc tggagaagga gaatgaagaa taatatgtgg   31740
aatcttaccctt ttacttgtaa tagatttaaaa ggtttcttta tcaaaagcgg gaagaataca   31800
ttcatcgata gtagatggac gatatttctg ttcaagaatg tgttcttttt catttacagt   31860
aatcataatt tcctcattca agttttagtg taaattataa aggccgaagc cctctattaa   31920
aaatcgtggg tagaatcagc ttcaagagct accacataat tcgcgtgttc accttcaaat   31980
ttagcagcac cttgtttacc ttttgcccaa agcagaagtt tataatttcc tggttgcatt   32040
ttcatatttg ccatattgat aatgaaatta aatgtatttt caccatcata atcaccaaga   32100
gtcaaagaat atttaacacg ggtcagagca gaatcttcta cttttattaaa accgttaatt   32160
acgattttac cttcttttac cgtgatagca attgtatcaa tttgcagacc acgagataca   32220
cgcaacagct gttgaaggtc ttcagcttta atttcagtaa cagcagatgc taccgggaat   32280
ggaattggtt tattaggagc aactactgta ctcggatcgg ctgctggcca aaaaattgtt   32340
gagcgggcat cagcaatttt aatatttcca tcttctgact gggaaatttc tgcatcatca   32400
ttaactaaag acagaatacc gagaaaaccg ttcaaatcgt aaattgctac atcaaatca   32460
ataacgtcag aaatatttgc ttccgcataa gttgtaccat taactgcgcg agtcataata   32520
aattgaccgg atttaagcat aataccagag ttaatagtag cgaaattttt aagcagagca   32580
gtagtatctt tagacagttt catgtaattt ccttcaattc aaatgagatt taattttata   32640
actaattttaa taaagcaatt aacgattaaa atcagccgca attgtttccg caacaatttg   32700
agcagcaaca attagacgtt catctgcatt accgcaataa tcatcttcaa ggcgttcacc   32760
acatgaagtc ataataaatt tagcaccggc gtttagggat tctgtagtat gtttgcgcat   32820
tagttcaatc catttattac ttacttcacg atcgatagct tcataatacg catgacgagc   32880
aggtgcagat ttaattttgt tctgaataac ttccattgcg ttatcagaaa gagacaaaac   32940
ccatgctcga cgaattttat tttggttttg tggatttgat tcagaacgca cgtgttttgg   33000
ctgaatatct tttacatcaa cagtataatt cacagtaatt ttagtcataa tacaccttta   33060
gtcataataa tcagtaacag tccaagcttc atttctattg acattatttt ttgtatattc   33120
tgctttaaat gcattcctaa gcatagattc agtaactata tgctcttcat tagaaaaatt   33180
atttctcaga atatatcgtt ttatttcagg aatagttaat agatgctgtc cagttgaata   33240
ttccatgttt ttcctccata gagattatac tctaataaat taaagcataa tctcttataa   33300
attaaaccat tacagtaaat cgaccaactt tcttcatttg aagatgctga ccatattctt   33360
gcgggtcatg gtctttatgc gaaattataa aaacgttagt gtttttcatt gaatttataa   33420
tattagctac acctttaata ccttcggcat caaatgaccc atcaaacact tcatcaagaa   33480
ttaatgtact aatactaaca ccagatacga tagaagcaat atcacgccaa gtaaataaaa   33540
gagcaatatc gattcgtgcc ttttcacctt cactaaatga agcataacta aaatcttcac   33600
gaccacggga tttaattgtc tcattaaatt cttcatctaa tgtaaacaca taatccgctt   33660
ccattatttt aagataatgg ttaatctgct tattaaataa tggaatgtac ttttttaataa   33720
tagcaccttt aataccagaa tctttgagca tatcagtcaa aattcctcgg tggtattttt   33780
ccattactaa attagttttt gtcttaacaa ttttatcaag ttcttcttga agcagtgcta   33840
tttcatcagc atggtcaata aactcagaag atgctttttc tatagccgct ttaacttttt   33900
tagctttatc tactgctgcg atcagagatt gcttttatt gcgaatatca tttgccaacg   33960
actgctgggt tttaatatta tctcggtatt catcaacaag aacttttaaa ttatcacgat   34020
gtgttgaaag ctgttcaaac gaatgtgtgc attcagaaac tttatcttta atttagaaa   34080
caactttatc accggaactc aattgtgaca aacaggttgg acataatcca ccttcgtgat   34140
acatattaat gactttatta tacgagtcaa ttttttgattt aattaaaaat gcttcttgac   34200
cgattttatt aaatgcatca gtcgggtctt cgtccaaaac aatattaact aatctttcgt   34260
tagcttcttc tatttccgat tttagcgttc tagcttcttt tgccaaatca tcatacatat   34320
tttgtagacg agtaaggttg tcacccgtta attttttctg gcgttcaaca ttatcattat   34380
atttttaat ttgttggata atactatctt ttttaacatc aagcacttgg ttctgcgaat   34440
ttaattcacg tattagtgct ttattaagct tatccatttc agctaatgtt cctacctcaa   34500
gcaggtcttc cacaagcttt cttcgcgcag gggtcgacaa acccatgaaa gggggtatacc   34560
ctgctgtacc aaggacaaca atcgtcttga aactggcata tgacattccg ataagctgtt   34620
caaattctgc ttggaaatct ttactgctgg cagattcatt aagacgtgta ccgttaacgg   34680
tgatttcgaa aacgtttggt ttttgtcctc ttttgatata gtacttttc tcatcatatt   34740
```

```
ccatccacag ttcaactaaa agttctttct tatttgtgct gtttattaat tgaccttct   34800
ttacatcgcg aaatggctta ccaaaaagcc caaatgtgat ggcttctagc atagtagact   34860
taccaccgcc atttcgtcca gtaataagag ttttttgaac cttatctaat tgaatgtcaa   34920
tcccattttg accaactgac attatatttt tatattttac tctattaagt ttaaaattct   34980
tcacaaaaga ttcctttaa tgtatctttt agaccattct atcatatcat cataatctaa   35040
aaagtattca tcaaattcag ccatgcaaac aacgccttgt gctgtttttg atgtgatata   35100
aattattcca acatatctag aatcttcttc ggtataatca atatttgcta tgaattcatc   35160
attaatgtca aatgtcgaaa acttcacagt atgcatcctt aatacaagat acagccatat   35220
ctcgtaatga tttaggtgtg tcattatcta aaatgttgaa gttaaaagat acagcccagt   35280
cagtgcagac agtaacctt ttaatacaat tatcttcaac ctctaacggt tcaaaccagt   35340
attcaataat ttcttatga ccaatatcat cttttacttc acattaaaa tgctgactca   35400
tcataacatt tttaaattca tcaaaagtca ttgtgttgcc tctacatata gctgatttgc   35460
atattgaata agtgcttcac ggtcagaatc agtgatgtct ggaattgcat taatatactc   35520
ttccattaat gtctgaagcg attgaacttc aacttcttca ctgtcatctg actcgacaga   35580
gttatcaatc tttgacacaa ctcgtaatga atgcacaact tttctagtt cagattcgaa   35640
cttcgtcaga tttttgtcta cttcagttac tataacacgt actgatagat ttgtaaaatc   35700
tttatagtca attttttcctt taaatggata atgaattcta cgatgccagg tagtattgtt   35760
tggaataaat tccgttcgtt ctgttctgt atcaaacatc cagaacccac gagggtcatt   35820
ctcgtcacct gcggttagtg tccatgtgt cccaatatat ctgacgtttg cagcctcaga   35880
aatagtatgg aagtgaccag accacactc tttataagtc ttaaggaaat cgggttcaag   35940
accatgagat ttcattcctt tataaaaata aaatccattc agttcccagt gaccaacaca   36000
aaaagaagca gatgaagttt tgatatgctc aagaatttca ccagtatttt cttcgcacat   36060
ccaaggaatc aaatcaatca aacacccgtc aaaatctact gtagtaggct tatcatacac   36120
tttaacatta ggatatttag ccaaaagctc agtagaagca tttggatgca ttacattttt   36180
atagtggaga tcgtgatttc ctacaatagt gtgtaatgta attccagcat catcaagcgt   36240
ttgaactatt tcacgggcaa actccatagt tttatgtgt atcgctttc gcacatcaaa   36300
aatatcaccg tattgaatcc aggtagtaat tccattttc ttagaatatt ctatcgcttg   36360
cttaattcca tcaatttgaa taccgcgaat ccactcatca tcagctttaa cgcctaaatg   36420
ccaatccct aaatttaaaa ttttcatata tcaagaaccg tcattgaaat gcaaaataaa   36480
attattgaaa taaatccatc tggagtgcta aagaacccaa tccaacatgc tctagtgaat   36540
agataaaatg caagaaaaag tatcacatat ccaagaaata tcattatatc aaactccgta   36600
taaagctaaa gggccgaagc cctttattt gtaataatgt caaactgttc tttaaagcag   36660
aagcttgaat cttgatgctg atacaaaaat tcatatgctt tttctcgctc acggtcataa   36720
agagctcggt cagatgacag ttctttaata cgttcaaatg ttgattccat atcattttca   36780
tcaaaccaaa tgataccgct atcatgcgag gtcaaaggag tattatcaac acggaatttt   36840
aaatttttcgc cagtagattt ccaaaatacc ggaattgttc cacatgcacc aagctcgaga   36900
tgagtatatt cgagtgagcg ttgtaagtat ttctggttaa gtttactcaa ctgatatcca   36960
aagccagatt tactcattcg ttcaagcatt tcactattaa tataacaatc taggattgt   37020
gccggttgat tcggcgcgag attcatttta tcaatctcac gattaccgta atattcatac   37080
ggaatacctt tttccttaat tgcaataaaa gcagggaac gttccagacc ttccattaca   37140
gtggattac cagcaggttt taagaatttt tcatgaaaat caaacatctg gtaaaaaccct   37200
ttccatgtag tcgtacgacc aatccaacgg ttgatattca tgttaatttc agaaacatct   37260
ttccaataag ttgaccgaac cttcacaata tccataggag gctgaaaatt atatactgt   37320
ggtgcttctt caatatcatc aaacagagaa acagtttctg gataccattc tttcatcaga   37380
actttattaa aatcaccatt atcagaatgg ctaaaaataa catcagctcg acgaacagtt   37440
tcttctaatc ccaaatttcg acgcaaagaa agaacagaat gatcatgctg ataaactaca   37500
acacgaatag aaggtttaat attatctaaa agttttttat agttattaat cgtagcttct   37560
tgaacggaag tagcaggaac agaattaata attagaatat cacaatcatt tactagctta   37620
agtgctttat cgtattcttt agctaaaata actggaattg aaaatgattt gtggtcatga   37680
gaacttgtac gagtaaatga tttatcttta gcataaacca aagttacttc atgaccattt   37740
ttaataaacc aattcacgttg ctcgagtgag aattttgtta caccacaacc ttcaagacct   37800
cgagccataa aaatgcaaat acgcatagtt ttcctctttt catttaataa atcatgtaaa   37860
taatatttta ttttcatta aacgctacga ataggcccaa acatatccat aagcaatttt   37920
gcttttccca gatatgcact ttttaatatt agacatgcat cctttaacgg atacagctgc   37980
gtctttaatt ctaggaaata ctcgtaataa ttttccagta gtatcatatt gaaatactgg   38040
cacatttctt ttctgagtta tcccacgttt agatttagac atttttgtt tagttgcatt   38100
agacatccta gagggctttc ctatgttatc agaataataa tatttccatt gaaatcctcc   38160
agcggttttc cttttaccat ctacacattg tttaattgaa gttgaacagc tatatgacat   38220
atcttctgca gcatctgtaa tacatctata tttgcgaata aaatttccat ttaaatcata   38280
ttgataaatt ggttttccag catttcgtct agcgttagac atgtatttt tattatcatc   38340
atctttccag aactctttca tgctttccga tattgaagaa gatacagctg ttttaatcca   38400
tccatacatt ttattattta gtcttgttcc gtcagaacta taacacatca tacgaatagc   38460
taaagccaat ttaggaagtc tataaattt aaataataat aaatgcgcgg taaaatgttc   38520
ttctggtgtc aaaagaacta aattagtttt atcatctgta ccacccatac atctaggaat   38580
tatatgatgt gtttcagtat agtatgtcaa aagactttta tcattgcctc tgtttagtcc   38640
ttttttcgatc agtaaattat atatgtttaa ataattcatt ttagtttatt ttaccaaaaa   38700
atttataaag caatatagga gccgaagctc ctatccacat aatacgccat acagaggctc   38760
gttagaactt ttaaattta tgcgcttata ccttctgctt tagctttatc   38820
atgagcctct ttaaagcgtc tcatcattc ctctctagag gaacgattt tattataatc   38880
tatttcagaa gtcggatgtt catctttcac agttgccacc attttttgac ttgataagaa   38940
tcaacccaca ctttcatatt agggtctgct cttacaatag gaggattaac ttctttgatt   39000
gaactatcac ggtattcttt ttcagaaatt ttcacgcaaa gatgaccatt caaagattca   39060
gtaaatcctg cattaatttt aagacgcttg aattttacgt gtgtaagcat caatcatatc   39120
ctcaatctga gatctagtag tcttccaaag aatactgata gttcatcgt tatatggctg   39180
ttttagaata tccgactttt tcttgatagc atattcgtat tgagcaaaat tattattttc   39240
agctgcgatc tgagcgtgct tataaagacg attcagttcg cgtttgtttt tagacaataa   39300
cttatttgct tttctttctg cttcaagacg gttctttct tcaatagaag aaataagctt   39360
ttccacttca tcattaattt cgggtttatc agtcatatta ttctctaat ataaaataaa   39420
aatcatcatc tgttaaatga taccgatagt ttaattctac accattagat ttaaaagcgg   39480
```

```
tatcatacgg attttctgga tcaatatcaa tgtcaagagc taaaacttcc ctgagataca  39540
ttttaagtaa atagggaata gcttcaactt caggtatttc ttccaagaat ccggagaggt  39600
taatcgttag cctcatataa aaaatccaaa ctaggagaat catctacaac acttttcttt  39660
tcagcccccg tgttctata  ggttgattct tcgtaatgcg tcattttatc atagatgtct  39720
tgaataaaag tttcatctac taacgcaacc atatcgtcgt cacggctgtc atagacattg  39780
tgaacgaagt aactatattt ctttgcaact tccttacgtt ctttttttaat acgttggacg  39840
aatgcattaa aacaagcttg agttatatac gcatgtgggt ttttatattt cgtttcatca  39900
aaaattgtgaa gccccttaat agaagcttct ataccatctg caatcatttc ttgtttccaa  39960
gactgggtgt atcctgaaaa gttgaaacgt ttagataagc cttctgcaat aagcataatg  40020
gctaatccga tagtatcatt ctgacgaact acttttatttg ggtctttatt atttgctaat  40080
tctgttttcc aatcaataat agcttgtaaa agctctttat tgtttacgta attatatttta  40140
ggcttagttt ctgacatttt cacctcttag ctcaattcat agatctatta tatcataata  40200
tttgaagacc tatcttaaag catagaggat gaatcaattc caagcacttc atcagattag  40260
ccgctccaag agctgcatct agtgaatcaa attggtcaac atattcaatt aattcgccgt  40320
aattagcgta taaccaccat tggctaaatt catactcaag gatgaatcca tttccttcaa  40380
tttgagttaa accaatgcca tttgtattta cttcataccc agcgagacgt aaatcgttaa  40440
taagagcttc gttcataatt ataccttagt aattttcagg tctgcaaatt ttttcttgcg  40500
ttgattttttc atgcgacgaa tagttttatc ggaaatttca tgcttttgat aagctttaga  40560
ttctacacca aaagctttaa catcaaattc tgacaagata tattgaacca acaattcacg  40620
gacagtattg cgtccaatct tctgatcatt ctgtttcatc gtttgatgaa gctcttttc   40680
ccatttatcc aaaatttgag gagttacaat atcgcctttt tctagcaaag aaactacttt  40740
atcatatgcg taagaattga tggcgttttt aatttgaata gtcatacatt atcctcaatt  40800
acgttaaaat tttattatcc aaaaaggccg aagcccttag gctaaacttt ttggcaccct  40860
tccagccttc gtacatcatt gcgactgaca atgacaaagc tccttcacat gctgcatact  40920
tattattcca gaaccaattt agaaaaactt catcctcaat accgttgtgt ttcatgttct  40980
ggaaaaattt ggcgcgttct tcagcaattc gctgcgataa tttagattca ggattcattt  41040
aaatttccca attgccattt tcatcaataa atttaatcca gtcatttact gaccacttgg  41100
tcgtatcgcc ttttggagta acatttaaag tgtatagccc ttgcttaaaa agcatgcgtt  41160
tgatattcat attttcctca gctgtaacga taacactcgt ttgatttacg tttagcaact  41220
cgttgagaag tattataatc aaaatcatca tcaatgtaaa ctgattttt  caactttctt  41280
acttcaccgc gtaattgacg atttaactca tctttaactt ctgaatcaat acctttcatt  41340
ctacgccatt tatctgagcg aaaaatgttt tcaaccatat ctttatgact tacccccatca 41400
ggagctttac gctttccgaa atagtcataa tcacgcactt ttaagtcttt acgacgatac  41460
gttttaccca tggagtttaa tttccttagc aactgaacta aatacagcac gatcacaaat  41520
catacgttta tgtaacttga gtataagata gtaaacatca aaaccattta cataagtaac  41580
acgaacaaca ttaccattca cgagataata ctgtcccttt ttaatctctt tatcaaccac  41640
aaccatatca attcctcaaa ggtaattcat atgttaataa taccacggtt tgaacttgtt  41700
gtaaacaact ttgtgaaaaa tattttaggg aatgataaga aaggaacgat agcttagaat  41760
ggtaatatac agaatgtgag aaagaaaggc ccagagggcc cgtcttaatc ttctatgata  41820
tctctatcat atccaagtga aatgagagtt tctttgaagt gtttaatgtt cttttgtcta  41880
gaatcattaa tgaaaatgac tggataacga atgttaagag atgtgaatcc agcgcgttta  41940
gcaagagata caatcagcgg acgatcatac tcaatcttac cattatttgt aagaacttta  42000
tagaaagtaa aaggagcatt gagctccttt agaagttttta taactgattg acatccagga  42060
caacgaccta cttcatctgg aattccatag acttcaatct tatttttgttt cacaactatt  42120
ccttactaag agcagcattc agcttgttag taatttttatc cagacgctca ttgaattcac  42180
tagaagataa gcccttttct ggagaaatca aactaatcac gaaaaatata gcaataaaag  42240
gaataaggaa aatagctcca actgccataa acagaaaaga tgttacagtt gtaagaaaat  42300
cagctaaacc tttacgaaat ttatacattt acatttacct ttaattgatt aaccaagcat  42360
tgataagcac taaactatac tgcgaataaa attctggacc aaaatgaaaa tcatatcatt  42420
tatagtatcc ataatgtaat tcaatttaat catgttccca caccccatcg gtatttgacc  42480
aaagtcgctg attatctgat cctcgccaca gcttttttgt cggaagattt ttctcatact  42540
tcccatcaat aataacatca acatatttaa gcatttctag ttgtttaata tcttcaaact  42600
tatatcctgt ccacaaccag atatctttct ccggaaatct tgctttaacc caagaaacta  42660
aatttgaaat ctcttctcgg ttctgtggat aaagtgggtc accgccggtt aaggtaaggc  42720
cttggatata cgatttgctt aaatgggacg caagttcttt aacggtattc atagtgaata  42780
actgtccgtt acgagcattc caagtactac gattataaca accttcgcat ttatgcaaac  42840
atccagtgac gaagagaacg accctacatc cagggccgtt aacgaaatcg catggataaa  42900
ttctatcata attcatcttt atatttccaa gtatatccct tatgaataga ttgaattcct  42960
ttgcaacatt tataaacagc agaatgaaaa aatcctgcat ttcttatttc agttgctcca  43020
gttagtccta ttgtatttcc gtctggtgaa tagccaataa ccgttttggt gttaaagcga  43080
tttctagaac tattttttgat atgctcttta tgattagtag acaaagttct tcctgttagc  43140
ccatcagata tccttttttcc aaaatcatca ggaagagtta ctttagacct agctatgctc  43200
attagcttct tagttttatc gcttcttttt gcgccacgct gattttcaaa tttcttagct  43260
tttgcatacg cgtattgtga agaagtaact tttctatgct tactattact cattatccaa  43320
tatgcatcat acatctttcc accatatatt ttagccaata aatggtgagc agtatagtgg  43380
gccttataag ttaaaaatac taagttgtct aaatcatctg aaccaccccat acttcttgga  43440
attatatgat gaagttcata cccggcttta gtttgacggg gctagatgg  gtgttcagca  43500
gaattaacta gatttgaata gattctgtca taattcattg gtgcttaacc ctatgcatga  43560
tttctttatt tttaccgaga ttaaatccgc gttcgttcga atttcccaaa taaccacatg  43620
ttcttcttat ggtattcatc tttttaggat cagtttctcc acaaatagaa caaacaaatc  43680
cgttttcagt aggagtcatt tcatgggtac ttccacatgt aaaacattta tctactggca  43740
tattaacacc aaaataatct aaatgctgtg cagcataatc ccacacgccc tcaagacctt  43800
ttaagttatt tttcatatca ggaagttcaa cataagaaat gtgaccacct gtcgcaatga  43860
aatgatatgg cgcttcacga gaatcttttt caaacggagt aatattttct tctactgaaa  43920
catggaaact gttagtgtac cagccttat cggtaacatc ttttacgctt ccatattttt   43980
ctgtatcgag tttacagaag cgataacaca ggttttcagc aggagtcgaa tataaactaa  44040
aagcaaatcc ggttctttca gtccactgtt taagatgagc attcatttta gttaaaattt  44100
ctcgtccaat atcacgaccg acaagaatat tcaattcgtg aataccaatg tatcctaaag  44160
acactgaact tctaccgttt ttaaataact caattatgtc gtcatcaggt ttaagacgaa  44220
```

```
ccccgaatgc accttcttgg taaagaatag gagcaacagt agctttaact ccttttaagg    44280
aactaattct acacatcaaa gcttcaaaac ataaatccat tcgttcatta aatagctcaa    44340
caaatttctg ttcattgaac tgtgttccaa tataagaatc taacgcgatg cgaggaagat    44400
tcagtgttac aacaccaaga ttattgcgtc catcaagaat ttcattgcca gtcgaatctc    44460
tccatacgct caagaaacta cggcaaccca tcggagaaac aggaacagat gaaccagtga    44520
tagctttatt gttcttagct gaaataatat caggatacat ccttttgctt gcgcactcta    44580
gagcaagctg tttaatatca tagttcggat cgtctttata aagattaaca ccttcttcaa    44640
cgaacataac aagcttaggg aaaataggag ttatcccatc acgaccaaga cctttaatac    44700
gattttcag aattgctttc tgaatcattc gttcagtcga gtcagttccc gtaccaaatg    44760
taattgttac aaaaggagtc tgtccgtttg aactgaataa cgtgttcact tcatcaatgt    44820
gttcagtaga gttcgctact tctctacccg tttatatgaa acaatgtaat ttggataatt    44880
gtcatctaaa cacaaatctt taatacgact tgggtggagt tttaaatctt tagcagcatc    44940
cacaaatgat ttatagatat tgtcatttat tttaacatat tctgggacgg gatgaattgt    45000
tatttttata tctataacat ttggatgatt actaacctgt tcttcagagc atttaagaaa    45060
ttttgcagct gatttaaaac ttctaaattt atttccggat tttaaagcta tagaaacagt    45120
ctttttagcc gttctactac caatattatt tttaacatga gcttcacttc tactattatt    45180
tttataatgc tcaatcaatt tctctcgtat cttatcttta tgttttaaag ataagatttt    45240
acctttatgg gcattactaa gtttttgctt atgttcttct gaatccggat atttgttaaa    45300
tttatatcca cctatagatt tattaagaat aaattcgtta ttaaaatatt tcctaataag    45360
catttcttca tgtttaaggg ccgattcata agaatcaaaa acttgaagaa ttatccactt    45420
agctttataa tctttaagct tttctttaac aagcttagat gacgaattgt attctttcca    45480
atttgtatct ttaccatata tagttttgaa tttttaaaa cctatataaa aagacttatc    45540
aggaaatctt accatatagg taaatgctac agaattggca atttttaagc ttttctttaa    45600
tttccatttc atcgtttcac ctcgtattca tatttatacg aggataaaca gctgcatgtc    45660
accatgcagt tcagactata tcttcaactc ttagagttgt ctgccgtttc gggtcgcttg    45720
accctactcc cttacattca tcagggatag tcgttgggca tttacagcta ctgctgattt    45780
agcaacggat tgtctcagtg agagtttccc gttttaggca gattttacat gagcttgact    45840
tacgttaact cataagcttg gaatgcatcg tatacgtctt tttctgtttt agattgagca    45900
taattcaacg catcagcgat ttgccatttt tctgcatcct caatatgttt tgcataggtg    45960
cgtttaacat aaggagaaag tactttatct acattcgtte ccgtcgttcc gccgtattg    46020
tgagaagcaa cttgcgcagt aatttgtgcc ataattgcag tagcaactcc aattgattta    46080
ggagtttcaa tctgcgcatt accaagctta aatccgtttt caagcattcc ttttaaatct    46140
actaaacagc aattagtaaa tggaagagca ggggaataat caatatcatg cacgtgaata    46200
attccgtttt catgcgcttt cataataaaa gacgggacca tattttttgg caatgtgttta    46260
gacacaatac cagccataag gtccgttga gttggaaaaa cacgagaatc tttattagca    46320
ttctcgttta aaaggtcttt attagtttta tgaattaatc cttcaatttc ttttttcaatt    46380
gtcattttaa actcttctca agctgcttct tgaatgaagc tattaattgt gttttggtgt    46440
cagattcatt atattccaaat cctctttgaa gcatctcggc catcatttcc tcttttccta    46500
aacgagaaaa ttcctttgat ttatctccaa caaagttagg gtgaatatta tttttgggtgt    46560
aatcggattt taaataagta agtaaatttt ctaaccattc aagataatca acaccttgtc    46620
cctttaagcc agaacgatta aatttatgct tcatttgacc ttctgcagca ttgcatagat    46680
tacaaagcaa tccacgcacc tttcctgctt ttggtccatt taattcatgg tcatggtcga    46740
ggtgattagc ttgaacatca ggatttagtt ctcgttgca aattaagcat ttaccgttt    46800
gtgcatcata aaatttctgt ttttcttctt tgtataattt gccagtcaat aacataataa    46860
acccttacct taaatagata aggtattta ttatttcaa gtattgtaaa acatttgatg    46920
caatcgctta tattgctgaa tcattcggtc agaaaaagaa atttgagttt caagccattc    46980
aatgtactct gcggcagctt gcattaaatt tccttcatag ccatcgttat tttcttgtgc    47040
agctaattta gctaatgcgt atgaaatacg ttcaccttga aaatcggctt taggcttctg    47100
aacaacttga ttagttcgct ctacaacttc ttcaatttcg ccattttcta ctgattcagt    47160
attccacaaa caccaatacg taattggctt atcgtagatg ttaataatct ttccatcaga    47220
aagttcaatt tcaataattc cagtgtcagg ctctatatca tcttcacatt cttttacaag    47280
ttcacgaact ttaaagacag tacctgcact aagttccggc cagtaattac acagccctgt    47340
atcagcacga ttaattctaa accatttatc tactgtaatc atgtcccatc tccatatcaa    47400
ttaagtcatt tatcgttggt tcattataca ccgtttcttc atcagtgtaa accggttctt    47460
ccggctctgg ctctacagtt tcccatctag ccgcccacca aggttttata gcgtaatcca    47520
ttctcgtact gtctgagtta ctacacgttc tcgaagctca accagttcaa cagtaggaac    47580
tgcataatac cagtcagaat ggtaagaacc tgacgagat tcatttacag ccacatgtac    47640
attatgtttt ggactaaaat aaacacactg acgatattgg catttaccat cttgcaccca    47700
gtcttctatt tcgataggtt taagatagtc ggaaaaatcg aaatcatagt tttccgaaaa    47760
tgcatcatgg tcttcaatga tttcgctcag aactgcatca acatctaatt tattttcaat    47820
attcattttt cacaccacca actgcttact tcaaaatcgg gttcgccatg ttcccagaac    47880
caggggccga taggaatcca cttaccttca tcggtgacgt catattcttc ggatttaagc    47940
ccaacgtatc gccattcgac ttcataagcg gtaccaccga ttacaactgt gttctcgcca    48000
tacgggttag acacaacaaa gtctatacct tctgctttag ctaaccaaat catgtattca    48060
tagagtttat attccaggtc gccttctgtt ccatcgccta gaaaaataat tgttcattt    48120
aattctatca tttaaagtat tcccgcaatt ggtcaaatcc accaatatga cttccatcag    48180
gagcaaatac ctgaggcatt gttaagccga tttgagtatc acgacctagt ttagtcagaa    48240
gctcagcaat ttttcatca tcaaaaacac ctttttccgg cataatgttg ataaattcaa    48300
acggctgttt cttcacagtc aaaagacgtt ttgcattatc gcaatacaca catttatgaa    48360
tgttgctatc ataaccatat actttaaaca tattattcct taattcctag tacttgttta    48420
aaagtctcgt cgtaatcaag actttggccc gtttgttctt tatgcttgta tataatatca    48480
cttacttctg atagcatatt tttatatgaa cgagttaaag cagatttaag cacgctgtat    48540
ctatcaggaa atttaccgtg ttcattataa taagctattg ctaattcacg gactgccttt    48600
tcagcagtct ccatatattc tcattttct tctcggtcaa gtcggtgttt    48660
acaatggcga catttataac gaagattatt agtctgccaa tggaccaatt gcacctgttc    48720
agttccacat tcagggcaat taggaacgtt tttagaagcc ctttcgcgac gttcaaccat    48780
gaccattaca gaatcccaat taacaggagg gctataatca tcacaaccat aaatctttcc    48840
acgcatttcc agatcgtctt cttcaccagc cataataatt ttaattagac tagaattact    48900
tgaagctgca atgtcttcta atagacgctt tttcatttca atacctcaat agcattacgt    48960
```

```
aaaccatttg ctttggcggt taaatcctta agaactttag tatgctcttc aatctgtttt   49020
tcaacttcaa tcaaacgggt actgagatat tcgcgttctt ctttcatagt atcattccca   49080
tgattgggct ttggcgtagg tttaaattta ttagggtcct ttaacttaat aacaacttta   49140
gtttcaaaca gtgaaagacc ataattcgta ttatcatcaa aggattcaac tacgtccatt   49200
ttagacaata acgtacgaag tttataagtc aaagaacgaa tcgtttttat atgtttatta   49260
gcttcacatg gtttcatata tggaagattt ttatatattt catgcggagc acaaacaata   49320
attaacaatt caaatggtcc attctgagat gatggaatga atttagccgt aacccaatct   49380
tttacattta cattaatagt acgatcatcg ccatgacaaa acagtctacg agaatgctta   49440
aaaagcatat tcacattatt attaaattcg tgtgaaaact cactggcaaa tttttctttta  49500
ctatctttag aaaaccattc ttctaaataa gttcttttca cgtcgttaat aatattaaat   49560
gtaacaacat tatcatttga tacattagtc tcaatgtagc ttggatacat aaatttttta   49620
acattattaa cagctatcac agaagatagt aatcgggaac gtttgaacca ctcgagcaaa   49680
gaaccaagag aatgtgaata cgcattttgt gtatctttac aaatatggtt ttcccatcca   49740
atatagtcta aaaaatcacg aagaaatatta ttgattactt ctctatgtcc tttctgataa   49800
tcacgatgtt tagtaataag actgtcaaaa taatcaatat aatgtttacg agttttcatg   49860
ttcttctcac ttggttaatg atttatactc cgagccatcc ttggctttaa attttactta   49920
attaactgca aagcttgttc tagacgatca agacgattaa cggattcttc ccaaatcttt   49980
ttagcctgct catattcttt ctgcgcttta ttagaaattt ctagaacttc tttataagct   50040
ttttctagtg caataacttc tggacgaatt tctatcggtt caggtgaatc atcaagacat   50100
tccattagtt ccctcaagggt agtttcttct ttaggagtat tcacaatttc atcacatttt   50160
tgttggtaaa tttctttact agtaggtgaa taagcacatt tcacttcacg aaggctaatt   50220
acgagtttat atccttccca accgcatata ttcttaaaag gatatgtatg aatattttct   50280
actgtttcca tacaaagtaa tgcggtctct aattgacgag ttatagtgct agcaattgag   50340
aaaaatttat taatattctt ttggttagtt tctggtgtaa aaaatccata attcacaaaa   50400
atagatactt tattttatc aagttcatat tcttttatga taatcatatc agaagccaaa   50460
ggatgaattt gacgataatc gccataacat aatttagaag ctgattttag aatttgcttc   50520
ttgaaaagtc tgaaattact aatccaacga cgagtaaaaa tattctcagg gtcttcttta   50580
ttattgagat gataagaatt aacatcaccg aaccaattat atcctactac atctttagtt   50640
cgtttaattt ctttcccaaa attaccaaga atatcccgat taaccaaata tgaaagaaga   50700
cgagactctt taaaggtttt cttgataaca tcttttatcta cacggctaga attttttacga  50760
atttcatgaa taaatttagt agaagaaaca atacttgcat caacactatt gagccactga   50820
ttgataatag aaagaacgct attttggcca aacatcggta tagctttatc atcaataacg   50880
ctattgaatg atttgatata ttcgttacga gtcatattaa tctcctcagt agaaagtaag   50940
aacattatac cacatccttg tggcaaagta aactagttca gtgcatttag tgcattgttc   51000
agtttagaac gttgctttgt cagattttga acccttgact gagcttgttc taacgccttt   51060
tcagcttcta gcacttcatt ggtcgcttta actaattcag catctactgc cttaagagac   51120
ttctcaatcg catccgcgtg ccattttttca acaggtttaa gacttggatt ttcaacagga   51180
agaaaattca ctttattgaa tttccatgca tctttattac ctgagctatc catccaaaat   51240
ttaggatcgt ttgataagta attagataaa tttaagttat cttgcacttc ttgcttttttc   51300
tcttgtgtga cttcgtcctt tctcaaaaat tcatatttaa atgaaacgat catatcaagt   51360
tcatatgatg ttgtatctaa cttaaatcgt tcaaaacgag gtaaaatctt agattgaaca   51420
gcagcaacaa catccatata cttaaatgct tctgtcaact gcgatttaag gcattcgcaa   51480
attgaaagag attttttgt attaggttta aagctaattc gtgcagttct attatttttct   51540
tttaacggtc ttacttccat ctgaagagta taaccatcaa atttcagatt ctttaagtta   51600
atgtcagagc cttttaatcg actagcagta gacaaaattt gctttaattg tctacggaac   51660
agagcaataa atctccattc aatacgataa tgatttggat tgaaaaatcc agatgataaa   51720
tcgaccttac tttgaccaac gccttgaaca aatagaggat ttttataatc aatagtttta   51780
cagaaatcgg tgagctgttc acgagcagtc atttgagtaa tataccctgc tttactaaaa   51840
ttacgcaccc attcactgct attcgtatac ttaaagtgat gaataacacg attaacttta   51900
tcagggtcta aattattttc acacaaaaat gtcataacat cacgagtata gctggcatta   51960
cgaaccatat cttcaatttg agaacgagtt tcatggtgt tccttaagat ttaagtaaat   52020
caacaatttt aattaacttt tcacgctcag atttagcttt actactcaat ccagatagtc   52080
tgaaaatttc atcatcatat tgttgaatag aaatatcagc tcttcaattt gcttattaaa   52140
ataatcaatt tgttcagaat gtttttcgtt actacgaact ggtacaggtt ttgtaggcaa   52200
tttagttgaa ctggattcat tcgggcgata aattaaaatg caatttgaac caatcgggca   52260
tttagcacca gatgaatatt ctaacgttcc agcttctttt aaaacttcaa aagctaaaca   52320
gagatgatgc cccatattaa cataatcagt agagcgagct ctgatgtaat aatcatctcc   52380
acgagtgcta aatttaaagc atttaaggtc ttctgtatta ttagttttaa aaatcatttg   52440
tttatctaga cctttagcca atcgagcacc taatgctaat aatcgtcgtt gattttccca   52500
caaatctgcg atcatttggt caaatgataa tttcggcatt agccgaccat aaaggtcata   52560
tcctttatta taattgcgaa ggatttcact cgcattaata cgagacaacg ctccaatttt   52620
attaagggct ttcataatac gattagataa actcattcca gacccgtttg ttcgctgtaa   52680
atgttttttct aatccaaatc caatatcaac tttaaattta tctaaaattt cagcatgaac   52740
atctctgtca ataacattca aatccaaagt tgggttaaat ctatgaaaaa attatcggg   52800
ctctccacga cgtaaaacag tccattcatt catcattttt ttattaacta agatttaat   52860
tactgcgttg acattattaa ttactactga catattttcc tcactcaatt ttaccaatta   52920
cgcggaataa gattgaacag actatataag taccacatat agattgaact aatgccattc   52980
caaagaacca aacaatatta tcaaaccatg tctgtttttac gtcgaaagga cgtaaactta   53040
cagtaatatt atcacctttt tctattgaag aatacgtctc tggggaaata tattcactaa   53100
atctataacc gtctttgagt tcatatacag caataaacga taaactagac ccctttcctt   53160
gagttcctgt aagggtatta actacagtaa catcataatc tttataatgc atataatcat   53220
taattgcgta ataaccatat gcaattacta tacataaaca acatatcaat aaattcaatc   53280
tttaattat caactgtttc ataataatct caattaaaag gcttagaac cattatacca   53340
tgtataaagc ggtta tgcgagtacc gtatttaacc gtcttcaaa cttccgaaga    53400
gtgttctggc gttcagctct ttgcttttttg taagtttcaa tacgctctga aatgagagtg   53460
tatcgttcat ttactgattc tttcataaaa tcaggaattt ctcgagaagc tttaatctcg   53520
tcaaatttat caataacagc ttgctcttca gcaattaagt tatcatacat caaaatatct   53580
ttcttgatga actcaatatc ttcttgagtt acacgagata atttagatgc tttatccttt   53640
ttgtactgtt cgttagtatc acgagaccag tgtaatgtac gattttttatt cgtattcttg   53700
```

```
taaatttcta caataccaat ctcatcgata ataacgatcc aattccaacg ggatttgtaa   53760
atttgtcctc cattaacagt gatttcacct ccgattgaga tgtcattaaa gaacttgctt   53820
tgtgcttctg atttaaattt accatcgttg taatttacca ggttgaaaat atctttagcg   53880
ttcatttttgt gttcctccgt agttgatagt tgtatagtac cacagaggaa cggtcttgta   53940
aacaactaaa agaaacttct ttcacaattt tttccactga accaagcgct cactgctttc   54000
ttagtttcag gagcagtgtt atccataaac cattcaaagg cagccttttt atgattctgg   54060
agggcttctc gggctttaat ctgctcacgg tctattaaca ctaacatatg agcctttctt   54120
gtcaccaggg gcttcttatg atttttttgaa tactcccaat catttgtcca tcgcatcgtt   54180
gttgcgaatt gaaatacagc ttctttaatc ttagtttcgt aaatttcacg agcctttgag   54240
tataacatca ttacctccat ttaccagttt aattcagtc atctttttga tggcagtcca   54300
tataatctat ttctgaactg ccttttttgtc ttagaaggcc tcttatgaat ttatttcaga   54360
agagtaaccc gtagcgattt cttcccaacc gttttttgtcg gtcataataa agtcagcaag   54420
ataaagtgca gtacgcagtg aaacattacg taaacggtta acattgactt tcatccatga   54480
taatgcttta taagtttctt catcagaaag accacgcttt tgcatcatgt cggttgaaag   54540
aataacatct tcaaccctga ccataatttc ttcattagtg tgaacaccca aatccaaata   54600
aactgagcgg gacactaatg cttgtaaatg tggagcaagt ttagtaccac ggtctaattc   54660
gcggtcaatg tcaacgtttg tgataaaaac aattgttcct ttaaattcga gctcacgctc   54720
aatgcctttt tcttctaagt aagaagatgc agtgctccag cagactttac gggtctctcc   54780
agtgtccaga gcagctttca gaagattaag aatgtccata tcagagaaaa catccacatc   54840
atcaatcaaa aggacagaat tctcttcacg attattccaa agctgttcat aaagaccgat   54900
accagagatt ttaccgttaa tgcttttata ctcaatgtat ccaatatcat ttgctttatt   54960
caaagcttta tctaaagaat atgttttacc aatacccgcc gcaccagaga taattaatga   55020
acgaatattt ccgttaataa taccattcgt catcattccc ataacattaa atctttttatt   55080
aatgcgggtt ttcatatctt catatgattc tttaacttct tcaactttta caccatcata   55140
tgaaatgtct gatttgtaaa cccaaacacc gcgacgttta ccgtcaattt caacaaaaac   55200
tttaccatct ccttgtgcat ctaccggagc attatcaggg aaccattcac ctaagagctc   55260
aaaagttcca gagatttctt taccgaagta catcccctta ttgatagtta cagttttcat   55320
tttattctcc aaatccgtat cagttgatag ttgtatagta ccataaagct ttatgcttgt   55380
aaaccgtttt gtgaaaaaat tttgaaataa aaaagggagc ccgaaggctc cctatcattt   55440
ataataactt cgatggtttt caagataaac cctctcaagg aagtcatccc agaaactcat   55500
gtctactttt tgctgcatac cgttcttaga agcttcagta gatgctgctt ctacttgatc   55560
gaccacatct tccaaaaact cttgaacggt tttaaatgga tgcttaccca acttcacgtc   55620
gagaataaat ggagcatctt ggagtggata aaccaagtca ccagttttgt aaatttccaa   55680
tagttgaagt ccaccacgac aagcatggct cagagctttc cagtcaatgc cttcattggc   55740
ttcggcctta cgagcacgtt cgccgtattc agcatctaat ttgttcagtg actgcttaag   55800
ctcaataaga gaaagcgttg tctgatattt acgacccaac actgtgtaaa acgtttgtgg   55860
gcctgttttc tcatgattat ggaacaccca ttcacagaat tcgttttctg gaagacgatg   55920
cttaatatct tcaactttag tacgacgctg cttaatggaa ccatctcttc ggtaatcaac   55980
ccattgctca gggatttgat taactacttt caatacatcg cgtaatgcag ccaaacgaga   56040
acccttgacg ccgtatttag aagcttgctt gcggacatat cctaaatatg atttcatgtt   56100
agtcgtataa aaacgagaac ggtgtcttg aataaacttc camacatcag gcaaatcgga   56160
tttaaccact agttcaggtg gagtgtgaag catatccaat gctacaggtt caccatctgc   56220
tgctaattta aagaaatact taagactata caattcgtgg tcaatattat ctttagtgtt   56280
tttagatgat gtgttgttgg tatttttact catgtgctct ttgacgtttc caataagaat   56340
atcgcgagca ggaggaacaa agatttcttt aaaatctaca tcagattctg gagtagaagt   56400
tccataaaga tgactaccaa aataagactt aactacagtt tcattatta gacctttcat   56460
aatcttcatt aaattgtaca atcaatcgat gataatttaga ttttggatat cctaatttac   56520
ttatataagt tccgaatgac ccacgtttag gtctatttaa tttaatccat aacttataaa   56580
gtaagtcata gtcttgccaa tgtttaccag ttctttgtct aattttagat gaatttgatt   56640
gtttcttttt agcttcaaaa ttattcaaag atttttttgac tgcagcagag tgttttcttt   56700
taactcccgg tcgtttaaaa gcagctttca ccccttttga tattttttct ttaacttccg   56760
gtttgtttttg tgcttctaac tgggattctg aaatttttagc ccttatttca ggaagactta   56820
atgttatcga acgttttttct ctgtattcat tagacttcca catttctttc attgtattag   56880
aatgtatttt tgaaaatttt tctctaacta actgatatcc tcttgaagtt aatttgagat   56940
ttcttcctaa agaatcttct ccaaaattat aaaatgacca ccatgcataa attaatccag   57000
gcgaattgta atgaatttta gctaaaagcc aatgggctat aaaatgctct ctagctgtta   57060
ataaaactag attatcagaa tcatcattac caccaataca agatgaaata atatgatgct   57120
tttccgtata aaaatttaat ttagatttat ctaatttttct gagttttcct ttcttaatta   57180
aattattata tactttagta taattcattg gttcttcgtc tcatttaatt ttgctttgca   57240
tttataacac atgtctgttc cacttgaaat aaacatattt cctcactttg aaatcatagt   57300
tggaataaca gaatcaagat aagtcttag tgcaatagct tcctctttct ttaatgtaat   57360
gatatgtgat cgaaaatcat caatttgacg aatagatact acatctccct cttcatagca   57420
ttttgaaaca tttaaaatag tttcatcatt ctgattacag gagttagtaa taatagcatt   57480
acattttttta aaccatttta aattatgttt tcttttagta gaatcataaa aatatttaat   57540
gttagttata aaattatccc aattattaat tgataagcac attgactcgc ttttaatatt   57600
aaatcctggg catgaagaat aaaaatgaat tttatgctca tcattaatgc ttacaatttt   57660
atcagtgtaa gcatattcaa tttgggttaa acgaacaatt tcgctaggcg taaaaataaa   57720
catgtcatct tcttgcgtca aacgatacat gttatttact ttttctatag ccaattcacc   57780
aaaaagtgga ctaacttcta atactagtcg tttcgcctcg ctcatcatta catactcctc   57840
tgaatcatat taataatgtt attcaccaga ttataagtaa acattgggta attatattga   57900
atcatcacat atataacaaa caaaactttc attctcttct ccttggcagt tgacaagatt   57960
actataccat aatcttgtca acttgtaaac cattaaatga cgttttcgat aaaatttga   58020
agctttgtat gagcatcaac catgattttc attcttcct tggaaaagct gtgcctcttt   58080
cccgagaga acattcatag tcagaaactg cattagcata ttcttcaatt agcttcatta   58140
aaaacatctg tttttcagtt ttcattattc cacctaatca tttcaagata ttgaactaac   58200
ttagctttgg atttatccaa atccctttta gctgcttcta taccgtcgta tgaatatcct   58260
tcacaatgct caactgctaa ttgatatgaa tctatttcaa tatcatgcgc taatttaatg   58320
atttttttcaa actgttcgcg tgttagcata cttaaactct cgtattatga tcgataattt   58380
catcaagaaa catatctaac gcttctacag cattattaac tttagcttca aattcttcaa   58440
```

```
tacctgataa ggcaaagtta atgcgttcct catctgcttt acgaattaaa gctaccaatt  58500
ccttaatttt atccgcttgt tcgatactaa tcattattcc accacatatg aaagagagaa  58560
tattgcacac gccatgtgag ttgcaacttc atcacacata ttataacgtt tcttaagaag  58620
ttctacaagt tcttcactag taacttcatc catgtcgacg aaaaaatcac cattaatgat  58680
gacgtagata tttccttctt gattgagtgc ttcaattttc atgatgttct cctctttatc  58740
cgatggttgt atagtaccac agctcaaacg gaaagtaaac cggtaaaatg aaaaaaagtc  58800
tcccgaagga gactaatgtt attcgaggga aagaagatac ttactctggt aaaacattcc  58860
agtaatatca tctatcgtgc tttggatggc tggaggcatt tctttataaa tgctgttaga  58920
ttggtctagt atgcgatcaa tcattttaat tgtgtcggta ggaagtttac tggcatctgg  58980
aattgaaggc gtgtattttc gaccagaata ccccaaatat tgctcaccaa atttatcaat  59040
caaatctggc aactcggaaa aaataaaatc gtatgctttg tgtctagcat aacttttagt  59100
ttcaaaatgt gcagaatgaa aataagcttg tgcagccatt aataaaccta agtattcatc  59160
tgcctttgaa ggttttccac tttgtgaaaa gtcgctgaat ttcattcagt ctccaattta  59220
atgttcataa ttctagcgta tgattgtgcc atctccgcgc ctcgctctat acattcaaaa  59280
tcagaagagc acgggtcatt tttataggtc gttctcataa aactatagaa ttgttcagac  59340
gattctacgc ttttattttc aaaaagcata taaacgtgcc taataccaga ttccataaat  59400
ttatcaaaat gaggatcgac attcgcttca atcgatggag ataaaacaaa tgacaatcct  59460
agcatggcaa aaagtgctgt tgcttttaag gccataaagg cctcctatca tttttgtcct  59520
gtatttactt tgtgccgatg cacggcctta actttatcaa ggtattttc aaaatttcgc  59580
aatctagtat agtctgccgg agattggttg agtgatactt ctcgacgcaa agctgaaatg  59640
atatttccaa cttccctacg aatttcatct aattgaagaa cagtaagatt gcgaagttgc  59700
ttttcagtta attgtagcat aatatcccct ttagttagat aaacctattt ataacttttg  59760
cactaaccga gcttttagt taattcattc caatgttttc tacacaaaga aacataaatt  59820
tcatcaccaa tacaaatttg attaccttct ttaactggtg ttccatcttc cattaatcga  59880
gctgtcataa tcgcttttt accacaatga caaactgctt ttagttcaat aagtttatct  59940
gcaatcgcta aaagttcttc agaaccttca aataattttc cagcgaaatc agtccttagc  60000
ccataagcca taacaggaac attatatgta tcaacaattc ggctcaattg atgcacctgt  60060
tcagttttta aaaactgagc ttcatctaca aatacgcaat gaatatcttt ttgtgcttca  60120
gcccatttat agaactcgaa aatatccata tcatctgtaa taatattcgc ttcctgctta  60180
attccaatgc gagaaacgac ttcacagaca gaatcgcgag tatcaatagc aggcttaaga  60240
actaatacac tcattccacg ttctttataa ttatgtgcag caatcaaaag agaagcagat  60300
tttccagcat tcattgctgc ataagtaaaa attaaactcg ccatcttagt ccttagttaa  60360
attttctaaa tatgtttcta aatcattttc agctttatcg atagatttta ctaattcgta  60420
atatgtttcg tgcatctccat attcagaaga tatttcaaaa gacaaatcct tttctaaact  60480
aataatttca ccaactaaaa ataaatattc gttcttttgt tcgcgagtaa tcataaggaa  60540
tttatataat caatgagttc ttgttctttta ttatcgaatt ctttagaaag ttcttcgtac  60600
tcgtttgcgc taaaaggacc gcattcatta caaactttt ccaattcact atttttatcc  60660
ataacttcgt ggataagaga aaagagtgtg tctttttgtt ctttgcttaa actcataacc  60720
atgtcacctt taagcagtat tcttctacat gctgtttacg accttctta tcaataaagg  60780
tatattcaac gaatgttcca atgtagtctt tatctcatc atgtggacta ttaattggac  60840
atttagtgcg acaaatgcgt tcccattgac gaataattac tgccttattc tttgggtcat  60900
atggatgtgg ataatgtata ttcataataa tggttcccaa tcaacaatca caatttctaa  60960
tttagaggaa tatgtatcta aaatcccctc aataatatcc cagttccctt tacctatgcc  61020
tgcaccaatc ctaggcatat agattgtagg tttaatcagt ttattttcac caaactcatt  61080
taattctaac atacaattca ttaaagcgga atactcaaaa tttggccctg gttgaaattg  61140
agtataaaga ttgaagcagt aagctttatg agtcctaaag tatttttcat agactgagta  61200
agaaccgagt ttagttacat caccccattc agtctgtaat ttatcagctt ccaaaatttt  61260
agggaaagct ttggttaatt gacccgctac gcctgaaccc atagtatgaa aacaattaca  61320
tccatgtgca atattttac cttcagcgaa aagggcgaca atatcgccct tgatatattt  61380
tacaatcatc tagtactcaa tcctcgatta taagaatcta ccaaacgtc aaccattgaa  61440
tgacaagcgg cttttatctt ctcctccgca actgaacatt ctaaggtatt ccactttta  61500
gcatatcgtt ttaacaatgt atcgttttgt tatctgcttg atttatctct ttctccgtct  61560
ttatatgcat atattaattt ctgtgcaaat tcagcttggc atgccttatt tttcccacaa  61620
taatctgccg cagtgcggtt tacatattct ctaatttcag tatatgatgt atctgctgac  61680
gcagaagcag aaaatgaaat taatcctata cataaaaacca aaatttttagt catttactat  61740
ttccaaaagt ttattattttt taaggtaatt agccttttct aggacttcag aagcatattt  61800
agaacctgct ttaacattcc atcccgaatt ataagaggat attgcttttc ttatatcgcc  61860
cttatgtata tttaaccaat aagaaagttc aatgtacgcc caggaagctg aattggatcg  61920
tttattcaac attcttttta tttcagcatc catatatta taaccaagtt ccttaactct  61980
tgctcgcata gtaggcaaat aattttgaa cattccgtag gcgtgatgct tggtttaga  62040
ttttaaatta actccgccag agcttttctt g ccataaaatg gcagccatta tatgacctaa  62100
tccgctcttg tggatatttt tgtgtgtttt atattttcca tccttagaaa attgttcccc  62160
gaattgatac gcgtaacgca tgttatcgag ttggacatta ctgaaagtat gctcggagct  62220
atgtgccatc attgaaatgg ccaataqacc agcgagtagt gcttttctca tgcttacctc  62280
attgagtttt aattactgct ttagaagcct ttcctggtaa acgacgactg ttgataattg  62340
ccatcctaca ttgaagtgac gggtctttga acttctcgtt aggttacaa actgtaaatc  62400
caagccaaag atttccatct gtgatttcta aacgtccagg acgatattca accccatcaa  62460
taaaatcctc gtcaatgtca ggacgcgag gcatactcag gaattcatta acttctaaaa  62520
catggtctttt tattttatgg aataattcaa aaacgtatgt ttcatcaatc tcccgttgaa  62580
ttgcgcgatc aagaagatgt tgagaatatt ttagatgaaa cgatgagact cctgctgctt  62640
ttgatgcctc acgaatctca ttgttaattt gacgaaactc cgactcaaag tgacgacgaa  62700
gcttatttcg acggataaaa acttctgtat tgatagtcat gttattctcc tcttaactga  62760
tagaaaaatt ataccacagt caagaggaaa agtaaacagt tattctttaa atctaatcaa  62820
tttattcata gactttgaaa cttcggcacg aacctcatgt agattttga gctgttcaag  62880
acgctgcgta tagtaagcaa tttcatcttc ttcgagacag tcctgcgaat cttctttaag  62940
ataacgtgca tagtcctgga aagcgttacg gactacttcc tggaagtcat caagactttg  63000
aattttctta ggagcaacag atacacgacg aggggcagta taatactcat aaccaaaccc  63060
tgcgcttaat tgagccatta gtattttttcc tctggttgga acactgcacg acaagccac  63120
atactggctt ctttgagttt cgttttagca atagttaact gatcgagact ttcagcataa  63180
```

```
ttcttcgcga attcacagtc ttcgcaatta tctagtgctt cccagaattc atcatataaa   63240
gcatcaaaga taagtcctaa acgaacttca gcgtctttaa tagcatttac tttaccgatt   63300
ttctcttcag tatgtggttt ataaccctta atatcttcaa tcatatttga cttcctcacc   63360
agtacataat acgtattcaa ctaaacgaat aggttcatga atgccatagc cttgaacaga   63420
aatttctgtc gtaggataaa ttccatcaat atcacccata ttccacgctt cattaaattg   63480
ctgttcgcct gagttactaa accactcgcg aaagcattta gcacatcttc agaaccttca   63540
ataattatct ttgccattac aaactttcag taaaggtacg agcgataacg tcgcgctgct   63600
gttccggagt cagagagtta aagcgaactg cataaccgga tacacggatg gtcagctgcg   63660
gatattttc cggatgctta actgcatctt ccagagtttc atgacgcaga acgttaacgt   63720
tcaggtgttg accaccttca attttaactg taggttgtgg ctcaatttca atttcacgag   63780
catgcaaacc atagaaaatt tctgggtcta caaaagagtc ctctttaaag gttttagaga   63840
caataattcg tgcttgaata ccatcttcaa aataaatagt acctttatgt gtgccttcaa   63900
gaatttgata tgctttcata taaacctcaa ttagaaaata aatttatcca agattgttct   63960
ttaattaaaa atggctcaga atcatatgcc attaaacttt gcgtaattaa tccttaaaa   64020
ggtccatcaa taaattccat ggtaaaatat ggaatttat tcattagccg tgcattagga   64080
gcagtgcaca aaactctgca tcctttgaat acgccttttt gtaatttgta ttgcttggga   64140
taaaattcgc tcaaaatgtt attttttgcc aaaatttcaa aatgattcac caatttattt   64200
ttaatagttt ttggcgaaaa ataaagatat tcgaaaagct gagtgtctgt catcattgca   64260
ttccgattac gaaaaactgt ggacgagtaa taccaccaat gcaacattta ctattacagc   64320
agtagtgtac ggtgtcaata tggacactat aaatcttatc catatcagga gatttgacag   64380
gctcatcaat tatatacaaa attcgcgaaa gctttaaacc tctgaacttg cttcctttat   64440
taccaataaa actgcgtaca gaatcagtaa ataaacgaaa acgtatatca tcattagaat   64500
aacgcgaaaa ttccttttg atgttatttg cagaaatttt agcataagct gaagtattag   64560
aaagaacaat aactgttccg ccatcataca accaattagc agcaaagtta gtcacagcaa   64620
ttgatttacc ggattgacgt ccaccatcta gtcgaagtgt acaatactgt ttaagtaagt   64680
cttcaaatgg cgggatatat tcgttttac aaatttcttc tactctagca tcagaatggt   64740
gtgtaaaagc attcatcagg gatagataag gaccagttaa aaatgttctc atttcttctc   64800
tataagctct ataagtttgg gccattccgt ggcacatgaa ttgtccattt ctgtatttac   64860
ccattaccgc gcttgggctc gaccttatta caggttggcg ggaatccctc atataatcat   64920
gaggtccagg ttgttccctt atgcataaat cgccttaccg tagtatttgt accaagtagg   64980
acgttgtgca atttttcat ctaaacgagc ttgtgatata gcaatagaag cttcatggtg   65040
aatataatca ccacggaatt cctgaggaat atcactaata tcctggactg tagtatcctt   65100
gatattaaaa ccacgtttta aacattcagc tataagctca atttgacgtt tacgtaagaa   65160
ctcgagctta tcgtaaaaga atgtaacatg acctgcgcca aggataaaag taggactgat   65220
tttaaaatca cgaacacgtt taccgttagc aacatgctta cgaactgcac caaaaacacg   65280
cggcaattca cgatattcag ccattaagtg ttggtcagcc aattcagata ctaaagtaag   65340
gttgatacga gtcattttag tgttctcctg tagttgatag gtctatagta tcataccta   65400
aggagatgta aactgttatt tatctttaat tgctttagct gcttcgatag ccgcttgctg   65460
aaggtcatcc atagacatgc cgaacttaga agcaaagtta tcaattttct tttcgacggc   65520
attcaaaggc ttggcctgtt taccttcatt agcgccagga agagcgagaa tacgctctct   65580
gtcaatataa aggcttacaa gtttcttacg gtctttatcg ggcaaatcat gaaatgaatg   65640
ggcctttta tttacagcgg cttctaattt acctgcgccc actcgcgctt cggcaataaa   65700
ttcttgatat gtttcatat gtttccttta aatgtaaata ttttattat tctatcctag   65760
aattgtgata atatattcac aattctagga gttgtaaact gcttttattt aagcgtccca   65820
agtataagct ttattaagaa ttaccacggg ctgcattagc aacggcgtaa gcgtactgaa   65880
tattagcgtc tttaaactta cctttagagg tatctatttc tgccttaaag ccgcctttag   65940
tcataacatc ggcaaattct ttacggaaag ccattgcatc aagaccttc catgatgatt   66000
tatgcttggc aaattcaaga cctgcgaagt tgacagcttt agccaattta ttatcaatga   66060
cccatttacc ggcttttaggc acaaacttcg ggcctttctg tttagagaac agttttaaat   66120
tccagcggcg aaggtctgca tcagctttaa caaattctga gtcaagtta ctagcaacaa   66180
catcttcaat atgagcaaat ttaagtccgt caacttcaat atttaaatcg gtacgccagc   66240
gaagtccttc ccaagcgaag gctttaaagt cggaagcctt tgtagctaag taccgttcaa   66300
taggagctgt tttagggtca aagccgtttc ctgatcggta ggtccactca tctttgttaa   66360
tgcctttggc ctttactaca gaagcttcgg caataaattc ttgatatgtt ttcatatgtt   66420
tcctttaaat atttaatta gtaattgtct attcaagtaa ttgtgaatat actatccaca   66480
ttccaagaga aagtaaacag ctttatagat ttttatacgc gtcccaagtg ccagttctaa   66540
acgttgtaat gactcgtttt gcgcgattag gtgtttgatt ataccatata cttttagcta   66600
agttaactgc tgcttcatcc cagcgttttt gttgaagcat acgtaaagag ttagtaaatc   66660
ctgccacacc ggtttctccc atttggaaaa ccatattaat caatgcacag cgacgaaccg   66720
catcaagaga atcataaacc ggtttttaatt tagcatttct cagaattccg cgaacagcag   66780
catcaacatc ctgattaaag agttttttcag cctcatcttt tgtaattaca ccattgcaat   66840
tacgcccaat agctttatct aattcagatt tagcagcatt aagtgatgga cttttttgtaa   66900
gcaaatgacc gatgccaata gtgtaatagc cttctgtgtc tttatagatt ttaagtctaa   66960
gacgttcatc tatacgtaac attctcaaata tattcataat acctcctaag tatttataga   67020
aggtatttat aaaattaaaa gaggttgttc attattcggt aaagtgaagg acccatcaca   67080
tattgccact gagtacgagg aataagagca aaagcgtcca tctctggaat cataacgcca   67140
tctttatttt caaaataaga ctcgcaacgg caatttctga acatctcatg ctctactgga   67200
atcgtgtaat aaaataactg taggtcttta ttactagaat attaaaatac acctaggtct   67260
tctagaaggt ctggattata attgctaaaa ccagtctctt ctaaacattc tcttcgtgct   67320
gcatctaatg cgcttaaatc agaatttct acacggccct ttggaatatc ccaacgatgt   67380
gccatcattc cagtcttacg agaaccagta acccgaccca taaataaatc tttatcttct   67440
gtcataaaga taataccagc tgataatgtt ttcattttaa tttcctgcat tcagtgataa   67500
agttatttaa attttgagca tatttctttt catcaaaaat cttttgctgt ctgcgtaacc   67560
gccatggcat ttcaatgaac atacgccata tccctagata ataccgctgc tgtaaaaata   67620
ttaacaagta tagttaaaag aatccaatcg cctattctgt ccattggatt tttataaaaa   67680
agtaaaatac gaatgatgat ataggaagac taatgatata ccacagaaga accttcttat   67740
ctgtgaacca atcagcattc gttaacttag cgcgaccatt ttgaatacac acgaatttat   67800
catctgttac agtaaatggc ttagctgctt gatatcccta tctaaactcc ctaattaatc   67860
gtttctttgt atcttcggaa caaccattcc aatcaactct atcaactgga atgccatcat   67920
```

```
ccccatcatc taaatcatac cagcgagttt ttaaaatcat ttaattttcc tgcaatcaat  67980
cacaaactct ttcattgatt cattttcaat ataagacatg tagctattat attcttttaa  68040
ttgtattttg taatccttt ttctttgcca atttattta aaattatcat aatgaaaata   68100
taaaatgata ccaagaatg aaaacaatga aataatttta gtataacaaa gctcgctcca   68160
aacttctatt atatctactg taccactgat ttttaaaata aaacagtcaa ttaatagtcc   68220
aataagacta cctgtaagag ctgcagccaa cgccacagca aaaattaaaa atgactcaga   68280
aaacgaatat ttgactttat ttagctttgg cttttgcatc gtgattcctt aacaaatttc   68340
ataatttcat taaattcata ctcagcaagt ttaagctggt gttccttttt aatcttttg   68400
cactgggctt tccaatcacg tacgcgttta cgataatgtc ttccttgata ccagtatcct   68460
atccaattta cgggtactaa taaaaatgga actaccaatg gaagagttag cattaacata   68520
attattacgc cagaatcaat atcagtcata acatctaaaa cacctccaat aatcaataga   68580
attacaaatg atatagctat cacaggacct attaatacat cagtagaaat tatctggcgc   68640
tttaattcat acttcaaagg tttacttgga aggtatagtg atggctttga catattctct   68700
acattcctta acaaattttt ctagtaataa atcactttca aaattaggat tttccactaa   68760
tttatcaaaa agatcatcaa caatattcaa gatatttctt ttactaagaa tacgtttatt   68820
ttcatgcttc gtttcagaat caactataag agtaaagaaa tatttctttc cctgaaattt   68880
taccgtagta tcaatataaa ataaatttga cttttgtaaa ttacgtttaa accatgcgtc   68940
acttaaacta taaacaccga gataatcaaa atcgtcgttt aaataacaaa ctgaccattc   69000
aggagaaatg aaatcagtaa attcaacatc aaaatcacat gtcaatgaat gaattgattc   69060
aatactgtta ataagtattc caggacgtat taaagacttt ttacctctgg aaaatcttcc   69120
agaaagactt tcatcagttt catatgaaga accccaataa taattacgtc cttttgccat   69180
atgttaaga gcatttagta attggtctgg aacatcaacg tgtctttgga actcttcaaa   69240
cattgaattg aaatcacttt gcattttcat tcctatttac tccaagtaat aggggccgaa   69300
gccccttatc attattcag agaattaata tattcctgaa catcggcaga ggtagtttca   69360
accccagaaa tattaccatt aaaggtttca actcgagcaa gagtatcttc aatatcaacc   69420
ttagtcagtg ctgcaatttc aactacatca tcagcagtaa taattccaag ggcatttgct   69480
gcacgagttt cacggatata ttccaattta actgcaagtt cttggcgagc atcatctaac   69540
tcaactactt tcttggcgat ttcaattcgc atttcagcat aaccatcagc tttagtagtc   69600
agctgttcag ctgttcgacg atatagcaag ccgagtttag catgcattgt tacatcttga   69660
ccttcggaaa gaagcttgcg aatttcacgc tcttttgatt cggcctgttt attcttttca   69720
acaataagtt cacgaatacg ttttttcttca ttaatagatt taacagaagc agttttttagg   69780
tctttaattt tatcaagtag ttttgctgct gcagcagtat actgttcttc aacagataga   69840
tttttagcca ttgcagaacc aagtttagtg cgaataaact caacaatttt cttcagtgtg   69900
ttcatagtat ttccttaggt tggtataatt agataatata atatcacgtt tctaatagat   69960
tgtaaactta ttcttcgtct agctcgtcga taaaggcgtt gatggcctcg ataatggcat   70020
cattgatagc caataaaata aaatcatcgt cagtaccttt agaagattct aaagcattga   70080
tatatgcttg gttgacgagt tcccaagcct tttaaaata aggagcttca tcatcaggac   70140
aaatatcccg cacgccttca aagatacgtt tggcataatc taacaccccat tgtacaggca   70200
tgttttgaga acgttcgtta aactctttaa agtccttaga ttcaaaaagc tcttcaggat   70260
aattatttct attacaaaaa gctttactaa agttacgttt cataatgttt tcctcatttg   70320
tataggctca taatatctca atcatsagcc tatgtaaact tatttcatat tattgaaata   70380
ttcttctgcg atttcgtcgt tatcatggta aactttagaa gacagtttaa cataactttc   70440
agcagtgaac atgttaatca caaccttac agtataccac tgaccgtctt cattacccat   70500
tactgcgtaa gtttcaaaca tcggatggtc aggaccgata actttaatat cattcaccgt   70560
acgaccgaaa tcttctgaaa cacatttcat aaagaagttg aaaagttcac cgtaattatc   70620
cattttattc tccaagttat tttctgtatc agtagttgat agttgtatag taccatggaa   70680
gaacaaggat gtaaacagtt ttgtgaaaaa attttaaaa agttttaggg aattctaggg   70740
cggagagggg caattaaaag ataggataat atattataaa gggtataaac taaatgatgc   70800
ctagagaggt ctggaaaggc ttagatacca aaaagcccca accttccggt cggggctaaa   70860
cgttgcggca accttgtcgg ggttccacct gccaaggcaa gtgtttgtac gaaacgccgg   70920
gattcgaacc cggttattaa gtagttgacg ctactcaata ttttaaaag gccatatctg   70980
aaccatatcc gaacgttccg tcaaaaacgc tactcggctt acggcaaaga tatttcctcg   71040
aatcgataat ttggtgcgcc gtttctgctg tgatgtaaga gggcatcaat aaacgcaaag   71100
attattaacg caattcctta ctcagggaac catcagtccg acgacttacc ggtagcgacc   71160
cggttctca tttggtatcc cgccctggga tcgaaccagg accgcaaact tagaaggatc   71220
gtatgctatc cattcaccca gcgggacgta atttaaaatt tcattttcg accttttaaac   71280
catccttctg gaattggtc agttttctta atacgtttag aaacttttc atctaatgaa   71340
tgaatccaca tcataccgaa ttgggaattc ttttcacctt tctggtgatt attttggcg   71400
tgagattctt tcattttatt aatagtttca ggagtatgat gcttatttag aaatctgcta   71460
ttatttaaaa attttttccct gtattcagga gttgaccaca aacgtttaaa tacattttgaa   71520
ccaatttttac gatatttttc ttgaagtaaa atatcatttt caaaacgtga cttaaacgat   71580
ttagctcctt ttaagctagc atctttcttc tggtttagca ttccaggaat atttacatga   71640
tcccatccac cttcaccgcc aagttttaaa ttatacacat ctggtctatt taaaaactct   71700
tctgtgacaa tattttctc ggcttcaagc atagattctt tatcgtcaaa atactctaat   71760
atttctttag aaaaattttc tataccatat ttatcttggg ctcttttaa taattacca   71820
gaacccatat atccatcatc taaatttcg gtagaatgca caccaatata aattttatta   71880
ttaatttat ttgttatttt ataagtgtaa tagaacataa atatctccta tttctaagag   71940
tatttatgtt ctcaaaatat gacccagacc agatttgaac tggtaacctt tccccttatga  72000
ggggactgct gctaaccatt gagctacagg gccttggtgc tgattgacgg aatcgaaccg   72060
ccgacatcct cattcaagt gaggtgctct acctactgag ctaaatcagc aaaattacgg   72120
aggcgatagg atttgaacct atgagtcgcc ggagcgactg ccggttttca agaccggtgc   72180
attaaaaccac tctgccacgc ctccagtctc catacaagga tttgaacctt ggacctcctg  72240
atcccaaatc aggcgctcta ccaaactgag ctacacggag taaattaaat tggagcggat   72300
aatgaccat gaactcacat catcagattg gaagtctgag gtaataccat tatacgatat   72360
ccgcaaattt ggtgcgagaa gtgggactcg aacccacaag gaaatcattc cgcagcattt   72420
taagtgctgt gcctttacca atttgaccat tctcgcgctg gaataaagg actcgaacct   72480
ttgcatctag cagtcaaagt gctatgcctt accaacttgg ctaattccca attattaaca   72540
aaggctctct aacaagaacc cttgatgata gagggtatta atcagtgcgg tatgagttaa   72600
taataacaaa taattcttaa agcatatta ccatttatga tgatacgtat ttacgataca   72660
```

```
ttcaagaccc aaaggattct tgaaaatatc atattcaaga ggacctttt  ctgtttcaat    72720
aaagaaatca aaatttactg tattaaattt acggtcttcc tttactaatt taacttgaga   72780
agatgaacga tcaatgtaaa cctttcaac  ttcaaaacac gttaaaatgc cataatcatc   72840
aatcaaggct ttagctgctt cttgatcata tttatatcca ttttcaacgg atgatacttt   72900
cgcataaaga atcatcatca acctctatca acaatagcat gagtatgggc atttacgatt   72960
tgccaccagt cgaaacgatt ggaaccataa tctggtttat tttcattttc tttaatgata   73020
tcacgcagtt tatcttctgt ttcagcatac gcaattaaat catcatatcc accacaagga   73080
taataattat cacctgcgaa taaaagaaaa tttaccttag atggatttac gtaataatgg   73140
tctttaggat atttagttcc tctccaatca gttacttcaa cataacggta agaaaatcca   73200
tttttactt caatccaact ccacgcttca aaaggagtat taaaaacttt atcaggtatt    73260
aaattacctt caaaatgaga aggatttgca taatccccgg cataaacata atattcgtta   73320
atactcattt attcacctt agaaaattta tccataacga tagcaattaa accaattaaa    73380
aatgctacta caagtgaaaa cacattttct gctgtagtta ataatccgca tataaatcca   73440
acaaacattg aaaaactaaa agcagaagca gaaattgcaa tagcaacatt tcgaattaat   73500
tcacagcgtt tcattttatt ctcctcagta gttgataggg taatagtatc acagctaaaa   73560
ccctatgtaa acaacttgt  gaaatattta ttacaaaaga tttttagcaa taatcttgag   73620
atgtgccgca gaaatgtgtt tagctttaaa caacgcagtt tcttcagcag gagagataac   73680
gattgtagca ccatccttt  tagcagacca cccatcacct aggtaaacag tacctttgat   73740
ttcttcgcca tcaaccagac taatcattgg tttaccttct cgtcctttat ttgctttaat   73800
aacttcagaa gtaagagtag cttcggtaat ggtagaaacc ggggtagttg tagaagtaaa   73860
ttcttaaat  gttttcattt ttattttcct aattaatttt gatgaggtaa tagtatcact   73920
acctcatcag tatgtaaaca acttttgtgaa attattttaa atcatctgcc caatcgagtt   73980
taagaggctc tttgtattca cgatctaata cgaccggaat ttgtacatca ccgctaaatg   74040
ataagggccc aacattataa gacaatgtta tatgcggtgt gtaatcatca aaatcatgtg   74100
tagcacctag tgcccgcgca tacatgtgtc gacagcgcag atattcagaa tctagcacaa   74160
gtacaagagt cgatccatct tgtgtttcc atacttctaa atgtccagaa gaagctactt    74220
caaaacttcc actcgatgga acatatgaa  catttactct tgaataacat atagtcgaat   74280
gaattttttc tctaggaact ggattaggaa cacgtaaaga gcgctgaagt tcttccagcg   74340
catcaagtgt taattctgaa aacttagctg ctacataaag acccgttgaa aagtctttaa   74400
attccatcat tcttcatctt ttgcttcatc tgcagattca gcagtaagat tttgacagc    74460
ttcaacgatt tcttcaactt tgatagtatc gccagtgata cctactgcac gagcaatttc   74520
agccaaagtt ccttgcagaa ttttggattc ttccatcaga cgagcagctt gatcctgcgt   74580
atcaagaatg cgagatttca gagttacgat ttcagcagac agttttgtt  caacagtttg   74640
ttcagacatt atagtacctt tagtgtattt ttaattttag aaaaaagttc ttcaagagaa   74700
ccatcgttg  taattactaa atcgccatca cgaattggca atccagcttc tgtaatatgt   74760
gtatcattgg atttttgacc aggacgaact acatgaatta ctgtagcacc catcgcccta   74820
gccgcatcca tttcatgatc ttgacgggta tcaggaacga tataataatc ataacctgag   74880
ttaaatttat caagataatc taaagcaaat aatttaccc  agtacatgcg gtcgaagtta   74940
ttaacaatca aatccgtacc tagggcttgc atcagacgac ggactgacca ttgatcttca   75000
atattattta taacgtcagt aatcttatta aatgctacga aattaactga ttctttccct   75060
tcgtcatcaa aacaaacac  acctttaatt gggctttac  cattaagata acaaaatgct   75120
tgttccataa tcgtgattac ttctaattta gtcagattta aattagtctc acgatcatag   75180
tcaattcctt caaactcttt acgagttaag caaggatagt cagtgtttgc tgcaaatact   75240
ccccatgcat aagccaatgc atccttaata ggaccagcaa gttggtattt aactgcagaa   75300
taattgctca tgataaaatc agcagtagta tctttttccac tacgctttac accgcttaaa   75360
aagattagtt tcatgtgtt  ctcctcaaat ttaattaaga ttataacaca caaaactgaa   75420
gcattaaaat tctgctataa ttttaccatc ttttctact  tgaaaatagg tgtaaggaat   75480
tgttgcagta catactaaag ccgggtctga atcttccgtg tagctaaatt ctacttcaga   75540
taggtcagaa acccaaggct tataaaaatt tattgacatc acgatttcag ttttgctatt   75600
atctaagatg taaagcgtaa tgtactcagg acctgttttt tgggcagtat tttcacctgt   75660
aagatagttg ctagttccta gcatccattc atacattcct atccacgact taagttcttc   75720
atcaactata aatctcacaa tgagtggatc atactcaaat gtaacacctg gacgttgtgc   75780
tcggcccagt ccaaacggcc cagtcacggg atcagtaaca ggtattctaa ttcctggaat   75840
aggaactgac tgagcattta aagtaaaagc agatgtagta ttactatgtg gtattgatac   75900
tacaaagtta gttgtatttg cttggttaaa aatttgttgc agagcttgcg acatatattc   75960
ctcataatgc tttataactg ttggtggtat aatgggtcta agtcccttcc attcaattcc   76020
atttagaaca aacaacagaa aagaatggaa gataatagaa ttagatattt gaccagactt   76080
tgtttgcaga gaaacgtttt ccttttgaaa cgaactgctg aagtggcatc aacacaacgt   76140
tcgcccagtc tttcggggcg atttcaacaa ggctacccat aatattacca ggtatatatg   76200
ccttaatcat ttggtctgca cccctaaatc cttcacttg  actccaatca atttttaatt   76260
tcgtttatt  agtaatagta ggtgtatttg catattgctt taaaagctct tctaggaatt   76320
gctgacgagc tttaggtgga atatagtgca agtttaatcc gtacattaaa ttatgcttac   76380
ctaaaccaag gtaattatc  aaaggaaatt tatcccagta aggaagagtt tccttgtgtt   76440
tagcatcata agcaaaagca tatattcgtc ccggctgcgg cgcaacaact ttatgtccnt   76500
ttacttgctt aatagtttca gcaaaccact ttctggtttt attattaatt gctgcgcctt   76560
cattacgaat tttcatcgc aatgtttgtc tgaatgaatt tatctaaagc agttgtcttt    76620
cttgcttatt gagtttattc attggttttg attcaagttt ttgaatcttt tcagccgttt   76680
taattcctga agcatatttt gacattgctg aagtaaacgt agagtatttg attcctcttt   76740
cttcagcaaa ttgctttcct gtcattcctt ttgctttggc ctttttatat tcaagaccta   76800
tctgaatcca ttctttttcg tttaatgatt gcttaacctt tggaacttgg gagtgctttt   76860
cattaattat ttgaaaaata gccattatgc ccccttaaag ccaagagctc gtaatccatc   76920
ttctgttaga attctaaatt ttattccacg cttttcagct aaagattgtg ctgctttcca   76980
tttgtcagtg ttcacagacc aggtataaat ttcattcata aatctttct  tcgctgcggt   77040
cgttagatgt gctggtttaa ctggtggttg tgttttta taggttta tttcaataaa       77100
aaattcttgt ccagaagaat ctttcatcca aatatccatg aagtatctac gtttttttcc   77160
ttctgcatta caaaaataag gaattactgc tgtttcacta ccccatgcaa taatttctgg   77220
attttatct  aaccattcaa aaaagaattt ttcccaattt gatctatacg taatttttt    77280
agggtcacct ctatactttg atatattttt aggaaccccat tttccagaat atgccattgg   77340
attctcctta taaatagata atatatttat aaacaggagg gcccatgctc ttttacatttt   77400
```

-continued

```
ttgatccgat tgaatatgcg gccaaaacgg tgaataaaaa cgcgccgact attcctatga   77460
cagatatttt tagaaactat aaagactatt ttaaacgcgc tcttgcggga taccgcttac   77520
gtacttatta tattaaaggt tcaccacgcc cggaagaatt agcaaatgct atatatggaa   77580
atccacagct gtattgggtt ttattgatgt gtaatgataa ttatgacccg tattatggat   77640
ggattacttc gcaagaagct gcttatcaag catctataca aaaatacaaa aacgtaggtg   77700
gagaccaaat agtatatcat gtgaatgaga acggtgaaaa attttataat ttaatatcat   77760
acgatgataa tccatatgtt tggtatgata aaggcgataa agctagaaaa tatcctcaat   77820
atgaaggagc gcttgctgcg gtcgatacgt atgaagctgc tgttcttgaa aatgaaaaac   77880
ttcgtcaaat aaaaaataata gcaaaatcag acatcaattc atttatgaac gaccttatac   77940
gtataatgga gaaatcttat ggaaatgata agtaataacc ttaattggtt tgtcggtgtt   78000
gttgaagata gaatggaccc attaaaatta ggtcgtgttc gtgttcgtgt ggttggtctg   78060
catccacctc aaagagcaca aggtgatgta atgggtattc caactgaaaa attaccatgg   78120
atgtcagtta ttcaacctat aacttctgca gcaatgtctg gaattggagg ttctgttact   78180
ggaccagtag aaggaactag agtttatggt cattttttag acaaatggaa aactaatgga   78240
attgtccttg gcacgtatgg tggaatagtt cgcgaaaaac cgaatagact tgaaggattt   78300
tctgacccaa ctgggcagta tcctagacgt ttaggaaatg atactaacgt actaaaccaa   78360
ggtggagaag taggatatga ttcgtcttct aacgttatcc aagatagtaa cttagacacc   78420
gcaataaatc ccgatgatag accgctatca gagattccga ccgatgataa tccaaatatg   78480
tcaatggctg aaatgcttcg ccgtgatgaa ggattaagat taaaagttta ttgggatacc   78540
gaaggatatc cgacaattgg tattggtcat cttatcatga agcagccagt tcgtgatatg   78600
gctcaaatta ataaagtttt atcaaaacaa gttggtcgtg aaattacagg aaatccaggt   78660
tctattacaa tggaagaggc gacgacttta tttgagcgtg atttggctga tatgcaacgg   78720
gacattaaat cacattctaa agtaggacca gtctggcaag ctgtcaaccg ttctcgtcaa   78780
atggcgttag aaaatatggc atttcagatg ggtgttggtg gtgtagctaa atttaacaca   78840
atgttaactg ctatgttagc aggagattgg gaaaagcgt ataagccgg tcgtgattca   78900
ttgtggtatc aacaaacaaa aggccgtgca tcccgtgtta ccatgattat tcttacgggg   78960
aatttggaat catatggtgt tgaagtgaaa accccagcta ggtctctatc agcaatggct   79020
gctactgtag ctaaatcttc tgaccctgct gaccctccta ttccaaatga ctcgagaatt   79080
ttattcaaag aaccagtttc ttcatataaa ggtgaatatc cttatgtgca tacaatggaa   79140
actgaaagcg gacatattca ggaatttgat gatcccctg ggcaagaacg atatagatta   79200
gttcatccaa ctggaactta tgaagaagta tcaccatcag gaagaagaac aagaaaaact   79260
gttgataatt tgtatgatat aaccaatgct gatggtaatt ttttggtagc cggtgataaa   79320
aagactaacg tcgtggttc agaaatttat tataacatgg ataatcgttt acatcaaatc   79380
gatggaagca atacaatatt tgtacgtgga gacgaaacga aaactgttga aggtaatgga   79440
actatcctag ttaaaggtaa tgttactatt atagttgaag gtaatgctga cattacagtt   79500
aaaggagatg ctaccacttt agttgaagga aatcaaacta acacagtaaa tggaaatctt   79560
tcttggaaag ttgccgggac agttgattgg gatgtcggtg gtgattggac agaaaaaatg   79620
gcatctatga gttctatttc atctggtcaa tacacaattg atggatcgag gattgacatt   79680
ggctaatata cttccaatga gcgctgattt aggagaatca atggaaggtt cttctatcga   79740
cgtcaccttt accgctcaat tagaaacagg tgaaacgtta gtatctataa atataactag   79800
ttacgaagaa actcctgggg ttttagtaga agaaaatcgc ttatatggaa catatgaatc   79860
tgtatttggt ttcggaaatg acgcgttgaa atatcgttta ggcgatgaat ttaaaactgc   79920
tgcttcatgg gaagaacttc ctactgattc tgatactacg ttgtatttgt ggaaagctcc   79980
tcaaaacctc cagaagacat tcacttacga agtaacatta atatatgact accaagaaca   80040
aagtgaatct gggggttctg gcagtaattc taggtcatct tctgatacta ctgaaccgac   80100
agatcctcct gctccagtaa gaaaaactct agttaaaaat tatactaaaa ctatagttgg   80160
aaattggagt cgttgggcta ataaactgag aaaaatatgc tatgcaagac cataaatatt   80220
tttatttgta ttcaataact aataaaacaa cagaaaaaat ttatgtaggc gtccacaaaa   80280
cttcaaattt ggatgatggg tatatgggtt ctggcgttgc cattaaaaat gccattaaaa   80340
aatatggcat agataatttt tataagcata ttataaaatt ctttgaatct gaaaagcta   80400
tgtatgacgc agaggcagaa atagtcacag aggaatttgt taaatctaag aaaacttata   80460
atatgaaact aggcggtatc ggtggcttcc caaaacataa cacagcgggt gctaaaaatg   80520
gattttacgg taaatctcat tcgcgtgaaa ctagattgaa aattagcatt aaatcgtcta   80580
gaaaagagg gcctagaggg ctagaggtaa aactctgaag atgtgtggcg ccaataaccc   80640
aaggtatggc aaaatagccc ctaatgctaa atctgttatt atcaacggcg ttttatataa   80700
aagtattaaa atcgcagcta aagctcttaa tataaattat agtaccttaa aggggcgagt   80760
taaagcgggg tattataaat gtcaggatta agttatgata agtgtgttac tgctggccat   80820
gaagcgtggc ctccaacagt tgtgaatgct acacaaagta aagtattcac tggaggaatt   80880
gctgttctcg tagcaggcga tccaattaca gaacatacag aaattaaaaa gccgtatgaa   80940
acacatggcg gagtgacaca acctagaact tctaaggtat atgtcactgg aaagaaagct   81000
gttcaaatgg ctgatccaat atcatgcggt gatactgtgg ctcaggcatc atctaaagta   81060
ttcattaaat aggatttaaa atggcaaata cccctgtaaa ttatcaatta acaagaacag   81120
caaatgctat tcccgagata ttcgtcgggg gtacatttgc tgaaataaaa caaacctca   81180
ttgaatggct taatggccaa aatgaatttt tggattatca ttttgaaggc tcaagattaa   81240
acgttctgtg tgaccttta gcttataata cattatacat tcagcagttt ggtaatgcta   81300
ctgtgtatga aagctttatg cgtactgcta acttacgaag ttcagttgtt caagctgcac   81360
aagataacg atatttacct acttcaaaat ccgctgcgca gaccgaaatt atgttaacat   81420
gcactgacgc attgaatagg aattacatta ctattcctcg cggaactcgc tttttagcat   81480
atgcaaaaga tacttctgtt aatccatata acttcgtttc tagggaagac gttattgcta   81540
ttcgtgataa aaataaccaa tattttccgc gtttaaaatt ggcccaggga cgtatagtaa   81600
gaactgaaat catttatgat aaaattaacac ctattatcat ttatgataaa aatattgata   81660
gaaaccaggt taaattatac gttgatggag cggaatggat taactggacg agaaagtcaa   81720
tggttcatgc tggttcaaca tcaacgattt actatatgcg tgaaactatt gatggaaaca   81780
ctgaattcta ttttggtgaa ggtgaaattt ctgttaatgc ttctgaagga gctttgaccg   81840
ctaattatat cggaggtctt aaacctactc agaactctac gattgttatt gagtacatta   81900
gtactaatgg tgctgacgcg aacggagcag tcggattttc atacgcagat acattaacaa   81960
atataactgt catcaatatt aatgaaaatc caaacgatga tccagatttt gttgggcag   82020
atggaggcgg tgatccagaa gatattgagc gtattcgcga attgggtact attaaacgcg   82080
aaacccaaca acgatgcgta actgcgactg actatgatac attcgtttca gagagatttg   82140
```

```
gttctattat tcaagctgtt cagactttca ctgattctac taaacctggg tatgcattta    82200
ttgctgctaa acctaaatca ggattgtatt taactaccgt acagcgtgaa gatattaaaa    82260
attatctcaa agactataat ttagctccta ttacgccatc aattatttct cctaattatc    82320
tttttattaa gactaattta aaagtcacat atgctttaaa taaactgcaa gaatccgaac    82380
agtggcttga aggtcaaata attgataaaa tagatcgcta ttataccgaa gatgtagaaa    82440
tttttaactc gtctttcgct aaatctaaga tgttgacata tgtagatgat gcagatcatt    82500
ctgtcattgg ttcatcagcg actattcaaa tggttcgtga agtacaaaac ttctataaaa    82560
cgcctgaagc gggtattaaa tacaataatc aaataaaaga tcgttctatg gaatctaata    82620
cgttttcatt taattctgga cgaaaggttg taaatcctga tactggttta gaagaagtta    82680
tattatatga cgttcgtata gtatcaacag accgagattc taaaggaatt ggtaaagtta    82740
ttattggtcc atttgcttct ggcgatgtta cagaaaatga aaacattcag ccgtatacag    82800
gcaacgattt taacaaatta gcaaattctg atggacgcga caaatactat gttatcggtg    82860
aaataaatta tccagctgat gtgatttatt ggaatatcgc taaaattaat ttaacatctg    82920
aaaaatttga agttcagacc attgaattat attctgaccc aaccgatgat gttatctta    82980
ctcgcgatgg ttcactgatt gtatttgaaa atgacttacg tccacaatac ttaactatcg    83040
atttggagcc tatatcacaa tgacagtaaa agcaccttca gtcactagtc tcagaatttc    83100
caagttatcc gcaaatcagg tgcaagtacg ctgggatgac gttggtgcta atttctacta    83160
ttttgtagaa atcgctgaga caaaaacaaa ctcgggggaa aatctcccga gtaatcaata    83220
tcgttggatt aatttaggat atacagcaaa taatagtttc ttttttgatg atgctgatcc    83280
attaacaaca tacattatta gagtagccac agctgcgcaa gattttgagc agtctgattg    83340
gatttatacc gaagagtttg aaactttgc tacaaatgct tatacatttc aaaacatgat    83400
tgaaatgcaa ttagccaata aattcattca ggaaaaattt actcttaata atctgaatta    83460
tgttaatttt aataatgata ctataatggc tgcattgatg aatgaatcat tccaattcag    83520
cccatcgtat gttgatgttt catcaataag taatttatt attggtgaaa atgagtatca    83580
tgaaatacaa ggttctattc agcaagtatg taaggatatt aaccgagttt atttgatgga    83640
atcagaagga attctatatc tttttgagcg ctatcaacct gtagttaaag ttccaaatga    83700
taaaggacaa acctgaaaag ctgtaaagct cttcaatgac cgtgtaggat atcctttatc    83760
taagacagta tattaccaat ctgcgaacac aacatacgtt ctaggatacg acaagatttt    83820
ctatggccgc aaatctactg atgttagatg gtcagccgat gatgtcagat ttagttctca    83880
ggatataaca tttgctaaac ttggcgacca attacatcta ggatttgatg tagaaatttt    83940
tgccacttac gcgactttac cagcgaatgt ataccgcatt gcagaagcta ttacttgcac    84000
cgatgattac atttacgttg tcgccagaga caaagttaga tacataaaaa cgagtaatgc    84060
acttatagat tttgatccat tatctccaac atattcggaa agactttttg aacctgatac    84120
catgactata accggaaatc ctaaagcagt atgctataaa atggattcta tctgtgataa    84180
agtttttgct cttattattg gtgaagttga aacattaaat gctaatccta gaacatcaaa    84240
aataattgat tccgctgata aaggaatata tgtttaaat catgacgaaa aaacatggaa    84300
aagagttttt ggtaataccg aagaagaaag aagacgtatt caacccggat atgcgaatat    84360
gtcaactgac ggtaaattag tttctctgtc ttcgagtaat tttaaatttt taagtgataa    84420
tgttgttaat gaccctgaaa ctgcagcaaa atatcagtta attggcgctg ttaaatatga    84480
atttcctcgt gaatggttag ctgataagca ttatcatatg atggcattta tagcggatga    84540
aacatctgat tgggagactt ttactcctca accaatgaaa tactacgcag aaccattctt    84600
taactggtct aaaaaatcta acacacgttg ttggataaac aactctgata gagctgtggt    84660
agtttatgct gatttaaaat acactaaagt tatagaaaat attccggaaa catcaccaga    84720
tagattagtt catgaatact gggatgatgg tgattgcact atagtaatgc caaatgtcaa    84780
attcactgga tttaaaaaat acgcatcagg aatgcttttc tataaagcct ccggtgaaat    84840
aatttcttac tatgatttta actatcgtgt gagagataca gtagaaatta tttggaagcc    84900
aactgaagta tttttaaaag cattttttaca aaaccaagag ctgagactc cttggtcacc    84960
agaagaagag cgtggattag ctgaccctga tttaagacca ttaattggca caatgatgcc    85020
tgattcttat ttgttacagg attcgaattt tgaggcattt tgcgaagcat atattcagta    85080
tctttctgat ggatatggaa ctcaatacaa taatttacga aatttaattc gtaaccaata    85140
tccacgagaa gagcacgcat gggaatattt gtggtcagag atatataaaa gaaacattta    85200
tttaaatgct gataaacgcg atgctgttgc gagattcttt gaatcacgta gctatgattt    85260
ttattctact aaaggaattg aagcatcata caagtttctt tttaaagttc tttataatga    85320
agaagttgaa attgaaattg aatctggggc tggtactgaa tatgatataa tcgttcaatc    85380
tgattctttg actgaagatt tagtaggaca aacgatttat acggcaacag gaagatgtaa    85440
tgttacttat atagaaagaa gctattctaa tggtaaattg caatggaccg taactattca    85500
taatcttttg ggacgattaa ttgctggtca agaagttaaa gcagaaagac tccctagttt    85560
tgaaggcgaa attattcgtg gggttaaagg aaaggatttg cttcaaaaca atatagacta    85620
tattaataga atagatcat actatgtaat gaaaattaaa tccaatttac cttcttcccg    85680
ctggaaatct gacgttattc gttttgttca tccagtagga tttggattta tagcaattac    85740
cctttttaaca atgtttatta atgttggttt aactcttaaa catcagaga ctataattaa    85800
taaatacaaa aactataaat gggattctgg attgcctact gaatatgccg acagaatagc    85860
taaattaact ccaaccggtg aaattgagca tgattcagta acaggcgaag caatttatga    85920
gcctggccca atggctggtg taaaatatcc tcttcctgat gactataatg ctgaaaataa    85980
taattcaata tttcaaggtc aattgccgtc tgaacgacgt aaattaatga gtcctttatt    86040
tgatgcatct ggaacaacat ttgcgcaatt tagagattta gttaataaac gtctaaaaga    86100
taatataggg aatccaagag accctgaaaa tccaacacag gttaaaatag atgaatgatt    86160
caagtgttat ctatcgtgcg atagttactt caaaattga aacagaaaaa atgttgaatt    86220
tttataattc aattggaagt ggtccggata aaaacactat cttatcaca tttgggaagat    86280
cagaaccgtg gtcatcaaat gaaaatgagg tgggctttgc cccaccttat ccaaccgatt    86340
ctgtattagg cgtaactgac atgtggacgc atatgatggg aacagtaaaa gttcttccat    86400
caatgcttga tgctgttatt cctcgcagag attggggaga tactagatat ccggatccat    86460
acacatttag aattaacgat attgtagtgt gtaactcagc tccttacaac gctactgaat    86520
caggcgctgg ttggttagtg tatcgttgtt tagatgttcc tgataccgga atgtgttcaa    86580
tagcatcttt aactgataaa gatgaatgcc ttaagttagg tggaaaatgg actccttctg    86640
ctaggtcaat gactccgcct gaaggtcgag gagatgctga aggaacaatt gaacccggag    86700
acgggtatgt gtgggaatat ctatttgaga ttccgcctga tgtatctata aatagatgca    86760
cgaatgaata tatcgtggtt ccttggcctg aggaattaaa agaagacccg actagatggg    86820
gatatgaaga taatctcact tggcaacaag atgatttgg attaatttac cgtgttaagg    86880
```

-continued

```
caaatactat ccgtttaaa gcatatttag attcagttta ttttcctgaa gctgcattac   86940
caggaaataa aggattaga caaatatcaa taatcacgaa tcctcttgaa gctaaagctc   87000
atccaaatga cccaaacgtt aaagctgaaa aggattatta tgacccagaa gatttaatga   87060
ggcattcggg tgaaatgatt tatatggaaa ataggccacc tattattatg gcaatggatc   87120
aaacagaaga aatcaatatt ctgtttacat tttaaattaa gggagcccat gggctccctt   87180
tttcttata aatactataa actcataagg aaaccgctat gttcattcaa gaaccaaaga   87240
aattgattga taccggcgaa attggtaacg cttctactgg tgatatctta ttcgacggtg   87300
gtaataaaat taatagtgat tttaacgcaa tttataatgc gtttggcgat cagcgtaaaa   87360
tggcagtagc aaatggcact ggagcagatg gtcaaattat ccatgctact ggatattatc   87420
aaaaacactc tattacagag tacgcaactc cagtgaaagt tggcactaga catgatattg   87480
atacctctac tgtaggtgtt aaagttatca ttgaaagagg cgaactcggc gattgtgttg   87540
aattcattaa ctctaatgga tcaatatcag ttactaatcc tttgacaatt caagctattg   87600
attcaattaa aggtgtttca ggtaatttag tagtaactag cccatatagt aaagttactt   87660
tacgctgtat ttcatctgat aattctacgt cggtttggaa ttattctatt gaaagtatgt   87720
ttggacaaaa ggaatcacca gctgaaggta catggaatat ttctacatct ggatcagttg   87780
acattccatt atttcatcgt actgaataca atatggctaa attgctagtt acgtgccaat   87840
cggtagatgg aagaaaaatt aaaacagcag aaataaatat tcttgtggat actgttaatt   87900
cagaggtaat ttcttctgaa tatgctgtca tgcgagttgg gaatgaaacc gaagaagacg   87960
aaatcgctaa tattgcattt agtattaaag aaaattatgt aacggcgact ataagttctt   88020
caactgtcgg tatgagagca gcagttaaag ttatcgctac gcagaaaatc ggggtggctc   88080
aataatgaaa caaatatta atatcggtaa tgttgtagat gatggtaccg gtgactacct   88140
gcgtaaaggt ggtataaaaa taaatgaaaa ctttgatgag ctttattatg aactcggtga   88200
tggtgatgtt ccatattcag ccggtgcctg gaaaacttaa aatgcttcat caggacaaac   88260
attaacagca gaatggggaa aatcatacgc tattaataca tcttctggaa gagtgactat   88320
aaatcttcca aagggtacag ttaatgatta caacaaggta attagagcta gagacgtatt   88380
tgctacatgg aacgtcaacc cagttacact agtagctgct tccggcgata cgattaaaagg   88440
gtctgcagta ccagttgaaa ttaatgttcg attcagcgat ttagaactag tgtattgtgc   88500
cccaggacgt tgggaatatg tcaaaaataa acaaattgac aaaattacca gttcagacat   88560
tagtaatgta gctcgcaaag aattttttagt tgaagttcaa ggacaaacag actttttaga   88620
tgttttccgt ggaactagtt aaatgtaaa taacatcaga gtaaaacatc gtggtaacga   88680
attgtattac ggcgatgtgt ttagcgaaaa cagcgatttt ggctctccag gcgaaaatga   88740
aggagaactg gttcctcttg atggatttaa cattcgatta agacagcctt gtaatattgg   88800
tgacactgtt caaattgaaa catttatgga tggtgtatca cagtggagaa gttcatatac   88860
aagacgtcaa attagattgt tagattcaaa attaacgtca aaaacttctt tagaaggaag   88920
catttacgtt actgatttat caacaatgaa atcaattcca ttttctgctt ttggattaat   88980
tccaggagaa cctattaatc ctaactctct tgaggttcgt tttaacggga ttttacagga   89040
attggctggc acagttggaa tgccattatt tcattgtgtt ggtgccgatt cagacgatga   89100
agtagaatgc tctgttttag gtggaacttg ggaacaatct cataccgatt attcagttga   89160
aactgatgaa aacggcatac cagaaatttt acatttcgat acgtatttg agcatggtga   89220
cattatcaat atcacctggt ttaataatga tttgggtaca ttattaacaa aagatgagat   89280
tattgatgaa actgataatc tctatgtatc gcaaggacct ggagtagata tttctggtga   89340
tgtaaattta acagacttcg ataaaattgg ttggccaaat gtagaagcag ttcaatctta   89400
tcaacgcgca tttaatgctg tttcaaatat ctttgatacg atttatccta ttggaactat   89460
atatgaaaac gctgttaatc caaataaccc tgttacatat atgggattcg gctcatggaa   89520
attatttggg caaggaaaag ttttagttgg atggaatgaa gatatttcgg accctaactt   89580
tgctctaaat aacaacgatt tagattcggg tggaaatcct tcacataccg caggtggaac   89640
aggtggttct acttctgtta cattggaaaa tgctaatctc cctgcaactg aaacagatga   89700
agaagttcta atagttgatg aaaatgatc agtcattgtt ggtgggtgtc aatacgatcc   89760
agatgaatcc ggtccaattt acactaaata ccgtgaagct aaagcatcta ctaactctac   89820
tcacactccg ccaacatcaa taactaacat tcaaccatat attacagttt atcgttggat   89880
aaggattgca taatgagttt acttaataat aaagcgtggg ttatttcccg cttagccgat   89940
tttcttggtt ttagacctaa aactggcgac attgatgtaa tgaatcgtca atcagtcggg   90000
tcagtgacaa tatctcaatt agcgaaagga ttttatgaac caaacataga atcagctatt   90060
aatgacgttc ataattttc tataaagac gttggcacaa ttattactaa taaaactggt   90120
gtttctcctg agggtgttc tcaaactgat tattgggcat tttctggaac tgtaacagac   90180
gattctcttc ctccgggttc tcctattacg gtattagtat ttggtcttcc agtttcagca   90240
acaactggaa tgacggcaat tgagtttgtt gcaaaagttc gcgttgcact acaagaagct   90300
attgcgtcat ttactgctat caattcatat aaagaccatc caactgatgg tagtaaatta   90360
gaagttactt atttagataa tcaaaaacat gtattaagca catattctac atatggaata   90420
actatttccc aagaaattat atctgagtct aagcctggct atggtacatg gaatttattg   90480
ggcgcacaaa ctgtaacttt agataatcag cagactccta cagtatttta tcattttgag   90540
agaacagcat gagtaataat acatatcaac acgtttctaa tgaatctcgt tatgtaaaat   90600
ttgatcctac cgatacgaat tttccaccgg agattactga tgttcacgct gctatagcag   90660
ccatttctcc tgctggagta aatggagttc ctgatgcatc gtcaacaaca aagggaattc   90720
tatttattcc cactgaacag gaagttatag atggaactaa taataccaaa gcagttacac   90780
cagcaacgtt ggcaacaaga ttatcttatc caaatgcaac tgaaactgtt tacggattaa   90840
caagatattc aaccaatgat gaagccattg ccggagttaa taatgaatct tctataactc   90900
cagctaaatt tactgtcgcc cttaataatg cgtttgaaac gcgagtttca actgaatcct   90960
caaatggtgt tattaaaatt tcatctctac cgcaagcatt agctggtgca gatgatacta   91020
ctgcaatgac tccattaaaa acacagcagt tagctattaa attaattgcg caaattgctc   91080
cttctgaaac cacagctacc gaatcggacc aaggtgttgt tcaattagca acagtagcgc   91140
aggttcgtca gggaacttta agagaaggct atgcaatttc tccttatacg tttatgaatt   91200
catcttctac tgaagaatat aaaggcgtaa ttaaattagg aacacaatca gaagttaact   91260
cgaataatgc ttctgttgcg gttactgcg caactcttaa tggtcgtggt tctacgacgt   91320
caatgagagg cgtagttaaa ttaactacaa ccgccggttc acagagtgga ggcgatgctt   91380
catcagcctt agcttggaat gctgacgtta ccagcaaaag aggtggtcaa attatctatg   91440
gaacactccg cattgaagac acatttacaa tagctaatgg tggagcaaat attacgggta   91500
ccgtcagaat gactggcggt tatattcaag gtaaccgcat cgtaacacaa aatgaaattg   91560
atagaactat tcctgtcgga gctattatga tgtgggccgc tgatagtctt cctagtgatg   91620
```

```
cttggcgctt ctgccatggt ggaactgttt cagcgtcaga ttgtccatta tatgcttcta   91680
gaattggaac aagatatggc ggaaacccat caaatcctgg attgcctgac atgcgtggtc   91740
tttttgttcg tggttctggt cgtggttctc acttaacaaa tccaaatgtt aatggtaatg   91800
accaatttgg taaacctaga ttaggtgtag gttgtaccgg tggatatgtt ggtgaagtac   91860
agatacaaca gatgtcttat cataaacatg ctggtggatt tggtgagcat gatgatctgg   91920
gggcattcgg taatacccgt agatcaaatt ttgttggtac acgtaaagga cttgactggg   91980
ataaccgttc atacttcacc aatgacggat atgaaattga cccagaatca caacgaaatt   92040
ccaaatatac attaaatcgt cctgaattaa ttggaaatga aacacgtcca tggaacattt   92100
cttttaaacta cataattaag gtaaaagaat gacagatatt gtactgaatg acttaccatt   92160
cgttgacggc cctcctgcag agggccagag ccgcatttcc tggattaaaa acggcgaaga   92220
aatattagga gctgacacac agtatggaag tgaaggctca atgaatagac ctacggtttc   92280
tgtactaaga aatgttgaag ttcttgataa aaacattgga atacttaaaa catctttaga   92340
aaccgcaaat agtgatatta aaacaattca gggcatctta gatgtatctg gtgatattga   92400
agctttggcc caaataggta tcaataaaaa ggatattttct gacctcaaaa cgctaaccag   92460
tgaacacaca gaaatattaa atggaactaa taatacggtt gacagtattc ttgccgatat   92520
tggtccattt aacgccgagg ccaactctgt atacagaacg atcagaaatg atttactgtg   92580
gataaagcgt gaacttggac aatacactgg tcaagatatt aatggtcttc ctgttgtagg   92640
aaatcctagt agtggaatga agcatcgcat tattaataat actgatgtca tcacttcgca   92700
gggaatacgt ttaagcgaat tagaaacaaa atttattgaa tctgatgtag gttctttgac   92760
cattgaagtt ggtaatcttc gtgaagagct tggaccgaaa ccaccatcat tttcacagaa   92820
cgtttatagt cgtttaaatg aaattgacac taaacagaca acagttgagt ctgacattag   92880
tgctattaag acctcaatag gatatccagg aaataattcg attatcacga gtgttaatac   92940
aaacactgat aatattgcat ctattaattt agagctaaat caaagtggag gtattaaaca   93000
gcgtttaacc gttattgaaa cttccattgg ttcagatgat attccttcga gtattaaagg   93060
tcaaatcaaa gataatacaa cttcaatcga atctctaaat ggaatcgtcg gtgaaaacac   93120
ttcatctggc ttaagagcga atgtttcatg gttaaaccaa atgttgaga ctgattctag   93180
cggtggacaa ccttctcctc ctgggtctct tttaaaccga gttttctacaa ttgaaacttc   93240
tgtttcaggc ttgaataacg ctgttcaaaa cctacaagta gagattggta ataacagcgc   93300
aggaattaaa gggcaagttg tagcgttaaa tactttagta aatggaacta atccaaacgg   93360
ttcaactgtt gaagagcgcg gattaaccaa ttcaataaaa gctaacgaaa ctaacattgc   93420
atcagttaca caagaagtga atacagctaa aggcaatata tcttctttac aaggtgatgt   93480
tcaagctctc caagaagccg gttatattcc tgaagctcca agagatgggc aagcttacgt   93540
tcgtaaagat ggcgaatggg tattcctttc taccttttta tcaccagcat aacatggggc   93600
cgcaaggccc caaaggattt taaatgtcag gatataatcc tcagaatcca aaggaactca   93660
aagatgtcat tctaagacgt ttagggggctc caattattaa tgttgagtta acacccgatc   93720
aaatttacga ttgtatccag cgtgccctag aattatacgg tgaataccat tttgatggac   93780
tcaataaagg ttttcatgtt ttttatgtag gggatgatga agaaaggtac aagaccggag   93840
tcttcgattt aagaggttct aacgtatttg cagtaaccg cattttacgc acaaatattg   93900
ggtcaataac atctatggat ggaaacgcta catatccgtg gtttactgtca tttcttttag   93960
gaatggctgg tattaatggc ggaatgggaa cgtcttgtaa tagattttat ggaccaaatg   94020
cctttggagc tgatttagga tattttaccc agcttaccag ttatatggga atgatgcaag   94080
atatgctctc tcctattcca gacttttggt ttaattcagc aaatgaacag ctcaaagtca   94140
tgggaaactt ccaaaaatat gatttaatta tcgtagaaag ctggactaaa tcatacattg   94200
atacaaacaa aatggttgga aatacagtag gatatggaac agtcggtcca caagatagct   94260
ggtcattatc tgaacgatat aataacccag accacaattt agtaggtcgt gttgtcggcc   94320
aagatccgaa tgttaaacag ggtgcttata ataatcgttg ggtgaaagac tatgcaacag   94380
ctttagctaa agaattgaac ggtcaaattt tagcacgcca ccaaggtatg atgcttccgg   94440
gcggtgttac aattgatggg cagcgcttaa tagaagaagc cagattagaa aaagaagcac   94500
tgcgcgaaga attatactta cttgatcctc catttggaat tttggtaggt taatatggct   94560
acttatgata aaaatctttt tgctaaattg gaaaaccgca caggttattc tcagaccaat   94620
gaaactgaaa tattaaatcc ttatgtaaat ttcaatcatt ataaaaacag ccaaatatta   94680
gctgatgtat tagtagctga aagcattcaa atgcgaggtg tagaatgcta ttatgttcca   94740
agagagtatg tttcccctga tttgatattc ggcgaagact taaaaaataa atttactaaa   94800
gcttggaaat ttgctgcata tttaaattca tttgaaggat atgaaggagc taaatcgttc   94860
tttagtaact ttggtatgca agtacaagac gaagtgactt tatctattaa cccaaattta   94920
tttaagcatc aagttaacgg aaaagaaccc aaggaaggtg attttgatata ttttcctatg   94980
gataacagct tatttgaaat taactgggtt gaaccatatg atccattta tcaattaggc   95040
caaaacgcta ttcgtaaaat tacggcaggt aaattcattt attctggaga agaaattaat   95100
ccagttctac agaaaaatga aggaattaac atttcagaat ttagtgaatt agaattaaat   95160
gctgttcgca atcttaacgg tattcatgac attaatattg atcagtatgc tgaagtagat   95220
caaattaatt ctgaagctaa agaatacgtt gaaccttatg ttgttgtcaa taacagaggc   95280
aaatctttcg aatctagccc atttgacaat gatttcatgg attaataaat attataaact   95340
aattaaagcc cggattagga gaagtcatgt ttggttattt ttataattcg tcttttagac   95400
gatatgctac cttgatggc gatttgtttt caaatatcca aatcaaacgt cagttagaat   95460
ctggtgataa gttatacgt gttcctatta cgtatgcatc aaaggaacac tttatgatga   95520
aattgaataa atggacatca ataaattcac aagaagatgt agctaaagtt gaaactattc   95580
tacctcgtat aaatttacat ttagttgatt ttagctataa tgctccattt aaaacaaaca   95640
ttttaaatca gaatttactg caaaaaggtg caacttctctg agtatcgcag tataatccat   95700
ctcctattaa aatgatttat gaattgagta tctttactcg ctatgaagat gatatgtttc   95760
aaatagttga acagattctt ccatattttc aacctcattt taatacaact atgtacgagc   95820
agtttggaaa tgatattcca tttaaaaggg atattaaaat tgtactgatg tctgctgcta   95880
tagacgaagc tatagatggg gataatttat ctcgtcgtag aattgaatgg tcattaacat   95940
ttgaagtaaa tggatggatg tatcctccag tagatgatgc agaaggatta attcgtacta   96000
cttatacaga ttttcacgcc aatacaagag atttgcctag aggt gttttgaat   96060
ctgtcgatag cgaagttgtt cctcgagata ttgacccaga agactgggat ggaacagtaa   96120
aacaaacttt cactagtaat gtaaatagac caacaccgcc agaacctcct ggcccaagaa   96180
catagaggtt attatggaag gtcttgatat aaacaaactt ttagatattt ctgacctccc   96240
cggaattgac ggggaggaaa tcaaagtgta tgaacctctg caattagtag aagttaaaag   96300
caatccacaa aaccgtactc cagacttaga agatgattat ggagtagttc gtcgaaatat   96360
```

```
gcattttcag caacaaatgc taatggacgc tgccaagatt tttcttgaga cagcaaagaa  96420
tgctgattct cctcgtcaca tggaagtatt tgcaactctt atggggcaaa tgactacgac  96480
gaacagagaa atactgaagc ttcataaaga tatgaaagac attacatctg agcaggttgg  96540
caccaaaggc gctgttccta caggtcaatt gaatattcag aatgcgacag tattcatggg  96600
ttcaccaaca gaattaatgg acgaaattgg tgatgcttac gaggctcaag aagctcgtga  96660
gaaggtgata aatggaacaa ccgattaatg tattaaatga tttccatccg ttaaatgaag  96720
ctggaaaaat tttaataaaa cacccaagct tagcggaaag aaaagatgaa gatgaaattc  96780
attggataaa atctcagtgg gatggaaaat ggtatcctga aaaattcagt gattaccttc  96840
gtctacacaa aatagtaaaa attccaaaca actctgataa gcctgaatta tttcaaactt  96900
ataaagataa gaataataaa agatctcggt atatgggtct tcctaacttg aaacgagcta  96960
atattaaaac acaatggact cgtgaaatgg ttgaggaatg gaaaaaatgc cgagatgata  97020
ttgtttattt tgcagaaaca tactgtgcca ttactcatat tgactatggt gtcataaagg  97080
ttcaattacg tgactatcag cgtgatatgc tcaaaataat gtcatctaaa cgtatgactg  97140
tttgtaatct atcgcgccag ctcggtaaaa ccaccgtagt agctattttc cttgcacact  97200
ttgtatgttt taacaaagat aaagctgtag gtattcttgc acacaaaggc tcaatgtctg  97260
cggaagtttt agaccgtact aagcaagcaa ttgaactgct tcctgacttt ttacaaccag  97320
gaattgttga atggaataag ggttcaattg aactagataa tggttcttca attggcgctt  97380
atgcttcctc tcctgacgca gttcgtggta actcgttcgc aatgatttac attgacgaat  97440
gtgcgtttat tccaaacttc catgattcct ggcttgctat tcaaccagta atttcatctg  97500
gtcgtcgttc gaaaattatt attactacga ctcctaatgg attaaatcat ttttatgata  97560
tttgactgc tgctgtcgaa ggtaaatctg gatttgaacc atatactgct atttggaatt  97620
cagttaaaga acgtctttat aacgatgaag atatttttag gcatggatgg caatggagca  97680
tacaaaccat taatggttct tcattagctc aattccgtca agaacatact gcagcgtttg  97740
aagggacttc tggtacatta atttcaggaa tgaaattagc tgttatggat tttattgaag  97800
taacaccaga tgatcatggt tttcaccaat ttaaaaaacc tgaaccagat agaaaatata  97860
ttgcaactct agattgctca gaaggtcgtg ggcaagatta ccacgctttg catattattg  97920
atgttactga tgatgtgtgg gaacaggttg gtgttttgca ttcaaacact atttctcatt  97980
taattctacc tgacatcgtt atgcgttatt tagtagaata caatgaatgc ccagtttata  98040
ttgaattaaa tagtactggt gtgtcagttg caaaatcgct ttatatggat ttagaatacg  98100
aaggtgttat ctgcgattca tatactgatt taggaatgaa acaaactaaa cgcacgaaag  98160
cagtaggatg ttccacgcta aaagaccttta ttgaaaaaga taagcttatt attcatcacc  98220
gagcgactat tcaagaattt agaacgtttta gtgaaaaagg cgtgtcttgg gcggctgaag  98280
aaggttatca tgacgattta gtaatgtctt tagtgatttt tggatggtta tcaacgcagt  98340
caaaatttat tgattatgcg gataaagatg acatgcgatt gacatctgaa gtattttcaa  98400
aagagcttca ggatatgagc gacgactacg cgccagttat atttgtggat tcggttcatt  98460
ctgctgagta tgttccagta tctcatggta tgtcaatggt ataaatatat taaagcatat  98520
taaagaggat taaaaatgac tttattatct ccgggcattg agctcaaaga aactacggtt  98580
caaagcaccg tagttaataa ctctactggt acagcagctt tggccggtaa attccagtgg  98640
ggtcctgctt ttcagattaa acaggttaca aatgaagtag atttagttaa tactttttggt  98700
caaccaaccg ctgaaactgc tgactatttt atgtctgcga tgaatttctt gcagtacgga  98760
aatgacttac gagtagttcg tgctgttgat agagataccc taaaaactc atcgccaatt  98820
gctggtaata ttgattacac aatttctacc ccaggtagta actatgcggt tggagataaa  98880
atcacggtca aatatgtttc agatgatatt gaaactgatg gtaaaattac tgaagtagac  98940
gcagatggaa aaattaagaa aattaatatt cctactggca aaaattacgc taaagcgaaa  99000
gaagtcggtg aatatccaac actaggttct aactggactg cggaaatttc ttcatcttcc  99060
tctggtttag ctgcagtaat aactcttgga aaaattatta ctgattctgg tatttttatta  99120
gctgaaattg aaaatgctga agctgctatg acagcggttg actttcaagc aaatctttaaa  99180
aaatatggaa ttccaggagt agtagcgctt tatccaggcg aattaggcga taaaattgaa  99240
attgaaatcg tatctaaagc tgactatgca aaaggagctt ctgcattact cccaatttat  99300
ccaggtggtg gtactcgtgc atctactgct aaagcagtgt ttggatatgg accgcaaact  99360
gattcacagt acgctattat agttcgtcgt aatgatgctg ttgttcaaag cgttgttctt  99420
tcaactaagc gtggtgaaaa agatatttac gatagtaaca tctatatcga tgacttttttc  99480
gcaaaaggtg gttcagaata tatttttgca actcacaaa actggccaga aggcttctct  99540
ggaattttaa ctctgtctgg tggattatca tcaaatgctg aagtaacagc aggagattttg  99600
atggaagctt gggacttctt tgctgaccgt gaatctgtca acgttcaact gtttattgca  99660
ggttcttgtg ccggtgaatc tttagaaaca gcatctactg tccaaaaaca cgtcgtttca  99720
attggggatg ctcgccaaga ttgcttagta ttgtgctctc ctccgcgtga aactgtagtt  99780
ggaattcctg taacccgtgc tgttgataac ctagtcaatt ggagaactgc ggcaggttca  99840
tacactgata ataactttaa tatcagttca acctatgcag caattgatgg ttaaccataag  99900
tatcagtatg acaaatataa ttgatgtgaat cgttgggttc cattagcagc tgatattgct  99960
ggtttatgcg caagaactga taacgtatct cagacttgga tgtctccagc tggttataat  100020
cgtggtcaga ttcttaacgt tattaaactt gctattgaaa ctcgccaggc tcagcgcgac  100080
cgtttatacc aagaagctat caacccgta accggtacag tggtgatgg ttacgttattg  100140
tatggtgata aacagctac ttctgttcct tctccatttg atcgtattaa cgttcgtcgt  100200
ctgtttaata tgttgaaaac gaatatcgga cgtagttcaa aatatcgttt gttcgaatta  100260
aacaacgcgt ttactcgttc atcattccgc acagaaactg cccagtactt acaagggaat  100320
aaagctctcg gtgaattta tgaatatcgt gtagtttgcg atacaacaaa taacactccg  100380
tcagtaattg atagaaatga gtttgttgca acattctaca tccaaccggc tagaagcatt  100440
aactacatta ccttaaactt cgtagcaact gctactggtg cagatttcga tgagttaact  100500
ggtcttgctg gttaatacgg tgcattctaa aggcctgttt cggcaggcca tataaataca  100560
ctatatcctt aattctttaa ttctatatgc cctaggttaa acatagggat ataaatacta  100620
cagaggctaa tatgtttgta gatgatgtaa cacgagcgtt tgaatctggt gattttgctc  100680
gacctaactt attccaagta gaaatttctt atcttggaca aaattttacg ttccaatgta  100740
aagctactgc tctaccagct gcgtattgtag aaaaaattcc agtcggattt atgaaccgta  100800
aaattaacgt agcaggcgat cgtacattcg atgactggac tgttacagta atgaacgatg  100860
aagctcatga tgctcgtcag aagttcgttg attggcaaag cattgctgcg gggcaaggaa  100920
acgaaattac tggtggaaaa cctgcagagt ataaaaagag cgctatcgtt cgtcaatatg  100980
ctcgtgacgc taaaacagta acaaaagaaa ttgaaattaa aggtctgtgg cctactaacg  101040
tgggtgaact tcaattagat tgggattcaa acaatgaaat ccaaactttt gaagtaactc  101100
```

```
ttgctctcga ttattgggaa taaaatgaat ggggagaaat ccccatcctg cttaaagcag   101160
agaagtccat tataaatata actataattc ccatttggag aatacaatga aatttaatgt   101220
attaagtttg tttgctccat gggctaaaat ggacgaacga aatttaaag accaagaaaa    101280
agaagatctt gtttccatta cagccccaaa gcttgatgat ggagcaagag aatttgaagt   101340
aagctcgaat gaagctgctt ctccttataa tgctgcattc caaacaattt ttggttcata   101400
tgaaccagga atgaaaacta ctcgtgagct tattgataca tatcgtaatc tcatgaataa   101460
ctatgaagta gataatgcag tttcagaaat cgtttcagat gctatcgtct atgaagatga   101520
tactgaagtc gtagcgttaa atttggataa atctaaattt agcccaaaaa ttaaaaatat   101580
gatgttagat gaatttagtg atgtattaaa tcatctatcg tttcaacgaa aaggttctga   101640
tcattttaga cgttggtatg ttgattcaag aattttcttt cataaaatca ttgatccaaa   101700
acgtccaaaa gaaggcataa aagaattacg tagattagac cctcgccaag ttcagtatgt   101760
tcgtgaaatt ataacagaaa ctgaagctgg cacaaaaata gttaaaggtt acaaagaata   101820
ttttatatat gatactgccc atgagtgcata tgcatgtgat ggtagaatgt atgaagctgg   101880
cacaaaaata aaaattccta aagctgccgt cgtttatgcc cattctggat tagtcgattg   101940
ttgcggtaaa aatatcatcg ggtatttgca tcgtgctgtt aaacctgcta accaattaaa   102000
attattagaa gatgctgtag tcatttatcg cattactcgt gctcctgacc gtcgtgtttg   102060
gtatgtagac acaggtaata tgcctgctcg taaagctgct gagcacatgc aacatgttat   102120
gaacacgatg aaaaaccgtg tagtatatga tgcatcaaca ggtaaaataa aaaatcaaca   102180
gcataatatg tctatgaccg aagactattg gttgcagcgc cgtgatggta aagctgtgac   102240
agaagttgat actcttcctg gtgctgataa tactggcaat atggaagata ttcgttggtt   102300
tagacaagct ctttatatgg cattacgtgt tcctctttca cgcattccgc aagaccaaca   102360
aggcggtgtg atgtttgatt ctggaactag cattacacgt gatgaattaa cgtttgctaa   102420
atttattcgt gagttacagc acaagtttga agaagtttc ctagatccgc ttaaaacaaa    102480
tcttttgctt aaaggtataa tcacagaaga tgagtggaat gatgaaataa ataatattaa   102540
gatagaattt catcgggata gctactttgc tgagctcaaa aagcagaaa ttttggaacg    102600
aagaattaat atgctaacca tggcagaacc atttattggt aaatatattt ctcacagaac   102660
tgctatgaaa gacattttgc agatgactga tgaagaaata gaacaagaag ccaagcaaat   102720
tgaagaagag tctaaagagg ctcgtttcca agacccgac caagaacaag aggatttta    102780
atggaaggtt taattgaagc tattaaatca aacgacctcg tagccgctcg taaattattt   102840
gctgaagcca tggctgcaag aacgattgat ttaattaaag aagaaaaat cgctatcgct    102900
cgcaatttct taatcgaagg tgaagaacct gaagacgagg atgaagatga agatgacgaa   102960
gatagtgatg ataaagacga caaaaaagac gaagactctg acgaagacga ggatgatgaa   103020
taatgcttct gatccctgaa actcatgaat tagttctcga gaatgtcgaa gcacttattc   103080
ctgaagcaca gggtcgcttt gacgaattgt cttctgcttt aaataaagac gatataaata   103140
caattgtcga gaatatgctt gatgatgaaa ctgatttagc ggttgcatta gcttctatta   103200
atgaaaatat gccgttaaat gaattcatcg ttaaacatgt ttctgcccgt ggtgaaatta   103260
ctcgcactaa agaccgcaaa acgcgtgaac gaaatgcatt tcaaaccact gggctgtcta   103320
aagcaaaacg tagacaaatt gctcgtaaag ctaccaaaac gaagattgcc aatccagcag   103380
gtcaatctcg tgctcagcgt aagcgtaaaa aagctcttaa acgccgtaaa gcattaggat   103440
taagctaatg aatgaacccc aattactaat tgaaacttgg ggtcaacctg gcgaaattat   103500
tgatggcgta ccaatgcttg aatctcatga tggaaaagac ttaggtttaa aaccgggttt   103560
atacatcgaa ggaatattca tgcaagcgga agtcgtcaat agaaataaac gtctttatcc   103620
aaaacgtata ttagaaaaag cggtaaaaga ctatattaat gacgaagtttt taactaaaca   103680
agctctcgga gaattaaatc atcctccacg cgctaatgtt gacccgatgc aagccgctat   103740
cattatagaa gatatgtggt ggaaaggaaa tgacgtatac ggacgagctc gtgttattga   103800
aggtgaccat ggtcctggag ataaaattagc agctaatatt cgtgccggat ggattccagg   103860
agttcttct cgtggattag gttcattgac tgacacaaat gaaggttatc gtatcgtaaa    103920
cgaaggattc aaattaactg taggtgttga tgcagtatgg ggtccaagtg ctccagatgc   103980
atgggtaact cctaaggaaa ttaccgaatc acagacggcg gaagccgata caagtgccga   104040
tgacgcctat atggctctcg cagaggccat gaaaaagcg ttataaatat tattatctaa    104100
acaacaggac tacaaaatgc ttaaagaaca actgattgcc gaagcgcaga aaattgatgt   104160
ttccgttgct cttgatagta ttttcgaatc agttaatatt tctccggaag caaaagaaac   104220
tttcggcact gtattcgaag ctaccgtcaa gcagcacgcc gttaaattag ctgaatctca   104280
tatcgctaaa attgctgaaa aagcagaaga agaagtagaa aaaaataaag aagaagccga   104340
agaaaagct gagaagaaaa tcgctgagca agcttctaaa ttcattgacg aacttgcaaa    104400
agaatggctc gctgaaaata aattagcagt tgataaaggc atcaaagccg aactgtttga   104460
atccatgctt ggtggattaa aagagctctt tgttgaacac aacgttgttg ttccagaaga   104520
atcagttgat gttgtagctg aaatggaaga agagctgcaa gaacataaag aagaatcgcc   104580
tcgtctgttc gaagaactga atatgcgcga cgcatatatc aattatgtgc agcgtgaagt   104640
ggcattgagc gaaagtacta aagatctgac tgagtctcaa aaagaaaaag tctctgctct   104700
ggtcgaaggt atggattatt cagatgcatt ctcaagtaaa ttgagtgcaa tcgtagaaat   104760
ggtgaagaaa tctaataaag atgaaagcac tattactgag agtataaata ctcctgatac   104820
tgaagcagcc ggactgaatt tcgtcactga agctgtgaaa gataaagctg cacagggtgc   104880
agaagatatt gtaagtgtat gtcgcgaaagt cgcatctcgt ttctaatttt aaaggttaac   104940
acaaatgact atcaaaacta aagctgaact tttgaacgaa tggaagccat tactgaagg    105000
tgaaggttta ccggaaattg ctaatagcaa acaagcgatt atcgctaaaa tctttgaaaa   105060
ccaggaaaaa gatttccaga cagctccgga atataaagac gaaaaattg ctcaggcatt    105120
cggttcttc ttaacagaag ctgaaatcgg tggtgaccaa ggttacaatg ctaccaacat    105180
cgctgcaggt cagacttctg gcgcagtaac tcagattggc ccagtgctta gggtatggt    105240
acgtcgtgct attcctaacc tgattgcttt cgatatttgt ggtgttcagc cgatgaacag   105300
cccgactggc caggtattcg cactgcgcgc agtatatggt aaagacccag tggctgccgg   105360
tgctaaagaa gcattccacc caatgtatgg tccagatgca atgttctctg gtcagggtgc   105420
tgctaagaaa ttcccagctc tggctgctag cacacaaacc acagtaggtg atatctatac   105480
tcacttcttc caggaaactg gtactgtata tcgcaagct tctgttcaag taacaatcga    105540
tgctggtgcg actgatgctg ctaaattaga tgctgaattt aagaaacaaa tggaagctgg   105600
tgcactggta gaaatcgctg aaggtatggc tacttctatc gctgaactcc aggaaggttt   105660
caatggttct accgataacc catggaatga aatgggcttc cgtatcgata agcaagttat   105720
cgaagctaaa tctcgtcagc tgaaagctgc ttactctatt gaattagcac aagacctccg   105780
cgctgttcac ggtatggatg ctgatgctga actgtctggt attctggcta cagaaaattat  105840
```

```
gctggaaatc aaccgtgaag ttgttgattg gattaactac tcagctcagg ttggtaaatc  105900
tggtatgacc ctgactccgg gttctaaagc tggtgtattt gacttccagg acccaattga  105960
tattcgtggt gctcgctggg cgggtgaatc ctttaaagct ctgttgttcc agattgacaa  106020
agaagcagtt gaaattgctc gtcagaccgg tcgtggtgaa ggtaacttca ttatcgcttc  106080
ccgtaacgta gttaacgttt tggcttcagt tgataccgac atttcttatg ctgcacaggg  106140
tctggctacc ggctttagca ctgatactac caagtcagta tttgctggtg ttctgggtgg  106200
taaataccgc gtatatatcg accagtatgc taaacaggat tatttcactg taggttataa  106260
aggtccgaac gaaatggatg ctggtattta ctatgctcca tatgtagctc tgactccgct  106320
gcgtggttcc gatccgaaga acttccaacc ggtaatggga ttcaaaactc gttacggtat  106380
cggtatcaac ccatttgcag aatccgctgc tcaggctccg gcttctcgca tccagagcgg  106440
tatgccttct attctgaata gccttggtaa aaacgcttac tttagacgtg tatatgttaa  106500
aggtatctaa tctctaacga tagaaacaca attttaggga accttcgggt tcccttttt   106560
ctattttata cgatagcaat caggcatatc atccgcattt atccaattgc gaatagtttt  106620
aggactaact ttaaaatgct ccgctgcgta atcaggatta tcaaatttaa cgcccttat   106680
acatattgga ataaatttt taataccacc aagttttca gaaatagctt tacgatgtga  106740
aatcgatata ggtttgtttt ttcgtggatg aacatgtgtt ttataatatt cattgcgccc  106800
tttaactcgc ttcgcaatag tttcatcaga ttgcttaacg cctgttttg cctttgatat  106860
ttttcgttta gcttccacag tcattccttc ttttgttcgt attgataaca tattacgata  106920
tgaaggatct tgcaaatgaa ctataactgg atttcctctg ccaccaatag cagcattata  106980
ggtatcagtt ctcataacga attcctcatt aactagtaaa gcttccattt tatacatctc  107040
ctcagatgag gagaaagaat aaagaattc tttttaag ttatgaatac catatttttt  107100
gatggatttt ttgatgttta cgccagaacc catataacca tcgttttcgt caagagtagc  107160
atgagctccg atgtaaattt ttccattgat gatattagta atttgatata ttaaatattt  107220
cattttaaac atcactccgt ttgtatatga ttataatatc atattacttt ggtcttgtaa  107280
ataactttat aaatagtatt atatttcaac aaggaaaata caatggctaa aatcaacgaa  107340
cttctgcgcg aatcaaccac aacgaatagc aactcaatcg gtcgcccaaa tctcgttgct  107400
ttgactcgcg ctaccactaa attaatatat tctgacattg tagcaacgca aagaactaat  107460
caacctgttg ctgcttttta tggtatcaaa taccttaacc cagacaacga atttacattt  107520
aaaactggtg ctacttacgc tggcgaagct ggatatgtag accgagaaca aatcacgaaa  107580
ttaacagaag agtctaaatt aactctcaat aaaggcgatt tattcaaata taataatatc  107640
gtttataaag tattagaaga tactccattt gctactatcg aagaaagtga tttagaatta  107700
gctcttcaga ttgcaatcgt tcttttaaag gttcgtctat tttctgacgc agcgtcaaca  107760
agcaaatttg aaagctctga tagtgaaatt gcggatgcta gattccagat taataaatgg  107820
caaactgcag ttaaatctcg taaacttaaa actggcatca cagttgaatt agcgcaagat  107880
ttagaagcaa atggattcga tgctcctaat ttcttggaag atttgcttgc aactgaaatg  107940
gcagatgaaa tcaataaaga cattctgcag tctttgatta cagtgtcaaa acgctataaa  108000
gttacaggaa ttactgatag tggattcatc gatttgagtt atgcatctgc tcctgaagct  108060
ggtcgttcat tataccgaat ggtatgtgaa atggtttcgc atatccaaaa agaatcaact  108120
tatacagcaa cgttctgtgt tgcttcagct cgtgccgctg cgattcttgc tgcatcaggc  108180
tggttaaaac ataaaccaga agatgacaaa tatctttcac aaaaatgccta cgggttctta  108240
gctaatggtt taccgcttta ttgcgatact aacagcccat tagattatgt aatcgttggc  108300
gtagtagaaa atatcggtga aaaagaaatt gttggatcaa ttttctatgc tccgtataca  108360
gaaggtctcg acttagatga ccctgaacat gtaggtgcat ttaaagttgt tgttgatcca  108420
gaaagcttac aaccatctat cggtttatta gttagatatg ctttatcagc aaatccttat  108480
actgtagcaa aagatgaaaa agaagcaaga ataattgacg gtggagacat ggataaaatg  108540
gcaggtcgtt cagatttgtc tgtttttatta ggtgttaagc taccaaaaat tatcattgat  108600
gaataaaaca aagggacctt tcggtcccctt tttatttaac ttaccaactc aatccaagct  108660
ggacgaagta catcttgtac cattttaact aattcctttt taatcaaaga aggattatct  108720
gcttgagtta gagtaatacc ttcacgagaa gtttcttcca aaatatcttg aacagttagc  108780
cccatcacct ttcaaaatc ctttggacca atttcgccaa ttttagaaat aacgttattt  108840
acgcggttca gtgtaacgta acaagctaaa attcccaaca atttgttatc agcttctgat  108900
agctcaactt tagctttaat aggcttatca gacttttttct tttcactaaa tttagagttc  108960
ttgcatttaa tcgctacacg atttccatta cgaagccaag aaggataaca aggtttcaat  109020
acatatcctt cagcagtaaa tacttcgcct tttgcttcgg cattccaaac gcatttattt  109080
gcatcaacta atccagcatg gtctactgta aaattataat cttggacgac agaatctaaa  109140
tcatttggca atttaataag ctcttcaaat ttaccgcgca ctaaaagtgg agccattta   109200
aatttaaatg tattacagaa tgattccatc atataatcat ctacataagt cacatcaccg  109260
cttttctgtag taacaataat gtcaaataca taaaaatctt tatcacaata atcaacattc  109320
ttctgaatgc caggtccagc gaattcgcca aagacttgat aagatacaac cgctgaggtt  109380
tccataatat cttgtacagc tttaatggaa tcagctaaat tcttcaaaat aatttcatac  109440
ccaaagaaat cttcagcagg aagaatcggt ccagtgcgtt tagcgcaagt cactttatca  109500
cgctcaataa tcaatgagaa atttgtgccg tgaatctttt cacgagctac ccactcccca  109560
ccagtcaatc ccaagctata aagtttttca ataaatttag agttgtaatg attttcaaga  109620
ctgctatact ttttaaacat aattaatcct caaaatgtaa tttctaacca atcaccatca  109680
cgctgatcac tattgacttt aaagctgaat ccttcttttc tcagccaatc accaatttct  109740
tctgtaatca atttatcacg agcaatacaa taataattaa aatgtgtttt accttgttca  109800
gctgcttat tagcaagttc tgaaaaatct ttaataaaac actctagctt aaactgttta  109860
cttttaatg cttttcgcg taattgatta gcaaaagatt cattttcata aagatcatac  109920
tgttccattt ttcaccttt tattgatatg tcttttttca tagacaactt tttctcgagc  109980
ccataataca gccacttctt ttgcctgtaa gttaattca cgagcaattt caatgaatga  110040
ctttccagac tcatgaagag taaacaccac aacctcagtt ctcataatca atctcatgtt  110100
atcgagttgg tgccattata tacatcattt tctgattgtg ttttgtgtgc tttcaaaatg  110160
aagaaagggg ccgaagcccc ttatgattat ggataggtat agatgatacc agtttctaaa  110220
gcagttttat gaatgatgta tccattacgc gattcttgga catcaactc tggatagtct  110280
ttcatcatct tctggagagt gtaacgatgc aggtaatatt tactatctgg gtcgtcagtt  110340
ttccaatctt taccttcttc ggtcattttt tggatttcat ccataaccca ccaaccgcac  110400
cagatgtaag ctgagctacg gtgtggaaga ggatgaacat aaggtaattc accttctggt  110460
tctggagcaa ctttagccgt gactgttaca ttaccagttt tggtaacggt tacagggtta  110520
taatctgcag cagtaacagt tgcagtaact tcaatagttt gacttccaac agatgaggta  110580
```

```
tcgacagtat atacgttagt tgacccttct acaggagaag aatctttctt ccatgagtaa  110640
gtaatttgtg cttcttctgg agcacccgta acattagccg taaatgtagc cgaagcatct  110700
tgctgaacat taatagaagg aggagtcaat gtaacctgtg gattcattgt cttcttatta  110760
accgttaatg atacttcatt agaagtaacg cttagtgcat cataatctgt cgcggttact  110820
tgggctacgc atttaattct tttactcca cttgtagttg gagtatagct aaatgtagag  110880
ttagtttctc caccaacttg tgaatcatct acataccact gatacgtagc agatgctcca  110940
tcaggttgag aagctaaggc agcagtaaat tgaactgggg ttccaatcac tccagccgca  111000
ggactagcag gagttacggc taaggtagtc gtctgtgtct tatttttaac tgtgatagtt  111060
gttgtcgctt cagccgtttc cgggcctcct tcagaaagtg tatttgttgc aactacttta  111120
atagtctttt gaccggcagg tccttttagt acataactaa aagttgcttc agctccatct  111180
tgtggaacat tatctacgct ccaagcatat gtaatagttc cgcctccagt ttgaccactg  111240
ggtgtagcag taaactgctt agtttcatca ataacccctg taggtgtttt aggagttata  111300
tcaactgtaa aagtcataag ttatccttat tttaatgtta cgaaagaaga gttgcgtgtt  111360
tcacgaatta aaactgatcc atcgcgatta atgtaataaa ttaagctaaa taaagtttgg  111420
tgtgctgacg catgttcaaa actagttggg tgagatttcc aatcaggagt ttcagcaatc  111480
cattgataaa tccaccaagg aacagtacag aatcctagat ttttttccaat cagttgaaga  111540
ttcggactaa agttttccgg aagagtaaat acagacggct tttcagattc aataatctca  111600
gctacagcct gttcgaattt ttcttcaaca aaaggagtat cttcaatcaa aacatcggta  111660
ttttcaggaa ttttatccgt ttctactact tcaattttaa tgtcagattt aatcggagaa  111720
tcaatcagaa gtgctgcttc tggattgact tcttcatcgt catattttaa tccctctgcg  111780
gcatcagcag catcaattaa gtctttaata gataacccat cagtctctgg cataggttca  111840
ctagcgaact tctggagggc ttcttcaata tcaacaacga tattatcaaa agatttattc  111900
ttttgacct ttataccaaa ctgttcagca tattcagcta atttagcttt agcttctttg  111960
ttatcatcaa gagccttcag ctctgcaata taatctttat ctatcataat atttcctcag  112020
tataaatata gatatattta ttactcggaa aatagtatgt accactttgt atatgaaaca  112080
acaaatctaa taaatggtaa aaagtatata ggaaagcaat ctactgatga cttgaatgat  112140
ggttaccttg gttccggtaa ggcaattcag caggctataa agaaatatgg tgaaaacaat  112200
ttctctagaa caatactaaa agagtttaaa acttccgaag aagcgtacat gtatgaagaa  112260
gaaattataa ctcctgaact aataaaaagc aaaaattatt ataatatgaa acctggtgga  112320
attggtggaa ttgttatgac tacagatgtt atagcaaaga tgaaagaatc ttccgctaaa  112380
agatttgaaa actcaccggg cacggtatta ggtaaaactt gttatactaa tggaactaaa  112440
aatattttta ttaaacctgg agaacttgtt ccagaaggat ttgtaaaagg gatgttcat  112500
cctaatagaa agtccagaaa aggatgtaaa gtcaaaccga ctaccacagg aacttttgg  112560
gtcaataatg gcgcaataaa taaattaata caaccagacg gtattattcc cgacggattt  112620
attaaaggtc gtctcatgaa aagagattcc aaaggcaaat ttagtaaggc ataattatgt  112680
atattaaagt acattttcac gacttcagtc atgtacgcat cgattgtgaa gagagcacgt  112740
tccacgaatt aagagatttc ttttcgtttg aggccgatgg atatagattt aatcctcgct  112800
tcagatatgg caactgggat ggacgaatcc gtcttttaga ttataatcgt cttcttccat  112860
tcggcttagt cgggcaaatt aaaaaattc gtgataattt tggctataaa gcctggattg  112920
acccacaaat taacgaaaaa gaagaattat caagaaaaga ttttgatgaa tggctttcta  112980
aattagaaat ctattcagga aataaagaa ttgaaccgca ctggtatcaa aaagatgcag  113040
tgttcgaagg attagttaat cgtcgtagaa ttcttaatct tccaacatct gcaggtaaat  113100
ctttaattca agctttgctt gcgcgatatt atttggaaata ttatgaaggt aaaaattctta  113160
tcattgttcc aacaactgct ctgacaactc agatggctga tgacttcgtc gactatcgtt  113220
tattcagcca tgcaatgata aagaaaattg gtggcggagc atcaaaagat gataaatata  113280
aaaatgatgc accagtcgtt gttggtacat ggcaaactgt agtaaaacaa ccgaaagaat  113340
ggttctcaca gtttggaatg atgatgaatg ataatgccta tcttgctaca ggaaaaagta  113400
tttcatctat catatcaggt ttaaataact gcatgttcaa attcggtttg tctggttcat  113460
tacgtgatgg caaagccaat atcatgcagt atgttggaat gtttggtgaa atatttaaac  113520
cagtaacgac ttctaaatta atggaagatg acaagtaac tgagctaaaa attaatagta  113580
ttttttcttcg ctatcccgat gagttcacta ctaaattaaa gggaaaaact taccaagaag  113640
aaataaaaat tattactggg cttagtaaaa gaaataaatg gatcgctaaa ttagctatta  113700
agcttgcgca aaaagatgaa aacgcttttg tcatgtttaa acatgtatcg catggtaaag  113760
ctattttcga tttaattaaa aatgaatacg ataaagttta ttacgtatca ggggaagttg  113820
ataccgaaac ccgcaatata atgaaaacct tagctgaaaa tggtaaagga ataattatag  113880
tagctagtta tggtgtattt tctactggta tttcagttaa aaatctgcat cacgttgttt  113940
tagcgcacgg tgttaaatca aaaatcattg tattacaaac aatcggtcgt gtattacgta  114000
agcatggttc taagacaata gcaacagtct gggacctcat agatagccgca ggcgtcaagc  114060
caaaatctgc taatacgaaa aagaaatatg ttcatttgaa ctatctttta aaacacgaca  114120
ttgatcgtat tcagcgctac gcagatgaaa aatttaatta cgtaatgaaa acagttaatt  114180
taataagctt cggccctttg gagaaaaaga tgttactaga atttaaacaa tttctttatg  114240
aagcttctat tgatgaattt atgggtaaaa ttgcctcttg tcaaacatta gaaggtttag  114300
aagaacttga agcttattat aagaaaagag tcaaagaaac tgaattaaaa gatactgatg  114360
acatctctgt gagagatgct ttggcaggaa aaagagctga attagaagat tcagacgatg  114420
aagtagaaga aagcttttaa attaaaaaag gcccaaccaa aaaggaaggg ccaaaactat  114480
agactaaagg tcacactata gcaaagttg tgtttcattt aattgttctt ccgaactttc  114540
tgaaactggt agttctttaa tgtaattata gcaaggccca ggatgtacag gaccttttgtc  114600
tgtttcaaca accaatgcag aatcgattgg agttttacag acaacacaa tcttatctga  114660
catgattgtc tcctctgaat tatatctatt tatacaactc tcatatgcat atcaatgccc  114720
atatctttag aataaaaata ttcatcaaga tatccggcaa attttccttt aatataaagg  114780
acatcttcac cacacgggtg gtcggccagg atacgaatat cctgacgctt aagattatgc  114840
tttttcatta agaattgaat ttccgtttca aattcttctt cataattaaa agcatcatca  114900
atgctatatc tcattatttt ccagcctcaa atgctcgcat gtcttgaata tgcttaatag  114960
caaatccacg tgatttaata gcatcaagag ctccgctaca gaaatctaat aaaatccccc  115020
aatactgcaa cgaggtatca acctttaaaa catccttatc cgctgataga actgtcttca  115080
tttctgattt ctcgtaacga tccatactaa attcatcacc atctcctcgt cccgagtagt  115140
agtctaatct agctttaaga gcaacttttt tctgtgcttc aattctaagc atttcctttt  115200
taatacttga atgcttatta agccatttac tatataacac cacattatta gctgcttcat  115260
actgtaattt agtcgaatct ataaacacat cttttcttcaa ttcttcttga agatcttcta  115320
```

```
atctcatatt gttctctatt caattgttat tggttgttat tggatggact tagattcatt    115380
ataccacgtt ttaacgtgaa gcattatact ctattactgg aagccagctg cagttttatc    115440
tgctcaatat catcaggatt atcgatgacc gaaaagcgta tttctactat cagagtataa    115500
tcgtcataaa cgggtatcac attaactgct aatttatcaa tacgtggctc atagtttctt    115560
actgcgcttt cgatattgcg ttcaaccgtg tcagcagtaa gaggagtcat attttcaaaa    115620
agctggtctg ataaatcaca tccaaattca gggtcaaacg gtcttgaacc ttttcttgtt    115680
gtaataattc ccaaaagact gttttaatt gaccttaatc caagcgatct ggaaacgtct     115740
ttgttccaat ccatttcat ttccgggtca atatcagaat aaagcttatt aatatttgcc     115800
attatagtaa ctcaaagaac tctttgaggc ctcttattac gtgagcatgg gtttttccac    115860
actctggaca cttaattgga acagccaaat aaacggtagg ctttaaaagc atatctttta    115920
tagctacaat atctgactct gtgatgatag aatataaatc ttctagttcc ttttcattta    115980
agtcttcaac tggaatgctt tccccgttag catgaatcgt ttctatacat gatactatca    116040
tgtgggctat attttatca tcaaaaattt tagggtatcg gaatttaatt ttaatgtcac     116100
ctagtgtata ccagaggtct tctggtgcat ctatttgtgt atgtaataga tttatatggg    116160
ttggtatttc agttccacag gtgcacttcc aggagttttc gtgattaact tcaccgagag    116220
aatgtgccca taaatgaatc aacaatagtt ctgattcttg gcggtttaaa tcttttgcat    116280
ttgtgcagtc tttgattagc ttttaacaa ttacttctac ggaaccatta tttttggcag     116340
taataagttc tagatattct ttaagcgtga atgcgcgaca attgattatt ttagaaccaa    116400
ctctcacatc aaatttgtat tcatacatat ttagctcctt tatttatcat atttataaat    116460
agaataaaag gagcatctat ggcaaacatt attcgttgta aattaccaga tggtgttcat    116520
cgttttaaac catttacggt agaagattat cgagattttt tgttagttcg aaacgatata    116580
gaacatcggt caccacaaga acaaaagcaa ataattactg atttaattga tgattatttt    116640
ggagactatc cgaagacttg gcaaccattt atatttttgc aggtatttgt agggtcaata    116700
ggtaaaacta aaagtacggt cacatttata tgtccaaaat gtaaaaaaga aaagacagtt    116760
ccatttgaaa tatatcaaaa agaattaaag gaccttgttt ttgatgtagc taatgttaaa    116820
attaaattaa agtttccttc tgagttttat gaaaataaag caaagatgat tactgaaaat    116880
attcattctg ttcaagtaga tgaaatatgg tatgattgga aggaaattag cgagtccagt    116940
caaatagaac tagttgacgc catcgagata gaaacattag aaaaaattct cgatgccaatg   117000
aatcctatta atttaactct acacatgtca tgctgtaata agtacattaa aaaatacact    117060
gatatagtag acgtgtttaa gctattagtt aacccagatg agatatttac tttttatcaa    117120
attaatcaca cactcgtaaa aagtaattat agcttaaatt caataagtaa aatgattcct    117180
gccgagcgcg gattcgtatt aaaactgatt gagaaggata aacaataatg agtatgttgc    117240
aacgccccgg atatccaaat ctcagcgtta aattatttga tagctacgac gcttggagta    117300
ataatagatt tgttgaatta gctgctacta ttaccacatt aactatgcgg gattctcttt    117360
atggccgaaa tgaaggaatg ctgcagttt atgattctaa aaacatccat acaaaaatgg     117420
atggaaatga aataattcag atttctgtag ctaatgcaaa tgatattaat aatgttaaaa    117480
cacgaattta tggatgtaag cattttccg tgtcagtaga ttcaaaaggt gataacatca     117540
ttgctattga attgggaact attccattcta tagaaaatct taaatttggt agaccattt     117600
tccctgatgc aggtgaatct ataaaagaaa tgcttggtgt catttatcag gatcgcacat    117660
tattaactcc agcaataaat gctataaatg cttatgttcc tgatattcca tggactagca    117720
catttgaaaa ctatttgtca tatgtaagag aagttgctct agctgtagga agcgacaaat    117780
ttgtatttgt atggcaagac atcatgggcg ttaacatgat ggactatgat atgatgataa    117840
atcaagaacc atatccaatg attgtcggtg agccatcttt aataggtcaa ttcatccaag    117900
aattaaaata tccattagca tatgatttcg tttggttgac taaatcgaat cctcacaaac    117960
gtgacccaat gaaaaacgct actatctatg cgcattcatt tttagattct tcaataccaa    118020
tgattactac aggaaagggt gaaaactcta ttgtggtgtc aaggtcaggt gcttattctg    118080
aaatgactta taggaatgga tatgaagaag ctattcgtct tcaaactatg gcacaatatg    118140
acggctatgc taaatgttct actatccgta atttttaactt gactcctggt gttaaaatta    118200
tttttaatga tagtaaaaac caatttaaaa cagaatttta cgttgatgaa gttatccatg    118260
aattatccaa taataattca gtaactcatc tatatatgtt cactaatgca acgaaactgg    118320
aaacaataga cccagttaag gttaaaaatg aatttaaatc tgatactacc actgaagaaa    118380
gtagttcttc caataagcaa taaagaagtt tctattccta aaatgggtct taaacattat    118440
aacatttaa aagatgttaa aggtcctgat gaaaatttaa aacttctcat tgattctatt     118500
tgtccgaatt tatcaccggc agaagttgat ttcgttctta ttcatttatt ggaatttaat    118560
ggaaagatta aatctgtaa agaaatagat ggttatactt atgacattaa tgatgtttat     118620
gtatgccaaa gattggaatt tcaataccaa ggaaatacat tttatttag acctcctgga     118680
aaatttgaac aatttttaac ggtgagcgat atgttatcta aatgcttact tagggtcaac    118740
gatgaagtta aagaaattaa ttttcttgag atgccagcat tcgtttaaa atgggcaaat     118800
gatatttta caactttagc aattcctggc cctaatggtc caataactgg aattggcaat    118860
attattggat tatttgaatg aaaaagccac aagaaatgca aacgatgcgt agaaaagtta    118920
tttcagataa taaccaaca caggaagcgg ctaaatccgc ttctaatact ttatctgggc    118980
ttaatgacat atctacgaaa ttggatgatg ctcaagctgc ttctgaatta atagctcaaa    119040
ctgtcgaaga aaaatcgaat gaaataattg gagcaattga caatgtagaa agcgcagtga    119100
gtgatacatc tgccggttct gagttaattg ctgaaactgc cgaaattgc aacaatatta     119160
ataaagaaat cggtgaatcg ctcggaagca aattagataa attaacaagt ttactagagc    119220
aaaaaatcca gacagtcgga attcaacaga ctggaactag tttagctacg gttgaaagcg    119280
ctattcctgt taaagtcgtt gaggatgata ctgctgaatc tgtgggtcct ttattaccag    119340
ctcctgaagc agttaataat gatcctgacg ctgattttt ccctaccct cagccagttg      119400
agccaaagca agaatcacca gaagaaaaac agaaaaaaga agcatttaac ttaaaattat    119460
ctcaagcttt agataaatta acgaagactg ttgatttgg atttaaaaaa tccatttcaa     119520
ttactgataa aatatcaagc atgctattta agtacaccgt cagtgctgct attgaagctg    119580
ctaaaatgac tgcaatgata ttggctgttg ttgttggaat agacctttg atgattcact     119640
ttaaatactg gtcagataaa ttttcaaaag cctgggattt gtttagtaca gactttacca    119700
aattctctag cgaaaccgca acttgggtc ctttattaca ggcatctttt gattctattg      119760
ataaaattaa acaactttgg gaagcgggag attggggtgg attgacagta gctattgttg    119820
aagggcttgg aaaggttctt tttaatttag gtgaacttat tcaattaggt atggctaaat    119880
tatctgcagc aattcttcga gtcattcctg gtatgaagga tactgctgat gaagtagaag    119940
gaagagcatt agaaaatttc caaaattcta ctggagcatc tctcaataaa gaagaccaag    120000
aaaaagtagc aaattatcaa gataaacgaa tgaatggaga ccttggccca atagcagaag    120060
```

```
gactagacaa aatctctaac tggaaaactc gtgcatctaa ctggattcgt ggtgtagata  120120
ataaagaagc gctgactacc gacgaagagc gtgcggcaga agaagaaaaa ttaaagcaac  120180
tttcaccgga agaagaaaaa aatgctttaa tgaaggctaa tgaagctcgt gctgcgatga  120240
ttcgttttga aaaatatgcc gattcagctg atatgagtaa agactcaacg gttaaatcag  120300
ttgaagctgc ctatgaagac cttaaaaaac ggatggatga cccggattta aataattcac  120360
cggcagttaa aaaagaactt gctgctagat tttctaaaat tgatgctact tatcaagagc  120420
tcaagaaaaa tcagcctaat gccaaacctg aaacttctgc taaatcacca gaagcgaaac  120480
aagtccaggt gattgaaaag aacaaagcac agcaagctcc tgttcaacaa gcatctcctt  120540
cgatcaataa tactaataat gttattaaga aaaatactgc cgttcataat atgacacctg  120600
taacgagcac gactgctcct ggtgtatttg atgcgactgg agttaattaa ggaataatat  120660
ggcaattgtt aaagaaataa ctgctgattt aattaaaaag tccggtgaga aaatttcagc  120720
cggacagagt actaaatcag aagtaggaac taaaacatac acagcccagt ttccaactgg  120780
gcgtgctagt ggtaatgaca ctacagagga cttccaggta acagatctat ataagaatgg  120840
attattattt actgcataca atatgtcatc tagggattct ggaagtctta gatcgatgag  120900
atctaactac tcttcttcat cttcgagtat tttacgtaca gctagaaaca ctattagtag  120960
tacagtatca aaactatcaa atggattaat atcaaataat aattcaggaa caataagtaa  121020
atctcctatc gcaaacattc ttttaccgag atctaaatct gatgttgata catcatcaca  121080
tagatttaat gatgttcaag aaagccttat cagtagaggc ggaggtactg ctactggtgt  121140
gctaagtaat attgcttcaa ccgcagtatt tggggcactg gaaagtataa cacaaggtat  121200
aatggctgat aataatgaac agattttatac gacagccaga agtatgtatg gtggtgctga  121260
aaatagaact aaagtgttta catgggattt gactccacgt tcaacagaag atttaatggc  121320
tattattaat atctatcaat attttaacta tttttcttat ggtgaaacgg ctaaatctca  121380
atatgctgct gaaataaagg ggtatttaga tgattggtat cgttctacgt taattgaacc  121440
tttatctccg gaagacgcag ctaaaaataa aacactattt gagaaaatga catcgagttt  121500
aactaacgtt ctagtagttt caaacccgac agtttggatg gtgaaaaact ttggcgcaac  121560
atctaagttt gatggaaaaa cggaaatatt tggtccatca caaatacaga gcattagatt  121620
tgataaaaca cctaatggta actttaacgg attagctatt gctccaaacc tccctagtac  121680
atttactctc gagattacta tgagagaaat tatcacgtta aaccgtgctt ctttatatgc  121740
ggggactttt taatgtattc tttagaggaa tttaataatc aagcaataaa cgcagatttc  121800
caacgtaata atatgtttag ctgcgttttt gcgacaactc catcaactaa aagctcttcg  121860
ttgataagtt caattagcaa cttttcttat aataacttgg gcctaaattc agattggtta  121920
ggattaactc aaggtgatat taatcaggga attaccacgc taattacagc tggcacacaa  121980
aaactgataa gaaaatcagg agtcagtaaa tatcttattg gtgccatgag tcaacgtaca  122040
gttcaaagtt tattaggctc atttacagtt ggtacatatt taattgactt ctttaacatg  122100
gcatataact catctggatt gatgatatac tctgtaaaaa tgccagagaa tagattatcc  122160
tatgaaactg actggaacta taattctcct aatattcgta taaccggaag agaattagac  122220
cctttggtta tttcatttag aatggattca gaagcttgta actatcgtgc aatgcaagac  122280
tgggttaact ccgttcaaga cccagtaact ggactgcgtg ctttgccaca agatgtcgag  122340
gcagatattc aggttaatct tcattctcgc aatggattac ctcatactgc ggtgatgttc  122400
acgatgcatt caatatcagt gagcgctcct gagttatcat atgatggaga taaccaaata  122460
actacatttg atgttacttt tgcgtacaga gtgatgcagg ctggagcagt tgataggcaa  122520
cgtgcgcttg aatggcttga atctgctgct ataaatggta ttcaaagcgt tctcggaaat  122580
agtggaggtg ttactggact atctaattcg cttttcacgac ttagtagatt aggggggaact  122640
gcaggaagca tttcaaacat taatactatg acaggaattg tcaattcgca gagtaaaata  122700
ttaggagcaa tataacaatg gggaccgaaa ggtccatatt tttatttacg gaatgaaatg  122760
aaaagcagca ctgaagcaac taaactgtct tcaatataaa cttcaatttt tacaggagct  122820
tctgactcaa atttacctgt tactacacc tgaaaaatac tttcagtcgg ttctggcttt  122880
gaaaaatttt cagaaggaaa aattccgaac tttttatctg ttccaaaaat tttgataaat  122940
tcatcgtaaa ccgcttcgtt aaaagcatta tcagcaggaa taacgccttc aactacaagt  123000
tcttgaccta aaaagcgtaa agaagatttc attttgtgtt cctcatgtta tgttagtaag  123060
actactataa cacaacacga gggacttgta aactacattt tgaacttttt agtacgcgta  123120
ataggcatgc gtcgatttta tactgtttca ttgtttgaag agcagtatca aaaacagcat  123180
taatgacacc aattggattt ccacccaagt tttaagcttt aactaatgat agtttctcat  123240
taacacctat cattacgata tgcatcattt tatcgcctgg tttaacgttt tatttgtatc  123300
accgccagag gtgtatgtac aaaatctaaa tccaggaagt acactttttt caccggcttg  123360
aatagcaaaa atttgtggta ttttatgctt aggatttaat gtaacaaccg gcgccgaagc  123420
gccgtcaaat aattctgtaa taagttccat gatttatcct tgaacgaact tgtaaggcat  123480
gtttgcaata tctatgcaag acgcaataat tccaagagat gattctactt tctgtttaac  123540
atttgatgaa acaaatgatg caaagtcaac tctatcttct atatcacctg tcattgtaac  123600
caattcacca gtttccatta aatggtctcc gtcatagatt accgattcgg tgagttcttc  123660
tgtggtcata acttcagctt gaataagctt gttgttagtt ttaactgttc catcattgta  123720
agatgcatcg gttatttttat taactttgac cattaatcca cgtggcaaaa tgacttccat  123780
ttcatttgaa ggcgctaaac ttccaccggg taaaacaaca ttgaccttat cagccccagt  123840
aataacccat ccaattccaa ctaaattatc gctagaattt acaagtcctt catcagtttt  123900
atcaatagaa acgcttaaac gcttttcgtc tggtaaaaca cctatagatg aatcagtcat  123960
ccaagtacca aaaatatttg gatataatga tgttgacaca aagttctaa aataaaaaac  124020
tcgatttttt accattgctt cgtatattga aggtaacatt cgttgtgaac gatacaaagt  124080
aataccttt ggtaatcgtt caccattttt aaaggctgaa tctaaattat caatagcttt  124140
ttctatgtca gatgctgtca aaatacttgt acgctcatct ggattatata atcccaaaag  124200
agcattattt atgtctacat atcctgaacc tacgtattca cgaattccgc gttttttgcgc  124260
tggtgtgtat ttagatgaat ctttattttc gactatagga tgtaatgacc atccagcggt  124320
aagagcatat ccacgtaatt ctcttcgaat aatctttgtt tttattgcat tccaagaatt  124380
ttgtactaac tcatttgcag catctggtt taaatgcgaa tgtttgttaa tatttctttc  124440
aaaccaagca cccttatatt tttctaaagt atcatcgacg atagaagcaa tagttctaa  124500
ggtttttatt gaagtaatag attctttccg taatcttttct aaagcttat ttttatttc  124560
tgcgttaata atggattctt tatcttcagg aattatagaa gcttctctga atgccatccc  124620
agctgtaaca ctgctaagag cattctctag tgcaaatcct gaagtagaaa ttaccgttaa  124680
ttcattagaa tcagaaatta aaggcgcgtc cgctggttta tttaattcgg ccgctgaagc  124740
ctcaaatttt tgaaacattg gtgtttcaaa tctagaagat tccaatgact gactttgcgc  124800
```

```
aattgctcta cgggaaattt taactttaac gattacagct tggtcagaac gtttatcatt   124860
ttcttgcgca atagatgctg caattgcctc atttttagtt acttgagccc cagtatcttt   124920
attgatataa acatcaccga ccttcgattc aactttagta aagagctcgg tactaatttc   124980
cggaactcct ggaatgtctt ctagtgatac attttttgcga tgtataagaa tatatgcata   125040
cttttatcg taatcccaga gttccttaag aaggacgtat ctaccacctg aacgactacg   125100
gataagtcta tcagcaataa cttgaattg tcgagcttgg ccagcagttt tagacttaag   125160
aatacggagc ataccaggcat caattttata ctggcgcatt gtttgcattg caacagtaaa   125220
aactgaattg atataattaa ttgggcttgg accaagacct tttaatttag caattgaacc   125280
tttagcagtt aatgtaaaag gaacaatatg catcatttta tcgcccatct ttaaatcacg   125340
attagtatca cctccagatg tataggtaca taaacgaaag cctggttgtt caattgcatc   125400
atcaacatga actgaaaaaa tttgcggtat tttcttcttt ggatataagt ttgtaattgg   125460
aagagtagta tcttcgtcaa ataattctgt aataagttcc atcatatcct ctctagtgtt   125520
tattctattc tatttataaa attaaaggcc cgaaggcctt taataatcta ttggtaagag   125580
agtacgatat atttcaaact ttggacctt tccataagca tcaaatgttt ctgtgaattt   125640
attataagca tatgcatcta taaattcaat catgatttgt gatacagaag tagaaacatc   125700
tccaccttct ttttgagcca cgacaattgt ttctaagtaa gctttcatag accagttacc   125760
tcatgaaaat caccaaatac atcttcgaat gtattagctt tagttttatc ttcacgtaaa   125820
cgaatccgaa tcggaagaaa taatttaacg taatcagtgc ggccatcaga ttttaaccaa   125880
ccgttgcatt cgcactctag aatttttcca atataataat tttggttttc cataatgcga   125940
gtacggtcaa gttcatgcga ttttacaccg gctttatctt ttaagcctga accagcattt   126000
accttaattt ttccacactc tgactcaaga ataaatccac ccgctttagt agggtcttta   126060
cggtgaggat aaattcctac aattttttaaa tcaacatcaa ttacttcttt aaattttaaa   126120
agatttttg aacgagcatt ttcccataat ccatcgatat ttttgagaat aataccttca   126180
agaccttggt caatatactt tttataaatt accttagctt catctaggtt atttactacc   126240
tggttttcaa ttaaaattac tttatcatat ccagatgtca tttgttctag tttagaaaaa   126300
cgtacatcat atttcaaacg aaatgcagga agactgttta ttctaccaa cgggacataa   126360
tcccagacct gaaacttcat gcattgtgct tctttttcag aaatggttcc ctttaaagat   126420
ttattggcga ttccattaga agcagtacg gattcagcta cttcggcgaa ttcttttagct   126480
ttactgtttt caggataagc atcaaaaaga aaatctaggc cttctggctc cttttttaact   126540
tgctcatggt ataccaattc gccatcaatc aacacacctt ctggatgaat ctggcgggct   126600
tcagcggtca ttttaattaa ctcttcctta agaagatcta atcctagata ttcattacca   126660
gctcgtgata aaagacgaac atcatctaat tcatcacctc taacttcagc aaaacaccga   126720
gctccatcag cttttaactg agcaaaggct ggaaatttga tattcttatt aatgcctttt   126780
tcatcataag aacttgcgag catttgaggt tgttcaggaa ttaaacctgg ccaaactttg   126840
tttgcaatag atactcgaagc accacattca aggtctcgca acgcaaaact   126900
tcaacatcat cttttttacc atcggtgata tatccagtta attcctcaat tgctgcattt   126960
ccagtcaatt tccgagtagc taatgtgaat tcaatgaagt caagcatatc ggtaagagtc   127020
aacattccaa aactctgggt agcaatacca ggtttaggcc atttcttgat ataatactgt   127080
aacccacgag aataagtcag acgatatact cgtttaagca attcattac tttattcttt   127140
tcaagaattg cttgcttctg tttagttgaa ccaatagatg ctatttcgtt cagaattta   127200
agaatcattg ttcatccttt agagtttggt ttacagctct attataaatc aattcatcat   127260
taagctcagt caaagacctg tggtacgtgg ttctaacttt atttccttgc atccagtgct   127320
tgatataat gaaaccttgc tctacacatt ttttaaaaat tcgttcgtct ttttgagctc   127380
ggaattctgg attgcatcta aaaaattgat ttacgtgacc gtaatcacgt gtagtattac   127440
cttcatttttc ataaatagtg tgaacaacaa acattagaat gctccttgga aaatattatc   127500
accacaagta ggtctattat acaaatactc tataccgccg ggcttaatat agttccatgt   127560
ctgaaacgga tgcgtctgat atggatgata tggattataa ggattaaatc caggagttct   127620
ccaggtagtg ttccaaggaa aagaatcgtt tttaatcatc ttttcaatta catctttat   127680
agcttttca ctatcaaaac tttctttatt ttccttggt gaaaaagct tattctctac   127740
atcgttccat gtataaactc gctgagcagt ttttggaata ttgtcacgct ctcctcgagc   127800
catccaatac acaggaacac gtaatatttc actcgcgtga tcgcagtggt gagcgagatc   127860
gtcaatataa caaattacgt tatatttctc ttttgctttt ttgaacaact cttcttttga   127920
agaatcatga ctacacatca gtacttctga gaaagcacca ggaaaaagag cattcaaatt   127980
aaattgacga tttaatagag cgtcaatag atcacccaat gctgtaacag caacaaaatt   128040
ataatcttct tttaatttgt taattacaca cagagcatct ttatatggaa acaagtaacg   128100
aataaaatcc gaacgattgt attttttcaat taacttgacg ccaagttctt catccacagtt   128160
aaagagttta ccaggagaaa taaatttctc atcttggatc attttttaaa tatgttctaa   128220
cggaagatta tatttctgag caaaataagg aaggcctgat tgccagctta acatactcc   128280
atcaatatca gttaaaatag taggcttcat agagagtctc ttaataggtt taacacatca   128340
ataaattcag cttcggttag tattgtatca tcttttgtta gaccactagc aatgctgtgc   128400
ttcaaaactt ttccttttcga ggcttgtaat gcatcacgaa agcccttgtt ttgaatcgct   128460
gcttcaaaat atgcatttgt gtataattct tccacgccg gggagtatct tgaaacggaa   128520
actccaagcc aaaagagggt cccacggtcc tgagctctag cataagacct tccagctgt   128580
tgggcggcaa gcccggataa cccaaatata cgacgttgtt gttcaacatt tttcaccta   128640
caccettgga ggaatccttc aagacctcca aattgaatac catccataac gaaaggccat   128700
tgggcgaaat tacttaatgc acatgatggc cacctaaaat tgcttctaat ctctaactca   128760
gacattttca atgcttataa tttcaacatc agccaatga ccatagcaag gaagacgaaa   128820
ttcaactggc cagttagggt cccttttctaa tataatagac tcaactttgtg gttcttcgtg   128880
ttcatcagta tacggatttt tatctgttac tttatatgtg accttaatgt actgaattct   128940
aaaaatcta ttaattatat tcatactaat tcctttaatc cgtagatagg agataattca   129000
tcacccatac gaaggtcttc atttccatct acccaggaaa caatataagc ctcttttatt   129060
tgaataccac tccatttaaa tggaggtaga acctagaaaa ttaatccagg tataccaact   129120
cccttttatt caacagtttg acctaaaaag aattgcatta gaacctcatc tgaaaaccgt   129180
gcgattaac attaccgccg ccaatatcag aaatgttaat ttcacgccgca attgaagggt   129240
caatgtcaat ttcacgattg agtttagtga tagctaaagt atcacgccca tttacagtac   129300
ggaactctaa aggacaaacc acatcaacgt agttttaat cgattcgcta gtaagttgca   129360
aatgtgcagg aaggtcttta ggtgcctttg agaaaaccac ttcacagaaa tttttgcggg   129420
tatcaaaata agtagtcata aacataatat tttcctcagt aaggggctga agccctcat   129480
tttattttaa atatcaaatt cattaagaac tacatcaaag attgcttcaa gatgctcagg   129540
```

-continued

```
tttagctctg ttactcagaa tatgacgaat ccaagtttta actaagagtt tacgattagc  129600
accattccag caaggatgag tccctaaatc gcgttggcgg aaatcatcat ccagagcgat  129660
tttgaagttg gaacctttca tcgtgattga aaccgtgata ccgttttcaa atcgcatata  129720
aacgtagtta ggagtcatat actgttcaat ttcgcatact gatccatttt gatgtttcca  129780
gaggcaaata gtatcaatag aacctgcaat accattagaa acatatttac gttcaaagtt  129840
aatgtagttc atttttattc tccgagatgt ttaattgcgg tacaggtata taatatcata  129900
tcctgtacca aagtaaacaa ttattttact actttccaat gctgcatgtc aagtttacca  129960
acttttttca tcttctcaat taagcgttct gcacgttggc gagctgtaac ataatgccat  130020
tcgcctaatt cattttgttc aattttttcca acgattactg tattcaattc ataaatccaa  130080
ccagtaaaga aattatgaac ttgaattgta aaggtgaaat ctgttcccat accttctgtt  130140
gtttctactt caataatatc accttcaact gccattaaga accacatagt ttcatcatat  130200
ttaccattga agcatttagt tttaactgca gcgttcagat taatcgtttt catttttattc  130260
tcctttgttt gtgtaagata atactatcac aaaggaacta tactgtaaac aactttgtgc  130320
aatctttgga aaataaaaaa ggactcccga aggagtcctc aacttatgct ttctgcttac  130380
caaaacgaga agcatcatct cgaagaaccg cacgtgctcg gcgcatgatc ttctcaacag  130440
tttgattgat acgagagttc gacccacgct tgtagccagc gcgtttagaa tcaccaactt  130500
tcttttcaac tgctttcttt gctttagctt gttttgccat tataaattct cttttaaatg  130560
aaaatgcagg acttattggc attgcctgcg caagccctca agggggaacat aggttttttgg  130620
atatttaacg accaggataa ccataaaccc gtcatcattc acattcaaga ggtacaccgt  130680
aaaactgtcg gggtcttaaa actataatga ttcgcaaatc attaatcaga cagttcgacg  130740
gctcctcgat ttagctcaca ctaaggcagt gaatctccaa taaattactt cagtgttacc  130800
acaaagtgac gaactgcttt tcgtgcagca gaagccagag gcttagcata tttaagttca  130860
tcttttttcct gaagctcagc agctaatgca gtttgagcag gattcagatg tttgaaataa  130920
cgcaggattt caagagcttc ggcttcaaca tcaatagatg cgccatagtt ttcgtgacca  130980
ttattccatg cgtttcgttg cagttcaaga gcgtgttgta attgtttaat catttaaaaa  131040
ttctcgttag agattaaaac tcggtagtca cgttcttctg aatttcatct tctttcgaca  131100
gatctctcag ttgtagacta ccacatagaa ttgttcggtt aacttattat tccgacaccc  131160
aattcatatt attatttata tcacttataa agacacggaa tagctttata gtgacaggta  131220
acgaattttt gtttaatttc ttttggctgc ttaagaccca gagctacaaa aggatgcgga  131280
acatttcgaa tttgaccaac tggaagagaa gtcaaatcac caacttcgca gaaaccttca  131340
ggaacatcag gaccgacaga gtgaactaca cacagttcag gaacttcacc ttgaacacgt  131400
ttaccgataa taagtcctga ttctgtaact tcttcatcac cggcttgtgc aggttcagaa  131460
actaaaataa catattcacc gacagcacga attggtagct gttgtacttc agacatcgtt  131520
tttcctttt gttaacagat gaattaataa taacaaatag ttcttaaagc atttatttac  131580
caataaaattg aagcaaatgc tcaactttca taccattaac ggaaatcaat ttgtcaatag  131640
aaaaacctcg ccacgcacca agctcaacat caaatactgg aatcatgtca gtagattctt  131700
tccgagtaga ttcagtcaat ttgccagttt gcatggttgg cataaagtct gcatcacgag  131760
tacctttcat agtacgaata gtaccatcag acttttcaaa aactacgttt gaaacacccca  131820
tggacaattt agttttcaaa atttcacgaa ttgctacttt ctgctcagtt gtcagtttca  131880
tttatttacc tattacagtt ttaatatgag ttgttccacg ttctttaagg gtggaaagta  131940
attttttggca ttttttctaaa tcagatttcc aactatatgg tctatcaata caaacccaat  132000
ttgtcttata atactgtttc catttagaga aaaaatattt cttatactct acagcaaatg  132060
agatgtctc gttagaataa gaactaattg ctgtgagttt taccaaacga aatttcatta  132120
ttcaccacag aattcgttga tattttccca gtttaactta ttcaagttttt cttaggaac  132180
attaaacact tcaatacctg catttcgcag aatatcatcc caaccgggtt tatttttgtc  132240
gtatgtttca caataaacca gctttttaat accagattga gctatcgctt ttgcgcaatc  132300
tggacaagga gaaagtgtta catacatagt agcaccttca atagaagaac catttcgttg  132360
agcaaacaaa attgcattta gttcagcatg aatttcattt ttagatgacc attccgagtg  132420
agcactacga tgttctttcg ccaaaacaaa acgatcagtt gaaccaaatg atacgcattc  132480
aggcttatga ccttgaatga tagcatgttt aggcttattc aacaaccatc cttgctcagc  132540
agcataatca caacagttca caccccctgc gggtgaacca ttataccccag tagaaataat  132600
acgtccattc tttttcaatta ctgctcctac cttccaggag caacattttg attcctgcga  132660
tactaaaatat gcaatttgaa gtactgtact cgctttcatt tcataatcac cagataagca  132720
gatttagcag tttcaacacg ataaatttcg tgacgaagtt tagttatact tttaataaca  132780
gaactaatta tattctgccc atctttaaag cggtttttct tatcaataaa aactgcgcca  132840
gtcatctttt tgtgaagctc aactggatac ttcgtcacaa taatagcatc atacacagaa  132900
ggatgaatac tattcaccag agtatcattc attaaagtta ttctaatgaa ctgtgctgtt  132960
tcagaatcaa gcgctctatg atcgccagta tcatttcaa gacaattatc aattatatca  133020
gttaaattca tcatagtacg ccatacaccc tttgtgcttc aactaatcca tcaaaatcca  133080
gtttaagatg cgatatttga tcgccatcac ctggattcac aattactaat actgaaccgag  133140
gagtttcggt aataacacga accgatgttt caggaaatcg ttcagaaacc ttatttacta  133200
attcctgcgc aaatagttta actttttctt ggaattcctt taacagtaat cggttttttca  133260
cttagcaaca ttttgttttc ctcatttgtt ttggtagagc tataatatca caactctacc  133320
gtaaagtaaa ccattaaatc gctttgaatt ccgcagtttg aggttcaaag cgaatatcgc  133380
ctttgataac aagctcagca tcaagaccaa atacgacaat gatatgcgcg aacctggat  133440
acagtgtaat ggcaatagaa tccacctggt ctggaagcaa agtgttcaat acatgagtca  133500
cttgagcatg gattcgaagc tcagctgcgt tatcaagttc tcaaacata ttattagcga  133560
taatttggct aaacactact tctacgattt tagagtaagt cggaaacata tttaccttca  133620
ataattttct tcaagccaat caataacatc caacgcatta tcaaaagttg aaccatctac  133680
tctgtcttct gtttcataat caagaacatc taggcctact cttccgtcaa caataggcca  133740
tagacaaaat agatatttct ttctctttttc aattttatca caaagacgat aaatctttttc  133800
taggttattc ataagttttc catggtaaag gcagtttagt tttctttact actagttcaa  133860
catcgggatt cttttctctt aatttaagac attcctccca tgctctattt tcactagtaa  133920
atacacaaaa ttgcccatta ctagtaccaa ctaaaccgct atttacaata acaatagccc  133980
aagtttcatg gtgccaagcc attaaaaatc tcccgaagcg acttgccagc attcaacacc  134040
gatacgacgc cacatttcaa ctacttgagt tcggtcatca atagctaatt tcacgtcaaa  134100
atgcggtgca atgtgttttcc agaaaatttc ttctttaact acatcgtctt tacgggatc  134160
gccttgttcg cgctgacatt gcataactaa tggaacgcca gcaatgtcct caacccattt  134220
acgggtcata cgataatatt tcgttgggtc ttctttagtt ccactttcac gacctgaaac  134280
```

```
gactacgatt tgataaccca taagagcata catcttagac agttcaacaa ccataggatt    134340
gataacatcg gtatcgcatt tttcaaggtc ataaggacca cgaccattca ttttagctag    134400
tgtaccatca acatcaaaaa taactgcttt tggtttacca ggagtccatt tatatactgg    134460
aagaccgaga tactctcgca tgcttttata cattgaacgt aaaacatcaa ttggtactgc    134520
tttagttccg cgttttgagt tacgtttaac caattcagtc caaggaacat caaacacttt    134580
atgttcaact ttccagccgt attctttggc aaaagtttcc catgctaggc gacgttcagg    134640
attcaggtta gtatctgaaa tgattactcc cttaacagaa tcgccaccgt acagaatact    134700
tttagctgta tcaaactgca taccagttac gataccttct ttcttttttgg tatacttgta    134760
ctcatcgcgt tcttcatgcg ccataataga ttggcgatag tcatccacgat tgatattata    134820
aaacccggga ttcttagcaa taaattcacg agcccaagta ctcttaccag aaccaggaca    134880
gccaatagtc aaaataatct ttttcattta ttttttctca actaatgatt gaatataatc    134940
atgtaggtct ttagatgctt tacccccactt attttgatat tcattttttga gattagcacg    135000
tgattgagct aataaaacat cattagttgg aggtaaagat tctaaccgct gaatctggcg    135060
tccataaatc attgcagcca tctcggattc ataaatccct ccttttgagat gttcaaattg    135120
atgccatgaa atcattttaca tttatcctct tttagctctt gacgataata acatrtcata    135180
gttttctggt catgtacata tcgttttaca tcattaagcc aaatacgaaa ttcctgagaa    135240
tcttcaaatg gcataccgac ccaggcttta ccatcaataa ctttaacttg ccaagatagt    135300
ttagcttcat catatgactt tatttgcaca ggccaattag gatgaactgt ttcttttcttt    135360
acttctagag gctttgtcga acaaccaact agaagaccaa tagataatat tactgctgat    135420
agttaatca tttagaaagg tcctggatgt cttctgcgaa cttgttgaag gagttgttga    135480
tttgttttttc aaccaatcct ggcttatgag ccaccacatc cgccttcttt gcatctttgc    135540
gcagttttttc attttcacgc tcaatagcag caattgccct acgattttta ttattcatcg    135600
catcaatata attatactga attcgcaaat tatttaatgc taaggcgttt tcattggccg    135660
tttttgtaat ttcagtaact gatgtttcta atctttctac cttatgtttt aaaataatag    135720
atgttccgcc aaatgctatt acaagtaata gcaatccagc tgtaaaatta cttacatgca    135780
taaagttttta ataacctcta caatatcgtc ttgagaaaga ccgttaatta aaatatgatg    135840
ttcagctgga gatttagaaa ttttaaagca tgcctcaaca tcttctgcca tatccgatgc    135900
actacgattt ggattactaa taccaaggcg atgtttccc gtcaaaggat taacgatgat    135960
atagcatttg cagctattga tatgaacatt gggttgagtc tgattaatga acacttcaca    136020
atcatactta gcaagttgat tttctaaaaa gactttcatc tcttcaaccg catcaggaag    136080
catatcacgg gcttgctcaa gacgacgatt tcgatattct ttaatggtcg ttttccgctt    136140
gacttgctta gctaaatctt tcttaagacc agtgatatat ccaactcgac gatttccttt    136200
gaatacagaa atcccatctg tagtatcacc gtatgcttca acgaccattt cagtagtaat    136260
aagttgtaaa tccatcataa agtcctcatg ttatgtcagt aagctacta taacacaaca    136320
cgagggactt gtaaacaact tagtatcctt ctgggataaa tttttttataa ttttttcaaaa    136380
aattctgttc gatttcacac atgacctttt cttgactatc gtaccctgg tataagctca    136440
tgatgatacc gaacaggtga tccattccag caccttttagc aacaccttgt gcttccattg    136500
cataagtctt tctatccttta ccgcaatgct tattatgaca gtcaagaact aaaaacagag    136560
ctcggtctaa gtacttcaga taagtcgttt caaatgcttc aattttttctg tatgaatatt    136620
catcgtcagc atacattgct ttaagatcat ctgatgcacc atcaataata gtcttaaaca    136680
atttttctgg attatctaat gaactttttg tactatgaag agcacgtac cagtcagact    136740
taattttaaa atgagaacca tctttcatca cagcaacata gccttcgatg ttttctgcat    136800
ttttagcttc ttctatccat ttagggctat cgatttcgta tcgttcaact agatacggac    136860
gaagagtagc atcttttataa atatcatcgt atgaaatgta ttcacccgtt tcgtttttcac    136920
gaacattcag taaaataatt ttcatctctt gataagcaag aacgattcta ttcgtcgggg    136980
caacgaattc gaagttagca gtaaatccat cttcagctaa ttcttttaagt ctatcacgca    137040
accgatggtg attaatattc atcaaaattc cattagccat taaagcctgc tcagatttga    137100
ttgaacccttt tgatttgaac agaatttcat caccgtctaa ataagttgat accaaagacc    137160
cgtcttcttt tgttagaata taatcaacat cgtttaaatc gatattcatc gtgaacggat    137220
tttcattcaa gttaaaaaac ttttccatag gacgagaagc aattcttact ggttttttctc    137280
catccatttc aaacataatt ccacgacatt ctagtgcatc tggaagtaac cattcagaat    137340
aagatgcata attatatgag aaaattctgt aagttcttcc agatgcactt acatcatctg    137400
agtaaaaaaa cttacgctgc gaatccttac atagttccat taaattgtta aaagttcttt    137460
gcattgtgta tcctctttttg tgttttgaat atagtaccac actccatgtg gaagcatcat    137520
ttttttcttgt gttgaatatt ccaaggcggg ttaaacagtt taatgaatag aggctcctct    137580
aagtcaatcg ttgcgattgt cattgtacct aactcatttg tcatagaaag attaaaacat    137640
tggcgggcgt aaaattcaac tttgcttcct tcctttagcg cagaatgaat taatgcagat    137700
ttagtagaat cagacgtttt gtctttgcgg ttaatagcag ttctataata gtttattctt    137760
ttacgtaaat ttttagttttt tccaatataa acaagctcat catttatagc aatagcataa    137820
attacgttat acttgtttgg aatagataat tgttttatac ttccattgtc gtctaattct    137880
agctcagtat atttaataaa tgaatattct gttgcaattt ctttcataat aaaatgggcc    137940
ttgcggccca ctccttaaaa gtatttttta aaactcatca taactttatc atcaacatca    138000
ttatcaatct gtgcaacaag gtaagatgac agttctactt cttgcggcgc ggattgaaca    138060
ttatcagaat taagatattc acgaatccaa ggatatggat gtttaaccgg agcatcggta    138120
attgggcatg gaagaccgca ctgtttcata cgagatacag ttaagtaatc aataaagctc    138180
cacatgctat ttgtatttaa tccaggaaca tcaccatctt taaataaatg aactgcccag    138240
tcttttttcct ggcggttaac ttccatgaaa atatcaactg cttcttgttc acactcttgg    138300
gcaattttaa cccattcatc accatcagta ccggatgaa gttgacgaat aatatattgg    138360
gtgcctttaa ggtgaagctg ttcatcacgt gcaatgaact tcataatctt ggcattacct    138420
tccatgattt ccatgttctt atggaagtta aaggtaccgt atgttcgatt gagctcgcta    138480
attctcaacc cgttctctta tgaactgctg catgttacca tgcagtccag actatatcac    138540
aatcccggag ggattctccc catttcgagt cgcttgaccc tacgtccgaa gactagtcgt    138600
tgaaccttgt tttgcaattg tcgccgtgcc atcgtttata tgttgatggt gataaatctt    138660
tactaaca atatggacaa ttcaattgaa ttctatttgg atttaatttta catctgtcat    138720
tatgtttttag ataaaatcca ggaccttttac caatgtgacc acagaaatca catgtgattt    138780
cttttttgtgc aggatgggtc ccgttcttaa ccatttctaa tgttttttgct gatgttcttt    138840
tcttatgttc ttccatcaga atctttaggt ataggtccgt tagcatctat ccaaattttt    138900
ctatagttca attgtgcatc ctcttaaaag tataatcata tttatattat actaattaaa    138960
ggtgcaagca aaaccttggc tgctagttttt ccataaagga ctttccagca attaaaggag    139020
```

```
ttttcgataa acgttaccgt ttaaaggcgc attttacgca aaagatacat aaaaacgaat   139080
agcttctaag gcattaataa cgtgcaaaca gaggtaaaga gatttcatca gatctcgttt   139140
agctctttgc tcaacgtctt tatcagctag aattagacct tggtctttat aatattcaac   139200
catgtcttta gcattttccc attcacgggt tttaaccaag acatcatcgt aatatcgccc   139260
aatggactca gcacgtttca taatagcttc atctaataca atctcatcaa acaccttcga   139320
tggatcagta taaagatttc gcatgatatg agtatatgaa cgactgtgaa tagtttcact   139380
aaaagtccat gtagcaaccc atgtatcaag gcttgggtct gaaattaatg acataagtac   139440
agcagatggc gcacgaccct gaatgctatc caaaagtgat tgatacttca ggttgttagt   139500
aaaaatattt tgctgatact gaggaagctt attaaattgc gcagcatcca tcattaagtt   139560
tacttcttca ggacgccaaa aaaaactgat ctgccgctca atgagttctt caaatactcg   139620
atgtcgttga atatcatatc gagctaaacc taatccagaa ccaaagaaca tcggttcatt   139680
caaaacatca actggatttg tattaaaaac tgtactcatt tagaatcctt aaatttacat   139740
ttatcataat gccatcttaa agcattgcct ttattaactt tcttaccaca gtgcgggcaa   139800
ggtggatact ctgctccttg tttagttctc aaagaaatca aatcacgggt ttctttagta   139860
tgaggaacat ctccttgtcgg agaaattgta ccatacatcg gattaagcac gccgacttta   139920
gcagcagcta tattctttt agcttcttca gttttaggct ttctcatctt tttcttaggt   139980
ttcttcgctt ttagccctc ctttggttgc cgccgatatt ttgtgtttgg tttcttctgt   140040
taaacgcaga cctgttttcg cttttgaca ttttcagtct cgtttcttca gaaatgaccg   140100
taccttttgcg aaattgcgaa tttaacttct ttgcatgggc atatatttta gaatgaactt   140160
tataatgacg tttcttagtt cctttcatat tgcacatcat gaaaaatgcg aatataacag   140220
attttaccgg ataaatcttt gataaaatag catgcgctat aaaatgctct ctagctgtta   140280
attcaactaa attttcttta tcatcagaac ctcccatgca tctagggatt atatgatgtg   140340
tctctttata ttcggataaa ggttcccgag cctgagctcg ggaaattagg tcgttataga   140400
tttttttgata attcattaca atttacacgc tgcacaatca tcggctttag gagtttctat   140460
ttcataatca tcagtaccag aaccatcacg ggtattatga taatagaaat ttttaatgcc   140520
ataataccat ccgtatagca tgtcatcaat cattattgac attggaacct ttcctttggg   140580
aaaaatctgc gggtcataat atgtattcgc tgaagctgat tgacataccc atttcagcat   140640
aatagctacc tgcgtaagat aaggtttatt acctttctta gctaatttcc atgtataatc   140700
atagaggtct atgttatgct caatattggg cacgacttga ttaaaggaac cctcttttga   140760
ttctttaaca cttaccggtc cacgtggagg ctcgtagccg tttgtactgt tagaaacttg   140820
ggaagatgac tcacatggca taagtgctga taatgtgcta ttacgatgc caaatagctt   140880
aaggtcttcc cgcagcgccg accagtcaca aacgtatttt ggagctgcga tttggtcaat   140940
cttttattg taccagtcga taggtaattc gcctcgagac caacgagtgt ctgaataata   141000
ttccgaaggt cctttttctt tggcgagctt aatggatgct ttaatgagtc catactgtaa   141060
tctctcaaat agttcatgtg ttaaatcgtt agcatcttca taagaagcaa agttacttgc   141120
cagccaagct gcatagttgg taacacctac accgaggtta cgacgctttt tagctttttc   141180
tgcttcagga accggatatc cttggtaatc caacagatta tcaagagcac gaacttgaac   141240
ttctgccaat tcattaattt tatcttggtc ttgccagtca aaattatcta atacgaatgc   141300
agagagagta cacaatccaa tttcgacatc agggctattc acatcatttg ttggaatagc   141360
aatttcacag cacaagttac tctgacgaat aggtgccttt tcacgaataa acggagtata   141420
gttattcgta ttatcaatga actgcacata aatccttgct gttcctgaac gttcagtcat   141480
gagcaattca aatagttcac gggctttaat acgcttttta cgaatattag ggtctttttc   141540
tgctgcttcg tataattcac ggaaacggtc ttggtcttta aaataagaat aaaaagctc   141600
gccacccatt tcatgcggac tgaacaaagt aatgtaatcg ttttttccaa aacgttccat   141660
catcaaatca ttcagttgaa caccataatc catatgacga atgcggtttt cttctacgcc   141720
tttgttattt ttcaaaacga aagattttc aacttccaaa tgccaaatag gataataagc   141780
agtagcagcg ccgccacgaa ttcaccctg tgaacatgat ttaactgcag tctgaaaatg   141840
tttccaaaaa ggaataacac cagtatggcg tacttcaccc atgccaatct tagaaccttc   141900
ggcacgaatc ataccaacgt taataccaat tccagcgcgt ttagagatat attcaacaat   141960
tgaagcagaa gccttattga tagacttcaa tgaatctcct gcctcaataa caacacatga   142020
actaaactgt cgagtcggag tacgacaacc agccataata ggagttggca atgaaatctg   142080
tcgagttgat actgcttcat aaaaacggat aacatgtttt aatctatcaa caggttcatc   142140
ttgatgcagt gccattccaa tagtcataaa tgcaaactgt ggagtttcat aaatttgacc   142200
agtggtttta tctttaacta gatatttttc ttttaattgc attgccccgg aataagtaaa   142260
ttccatatcc cgttcgtgct taattttga ttctaaaaat gtaatttctt ctgctgaata   142320
ttttgacaat aattcagggt cgtatttacc tgcatttaca caataagaaa tatggtcaat   142380
aaatgaacgt ggttcatact gcccataaac atgcttacga agagcaaaca ttaaacagcg   142440
tgcagctaca tattgataat caggttcttc aaccgaaata gaattcgcag cagccttaat   142500
gacaatagtc tgaatatcat cagttgtcat tccatcaacg agataagtt taatattttc   142560
atataattca taaggatcta ctgatgttcc ttcagctgcc caagataaaa ctttaataat   142620
tttttgtggg tcaaagctct gagaaacacc actactttg ataacattaa ttaattgcat   142680
aagtcctcaa cttgaaaatc gtctttaaac aatcggttaa ctatatgagc tattatatca   142740
ccatgacacg gctttggttt acatgtgcat cctagcctca ttccacgtaa aggctctaaa   142800
tgtgctttag ttatttctcc ggatttaatt cgacgtataa aatctttttt gaataattca   142860
atggcagcct cccggctgcc agcatcttta ccgacgtaat ttccccaaaa tgtaccgcgg   142920
tgaatattaa catcaaagtc ggatttatat ttattcacta cccggcatag acggcccacg   142980
ctggaataat tcgtcatatt gttttccgt taaaacagta atatcgtagt aacagtcaga   143040
agaagtttta actgtggaaa ttttattatc aaaatactca cgatccattc tatgagtata   143100
gtatttttta ccataaatgg taataggctg ttctggtcct ggaacttcta actcgcttgg   143160
gttaggaagt gtaaaagaa ctacaccaga agtatcttta aatcgtaaaa tcatatatcc   143220
tcgcaataat aaaattacac cgccatcttt cctttaatag gagggtgtga tacatagttg   143280
ttaagaacga aatctttagg cctaagttta agaacatatt ttaattgttc tttagtagaa   143340
agatatcgga atttataagg tagaccactt attaccagct cacaaagctc tttaggttca   143400
cgcctcaaaa tttctttaca ttgttctacg tgattcatat agatatgagt attaccacca   143460
gaaaatatca aatcccctgg aataagatta cacatcttag ctacaatatg aactaacgta   143520
gcatatgacg caatattaaa cggtagcatt atgttcagat aaggtcgtta atcttacccc   143580
ggaattatat ccagctgcat gtcaccatgc agagcagact atatctccaa cttgttaaag   143640
caagttgtct atcgtttcga gtcacttgac cctactcccc aaagggatag tcgttaggca   143700
tttatgtaga accaattcca tttatcagat tttacacgat aagtaactaa tccagacgaa   143760
```

```
attttaaaat gtctagctgc atctgctgca caatcaaaaa taaccccatc acatgaaatc    143820
tttttaatat tactaggctt tttaccttta atctttctg atattttaga tttagttatg    143880
tctgaatgct tatgattaaa gaatgaatta ttttcacctg aacgatttct gcatttacta    143940
caagtataag cagaagtttg tatgcgaaca ccgcacttac aaaacttatg ggtttctgga    144000
ttccaacgcc cgttttact tccgggttta ctgtaaagag ctttccgacc atcaggtcca    144060
agtttaagca tcttagcttt aacagtttca gaacgtttct taataatttc ttcttttaat    144120
ggatgcgtag aacatgtatc accaaacgtt gcatcagcaa tattgtatcc attaatttta    144180
gaattaagct ctttaatcca aaaatttct cgttcaataa tcaaatcttt ctcatatgga    144240
atttcttcca aaatagaaca ttcaaacaca ttaccatgtt tgttaaaaga cctctgaagt    144300
tttataaag aatggcatcc tttttctaaa tctttaaaat gcctcttcca tctcttttca    144360
aaatctttag cacttcctac atatacttta ttgtttaaag tattttaat ctgataaatt    144420
ccgcttttca taaatacctc tttaaatata gaagtattta ttaaagggca agtcctacaa    144480
tttagcacgg gattgtctac tagagaggtt ccccgtttag atagattaca agtataagtc    144540
accttatact caggcctcaa ttaacccaag aaaacatcta ctgagcgttg ataccactgc    144600
aaatccaaat agccattacg cacattaaac tgatagaaca tatgacaagg cggtaatgcc    144660
atatatttaa gttcagctgg attccatgca gaaacaattt gacgcctatc atttggcagt    144720
tttttaatac gatcaataac ttctataatt tggtctacac caccaaaatc acgccactgt    144780
tttccataaa ttggaccaag ttcaccgcta tggtatccta aatcttttgc ttgattttcg    144840
taattttcat cccagactgt tttgccttgg attaacgaat cgtgttgaat taatcgtaaa    144900
tcattgacat ttgtgcttcc tgataaaaac catattagct cagcaatgca agcttttccag   144960
gcgagcttct tagttgttac cgcaggaaaa ccttagtta aatcccagcg taatttagat    145020
ccgaacagag caattgttcc tgtgcgttga cgatcatcga tttcataacc atttttcaaaa   145080
atgtctttaa ttaaatcttg gtattgtttc atttatatac tgattccgta agggttgtta    145140
cttcatctat tttataccaa tgcgtttcaa ccatttcacg cttgcttata tcatcaagaa    145200
aacttgcgtc taattgaact gttgaattaa cacgatgcct tttaacgatg cgagaaacaa    145260
ctacttcatc tgcataaggt aatgcagcat ataacagagc aggcccgcca attacactta    145320
ctttagaatt ctgatcaagc atagtttcga atggtgcatt agggcttgac acttgaattt    145380
cgccgccaga aatgtaagtt atatattgct cccaagtaat atagaaatgt gctaaatcgc    145440
cgtctttagt tacaggataa tcacgcgcaa ggtcacacac cacaatatgg ctacgaccag    145500
gaagtaatgt aggcaatgac tggaacgttt tagcacccat aatcataatt gtgccttcag    145560
tacgagcttt aaaattctgg aggtcctttt taactcgtcc ccatggtaaa ccatcaccta    145620
aaccgaatgc taattcatta aagccgtcga ccgtttagt tggagaataa cggaatacca    145680
atttaatcat tacgtaaatc ctatttaat tgaaaacgaa tgcttacttg gataatttca    145740
atgacataca taatattttc ctcaaacaga cttttcaca attttccaat cagctttaaa    145800
ctgctcgacg tcagaatggt aaatccaaaa tcctgcgctt tctccgtctt cataaagagg    145860
acatccatcg cattcatctt cccatcccat atcacgtaaa agatgttcag cttttttcaac   145920
aagttcagaa tctttaccga tgatattaaa ataccattta cctctaactt ctgaatcttt    145980
gatgctctgg cgttgtaatc tcattttatt ctccttagca agctttaatc aaaagatata    146040
aacagaccaa cataactgct gccataatat aaggtgcaaa cattttcttt tctccattag    146100
ttttgatagg gtaatagtat cacactacta ccctgatgta aactacttt tgaaagtttt    146160
tcgcaaaagt tcaatgattt catctacatt gttttcgtca acaatgcagt gaattttgt    146220
tacgccagaa accttgtctt tgacttcatc ttcttcagaa gtcggttctt tatattcgcg    146280
gaaacaataa aactcttctt cactaagttc aaaataatca tcacccatac catcatcatt    146340
atagatttca ccattagcac aaatgatttc ggttacataa tcaaagccat ctaaacttga    146400
tattgattta acttcaaacc aaccgccatt tccttgaatg atgccgacca tactagcatt    146460
tgatgaacta atatcaatga agatttaat acgatgtgga tttaactcgt attttttgcc    146520
gatttccatt ttgattttcc tcattttaat agggggcttga tagcccccttg ataattattg   146580
ttcaatcagt cccatgtaaa attctgcgtc ttcagaatcc atgccatcac aatattcatt    146640
agccataaag cgggtgaggt cttcaagagg accttcaata acgatttgaa tactccaaaa    146700
cttagaatct tgcacgcttg tgatactaag ttcaggataa cgattacgaa taatctcttc    146760
aatatattca aaatcaacga tgtcaatatc aactttagcc atattatttt cctcttttaa    146820
tattagcagt attgccgata gttgtatagt accataaagc tttatgcttg taaaccgttt    146880
tgtgaaaaaa ttttaaaat aaaaaagggg acctctaggg tccccaatta attagtaata    146940
taatctatta aaggtcattc aaaaggtcat ccaggtccgt gtcatcagca ctagatgaac    147000
taccagagct tgagctcata aaatcatctt cagtttttgt attgaagtca tcaacattga    147060
atgcatccaa atcatcagcc acttatcag ctttcttagc agcagttgca gcagcaccgc    147120
ccatcacagc agttcccata acttgaccga atttagtatt aagttcttca aacgatttga    147180
atttatcttt agaagtcatt tcagaaaggt caaccattg ttcgaacagt tctttctgga    147240
aagattcatc gtcaatgttt ggaatcgcag attgattcag gaatttagat tcatcgtagt    147300
tactaaatct agaaacttgt ttaacttca gtacaaagtt agcacctcc cacggacaag    147360
ttacatcaac tggagtttca ccattttcaa catcaaccgc aatcattgca ttgatttat    147420
cccagatttt cttccaaag cggtatttaa atactttacc ttcgttttct ggagcagctg    147480
ggtcttttac tacaagaatg ttagcccagt aagaagtttt acgtttaaca agactgtact    147540
ctttattgtc agtgttgtat agatcatttt tactgatgta ttgacatact gggcaagaat    147600
cgtaatcacc atgggtagat gaacatgttt caatatacca tttacctt tcttgaaac    147660
cgtgatttac aagaattgcg aatggtgctt gttcatcatt tttagacgga agaaacgaa    147720
ttactgcttg accgttaccc gcattatcga gtttcagttt ccactcgcct ttatcttcag    147780
aagaaaaacc tttattgcca ttcagtttag ccatttgtgc agcagagttca gcagtagatt    147840
tacgtttaaa cattttttatt tccttttaa ttaatttaa taacagttg gtgctatgac    147900
actttacctc atagctggca taattcgcaa tactctgggt cttcgagagg tatccaacct    147960
gagttgaaat actttaccat cgatttagca gttgtatcag ttatattat attacctta    148020
actcttcgcc atccaggagt tttaccgtac agattagagg ataataataa cacataattc    148080
tcgtaagcaa tatgagataa tttccaagac tctatattag ctcgtgatgt tttccaaggt    148140
ctaaaatcgt cacggttcat ataattagcc aatctctcaac gctctctaac ttccgggtct    148200
ttggctggat gagtttcacc actcacacca aatccaccac cagcatatac cagattaaaa    148260
tagtctggat tatctctggc atttacttca agttggtatt tcgttctgc ttcaataaca    148320
tccagtgtcat catcaatttg aattattta acgctcggtt tttgaagcat tagcgcattc    148380
aaaaatcttt tttgttaca tgagctccag tattcctttc cggaagagtc atatatatt    148440
ccgttctcaa atgagcaatt taatttacta ccgatatagt agtatggcgg agtcttattt    148500
```

```
ttgacacggt cttcaaatgt aaaccaatat actatattca tatcaatact tgcaagattt  148560
cacagtttca atgaaaacat ttttagcttt ctgtgaatca atatttaaaa ttttttctata 148620
agcctttaac tttatagaat aattattcca gactaaatta tcagtctgtt catcatgttt  148680
atcaattata tttaaaaacg aatcaagcaa gataaacgtc tcaaacgaaa ttatgttcga  148740
ttgcagaagt ttaaaaatat aacttgattg aacttttgta ttatactcaa aaatttcttt  148800
aaaagcagaa acttcaactt ttttactaaa ataataaatg ttgcgaatat cttcttcaaa  148860
cttaaattta atttgcttta agcgtccgat atattcacga taaaacacaa gtgcatcagc  148920
gtcagagatg tcaccaatcc aagcatcttg gttagcaacc aaattgctta taagattaa   148980
agcaagttcc tttaatttat atttttctga taacttctgg aaaaaatact tatcccttcg  149040
cttttgataa gcggcatcag acacccgcat gcaccaatta tacttaatta catcatactt  149100
tccattcata tgttgtttta tcattaagta taatttataa actgatttac catcaatgta  149160
tctttcacca ccagcaggca tgcggagttt aatcatagta gaaaatcaa  tgtattagtt   149220
ttttcacaac gaacaacaga aggacgtaaa agattttcgt caatagcttc tgactgaatt  149280
ttttcaatta tacccgaagg aataaattta gcaaattgaa tttcaggaat agaattttct  149340
tctaagaatg ctgttgtagc ttcaagataa ctcattccaa actcttctac cattttttca  149400
ataataaatc cattttcttg gcggtcaaga agctttgcta tttcatcctt ttctttctta  149460
attgaaagtt ctttttctga aagaccggtc tcatcgaccg gacgaaatatc atttagagaa 149520
aactgtgtca taaagttcaa ctaccttctc agtttcagct tcaaacacat cacggttatc  149580
tttatgatac aaagctaata gacgattaaa catcttacca tcaacgccaa gttcatcttt  149640
agcacgaatt cgaatatctt taatcagttc attataaccg gaaattttca gtttatgatc  149700
agatgcttct ttaataaatt tagccaagtc ttcgccatgg atagcttcat caaattcaac  149760
catttctttt ttagccatta ttcaccttcaa aattcattaa tgctattagt taatttagaa  149820
agacccgctt ttacaaaata tgaataaatt ttgccacgcg gtggtaattt atatgaatta  149880
tagtaattca caatgtttga agcaatatta tcaggaatat aatcaaaatc aattagaact  149940
aaattttctt tataacgatt atattcagat tcagtgagaa gcaccttagc ttgctcacgg  150000
tcattagcaa tagcttcaac gattgaagtt ttcattgaag gagttcgttc accttcaact  150060
ctggtaaacc aaaagtcaga tcgtacttta actgaagcaa cgttatcctt tttgtcgcct  150120
ttaaggattt tagtcataca gtcaatttca gcagaaccgc ttttaatttt aacccatttc  150180
ttatgcatcg gagaccattg cttaacattt ggatatttgt gaagctgagt aaagtcacca  150240
tctgacgaaa tgattaaaat cttatgtcct tctaaagaga acttttttaac aagaacagca  150300
atgtggtcat ctgcttcata cttatcaata tccataacaa tgtatggcat ataagctttc  150360
aattcatcta taactttatg gctggattca aaataacctt cccagtccca agtagattct  150420
tctcgtgctt ttccacggtt tttcttataa taataagcga aatcacgacg ccaatatcca  150480
gatttcgcgt tatcaataca cagtacaatt ttagtgtatc caagcgtttt tgctttttg   150540
acattaaact taattgagtt caatatcaaa tgacgaacca ttgataaatt aattttttct  150600
ttatctggga agtttaccaa agcagttgaa agcgcaattt gactaaagtc aattaagcag  150660
attccttctt tgtaatcttc atccaacatc atttctaaat ccatatgaac ctcgttcaat  150720
tagtgagatt tctattatat accatccaaa tcttaaagta aacaagtata aatacttatt  150780
attgaaaaca caataggagc ccgggagaat ggccgagaat aaaagagaat tcagagcaga  150840
agatggtctg gacgcaggtg gtgataaaat aatcaacgta gctttagctg atcgtaccgt  150900
aggaactgac ggtgttaacg ttgattactt aattcaagaa aacacagttc aacagtatga  150960
tccaactcgt ggatatttaa aagattttgt aatcattttat gataaccgct tttgggctgc  151020
tataaatgat attccaaaac cagcaggagc ttttaatgac ggacgctgga gagcattacg  151080
taccgatgct aactggatta cggtttcatc tggttcatat caattaaaat ctggtgaagc  151140
aatttcggtt aacaccgcag ctggaaatga catcacgttt actttaccat cttctccaat  151200
tgatggtgat actatcgttc tccaagatat tggaggaaaa cctggagtta accaagtttt  151260
aattgtagct ccagtacaaa gtattgtaaa cttttagagt gaacaggtac gttcagtact  151320
aatgactcat ccaaagtcac agctagtttt aatttttagt aatcgtctgt ggcaaatgta  151380
tgttgctgat tatagtagag aagctatagt tgtaacacca gcgaatactt atcaagcgca  151440
atccaacgat tttatcgtac gtagatttac ttctgctgca ccaattaatg tcaaacttcc  151500
aagatttgct aatcatggcg atattattaa tttcgtcgat ttagataaac taaatccgct  151560
ttatcataca attgttacta catacgatga aacgacttca gtacaagaag ttggaactca  151620
ttccattgaa ggccgtacat cgattgacgg tttcttgatg tttgatgata atgagaaatt  151680
atggagactg tttgacgggg atagtaaagc gcgtttacgt atcataacga ctaattcaaa  151740
cattcgtcca cattgaagaag ttatggtatt tggtgcgaat aacggaacaa ctcaaacaat 151800
tgagcttaag cttccaacta atatttctgt tggtgatact gttaaaattt ccatgaatta  151860
catgagaaaa ggacaaacag ttaaaatcaa agctgctgat gaagtaaaa  ttgcttcttc   151920
agttcaattg ctgcaattcc caaaacgctc agaatatcca cctgaagctg aatgggttac  151980
agttcaagaa ttagttttta acgatgaaac taattatgtt ccagttttgg agcttgctta  152040
catagaagat tctgatggaa aatattgggt tgtacagaaa aacgttccaa ctgtagaaag  152100
agtagattct ttaaatgatt ctactagagc aagattaggc gtaattgctt tagctacaca  152160
agctcaagct aatgtcgatt tagaaaattc tccacaaaaa gaattagcaa ttactccaga  152220
aacgttagct aatcgtactg ctacagaaac tcgcagaggt attgcaagaa tagcaactac  152280
tgctcaagtg aatcagaaca ccaattctc ttttgctgat gatattatca tcactcctaa   152340
aaagctgaat gaaagaactg ctacagaaac tcgtagaggt gtcgcagaaa ttgctacgca  152400
gcaagaaact aatgcaggaa ccgatgatac tacaatcatc actcctaaaa agcttcaagc  152460
tcgtcaaggt tctgaatcat tatctggtat tgtaaccttt gtatctactg caggtgctac  152520
tccagcttct agccgtgaat taaatggtac gaatgtttat aataaaaaca ctgataattt  152580
agttgtttca cctaaagctt tggatcagta taaagtact ccaacacagc aaggtgcagt   152640
aattttagca gttgaaagtg aagtaattgc tggacaaagt cagcaaggat gggcaaatgc  152700
tgttgtaacg ccagaaacgt tacataaaaa gacatcaact gatggaagaa ttggtttaat  152760
tgaaattgct acgcaaagtg aagttaatac aggaactgat tatactcgtg cagtcactcc  152820
taaaacttta aatgaccgta gagcaactga agtttaagt ggtatagctg aaattgctac   152880
acaagttgaa ttcgtcgcag gcgtcgacga tactcgtatc tctacaccat taaaattaa   152940
aaccagattt aatagtactg atcgtacttc tgttgttgct ctatctggat tagttgaatc  153000
aggaactctc tgggaccatt atacacttaa tattcttgaa gcaaatgaga cacaacgtgg  153060
tacacttcgt gtagctacgc aggtcgaagc tgctgcggga acattagata atgtttaat   153120
aactcctaaa aagcttttag gtactaaatc tactgaagcg caagagggtg ttattaaagt  153180
tgcaactcag tctgaaactg tgactggaac gtcagcaaat actgctgtat ctccaaaaaaa 153240
```

```
tttaaaatgg attgcgcaga gtgaacctac ttgggcagct actactgcaa taagaggttt  153300
tgttaaaact tcatctggtt caattacatt cgttggtaat gatacagtcg gttctaccca  153360
agatttagaa ctgtatgaga aaaatagcta tgcggtatca ccatatgaat taaaccgtgt  153420
attagcaaat tatttgccac taaaagcaaa agctgctgat acaaatttat tggatggtct  153480
agattcatct cagttcattc gtagggatat tgcacagacg gttaatggtt cactaacctt  153540
aacccaacaa acgaatctga gtgccctct tgtatcatct agtactggtg aatttggtgg  153600
ttcattggcc gctaatagaa catttaccat ccgtaataca ggagccccga ctagtatcgt  153660
tttcgaaaaa ggtcctgcat ccggggcaaa tcctgcacag tcaatgagta ttcgtgtatg  153720
gggtaaccaa tttggcggcg gtagtgatac gacccgttcg acagtgtttg aagttggcga  153780
tgacacatct catcacttt attctcaacg taataaagac ggtaatatag cgtttaacat  153840
taatggtact gtaatgccaa taaacattaa tgcttccggt ttgatgaatg tgaatggcac  153900
tgcaacattc ggtcgttcag ttacagccaa tggtgaattc atcagcaagt ctgcaaatgc  153960
ttttagagca ataaacggtg attacggatt ctttattcgt aatgatgcct ctaataccta  154020
ttttttgctc actgcagccg gtgatcagac tggtggtttt aatggattac gcccattatt  154080
aattaataat caatccggtc agattacaat tggtgaaggc ttaatcattg ccaaggtgt  154140
tactataaat tcaggcggtt taactgttaa ctcgagaatt cgttctcagg gtactaaaac  154200
atctgattta tatacccgtg cgccaacatc tgatactgta ggattctggt caatcgatat  154260
taatgattca gccacttata accagttccc gggttatttt aaaatggttg aaaaaactaa  154320
tgaagtgact gggcttccat acttagaacg tggcgaagaa gttaaatctc ctggtacact  154380
gactcagttt ggtaacacac ttgattcgct ttaccaagat tggattactt atccaacgac  154440
gccagaagcg cgtaccactc gctggacacg tacatgcag aaaaccaaaa actcttggtc  154500
aagttttgtt caggtatttg acggaggtaa ccctcctcaa ccatctgata tcggtgcttt  154560
accatctgat aatgctacaa tggggaatct tactattcgt gatttcttgc gaattggtaa  154620
tgttcgcatt gttcctgacc cagtgaataa aacggttaaa tttaatgggt ttgaataaga  154680
ggtattatgg aaaaatttat ggccgagttt ggacaaggat atgtccaaac gccatttta  154740
tcggaaagta attcagtaag atataaata agtatagcgg gttcttgccc gctttctaca  154800
gcaggaccat catatgttaa atttcaggat aatcctgtag gaagtcaaac atttagcgca  154860
ggcctccatt taagagtttt tgacccttcc accggagcat tagttgatag taagtcatat  154920
gccttttcga cttcaaatga tactacatca gctgcttttg ttagtttcat gaattctttg  154980
acgaataatc gaattgttgc tatattaact agtgaaaagt ttaattttcc tcctgaagta  155040
gtatcttggt taagaaccgc cggaacgtct gcctttccat ctgattctat attgtcaaga  155100
tttgacgtat catatgctgc ttttatact tcttctaaaa gagctatcgc attagagcat  155160
gttaaactga gtaatagaaa aagcacagat gattatcaaa ctattttaga tgttgtattt  155220
gacagtttag aagatgtagg ggctaccggg tttccaagga gaacgtatga aagtgttgag  155280
caattcatgt cggcagtttgg tggaactaat gacgaaattg cgagattgcc aacttcagct  155340
gctaaagta aattatctga ttataattta attcctggag atgttcttta tcttaaagct  155400
cagttatatg ctgatgctga tttacttgct cttggaacta caaatatatc tatccgtttt  155460
tataatgcat ctaacggata tatttcttca acacaagctg aatttactgg gcaagctggg  155520
tcatgggaat taaaggaaga ttatgtagtt gttccagaaa acgcagtagg atttacgata  155580
tacgcacaga gaactgcaca agctggccaa ggtggcatga gaaatttaag cttttctgaa  155640
gtatcaagaa atggcggcat ttcgaaacct gctgaatttg gcgtcaatgg tattcgtgtt  155700
aattatatct gcgaatccgc ttcaccccg gatataatgg tacttcctac gcaagcatcg  155760
tctaaaactg gtaaagtgtt tgggcaagaa tttagagaag tttaaattga gggacccttc  155820
gggttccctt tttctttata aatactattc aaataaaggg gcatacaatg gctgatttaa  155880
aagtaggttc aacaactgga ggctctgtca tttggcatca aggaaatttt ccattgaatc  155940
cagccggtga cgatgtactc tataaatcat ttaaaatata ttcagaatat aacaaaccac  156000
aagctgctga taacgatttc gttttctaaag ctaatggtgg tacttatgca tcaaaggtaa  156060
catttaacgc tggcattcaa gtcccatatg ctccaaacat catgagccca tgcgggattt  156120
atggggggtaa cggtgatggt gctacttttg ataaagcaaa tatcgatatt gtttcatggt  156180
atggcgtagg atttaaatcg tcatttggtt caacaggccg aactgttgta attaatacac  156240
gcaatggtga tattaacaca aaaggtgttg tgtcggcagc tggtcaagta agaagtggta  156300
cggctgctcc tatagcagcg aatgaccta ctagaaagga ctatgttgat ggagcaataa  156360
atactgttac tgcaaatgca aactctaggg tgctacggtc tggtgacacc atgacaggta  156420
atttaacagc gccaaacttt ttctcgcaga atcctgcatc tcaaccctca cacgttccac  156480
gatttgacca aatcgtaatt aaggattctg ttcaagattt cggctattat taagaggact  156540
tatggctact ttaaaacaaa tacaatttaa aagaagcaaa atcgcaggaa cacgtcctgc  156600
tgcttcagta ttagccgaag gtgaattggc tataaactta aaagatagaa caattttac  156660
taaagatgat tcaggaaata tcatcgatct aggttttgct aaaggcgggc aagttgatgg  156720
caacgttact attaacggac ttttgagatt aaatggcgat tatgtacaaa caggtggaat  156780
gactgtaaac ggacccattg gttctactga tggcgtcact ggaaaaattt tcagatctac  156840
acagggttca ttttatgcaa gagcaacaaa cgatacttca aatgcccatt tatggtttga  156900
aaatgccgat ggcactgaac gtggcgttat atatgctcgc cctcaaacta caactgacgg  156960
tgaaatacgc cttaggggtta gacaaggaac aggaagcact gccaacagtg aattctattt  157020
ccgtctctata aatggaggcg aatttcaggc taaccgtatt ttagcatcag attcgttagt  157080
aacaaaacgc attgcggttg ataccgttat tcatgatgcc aaagcatttg gacaatatga  157140
ttctcactct ttggttaatt atgtttatcc tggaaccggt gaaacaaatg gtgtaaacta  157200
tcttcgtaaa gttcgcgcta agtccggtgg tacaatttat catgaaattg ttactgcaca  157260
aacaggcctg gctgatgaag tttcttggtg gtctggtgat acaccagtat ttaaactata  157320
cggtattcgt gacgatggca gaatgattat ccgttaatgac cttgtagta gtacattcac  157380
tacaaattc ccgtcagtg attatggcaa cgtcggtgta atgggcgata agtatccttg  157440
tctcggcgac actgtaactg gcttgtcata caaaaaaact ggtgtatttg atctagttgg  157500
cggtggatat tctgttgctt ctattactcc tgacagtttc cgtagtactc gtaaaggtat  157560
atttggtcgt tctgaggacc aaggcgcaac ttggataatg cctggtacaa atgctgctct  157620
ttgtt ctgtctgtt caaacacaag ctgataataa caatgctgga gacggacaaa cccatatcgg  157680
gtacaatgct ggcggtaaaa tgaaccacta tttccgtggt acaggtcaga tgaatatcaa  157740
tacccaacaa ggtatggaaa ttaaccggg tatttgaaa ttggtaactg gctcaataa  157800
tgtacaattt tacgctgacg gaactatttc ttccattcaa cctattaaat tagataacga  157860
gatttttta actaaatcta ataatactgc gggtcttaaa tttggagctc ctagccaagt  157920
tgatggcaca aggactatcc aatggaacgg tggtactcgc gaaggacaga ataaaaacta  157980
```

```
tgtgattatt aaagcatggg gtaactcatt taatgccact ggtgatagat ctcgcgaaac  158040
ggttttccaa gtatcagata gtcaaggata ttatttttat gctcatcgta aagctccaac  158100
cggcgacgaa actattggac gtattgaagc tcaatttgct ggggatgttt atgctaaagg  158160
tattattgcc aacggaaatt ttagagttgt tgggtcaagc gctttagccg gcaatgttac  158220
tatgtctaac ggtttgtttg tccaaggtgg ttcttctatt actggacaag ttaaaattgg  158280
cggaacagca aacgcactga gaatttggaa cgctgaatat ggtgctattt tccgtcgttc  158340
ggaaagtaac ttttatatta ttccaaccaa tcaaaatgaa ggagaaagtg gagacattca  158400
cagctctttg agacctgtga gaataggatt aaacgatggc atggttgggt taggaagaga  158460
ttcttttata gtagatcaaa ataatgcttt aactacgata aacagtaact ctcgcattaa  158520
tgccaacttt agaatgcaat tggggcagtc ggcatacatt gatgcagaat gtactgatgc  158580
tgttcgcccg gcgggtgcag gttcatttgc ttcccagaat aatgaagacg tccgtgcgcc  158640
gttctatatg aatattgata gaactgatgc tagtgcatat gttcctattt tgaaacaacg  158700
ttatgttcaa ggcaatggct gctattcatt agggactta attaataatg gtaattccg   158760
agttcattac catggcggcg gagataacgg ttctacaggt ccacagactg ctgattttgg  158820
atgggaattt attaaaaacg gtgattttat ttcacctcgc gatttaatag caggcaaagt  158880
cagatttgat agaactggta atatcactgg tggttctggt aattttgcta acttaaacag  158940
tacaattgaa tcacttaaaa ctgatatcat gtcgagttac ccaattggtg ctccgattcc  159000
ttggccgagt gattcagttc ggtcggatt tgctttgatg gaaggtcaga cctttgataa  159060
gtccgcatat ccaaagttag ctgttgcata tcctagcggt gttattccag atatgcgcgg  159120
gcaaactatc aagggtaaac caagtggtcg tgctgttttg agcgctgagg cagatggtgt  159180
taaggctcat agccatagtg catcggcttc aagtactgac ttaggtacta aaaccacatc  159240
aagctttgac tatggtacga agggaactaa cagtacgggt ggcacactc actctggtaa  159300
tggttctact agcacaaatg gtgagcacag ccactacatc gaggcatgga atggtactgg  159360
tgtaggtggt aataagatgt catcatatgc catatccatac agggcgggtg ggagtaacac  159420
taatgcagca gggaaccaca gtcacacttt ctctttttggg actagcagtg ctggcgacca  159480
ttcccactct gtaggtattg gtgctcatac ccacacggta gcaattggat cacatggtca  159540
tactatcact gtaaatagta caggtaatac agaaaaacacg gttaaaaaca ttgcttttaa  159600
ctatatcgtt cgtttagcat aaggagaggg gcttcggccc ttctaaatat gaaaatatat  159660
cattattatt ttgacactaa agaattttac aaagaagaaa attacaaacc ggttaaaggc  159720
ctcggtcttc ctgctcattc aacaattaaa aaacctttag aacctaaaga aggatacgcg  159780
gttgtatttg atgaacgtac tcaggattgg atttatgaag aagaccatcg cggaaaacgc  159840
gcatggactt ttaataaaga agaaattttt ataagtgaca ttggaagccc ggttggtata  159900
actttcgatg agcccggcga atttgatata tggactgatg acggttggaa agaagacgaa  159960
acatataagc gagttttaat tcgtaataga aaaattgaaa aattatataa agagttccaa  160020
gttttaaata atattgattga agcttcgtc gccaataaaa aggaaaaatt ctattataaa  160080
aaccttaagc ggttctttgc tcttttagaa aagcatgagc atttaggtgg tgaattccct  160140
tcatggcctg aaaaagaaca gaagccttgg tataagcgtt tattcaagca ttacgtataa  160200
atatcttaaa aggagggtct atggcagcac ctagaatatc attttcgccc tctgatattc  160260
tatttgtgt tctagatcgc ttgttcaaag ataacgctac cgggaagtt cttgcttccc   160320
gggtagctgt cgtaattctt ttgttataa tggcgattgt ttggtatagg ggagatagtt  160380
tctttgagta ctataagcaa tcaaagtatg aaacatacag tgaaattatt gaaaaggaaa  160440
gaactgcacg ctttgaatct gtcgcccctgg aacaactcca gatagttcat atatcatctg  160500
aggcagactt tagtgcggtg tattctttcc gccctaaaaa cttaaactat tttgttgata  160560
ttatagcata cgaaggaaaa ttaccttcaa caataagtga aaaatcactt ggaggatatc  160620
ctgttgataa aactatggat gaatatacag ttcatttaaa tggacgtcat tattattcca  160680
actcaaaatt tgcttttttta ccaactaaaa agcctactcc cgaaataaac tacatgtaca  160740
gttgtccata tttttaatttg gataatatct atgctggaac gataaccatg tactggtata  160800
gaaatgatca tataagtaat gaccgccttg aatcaaatatg tgctcaggcg gccagaatat  160860
taggaagggc taaataatta tttgttcgta tacatctcta gatatcgata tacaccctca  160920
aaaccctcgt tgaattcgtc gatgagggtt ttcttatctt cttgagttaa ttcagaaaca  160980
attttacgga gtgaatttttg atttaactt ctaccttcgt gcgttactcc aatctcattt  161040
agaaatgcaa taaattagc acgattctca acaatatctc ctctggaaaa tttaatcaaa  161100
atagatgcaa cagtaataat ttcacgaact gtatcaatgt ttttattcat taactatacc  161160
actcaattag ttgactttgt tataaatatca tcagacgctt gatttgtaaa ctggtctgtg  161220
taattttctt caaaaatttt ttctacgaat tccttgaacg attcacgttc ctgagctaca  161280
ttatgctcga ttacctttttc aagattatga ctcattcgaa ataatcttca atttcataat  161340
catggacata aatcattata gtttttaata catcatcaat atttttttcct ggagctggaa  161400
ttacgtaaaa ataccctgct tttgagaggt ctttataagt tccaatcaag aaatcattat  161460
tctcaagatg taactcttca actaattcat tgacaattga atggtataag tttggcagaa  161520
acttatatag cttttctaga atatcaattt tgaatgtata ttgaaccacg gactgagaat  161580
caataatcat agaccttccc cttatgtttc tgtttgcgat tagattcttt aaacgctttc  161640
ttcttatcct tatgaacaga agctttatta aaattatgct ttgcgactaa attgttcata  161700
gtgctgaatt acctctctta aacatttgca tgtgaatgaa aacttttag ctacaccaca  161760
ttcaaatata tgttctctta aatcgcgtgt atcggtatat cccatctcaa caataaaatg  161820
ccgtattaga tttttatctt tatcgtttag agaattaaaa taatcagatt ttgaattaat  161880
ttccctggcc aaattgaatc accttcagtt gacgttttaa ctcttttatc atctcttcgt  161940
tcatcgcaat ataagatcg cgtagagcag gtttagcat tccatttact ggagaactaa  162000
atggacatac ataatcttttt cctacgagct ttttagtgaa ttccatatca cagaactgaa  162060
atcccggctc attggtataa attccccaat tagttgacat cattttattg gcatattcca  162120
gtgcctggat ttgattcata attccatcaa tttgaaactt tttaatattc attagtaaag  162180
gtcctcagag taaagttctt tttcactacc acgttcaata cttacttgtc cagcgtaagt  162240
tgcaataatc attgcttctt cacgtgtcca ataattacta tattggtcaa taaacccttg  162300
gtcatcatca caaacttgct gagtaactaa ttgaggttta actacatcta aaacttctgc  162360
catatcttta gaataatgac gagcacctgg aataataaga gttcgtccat cttttaattt  162420
aaaacggttg gctgcgcaaa caattcgtcg ttgatacttt tggttttcat cccagtacgc  162480
agtctgccaa cagatttcag gaactcttt cagaatatct tcttctgtgc atttataacc  162540
atgcgcttta aattttcaa caagactttc tggagtttca cgagataaag gaacattcag  162600
catttttaaa cgattgataa atgggttcat ttaaaccatc ctttaatacg ctgccacaaa  162660
gttttctgtt gagctttgtt gacgccaatt gagcgaataa ccggttgaga ttcctggaat  162720
```

```
tctttataat cagcaaggta aatttcgtaa gctgcatccg taaatgaact tatcgctgcc  162780
ataaaattat tgcgaatacc tactggagca tctttacttt cacgaatgat catgtattta  162840
ccagtcttaa tctttacgat agttccaaga taagctccat ggtaccaaat atcccaaccc  162900
tcttgagtag gttctgcgca acgacgaagt tcattgacaa tttctaactt gtttattatt  162960
tattcctcac agttcagatg ctacagtgat tacagcttca atgtttttctg ccgagcgttt  163020
aatgtcaaga tacacattac cgtttttagc gattttacat gacattccga tgtcagtaaa  163080
tttctgaata tgatgttcca tcattttgta tccaaaaatt cgcatatttc cattgttatt  163140
aatttcaaaa ttacgaattc cgttagtgcg tttttctaaa atagcaagat aattactacg  163200
ataaatttca acctttttaa gaacaaatcc atttttatct aaaagtttta acatgaggtc  163260
tttatcttct tccatatcgg aagtaatctc gcgagcttta cgagttgctc gttttttcag  163320
cagttccgga gcattttcct gtgcatataa agttgctgca tttgaaataa tatcctgagc  163380
ttcaccagta atgattaatc catcaccaga tttctccacc aggccttttt taatcaatac  163440
cccaatatta ctattaacta ctgcgttacc taaatctgga tgcacctcac gaacttctgc  163500
agctgtaatg aaatcttctc tagcaatggt aattaaaatc gtagcagttt tttcattcag  163560
aacatcgtta gaagctttga tgatgtaagt tactttagac attttctaat ctccgtaatt  163620
ctgtatcagt agttgatagt tgtatagtac cacagtatgc tttggttgta aaccgttttg  163680
tgaaaaaatt tttaaaataa aaaagggaga gcctcggctc tccctaaaat tactgcatga  163740
ctgtgataac tgtcatgata acacgttgaa ttccgaacgc aagaagacct cctgctacgg  163800
ctggaacaac gcctaaaccc gccagtaaaa tgctaccaga tactaatgca gcgcttgtaa  163860
taccaatgaa tggactcatt tgatttcctc taaatctttg gtgtattcag taactacatc  163920
agtagttttc caatattcgt tttcttcttt tttagcttta gcttcttcag caagtttctt  163980
tgcttcatcg gaagtcatat gaaaaatatt cattccaact agtttatcaa cataagaaga  164040
atacatatcg attttcgaaa gttcttcggt cagttcttta cgagttttac cctgtacaac  164100
aatttcacct gaaattactt tcttaatgaa atgtgctttg gcaaaggcta aacgaaaagc  164160
tgactcagtt tctttaattt tgttatcaat tcgttttttgg acataagttt tacgaacttc  164220
aacaaagtct ttaattaaat caactacgtt atcgtaaact tgcagctttc cttttctcatt  164280
aataaccgta atattctggg aacgacgctc aatcagtccg aagtcttttca taatttttgc  164340
atggcgttct tcttcgttat cgctcaaaga atatctttg cggaatttaa ctttgaagcc  164400
aaaaccatgc tcaccacaag catcatccca tgtaatgaag cctttatttt caagtgggtc  164460
taagatttta ctcacataag tttcacgatc atacttatac ggaatctcag tgatatgcat  164520
ttgagttcgt gaagtaaact tatatgttcc acgaatttca tattgcccat caatttcaac  164580
gacttcacca cgaaattctg ggaattctac tttcggttta gttactttct ttccttgaag  164640
agcttgcagt acagctttct tgacagaaga aacactatga ggaagaatgt aagttgcata  164700
accagttgca ataccggaaa cgccattaag aagaacagta ggaataatga gcaaatagaa  164760
agcaggcgga atgtgttctt tatcttgatg taccggagca tattcagtat ctttatatac  164820
gttatagaaa ttttttactta cacgagcaaa aatataacga cttgccgctg cctttttggac  164880
agtacgagaa ccaaagtttc cttgaccatc taacagagga aagttattat tccaagtatt  164940
agccatcaaa gcacctgcgt cttgtgcaga gttttcacca tgatgatatc caaggtccgc  165000
tacaccacct gcaatagaag cgagtttgtg aaacttatct ttatttcctc gtgccaaatc  165060
aagagctcga gcaataacaa atcgttgaac tggcttaaat ccatcaatca tatttgggat  165120
agcacgattt tcaaccgtgt acatagcata agccaatgct tcattatcaa tgatactttt  165180
taaatcgcga ttattcagtt gcataaattt accatactag tgaatgtagt gccataataa  165240
catcagaaat gaaaagcacg acttgaatta atccgtaata tactccgtaa tatagtgcta  165300
ccaataaagc agcaagggct aatgaatagc ccaagatttc cttaatcatt agataacaac  165360
acaaatgtta aatatgcaca catcccctgg gctaaagctt gtgaaaacac actgctagca  165420
tcgatacaga tagttaaaac acatgctact atccaacaaa taaatgaaat aactcctaat  165480
aattttgcaa tattcatatt ttcctcactg gcgtccgaag acgccttttag ttttaagatt  165540
gttacgatag aactgcatca cgtgttcgtt atggaaatta ctcattaata tgcctgtaaa  165600
acaaatttaa agttatcagc caacatacgg ttcatttctt cgagtgtttg atactcagaa  165660
tgatgattac gagtaaacgc caaagctagc tgaccttttc caaatcccgt cgttagaggt  165720
ttcatcttag aagcaggcag ataaaacact gtgtatggaa cattgttatt tgcaatgata  165780
cgcgcaagtt gagaccggcg ttgacgaata tgacttaaaa ccgcactgaa tccttgctta  165840
gaacgctgat tacctacata aaatcgtgca gatacgcatg gattactaaa tggaccaccg  165900
agtttactca ctaaaaagta aaatccaggt ttagataaaa tatctttatg cggagttcct  165960
aaaaaccatt caccacccctt gattgtacca ataacagtag cgcctgcatc attcagatca  166020
gtaacagtca tatatttcat attaatttcc tctaaattat tttctactcc aaggccgcat  166080
gaatacacac ggccattaaa ttactcgtcg cagtcgacgc tcaattccca aaactcttct  166140
acagtataag tttcagtatc attttcaata cagaaacgtt cattactatt atttgctaaa  166200
gtagcattaa ctgtcatttt ttcgctagtg tcttaagag gtgaaatacg aattaactga  166260
tcaccgttat ctaaacaaaa aatttcacca acttttacat cttaaaaact tttcataatt  166320
cacctcaagg agtataaaat ccaaatgcag ttgttgacca tcccatccaa tatggaaat  166380
ttacaccaat gtaaaacata agaatataaa accaaccgct cagcaaattc atcatttac  166440
accattccaa attgtttcaa ccacggattt taaaccattt tgatgaatat ccattcctac  166500
taccgccatc aataaaattc caactacaac tgaacctaag gcaaaaatca gcatgaaaat  166560
gaataaagcc ggaaaaatat tatcgaaaaa ccattcaata aatgtaaaag cactgcgttt  166620
acgttcatat tttcctcaca taaatccaaa gtaaacgttt aatacatcaa tcattaaaac  166680
gattgggaat atactcaaaa ctattagtat tataactaca ttccatatag ctttaataat  166740
cttttcatt ttctgttcct ccatagttga tagggtaata gtaccacgga agaacagtct  166800
tgtaaacaac tttttaaaa atattcgtaa taatgtaa taccaactac taccgctgaa  166860
acctgtcaa cccaccacgc acaagcaata agtacagaat tcaaaatttt cataataacc  166920
tcattacaaa agtaaatgtt aaacaaatta ctggaatact aattaaccaa acaaaacacc  166980
accataatga actcatagtt caatctcagc gattttcatt ttattctcca aatccgtatc  167040
agtagttgat agttgtatag taccacggtc cttgtggtat gtaaactgtt ttgtgaaatt  167100
ttttaaatgg aaagatacca tccgttgtag ttgctttctc ttacaacttt acgaaggtct  167160
tctctgtcac cgatgaactt cggagtgtac tggatgacac ctggatgaat ttctttagtg  167220
ttgaatataa ttatacagtc agcgacttga tgatttagaa tgggcccttag atttattcca  167280
gaaccatatg gatactctcc gctgcatccc gttgttaccg aaatccaacg tgagtcagtt  167340
tgatgtgtct taacttctac acgaagcccg cagtattttg gatgagccaa tacatcccat  167400
gcatatgtgt acggatcatc gacatcctct tggcctttat tgacatatcc actcaaccaa  167460
```

```
tctgccacaa aaaactctgc gtacacagcg atacggcatc tttcgataac ttctgcctta    167520
tcttgatttg ggttttgttt taaagagtat cttgcagtat cagcaatttt gaccttcatt    167580
tcacaggtca agtcactgtt cgatagggta aatgtcggaa tctgaaatag tctctgtaac    167640
ccaggattcg ttttctgcat ttaaactttc ctttatgtcg gaatccccga tattcatata    167700
aatcataatt tctcttaaaa caaaaggccg aagcccttta ttttacttga attgtgcaat    167760
tcttttctct agacattcag cataagattt cattgagatg aactgcgaaa gtagcagttc    167820
ttgctcaact gcgctaactg ttagaaactt tgcgctttct aaaaatttgc tcagtgcatt    167880
aattttgagc attaattgat cgtattcttc ttttactcgt gcttgataag ctaacataat    167940
tttccttagt taagggccga agccttattt aaattgttca gtaacgtctt caactacttc    168000
atattggcag gtacgcattt tagcatcgtt gtaatcaatc ggaattgata ctacatcgcg    168060
aggatgaact ttaactttta caactcggct ggttgaacta ccaaagtgac gaatataaga    168120
tttagaacac acatgcaaac cacgagaaca agtttgtgta tcatcgtcat tcacacgagt    168180
acgtggcatt ttaactactt tacccggact gttatcaaag gtgtttgagt gacagtcaaa    168240
gtaattgctg cgaactactt tccaagcata gaagtaacca tcttctgtaa tttcaatatc    168300
gtttgctacc aagaaatcaa agagtcgaga taccgctttt tggcttgggt tttccaacag    168360
attttccaag aacggaaaat aaaattcaaa gttttcgcct ttttccatcg agtcaagaat    168420
acgatcaacc aaaccagacc gcaattcaat attttgatag aacaagcttc caccttcaat    168480
tcgaacatcg ccggaaatat atttttcaac agcacgacga acattaattt tttgtgccgc    168540
ttcttccaac ttatccgcta caagcagatt aagaattttcc tggaagtttg aatgagtatt    168600
aggagttgcg ttataagtta cgccatcaac agtaattgaa atgaattttt tagatgcatt    168660
ccaaataatg tcagatttag caactggagc aataactgca tcgctattaa ctttaactgt    168720
aatatcaccg ctaatagtaa ctttagggcg tttagcttct tcagcatttt tcaaaacacg    168780
acggattgtg tcaaccgata caccttgcca atcagccaat tcctgttggg tgtaattacc    168840
acttgaatac agtttaacaa tttcagcttg ttcgtttttg gtcaggcatt taatattgta    168900
cat                                                                   168903

SEQ ID NO: 6           moltype = DNA  length = 32
FEATURE                Location/Qualifiers
source                 1..32
                       mol_type = other DNA
                       organism = synthetic construct
SEQUENCE: 6
cgaatgacca ggcatttacc gaccagccca tc                                  32

SEQ ID NO: 7           moltype = DNA  length = 32
FEATURE                Location/Qualifiers
source                 1..32
                       mol_type = other DNA
                       organism = synthetic construct
SEQUENCE: 7
agtgggaagg gttgcaggac accgtctttg cc                                  32

SEQ ID NO: 8           moltype = DNA  length = 32
FEATURE                Location/Qualifiers
source                 1..32
                       mol_type = other DNA
                       organism = synthetic construct
SEQUENCE: 8
ccgatgttac cttcctgaat caaatccgcc tg                                  32

SEQ ID NO: 9           moltype = DNA  length = 32
FEATURE                Location/Qualifiers
source                 1..32
                       mol_type = other DNA
                       organism = synthetic construct
SEQUENCE: 9
tgattgacgg ctacggtaaa ccggcaacgt tc                                  32

SEQ ID NO: 10          moltype = DNA  length = 32
FEATURE                Location/Qualifiers
source                 1..32
                       mol_type = other DNA
                       organism = synthetic construct
SEQUENCE: 10
gctgttaacg tacgtaccgc gccgcatccg gc                                  32
```

TREATING AND PREVENTING E COLI INFECTIONS

CROSS REFERENCE TO RELATED APPLICATIONS

This application claims benefit of Great Britain Application No.: GB2209518.6, filed on Jun. 29, 2022, the disclosures of which are herein incorporated by reference in their entirety.

REFERENCE TO AN ELECTRONIC SEQUENCE LISTING

The contents of the electronic sequence listing (786212001400SEQLIST.xml; Size: 181,640 bytes; and Date of Creation: Jul. 12, 2022) is herein incorporated by reference in its entirety.

TECHNICAL FIELD

The technology described herein relates to methods and compositions for treating or preventing an infection by $E$ $coli$ cells in human or animal subjects. The method comprises administering to the subject a plurality of transduction particles that encode a nuclease for targeting the genomes of B2 phylogroup $E$ $coli$ cells.

BACKGROUND $E$ $coli$ infection has been identified as harmful or life-threatening in various settings, such as UTI infections, transplant patients, cancer patients and other patients that are immunocompromised or on immunosuppressant.

Nuclease targeting of $E$ $coli$, such as by means of CRISPR/Cas systems, has been proposed with delivery using transduction particles that can target the nuclease to $E$ $coli$ cells for chromosomal or episomal cutting, thereby killing cells or reducing their growth or proliferation. Suitable transduction particles are phage or engineered particles (such as non-self-replicative transduction particles) comprising capsids that contain nucleic acid encoding at least crRNAs or gRNAs (or additionally a Cas nuclease) for targeting. Advantageously, selective targeting can be achieved which is not possible using conventional antibiotics, such as broad-spectrum antibiotics. Such selective targeting can avoid killing of beneficial species and strains in treated patients. Indeed, disturbances of the microbiome with broad-spectrum antibiotics is a risk-factor in the prophylactic management of cancer patients at risk of febrile neutropenia.

Bacteriophage (phage) therapy has been used prior to the broad availability of antibiotics, but has now re-gained interest due to the rise in bacterial antimicrobial resistance (AMR) combined with several successful individual case reports.

Bacteriophages (phages) are a phylum of viruses that infect bacteria, and are distinct from the animal and plant viruses. Phages can have either a "lytic" life cycle, a "lysogenic" life cycle that can potentially become lytic, or a "non-lytic" life cycle. Phages replicating through the lytic cycle cause lysis of the host bacterial cell as a normal part of their life cycles. Phages replicating through the lysogenic cycles are called temperate phages, and can either replicate by means of the lytic life cycle and cause lysis of the host bacterium, or they can incorporate their DNA into the host bacterial DNA and become noninfectious prophages.

The natural capability of phages to infect and kill bacteria, together with the specificity of the phage-bacterial interactions, is the basic phenomena on which the concept of phage therapy is built.

Therefore, phages that possess lytic life cycle are suitable candidates for phage therapy.

International Patent Application No. WO 00/69269 discloses the use of certain phage strain for treating infections caused by Vancomycin-sensitive as well as resistant strains of $Enterococcus$ $faecium$, and International Patent Application No. WO 01/93904 discloses the use of bacteriophage, alone or in combination with other anti-microbial means, for preventing or treating gastrointestinal diseases associated with the species of the genus $Clostridium$.

US Patent Application No. 2002/0001590 discloses the use of phage therapy against multi-drug resistant bacteria, specifically methicillin-resistant $Staphylococcus$ $aureus$, and International Patent Application No. WO 02/07742 discloses the development of bacteriophage having multiple host range.

The use of phage therapy for the treatment of specific bacterial-infectious disease is disclosed, for example, in US Patent Application Nos. 2002/0044922; 2002/0058027 and International Patent Application No. WO 01/93904.

US20160333348 describes the use of CRISPR/Cas systems delivered to host bacterial cells using phage as vectors.

Amongst the several phylogroups of $E$ $coli$, it has been observed that antibitic-resitant (eg, fluoroquinolone (FQ)-resistant) and multi-drug resistant (MDR) strains are frequently found in the B2 phylogroup. B2 strains ST131 and ST1193 have been found that are associated with antibiotic resistance. ST132 is a globally dominant multidrug resistant clone associated with high rates in rUTI. ST131 is a major contributor to hospital- and community-acquired UTI, as well as $E$ $coli$ bloodstream infections and infections in companion animals and poultry. Originally identified in 2008, ST131 is associated with the worldwide spread of the CTX-M-15 extended spectrum β-lactamase (ESBL) resistance gene. ST131 is now strongly associated with multidrug resistance (MDR), including resistance to fluoroquinolones. Recent reports have also identified strains that are resistant to last-line carbapenems. Sequence type 1193 has recently emerged as a new, virulent and resistant lineage among fluoroquinolone resistant $E$ $coli$.

Classic antibiotics, such as FQ and broad-spectrum antibiotics are not, thus, sufficiently effective for combatting such infections. There is, therefore, a need to find alternative means to address these infections.

SUMMARY OF THE INVENTION

The invention provides means for treating or preventing B2 phylogroup $E$ $coli$ infections in humans and animals by combining the use of selective killing with nucleases targeted using specific types of transduction particles. The particles of the invention target by adhesion to LPS, LamB or Tsx, which has surprisingly been found highly advantageous for killing and inhibiting growth of B2 $E$ $coli$ cells of many different strains (including the potentially lethal ST131 and ST1193 strains). As exemplified herein, surprisingly more than 10 different ST131 strains were killed (plaques formed) and more than 10 different ST1193 strains were killed (plaques formed).

The invention finds utility, for example, to treat or prevent potentially life-threating B2 phylogroup $E$ $coli$ infections in patients, such as in immunosuppressed, cancer, transplant and UTI patients, who are susceptible to infection by B2 strains (and often by multiple different B2 strains). As demonstrated in the Examples, the invention is useful for preventing *E coli* B2 phylogroup bacteraemia (infection of the blood stream by *E coli*) in a subject.

To this end, the invention provides:—

In a First Configuration

In a First Aspect:—

A composition comprising a plurality of transduction particles for use in a method of treating or preventing an infection by *E coli* cells in a human or animal subject, wherein the method comprises administering the particles to the subject, wherein
  (a) each particle comprises a nucleic acid encoding a nuclease for targeting the genomes of *E coli* cells, wherein the said administered particles contact the cells and introduce therein the nucleic acid, wherein the nuclease is expressed in the cells and cuts genomic DNA of the cells, thereby killing the cells or reducing growth or proliferation of the cells in the subject;
  (b) the *E coli* cells are cells of *E coli* phylogroup B2; and
  (c) each particle comprises an adhesion moiety for recognising and binding to a cognate moiety selected from a LPS, LamB and Tsx displayed on the surface of the phylogroup B2 *E coli* cells.

In a Second Aspect:—

A composition comprising a plurality of transduction particles for use in a method of treating or preventing *E coli* bacteriaemia in a human or animal subject, wherein the method comprises administering the particles to the subject, wherein
  (a) each particle comprises a nucleic acid encoding a nuclease for targeting the genomes of cells of said *E coli*, wherein the said administered particles contact the cells and introduce therein the nucleic acid, wherein the nuclease is expressed in the cells and cuts genomic DNA of the cells, thereby killing the cells or reducing growth or proliferation of the cells in the subject;
  (b) the *E coli* cells are cells of *E coli* phylogroup B2; and
  (c) each particle comprises an adhesion moiety for recognising and binding to a cognate moiety selected from a LPS, LamB and Tsx displayed on the surface of the phylogroup B2 *E coli* cells.

In a Second Configuration

In a First Aspect:—

A method for treating or preventing an infection by *E coli* cells in a human or animal subject, the method comprising administering to the subject a plurality of transduction particles, wherein
  (a) each particle comprises a nucleic acid encoding a nuclease for targeting the genomes of *E coli* cells, wherein the said administered particles contact the cells and introduce therein the nucleic acid, wherein the nuclease is expressed in the cells and cuts genomic DNA of the cells, thereby killing the cells or reducing growth or proliferation of the cells in the subject;
  (b) the *E coli* cells are cells of *E coli* phylogroup B2; and
  (c) each particle comprises an adhesion moiety for recognising and binding to a cognate moiety selected from a LPS, LamB and Tsx displayed on the surface of the phylogroup B2 *E coli* cells.

In a Second Aspect:—

A method for treating or preventing an infection by *E coli* cells in a human or animal subject, the method comprising administering to the subject a plurality of transduction particles, wherein
  (a) each particle comprises a nucleic acid encoding a crRNA or guide RNA that is operable with a Cas nuclease for chromosomal targeting in the cells, wherein the said administered particles contact the cells and introduce therein the nucleic acid, wherein the crRNA or guide RNA is expressed and guides the Cas nuclease wherein the nuclease cuts the chromosomes of the cells, thereby killing the cells or reducing growth or proliferation of the cells in the subject;
  (b) the *E coli* cells are cells of *E coli* phylogroup B2; and
  (c) each particle comprises an adhesion moiety for recognising and binding to a cognate moiety selected from a LPS, LamB and Tsx displayed on the surface of the phylogroup B2 *E coli* cells.

In a Third Aspect:—

A method for treating or preventing *E coli* bacteriaemia in a human or animal subject, the method comprising administering to the subject a plurality of transduction particles, wherein
  (a) each particle comprises a nucleic acid encoding a nuclease for targeting the genomes of cells of said *E coli*, wherein the said administered particles contact the cells and introduce therein the nucleic acid, wherein the nuclease is expressed in the cells and cuts genomic DNA of the cells, thereby killing the cells or reducing growth or proliferation of the cells in the subject;
  (b) the *E coli* cells are cells of *E coli* phylogroup B2; and
  (c) each particle comprises an adhesion moiety for recognising and binding to a cognate moiety selected from a LPS, LamB and Tsx displayed on the surface of the phylogroup B2 *E coli* cells.

In a Fourth Aspect:—

A method for treating or preventing *E coli* bacteriaemia in a human or animal subject, the method comprising administering to the subject a plurality of transduction particles, wherein
  (a) each particle comprises a nucleic acid encoding a crRNA or guide RNA that is operable with a Cas nuclease for chromosomal targeting in cells of said *E coli*, wherein the said administered particles contact the cells and introduce therein the nucleic acid, wherein the crRNA or guide RNA is expressed and guides the Cas nuclease wherein the nuclease cuts the chromosomes of the cells, thereby killing the cells or reducing growth or proliferation of the cells in the subject;
  (b) the *E coli* cells are cells of *E coli* phylogroup B2; and
  (c) each particle comprises an adhesion moiety for recognising and binding to a cognate moiety selected from a LPS, LamB and Tsx displayed on the surface of the phylogroup B2 *E coli* cells.

In a Third Configuration

In a First Aspect:—

Use of a composition comprising a plurality of transduction particles in a method for treating or preventing an infection by phylogroup B2 *E coli* cells in a human or animal subject, the method comprising administering to the subject the composition, wherein
  (a) each particle comprises a nucleic acid encoding a nuclease for targeting the genomes of *E coli* cells, wherein the said administered particles contact the cells and introduce therein the nucleic acid, wherein the nuclease is expressed in the cells and cuts genomic DNA of the cells, thereby killing the cells or reducing growth or proliferation of the cells in the subject; and
  (b) each particle comprises an adhesion moiety for recognising and binding to a cognate moiety selected from a LPS, LamB and Tsx displayed on the surface of the phylogroup B2 *E coli* cells.

In a Second Aspect:—

Use of a composition comprising a plurality of transduction particles in a method for treating or preventing an infection by phylogroup B2 *E coli* cells in a human or animal subject, the method comprising administering to the subject the composition, wherein
- (a) each particle comprises a nucleic acid encoding a crRNA or guide RNA that is operable with a Cas nuclease for chromosomal targeting in the cells, wherein the said administered particles contact the cells and introduce therein the nucleic acid, wherein the crRNA or guide RNA is expressed and guides the Cas nuclease wherein the nuclease cuts the chromosomes of the cells, thereby killing the cells or reducing growth or proliferation of the cells in the subject;
- (b) the *E coli* cells are cells of *E coli* phylogroup B2; and
- (c) each particle comprises an adhesion moiety for recognising and binding to a cognate moiety selected from a LPS, LamB and Tsx displayed on the surface of the phylogroup B2 *E coli* cells.

In a Third Aspect:—

Use of a composition comprising a plurality of transduction particles in a method for treating or preventing phylogroup B2 *E coli* bacteraemia in a human or animal subject, the method comprising administering to the subject the composition, wherein
- (a) each particle comprises a nucleic acid encoding a nuclease for targeting the genomes of cells of said *E coli*, wherein the said administered particles contact the cells and introduce therein the nucleic acid, wherein the nuclease is expressed in the cells and cuts genomic DNA of the cells, thereby killing the cells or reducing growth or proliferation of the cells in the subject; and
- (b) each particle comprises an adhesion moiety for recognising and binding to a cognate moiety selected from a LPS, LamB and Tsx displayed on the surface of the phylogroup B2 *E coli* cells.

In a Fourth Aspect:—

Use of a composition comprising a plurality of transduction particles in a method for treating or preventing phylogroup B2 *E coli* bacteraemia in a human or animal subject, the method comprising administering to the subject the composition, wherein
- (a) each particle comprises a nucleic acid encoding a crRNA or guide RNA that is operable with a Cas nuclease for chromosomal targeting in cells of said *E coli*, wherein the said administered particles contact the cells and introduce therein the nucleic acid, wherein the crRNA or guide RNA is expressed and guides the Cas nuclease wherein the nuclease cuts the chromosomes of the cells, thereby killing the cells or reducing growth or proliferation of the cells in the subject;
- (b) the *E coli* cells are cells of *E coli* phylogroup B2; and
- (c) each particle comprises an adhesion moiety for recognising and binding to a cognate moiety selected from a LPS, LamB and Tsx displayed on the surface of the phylogroup B2 *E coli* cells.

DETAILED DESCRIPTION

Figure 1:
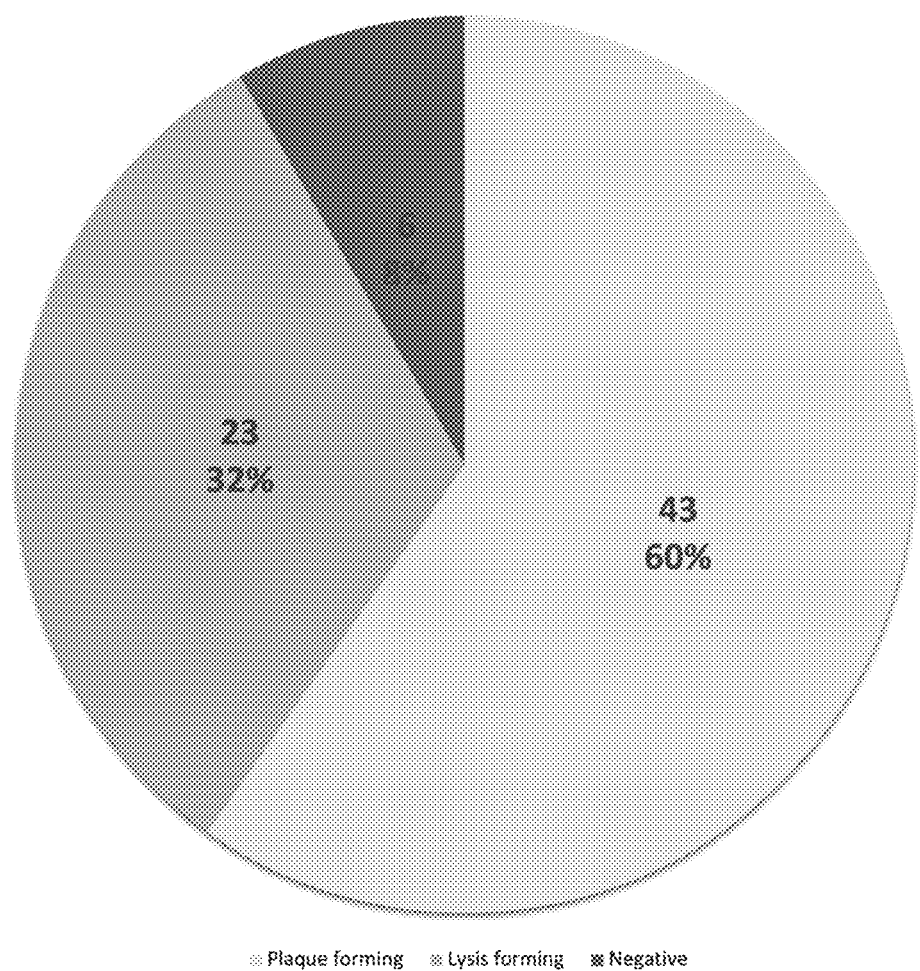
FIG. 1: Killing and growth inhibition activity of a composition of the invention when tested against *E coli* of several different phylogroups and different strains within each group (*E coli* taken from clinical samples); the composition was surprisingly highly effective at killing across many phylogroups (and particularly in the B2 phylogroup, where multiple strains—including those known to be potentially life-threatening and related with antibiotic resistnance—were killed or whose growth was effectively inhibited). The 6 negatives comprised non *E coli* and non FQ resistant samples.

The invention finds application to combat harmful or life-threatening B2 *E coli* infections in various settings, such as UTI infections, transplant patients, cancer patients and other patients that are immunocompromised or on immunosuppressant.

Cancer treatment continues to advance and survival rates for people with hematological malignancies are increasing. However, this population is immunocompromised and chemotherapy regimens cause bone-marrow suppression and gastrointestinal mucositis with associated increased intestinal permeability. Translocation of gut bacteria, including *E coli*, from the gastrointestinal tract is a frequent cause of bloodstream infections (BSIs). The mortality-related to BSIs can be up to 50%; thus, antimicrobial prophylaxis is applied in people at risk of febrile neutropenia. There are no approved therapies for the prevention of BSIs in patients with hematological cancers, yet fluoroquinolones are used off-label in the United States. This antibiotic prophylaxis practice is at odds with the emerging paradigm that maintaining a normal microbiome is important for upholding immunological tonus potentially benefiting the outcome of oncology treatments. Indeed, disturbances of the microbiome with broad-spectrum antibiotics is a risk-factor in the prophylactic management of patients at risk of febrile neutropenia. Beyond the side effects of fluoroquinolones, including safety warnings and precautions, bacterial resistance is rising and approaching 60% in USA.

In immunocompromised patients with hematological malignancies at risk of developing neutropenia, *E coli* is responsible for 25.1-30% of all bacteraemia cases with a 35.8% 90-day mortality rate. Moreover, up to 65% of *E coli* isolated as the causative pathogen from BSIs in patients with hematological cancers undergoing hematopoietic stem cell transplantation (HSCT) were resistant to fluoroquinolones. Accordingly, novel narrow-spectrum treatment and prophylactic options are needed to prevent infections in these vulnerable patients. The invention addresses this need.

To this end, the invention provides compositions, methods and uses according to the above Configurations. There is, thus, provided the following description with numbered Embodiments.

1. A composition comprising a plurality of transduction particles for use in a method of treating or preventing an infection by *E coli* cells in a human or animal subject, wherein the method comprises administering the particles to the subject, wherein
    - (a) each particle comprises a nucleic acid encoding a nuclease for targeting the genomes of *E coli* cells, wherein the said administered particles contact the cells and introduce therein the nucleic acid, wherein the nuclease is expressed in the cells and cuts genomic DNA of the cells, thereby killing the cells or reducing growth or proliferation of the cells in the subject;
    - (b) the *E coli* cells are cells of *E coli* phylogroup B2; and (c) each particle comprises an adhesion moiety for recognising and binding to a cognate moiety selected from a LPS, LamB and Tsx displayed on the surface of phylogroup B2 *E coli* cells.

2. A method for treating or preventing an infection by *E coli* cells in a human or animal subject, the method comprising administering to the subject a plurality of transduction particles, wherein the method comprises administering the particles to the subject, wherein
(a) each particle comprises a nucleic acid encoding a nuclease for targeting the genomes of *E coli* cells, wherein the said administered particles contact the cells and introduce therein the nucleic acid, wherein the nuclease is expressed in the cells and cuts genomic DNA of the cells, thereby killing the cells or reducing growth or proliferation of the cells in the subject;
(b) the *E coli* cells are cells of *E coli* phylogroup B2; and
(c) each particle comprises an adhesion moiety for recognising and binding to a cognate moiety selected from a LPS, LamB and Tsx displayed on the surface of the phylogroup B2 *E coli* cells.

Optionally, the genomic DNA is chromosomal DNA of the cells. Additionally or alternatively, the genomic DNA is plasmid DNA of the cells.

Optionally, each particle comprises a nucleic acid encoding a nuclease for chromosomal targeting, wherein the said administered particles contact the cells and introduce therein the nucleic acid, wherein the nuclease is expressed in the cells and cuts the chromosomes of the cells, thereby killing the cells or reducing growth or proliferation of the cells in the subject.

The human may be a male or female. The human may be an adult or child. The human may be 18 years of age or older, eg, 40, 50, 60, 70 80 or older. The human may be younger than 18, eg, a teenager, eg, a baby, eg, up to 5 years of age, eg, up to 2 years of age. The animal may be be a livestock or companion animal eg, a dog or cat). The animal may be a bird (eg, a poultry bird, eg, a chicken, turkey or duck, preferably a chicken), cow, sheep, goat or pig (eg, a neonatal swine or a swine under 6 months of age).

The infection may be a bloodstream infection. The infection may be a nosocomial infection.

In an example, each adhesion moiety is a tail fibre protein. In an example, each particle comprises a phage tail fibre that comprises or is fused to a said adhesion moiety. In an example, each adhesion moiety is an antibody fragment, eg, an antibody single variable domain. In an example, each adhesion moiety is a nanobody. In an example, each adhesion moiety comprises an antibody binding site that is capable of binding to the cognate moiety. For example, each adhesion moiety comprises an antibody single variable domain (ie, a dAb), such as a nanobody. In an example, each particle comprises one or more phage tail fibres or spikes, each fibre or spike comprising a said adhesion moiety.

For example, at least 2, 3 or 4 different types of said transduction particle are administered to the subject and each type comprises one or a plurality of types of tail fibres comprising adhesion moieties, wherein the other particle types do not comprise said one or plurality of tail fibre types. In an example, each type of said plurality of tail fibre types differs from the other types by the type of adhesion moiety it comprises.

Optionally, the particles comprise adhesion moieties for binding to LPS, LamB and Tsx. Optionally, the particles comprise adhesion moieties for binding to LamB and Tsx. Optionally, the particles comprise adhesion moieties for binding to LPS and Tsx. Optionally, the particles comprise adhesion moieties for binding to LPS and LamB.

In Gram-negative bacteria, the peptidoglycan layer is relatively thin and is located inward of the outer membrane, the major component of the cell wall. These two layers are connected by Braun's lipoproteins. The outer membrane is a sophisticated structure composed of a lipid bilayer ornamented with proteins, polysaccharides and lipids; the latter two molecules form the LPS layer. LPSs are complexes that consist of three parts: lipid A, the core polysaccharide and the O-polysaccharide. Lipid A is, in general, composed of fatty acids attached to glucosamine phosphate disaccharides. The core polysaccharide is connected to the lipid A through a ketodeoxyoctonate linker. The core polysaccharide and the O-polysaccharide (O-chain or O-antigen) contain several units of sugar residues extending outward to the outer membrane. Cells that contain all three components of the LPS are denominated as smooth (S) type and those that lack the O-polysaccharide portion are distinguished as rough (R) type.

Optionally, the LPS is smooth LPS or rough LPS.

For example, the particles comprise at least one type of particle whose adhesion moiety is capable of binding to O-antigen of LPS.

*E coli* is a very versatile species for which diversity has been explored from various perspectives highlighting, for example, phylogenetic groupings, pathovars as well as a wide range of O serotypes. The highly variable O-antigen, the most external part of the lipopolysaccharide component of the outer membrane of *E coli*, is linked to the innermost lipid A through the core region of LPS of which 5 different structures, denominated K-12, R1, R2, R3 and R4, have been characterized so far. Phylogroups B2 and C strains are mainly dominated by the R1 type. Strains within phylogroup B2 may carry a K-12 core, eg, belonging to the complex STc131, one of the major clone of extra-intestinal pathogenic *E coli* (ExPEC) strains.

Preferably, the LPS comprises a R1 core region. In an example, the LPS comprises a R2 core region. In an example, the LPS comprises a R3 core region. In an example, the LPS comprises a R4 core region. In an example, the LPS comprises a K-12 core region.

Optionally, the LamB comprises the amino acid of SEQ ID NO: 1 or an amino acid sequence that is at least 70, 80, 90 or 95% identical to SEQ ID NO: 1. Optionally, the Tsx comprises the amino acid of SEQ ID NO: 2 or an amino acid sequence that is at least 70, 80, 90 or 95% identical to SEQ ID NO: 2. Optionally, the LamB is encoded by the nucleotide sequence of SEQ ID NO: 3 or an amino acid sequence that is at least 70, 80, 90 or 95% identical to SEQ ID NO: 3. Optionally, the Tsx is encoded by the nucleotide sequence of SEQ ID NO: 4 or an amino acid sequence that is at least 70, 80, 90 or 95% identical to SEQ ID NO: 4.

The *Escherichia coli* tsx gene encodes an integral outer-membrane protein (Tsx) that functions as a substrate-specific channel for deoxynucleosides and the antibiotic albicidin. In an example, the Nucleoside-specific channel-forming protein Tsx of *E coli* has a Uniprot Accession Number of P0A927 or is a homologue thereof. In an example, the maltose outer membrane porin (maltoporin) LamB of *E coli* has a Uniprot Accession Number of P02943 or is a homologue thereof.

Homologue: A gene, nucleotide or protein sequence related to a second gene, nucleotide or protein sequence by descent from a common ancestral DNA or protein sequence. The term, homologue, may apply to the relationship between genes separated by the event of or to the relationship between genes separated by the event of genetic duplication.

In an embodiment, the *E coli* cells comprise UPEC *E coli*. In an embodiment, the *E coli* cells comprise intestinal pathogenic *E coli* (ExPEC) cells.

3. The composition or method of Embodiment 1 or 2 respectively, wherein the method is for treating or preventing infection of the subject by an *E coli* strain selected from the group ST131, ST1193, ST648, ST315, ST405, ST361, ST88 and ST453.

In a preferred example, the strain is ST1193. In another preferred example, the strain is ST131.

4. The composition or method of any preceding Embodiment, wherein the method is for treating or preventing infection of the subject by a plurality of different phylogroup B2 strains of *E coli*; optionally wherein the plurality comprises *E coli* ST131 and ST1193 cells. *E coli* ST131 and/or ST1193 have been found to be virulent and associated with fluoroquinolone resistance. As shown in the Example section herein, the invention is useful for treating or preventing infection by such strains. Optionally, said plurality of strains comprises *E coli* ST131 and/or ST1193 strains. Optionally, said plurality of strains comprises fluoroquinolone-resistant strains. For example, said plurality of strains comprises *E coli* ST131 and/or ST1193 fluoroquinolone-resistant strains. *E coli* strains B2-ST73 (CH24-30); B2-ST73 (CH24-103); B2-ST131 (CH40-30); B2-ST141 (CH52-5); B2-ST372 (CH103-9); B2-ST404 (CH14-27); B2-ST404 (CH14-807) and B2-ST1193 (CH14-64) have been found in UTI settings. In an embodiment (eg, wherein the subject is suffering from or at risk of UTI), the B2 *E coli* comprise one or more strains selected from B2-ST73 (CH24-30); B2-ST73 (CH24-103); B2-ST131 (CH40-30); B2-ST141 (CH52-5); B2-ST372 (CH103-9); B2-ST404 (CH14-27); B2-ST404 (CH14-807) and B2-ST1193 (CH14-64).

5. The composition or method of any preceding Embodiment, wherein the subject is a transplant or cancer patient (optionally a haematological cancer patient), or wherein the patient is suffering from or at risk of a urinary tract infection (UTI); and optionally wherein the transplant is a solid organ or stem cell transplant (optionally a haematopoietic cell transplant) or wherein the transplant is a transplant of a medical device.

For example, the subject is a haematological cancer patient suffering from neutropenia. For example, the subject is a haematopoietic stem cell transplant patient.

A suitable medical device may be, eg, heart device (eg, ventricular assist device, such as a left ventricular assist device (LVAD)), a catheter (eg, a biliary catheter) or a prosthesis (eg, a joint) prosthesis.

In an example, the patient is suffering from a sequestered B2 phylogroup *E coli* infection. In an example, the *E coli* are sequestered B2 phylogroup *E coli*.

For example, the subject is suffering from or at risk of acute bacterial sinusitis, pneumonia, urinary tract infections, chronic prostatitis or gastroenteritis caused by B2 phylogroup *E coli*. For example, the subject is a male human prostate surgery patient.

6. The composition or method of any preceding Embodiment, wherein the method is carried out prior to the subject receiving a transplant.

For example, the transplant is a solid organ or stem cell transplant (optionally a haematopoietic cell transplant).

7. The composition or method of any preceding Embodiment, wherein the B2 *E coli* cells comprise a strain of *E coli* that causes sepsis, septicaemia or diarrhoea in humans.

Enterohemorrhagic *Escherichia coli* (EHEC) serotype O157:H7 is a human pathogen responsible for outbreaks of bloody diarrhoea and haemolytic uremic syndrome (HUS) worldwide. Conventional antimicrobials trigger an SOS response in EHEC that promotes the release of the potent Shiga toxin that is responsible for much of the morbidity and mortality associated with EHEC infection. Cattle are a natural reservoir of EHEC, and approximately 75% of EHEC outbreaks are linked to the consumption of contaminated bovine-derived products. EHEC causes disease in humans but is asymptomatic in adult ruminants. Characteristics of *E. coli* serotype O157:H7 (EHEC) infection includes abdominal cramps and bloody diarrhoea, as well as the life-threatening complication haemolytic uremic syndrome (HUS). Currently there is a need for a treatment for EHEC infections (Goldwater and Bettelheim, 2012). The use of conventional antibiotics exacerbates Shiga toxin-mediated cytotoxicity. In an epidemiology study conducted by the Centers for Disease Control and Prevention, patients treated with antibiotics for EHEC enteritis had a higher risk of developing HUS (Slutsker et al., 1998). Additional studies support the contraindication of antibiotics in EHEC infection; children on antibiotic therapy for hemorrhagic colitis associated with EHEC had an increased chance of developing HUS (Wong et al., 2000; Zimmerhackl, 2000; Safdar et al., 2002; Tarr et al., 2005). Conventional antibiotics promote Shiga toxin production by enhancing the replication and expression of sx genes that are encoded within a chromosomally integrated lambdoid prophage genome. The approach of the present invention may rely on nuclease cutting of target cell genomic DNA. Six induction also promotes phage-mediated lysis of the EHEC cell envelope, allowing for the release and dissemination of Shiga toxin into the environment (Karch et al., 1999; Matsushiro et al., 1999; Wagner et al., 2002). Thus, advantageously, the invention provides alternative means for treating B2 phylogroup EHEC in human and animal subjects. In an example, the subject (eg, a human) is suffering from or at risk of haemolytic uremic syndrome (HUS), eg, the subject is suffering from an *E coli* infection, such as an EHEC *E coli* infection.

8. The composition or method of any preceding Embodiment for preventing haemolytic uremic syndrome (HUS), a UTI infection, sepsis, septicaemia or diarrhoea in the subject.

The composition or method may be for treating or preventing a blood stream infection by pathogenic B2 phylogroup *E coli* cells in the subject.

9. The composition or method of any preceding Embodiment, wherein each particle comprises a phage capsid containing the nucleic acid; optionally wherein the capsid comprises capsid proteins of a T-even (optionally T4) or lambda phage.

As is known the to the skilled addressee, transduction particles are operable to infect their cognate host cells to introduce therein nucleic acid by transduction.

10. The composition or method of any preceding Embodiment, wherein each particle is a phage (optionally a lytic phage) or packaged phagemid.

11. The composition or method of any preceding Embodiment, wherein at least 2, 3 or 4 different types of transduction particle are administered to the subject.

For example, each particle types comprises a type of adhesion moiety or collection of adhesion moiety types that differs from the other types of particles.

In an example, 2 different types of transduction particle are administered to the subject. In an example, 3 different types of transduction particle are administered to the subject. In an example, 4 different types of transduction particle are administered to the subject. In an example, 5 different types of transduction particle are administered to the subject. In an example, 6 different types of transduction particle are administered to the subject.

12. The composition or method of any preceding Embodiment, wherein a first type of transduction particle and a second type of transduction particle are administered to the subject, wherein the first type of particle comprises a first adhesion moiety that is capable of recognising and binding to a first cognate moiety selected from the group LPS, LamB and Tsx displayed on B2 *E coli*, and the second type of particle comprises a second adhesion moiety that is capable of recognising and binding to a second cognate moiety selected from said group, wherein the first and second adhesion moieties different from each other.

For example, the first and second adhesion moieties different from each other by their tail fibres, optionally wherein the first adhesion moiety is cognate to LPS and the second moiety is cognate to LamB; or optionally wherein the first adhesion moiety is cognate to LPS and the second moiety is cognate to Tsx; optionally wherein the first adhesion moiety is cognate to Tsx and the second moiety is cognate to LamB.

For example, each particle comprises a phage capsid containing a said nucleic acid; wherein at least 2, 3 or 4 different types of transduction particle are administered to the subject; and wherein a first type of transduction particle and a second type of transduction particle are administered to the subject, wherein the first type of particle comprises a first adhesion moiety that is capable of recognising and binding to a first cognate moiety selected from the group LPS, LamB and Tsx displayed on B2 *E coli*, and the second type of particle comprises a second adhesion moiety that is capable of recognising and binding to a second cognate moiety selected from said group, wherein the first and second adhesion moieties different from each other.

For example, each particle comprises a phage capsid containing a said nucleic acid; wherein at least 2, 3 or 4 different types of transduction particle are administered to the subject; and wherein a first type of transduction particle and a second type of transduction particle are administered to the subject, wherein the first type of particle comprises a first adhesion moiety that is capable of recognising and binding to LPS displayed on B2 *E coli*, and the second type of particle comprises a second adhesion moiety that is capable of recognising and binding to LamB displayed on B2 *E coli*.

For example, each particle comprises a phage capsid containing a said nucleic acid; wherein at least 2, 3 or 4 different types of transduction particle are administered to the subject; and wherein a first type of transduction particle and a second type of transduction particle are administered to the subject, wherein the first type of particle comprises a first adhesion moiety that is capable of recognising and binding to Tsx displayed on B2 *E coli*, and the second type of particle comprises a second adhesion moiety that is capable of recognising and binding to LamB displayed on B2 *E coli*.

For example, each particle comprises a phage capsid containing a said nucleic acid; wherein at least 2, 3 or 4 different types of transduction particle are administered to the subject; and wherein a first type of transduction particle and a second type of transduction particle are administered to the subject, wherein the first type of particle comprises a first adhesion moiety that is capable of recognising and binding to LPS displayed on B2 *E coli*, and the second type of particle comprises a second adhesion moiety that is capable of recognising and binding to Tsx displayed on B2 *E coli*.

For example, each particle comprises a phage capsid containing a said nucleic acid; wherein at least 3 different types of transduction particle are administered to the subject; and wherein a first type of transduction particle, a second type of transduction particle and a third type of transduction particle are administered to the subject, wherein the first type of particle comprises a first adhesion moiety that is capable of recognising and binding to LPS displayed on B2 *E coli*, the second type of particle comprises a second adhesion moiety that is capable of recognising and binding to LamB displayed on B2 *E coli*, and the third type of particle comprises a second adhesion moiety that is capable of recognising and binding to Tsx displayed on B2 *E coli*.

For example, each particle comprises a phage capsid containing a said nucleic acid; wherein at least 4 different types of transduction particle are administered to the subject; and wherein a first type of transduction particle, a second type of transduction particle, a third type of transduction particle and a fourth type of transduction particle are administered to the subject, wherein the first type of particle comprises a first adhesion moiety that is capable of recognising and binding to LPS displayed on B2 *E coli*, the second type of particle comprises a second adhesion moiety that is capable of recognising and binding to LamB displayed on B2 *E coli*, the third type of particle comprises a second adhesion moiety that is capable of recognising and binding to Tsx displayed on B2 *E coli*, and the fourth type of particle comprises a second adhesion moiety that is capable of recognising and binding to LPS displayed on B2 *E coli*, wherein the adhesion moieties of said particles are different from each other.

For example, each particle comprises a phage capsid containing a said nucleic acid; wherein at least 4 different types of transduction particle are administered to the subject; and wherein a first type of transduction particle, a second type of transduction particle, a third type of transduction particle and a fourth type of transduction particle are administered to the subject, wherein the first type of particle comprises a first adhesion moiety that is capable of recognising and binding to LPS displayed on B2 *E coli*, the second type of particle comprises a second adhesion moiety that is capable of recognising and binding to LamB displayed on B2 *E coli*, the third type of particle comprises a second adhesion moiety that is capable of recognising and binding to Tsx displayed on B2 *E coli*, and the fourth type of particle comprises a second adhesion moiety that is capable of recognising and binding to LamB displayed on B2 *E coli*, wherein the adhesion moieties of said particles are different from each other.

For example, each particle comprises a phage capsid containing a said nucleic acid; wherein at least 4 different types of transduction particle are administered to the subject; and wherein a first type of transduction particle, a second type of transduction particle, a third type of transduction particle and a fourth type of transduction particle are administered to the subject, wherein the first type of particle comprises a first adhesion moiety that is capable of recognising and binding to LPS displayed on B2 *E coli*, the second type of particle comprises a second adhesion moiety that is capable of recognising and binding to LamB displayed on B2 *E coli*, the third type of particle comprises a second adhesion moiety that is capable of recognising and binding to Tsx displayed on B2 *E coli*, and the fourth type of particle comprises a second adhesion moiety that is capable of recognising and binding to Tsx displayed on B2 *E coli*, wherein the adhesion moieties of said particles are different from each other.

13. The composition or method of Embodiment 12, wherein the first and second cognate moieties are different from each other.

In an alternative, the first and second cognate moieties are identical. In an alternative, the first and second cognate moieties are LPS. In an alternative, the first and second cognate moieties are Tsx. In an alternative, the first and second cognate moieties are LamB.

14. The composition or method of any preceding Embodiment, wherein the nucleic acid of each particle comprises a nucleotide sequence (N1) encoding said nuclease, wherein each particle is a synthetic T-even phage (optionally a T4 phage) comprising an insertion of N1 into the genome of the phage, wherein the region is between the pin (protease inhibitor) gene and the iPII (internal protein) gene.

Optionally, the phage is
(a) a synthetic T-even (eg, a T4) phage that comprises a deletion of DNA from, and/or an insertion of heterologous DNA into, a region of the genome of the phage corresponding to a region between coordinates
   (i) 1887 and 8983;
   (ii) 2625 and 8092;
   (iii) 1904 and 8113;
   (iv) 2668 and 7178;
   (v) 7844 and 11117;
   (vi) 8643 and 10313;
   (vii) 9231 and 13383;
   (viii) 9480 and 12224;
   (ix) 8454 and 17479; or
   (x) 9067 and 16673;
wherein coordinates are with reference to wild-type T4 phage genome (SEQ ID NO: 5);

15. The composition or method of any preceding Embodiment, wherein said nuclease is a guided nuclease, optionally a Cas, meganuclease, zinc finger nuclease or TALEN.

16. The composition or method of any preceding Embodiment, wherein the nuclease is a Type I, II, III, IV, V or VI nuclease, optionally a Cas9 or a Cas3.

17. The composition or method of any preceding Embodiment, wherein at least $1 \times 10^7$ PFU of particles are administered to the subject.

In an example, $1 \times 10^8$ to $1 \times 10^{13}$ PFU of particles are administered to the subject. In an example, $1 \times 10^8$ to $1 \times 10^{12}$ PFU of particles are administered to the subject. In an example, $1 \times 10^{10}$ to $1 \times 10^{12}$ PFU of particles are administered to the subject.

18. The composition or method of any preceding Embodiment, wherein the particles are administered to the subject at an MOI (multiplicity of infection) of at least 0.01.

Optionally, the particles are administered to the subject at an MOI of no more than 1. Optionally, the particles are administered to the subject at an MOI from 0.001 to 1. Optionally, the particles are administered to the subject at an MOI from 0.01 to 1. Optionally, the particles are administered to the subject at an MOI from 0.1 to 1.

19. The composition or method of any preceding Embodiment, wherein the strain or at least one strain is an antibiotic-resistant or MDR strain; and/or wherein the strain or at least one strain is a B2-I strain.

For example, the strain or at least one strain is a strain selected from B2-I (STc131), B2-II, B2-IX, and B2-VI.

For example, at least one MDR strain is resistant to fluoroquinolone and the strain is a beta-lactamase (ESBL)-producing *E coli*.

20. The composition or method of Embodiment 19, wherein the antibiotic is fluoroquinolone (optionally levofloxacin), carbapenem or vancomycin; and/or wherein the *E coli* are beta-lactamase (ESBL)-producing *E coli*.

Optionally, the antibiotic is selected from ciprofloxacin (eg, Cipro™), gemifloxacin (eg, Factive™), levofloxacin (eg, Levaquin™), moxifloxacin (eg, Avelox™), and ofloxacin.

For example, the *E coli* produce CIX-M-15. CTX-M-15 is the most abundant enzyme in ESBL-producing *E. coli* causing human infections.

Preferably, the antibiotic is fluoroquinolone (FQ). For example, the FQ is levofloxacin. Levofloxacin, sold under the brand name Levaquin™ among others, is an antibiotic medication. It is used to treat a number of bacterial infections including acute bacterial sinusitis, pneumonia, urinary tract infections, chronic prostatitis, and some types of gastroenteritis. Levofloxacin prophylaxis is recommended to prevent gram-negative bloodstream infections (BSIs) in patients with prolonged chemotherapy-induced neutropenia. However, increasing fluoroquinolone resistance may decrease the effectiveness of this approach (eg, Clin Infect Dis. 2021 Oct. 5; 73(7):1257-1265. doi: 10.1093/cid/ciab404, "Colonization With Fluoroquinolone-Resistant Enterobacterales Decreases the Effectiveness of Fluoroquinolone Prophylaxis in Hematopoietic Cell Transplant Recipients, Michael J Satlin er al). This study found that in the patients tested, nearly one-third of hematopoietic cell transplantation (HCT) recipients with pretransplant fluoroquinolone-resistant Enterobacrerales (FQRE) colonization developed gram-negative bloodstream infections (BSIs) while receiving levofloxacin prophylaxis, and infections were typically caused by their colonizing strains. In contrast, levofloxacin prophylaxis was highly effective in patients not initially colonized with FQRE. The authors found that 23% of patients admitted for HCT were colonized with FQRE and *E. coli* was the predominant species. Patients with hematologic malignancies who receive intensive chemotherapy, including those undergoing hematopoietic cell transplantation (HCT), frequently develop severe neutropenia and gastrointestinal mucositis, placing them at high risk of developing bloodstream infections (BSIs) from gram-negative enteric bacteria (Enterobacterales). Neutropenic patients often suffer severe consequences from BSIs caused by Enterobacterales, with mortality rates as high as 15%-20%. Moreover, many fluoroquinolone-resistant Enterobacterales (FQRE) also harbor extended-spectrum β-lactamases (ESBLs); thus, breakthrough infections that occur despite fluoroquinolone prophylaxis may be resistant to first-line antimicrobial therapies for fever and neutropenia. Finally, adverse effects of fluoroquinolones have become increasingly apparent, including *Clostridioides difficile* infection, aortic dissection and rupture, dysglycemia, tendinopathy, QT interval prolongation, and mental status changes. Thus, fluoroquinolones should only be administered to patients when they are likely to provide clinical benefit to justify these potential adverse effects. Thus, Although fluoroquinolones may decrease the risk of gram-negative BSI in many patients, those who are colonized with FQRE may not benefit from fluoroquinolone prophylaxis.

The high rate and absence of risk factors for FQRE colonization suggest that FQRE are prevalent in the community. Indeed, a study of urinary isolates among outpatients in the United States demonstrated that 12% of *E. coli* isolates from young women and 29% of *E. coli* isolates from elderly women were fluoroquinolone resistant. A surveillance study of 1831 urinary *E. coli* isolates from 2017 found that one-quarter were FQ resistant. Furthermore, 13%-16% of men undergoing transrectal prostate biopsies were found to be colonized with fluoroquinolone-resistant *E. coli*. Nearly one-half of fluoroquinolone-resistant *E coli* isolates in the study were ST131, a common sequence type that has spread throughout the world and whose isolates are frequently fluoroquinolone resistant and ESBL producers.

Bacteraemia caused by extended-spectrum β-lactamase (ESBL)-producing Enrerobacreriaceae (ESBL-E), such as *E coli*, is associated with inadequate empirical therapy and substantial mortality in neutropenic patients (see eg, "Colonization With Levofloxacin-resistant Extended-spectrum β-Lactamase-producing Enterobacteriaceae and Risk of Bacteremia in Hematopoietic Stem Cell Transplant Recipients", Satlin M J et al, Clin Infect Dis. 2018 Nov. 13; 67(11):1720-1728. doi: 10.1093/cid/ciy363). The study found that HSCT recipients who are colonized with levofloxacin-resistant ESBL-E pre-transplant and receive levofloxacin prophylaxis have high rates of bacteraemia from their colonizing strain during neutropenia. In this single-centre study of 312 HSCT recipients, it was found that 10% of patients were colonized with ESBL-E prior to their transplant. Nearly one-third of patients with pre-transplant ESBL-E colonization developed subsequent ESBL-E bacteraemia while neutropenic after their transplant, compared to <1% of patients who were not initially colonized with ESBL-E. Furthermore, the bloodstream and gastrointestinal ESBL-E had identical MLST and PFGE profiles in all cases, suggesting that these patients developed bacteraemia from their colonizing isolates.

In an example, the composition or method of the invention is for preventing the translocation of B2 phylogroup *E coli* from the gastrointestinal tract to the blood stream of the subject, thereby preventing or reducing bacteriaemia in the patient.

In an example, the composition or method of the invention is for preventing the translocation of B2 phylogroup *E coli* from the urinary tract to the blood stream of the subject, thereby preventing or reducing bacteriaemia in the patient.

In an example, the *E coli* are comprised by the gastrointestinal tract of the subject. Optionally, in these examples, the composition is administered orally to the subject.

In another example, the *E coli* are comprised by the urinary tract of the subject. For example, the infection is a kidney, bladder or urethra infection. Optionally, in these examples, the composition is administered to the urinary tract of the subject, such as by a catheter.

21. The composition or method of any preceding Embodiment, wherein
 (i) the nuclease is a Cas,
 (ii) each particle comprises a phage capsid containing the nucleic acid; and
 (iii) wherein a first type of transduction particle and a second type of transduction particle are administered to the subject, wherein the first type of particle comprises a first adhesion moiety that is capable of recognising and binding to a first cognate moiety selected from the group LPS, LamB and Tsx displayed on B2 strain *E coli*, and the second type of particle comprises a second adhesion moiety that is capable of recognising and binding to a second cognate moiety selected from said group, wherein the first and second adhesion moieties different from each other.

22. A method for treating or preventing an infection by *E coli* cells in a human or animal subject, the method comprising administering to the subject a plurality of transduction particles, wherein
 (a) each particle comprises a nucleic acid encoding a crRNA or guide RNA that is operable with a Cas nuclease for chromosomal targeting in the cells, wherein the said administered particles contact the cells and introduce therein the nucleic acid, wherein the crRNA or guide RNA is expressed and guides the Cas nuclease wherein the nuclease cuts the chromosomes of the cells, thereby killing the cells or reducing growth or proliferation of the cells in the subject;
 (b) the *E coli* cells are cells of *E coli* phylogroup B2; and
 (c) each particle comprises an adhesion moiety for recognising and binding to a cognate moiety selected from a LPS, LamB and Tsx displayed on the surface of the phylogroup B2 *E coli* cells.

Each nucleic acid preferably encodes a plurality of different cRNAs comprising spacer sequences that target *E coli* chromosomal genes. For example, Each nucleic acid preferably encodes a plurality of different cRNAs comprising spacer sequences that target 2, 3 or 4 *E coli* chromosomal genes selected from fimH, bolA, rpoH, lptA and murA.

Optionally, each crRNA or guide RNA comprises a spacer that targets an *E coli* gene selected from the group fimH, bolA, rpoH, lptA and murA. Optionally, each nucleic acid encodes a plurality of different cRNAs or guide RNAs, wherein the cRNAs or guide RNAs target at least 2, 3 or 4 (or targets all of) *E coli* genes selected from the group fimH, bolA, rpoH, lptA and murA. Optionally, each nucleic acid encodes a plurality of different cRNAs or guide RNAs, wherein the cRNAs or guide RNAs target fimH and bolA. Optionally, each nucleic acid encodes a plurality of different cRNAs or guide RNAs, wherein the cRNAs or guide RNAs target rpoH and lptA. Optionally, each nucleic acid encodes a plurality of different cRNAs or guide RNAs, wherein the cRNAs or guide RNAs target fimH and murA. Optionally, each crRNA or guide RNA comprises a spacer sequence that is complementary to an *E coli* gene selected from the group fimH, bolA, rpoH, lptA and murA. Optionally, each crRNA or guide RNA comprises a spacer sequence that is at least 80, 90 or 95% identical to a nucleotide sequence selected from the group SEQ ID NO: 6-10.

Optionally, each nucleic acid encodes a first crRNA, second crRNA, third crRNA, fourth crRNA and fifth cRNA, wherein the cRNAs are different from each other and each crRNA targets a B2 phylogroup *E coli* gene. Optionally, each nucleic acid encodes a first crRNA, second crRNA, third crRNA, fourth crRNA and fifth cRNA, wherein the cRNAs are different from each other and each crRNA is complementary to a B2 phylogroup *E coli* gene. Optionally, each nucleic acid encodes a first crRNA, second crRNA, third crRNA, fourth crRNA and fifth cRNA, wherein the cRNAs comprise respectively SEQ ID NO: 6, SEQ ID NO: 7, SEQ ID NO: 8, SEQ ID NO: 9 and SEQ ID NO: 10. Optionally, each nucleic acid encodes a first crRNA, second crRNA, third crRNA, fourth crRNA and fifth cRNA, wherein the cRNAs comprise respectively a nucleotide sequence that is at least 80% identical to SEQ ID NO: 6, a nucleotide sequence that is at least 80% identical to SEQ ID NO: 7, a nucleotide sequence that is at least 80% identical to SEQ ID NO: 8, a nucleotide sequence that is at least 80% identical to SEQ ID NO: 9 and a nucleotide sequence that is at least 80% identical to SEQ ID NO: 10. Optionally, each nucleic acid encodes a first crRNA, second crRNA, third crRNA, fourth crRNA and fifth cRNA, wherein the cRNAs comprise respectively a nucleotide sequence that is at least 90% identical to SEQ ID NO: 6, a nucleotide sequence that is at least 90% identical to SEQ ID NO: 7, a nucleotide sequence that is at least 90% identical to SEQ ID NO: 8, a nucleotide sequence that is at least 90% identical to SEQ ID NO: 9 and a nucleotide sequence that is at least 90% identical to SEQ ID NO: 10. Optionally, each nucleic acid encodes a first crRNA, second crRNA, third crRNA, fourth crRNA and fifth cRNA, wherein the cRNAs comprise respectively a nucleotide sequence that is at least 95, 96, 97, 98 or 99% identical to SEQ ID NO: 6, a nucleotide sequence that is at least 95, 96, 97, 98 or 99% identical to SEQ ID NO: 7, a nucleotide sequence that is at least 95, 96, 97, 98 or 99% identical to SEQ ID NO: 8, a nucleotide sequence that is at least 95, 96, 97, 98 or 99% identical to SEQ ID NO: 9 and a nucleotide sequence that is at least 95, 96, 97, 98 or 99% identical to SEQ ID NO: 10.

23. The method of Embodiment 22, wherein the method is according to any one of Embodiments 1-20, optionally except that the nuclease is an endogenous nuclease of the cells and is not encoded by the nucleic acid comprised by the particles.

24. A composition comprising a plurality of transduction particles for use in a method of treating or preventing an infection by E coli cells in a human or animal subject according to Embodiment 22 or 23, wherein
   (a) each particle comprises a nucleic acid encoding a crRNA or guide RNA that is operable with a Cas nuclease for chromosomal targeting in the cells, wherein the said administered particles contact the cells and introduce therein the nucleic acid, wherein the crRNA or guide RNA is expressed and guides the Cas nuclease wherein the nuclease cuts the chromosomes of the cells, thereby killing the cells or reducing growth or proliferation of the cells in the subject;
   (b) the E coli cells are cells of E coli phylogroup B2; and
   (c) each particle comprises an adhesion moiety for recognising and binding to a cognate moiety selected from a LPS, LamB and Tsx displayed on the surface of the phylogroup B2 E coli cells.

25. A method of detecting the presence of a B2 phylogroup E coli in a sample, the method comprising contacting the sample comprising B2 phylogroup E coli with a composition comprising a plurality of transduction particles, wherein
   (a) each particle comprises a nucleic acid encoding a nuclease for targeting the genomes of said E coli cells, wherein the said administered particles contact the cells and introduce therein the nucleic acid, wherein the nuclease is expressed in the cells and cuts genomic DNA of the cells, thereby killing the cells or reducing growth or proliferation of the cells in the subject;
   (b) each particle comprises an adhesion moiety for recognising and binding to a cognate moiety selected from a LPS, LamB and Tsx displayed on the surface of the phylogroup B2 E coli cells; and
   (c) the method comprises detecting that B2 phylogroup E coli cells have been killed or the growth or proliferation thereof has been reduced.

26. A method of detecting the presence of a B2 phylogroup E coli in a sample, the method comprising contacting the sample comprising B2 phylogroup E coli with a composition comprising a plurality of transduction particles, wherein
   (a) each particle comprises a nucleic acid comprising or encoding a detectable label, wherein the said administered particles contact the cells and introduce therein the nucleic acid, wherein optionally the label is expressed in the cells;
   (b) each particle comprises an adhesion moiety for recognising and binding to a cognate moiety selected from a LPS, LamB and Tsx displayed on the surface of the phylogroup B2 E coli cells; and
   (c) the method comprises detecting B2 phylogroup E coli cells comprising the label.

27. The method of Embodiment 26 or 27, wherein the composition comprises the features of the composition of any one of Embodiments 1, 2-21 24 and 25.

28. The method of any one of Embodiments 26-28, wherein the E coli comprise one or more E coli strains selected from the group ST131, ST1193, ST648, ST315, ST405, ST361, ST88 and ST453.

29. The method of any one of Embodiments 26-29, wherein the sample is a patient sample (eg, blood, urine, stool or saliva sample), wherein the subject is a transplant or cancer patient (optionally a haematological cancer patient), or wherein the patient is suffering from or at risk of a urinary tract infection (UTI); and optionally wherein the transplant is a solid organ or stem cell transplant (optionally a haematopoietic cell transplant).

30. The method of any one of Embodiments 26-30, wherein the nucleic acid of each particle comprises a nucleotide sequence (N1) encoding said nuclease, or comprising or encoding the label wherein each particle is a synthetic T-even phage (optionally a T4 phage) comprising an insertion of N1 into the genome of the phage, wherein the region is between the pin (protease inhibitor) gene and the iPII (internal protein) gene.

31. The method of any one of Embodiments 26-31, wherein at least $1 \times 10^7$ PFU of particles are contacted with the sample.

32. The method of any one of Embodiments 26-32, wherein the particles are contacted with the sample at an MOI (multiplicity of infection) of at least 0.01.

Labelling for detection methods is routine for the skilled addressee. The label may, for example, be a fluorescence label, eg, GFP. The sample may be a blood, spit, sputum or cell sample.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims. All publications and patent applications mentioned in the specification are indicative of the level of skill of those skilled in the art to which this invention pertains. All publications and patent applications and all US equivalent patent applications and patents are herein incorporated by reference to the same extent as if each individual publication or patent application was specifically and individually indicated to be incorporated by reference. Reference is made to the publications mentioned herein and equivalent publications by the US Patent and Trademark Office (USPTO) or WIPO, the disclosures of which are incorporated herein by reference for providing disclosure that may be used in the present invention and/or to provide one or more features (eg, of a vector) that may be included in one or more claims herein.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" or similar as used herein refers to all permutations and combinations of the listed items preceding the term. For example, "A, B, C, or combinations thereof is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

Any part of this disclosure may be read in combination with any other part of the disclosure, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The present invention is described in more detail in the following non-limiting Examples.

EXAMPLES

Example 1: Particle Composition for Surprisingly Targeting a Plurality of Different *E coli* Strains, Including B2 Phylogroup Overview Patient samples containing various different *E coli* strains were challenged with a particle composition. The composition comprised a plurality of transduction particles bearing adhesion moieties that are able to bind to LPS, LamB or Tsx present on *E coli* cells. The particles comprised capsids comprising phage capsid proteins, with the capsids containing nucleic acids encoding CRISPR/Cas systems for chromosomal targeting in *E coli*. Each nucleic acid encoded a plurality of different cRNAs comprising spacer sequences that target *E coli* chromosomal genes. The ability to kill or reduce growth of *E coli* in the samples was determined using a plaque assay as described below. Whole genome sequencing and genome assembly were used to assign susceptible *E coli* strains to phylogroups. It was surprisingly seen that use of such a particle composition was able to very effectively and extensively target a plurality of different *E coli* strains (these strains being clinically relevant from actual patient samples). Furthermore, advantageously a large number of different strains of the B2 phylogroup were targeted and killed. This is significant, because B2 *E coli* strains often display antibiotic resistance (such as MDR), eg, resistance to fluoroquinolone, that causes potentially life-threating infections in patients, such as in cancer, transplant and UTI patients. In addition to the B2 group, we surprisingly also were able to successfully kill or inhibit the growth of multiple strains of *E coli* phylo groups B1, D, F and G.

Patient Sampling

The samples tested (n=71) were obtained from two prospective observational studies enrolling adult (≥18 years) patients who were admitted to hospital for an autologous or allogenic hematopoietic cell transplantation (HCT) and who received levofloxacin (a fluoroquinolone, FQ) prophylaxis starting the day before the transplantation (Day −1) (Satlin 2021 and Satlin 2018). Trimethoprim-sulfamethoxazole (TMP-SMX) was administered to allogenic HCl recipients from 2 to 4 days prior to the HCT. The antibiotic treatments do not eradicate all *E coli* in the patients; for example, fluoroquinolone-resistant *E coli* would persist and thus sampling obtained *E coli* from patients. *E coli* isolates were derived from either anal swabs or fecal samples obtained upon admission for transplantation. The timing of sampling varied from Day −7 (7 days before transplantation) to Day 0 (the day of transplantation).

General Plaque Assay: Spotting for Coverage

This procedure describes the method to assess the coverage of phage particle lysates on a panel of bacterial strains.

| Section | Procedure |
|---------|-----------|
| Step 1 | Prepare bacterial indicator strains by inoculating 5 µl of a frozen stock into 250 µl of LB broth on a 96 well plate. Incubate overnight at 37° C. and 250 rpm. This step is done the day before the assay is performed. |
| Step 2 | Pre-acclimatize the LB plates to room temperature. Melt and acclimatize the top agar to 55° C. and add CaCl₂ and MgSO₄ to a final concentration of 5 mM. |

-continued

| Section | Procedure |
| --- | --- |
| Step 3 | In a culture tube mix 100 ml of the overnight indicator strain with 3 ml of pre-warmed top agar. When working with many strains, the top agar can be distributed to culture tubes and kept at 60° C. before use. |
| Step 4 | Pour the mixture on top of the room temperature LB plate and distribute evenly by swirling. Let plates solidify in a biosafety cabinet or lab bench for 5-10 minutes. Keep the lids closed. While solidifying avoid stacking plates to keep the layer of the top agar even across the plate surface |
| Step 5 | In the meantime, dilute the sample(s) or the stock of phage to the required dilutions (10-fold dilutions). Use PBS for dilutions. |
| Step 6 | Spot dilutions 0 to −9, 5 µl of each on top of your overlays and let them dry for 20 minutes (or until the spots are completely absorbed by the agar) on a bench with the lids open. Incubate plates upside down at 37° C. overnight. |
| Step 7 | Evaluation of the results: |
| | 1. If visible plaques appear, they are counted, and phage concentration is calculated. The result is recorded as YES. Calculation of phage concentration: number of plaques × 200 (to make it into ml) × dilution where you counted, i.e: If counted 5 plaques on dilution − 6: 5 × 200 × 1e6 = 1e9 pfu/ml |
| | 2. If there are no visible plaques, but inhibition of growth is observed the result is recorded as LZ (lysis zone) and the lowest dilution of inhibition is noted. |
| | 3. If no plaques or inhibition is observed, the result is recorded as NO |

Spotting was performed according to the above general plaque assay. Bacterial strains were prepared by inoculating 5 µl of a frozen stock into 250 µl of LB broth in a 96 well plate. The plate was incubated at 37° C. and 250 rpm overnight. Next day, in a culture tube 100 ml of the overnight strain was mixed with 3 ml of pre-warmed top agar (at 55° C.) containing 5 mM $CaCl_2$ and 5 mM $MgSO_4$. The mixture was poured on top of pre-acclimatized LB plate and distributed evenly by swirling. The plates were left on the lab bench for 5-10 minutes to solidify. In the meantime, the particle composition was diluted in PBS buffer from $10^0$ to $10^{-9}$ and 5 µL of each serial dilution were spotted on top of the overlays. Plates were left on the bench with the lid open for 20 minutes or until the spots are completely absorbed by the agar, and then incubated upside down at 37° C. overnight.

Evaluation of the Results:

If visible plaques appeared, the results were recorded as positive, plaques were counted, and phage concentration was calculated. Calculation of phage concentration: number of plaques×200× dilution where plaques were observed. i.e: If counted 5 plaques on dilution −6: 5×200×1e6=1e9 pfu/ml If there were no visible plaques, but inhibition of growth was observed, the result was recorded as lysis zone and the lowest dilution of inhibition is noted.

If no plaques or inhibition was observed, the results were recorded as negative.

Whole Genome Sequencing

DNA extraction was performed using Omega Bio-tek, Mag-Bind Bacterial DNA 96 Kit. The protocol was followed, and samples were eluted in 100 µL Elution Buffer.

Sequencing libraries were generated using Illumina Nextera XT, and sequencing was performed with paired ends on an Illumina MiSeq instrument with a V2 flow cell (300 cycles). The average sequencing depth for all samples was 48×(range: 31-72×)

Genome Assembly and Phylogenetic Tree Reconstruction

Raw data was trimmed for adaptor sequences and low-quality bases using fastp 0.22.0 (Chen et al 2018). Genomes were assembled using SKESA 2.4.0 (Souvorov et al 2018). The phylogroup of each sample was determined using EzClermont 0.7.0 (github.com/nickp60/EzClermont). Genomic distances were estimated using Mash 1.1 (Ondov et al 2016) with a kmer size of 17 and 1000 sketches. A neighbour joining tree was constructed using rapidnj 2.3.2 (Simonsen et al 2008). The final tree visualization was generated in Interactive Tree Of Life (iTOL) version 6.5.3 (Letunic et al 2021). Strain phylotyping was carried out in silico using the method disclosed in Microb Genom. 2018 July; 4(7): e000192, Published online 2018 Jun. 19. doi: 10.1099/mgen.0.000192, PMCID: PMC6113867, PMID: 29916797, "ClermonTyping: an easy-to-use and accurate in silico method for *Escherichia* genus strain phylotyping, Johann Beghain er al. The set of primer sequences described in Table S1 (available in the online version of this article) was used.

Results

Figure 2:
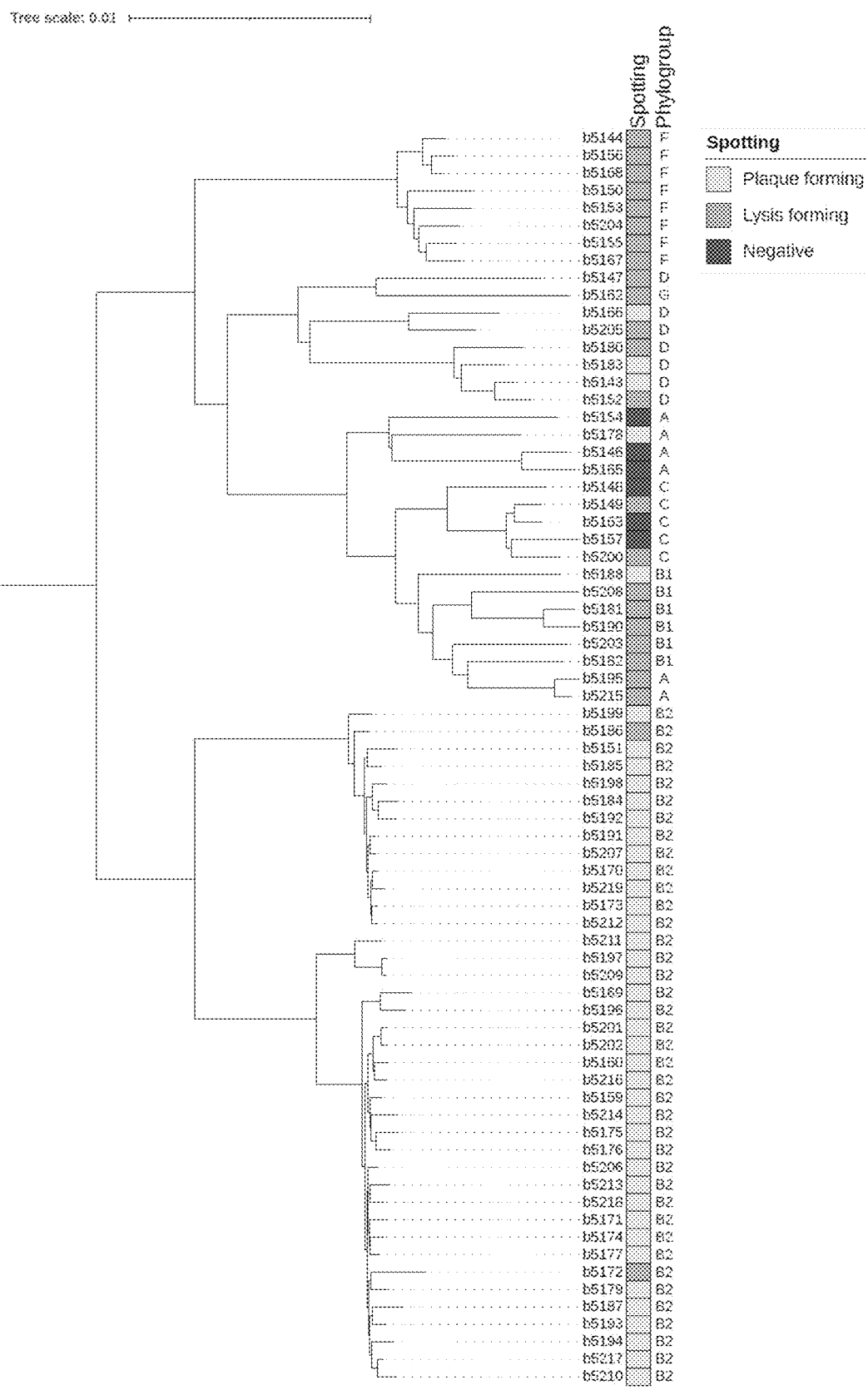
FIG. 2: Phylo-grouping of strains used in the study and showing particularly advantageous and extensive targeting of many clinical B2 phylogroup strains.

It was surprisingly seen that use of such a particle composition was able to very effectively and extensively target a plurality of different *E coli* strains (these strains being clinically relevant from actual patient samples), see FIG. 1. Furthermore (see FIG. 2), advantageously a large number of different strains of the B2 phylogroup were targeted and killed. This is significant, because B2 *E coli* strains often display antibiotic resistance (such as MDR), eg, resistance to fluoroquinolone, that causes potentially life-threating infections in patients, such as in cancer, transplant and UTI patients. More than 10 different ST131 strains were killed (plaques formed) and more than 10 different ST1193 strains were killed (plaques formed). Sequence type 1193 has recently emerged as a new, virulent and resistant lineage among fluoroquinolone resistant *E coli*. *Escherichia coli* ST131 is a globally dominant multidrug resistant clone associated with high rates of rUTI. Uropathogenic *E coli* (UPEC) are the primary cause of urinary tract infection (UTI), being responsible of ~90% of all cases. UPEC strains largely belong to the *E coli* phylogenetic groups B2 or D and are often clonal, with the most common sequence types (STs) isolated worldwide being ST69, ST73, ST95 and ST1312. The recently emerged and globally disseminated ST131 clone is a major contributor to hospital- and community-acquired UTI, as well as bloodstream infections and infections in companion animals and poultry. Originally identified in 2008, ST131 is associated with the worldwide spread of the CTX-M-15 extended spectrum β-lactamase (ESBL) resistance gene. Most ST131 strains are now strongly associated with multidrug resistance (MDR), including resistance to fluoroquinolones. Recent reports have also identified strains that are resistant to last-line carbapenems.

Significantly, we included clinical samples from patients that went on to develop *E coli* bacteraemia (despite pre-treatment with FQ/fMP-SMX). The composition could kill or reduce growth of *E coli* strains in these samples (and this is indicative of the possibility of using the composition for prophylaxis of bacteraemia in subjects). This included strains of the following Multi-Locus Sequence Typing (MLST) types (see FIG. 2): ST648, ST315, ST405, ST361, ST88, ST453, ST1193 and ST131.

In addition to the B2 group, we surprisingly also were able to successfully kill or inhibit the growth of multiple strains of *E coli* phylo groups B1, D, F and G.

REFERENCES

Shifu Chen, Yanqing Zhou, Yaru Chen, Jia Gu; fastp: an ultra-fast all-in-one FASTQ preprocessor, Bioinformatics, Volume 34, Issue 17, 1 Sep. 2018, Pages i884-i890, doi.org/10.1093/bioinformatics/bty560

Alexandre Souvorov, Richa Agarwala and David J. Lipman. SKESA: strategic k-mer extension for scrupulous assemblies. *Genome Biology* 2018 19:153. doi.org/10.1186/s13059-018-1540-z Ondov, B. D., Treangen, T. J., Melsted, P. er al. Mash: fast genome and metagenome distance estimation using MinHash. *Genome Biol* 17, 132 (2016). doi.org/10.1186/s13059-016-0997-x Martin Simonsen, Thomas Mailund and Christian N. S. Pedersen. Rapid Neighbour Joining. Proceedings of the 8th Workshop in Algorithms in Bioinformatics (WABI), LNBI 5251, 113-122, Springer Verlag, October 2008. doi:10.1007/978-3-540-87361-7_10

Letunic I and Bork P (2021) Nucleic Acids Res doi: 10.1093/nar/gkab301 Interactive Tree Of Life (iTOL) v5: an online tool for phylogenetic tree display and annotation Michael J. Satlin et al, Colonization with Fluoroquinolone-resistant Enterobacterales decreases the effectiveness of fluoroquinolone prophylaxis in hematopoietic cell transplant recipients. Clinical Infectious Diseases 2021.

Michael J. Satlin et al, Colonization with Levofloxacin-resistant extended-spectrum β-lactamase-producing Enterobacteriaceae and risk of bacteremia in hematopoietic cell transplant recipients. Clinical Infectious Diseases 2018.

Sequences

Amino acid sequences are written in N- to C-terminal direction and DNA sequences are written in 5' to 3' direction.

Protein

```
>LamB                                                          (SEQ ID NO: 1)
MMITLRKLPLAVAVAAGVMSAQAMAVDFHGYARSGIGWTGSGGEQQCFQTTGAQSKYRL

GNECETYAELKLGQEVWKEGDKSFYFDTNVAYSVAQQNDWEATDPAFREANVQGKNLIEW

LPGSTIWAGKRFYQRHDVHMIDFYYWDISGPGAGLENIDVGFGKLSLAATRSSEAGGSSSFAS

NNIYDYTNETANDVFDVRLAQMEINPGGTLELGVDYGRANLRDNYRLVDGASKDGWLFTA

EHTQSVLKGFNKFVVQYATDSMTSQGKGLSQGSGVAFDNEKFAYNINNNGHMLRILDHGAI

SMGDNWDMMYVGMYQDINWDNDNGTKWWTVGIRPMYKWTPIMSTVMEIGYDNVESQRT

GDKNNQYKITLAQQWQAGDSIWSRPAIRVFATYAKWDEKWGYDYNGDSKVNPNYGKAVP

ADFNGGSFGRGDSDEWTFGAQMEIWW

>Tsx                                                           (SEQ ID NO: 2)
MKKTLLAAGAVLALSSSFTVNAAENDKPQYLSDWWHQSVNVVGSYHTRFGPQIRNDTYLE

YEAFAKKDWFDFYGYADAPVFFGGNSDAKGIWNHGSPLFMEIEPRFSIDKLTNTDLSFGPFK

EWYFANNYIYDMGRNKDGRQSTWYMGLGTDIDTGLPMSLSMNVYAKYQWQNYGAANEN

EWDGYRFKIKYFVPITDLWGGQLSYIGFTNFDWGSDLGDDSGNAINGIKTRTNNSIASSHILA

LNYDHWHYSVVARYWHDGGQWNDDAELNFGNGNFNVRSTGWGGYLVVGYNF
```

DNA
```
>LamB                                                          (SEQ ID NO: 3)
ATGATGATTACTCTGCGCAAACTTCCTCTGGCGGTTGCCGTCGCAGCGGGCGTAATGTCT

GCTCAGGCAATGGCTGTTGATTTCCACGGCTATGCACGTTCCGGTATTGGCTGGACAGGT

AGCGGCGGTGAACAACAGTGTTTCCAGACTACCGGTGCTCAAAGTAAATACCGTCTTGG

CAACGAATGTGAAACTTATGCTGAATTAAAATTGGGTCAGGAAGTGTGGAAAGAGGGCG

ATAAGAGCTTCTATTTCGACACTAACGTGGCCTATTCCGTCGCGCAACAGAATGACTGGG

AAGCTACCGATCCGGCCTTCCGTGAAGCAAACGTGCAGGGTAAAAACCTGATCGAATGG

CTGCCAGGTTCCACCATCTGGGCAGGTAAGCGCTTCTACCAACGTCATGACGTTCATATG

ATCGACTTCTACTACTGGGATATTTCTGGTCCTGGTGCCGGTCTGGAAAACATCGATGTT

GGCTTCGGTAAACTCTCTCTGGCAGCAACCCGCTCCTCTGAAGCTGGTGGTTCTTCCTCTT

TTGCCAGCAACAATATTTATGACTATACCAACGAAACCGCGAACGACGTTTTCGATGTGC

GTTTAGCGCAGATGGAAATCAACCCGGGCGGCACATTAGAACTGGGTGTCGACTACGGT

CGTGCCAACCTGCGTGATAACTATCGTCTGGTTGATGGCGCATCGAAAGACGGCTGGTTA

TTCACTGCTGAACATACTCAGAGTGTCCTGAAGGGCTTTAACAAGTTTGTTGTTCAGTAC
```

-continued

```
GCTACTGACTCGATGACCTCGCAGGGTAAAGGTCTGTCGCAGGGTTCTGGCGTCGCGTTT

GATAACGAAAAATTTGCCTACAATATCAACAACAACGGTCACATGCTGCGTATCCTCGAC

CACGGTGCGATCTCCATGGGCGACAACTGGGACATGATGTACGTGGGTATGTACCAGGA

TATCAACTGGGATAACGACAACGGCACCAAGTGGTGGACCGTTGGTATTCGCCCGATGT

ACAAGTGGACGCCAATCATGAGCACCGTGATGGAAATCGGCTACGACAACGTCGAATCC

CAGCGCACCGGCGACAAGAACAATCAGTACAAAATTACCCTCGCACAACAATGGCAGGC

TGGCGACAGCATCTGGTCACGCCCGGCTATTCGTGTCTTCGCAACCTACGCCAAGTGGGA

TGAGAAATGGGGTTATGACTACAACGGCGATAGCAAGGTTAACCCGAACTACGGCAAAG

CCGTTCCTGCTGATTTCAACGGCGGCAGCTTCGGTCGTGGCGACAGCGACGAGTGGACCT

TCGGTGCCCAGATGGAAATCTGGTGGTAA
```

>Tsx (SEQ ID NO: 4)
```
ATGAAAAAAACATTACTGGCAGCCGGTGCGGTACTGGCGCTCTCTTCGTCTTTTACTGTC

AACGCAGCTGAAAACGACAAACCGCAGTATCTTTCCGACTGGTGGCACCAGAGCGTTAA

CGTTGTCGGAAGCTATCACACCCGTTTCGGACCGCAGATCCGCAACGATACCTACCTTGA

GTACGAAGCATTCGCTAAAAAAGACTGGTTCGACTTCTATGGTTATGCGGATGCGCCGGT

ATTCTTCGGCGGTAACTCCGATGCAAAAGGTATCTGGAACCACGGTTCTCCGCTGTTTAT

GGAAATCGAACCACGTTTCTCCATCGACAAGCTGACCAATACTGACCTTAGCTTCGGTCC

GTTCAAAGAGTGGTACTTCGCGAACAACTACATTTACGACATGGGTCGTAATAAAGATG

GTCGCCAGAGCACCTGGTACATGGGTCTGGGTACCGATATCGACACTGGCCTGCCGATG

AGCCTGTCCATGAACGTCTATGCGAAATACCAGTGGCAGAACTATGGCGCAGCGAACGA

AAACGAGTGGGACGGTTACCGTTTCAAAATTAAATACTTTGTGCCGATTACCGATCTGTG

GGGCGGTCAGCTGAGCTACATCGGCTTCACCAACTTCGACTGGGGTTCCGATTTAGGGGA

TGACAGCGGTAACGCAATCAACGGTATTAAGACCCGTACTAATAACTCTATCGCTTCCAG

CCATATTCTGGCTCTGAACTACGATCACTGGCACTACTCTGTCGTAGCTCGTTACTGGCAC

GACGGTGGTCAGTGGAACGACGATGCAGAACTGAACTTCGGCAACGGCAACTTCAACGT

TCGCTCTACCGGCTGGGGTGGTTACCTGGTAGTAGGTTACAACTTCTGA
```

>NC_000866.4 Enterobacteria phage T4, complete genome (SEQ ID NO: 5)
```
AATTTTCCTTATTAGGCCGCAAGGGCCTTCATAGTTTTAGCGATTTGGGAAACTTCATCATCACTTAAAG

AGTTGCGATAACCGATGAAGTCGGAAACAATACGGAATTTCTTGGTAAACTCAGCAACCATTTTATCACT

GTTTTTTGAAGCATTATTTGATAATACATCAAAAAGATTAGTTACTGTCCAAATGTCATGACCGATGGTA

TCTTTTCCACCATTAAAATATACACCCTGTAATGAACTAACCATATTAGCGAGTCGTGTATATTCTTCAG

AAACTTCATCTATACTGAAGTACTTCATCATAAAATCTAACTCAGGATACTTGATAATTTTATCAATATA

TCGTTTAGCTGAACTTGAATAACCTACATACTTATCATAATCTACATCATCAAAAGCATCTACATATAAA

TCACGCAAAGCTTCAAAAATACATTGGCACTGACCGAGTTCTTTTACCTTTTTCTGTAAAAGCGGACGAA

TAACATAAAATTCATTAATGCCAATAAGATTAGCCATACGAATCAAAATATTCATAGATGGATGACAAAG

AGATGTAGTACCATCCATAGAGAAAATATCAGAACGATGCATATACGCTACATAACCAGTAATTTCATCT

GCTTCTGATGTGAGGCGTAAATAATTCCTCTTTTCCCAGCGCCCGTCTTTAATTTCAAACTTAAACGCTG

TAGCAGCTTTAGGACGAGGAGCTTTACTTTTAACTACCTTTGGAATATAACTTTTTACTAAAGCTTCAAT

TTCTGACAAATAATGAATGTTAACTTCATCACTTTCAAACATCGCCATAATATCAGGAAGCAAATCAATC

TGCGATTCTACTTCTGGATTAATAAACAGAAGACGTTCGTTATGATGAATATTCAAAGTGTTATTAAATT
```

-continued

```
CACTATCATCTAACGCACGTGCTAATCCACGGACAATATTAACACGATTTTTAATATTATCAATAACGAT

ATTAATTTTTGTTGTATTAATACCAAACAGACGATAACTTGATGCAACGGCTGAAGTTTCATGACTTTGC

TTAATGCGCTTCAGTCGAGGGTCAAGATTTACTTCATACACAACTCCCGCGTTGCATAACTTACTGTCAG

GTTCAAACATGCTCTGCATCTTTTTATATGACAGATTTTTAGTCGTGAATTTGACTGAATTACTAATCAT

ATAATCTCGAGCAGAATACCCCATCTTCATCAATTCACGATATGTGTGACGAGGAGATGTAGATTCTTTA

AATCGTTTTACATCTTCATTAAATGCTTTCTCACTGAGTTCTTTAACTCGTTCAATAATATTTTTACGAG

TGCGATCATCCAGTGAAAGAGCCTCGCGAGATGGAGCAATATCAAGTGAACCCATTGGAAACTTAATGTA

ATTCACTTCATTGCGAATGCTTAGCCAGTTACGGTCTCTAATAACACCATCGATAGGATAAACAATACCA

CCGTAGATAGCATATAATCCACCACGATCAGGCCAGTATCTTTCTGGATTTACACCGTAATAGTCATCAA

AATCCGGAAAATAATCAATTTCGCGGTCAAGACCATTAATGATAGCCAAATCTTTGAACGGTCGCATGAT

ATAAGAAACTTCATAAGCAAAGTTTCTAAAGTCTTTTTCTTCAACTGGAACTACGATTTCAATACCAGTT

TTATCATCTGGACCCATTTCTTTTACGAATGTAGGTTTAATCTGTGGACCATCACCATCCATGTAAGCTA

CATAACCACGAATTTCACCTTTATGATACGAAGTAATACTAAACGTATCAGTATAACTAAACGGAGATTT

AGAACCTAAACCAAATCCGCCAATAAAGTCATTAGATTCAGCTTTAGATGAACTGAAGTATGAATTATAC

AACCCAGGAGAATTATCATCACCTTGAATATCAAAATCACTCATACCCGGACCAAAATCTCGACAAACAA

ATCGTGGGTCTAAACGTCCAGGAACTTGTATGATAAATTTTTCAGGATTTCCATTAAGTGCATGAGCATC

AATCATGTTAGTAATCAATTCACGGACTACTGCGCGAATCTTGTTTGTATACAAATCAGATGACAGAATT

TTAAATACTTTAGGAGATGCTGTGATGCTAAATGCTTTTGATTTAGAACCATTACCAAGAATTGTTTCTT

TTTCAGTGGTGATAATCATAATTTCCTCATTAATTCATATTACGCTTAATAACTTCAGCAACTTCTAGTA

GTTCATCTTTAGTTGCGGTGTCGGATTGAATTTTATCTCTAATATCTTTAAAGCGGGTTTTAAATTCTTC

GGCTTCTCCCATATCGAAAAAGCGTTGAATGATTCTATATTCTCGATGAACTGCTTTATCAAAAGTTCT

AAATTTACTTTATATGATTTCATTTCAATATCCTCATTTGCCCAATTAATTATACCACATCCTTGTGGTA

AAGTAAACTACTGGCTCATCCATTCTTTACGAAGGTCAGCATTATCTCCCATGAGCATTTCAAAAAGCTC

TTTCCAGTTCTCAGGAAGTTTAACAACATCATATACTGGGTTTTGAATCATCTCACGATATTCAGATTTT

TCCAAAGAGCCAAGTCCCTTAATATAACGGATGCTATGTTTAGGTAGAGCATCTTTGGCACTCTCATATT

CAGCGACTGTATAAAACCATTCTTGTTTTTTACCGACCTGAGCGATGATTACAGGAGTTTTGACAAAGCG

AATTCGTCCTTGCTCAAACAATTCTGGCCAATTACTAAAAAATCCGAGCAGAGAAGGATAAATAGAACCT

AATCCAATAATCTCTTAATTATGAGGTATTTCTATAGATAGCCCGAAGGCTATCCATCGTGATCTGCGTC

TGTCATAATAGCGACATTCGCATAGTTCATTGAAGAGGATTTAATAGAACGACGAACATTGTTCTGCAAT

TTATATTTTTTCATATCAACGCTAGAAGAATCAATTTTTACAAATTTCATTATACACCTCATAGAACTTT

TCATCAGGAATCCAACCGCGTTTAAATTCATTAAATGCTCGGCCGAATAATTTTGAATTCACAGTTATAT

TATTAACTGATTTCCATTTAGCAACTCCCGTTCGTTTATAATGATCGGGGTCATATTTCGTGACGTACCA

TTCATATAAATTTGGTATTAATTTTACAGCCTCTGGATTTGTCGCTGATTTATTATACCATGGTTTCGCT

TTTTCAAGTTCAGCTGCTTTTGCAGTAGCAGCAACAGTATTTCCAACACCAACTAATTTTTCAGTTTTAA

TGCGTGGATCATTAACATGAAGACGAAAAACTTCGCCCTTTTCATTTTTAAAGCATGTCATGCCTTTAAT

TCCAGGAAGCTTAACACCTTTATTAACACCGCATCATTCCTTTGGGTTAAATGATCCTTTAATTAATAAG

GCGCATTTACCCGATTTAACTACTTCTCATTCAACAACTTTATCTTTCATAACGTTTTTTGACCATTCAG

ATACTGCTCTTTGATGGCTAAATTCTAGCAATTTCACTATAATTTGCACTAGAACGTAAACTATTTTTCA

GTGTTTCAACATTCTATTCATCGCATATGCCATTTCACGATTACGATGAATTTTATATAGTAGAAAATAG

TGCTAAAAAGTGTTCACGAAAAGTCATGTTTCACCAAATTTTCGTTATCATCAGAACCTCCCATTGATCT

TGGAAGGATATGATGAATTTCACCCTTAAATTTAGAAACGCGGGTTTTACCCCGCACTATTAAGTCATTA
```

-continued

```
TAGATTTTTTCGTAATTCACCTACTGTTATCCATTTACCATTAATCTGTACTTCATCATTTTCATTTACG

ATAATTGTATCGCCATTTAGCTCGAAAGTAAACCACTCGCCATCTTCTTTTTCTTCAAACGCTTTTTCAC

CGAGAACTAGACCAGTGATTGCGCAAATATCAAATAGTTCTTTGTTTTTAAGCATATCTGCATAAGACAT

ACCCCAACTGTTGAGAACTTTACCACGCAATGGATAACCACCGTGAAGTTCTTTATCACGAACATCAATA

AGATATCCGATAGCCGAATCACCCTCAGTCAAGAAAAGAGTAGTATCAGCATCTTTACCGCAAAGATTCG

CTTTGATATGTTTATGAACCTTAGCTTTAGAAGCCTTTTTAGCTGCTTTAGTTTCTGCTGCTTTTTCTGC

CGCCAATTTACGAGCCAAAGCAGCTTCAATAATCGGCATTAGAATTGCTTCATTATTTAGAATATCACGT

GAAATCTTTTTAGCATCAAGTTGAATATGACTACGAATTTCGCCAAATGGAGAAGTCAAACGCTCTTTAG

TTTGACGAATCAATCGCATGTTTTTCATATCACGAACAAACATAACGATAGTCAAACATTCTTTGACACG

TGCTTTAGTCACATCAATTTTGAACTTACGTTTGATTTGTGGAATAAGGTCTTCACAAATATCATCCATA

GCGCAGTCAATGTGATGGCCACCATTCTTAGTATGAATGTTATTGACGTATGTTAATTGACGAAAACCAT

CCGGTGAACGACCAACCGCAATAGAACAATTTTCTTGCTCTTGAACAATAGCATGTTCATCATACTGCCG

TGCATATTTCTTAAAATTGCCCTGAACCTTTTTACCATTAAAGGTAAATTGAATATCAGGATAAACTACA

GCAAGTGTCTGGAGACGATCCAGTGTAATGTCAAGATAAACTTGGGACAGCTCATTAGTTTCAAATGACA

TAAAATCAGGAATGAAAGTAACACGAGTTCCTTTCCATTTTCCAGGAATATCTTCCCATGATTTATTTTC

CATGCCATTTGAACAACGAACTACAATATTATTTTGACCGTCGCCAGTTTCACCGACAAACATCACAGAA

AAAATGTTTGTCAAACTAGAACCAACACCGTTCATACCGCCGGTGACGCGTTCTTTATCATCACCAAAGT

TACCACCTGCTTTTGGAATAGTCCATGCGGCAACAGGACCAGGAATTTCTTCACCGGTAGGTGTTTTAAC

CATCGCTTGTGGAATACCGCGACCGTTATCTTCAACTGTTACTTGATTGTTTTTAATAGTAACATTAATT

TTATTCGCGAATTTAAACTTAGTACGAATACCTTCATCTACTGAGTTATCGATAATTTCATCAATAAGCT

TAACAAGACCAGGTACATACTGAACACTTTCCCATTTACCAAACATAAAGCGCTCATGCGTTTCATTAGC

AGAAGAGCCAATGTACATGCCACTACGCTTTTTGATATGTTCAATATCGCTCAGAATTTTAATTTCATTC

TTAATCATCACTTATCCTCGTTTGGTTTCGGGAATATTATACTCCGGTAATCATAAAGCTAAAGGCCCGA

AGGCCTTTTATTTAAAACGAATAGTTGAATCCTTAAAGAACAGCCCAGAACATACTGTTCCTTCTACTTT

CTGCCCGGTAGGTCCAATAGCACGAAATCCAGTATGCTGGAAATCATTTTCAGAGCAACCGAACCAATTA

TATCCAGTGATTTCAATATTAGTAAAACCACTTGAAGACAAAACTTTGGTTGCATTAATCAGCATCAGTA

CTATTAATTAAAGACACTGCTAATACTAATGCTGCAATTGAACGACTAATATATTTCATAACTACCCTTT

AAGCAAGTCGTAAAATCCATTATTCCCATGCTTAGGAAGCGGAAACTAACCGAACAGCCAGCCGATGACA

ATCAGGACATACACCAGTATCTCTTCCAGAAATTTTCTTGATTTTTTCGTATTCTTTTGCACAGTCTTTG

GATTGACATTTATAATCATAAAGCGGCATAATTATTCCTTAAAGTAAGCTTTCAACATCTGATATAAAGA

CCACGCCTGATCATTATTTTCAATAGTAACTTTCATGACTGGGAATTCTGTGAAATCTTCTATTTGTTCT

TGCTCTTTCTCTTCCTGCTCTTGCTCTTCAACCGCCTGATATGGATTTTCCACTTCATCAAAGAACCCAG

CTTCGTTAGTAGAGAGCCAGATAAAGTTTTCGTCAAGGATATCACCGCCGGCACAACGTTTGAGTACACC

TATGGATGTCATAATTTTAGTAGGACGCCCAAGATAATCAGCATCTAAAATTTTAAAAGGCTCCATACCT

AAACGTCGTGCATAGATTCCGTTATCAGTATGGTCTTTAATAAAATTTTCTTGAGCTTGTTTATTTTTAA

ATTGATACCATTTATTAACTTCAAATTTAATAGCCATTAATAAATTTCCTTCCAGTAAGTTGTGCCGTCT

TCAGTAATTTCACGAAATACACCATAAATTGGCTGTTTATCACCGACTTTCTCATACACATAAACAGAAG

TCAAGTGAGTAAACTTGCTAGTATGTTCCTTTTGAACTACTACCAAATTTGGATCAAATAATACATCTTC

AAATTCATCATTAGTGCAATTCTGAACAATTTTACGTTTCATTACAATTTCCTCATTAATTGAACAGTGG

AGCGATACGTTTCAGAAGAGTATCAACACCTTTAGCGAATTTTCCATTTTATTCTCCAAGTTGTTTTCTG
```

-continued

```
TATCAGTAGTTGATATTGATATAGTACCATAATCAACTACTGATGTATATAGTTTTATGAAAAATTTAAA

CTTTATGCATAGAGAGCATTGCTATAGTGTTTAATCCAACTTTCAGGAATGACTTTGTATGTTCCTAAAA

ATACCACGTTGTACAACTTAACACCATCTTCTACCCATTGATCGGTAATGTATCCACACATAGCGCGAGT

ATAAACAACCCTTCCATCATCTTTAATAAAGTTAAATTCACAAGGAGCAATGAACTTGATAGCCTGACCG

AGTTTCCACTTAAAGTCTACACCTACATGCGAAGTATCAATCGTTTCAATTCCTTTAGCAGGAACAGCTT

TTAAAAACGCAGACTCAAGAAATTTCGCACGAACATAGCCAAACTGGGGTTTAGACTTTCCATCTTTAGG

AATGATACGCACTTTTACTTCAGAATCTTCATCTTTAACACCATGCTTAAGCTGAATGCTTACAACTTCG

ACCAATTTTCCTGCTGCTTTAGAACGGGATTTATCAGATACACGAGCTAATTCACCAATATTAATAATCA

TAGTTATCTCTCACTTGTTAAAAAGATTTTATACTCCACGGGACCATTATACTCTGGTCCCAAGAGTTTG

TAAACTATTAATTCAAAATAGCTACCACTGCACTACGAGGAACTACGGAGTACTCTCCAGCATGAACTAC

GTTCAGAAGTTCAACGCCATCTTCCAATCCATTGGTCAGTTACCCAACCACCAATCGGATTCGCAAATGG

ACGACGAATGTAAACTGCCTTACACAACAAATCAGTCGGGTCTTCAGGTTTTTCAATTTCTGTCAATAGA

TTAAAATCTTCTTCATGATGATGAATGATGATACCCTTCCATAATAGTTTCTAATTTCCATGTACACTG

TACCAATGAGAATTCCACTATTAACACTAATGACAGTAAAAGGATATCCGCCAGTTGTACCAAGAAGTTC

CCAAAATTTGCTATCAGTCGTATTCGACATTGTCTGAAAATCAATTTCAGATGGTTTTTTCATTTGATAC

GCAGTATTAATTTTAATCATAATTTTCTCTTTAGTTTAAGGTAATAAAGCCTTTTAGTTCGGCATAGGAT

TTACGGAACATTACTTGATGCCCGCCAATGATAACTTGGTCATCTGGTACTTCGTATACAGCAAGATAAA

ATCCTTTCGAAGCTAATTCTTCACGCTCTTCTCGTGTGAACCATTTCATCATATCATATTCGCTAGCAAA

AGCAAAATGATAAAGAGCTACAAACCATCCGGGAATATGATATTCTACTCCAACATAATCTTTCTTGAAC

TTAGTATTAATTACGATATTAGCATTTTTAACTAATAGTTTGTCTTCGTGCGGCACAGGAATTCTTTTAT

TATCATTACTATGATGCATAAAATTAGGTCTGTCATAACCTACATGTAATAACCACTCTTCACTCCATGA

ATCTATTATACTTCTATACGGCGTTATTTGAACACAAAGATCTCGGCGTATTGTTATAGCGTCTTCATAA

TTAAGAATACTAAACGATGATTCAACACGATAAATTTTCATTTTATTATCCTCAGTAGCTATGGTGTTAT

AGTACCACAACTAACCGAGGAAGTAAACAACTTTTTATCGTTTTGTTGGAAGAGATAGAGGATCGCATTC

TTCCTCTGATGGAGCATCTTCAAGACCCATAGCATATCGCAAAGCATACTTCATCATCAGGATGTCTTTC

GCACAGTCATGAATAGAATCATGTGCAACGAATCCATCTAAAGTTCCCTTTGGAAGAGGACACGTTGTCA

TATCACGAACAAGCAGAAGTGCTTCAATTCTAGTACGAATATCACGCTGATTCCAAAATTTACAAGGTTC

TAACTTAAATGTATCAAGCTCATTCTCGGAAACGCCGTTAAGACGTTGAATATCGCGAATAAGATCGACT

AAAATTGGAAAATCAAACGACATTCCACGGCACCAGCCTTGAGATTTCCAAGGATCGATATTATGTGCAT

TGATGTAATCATTAAATTTTGCAATACCGTCGATAGTGCTTACATCTTCATCGGATGGTGCAATATTTTT

TCGAGCTTCAGGAGATTGATTCTTCCACCATTCGATAGTACTTTTAGTAAAAAGACGGTGTCCTTTTTGG

CTTTTTAAATCAAATTTGATTTTAATGCCACGTGAAACTAATTCATCGAATGTTTCAACTACTTCTGGAT

TAGGGTCAAAAGCAATTACAGCCAAATCAATAACCGCTGCTTTTTCACCACTTCCCATTGTTTCAAAATC

TATAATAAAATCAAACATTAAATTTTCCTCGCTAAATCACGAATTTGACCTACAGTATAGTCTTGAATAT

AAACTTTATTAATAGGCTCATCAATAAATTTTGCCATAGATTCAATATCTTTTTGTATTTCTTCAAGACT

GTATACTATCTTTGAAGCTTTTTCGCGAATAGTGATATTTTCAGGACCCGGATTTTCTTGAATGACAACT

TTAACATTTGTCATAAGAGATTTAAACTGGTACCAACTTAATTCAATCATTAATAATCGCCTCATAAAGA

TAGCTAATTTCGCCTAAAACATAATCATTGATTGTAACAGTTTTAACTTCACCGCAAAAGAATTCTAACG

CAATTAAATCTCGTTCAATTTCTTCTAATTGAAGCATCAACTTACTAGATTCAATTTTTACAGTTTCACG

ATTTTTGCTATAAGCTATTTCATAAATTTCGCTTACTTTATCTTGAAGAAGATAAAACTGATCTTTAGTT

ATTTCCACGAATAGCTTCCTCAAATTTAATCATACATAAAACACATCATAACGACCACGGGTGACACCAA
```

-continued

```
CATAAAGAAGTTGTTGAGCTAATTCAACATCTGCATAATGAATACAAGGCGTATAAATGAAAGCACGGTC
TACAGACATACCCTGCGCTTTATGGAATGTTGATGCAGGAAGTGCTTTCACTTTACTAAACTGTGATTTA
GCATCCCAAAAATCACTCCACGGAGCTTTTCCGCCTTTGTTCCAATTTTTATAAGTTTCTGCTGTTTTAG
CTAAAAATAGGTTAAACTTATACAATTCTTCGTCAGATGAAATTATTTTAATCTTTTCACGATAATATTC
ATCATCGCCATAAGTTTCTACTGTTAAATCCCAATGACGAATTAGATATTCTCCAGGAACACCACGGGCT
TTAACAAACGTTGATGTATACTCTGCTTCTATAATACGAACTAATTGTCCGTTATTAAAAATAATTTCTG
ACACAGGCTTTCCATCAATTTTATATGTTTTAAATAATGGTTCCTGCATTACAATAATTTCACCGACAAT
AAAATCTTTATCAGTTTCAAAAATCTTTTTACGAATAATGCTATTTAACTTGTCAACAGATTTATTCGTA
AATGCCATTACGCGATTTTCAAACAAATCATCTAGTGATTTGACGATTGAAAAATAATTTACCATAAAAT
CGCGTAAAGCGGTATCACCAGTAAATCCACGTACTCCATGCCCGTCAACAACTTTATCATAATTCCACTT
ACCGTTGCGAACGTCAGTAGCTACATCAATAATAGGAGCATTACTGCGTTTAACTTCAGTGAGTTCACAC
TGATAAAAATCTTTATGTGTAAAGAATGGACTGATATAAGCAGTATTTTCTCCTGGTTCAACAGGTCTGA
TTTGCTTATTATCCCCTATTCCAATTATAGTACACCAAGGTGGAATAGTTGAAAGCAGAATTTTAAATAG
CTTTCTATCATACATTGACACTTCGTCGCAGATTAATACTCTGCATTTGGCTAAATCAGGTACTTCTTTT
TGTTCAAAAAGAACATTTTCTTCATATGTTACTGGGTTAATTTTAAGAATACTATGAATAGTACTCGCTT
CTTTCCCTGATAGTTTTGAAAGAATCTTTTTAGCTGCATGTGTAGGAGCTGCTAAAATAATACCAGTTCC
ACCCGTAGATATTAAAGCTTCAATGATGAACTTAGTAAGAGTAGTCTTACCGGTACCAGCAGGTCCATTA
ATAGTTACATGATGTTTCTTTTCTTTAATAGCCTTCATAACAATGTTAAAGGCATTTTTCTGGCCTTCGG
TCAAATCATCAAATGTCATCGTAAATTCCCTGCAATTGGTATACTAACAATACGCCCAGTATCTAAAATT
CGCTGATATAATCTTTGCGTGTCTACGTCAGGCTTAACATGTTTAACTTCTATTTTATTAAACCAAAATT
TACGTGGAGTCTCAACTAATCTTGGAATTCCCTTACCTAAAGCTAATCGATACTGCTCTTTAAGAGTGGT
AAATACTTTATCAGCAATCTTCCATTCAAAAAATACAGCAGGACGATGTTCATCAAGCGGAACTGGCGCT
GTAAATCCGTCTTTGTCTCGGTAAACTATCGCATATACATAAACCATATTATCCTCGGATAAGTTTAAAA
ATTGAACAATTTAGCGGATATCCTCTTTTCAGTTTAAGTTTATCAATAAAAGACAAATTTTGATACCGCT
CTACACCTTGAATAATTTTATCACACATATCATATTGCATTTCTGCTTCTGACAACTTTTTCACAATTTT
CCAATCCGAGCCTTTAAGAAGAACGTTCAATTTAACAACTTCAGCGCCTTCTGCTATGCGAGAACCATCA
ATACGTGCTTTAAGTGCTATAATTCTCAGCTTAATGTCAGAGGTCTGTTTTGATTTAGAAAGCTGAGAAA
TGTGTTCAATTCGATTTTCACGTTTTTTCTGTATAGCTTTAATTTGATTATAAGTCTTTTTGATTTTAGC
CCATTTCTTTTCATCTAAATTTAGTTTATGAACTTTTTTCGCAGATGAACGACCAATTCGCAAAGCAAAT
AAATCACGCTTTTCAATCAACTCTTCTAAAGTATAATCAGAACGAAATGTATTATACTTTTTCTTTACTG
CAATAACATTCCCTTTAATGTATCCAACGTTATTATCAAAACGTTCTAATGATAATTTCTCTCCTTCAAT
ACGATTATCAAAAGGTTCTCCCGAGTAAGCACAAACTTTTTGATCTAAAATGTTCTTAATGTAATTGAAG
TCTAAGTTAAAATCTTTAGAACGTCTTTTTGCAGATGCCTGAGTATGCTCTAAACGACGTTTAATTTTAC
GAATTTGGTTATTAGACAGCTTCATATTTTTCTCACATCTTACGGACGGTTAACTACTTATACTATAACA
TTTTTACTTTAACTTGTAAACAACTTTATGAAAAATGCTTTAAAACTTTCATGGTATAATGAATCTAAGT
CCTTCCATTATAGATTAAATCCTTCAAAATCAAGAGTATAGATAGTGTATGTTGAACACTTTTTATACTC
ATATCTATCTGCAATTCTAAATACACTTCCAGCTGGTATCATTACTTCTTGTTCATCTGAAACTAATTCC
ATATTACGATAACGATGACTATCCGGAAACTTAAAGTTTGGATTGTATTCTTTACAGCGTAGAGCTTTTA
TAGCATACTCCTGGAAATTGAATACCATAGGAGCTTTGAATTCAAAAATAACTTGTGTGTTATACTCTAA
ACCAGAAGCAAAATGTAGAGCTATATTTTTATCATATGAAGCTGATACGACTTTATCAAATGTAATAATA
```

-continued

```
TCAATTCCTTGATTTAATACTTGTTTAGTCTCAGCTGGAACACCTCTCCAAAGAGGTTTATCGTTTGGAA

CCAAACGAGATTTGATTATTTCATTTAACCAAGAATGGTCATCTGGTTTATTAGTAATACAATGAATTAA

AAGTTCAATTTCAGATAAATTAAACCCTTCAGAAAGTAATTCTTCACGAATAGAAGCACGCACCGATGCA

TCCATTGATTTTATTTTAAAATCTTTTAGTTGCATTACTGAGTATTTCATTCAACTACCTCAATATCATA

AACTTTAAATGTTCCAAATGAATCGTGTAATTTTTCTTTTGAAATAGAAGTTATTTTATACTTTCCAATT

GGAATCATCCATTCTTGTTCACGCACAATCATCATTAAGTTATCAGTACGCTCTGAATCTAATCCATCAG

TATCTTCATACGTGTACTTAAACTCAGTATTAGGAGAAGAAAGTATAATATCGCTGATATGGTCAGAATA

ATTAAAAGCTTTATCAGTTTTTAAACGAAGTATTGTTTCAGTGAAATATTCAGCATAAGAAAAAGAACAC

GCTGTATGCAAACTAGTAGTAAATGAATCTACCCTGTTCGTTGAAAACACTTCTCCAACTTGTAAATCTT

TAATGAGTTCTTTTGTCGATTTTGATATACCACGATATAATTGATAAGGCGATTTAGTTAAATGCTTTTT

AATGATTTCATTTAAATGCTTATGAAGAGCTTCATTCTTTTGGCTTCCATACATTGCCAAAGAACAGAC

TGCTCAAAGTCAGTAAATTTTTCACAGACCTTTTATACATATCATATTGAAATCAACGCTTTCAGCTT

TTATAGATAACTGTTCAACATCTGCAAGATTAATAATCATGATAGCCTCCGTATACTTCAGAAGCTATCA

TATCATCGTTAGAAAGGAAAGTAAACAACTTTTTGAATTATTTTGCCCAGGGAGCCCAAGGCGGAGGGTC

AAGATGGTATGAAGCTAGTTCTTCTAGAAGAGCATCTGGGGCTTCAATTCCATAATTCTGTAATACTATA

CGGTACTCTTTCTTATAATCACTAGAATCATTCTGGTTATTCGTAGAATGATTATCTTCTAACATCTCAA

ATAAATCCATATTAATTCCTAGCGATAAAAACCAAATTTACGATTAGTTTCAATGATCTTTCTTTCTTCT

TCGGACATTCTCCAGCGTAGTCCAACATCAAAATGAGCCCAGACCATCCTAACAAATGCATTTATATCTT

TAATATCTTCAATAATGAATGTTTTACTTTTAGAAGGTTGACTCGCTAATTTAACTTTATCGTCTTCAAA

CATGTCAAAAGACCATATTCATGAGCTCTTTTATAGCCTTTAATAGTTAAAGCTTCAGAAGAAGAAAAT

GGTGAATCTGTATTCTGCAAAATATCTTCAGTATGCTTTATAATTAGAATAATATTTTCTGGATATTTTC

TTTCTTTTATATCTTTAATTAAAAAATCCGGATTTTCTGCTAAAGGAATAATTAATGAGCAATTTTTATC

AAGTGTATTTACTGATTTACCTTCTTTAGACATAAATTCTATTGAATATAATTTTGCTACTTCAATCATG

TGATTTCCTTTTGCCTACTAATGGACCGTCAGGAATTTTATTTTCCTGGATATATTTCTCATTTTCTTCC

ATCATTTTACTGCCAATTTTAAGAAGCAAATCCATTGCTTCATTTGCTTTTGCTTTAGCTTCTTCTAACG

TCATATCTTTGTTCATGATTTATCACCATAGATGTCTCTCATCAATTTAAGCGCTGAGCGTTCTAGTTTC

TTTTCTTTCTCAGCACTAATCATTGATTTCATCCATTCTTCTGATTCATTCTGCATTTCTTTATTTGCTT

GTTCAACCCAACCGTCATCAATATACATTGAGTTTGGTCTATTGAACCATTCAAGCATCTTCTTCAGAAC

TTTCATTCGTTTTACCTAAAACAATAGTAGGAGCATCGTCAAATTTATGAATTTTTAGCAAATTTGGATT

TAAATTATTCCATAAAGAGGTAATAAAATATGATAGCGCACTTTCGTCCGTAATTATAAATTTATTTCCT

TTATCTATTTTCCAATCATATATTGAATCATATGAATAGAAGGATAACGGTTTATTATTATAATATGCTT

CAGCAACATCAATATAGTTAGATTTAGTAAATGCTTGAATTGCCATAAATGGAGAATTTTGTACAGTTTC

AATAATTCCGATCTTTTAAGTTTTATTTCAACATCTTCTGGAATTGGCATTGAAATAAAATCTTCTACT

AGATACATATTATTGTCATATCTTTTATCAATCATTACTGCTACAGTAATTGGAACATCCTTGACAAACG

CCATACTAATACTATTGATAGACATTTCAAACAAATTGCTTCCATAATTTTCCTCAATCACAAGATGTA

GATGAACAACTAGAATCACAAGAACTTCCACATGAATCACCTGCCCATACATGAACAGGAACATTAGTAT

CATATGAATCAGAACTAGACTGTGTATTCTGTGTGTTAGATGATGTAGTAGGTGTTGACCAGCGCCAAGG

ATTTTTATAATATTCTTGGGCTTCTTCATAAGTCATAGTAACTGCTTCTACTGTTCCATCTCCCATATAA

ACATATTCAACTACAGTTAAAGGAAGGTAGTCATTTGAAATAGGAACTACACCTTCCCCAGGAGTTGTAG

AGAAAAAATCCGTAAAGAAACTTTTAAACCAATTAAAGATAAACATTACAAAAAGCCTCTTTTGAATTCG

ACTTGCTTCTCACCATAATCATATCGAATCTCTACATTAAATTCGACAGAACCATCTGCGTACATCATAA
```

-continued

```
ATGAATGCACAACAACTTCTGTAGACCATGGTTGTAGTTCATATTTCTTCATTACATGTCGTGAAATGAT
AATATCTAAATCTTCATTTGGTTTAATCCAACGATTTAACATAGTACTCTCCTCTATAAGATAATTCTAT
TATACCATACTCATTTTGGAAAGTAAACCATTTAAATGAAAAAAGGACTCCCGAAGGAGTCCTTGAGTTA
TTAACCAGTTACTTTCCACAAATCTTCATTTGCAGCAATCCATTCAGTACGTTGATTTTCTTCATATACT
GTAGAATATGCTGCTTTTTCTGAAGGGAATGTCTGGTAATGAGCGCCAGAAATTTTGTGAACGTCAGAAT
AAAGAGGGAAAGCTACAGAAATTTCCTTTCCTTCAATTTTCTTATTTCCATCTAATTTCTGCTCAAATGT
TTTGATATTAACATAACCGCGAGTACTAGCCATGTAATTCTCCTTTATTTAAATTACATGATTATTTATA
CATCTTCTTTTCTGAATAAGTAAATTAAATTCTTAAGAGCCGAACTTGTTACATCATATTTTCCTTTAAG
CGCCTTTACAACCGGGCCTGTTGCTGGTTTACCTAAAGAAACCCATAACTCGTGTATTTCGCTTTTAAGT
GGTTCATGCCAATGCGGTGCTTTTCTTTGCGCCCTTGAAGTTCCTTCTGAAATCTTTTTATTTCCGCCAT
TCGAATAAAACTTTTTCATTACTTCAGATTGCCGAGCTTTTCTTTCTGCCCTATTTTGGGCTATACGTTG
TGAATTCTTCATCCGAGTTTTTGTTTCAGGATTGTTTAATCTAAGTTTATGTTCTAATCGTTGTTGCTCA
GTCCATTTTCTTCCTTCTCCACCCTGACCACCAGGAGAAATATTAATGCAAGTATCTGGGTGTTTACGTT
TTAATGCAGATATTAGCTCACGTTCAACTTCATATGATTTTTCTCTAGAACCATGGCATTTTGACCATCG
TATTTTATAATTAAATCCATACTTACGATATATGTTCCATAGTATTTTACCTGAACCCGGATATTTATCA
TTATATGGATTTACAATAAATGATTCATGTTTCCCAGCGTACCAAAAGACGCCTTTCGGCGTCCTAACTT
TTACTATATATGTTCTATAAAATTTTTGTTTAATATCCATTATCTTGACGTTCAAAATTATGTTTGTTCT
TCAGATAATAAAGTTTAAAGATTTCTTCCGCATTCATTCCAAGGCCAACAAACATATTTAATACGAAATG
AAATATATCCACAAGCTCAAATTTAATTTCGAGCTGGTCTTCGGGGACATTTCATCAATGCGTTTTTCT
TGCGCTTCAATATAACGTGCTTTCCATTTTTTCCATACAGCAGAAGCTTCTTTTTCACCACGTGACATTT
CACCAAGAGAAGTCAGAAGTTCGCGGAATTCATCATCAATACAGTCTTTTTGTTCACGCATCCAAGAAAC
AACATCACCGGCAGTTTCTAATTTATCTGGATGATAGCAGTATTCGCGGACATTAGCCAAACGAATCTGT
AAAAACCGCTGCATATCAAGCATAACTTGCAGCGGATCTTTTTCATCACCGAGAATATCCCAGTATTCAT
TTTGAGCTTTATCAACACCTTCGATCAAATGAGCACATTCATTAAAGTGAGCCATTAGTTTTCCTTTCAA
TTCATTAATAAGTTAAATAATTATATCATTTGAGTATGTAAGCAATTAATTAAAAATATATACTTCATCA
GTTCCATTCTTTTCTTTGGAATGTATATATGTTAAAGACGTATTTTTTATTAAGATGCTTTACATTATATT
TTTTAGACCATTCTTTAAGAAGAGTGTTTTCCTTTCCGTGGTGTTCTAAAACATTCGACTGCCCAAATTT
TATTCCTCTATCATTTAAAGAATCTAAAAGATTTAAAAGGTCTTTTTCTTCATCTTCTGACCAAAATTTA
TTATAATCAGCAACTGTTATGAGATACGGAGGATCTACATATACAAAATCGCCGTCTAAAATTTTAACAT
CTTTAAAATGCAATGAACTAAAGATTATTTTATCACAATTTTGTTTAAAGTGATTATATTGTTTTTCACT
ATTTTTGTTTATAGTTCTTTTTCCAAACGGAGTAGTAAAATTTCCTTTATCGTTTATACGAATCATATTA
CTAAATCCGTGAAAATGAAGAACATAAAGTAAAAGAGGATCTCTAGTTTTATTATAATCTTCACGTAATT
TCAAAAACTCTTCTTTTGATGTTTTTGATAGTTTGTATTGCTTTATTACTTTTAAAACGTCATCCCATGA
TACATTAATAAGACGCTTATACATTTCAATAATTGGTTCTTGAATATCATTGGCCAATACAGGGCCATTA
ACATTCAAAGACACTGATAAACCTCCACAAAATAAATCCACGAATCTGTTATATTTTGGAAAGTGAGATT
TGAGTTCAGGTAATAATGATTGTTTATTACCTGTATACGCGATAGCTCCTAGCATTATATTCTCTCATTT
ATTGCAGCAAAAATGAATTATACAATTCTTCATCATATGTATTTGATAGTAATACTAACACGTTTTGCGA
TAAATATTAATTTAAAGGAGGATATATATGGTACAAAAATTAATGGCACTTGTTAATGCCATAAAAGGTA
ATAAGAAACGTATAGCTTTACTATTTCTACTATGGTAGGAATTTTACTCTGGAACTTTATTTTATCACC
TGTTGCAATTGCACATGGTGTTAATATTCCAGTAGTTACTCTTGATACATTCGTAGATTTAGCATTTGCT
```

-continued

```
TTAGTTGGGTTAATTTAAATCTTAGCATATTTAGATAGCCGCATTTTAGCCATTAACCCCTGGGCAATAT
TATTTTTCATATATTCCATAATTTGTTCAGGGGTTGCACCTTCCTTTCTAATCATATCATTAACATCTTT
TGATTTCCAGGGAGATTTATCCCAAAACATAACCCTTTCTCCTGCATCAACTAATTTAGTCATTCGTTTA
ATAGTGTCAGGGTGACGAGGTTCATTATCTAAGACCCACACACGTCTATCTTTAAATGGAACAACTTCTA
GGTCTAATTGACCGCCCGTAATAGCTATACCATTTTCAATAAAAAGTGAATCTATAGGTCCTTCTAGAAC
ATATACATCACCATCTTTAACTCGTTCGACTCCATAGATTTTGTTGCCTCAGGATAAGCTTCGATGGTG
ATATATTTTTGAGGAGCATCTTTCTTTAATGCACGTCCTTGAAAAGACTCAGCTTTTCCATTAGCATTAT
AAATTGGAATAACAAGACGAGGCTCAGAAATTTCCTTTTTGTATGTTCCCGGTGCTATGCTATTAACTAA
TTTAGGCCATTCGGTTGTAAACCAAAGATATTTCCATTTATCCTTTGGAATACAACGAGCTTTTACGTAT
TTTATAATTGGATGGTCTTCCGCCAGTTTATCTAATCTAACACATGACGGAAGAGATTTAATTATTTTCT
TCTCGGGTTGTTTAGGAAGTTCTTTAGGTTTTTCTATTGGACGACTTTTACCTTTTTCTTTTCTTATTTC
AAAGATATACTCACGATATAAATCGGGTTCAAACTCCTTTAAATATATTCCGATTGGTGCATGATAGTTA
CAGTTATAACAATGAATATTTCCTTCATTATTATCACCATAATACCATCCACGGGCTTTATTCTGGTCGG
TTTTTGAATCTCCACAAACAGGGCATCTAAACCGTAATTTAAAAGTTGAACTATTATTTACTTGTGTGAA
TTTAGGTAAATGAGCTAATGCACGGTATGCAAACTCATTATCAATCCAAGGTATTGATGACATTTTTACT
CTTCTTTTTCTTTAGATTCCTCTTTTTTCTTTTTAGGAATCTGTTCAGGACCTTTATTTACTACAGCGCC
TGATGTTGTTCCAATAGAGATATTTTCAGGATTACCACCTGAATCTCCAGCGACCATATCTTCTTTGATA
AATTCTTTAAATGTTTTCATATTAACCTCTATTCATAAAAGCATTAAAAATTTGGTCATCAATAGAAACA
TTTACTTTAGGCTGTTTTTCAGATGGCAATTCATATCCACATATTACAATTTTATGATCAATATCAAAT
ACACAGAAGCAATATGATTAATGATATTTTCAGTAAAGTCTAAATCAACATCAATATCTTTTTGACCAAA
GCCCAAAGGATAAATAATGCGAGTAATTCGATTATCTTTAACAAAGATTCCACCGACATACTCTGTGCTG
CGTTTAAAGTCTACACGCCGACGAAATGAAAAATATTCAGGCTCTTTATGAGCTCGGCTCATAGGACACA
ACGAATAACTAGAATAAGAGATGTCAAATCCTACGCCTTCAATATGAACTAAATTGTCATGATTAAACCA
ATTATAATCATATGCCAAGTCCATTAGATTGTCATATGTGAAAAGCACCGGATTAACATCATTGGTCACA
AGCATATAATTAGCAACTGCTATAATTTCATTATTTTTAACGAATACAAACCGTGATTGATGCGAATGGC
CTGGACCTGCGTTTTCACGATTAATGATATAACACTGGGCACCTTTATATTTGTACGTGTCTTTACACTT
GTGCATTTGATAAAGCATTATTCACCTACCACTTCAGCGATGATATTTTTGTTATTAAAGTTTTTATCGC
AATACAGAACATAATTATACTGCATTACACCACCAGACTTAAGCTGTTTTTGCACTTCAGCTTTCATTTC
AGGACGATCACGCTTAACGATATTCATAATATCTGCTTCAATTTGAGTTTCAACCTCAGTCTGATCCGCA
GTCATAGACCATTCGCACAAATCTTTATCATAACCTGCCATAGCAGGCTGAGCAGCACAAGAAGCTAAAG
CAAAATTGTAGCAAAGATGAATTTTTTCATGATAATCTCCTCAGTAGTTTATGTTTATATAGTATCTCA
ATTTCCAACAAAAGTAAACAGTTATTTTAAAATTTCTGCGTAATCACATGTTACAAACTGTTTCTCTAAC
TTGACGATTTTACGAAAGTATCTTTTGCATTGGCGAATCTGCCTCTTCGTAGGGCGAACAGCAAACTTAA
TAAATTCCACTCGACCAAATGGAGGGCTTTCTTCTGCTGGAATATCTAACACCAATTCCCACGTATCTGC
AATAAGTGCTTTGAATTGCGTATTTTTCCTGACGTTATACGGAGTAGGTTTAAATAAAACAATATGCATA
TTATCCTCGGCAATCCACTTCACATACTTTCTTGTCATCAATGAAAGCTTTAACTAATGCTTTATTAACT
TCAGCATATTGAGTAGTAGCCCATTGAACGTCATCTTTCATCATTGTGATTTCTTTAGTAAACATGCTTT
CATTCTTAAACCACCCCATAAAAACTACCTTTACCAATTCCATAACAATCTCCTCATTTAACCGACAAGA
CTACTATACCATAGTCTTGTCAGCTTGTAAACTAAAATTTTAATTCATTCGCCAAAGCATCTAACTGAGC
TCGAGTCGATTCATTTCTTTGATAGCGATTCTGCTCAGCCTGAATCTGTTGTGAACCTGCTACTTCGTTC
ACTTCAGTTGGAGTAGAATCTTGTTCAATTTCTACCCATTTTTGATTTCCTTTTTGAACACCCATCAAAA
```

-continued

```
ACTTATTCCACTTATTCTTATCACCATATCGTGATTTGATTTGCTTAATGAGTTGTTGTTCAGCAGCTGC

TAGCTCCTCGGTTTCAATGACCGCAAGCATAAAATCGGCTGTTGCTGGAAGACCGGCAGATTCTGCAATA

TCGCTCATGTTAACATCGGAAGAGTCCCAAGCTTGTTTACCAACCTGTGCTGCAGTCCAAAGAACAGTTT

CGGTTTCAACAGCCAGAGCACGTAATTCCTCTGCAATAGCTTTAACAGTTGTGTAACTATTTTCTGAATA

AACTCTAATGCGGCAAGATTTACAAATACCTAGATAGTCGACAATAATGATTGTTGGAACAAAATTCTTC

TTGAGCTTCAATTCGTTTAAAAGTGATCGAAATGTATTAGCGTCTGCTCCACCAGTAGGATACTGTTTAA

CGATTAAACGACCAAGAGTAGATTTCTCACGCCATTTTTCCATTTTTCCTTTATACTCAGCGTAAGAAAT

ATGCCCATCATCAATGTCATCAAGAGAAACATCAAGCATATTAGCGTCAATACGTTTAGCACAGACTTCT

TCTGCCATTTCCATGGAAATGTAAAGAACATTATGTCCGAGCTGTAAATAATCTGCCGCTAATGAACACA

ATCCTAATGATTTACCAACGTTAACGCCAGCCATTAAAACGTTCAGTGTTCCAGTTTCAGCTCCGCCTTT

CGTAATTTTGTTCAGAATTCTGAGTTTAAATGGAACCTTACGAGCTTTATTCATATAAGATAGCCAACGT

GCTTCGTAGTCATCCATCCAATCATGACCAACGTAACTATCAAATGAAATTGATAATGCCTGGCGCATGA

TGTCAGGAATAGCACCAACATCCGGCATTTTCTTATTTCGTTTTTCCGGAGGAAGCTCAGCATTAGTTTG

AATTTCGATTATTTTAGACGTAGCATTAAACATCGCCCTTTGCTGAACATATTTTTCTGTTTCTTTTACT

AACCAGCTGTGGTCTTCCGGAGAATCAGCCAGTTTTGAAATAAGTGTTTTTACACCAGAATATTCTGTTT

CAGTAAATGAACTATTTTCTAATGCAACATTTAACGCATTAATAGATGGAACGCTATGGTACTCATTAAC

ATGAGATTTAATTAATTTGAATGTATTTTAGCTGGACCACTTTCAAAATATTCTGAATCCATATATGGC

CAAACTTTTGAAAAATAAGCTTGATCAAATATGAGATGAGAAAGAATAATTTCTACCACACTTACTCCTT

AAAAGAATTTAAATTTTTCTTTGACCTTTTATTAAATGCATCTTGCAGTTGCATTGTAATACATTTTTC

TACATGAGGAGCTAACTCAGCTTTTCTTTCTTGGTCAAGAACAGCAAAGTCCATTACAACCTTTCCATCA

ACCCAATCCAGTTTAGTTACATACACTATATGCGTAGAACCATCTTCTAGTTTAATGACAATCTCCTGGA

TAACATTTTCCATAGCAGATTTAATTATCTTAAGAGACTCATTAAAAAGACGTTCTTTTCTTTCTTCTTC

CCCCTCCGAAGAGGGGGATTCATCGATAATTTCTAGATCTAAATCTAAATCATCTTTATTCATTAAATTC

TTCCATATCACTTAGCTGTTCGAGGTCAGTTTCTAAATCAGCAGCTGATTTACTTTTACTTTCTGGAGAT

TTAAATTTTTCAACCTTTGAGTTAATCAATTCATCAACTTCAGCTTCAACAATTTCATTACTATCAATAG

CACCTAACTGATAAGCACGTTTAATAGCATCTCGGAATGGTTGATGCTTAAATAAAGGACCCCAGAATGT

AGTGCAGTTGGTATCTTTTGCACGCCAAGATTTTTCTTCGCGAATCATCTCGCCAGTTTCTTCGTCAAGA

AATTCACGAGCATACCAGCCATTTTTAGGTTTTACCACGAATCCTAATTCTAGAGCCATATCTAACAATC

CAGAATAAGGATCGATACCACCGTCAAATTTAACATCAATAAAGAATTTACTTTTTTCTTTAACGGTACG

AGATTTTTCTACATTTAGAACAAATTGATACCCCTGAAGATCAGAACCATCTTTAATCTGGCGTTTACCG

ATAATGAATACGGTATCAGCCAATACATCGGTCCAGTACCACCTCCCATAACTGTTTTACTAAACATTT

CTTGTGTTTCGTATGTATGGTTAATAGCAATACATGGAATATTTTAGTACTAAAATAGGGAGTTACGAT

ACGAAATAAGCTTTTCATTGTTTTAGCTCTAGTCATATCACTAACAACTTTTTCATTTAAAGCATCTTCA

GTTTCTTTCTTAGAAGCTAAGTTACCAAGTGAATCGATAAAAACGACTACCTTTTCGCCGCGTTCAATTG

CATCCAATTGATTAACCATGTCAATACGTAATTGCTCAAGTGATTGAACCGGAGTATGAATTACTCGTTC

TGGATCGACTCCCATAGACCGCAAATAAGCAGGAGTAATACCAAATTCACTATCATAAAACAAACATACT

GCATCAGGATATTGACGCATGTAAGATGACACCATTGTTAATCCAAAGTTTGATTTAAATGATTTTGATG

GACCTGCCAAAATTAACAGACCAGATTGCATACCACCAGTAATTTCACCAGAAAGTGCAATATTCATCAT

AGGAATTTTGTCGAACTACATCTTTTTCATTAAAGAATTTAGATGCTGTTAATTCTGCAGTCAATTTA

GAAGTAGAAGCTTTAATCAAACGAGATTTTAAATCAGACATATAATACCTTATAGTAGTGTTCTTGTTCC
```

-continued

```
ACGAAATACTTCGAGCATTCTTGCATAAGATTTATTTGGAAATCCAGCTTCAATTGCTAATTTTTTAAGC

TTAATAGCACCGGATTTTCCAGAGTTTTCCCATATTTCTTTAATCTTTTCAATGTTATCCCACATTATTG

GGTCACGTTTATGTGATGGTTTATTTCTATTATAACCATATGGATTATTAAGCAAAGCTTCTTTTCGTTT

TGCTTTAGTTTCTTCTGACTGCTTTTTGCCTAGCTGGGCTTTCCGGCAAACATCACTAAATCCAAGATGT

TTTGGTTTTCCTTTTTGAGCTTTTGAAATTTTTTCTTTGGTTTCTGATGAAACTCTATAACCAATTCTTC

TACCACCCTCTCCACCAATTTTTAAATTATAAGTCATAGGATCATTTACCACATCTATTGTTACTAATTC

TCTTTCAGCATCACGGGCTGATTTAAAATCTTTATAAAACCCAAGAATGCTTAAATTAAAATTTTTCTTA

CCATACTTTTTCTTGGCTTGTGCTAATAAAGTTCCTGATCCCATATAACCATCATTTAAATCATCGGTTG

AATGAGTTCCATAGTAAATTTTATTATTAACTAAATTAGTTATAACATAAGTATAATTATATTTCTTTTC

TTTATGTCTTTTCATGTCATTAATCAACTGCTATTCGATGAACTTCTCTCTTTTCTAATCAATATAACAA

AAGAAGTCCCAAAAAGCAAACAGACCTAAACCGATAATAAGCAATAAAGGTCCTAACATTTATTCCACCG

GTTAAAGATAAATAACTTTCTAATAATAGTTCATAATTTTTATAAATCAATAGCTTTTTTGAACGCATCT

TGCCATTCGGCTTTCTTTGCACGGGTTTTATTTAAAATATCATGTTGAATAGAAAGCATCTCTTTACGCA

AAACATCACTGTGTTTTAACTCATTGACTCTATCAATGAGTTCAGCACGATTATTTACATAAAAACGAGC

ATCATTAATAATTCGATGTTTGGTATCAAATTCTTCGTCAATTAGCATCACTGCATCAGATGCCATTGTT

TCCCAGACGCGTAAGGTAATAAAGTTGTCATTATAATTCTTGTCACCAATAATTAATGCAGCAATAGCTT

GACTATTCTTTTCAGATACCATGTTCATAGGAATTTTTCCAGTGAACACCGGAGCTTTGGTCCAAGGATA

TTTAGGATTTTTAAACTGTTTTTCTCGTGCATTGCCAAAAAACTCAATATTTAAACCGGTGTCAAATAAG

AATTCTACCATCTTGGATTCGCGTTGACCGGACCGAAATGAACCGCCATAAATAACATCCAAAGTTTTCT

TGGTAGGCTTAGATAATTGAAAATCGTTCATATGAATTTTATATTGTTCAATAGGAAAATATTCAAATTC

AATAACATTATCAACTTTCTTATGCGCAGCCTTAGCAATGTCTAAATTTATACCTTGGGAAATCACTTTA

ATTGGTGATTTAATTAATAGCTCTTCTTCAGTGTACAAATATGCCCATGGTCTATTTTTAACATTTGGCC

AAGACTGCGAAAACGGCAAACGTATATCTGTAAATAAATAATAAATTTTACTTTTGTATTTTGCCATAAA

TTTTTGCGCAGATAAAATTGCTAAATTAGGTTTACCGCCAAAAAAGTTAATAGAAGAATTAACAACTATC

AAACGGTCATAATCATTAACATCTACTTCATCAAAAGATTTAGTGTAAACACCATTTTTAAGAGAAATAA

TGTCGACATTAAGACCCATTTCAGAAATAACTTTAAAAAGATAAATAGTTTCAGAAGATGGAACAGTTTT

AAAATTAATAACATTATTACCCATATTAATTATAGCAATTTTCATATTATTCCTTTTATGTTAAACGATT

AAGCGTATTTTCCTACATAATCTTTTTTCGAAATATGTGTTTCGCCAGTTTTCCACCAATGATCAACCAA

ATAAAAATGACGAGAATACACATGTAGGCTTCCAACATTCCATATAATGGAACCTGCTTTATACTGGCGA

GTTGAATCACCTGCATTCAAATCAGATACTAATTTATCTAATACGTATTTTTGCCATGCATAATCATTAC

GGAATCCGAAGACCACGTCATTTGAGCGCATGTTAACAACCGCATTGATTTCTTGTCACGAATCAGGTA

TTGTACTGTATTCGTGCACATGAAATCTGACATACCATCTTTATTATAGTCAAACTGCATAGATGGACGA

GTATAAATCATGATACCACGTCGAGAATCAGGATTTTGACCAAGTTCAGCTAAACACATGTCATACTGAG

CATAGTTATCTTCTGACCAGATAGCCCAACCATAATTCGAGTTAATTTCACCTTTAGAAGATGCTACTTG

TTGCCAAATCTTCGGTGTTTCACCCGGAATATCTTTAACGAACAAGCTTTTAGATTTATACCATTCAAGT

TCACGCTGAATGTATTCATCATTAAGAGCGCCAAAAATAAACGGTTCATCTGCTACAAATGATGCGCCAA

TAATTTCAATAGTTTTAACACCTGTTTTATCAACTACGAAATCTTTTTCTTTTAATGCAAGCCCCAAATG

AAGACGGATTTCTTCAACTGTCATAGAGTCACTAATCATTTAAACCTCAATTGATACATTCATATTTAAC

TTGTAACAGTAATAAACTCCAACCTAAAATAATAGTTGGAATCATAAGAGGAACCGTTACACTATAGTAT

ATACTTATTATAATCATCAAGATTAAAAGCAATGCTGCTATAATTTTGCTTTTCATTCCTTCTCTCTGAT

GATAATTACCTGATTTGGCTGCGCAGACTTTTTAGTTTCACCTGCAATTGACCAAATAAATGTAATAAAC
```

-continued

```
CAACCAATAATTGACCAGTTAAACAGTAAAGATGCGAAAAAGATTCCTACTGTCGATTTTGACCCACGCA

TCAAGGCGATAAACCATGGAAGCATGTATATAATAATAGCCAACACGCCTGAAACTAAAACCATAAAAAT

TGAACCTGCTACTAAAGTTTCCATGTTTTCCTCACTTAGGTCAAATTTTTTACACATGAATTATAAGAAT

TCACTACATACTCCATCGGAGCGTTTTTACCTGTACGCCACTGGTAATTATTAGCCCAATTTGCCCAAAG

CTCAGCGCAGTAGTTTTCAATTTTTTCTTCGCGTGTAATTACATCTGAATTACGATATGCTTGAGCAGAT

TCATCTGGACGAATAGCTTCGTCAAAATTCGCCTGCATTTGTTCTACTGTCTGTTTTGGAGCTTCTTTAT

AACACTTGACATTAGGATTATAAAATTTGCTTGAACAGTTTACAATTTTTCCTACATCAGACTGATTTAC

TACCGGTCCTTGAGCTACACAACCAGCAAGACCTAATGCAATAACCAAAATAGCGATTTTCATTTCATTC

TCCAAATCCGTATCAGTAGTTGATAGTTGTATAGTACCATGGAAGAACAGTCTTGTAAACAGTTTTGTGA

AAAAATTTTTAGGGAATCCAAAGGGTCCAGAATCATCTCTTTTTCATAAGTATAGATTTATATTACTTGT

ATGAAAAAGGGACCTGGAGGTCCTAGATTTATTCTATCAGCCAAACAGGAAGTCTAACGAAGCTTTTTCT

TCATAGTCCATGCCAGCCGATTCACACATACCCGCAAGCGGTTTAACAAACGATTTTTGGAACAAAGTTG

AGTGGTCAATCCAAGATAGCACATCAGAACGAATTTCTTTTGGAAGTTCTGTACCCGATGGCCAAGCAAT

GCACTTGTCACCAAATGGATTTCCTTCACGTAATGGAAGAACCATTACTTTATTTCCATCCAAAATTGGA

GCTACACCTAAACCGCTAACAGCTCGACGATAAGTTAGCACACCACGAATATGGAACGGGCATTTAAATC

CTGGCCAACCTTTATCATCATATTTCGCTATATCGTTCGCAGTTTTTACTTCAGCAATAACTTTATAGTC

AAGTTGACGATATTCTTTCTCGAAGTTCTTGTAGTATTCTTGGACAGACTCTTCACCTTCCTGAAGAATA

CGACGAATACTTTCTTCGAGAGCTTCTTGCACTGCTTTTGGTGTTGAACTCTGCTGAGTTTCCATACCCA

TGATTTTTAGATGCGGTTCAGCAAATCGCTTATCTTCCATATCATAAACGTTCAGAGCATAACGCTTTTT

CGCTTTCCAAAATCCACCAACGCCCTTTGAACCAAGCGGAGGGCAAGAAATAGCTTCACGGTCCATATGC

ATCAGATGCTCGCGGTTATTCATATAATCACATAACTCACGATATGCAACATCAATCATAGGTTCCATCT

TTTTCTTACCGAACTGATTCATGAATTCAACCAAATCGTTCTGCTCTTTGAATCGGTCAAGACCAACTTT

TTCAATAACTTTATCTACGCAAACATATACCGAATCAGTATCACCTGCTGCAATGAAATCTTCATCATTA

GTTCCGCATACTTTATTCAGATATTCATTAATTTTACGAGCAATCCACTGAATACCGACTTGGCCGAAAA

TTGTGATAGCAGTAGCATTTCGCAAATCATAGTAACGGAAATGAATATTACCAAGAGCACCATAAAGACT

GTTAATGAGAATTTTACGGTTCAGCTGATTTGTATTAGCAAGTGTAGCTGCTTTTTCACATTCTTCAATC

AGACTATTGAGAACAGATTCGGTGTAATTCGATAGTTCATTTAAGAAATCATCACTGAACTTAACATATC

GTTCAACTTCTGGTTTAGTTGAACAAGACCCTGCGCCTTTCATAATAATCTTTTTAATAGCTTCGGCATT

CATTTCTTCAGCGAACATTTTCTTTTTCCAGTCTTTACGCTGGAAAAATACTTTAGCGATTTCCTTTGGA

ATGATACCTTCTTGATGTTTATCATACATCCATCCATTCGGAGAACAAGAATATTCATCACTCGGTTTAG

GAGCTGTTCCTGCGATATATTCATGAATTGGATGAACTTTAAACTGACCACGAATAGTTTCAGGACTAAT

GTTAACCTGGCGAATAATGCTCGGATACAGAGACGTCAAGTCAAAACTCATAATGTATCGACGTGCAATT

GGTTTAGGTTCAAACACAAATGCACCCGGAAAACTCTGTTTAACGTGCGAACCTTGTTGAGGAATAACCT

TATGTTCACCTTTCAATGAGTTAAAAATAATAGCATCCCAAGTTTTAATAGGACTCATTACACCAGAAAA

AGGCATTTTAGCGTAATAAGACATACTTAAAACTAGATCGATAAACCCACGAATTTTATCGATTGCTTGA

ACTGATTCTACGTCAATGATGTTATAACTAATGTATCGTTGATGATTAGTCTCACGAAGTTTATTAATAG

GACCGTCGTATGGTAATTTACCTTTTTTGGTTTCATGTTGAGCAACTGATTCCAAAGAGAATGACGGCAA

ATTAGTAAAAGCGAATTTCTTGTACAAATCTAAATAATCAAGAATAGATACGCCATCAATAGAATAAATT

TCTTTGCTACCGTACATATTTTGAATTAGTTTAGATTTTACCCGACCGATTGGGAGAGAAACGTTTCATAC

TACGTTCACCCAGAATCATTTTAACACGATTCATGATATACGGAACGTCAAACCCCTCAATATTCCAACC
```

-continued

```
AGTAAAAATAGCAGGTCGTTTCTGTTCCCAAAGATTGATATATTCCATGAGCATATCACGCTCATTATCG
AATGGCATATAAATTACTCGGTCAAGAATTTCTTGAGGAACTTCATCACCACCTTCACAGTCAAGCTTAG
CAGCTAACTTTGCATCCCATTTTGATACTGAACCGTACATTGAATTCAAAAGGTCGAAAACATAAAAACG
ATCGTCAATTGAATCGTAATGAGTGATAGCATCAATTTCATATTCTGCTTTCATTGGGTCAGGAAATTTA
TCACCAGTAACCTCAATGTCACAGTTAGCTACACGAACAAATTTTCGGTCATAAACAATTTCTGAACCAT
ATGTATCACTTATATAAGCGAGTTTAAAATCGTTCATACCGAGAGCTTCGAGACCGATGTCTTCCATTCG
CTTCATCCAATCTCGAGCATCTTTCATTGATGGAAATTTTTGAGGAGCGCAGTTTTTACCATAGATGTCT
TTGTATTTTGACTCTTCCTTACAATGCCTAAACATAGTTGGAAGATATTCTACTTCACGGGTACGTTCCT
TTCCATTTTCATCAATATAACGTTCAACAATGTTATTTCCGACTGTTTCAATAGAGATATAAAATTCTTT
CATAGATATTCCTTAGTTTATAGCCCGAGTTATTAGGCTCTTGATATATTATACTCCAAATAAGGGGCCG
AAGCCCCTTGCTTAATTACCAATCGTATATTTAGGAACGAGCTTCCATTCATGTTTTTGTTTAAAAGAAA
TAACTCGGAAGTTATTAGTTAAATCTTTCATAAAAGTTCTTTGACCAGGAACGATTTCAATTAGTCCCCA
ATCTTCTAATAGCCATGCAATCGAATCACGACGAACTTCATCTTCTTCTGTCATTTCAACTTGACGACCA
TCCATACGAAGCATTTCTTTAAAATGAACGATATAGTATAGTCCTTTTTTCTGAAGAATATGACAGGACT
GATATAGAACTTTATCTTTATTATTAGCAATTCCCATACGAGTCAAAGTTTCTTTTACTTTCAGAAAATC
TTCAGGTTTTTTAAGAGTAATTTCAATCATTTTACCATTCCAATGCTAGTTTTTTGAGTTGTTTCTGTTC
TTTTACGTTCTTAGTCACTTCTTTCAAAAAATCATCCGTGACTAAACCTTTTAGTTCTTTTAATACTAAA
GGAAGTTTTCCATTTTTAGTAAGAATTGATTTATAGTTAATTGCATCATTTGTATTAACTTGATACCGCT
TAGCAAGTAACTTAATAATCAATACTTCGGTGGAATCTTCAACCAGTTTTGCCCATTTACCATATCTTTT
ACCACGAGGAACTGCAGCCATTAGATAATTAAAATGAGCTTCATCACTTAAGCCTGATCCAATTAAATTC
ATAGCATATACAGCTGGCATACACTCTGGAAATTGTGATAATGCATTTTCAACCATGAATTTTGAATAAT
CTTTTTGAGCAATAGAGCATTTAGTTTTATTATTAATAGCTCCAATTATTTCAAAAAATTCATTTTCTGC
TTTTTCTTTAAAAGAATCAGCAGCGGATTGGACAGCTGTCCAATCTTTTGAATACCAAGCAACTTGATGC
TCGTTTAATTGAATATCATCTTTAAATAAGCTCATATCACTTCCACTGCATTTCGCATGCTAATTGAATG
AAAAGATAAGCTAAATGCAATTCAGTATTAGCTGCAATACCATGATACTGATTATTTTCGCCGACAATTT
CGTACATACGAATAATACTTTGTGGAGTTACACGTGAATAGATTTCTTCGGCAAGTTTACCCACGAACCA
CGAATAATCAGCCGCATATTTTGGTGCTAAAGCTCTGAGTTGTTTAACATCTTTATTTTTGAGAGACTCA
AGAACATCATCAATAGCACCACGATCGTTAGTAACCAGTGATAAAATACCAGCATCCAAAACACCTTTAG
ACGAATAACTATCGAGCTCGCCAATAGTTTTACGAAAATCAGGAAAATTCTTTTTAACCAAAGCTGCTAC
AACTTTCATATCAGCTATAGCAATTCCTTCATGCTTGCAGATTTCAGTCAATCGACGAATCATCTGCTTC
ATCATTTCAATTTTATCTTCATCAGTTGGTTGACCGAATGTAATAACTCGGCAGCGTGACTGAAGCGGTT
TAATAATACCATCAATATTATTAGCAGTAATAATAATACTACAGTTTGAACTATAAGCTTCCATAAAGGA
ACGAAGATGTCGCTGAGACTCTGCTAACCCTGAACGGTCAAATTCATCAATAACGATTACTTTTTGACGA
CCATCAAATGAAGCGGCGCTGGCAAAATTAGTCAAAGGACCACGAACGAAATCAATTTTACAATCTGACC
CATTCACAAACATCATATCAGCATTTACATCATGACATAATGCTTTTGCTACAGTTGTTTTACCTGTTCC
TGGAGAAGGAGAATGAAGAATAATATGTGGAATCTTACCTTTACTTGTAATAGATTTAAAGGTTTCTTTA
TCAAAAGCGGGAAGAATACATTCATCGATAGTAGATGGACGATATTTCTGTTCAAGAATGTGTTCTTTTT
CATTTACAGTAATCATAATTTCCTCATTCAAGTTTTAGTGTAAATTATAAAGGCCGAAGCCCTCTATTAA
AAATCGTGGGTAGAATCAGCTTCAAGAGCTACCACATAATTCGCGTGTTCACCTTCAAATTTAGCAGCAC
CTTGTTTACCTTTTGCCCAAAGCAGAAGTTTATAATTTCCTGGTTGCATTTTCATATTTGCCATATTGAT
AATGAAATTAAATGTATTTTCACCATCATAATCACCAAGAGTCAAAGAATATTTAACACGGGTCAGAGCA
```

```
GAATCTTCTACTTTATTAAAACCGTTAATTACGATTTTACCTTCTTTTACCGTGATAGCAATTGTATCAA

TTTGCAGACCACGAGATACACGCAACAGCTGTTGAAGGTCTTCAGCTTTAATTTCAGTAACAGCAGATGC

TACCGGGAATGGAATTGGTTTATTAGGAGCAACTACTGTACTCGGATCGGCTGCTGGCCAAAAAATTGTT

GAGCGGGCATCAGCAATTTTAATATTTCCATCTTCTGACTGGGAAATTTCTGCATCATCATTAACTAAAG

ACAGAATACCGAGAAAACCGTTCAAATCGTAAATTGCTACATCAAAATCAATAACGTCAGAAATATTTGC

TTCCGCATAAGTTGTACCATTAACTGCGCGAGTCATAATAAATTGACCGGATTTAAGCATAATACCAGAG

TTAATAGTAGCGAAATTTTTAAGCAGAGCAGTAGTATCTTTAGACAGTTTCATGTAATTTCCTTCAATTC

AAATGAGATTTAATTTTATAACTAATTTAATAAAGCAATTAACGATTAAAATCAGCCGCAATTGTTTCCG

CAACAATTTGAGCAGCAACAATTAGACGTTCATCTGCATTACCGCAATAATCATCTTCAAGGCGTTCACC

ACATGAAGTCATAATAAATTTAGCACCGGCGTTTAGGGATTCTGTAGTATGTTTGCGCATTAGTTCAATC

CATTTATTACTTACTTCACGATCGATAGCTTCATAATACGCATGACGAGCAGGTGCAGATTTAATTTTGT

TCTGAATAACTTCCATTGCGTTATCAGAAAGAGACAAAACCCATGCTCGACGAATTTTATTTTGGTTTTG

TGGATTTGATTCAGAACGCACGTGTTTTGGCTGAATATCTTTTACATCAACAGTATAATTCACAGTAATT

TTAGTCATAATACACCTTTAGTCATAATAATCAGTAACAGTCCAAGCTTCATTTCTATTGGACATTATTT

TTGTATATTCTGCTTTAAATGCATTCCTAAGCATAGATTCAGTAACTATATGCTCTTCATTAGAAAAATT

ATTTCTCAGAATATATCGTTTTATTTCAGGAATAGTTAATAGATGCTGTCCAGTTGAATATTCCATGTTT

TTCCTCCATAGAGATTATACTCTAATAAATTAAAGCATAATCTCTTATAAATTAAACCATTACAGTAAAT

CGACCAACTTTCTTCATTTGAAGATGCTGACCATATTCTTGCGGGTCATGGTCTTTATGCGAAATTATAA

AAACGTTAGTGTTTTTCATTGAATTTATAATATTAGCTACACCTTTAATACCTTCGGCATCAAATGACCC

ATCAAACACTTCATCAAGAATTAATGTACTAATACTAACACCAGATACGATAGAAGCAATATCACGCCAA

GTAAATAAAAGAGCAATATCGATTCGTGCCTTTTCACCTTCACTAAATGAAGCATAACTAAAATCTTCAC

GACCACGGGATTTAATTGTCTCATTAAATTCTTCATCTAATGTAAACACATAATCCGCTTCCATTATTTT

AAGATAATGGTTAATCTGCTTATTAAATAATGGAATGTACTTTTTAATAATAGCACCTTTAATACCAGAA

TCTTTGAGCATATCAGTCAAAATTCCTCGGTGGTATTTTTCCATTACTAAATTAGTTTTTGTCTTAACAA

TTTTATCAAGTTCTTCTTGAAGCAGTGCTATTTCATCAGCATGGTCAATAAACTCAGAAGATGCTTTTTC

TATAGCCGCTTTAACTTTTTTAGCTTTATCTACTGCTGCGATCAGAGATTGCTTTTTATTGCGAATATCA

TTTGCCAACGACTGCTGGGTTTTAATATTATCTCGGTATTCATCAACAAGAACTTTTAAATTATCACGAT

GTGTTGAAAGCTGTTCAAACGAATGTGTGCATTCAGAAACTTTATCTTTAATTTTAGAAACAACTTTATC

ACCGGAACTCAATTGTGACAAACAGGTTGGACATAATCCACCTTCGTGATACATATTAATGACTTTATTA

TACGAGTCAATTTTTGATTTAATTAAAAATGCTTCTTGACCGATTTTATTAAATGCATCAGTCGGGTCTT

CGTCCAAAACAATATTAACTAATCTTTCGTTAGCTTCTTCTATTTCCGATTTTAGCGTTCTAGCTTCTTT

TGCCAAATCATCATACATATTTTGTAGACGAGTAAGGTTGTCACCCGTTAATTTTTTCTGGCGTTCAACA

TTATCATTATATATTTTAATTTGTTGGATAATACTATCTTTTTTAACATCAAGCACTTGGTTCTGCGAAT

TTAATTCACGTATTAGTGCTTTATTAAGCTTATCCATTTCAGCTAATGTTCCTACCTCAAGCAGGTCTTC

CACAAGCTTTCTTCGCGCAGGGGTCGACAAACCCATGAAGGGGTATACCCTGCTGTACCAAGGACAACA

ATCTGCTTGAAACTGGCATATGACATTCCGATAAGCTGTTCAAATTCTGCTTGGAAATCTTTACTGCTGG

CAGATTCATTAAGACGTGTACCGTTAACGGTGATTTCGAAAACGTTTGGTTTTTGTCCTCTTTTGATATA

GTACTTTTTCTCATCATATTCCATCCACAGTTCAACTAAAAGTTCTTTCTTATTTGTGCTGTTTATTAAT

TGACCTTTCTTTACATCGCGAAATGGCTTACCAAAAAGCCCAAATGTGATGGCTTCTAGCATAGTAGACT

TACCACCGCCATTTCGTCCAGTAATAAGAGTTTTTTGAACCTTATCTAATTGAATGTCAATCCCATTTTG
```

-continued

```
ACCAACTGACATTATATTTTTATATTTTACTCTATTAAGTTTAAAATTCTTCACAAAAGATTCCTTTTAA

TGTATCTTTTAGACCATTCTATCATATCATCATAATCTAAAAAGTATTCATCAAATTCAGCCATGCAAAC

AACGCCTTGTGCTGTTTTTGATGTGATATAAATTATTCCAACATATCTAGAATCTTCTTCGGTATAATCA

ATATTTGCTATGAATTCATCATTAATGTCAAATGTCGAAAACTTCACAGTATGCATCCTTAATACAAGAT

ACAGCCATATCTCGTAATGATTTAGGTGTGTCATTATCTAAAATGTTGAAGTTAAAAGATACAGCCCAGT

CAGTGCAGACAGTAACCTTTTTAATACAATTATCTTCAACCTCTAACGGTTCAAACCAGTATTCAATAAT

TTCTTTATGACCAATATCATCTTTTACTTCACATTTAAAATGCTGACTCATCATAACATTTTTAAATTCA

TCAAAAGTCATTGTGTTGCCTCTACATATAGCTGATTTGCATATTGAATAAGTGCTTCACGGTCAGAATC

AGTGATGTCTGGAATTGCATTAATATACTCTTCCATTAATGTCTGAAGCGATTGAACTTCAACTTCTTCA

CTGTCATCTGACTCGACAGAGTTATCAATCTTTGACACAACTCGTAATGAATGCACAACTTTTTCTAGTT

CAGATTCGAACTTCGTCAGATTTTTGTCTACTTCAGTTACTATAACACGTACTGATAGATTTGTAAAATC

TTTATAGTCAATTTTTCCTTTAAATGGATAATGAATTCTACGATGCCAGGTAGTATTGTTTGGAATAAAT

TCCGTTCGTTCTGTTTCTGTATCAAACATCCAGAACCCACGAGGGTCATTCTCGTCACCTGCGGTTAGTG

TCCATGGTGTCCCAATATATCTGACGTTTGCAGCCTCAGAAATAGTATGGAAGTGACCAGACCACACTTC

TTTATAAGTCTTAAGGAAATCGGGTTCAAGACCATGAGATTTCATTCCTTTATAAAAATAAAATCCATTC

AGTTCCCAGTGACCAACACAAAAAGAAGCAGATGAAGTTTTGATATGCTCAAGAATTTCACCAGTATTTT

CTTCGCACATCCAAGGAATCAAATCAATCAAACACCCGTCAAAATCTACTGTAGTAGGCTTATCATACAC

TTTAACATTAGGATATTTAGCCAAAAGCTCAGTAGAAGCATTTGGATGCATTACATTTTTATAGTGGAGA

TCGTGATTTCCTACAATAGTGTGTAATGTAATTCCAGCATCATCAAGCGTTTGAACTATTTCACGGGCAA

ACTCCATAGTTTTATGTGTGATCGCTTTTCGCACATCAAAAATATCACCGTATTGAATCCAGGTAGTAAT

TCCATTTTTCTTAGAATATTCTATCGCTTGCTTAATTCCATCAATTTGAATACCGCGAATCCACTCATCA

TCAGCTTTAACGCCTAAATGCCAATCACCTAAATTTAAAATTTTCATATATCAAGAACCGTCATTGAAAT

GCAAAATAAAATTATTGAAATAAATCCATCTGGAGTGCTAAAGAACCCAATCCAACATGCTCTAGTGAAT

AGATAAAATGCAAGAAAAGTATCACATATCCAAGAAATATCATTATATCAAACTCCGTATAAAGCTAAA

GGGCCGAAGCCCTTTATTTTGTAATAATGTCAAACTGTTCTTTAAAGCAGAAGCTTGAATCTTGATGCTG

ATACAAAAATTCATATGCTTTTTCTCGCTCACGGTCATAAAGAGCTCGGTCAGATGACAGTTCTTTAATA

CGTTCAAATGTTGATTCCATATCATTTTCATCAAACCAAATGATACCGCTATCATGCGAGGTCAAAGGAG

TATTATCAACACGGAATTTTAAATTTTCGCCAGTAGATTTCCAAAATACCGGAATTGTTCCACATGCACC

AAGCTCGAGATGAGTATATTCGAGTGAGCGTTGTAAGTATTTCTGGTTAAGTTTACTCAACTGATATCCA

AAGCCAGATTTACTCATTCGTTCAAGCATTTCACTATTAATATAACAATCTAGGATTTGTGCCGGTTGAT

TCGGCGCGAGATTCATTTTATCAATCTCACGATTACCGTAATATTCATACGGAATACCTTTTTCCTTAAT

TGCAATAAAAGCAGGGGAACGTTCCAGACCTTCCATTACAGTGGATTTACCAGCAGGTTTTAAGAATTTT

TCATGAAAATCAAACATCTGGTAAAAACCTTTCCATGTAGTCGTACGACCAATCCAACGGTTGATATTCA

TGTTAATTTCAGAAACATCTTTCCAATAAGTTGACCGAACCTTCACAATATCCATAGGAGGCTGAAAATT

ATATACTGTCGGTGCTTCTTCAATATCATCAAACAGAGAAACAGTTTCTGGATACCATTCTTTCATCAGA

ACTTTATTAAAATCACCATTATCAGAATGGCTAAAAATAACATCAGCTCGACGAACAGTTTCTTCTAATC

CCAAATTTCGACGCAAAGAAAGAACAGAATGATCATGCTGATAAACTACAACACGAATAGAAGGTTTAAT

ATTATCTAAAAGTTTTTTATAGTTATTAATCGTAGCTTCTTGAACGGAAGTAGCAGGAACAGAATTAATA

ATTAGAATATCACAATCATTTACTAGCTTAAGTGCTTTATCGTATTCTTTAGCTAAAATAACTGGAATTG

AAAATGATTTGTGGTCATGAGAACTTGTACGAGTAAATGATTTATCTTTAGCATAAACCAAAGTTACTTC

ATGACCATTTTTAATAAACCAATCACGTTGCTCGAGTGAGAATTTTGTTACACCACAACCTTCAAGACCT
```

-continued

```
CGAGCCATAAAAATGCAAATACGCATAGTTTTCCTCTTTTCATTTAATAAATCATGTAAATAATATTTTA

TTTTCTATAAAACGCTACGAATAGGCCCAAACATATCCATAAGCAATTTTGCTTTTTCCAGATATGCACT

TTTTAATATTAGACATGCATCCTTTAACGGATACAGCTGCGTCTTTAATTCTAGGAAATACTCGTAATAA

TTTTCCAGTAGTATCATATTGAAATACTGGCACATTTCTTTTCTGAGTTATCCCACGTTTAGATTTAGAC

ATTTTTTGTTTAGTTGCATTAGACATCCTAGAGGGCTTTCCTATGTTATCAGAATAATAATATTTCCATT

GAAATCCTCCAGCGGTTTTCCTTTTACCATCTACACATTGTTTAATTGAAGTTGAACAGCTATATGACAT

ATCTTCTGCAGCATCTGTAATACATCTATATTTGCGAATAAAATTTCCATTTAAATCATATTGATAAATT

GGTTTTCCAGCATTTCGTCTAGCGTTAGACATGTATTTTTTATTATCATCATCTTTCCAGAACTCTTTCA

TGCTTTCCGATATTGAAGAAGATACAGCTGTTTTAATCCATCCATACATTTTATTATTTAGTCTTGTTCC

GTCAGAACTATAACACATCATACGAATAGCTAAAGCCAATTTAGGAAGTCTATAAATTTTAAATAATAAT

AAATGCGCGGTAAAATGTTCTTCTGGTGTCAAAAGAACTAAATTAGTTTTATCATCTGTACCACCCATAC

ATCTAGGAATTATATGATGTGTTTCAGTATAGTATGTCAAAAGACTTTTATCATTGCCTCTGTTTAGTCC

TTTTTCGATCAGTAAATTATATATGTTTAAATAATTCATTTTAGTTTATTTTACCAAAAAATTTATAAAG

CAATATAGGAGCCGAAGCTCCTATCCACATAATACGCCATACAGAGGCTCGTTAGAACTTTTAAATTTTA

TGCGCTTATATGTTATAGTTCCTTCTGCTTTAGCTTTATCATGAGCCTCTTTAAAGCGTCTCATCATTTC

CTCTCTAGAGGAACGAATTTTATTATAATCTATTTCAGAAGTCGGATGTTCATCTTTCACAGTTGCCACC

ATTTTTTGACTTGATAAGAATCAACCCACACTTTCATATTAGGGTCTGCTCTTACAATAGGAGGATTAAC

TTCTTTGATTGAACTATCACGGTATTCTTTTTCAGAAATTTTCACGCAAAGATGACCATTCAAAGATTCA

GTAAATCCTGCATTAATTTTAAGACGCTTGAATTTTACGTGTGTAAGCATCAATCATATCCTCAATCTGC

GATCTAGTAGTCTTCCAAAGAATACTGATGAGTTCATCGTTATATGGCTGTTTTAGAATATCCCGACTTT

TCTTGATAGCATATTCGTATTGAGCAAAATTATTATTTTCAGCTGCGATCTGAGCGTGCTTATAAAGACG

ATTCAGTTCGCGTTTGTTTTTAGACAATAACTTATTTGCTTTTCTTTCTGCTTCAAGACGGTTCTTTTCT

TCAATAGAAGAAATAAGCTTTTCCACTTCATCATTAATTTCGGGTTTATCAGTCATATTATTTCTCTAAT

ATAAAATAAAAATCATCATCTGTTAAATGATACCGATAGTTTAATTCTACACCATTAGATTTAAAAGCGG

TATCATACGGATTTTCTGGATCAATATCAATGTCAAGAGCTAAAACTTCCCTGAGATACATTTTAAGTAA

ATAGGGAATAGCTTCAACTTCAGGTATTTCTTCCAAGAATCCGGAGAGGTTAATCGTTAGCCTCATATAA

AAAATCCAAACTAGGAGAATCATCTACAACACTTTTCTTTTCAGCCCCCGGTGTTCTATAGGTTGATTCT

TCGTAATGCGTCATTTTATCATAGATGTCTTGAATAAAAGTTTCATCTACTAACGCAACCATATCGTCGT

CACGGCTGTCATAGACATTGTGAACGAAGTAACTATATTTCTTTGCAACTTCCTTACGTTCTTTTTTAAT

ACGTTGGACGAATGCATTAAAACAAGCTTGAGTTATATACGCATGTGGGTTTTTATATTTCGTTTCATCA

AAATTGTGAAGCCCCTTAATAGAAGCTTCTATACCATCTGCAATCATTTCTTGTTTCCAAGACTGGGTGT

ATCCTGAAAAGTTGAAACGTTTAGATAAGCCTTCTGCAATAAGCATAATGGCTAATCCGATAGTATCATT

CTGACGAACTACTTTATTTGGGTCTTTATTATTTGCTAATTCTGTTTTCCAATCAATAATAGCTTGTAAA

AGCTCTTTATTGTTTACGTAATTATATTTAGGCTTAGTTTCTGACATTTTCACCTCTTAGCTCAATTCAT

AGATCTATTATATCATAATATTTGAAGACCTATCTTAAAGCATAGAGGATGAATCAATTTCAAGCACTTC

ATCAGATTAGCCGCTCCAAGAGCTGCATCTAGTGAATCAAATTGGTCAACATATTCAATTAATTCGCCGT

AATTAGCGTATAACCACCATTGGCTAAATTCATACTCAAGGATGAATCCATTTCCTTCAATTTGAGTTAA

ACCAATGCCATTTGTATTTACTTCATACCCAGCGAGACGTAAATCGTTAATAAGAGCTTCGTTCATAATT

ATACCTTAGTAATTTTCAGGTCTGCAAATTTTTTCTTGCGTTGATTTTTCATGCGACGAATAGTTTTATC

GGAAATTTCATGCTTTTGATAAGCTTTAGATTCTACACCAAAAGCTTTAACATCAAATTCTGACAAGATA
```

-continued

```
TATTGAACCAACAATTCACGGACAGTATTGCGTCCAATCTTCTGATCATTCTGTTTCATCGTTTGATGAA

GCTCTTTTTCCCATTTATCCAAAATTTGAGGAGTTACAATATCGCCTTTTTCTAGCAAAGAAACTACTTT

ATCATATGCGTAAGAATTGATGGCGTTTTTAATTTGAATAGTCATACATTATCCTCAATTACGTTAAAAT

TTTATTATCCAAAAAGGCCGAAGCCCTTAGGCTAAACTTTTTGGCACCCTTCCAGCCTTCGTACATCATT

GCGACTGACAATGACAAAGCTCCTTCACATGCTGCATACTTATTATTCCAGAACCAATTTAGAAAAACTT

CATCCTCAATACCGTTGTGTTTCATGTTCTGGAAAAATTTGGCGCGTTCTTCAGCAATTCGCTGCGATAA

TTTAGATTCAGGATTCATTTAAATTTCCCAATTGCCATTTTCATCAATAAATTTAATCCAGTCATTTACT

GACCACTTGGTCGTATCGCCTTTTGGAGTAACATTTAAAGTGTATAGCCCTTGCTTAAAAAGCATGCGTT

TGATATTCATATTTTCCTCAGCTGTAACGATAACACTCGTTTGATTTACGTTTAGCAACTCGTTGAGAAG

TATTATAATCAAATCATCATCAATGTAAACTGATTTTTTCAACTTTCTTACTTCACCGCGTAATTGACG

ATTTAACTCATCTTTAACTTCTGAATCAATACCTTTCATTCTACGCCATTTATCTGAGCGAAAATGTTT

TCAACCATATCTTTATGACTTACCCCATCAGGAGCTTTACGCTTTCCGAAATAGTCATAATCACGCACTT

TTAAGTCTTTACGACGATACGTTTTACCCATGGAGTTTAATTTCCTTAGCAACTGAACTAAATACAGCAC

GATCACAAATCATACGTTTATGTAACTTGAGTATAAGATAGTAAACATCAAAACCATTTACATAAGTAAC

ACGAACAACATTACCATTCACGAGATAATACTGTCCCTTTTTAATCTCTTTATCAACCACAACCATATCA

ATTCCTCAAAGGTAATTCATATGTTAATAATACCACGGTTTGAACTTGTTGTAAACAACTTTGTGAAAAA

TATTTTAGGGAATGATAAGAAAGGAACGATAGCTTAGAATGGTAATATACAGAATGTGAGAAAGAAAGGC

CCAGAGGGCCCGTCTTAATCTTCTATGATATCTCTATCATATCCAAGTGAAATGAGAGTTTCTTTGAAGT

GTTTAATGTTCTTTTGTCTAGAATCATTAATGAAAATGACTGGATAACGAATGTTAAGAGATGTGAATCC

AGCGCGTTTAGCAAGAGATACAATCAGCGGACGATCATACTCAATCTTACCATTATTTGTAAGAACTTTA

TAGAAAGTAAAAGGAGCATTGAGCTCCTTTAGAAGTTTTGTAACTGATTGACATCCAGGACAACGACCTA

CTTCATCTGGAATTCCATAGACTTCAATCTTATTTTGTTTCACAACTATTCCTTACTAAGAGCAGCATTC

AGCTTGTTAGTAATTTTATCCAGACGCTCATTGAATTCACTAGAAGATAAGCCCTTTTCTGGAGAAATCA

AACTAATCACGAAAAATATAGCAATAAAAGGAATAAGGAAAATAGCTCCAACTGCCATAAACAGAAAGAA

TGTTACAGTTGTAAGAAAATCAGCTAAACCTTTACGAAATTTATACATTTACATTTACCTTTAATTGATT

AACCAAGCATTGATAAGCACTAAACTATACTGCGAATAAAATTCTGGACCAAAATGAAAATCATATCATT

TATAGTATCCATAATGTAATTCAATTTAATCATGTTTCCACACCCCATCGGTATTTGACCAAAGTCGCTG

ATTATCTGATCCTCGCCACAGCTTTTTGGTCGGAAGATTTTTCTCATACTTCCCATCAATAATAACATCA

ACATATTTAAGCATTTCTAGTTGTTTAATATCTTCAAACTTATATCCTGTCCACAACCAGATATCTTTCT

CCGGAAATCTTGCTTTAACCCAAGAAACTAAATTTGAAATCTCTTCTCGGTTCTGTGGATAAAGTGGGTC

ACCGCCGGTTAAGGTAAGGCCTTGGATATACGATTTGCTTAAATGGGACGCAAGTTCTTTAACGGTATTC

ATAGTGAATAACTGTCCGTTACGAGCATTCCAAGTACTACGATTATAACAACCTTCGCATTTATGCAAAC

ATCCAGTGACGAAGAGAACGACCCTACATCCAGGGCCGTTAACGAAATCGCATGGATAAATTCTATCATA

ATTCATCTTTATATTTCCAAGTATATCCCTTATGAATAGATTGAATTCCTTTGCAACATTTATAAACAGC

AGAATGAAAAAATCCTGCATTTCTTATTTCAGTTGCTCCAGTTAGTTCTATTGTATTTCCGTCTGGTGAA

TAGCCAATAACCGTTTTGGTGTTAAAGCGATTTCTAGAACTATTTTTGATATGCTCTTTATGATTAGTAG

ACAAAGTTCTTCCTGTTAGCCCATCAGATATCCTTTTTCCAAAATCATCAGGAAGAGTTACTTTAGACCT

AGCTATGCTCATTAGCTTCTTAGTTTTATCGCTTCTTTTTGCGCCACGCTGATTTTCAAATTTCTTAGCT

TTTGCATACGCGTATTGTGAAGAAGTAACTTTTCTATGCTTACTATTACTCATTATCCAATATGCATCAT

ACATCTTTCCACCATATATTTTAGCCAATAAATGGTGAGCAGTATAGTGGGCCTTATAAGTTAAAAATAC

TAAGTTGTCTAAATCATCTGAACCACCCATACTTCTTGGAATTATATGATGAAGTTCATACCCGGCTTTA
```

-continued

```
GTTTGACGGGGCTTAGATGGGTGTTCAGCAGAATTAACTAGATTTGAATAGATTCTGTCATAATTCATTG

GTGCTTAACCCTATGCATGATTTCTTTATTTTTACCGAGATTAAATCCGCGTTCGTTCGGATTTCCCAAA

TAACCACATGTTCTTCTTATGGTATTCATCTTTTTAGGATCAGTTTCTCCACAAATAGAACAAACAAATC

CGTTTTCAGTAGGAGTCATTTCATGGGTACTTCCACATGTAAAACATTTATCTACTGGCATATTAACACC

AAAATAATCTAAATGCTGTGCAGCATAATCCCACACGGCCTCAAGACCTTTTAAGTTATTTTTCATATCA

GGAAGTTCAACATAAGAAATGTGACCACCTGTCGCAATGAAATGATATGGCGCTTCACGAGAAATCTTTT

CAAACGGAGTAATATTTTCTTCTACTGAAACATGGAAACTGTTAGTGTACCAGCCTTTATCGGTAACATC

TTTTACGCTTCCATATTTTTCTGTATCGAGTTTACAGAAGCGATAACACAGGTTTTCAGCAGGAGTCGAA

TATAAACTAAAAGCAAATCCGGTTCTTTCAGTCCACTGTTTAAGATGAGCATTCATTTTAGTTAAAATTT

CTCGTCCAATATCACGACCGACAAGAATATTCAATTCGTGAATACCAATGTATCCTAAAGACACTGAACT

TCTACCGTTTTTAAATAACTCAATTATGTCGTCATCAGGTTTAAGACGAACCCCGAATGCACCTTCTTGG

TAAAGAATAGGAGCAACAGTAGCTTTAACTCCTTTTAAGGAACTAATTCTACACATCAAAGCTTCAAAAC

ATAAATCCATTCGTTCATTAAATAGCTCAACAAATTTCTGTTCATTGAACTGTGTTCCAATATAAGAATC

TAACGCGATGCGAGGAAGATTCAGTGTTACAACACCAAGATTATTGCGTCCATCAAGAATTTCATTGCCA

GTCGAATCTTTCCATACGCTCAAGAAACTACGGCAACCCATCGGAGAAACAGGAACAGATGAACCAGTGA

TAGCTTTATTGTTCTTAGCTGAAATAATATCAGGATACATCCTTTTGCTTGCGCACTCTAGAGCAAGCTG

TTTAATATCATAGTTCGGATCGTCTTTATAAAGATTAACACCTTCTTCAACGAACATAACAAGCTTAGGG

AAAATAGGAGTTATCCCATCACGACCAAGACCTTTAATACGATTTTTCAGAATTGCTTTCTGAATCATTC

GTTCAGTCCAGTCAGTTCCCGTACCAAATGTAATTGTTACAAAAGGAGTCTGTCCGTTTGAACTGAATAA

CGTGTTCACTTCATCAATGTGTTCAGTAGAGTTCGCTACTTCTCTACCCGTTTATATGAAACAATGTAAT

TTGGATAATTGTCATCTAAACACAAATCTTTAATACGACTGGGTGGAGTTTTAAATCTTTAGCAGCATC

CACAAATGATTTATAGATATTGTCATTTATTTTAACATATTCTGGGACGGGATGAATTGTTATTTTTATA

TCTATAACATTTGGATGATTACTAACCTGTTCTTCAGAGCATTTAAGAAATTTTGCAGCTGATTTAAAAC

TTCTAAATTTATTTCCGGATTTTAAAGCTATAGAAACAGTCTTTTTAGCCGTTCTACTACCAATATTATT

TTTAACATGAGCTTCACTTCTACTATTATTTTTATAATGCTCAATCAATTTCTCTCGTATCTTATCTTTA

TGTTTTAAAGATAAGATTTTACCTTTATGGGCATTACTAAGTTTTTGCTTATGTTCTTCTGAATCCGGAT

ATTTGTTAAATTTATATCCACCTATAGATTTATTAAGAATAAATTCGTTATTAAAATATTTCCTAATAAG

CATTTCTTCATGTTTAAGGGCCGATTCATAAGAATCAAAAACTTGAAGAATTATCCACTTAGCTTTATAA

TCTTTAAGCTTTTCTTTAACAAGCTTAGATGACGAATTGTATTCTTTCCAATTTGTATCTTTACCATATA

TAGTTTTGAATTTTTTAAAACCTATATAAAAAGACTTATCAGGAAATCTTACCATATAGGTAAATGCTAC

AGAATTGGCAATTTTTAAGCTTTTTCTTAATTTCCATTTCATCGTTTCACCTCGTATTCATATTTATACG

AGGATAAACAGCTGCATGTCACCATGCAGTTCAGACTATATCTTCAACTCTTAGAGTTGTCTGCCGTTTC

GGGTCGCTTGACCCTACTCCCTTACATTCATCAGGGATAGTCGTTGGGCATTTACAGCTACTGCTGATTT

AGCAACGGATTGTCTCAGTGAGAGTTTCCCGTTTTAGGCAGATTTTACATGAGCTTGACTTACGTTAACT

CATAAGCTTGGAATGCATCGTATACGTCTTTTTCTGTTTTAGATTGAGCATAATTCAACGCATCAGCGAT

TTGCCATTTTCTGCATCCTCAATATGTTTTGCATAGGTGCGTTTAACATAAGGAGAAAGTACTTTATCT

ACATTCGCAAAAGTCGTTCCGCCGTATTGGTGAGAAGCAACTTGCGCAGTAATTTGTGCCATAATTGCAG

TAGCAACTCCAATTGATTTAGGAGTTTCAATCTGCGCATTACCAAGCTTAAATCCGTTTTCAAGCATTCC

TTTTAAATCTACTAAACAGCAATTAGTAAATGGAAGAGCAGGGGAATAATCAATATCATGCACGTGAATA

ATTCCGCTTTCATGCGCTTTCATAATAAAAGACGGGACCATATTTTTGGCAATGTGTTTAGACACAATAC
```

-continued

```
CAGCCATAAGGTCCCGTTGAGTTGGAAAAACACGAGAATCTTTATTAGCATTCTCGTTTAAAAGGTCTTT
ATTAGTTTTATGAATTAATCCTTCAATTTCTTTTTCAATTGTCATTTTAAACTCTTTCTAAGCTGCTTCT
TGAATGAAGCTATTAATTGTGTTTTGGTGTCAGATTCATTATATTCAAATCCTCTTTGAAGCATCTCGGC
CATCATTTCCTCTTTTCCTAAACGAGAAAATTCCTTTGATTTATCTCCAACAAAGTTAGGGTGAATATTA
TTTTGGGTGTAATCGGATTTTAAATAAGTAAGTAAATTTTCTAACCATTCAAGATAATCAACACCTTGTC
CCTTTAAGCCAGAACGATTAAATTTATGCTTCATTTGACCTTCTGCAGCATTGCATAGATTACAAAGCAA
TCCACGCACCTTTCCTGCTTTTGGTCCATTTAATTCATGGTCATGGTCGAGGTGATTAGCTTGAACATCA
GGATTTAGTTCTCGTTGGCAAATTAAGCATTTACCGTTTTGTGCATCATAAAATTTCTGTTTTTCTTCTT
TGTATAATTTGCCAGTCAATAACATAATAAACCCTTACCTTAAATAGATAAGGGTATTTATTATTTTCAA
GTATTGTAAAACATTTGATGCAATCGCTTATATTGCTGAATCATTCGGTCAGAAAAAGAAATTTGAGTTT
CAAGCCATTCAATGTACTCTGCGGCAGCTTGCATTAAATTTCCTTCATAGCCATCGTTATTTTCTTGTGC
AGCTAATTTAGCTAATGCGTATGAAATACGTTCACCTTGAAAATCGGCTTTAGGCTTCTGAACAACTTGA
TTAGTTCGCTCTACAACTTCTTCAATTTCGCCATTTTCTACTGATTCAGTATTCCACAAACACCAATACG
TAATTGGCTTATCGTAGATGTTAATAATCTTTCCATCAGAAAGTTCAATTTCAATAATTCCAGTGTCAGG
CTCTATATCATCTTCACATTCTTTTACAAGTTCACGAACTTTAAAGACAGTACCTGCACTAAGTTCCGGC
CAGTAATTACACAGCCCTGTATCAGCACGATTAATTCTAAACCATTTATCTACTGTAATCATGTCCCATC
TCCATATCAATTAAGTCATTTATCGTTGGTTCATTATACACCGTTTCTTCATCAGTGTAAACCGGTTCTT
CCGGCTCTGGCTCTACAGTTTCCCATCTAGCCGCCCACCAAGGTTTTATAGCGTAATCCATTCTCGTACT
GTCTGAGTTACTACACGTTCTCGAAGCTCAACCAGTTCAACAGTAGGAACTGCATAATACCAGTCAGAAT
GGTAAGAACCTGAGCGAGATTCATTTACAGCCACATGTACATTATGTTTTGGACTAAAATAAACACACTG
ACGATATTGGCATTTACCATCTTGCACCCAGTCTTCTATTTCGATAGGTTTAAGATAGTCGGAAAAATCG
AAATCATAGTTTTCCGAAAATGCATCATGGTCTTCAATGATTTCGCTCAGAACTGCATCAACATCTAATT
TATTTTCAATATTCATTTTTCACACCACCAACTGCTTACTTCAAAATCGGGTTCGCCATGTTCCCAGAAC
CAGGGGCCGATAGGAATCCACTTACCTTCATCGGTGACGTCATATTCTTCGGATTTAAGCCCAACGTATC
GCCATTCGACTTCATAAGCGGTACCACCGATTACAACTGTGTTCTCGCCATACGGGTTAGACACAACAAA
GTCTATACCTTCTGCTTTAGCTAACCAAATCATGTATTCATAGAGTTTATATTCCAGGTCGCCTTCTGTT
CCATCGCCTAGAAAAATAATTTGTTCATTTAATTCTATCATTTAAAGTATTCCCGCAATTGGTCAAATCC
ACCAATATGACTTCCATCAGGAGCAAATACCTGAGGCATTGTTAAGCCGATTTGAGTATCACGACCTAGT
TTAGTCAGAAGCTCAGCAATTTTCTCATCATCAAAAACACCTTTTTCCGGCATAATGTTGATAAATTCAA
ACGGCTGTTTCTTCACAGTCAAAAGACGTTTTGCATTATCGCAATACACACATTTATGAATGTTGCTATC
ATAACCATATACTTTAAACATATTATTCCTTAATTCCTAGTACTTGTTTAAAAGTCTCGTCGTAATCAAG
ACTTTGGCCCGTTTGTTCTTTATGCTTGTATATAATATCACTTACTTCTGATAGCATATTTTATATGAA
CGAGTTAAAGCAGATTTAAGCACGCTGTATCTATCAGGAAATTTACCGTGTTCATTATAATAAGCTATTG
CTAATTCACGGACTGCCTTTTCAGCAGTCTCCATATATTCTTTACGCTTTGTCATTTTCTTCTCGGTCAA
ATCGGTGTTTACAATGGCGACATTTATAACGAAGATTATTAGTCTGCCAATGGACCAATTGCACCTGTTC
AGTTCCACATTCAGGGCAATTAGGAACGTTTTAGAAGCCCTTTCGCGACGTTCAACCATGACCATTACA
GAATCCCAATTAACAGGAGGGCTATAATCATCACAACCATAAATCTTTCCACGCATTTCCAGATCGTCTT
CTTCACCAGCCATAATAATTTTAATTAGACTAGAATTACTTGAAGCTGCAATGTCTTCTAATAGACGCTT
TTTCATTTCAATACCTCAATAGCATTACGTAAACCATTTGCTTTGGCGGTTAAATCCTTAAGAACTTTAG
TATGCTCTTCAATCTGTTTTTCAACTTCAATCAAACGGGTACTGAGATATTCGCGTTCTTCTTTCATAGT
ATCATTCCCATGATTGGGCTTTGGCGTAGGTTTAAATTTATTAGGGTCCTTTAACTTAATAACAACTTTA
```

-continued

```
GTTTCAAACAGTGAAAGACCATAATTCGTATTATCATCAAAGGATTCAACTACGTCCATTTTAGACAATA

ACGTACGAAGTTTATAAGTCAAAGAACGAATCGTTTTATTATGTTTATTAGCTTCACATGGTTTCATATA

TGGAAGATTTTTATATATTTCATGCGGAGCACAAACAATAATTAACAATTCAAATGGTCCATTCTGAGAT

GATGGAATGAATTTAGCCGTAACCCAATCTTTTACATTTACATTAATAGTACGATCATCGCCATGACAAA

ACAGTCTACGAGAATGCTTAAAAAGCATATTCACATTATTATTAAATTCGTGTGAAAACTCACTGGCAAA

TTTTTCTTTACTATCTTTAGAAAACCATTCTTCTAAATAAGTTCTTTTCACGTCGTTAATAATATTAAAT

GTAACAACATTATCATTTGATACATTAGTCTCAATGTAGCTTGGATACATAAATTTTTTAACATTATTAA

CAGCTATCACAGAAGATAGTAATCGGGAACGTTTGAACCACTCGAGCAAAGAACCAAGAGAATGTGAATA

CGCATTTTGTGTATCTTTACAAATATGGTTTTCCCATCCAATATAGTCTAAAAAATCACGAAGAATATTA

TTGATTACTTCTCTATGTCCTTTCTGATAATCACGATGTTTAGTAATAAGACTGTCAAAATAATCAATAT

AATGTTTACGAGTTTTCATGTTCTTCTCACTTGGTTAATGATTTATACTCCGAGCCATCCTTGGCTTTAA

ATTTTACTTAATTAACTGCAAAGCTTGTTCTAGACGATCAAGACGATTAACGGATTCTTCCCAAATCTTT

TTAGCCTGCTCATATTCTTTCTGCGCTTTATTAGAAATTTCTAGAACTTCTTTATAAGCTTTTTCTAGTG

CAATAACTTCTGGACGAATTTCTATCGGTTCAGGTGAATCATCAAGACATTCCATTAGTTCCTCAAGGGT

AGTTTCTTCTTTAGGAGTATTCACAATTTCATCACATTTTTGTTGGTAAATTTCTTTACTAGTAGGTGAA

TAAGCACATTTCACTTCACGAAGGCTAATTACGAGTTTATATCCTTCCCAACCGCATATATTCTTAAAAG

GATATGTATGAATATTTTCTACTGTTTCCATACAAAGTAATGCGGTCTCTAATTGACGAGTTATAGTGCT

AGCAATTGAGAAAAATTTATTAATATTCTTTTGGTTAGTTTCTGGTGTAAAAAATCCATAATTCACAAAA

ATAGATACTTTATTTTTATCAAGTTCATATTCTTTTATGATAATCATATCAGAAGCCAAAGGATGAATTT

GACGATAATCGCCATAACATAATTTAGAAGCTGATTTTAGAATTTGCTTCTTGAAAAGTCTGAAATTACT

AATCCAACGACGAGTAAAAATATTCTCAGGGTCTTCTTTATTATTGAGATGATAAGAATTAACATCACCG

AACCAATTATATCCTACTACATCTTTAGTTCGTTTAATTTCTTTCCCAAAATTACCAAGAATATCCCGAT

TAACCAAATATGAAAGAAGACGAGACTCTTTAAAGGTTTTCTTGATAACATCTTTATCTACACGGCTAGA

AATTTTACGAATTTCATGAATAAATTTAGTAGAAGAAACAATACTTGCATCAACACTATTGAGCCACTGA

TTGATAATAGAAAGAACGCTATTTTGGCCAAACATCGGTATAGCTTTATCATCAATAACGCTATTGAATG

ATTTGATATATTCGTTACGAGTCATATTAATCTCCTCAGTAGAAAGTAAGAACATTATACCACATCCTTG

TGGCAAAGTAAACTAGTTCAGTGCATTTAGTGCATTGTTCAGTTTAGAACGTTGCTTTGTCAGATTTTGA

ACCCTTGACTGAGCTTGTTCTAACGCCTTTTCAGCTTCTAGCACTTCATTGGTCGCTTTAACTAATTCAG

CATCTACTGCCTTAAGAGACTTCTCAATCGCATCCGCGTGCCATTTTTCAACAGGTTTAAGACTTGGATT

TTCAACAGGAAGAAAATTCACTTTATTGAATTTCCATGCATCTTTATTACCTGAGCTATACATCCAAAAT

TTAGGATCGTTTGATAAGTAATTAGATAAATTTAAGTTATCTTGCACTTCTTGCTTTTTCTCTTGTGTGA

CTTCGTCCTTTCTCAAAAATTCATATTTAAATGAAACGATCATATCAAGTTCATATGATGTTGTATCTAA

CTTAAATCGTTCAAAACGAGGTAAAATCTTAGATTGAACAGCAGCAACAACATCCATATACTTAAATGCT

TCTGTCAACTGCGATTTAAGGCATTCGCAAATTGAAAGAGAATTTTTTGTATTAGGTTTAAAGCTAATTC

GTGCAGTTCTATTATTTTCTTTTAACGGTCTTACTTCCATCTGAAGAGTATAACCATCAAATTTCAGATT

CTTTAAGTTAATGTCAGAGCCTTTTAATCGACTAGCAGTAGACAAAATTTGCTTTAATTGTCTACGGAAC

AGAGCAATAAATCTCCATTCAATACGATAATGATTTGGATTGAAAAATCCAGATGATAAATCGACCTTAC

TTTGACCAACGCCTTGAACAAATAGAGGATTTTTATAATCAATAGTTTTACAGAAATCGGTGAGCTGTTC

ACGAGCAGTCATTTGAGTAATATACCCTGCTTTACTAAAATTACGCACCCATTCACTGCTATTCGTATAC

TTAAAGTGATGAATAACACGATTAACTTTATCAGGGTCTAAATTATTTTCACACAAAAATGTCATAACAT
```

-continued

```
CACGAGTATAGCTGGCATTACGAACCATATCTTCAATTTGAGAACGAGTTTTCATGGTGTTCCTTAAGAT

TTAAGTAAATCAACAATTTTAATTAACTTTTCACGCTCAGATTTAGCTTTACTACTCAATCCAGATAGTC

TGAAAATTTCATCATCATATTGTTGAATAGAAATATCAGCTCTTCAATTTGCTTATTAAAATAATCAATT

TGTTCAGAATGTTTTTCGTTACTACGAACTGGTACAGGTTTTGTAGGCAATTTAGTTGAACTGGATTCAT

TCGGGCGATAAATTAAAATGCAATTTGAACCAATCGGGCATTTAGCACCAGATGAATATTCTAACGTTCC

AGCTTCTTTTAAAACTTCAAAAGCTAAACAGAGATGATGCCCCATATTAACATAATCAGTAGAGCGAGCT

CTGATGTAATAATCATCTCCACGAGTGCTAAATTTAAAGCATTTAAGGTCTTCTGTATTATTAGTTTTAA

AAATCATTTGTTTATCTAGACCTTTAGCCAATCGAGCACCTAATGCTAATAATCGTCGTTGATTTTCCCA

CAAATCTGCGATCATTTGGTCAAATGATAATTTCGGCATTAGCCGACCATAAAGGTCATATCCTTTATTA

TAATTGCGAAGGATTTCACTCGCATTAATACGAGACAACGCTCCAATTTTATTAAGGGCTTTCATAATAC

GATTAGATAAACTCATTCCAGACCCGTTTGTTCGCTGTAAATGTTTTTCTAATCCAAATCCAATATCAAC

TTTAAATTTATCTAAAATTTCAGCATGAACATCTCTGTCAATAACATTCAAATCCAAAGTTGGGTTAAAT

CTATGAAAAAATTTATCTGGCTCTCCACGACGTAAAACAGTCCATTCATTCATCATTTTTTTATTAACTA

AAGATTTAATTACTGCGTTGACATTATTAATTACTACTGACATATTTTCCTCACTCAATTTTACCAATTA

CGCGGAATAAGATTGAACAGACTATATAAGTACCACATATAGATTGAACTAATGCCATTCCAAAGAACCA

AACAATATTATCAAACCATGTCTGTTTTACGTCGAAAGGACGTAAACTTACAGTAATATTATCACCTTTT

TCTATTGAAGAATACGTCTCTGGGGAAATATATTCACTAAATCTATAACCGTCTTTGAGTTCATATACAG

CAATAAACGATAAACTAGACCCCTTTCCTTGAGTTCCTGTAAGGGTATTAACTACAGTAACATCATAATC

TTTATAATGCATATAATCATTAATTGCGTAATAACCATATGCAATTACTATACATAAACAACATATCAAT

AAATTCAATCTTTTAATTATCAACTGTTTCATAATAATCTCAATTAAAAGGGCTTAGAACCATTATACCA

TCCTTGGTATAAAGCGGTTATGCGAGTACCGTATTTAACCGTTCTTCAAACTTCCGAAGAGTGTTCTGGC

GTTCAGCTCTTTGCTTTTTGTAAGTTTCAATACGCTCTGAAATGAGAGTGTATCGTTCATTTACTGATTC

TTTCATAAAATCAGGAATTTCTCGAGAAGCTTTAATCTCGTCAAATTTATCAATAACAGCTTGCTCTTCA

GCAATTAAGTTATCATACATCAAAATATCTTTCTTGATGAACTCAATATCTTCTTGAGTTACACGAGATA

ATTTAGATGCTTTATCCTTTTTGTACTGTTCGTTAGTATCACGAGACCAGTGTAATGTACGATTTTTATT

CGTATTCTTGTAAATTTCTACAATACCAATCTCATCGATAATAACGATCCAATTCCAACGGGATTTGTAA

ATTTGTCCTCCATTAACAGTGATTTCACCTCCGATTGAGATGTCATTAAAGAACTTGCTTTGTGCTTCTG

ATTTAAATTTACCATCGTTGTAATTTACCAGGTTGAAAATATCTTTAGCGTTCATTTTGTGTTCCTCCGT

AGTTGATAGTTGTATAGTACCACAGAGGAACGGTCTTGTAAACAACTAAAAGAAACTTCTTTCACAATTT

TTTCCACTGAACCAAGCGCTCACTGCTTTCTTAGTTTCAGGAGCAGTGTTATCCATAAACCATTCAAAGG

CAGCCTTTTATGATTCTGGAGGGCTTCTCGGGCTTTAATCTGCTCACGGTCTATTAACACTAACATATG

AGCCTTTCTTGTCACCAGGGGCTTCTTATGATTTTTTGAATACTCCCAATCATTTGTCCATCGCATCGTT

GTTGCGAATTGAAATACAGCTTCTTTAATCTTAGTTTCGTAAATTTCACGAGCCTTTGAGTATAACATCA

TTACCTCCATTTACCAGTTTAATTCTAGTCATCTTTTTGATGGCAGTCCATATAATCTATTTCTGAACTG

CCTTTTTGTCTTAGAAGGCCTCTTATGAATTTATTTCAGAAGAGTAACCCGTAGCGATTTCTTCCCAACC

GTTTTTGTCGGTCATAATAAAGTCAGCAAGATAAAGTGCAGTACGCAGTGAAACATTACGTAAACGGTTA

ACATTGACTTTCATCCATGATAATGCTTTATAAGTTTCTTCATCAGAAAGACCACGCTTTTGCATCATGT

CGGTTGAAAGAATAACATCTTCAACCCTGACCATAATTTCTTCATTAGTGTGAACACCCAAATCCAAATA

AACTGAGCGGGACACTAATGCTTGTAAATGTGGAGCAAGTTTAGTACCACGGTCTAATTCGCGGTCAATG

TCAACGTTTGTGATAAAAACAATTGTTCCTTTAAATTCGAGCTCACGCTCAATGCCTTTTCTTCTAAGT

AAGAAGATGCAGTGCTCCAGCAGACTTTACGGGTCTCTCCAGTGTCCAGAGCAGCTTTCAGAAGATTAAG
```

-continued

```
AATGTCCATATCAGAGAAAACATCCACATCATCAATCAAAAGGACAGAATTCTCTTCACGATTATTCCAA

AGCTGTTCATAAAGACCGATACCAGAGATTTTACCGTTAATGCTTTTATACTCAATGTATCCAATATCAT

TTGCTTTATTCAAAGCTTTATCTAAAGAATATGTTTTACCAATACCCGCCGCACCAGAGATAATTAATGA

ACGAATATTTCCGTTAATAATACCATTCGTCATCATTCCCATAACATTAAATCTTTTATTAATGCGGGTT

TTCATATCTTCATATGATTCTTTAACTTCTTCAACTTTTACACCATCATATGAAATGTCTGATTTGTAAA

CCCAAACACCGCGACGTTTACCGTCAATTTCAACAAAAACTTTACCATCTCCTTGTGCATCTACCGGAGC

ATTATCAGGGAACCATTCACCTAAGAGCTCAAAAGTTCCAGAGATTTCTTTACCGAAGTACATACCCTTA

TTGATAGTTACAGTTTTCATTTTATTCTCCAAATCCGTATCAGTTGATAGTTGTATAGTACCATAAAGCT

TTATGCTTGTAAACCGTTTTGTGAAAAATTTTGAAATAAAAAAGGGAGCCCGAAGGCTCCCTATCATTT

ATAATAACTTCGATGGTTTTCAAGATAAACCCTCTCAAGGAAGTCATCCCAGAAACTCATGTCTACTTTT

TGCTGCATACCGTTCTTAGAAGCTTCAGTAGATGCTGCTTCTACTTGATCGACCACATCTTCCAAAAACT

CTTGAACGGTTTTAAATGGATGCTTACCCAACTTCACGTCGAGAATAAATGGAGCATCTTGGAGTGGATA

AACCAAGTCACCAGTTTTGTAAATTTCCAATAGTTGAAGTCCACCACGACAAGCATGGCTCAGAGCTTTC

CAGTCAATGCCTTCATTGGCTTCGGCCTTACGAGCACGTTCGCCGTATTCAGCATCTAATTTGTTCAGTG

ACTGCTTAAGCTCAATAAGAGAAAGCGTTGTCTGATATTTACGACCCAACACTGTGTAAAACGTTTGTGG

GCCTGTTTTCTCATGATTATGGAACACCCATTCACAGAATTCGTTTTCTGGAAGACGATGCTTAATATCT

TCAACTTTAGTACGACGCTGCTTAATGGAACCATCTTCTTGGTAATCAACCCATTGCTCAGGGATTTGAT

TAACTACTTTCAATACATCGCGTAATGCAGCCAAACGAGAACCCTTGACGCCGTATTTAGAAGCTTGCTT

GCGGACATATCCTAAATATGATTTCATGTTAGTCGTATAAAAACGAGAACGGTTGTCTTGAATAAACTTC

CAMACATCAGGCAAATCGGATTTAACCACTAGTTCAGGTGGAGTGTGAAGCATATCCAATGCTACAGGTT

CACCATCTGCTGCTAATTTAAAGAAATACTTAAGACTATACAATTCGTGGTCAATATTATCTTTAGTGTT

TTTAGATGATGTGTTGTTGGTATTTTTACTCATGTGCTCTTTGACGTTTCCAATAAGAATATCGCGAGCA

GGAGGAACAAAGATTTCTTTAAAATCTACATCAGATTCTGGAGTAGAAGTTCCATAAAGATGACTACCAA

AATAAGACTTAACTACAGTTTTCATTATTAGACCTTTCATAATCTTCATTAAATTGTACAATCAATCGAT

GATAATTAGATTTTGGATATCCTAATTTACTTATATAAGTTCCGAATGACCCACGTTTAGGTCTATTTAA

TTTAATCCATAACTTATAAAGTAAGTCATAGTCTTGCCAATGTTTACCAGTTCTTTGTCTAATTTTAGAT

GAATTTGATTGTTTCTTTTTAGCTTCAAAATTATTCAAAGATTTTTTGACTGCAGCAGAGTGTTTTCTT

TAACTCCCGGTCGTTTAAAAGCAGCTTTCACCCCTTTAGATATTTTTTCTTTAACTTCCGGTTTGTTTTG

TGCTTCTAACTGGGATTCTGAAATTTTAGCCCTTATTTCAGGAAGACTTAATGTTATCGAACGTTTTTCT

CTGTATTCATTAGACTTCCACATTTCTTTCATTGTATTAGAATGTATTTTTGAAAATTTTTCTCTAACTA

ACTGATATCCTCTTGAAGTTAATTTGAGATTTCTTCCTAAAGAATCTTCTCCAAAATTATAAAATGACCA

CCATGCATAAATTAATCCAGGCGAATTGTAATGAATTTTAGCTAAAAGCCAATGGGCTATAAAATGCTCT

CTAGCTGTTAATAAAACTAGATTATCAGAATCATCATTACCACCAATACAAGATGGAATAATATGATGCT

TTTCCGTATAAAAATTTAATTTAGATTTATCTAATTTTCTGAGTTTTCCTTTCTTAATTAAATTATTATA

TACTTTAGTATAATTCATTGGTTCTTCGTCTCATTTAATTTTGCTTTGCATTTATAACACATGTCTGTTC

CACTTGAAATAAACATATTTCCTCACTTTGAAATCATAGTTGGAATAACAGAATCAAGATAAGTCTTTAG

TGCAATAGCTTCCTCTTTCTTTAATGTAATGATATGTGATCGAAAATCATCAATTTGACGAATAGATACT

ACATCTCCCTCTTCATAGCATTTTGAAACATTTAAAATAGTTTCATCATTCTGATTACAGGAGTTAGTAA

TAATAGCATTACATTTTTTAAACCATTTTAAATTATGTTTTCTTTTAGTAGAATCATAAAAATATTTAAT

GTTAGTTATAAAATTATCCCAATTATTAATTGATAAGCACATTGACTCGCTTTTAATATTAAATCCTGGG
```

-continued

```
CATGAAGAATAAAAATGAATTTTATGCTCATCATTAATGCTTACAATTTTATCAGTGTAAGCATATTCAA

TTTGGGTTAAACGAACAATTTCGCTAGGCGTAAAATATAACATGTCATCTTCTTGCGTCAAACGATACAT

GTTATTTACTTTTTCTATAGCCAATTCACCAAAAAGTGGACTAACTTCTAATACTAGTCGTTTCGCCTCG

CTCATCATTACATACTCCTCTGAATCATATTAATAATGTTATTCACCAGATTATAAGTAAACATTGGGTA

ATTATATTGAATCATCACATATATAACAAACAAAACTTTCATTCTCTTCTCCTTGGCAGTTGACAAGATT

ACTATACCATAATCTTGTCAACTTGTAAACCATTAAATGACGTTTTCGATAAAATTTTGAAGCTTTGTAT

GAGCATCAACCATGATTTTCATTTCTTCCTTGGAAAAGCTGTGCCTCTTTCCCGAGAAGAACATTCATAG

TCAGAAACTGCATTAGCATATTCTTCAATTAGCTTCATTAAAAACATCTGTTTTTCAGTTTTCATTATTC

CACCTAATCATTTCAAGATATTGAACTAACTTAGCTTTGGATTTATCCAAATCCCTTTTAGCTGCTTCTA

TACCGTCGTATGAATATCCTTCACAATGCTCAACTGCTAATTGATATGAATCTATTTCAATATCATGCGC

TAATTTAATGATTTTTTCAAACTGTTCGCGTGTTAGCATACTTAAACTCTCGTATTATGATCGATAATTT

CATCAAGAAACATATCTAACGCTTCTACAGCATTATTAACTTTAGCTTCAAATTCTTCAATACCTGATAA

GGCAAAGTTAATGCGTTCCTCATCTGCTTTACGAATTAAAGCTACCAATTCCTTAATTTTATCCGCTTGT

TCGATACTAATCATTATTCCACCACATATGAAAGAGAGAATATTGCACACGCCATGTGAGTTGCAACTTC

ATCACACATATTATAACGTTTCTTAAGAAGTTCTACAAGTTCTTCACTAGTAACTTCATCCATGTCGACG

AAAAAATCACCATTAATGATGACGTAGATATTTCCTTCTTGATTGAGTGCTTCAATTTTCATGATGTTCT

CCTCTTTATCCGATGGTTGTATAGTACCACAGCTCAAACGGAAAGTAAACCGGTAAAATGAAAAAAAGTC

TCCCGAAGGAGACTAATGTTATTCGAGGGAAAGAAGATACTTACTCTGGTAAAACATTCCAGTAATATCA

TCTATCGTGCTTTGGATGGCTGGAGGCATTTCTTTATAAATGCTGTTAGATTGGTCTAGTATGCGATCAA

TCATTTTAATTGTGTCGGTAGGAAGTTTACTGGCATCTGGAATTGAAGGCGTGTATTTTCGACCAGAATA

CCCCAAATATTGCTCACCAAATTTATCAATCAAATCTGGCAACTCGGAAAAAATAAAATCGTATGCTTTG

TGTCTAGCATAACTTTTAGTTTCAAAATGTGCAGAATGAAAATAAGCTTGTGCAGCCATTAATAAACCTA

AGTATTCATCTGCCTTTGAAGGTTTTCCACTTTGTGAAAAGTCGCTGAATTTCATTCAGTCTCCAATTTA

ATGTTCATAATTCTAGCGTATGATTGTGCCATCTCCGCGCCTCGCTCTATACATTCAAAATCAGAAGAGC

ACGGGTCATTTTTATAGGTCGTTCTCATAAAACTATAGAATTGTTCAGACGATTCTACGCTTTTATTTTC

AAAAAGCATATAAACGTGCCTAATACCAGATTCCATAAATTTATCAAAATGAGGATCGACATTCGCTTCA

ATCGATGGAGATAAAACAAATGACAATCCTAGCATGGCAAAAAGTGCTGTTGCTTTTAAGGCCATAAAGG

CCTCCTATCATTTTGTCCTGTATTTACTTTGTGCCGATGCACGGCCTTAACTTTATCAAGGTATTTTTC

AAAATTTCGCAATCTAGTATAGTCTGCCGGAGATTGGTTGAGTGATACTTCTCGACGCAAAGCTGAAATG

ATATTTCCAACTTCCCTACGAATTTCATCTAATTGAAGAACAGTAAGATTGCGAAGTTGCTTTTCAGTTA

ATTGTAGCATATATACCCCTTTAGTTAGATAAACCTATTTATAACTTTTGCACTAACCGAGCTTTTTAGT

TAATTCATTCCAATGTTTTCTACACAAAGAAACATAAATTTCATCACCAATACAAATTTGATTACCTTCT

TTAACTGGTGTTCCATCTTCCATTAATCGAGCTGTCATAATCGCTTTTTTACCACAATGACAAACTGCTT

TTAGTTCAATAAGTTTATCTGCAATCGCTAAAAGTTCTTTAGAACCTTCAAATAATTTTCCAGCGAAATC

AGTCCTTAGCCCATAAGCCATAACAGGAACATTATATGTATCAACAATTCGGCTCAATTGATGCACCTGT

TCAGTTTTTAAAAACTGAGCTTCATCTACAAATACGCAATGAATATCTTTTTGTGCTTCAGCCCATTTAT

AGAACTCGAAAATATCCATATCATCTGTAATAATATTCGCTTCCTGCTTAATTCCAATGCGAGAAACGAC

TTCACAGACAGAATCGCGAGTATCAATAGCAGGCTTAAGAACTAATACACTCATTCCACGTTCTTTATAA

TTATGTGCAGCAATCAAAAGAGAAGCAGATTTTCCAGCATTCATTGCTGCATAAGTAAAAATTAAACTCG

CCATCTTAGTCCTTAGTTAAATTTTCTAAATATGTTTCTAAATCATTTTCAGCTTTATCGATAGATTTTA

CTAATTCGTAATATGTTTCGGCATCTCCATATTCAGAAGATATTTCAAAAGACAAATCCTTTTCTAAACT
```

-continued

```
AATAATTTCACCAACTAAAAATAATATTTCGTTCTTTTGTTCGCGAGTAATCATAAGGAATTTATATAAT
CAATGAGTTCTTGTTCTTTATTATCGAATTCTTTAGAAAGTTCTTCGTACTCGTTTGCGCTAAAAGGACC
GCATTCATTACAAACTTTTTCCAATTCACTATTTTTATCCATAACTTCGTGGATAAGAGAAAAGAGTGTG
TCTTTTTGTTCTTTGCTTAAACTCATAACCATGTCACCTTTAAGCAGTATTCTTCTACATGCTGTTTACG
ACCTTTCTTATCAATAAAGGTATATTCAACGAATGTTCCAATGTAGTCTTTATCTACATCATGTGGACTA
TTAATTGGACATTTAGTGCGACAAATGCGTTCCCATTGACGAATAATTACTGCCTTATTCTTTGGGTCAT
ATGGATGTGGATAATGTATATTCATAATAATGGTTCCCAATCAACAATCACAATTTCTAATTTAGAGGAA
TATGTATCTAAAATCCCCTCAATAATATCCCAGTTCCCTTTACCTATGCCTGCACCAATCCTAGGCATAT
AGATTGTAGGTTTAATCAGTTTATTTTCACCAAACTCATTTAATTCTAACATACAATTCATTAAAGCGGA
ATACTCAAAATTTGGCCCTGGTTGAAATTGAGTATAAAGATTGAAGCAGTAAGCTTTATGAGTCCTAAAG
TATTTTTCATAGACTGAGTAAGAACCGAGTTTAGTTACATCACCCCATTCAGTCTGTAATTTATCAGCTT
CCAAAATTTTAGGGAAAGCTTTGGTTAATTGACCCGCTACGCCTGAACCCATAGTATGAAAACAATTACA
TCCATGTGCAATATTTTTACCTTCAGCGAAAAGGGCGACAATATCGCCCTTGATATATTTTACAATCATC
TAGTACTCAATCCTCGATTATAAGAATCTACCAAACGGTCAACCATTGAATGACAAGCGGCTTTATCTTT
CTCCTCCGCAACTGAACATTCTAAGGTATTCCACTTTTTAGCATATCGTTTTAACAATGTATCGTTTTTG
TATCTGCTTGATTTATCTCTTTCTCCGTCTTTATATGCATATATTAATTTCTGTGCAAATTCAGCTTGGC
ATGCCTTATTTTTCCCACAATAATCTGCCGCAGTGCGGTTTACATATTCTCTAATTTCAGTATATGATGT
ATCTGCTGACGCAGAAGCAGAAAATGAAATTAATCCTATACATAAAACCAAAATTTTAGTCATTTACTAT
TTCCAAAAGTTTATTATTTTTAAGGTAATTAGCCTTTTCTAGGACTTCAGAAGCATATTTAGAACCTGCT
TTAACATTCCATCCCGAATTATAAGAGGATATTGCTTTTCTTATATCGCCCTTATGTATATTTAACCAAT
AAGAAAGTTCAATGTACGCCCAGGAAGCTGAATTGGATCGTTTATTCAACATTCTTTTTATTTCAGCATC
GGTCATATTATAACCAAGTTCCTTAACTCTTGCTCGCATAGTAGGCAAATAATTTTGGAACATTCCGTAG
GCGTGATGCTTTGGTTTAGATTTTAAATTAACTCCGCCAGAGCTTTCTTGCCATAAAATGGCAGCCATTA
TATGACCTAATCCGCTCTTGTGGATATTTTTGTGTGTTTTATATTTTCCATCCTTAGAAAATTGTTCCCC
GAATTGATACGCGTAACGCATGTTATCGAGTTGGACATTACTGAAAGTATGCTCGGAGCTATGTGCCATC
ATTGAAATGGCCAATAGACCAGCGAGTAGTGCTTTTCTCATGCTTACCTCATTGAGTTTTAATTACTGCT
TTAGAAGCCTTTCCTGGTAAACGACGACTGTTGATAATTGCCATCCTACATTGAAGTGACGGGTCTTTGA
ACTTCTCGTTAGGTTTACAAACTGTAAATCCAAGCCAAAGATTTCCATCTGTGATTTCTAAACGTCCAGG
ACGATATTCAACCCCATCAATAAAATCCTCGTCAATGTCAGGACGCGGAGGCATACTCAGGAATTCATTA
ACTTCTAAAACATGGTCTTTTATTTTATGGAATAATTCAAAAACGTATGTCTCATCAATCTCCCGTTGAA
TTGCGCGATCAAGAAGATGTTGAGAATATTTTAGATGAAACGATGAGACTCCTGCTGCTTTTGATGCCTC
ACGAATCTCATTGTTAATTTGACGAAACTCCGACTCAAAGTGACGACGAAGCTTATTTCGACGGATAAAA
ACTTCTGTATTGATAGTCATGTTATTCTCCTCTTAACTGATAGAAAAATTATACCACAGTCAAGAGGAAA
AGTAAACAGTTATTCTTTAAATCTAATCAATTTATTCATAGACTTTGAAACTTCGGCACGAACCTCATGT
AGATTTTGAGCTGTTCAAGACGCTGCGTATAGTAAGCAATTTCATCTTCTTCGAGACAGTCCTGCGAAT
CTTCTTTAAGATAACGTGCATAGTCCTGGAAAGCGTTACGGACTACTTCCTGGAAGTCATCAAGACTTTG
AATTTTCTTAGGAGCAACAGATACACGACGAGGGGCAGTATAATACTCATAACCAAACCCTGCGCTTAAT
TGAGCCATTAGTATTTTCCTCTGGTTGGAACACTGCACGACAAGCCCACATACTGGCTTCTTTGAGTTT
CGTTTTAGCAATAGTTAACTGATCGAGACTTTCAGCATAATTCTTCGCGAATTCACAGTCTTCGCAATTA
TCTAGTGCTTCCCAGAATTCATCATATAAAGCATCAAAGATAAGTCCTAAACGAACTTCAGCGTCTTTAA
```

-continued

```
TAGCATTTACTTTACCGATTTTCTCTTCAGTATGTGGTTTATAACCCTTAATATCTTCAATCATATTTGA

CTTCCTCACCAGTACATAATACGTATTCAACTAAACGAATAGGTTCATGAATGCCATAGCCTTGAACAGA

AATTTCTGTCGTAGGATAAATTCCATCAATATCACCCATATTCCACGCTTCATTAAATTGCTGTTCGCCT

GAGTTACTAAACCACTCGCGAAAGCATTTAGCACATCTTCAGAACCTTCAATAATTATCTTTGCCATTAC

AAACTTTCAGTAAAGGTACGAGCGATAACGTCGCGCTGCTGTTCCGGAGTCAGAGAGTTAAAGCGAACTG

CATAACCGGATACACGGATGGTCAGCTGCGGATATTTTTCCGGATGCTTAACTGCATCTTCCAGAGTTTC

ATGACGCAGAACGTTAACGTTCAGGTGTTGACCACCTTCAATTTTAACTGTAGGTTGTGGCTCAATTTCA

ATTTCACGGGCATGCAAACCATAGAAAATTTCTGGGTCTACAAAAGAGTCCTCTTTAAAGGTTTTAGAGA

CAATAATTCGTGCTTGAATACCATCTTCAAAATAAATAGTACCTTTATGTGTGCCTTCAAGAATTTGATA

TGCTTTCATATAAACCTCAATTAGAAAATAAATTTATCCAAGATTGTTCTTTAATTAAAAATGGCTCAGA

ATCATATGCCATTAAACTTTGCGTAATTAATCCTTTAAAAGGTCCATCAATAAATTCCATGGTAAAATAT

GGAATTTTATTCATTAGCCGTGCATTAGGAGCAGTGCACAAAACTCTGCATCCTTTGAATACGCCTTTTT

GTAATTTGTATTGCTTGGGATAAAATTCGCTCAAAATGTTATTTTTTGCCAAAATTTCAAAATGATTCAC

CAATTTATTTTTAATAGTTTTTGGCGAAAAATAAAGATATTCGAAAAGCTGAGTGTCTGTCATCATTGCA

TTCCGATTACGAAAAACTGTGGACGAGTAATACCACCAATGCAACATTTACTATTACAGCAGTAGTGTAC

GGTGTCAATATGGACACTATAAATCTTATCCATATCAGGAGATTTGACAGGCTCATCAATTATATACAAA

ATTCGCGAAAGCTTTAAACCTCTGAACTTGCTTCCTTTATTACCAATAAAACTGCGTACAGAATCAGTAA

ATAAACGAAAACGTATATCATCATTAGAATAACGCGAAAATTCCTTTTTGATGTTATTTGCAGAAATTTT

AGCATAAGCTGAAGTATTAGAAAGAACAATAACTGTTCCGCCATCATACAACCAATTAGCAGCAAAGTTA

GTCACAGCAATTGATTTACCGGATTGACGTCCACCATCTAGTCGAAGTGTACAATACTGTTTAAGTAAGT

CTTCAAATGGCGGGATATATTCGTTTTTACAAATTTCTTCTACTCTAGCATCAGAATGGTGTGTAAAAGC

ATTCATCAGGGATAGATAAGGACCAGTTAAAAATGTTCTCATTTCTTCTCTATAAGCTCTATAAGTTTGG

GCCATTCCGTGGCACATGAATTGTCCATTTCTGTATTTACCCATTACCGCGCTTGGGCTCGACCTTATTA

CAGGTTGGCGGGAATCCCTCATATAATCATGAGGTCCAGGTTGTTCCCTTATGCATAAATCGCCTTACCG

TAGTATTTGTACCAAGTAGGACGTTGTGCAATTTTTTCATCTAAACGAGCTTGTGATATAGCAATAGAAG

CTTCATGGGAATATAATCACCACGGAATTCCTGAGGAATATCACTAATATCCTGGACTGTAGTATCCTT

GATATTAAAACCACGTTTTAAACATTCAGCTATAAGCTCAATTTGACGTTTACGTAAGAACTCGAGCTTA

TCGTAAAAGAATGTAACATGACCTGCGCCAAGGATAAAAGTAGGACTGATTTTAAAATCACGAACACGTT

TACCGTTAGCAACATGCTTACGAACTGCACCAAAAACACGCGGCAATTCACGATATTCAGCCATTAAGTG

TTGGTCAGCCAATTCAGATACTAAAGTAAGGTTGATACGAGTCATTTTAGTGTTCTCCTGTAGTTGATAG

GTCTATAGTATCATACCTACAGGAGATGTAAACTGTTATTTATCTTTAATTGCTTTAGCTGCTTCGATAG

CCGCTTGCTGAAGGTCATCCATAGACATGCCGAACTTAGAAGCAAAGTTATCAATTTTCTTTTCGACGGC

ATTCAAAGGCTTGGCCTGTTTACCTTCATTAGCGCCAGGAAGAGCGAGAATACGCTCTCTGTCAATATAA

AGGCTTACAAGTTTCTTACGGTCTTTATCGGGCAAATCATGAAATGAATGGGCCTTTTTATTTACAGCGG

CTTCTAATTTACCTGCGCCCACTCGCGCTTCGGCAATAAATTCTTGATATGTTTTCATATGTTTCCTTTA

AATGTAAATATTTTTATTATTCTATCCTAGAATTGTGATAATATATTCACAATTCTAGGAGTTGTAAACT

GCTTTTATTTAAGCGTCCCAAGTATAAGCTTATTAAGAATTACCACGGGCTGCATTAGCAACGGCGTAA

GCGTACTGAATATTAGCGTCTTTAAACTTACCTTTAGAGGTATCTATTTCTGCCTTAAAGCCGCCTTTAG

TCATAACATCGGCAAATTCTTTACGGAAAGCCATTGCATCAAGACCTTTCCATGATGATTTATGCTTGGC

AAATTCAAGACCTGCGAAGTTGACAGCTTTAGCCAATTTATTATCAATGACCCATTTACCGGCTTTAGGC

ACAAACTTCGGGCCTTTCTGTTTAGAGAACAGTTTTAAATTCCAGCGGCGAAGGTCTGCATCAGCTTTAA
```

-continued

```
CAAATTCTGAGTCTAAGTTACTAGCAACAACATCTTCAATATGAGCAAATTTAAGTCCGTCAACTTCAAT

ATTTAAATCGGTACGCCAGCGAAGTCCTTCCCAAGCGAAGGCTTTAAAGTCGGAAGCCTTTGTAGCTAAG

TACCGTTCAATAGGAGCTGTTTTAGGGTCAAAGCCGTTTCCTGATCGGTAGGTCCACTCATCTTTGTTAA

TGCCTTTGGCCTTTACTACAGAAGCTTCGGCAATAAATTCTTGATATGTTTTCATATGTTTCCTTTAAAT

ATTTTAATTAGTAATTGTCTATTCAAGTAATTGTGAATATACTATCACAATTCCAAGAGAAAGTAAACAG

CTTTATAGATTTTTATACGCGTCCCAAGTGCCAGTTCTAAACGTTGTAATGACTCGTTTTGCGCGATTAG

GTGTTTGATTATACCATATACTTTTAGCTAAGTTAACTGCTGCTTCATCCCAGCGTTTTTGTTGAAGCAT

ACGTAAAGAGTTAGTAAATCCTGCCACACCGGTTTCTCCCATTTGGAAAACCATATTAATCAATGCACAG

CGACGAACCGCATCAAGAGAATCATAAACCGGTTTTAATTTAGCATTTCTCAGAATTCCGCGAACAGCAG

CATCAACATCCTGATTAAAGAGTTTTTCAGCCTCATCTTTTGTAATTACACCATTGCAATTACGCCCAAT

AGCTTTATCTAATTCAGATTTAGCAGCATTAAGTGATGGACTTTTTGTAAGCAAATGACCGATGCCAATA

GTGTAATAGCCTTCTGTGTCTTTATAGATTTTAAGTCTAAGACGTTCATCTATACGTAACATTTCAAATA

TATTCATAATACCTCCTAAGTATTTATAGAAGGTATTTATAAAATTAAAAGAGGTTGTTCATTATTCGGT

AAAGTGAAGGACCCATCACATATTGCCACTGAGTACGAGGAATAAGAGCAAAAGCGTCCATCTCTGGAAT

CATAACGCCATCTTTATTTTCAAAATAAGACTCGCAACGGCAATTTCTGAACATCTCATGCTCTACTGGA

ATCGTGTAATAAAATAACTGTAGGTCTTTATTACTAGAATATTTAAATACACCTAGGTCTTCTAGAAGGT

CTGGATTATAATTGCTAAAACCAGTCTCTTCTAAACATTCTCTTCGTGCTGCATCTAATGCGCTTAAATC

AGAATTTTCTACACGGCCCTTTGGAATATCCCAACGATGTGCCATCATTCCAGTCTTACGAGAACCAGTA

ACCCGACCCATAAATAAATCTTTATCTTCTGTCATAAAGATAATACCAGCTGATAATGTTTTCATTTTAA

TTTCCTGCATTCAGTGATAAAGTTATTTAAATTTTGAGCATATTTCTTTTCATCAAAAATCTTTTGCTGT

CTGCGTAACCGCCATGGCATTTCAATGAACATACGCCATATCCCTAGATAATACCGCTGCTGTAAAAATA

TTAACAAGTATAGTTAAAAGAATCCAATCGCCTATTCTGTCCATTGGATTTTTATAAAAAAGTAAAATAC

GAATGATGATATAGGAAGACTAATGATATACCACAGAAGAACCTTCTTATCTGTGAACCAATCAGCATTC

GTTAACTTAGCGCGACCATTTTGAATACACACGAATTTATCATCTGTTACAGTAAATGGCTTAGCTGCTT

GATATCCCATTCTAAACTCCCTAATTAATCGTTTCTTTGTATCTTCGGAACAACCATTCCAATCAACTCT

ATCAACTGGAATGCCATCATCCCCATCATCTAAATCATACCAGCGAGTTTTTAAAATCATTTAATTTTCC

TGCAATCAATCACAAACTCTTTCATTGATTCATTTTCAATATAAGACATGTAGCTATTATATTCTTTTAA

TTGTATTTTGTAATCCTTTTTTCTTTGCCAATTTATTTTAAAATTATCATAATGAAAATATAAAATGATA

CCAAAGAATGAAAACAATGAAATAATTTTAGTATAACAAAGCTCGCTCCAAACTTCTATTATATCTACTG

TACCACTGATTTTTAAAATAAAACAGTCAATTAATAGTCCAATAAGACTACCTGTAAGAGCTGCAGCCAA

CGCCACAGCAAAAATTAAAAATGACTCAGAAAACGAATATTTGACTTTATTTAGCTTTGGCTTTTGCATC

GTGATTCCTTAACAAATTTCATAATTTCATTAAATTCATACTCAGCAAGTTTAAGCTGGTGTTCCTTTTT

AATCTTTTTGCACTGGGCTTTCCAATCACGTACGCGTTTACGATAATGTCTTCCTTGATACCAGTATCCT

ATCCAATTTACGGGTACTAATAAAAATGGAACTACCAATGGAAGAGTTAGCATTAACATAATTATTACGC

CAGAATCAATATCAGTCATAACATCTAAAACACCTCCAATAATCAATAGAATTACAAATGATATAGCTAT

CACAGGACCTATTAATACATCAGTAGAAATTATCTGGCGCTTTAATTCATACTTCAAAGGTTTACTTGGA

AGGTATAGTGATGGCTTTGACATATTCTCTACATTCCTTAACAAATTTTTCTAGTAATAAATCACTTTCA

AAATTAGGATTTTCCACTAATTTATCAAAAAGATCATCAACAATATTCAAGATATTTCTTTTACTAAGAA

TACGTTTATTTTCATGCTTCGTTTCAGAATCAACTATAAGAGTAAAGAAATATTTCTTTCCCTGAAATTT

TACCGTAGTATCAATATAAAATAAATTTGACTTTTGTAAATTACGTTTAAACCATGCGTCACTTAAACTA
```

-continued

```
TAAACACCGAGATAATCAAAATCGTCGTTTAAATAACAAACTGACCATTCAGGAGAAATGAAATCAGTAA

ATTCAACATCAAAATCACATGTCAATGAATGAATTGATTCAATACTGTTAATAAGTATTCCAGGACGTAT

TAAAGACTTTTTACCTCTGGAAAATCTTCCAGAAAGACTTTCATCAGTTTCATATGAAGAACCCCAATAA

TAATTACGTCCTTTTGCCATATGTTTAAGAGCATTTAGTAATTGGTCTGGAACATCAACGTGTCTTTGGA

ACTCTTCAAACATTGAATTGAAATCACTTTGCATTTTCATTCCTATTTACTCCAAGTAATAGGGGCCGAA

GCCCCTTATCATTATTTCAGAGAATTAATATATTCCTGAACATCGGCAGAGGTAGTTTCAACCCCAGAAA

TATTACCATTAAAGGTTTCAACTCGAGCAAGAGTATCTTCAATATCAACCTTAGTCAGTGCTGCAATTTC

AACTACATCATCAGCAGTACTAATTCCAAGGGCATTTGCTGCACGAGTTTCACGGATATATTCCAATTTA

ACTGCAAGTTCTTGGCGAGCATCATCTAACTCAACTACTTTCTTGGCGATTTCAATTCGCATTTCAGCAT

AACCATCAGCTTTAGTAGTCAGCTGTTCAGCTGTTCGACGATATAGCAAGCCGAGTTTAGCATGCATTGT

TACATCTTGACCTTCGGAAAGAAGCTTGCGAATTTCACGCTCTTTTGATTCGGCCTGTTTATTCTTTTCA

ACAATAAGTTCACGAATACGTTTTTCTTCATTAATAGATTTAACAGAAGCAGTTTTTAGGTCTTTAATTT

TATCAAGTAGTTTTGCTGCTGCAGCAGTATACTGTTCTTCAACAGATAGATTTTTAGCCATTGCAGAACC

AAGTTTAGTGCGAATAAACTCAACAATTTTCTTCAGTGTGTTCATAGTATTTCCTTAGGTTGGTATAATT

AGATAATATAATATCACGTTTCTAATAGATTGTAAACTTATTCTTCGTCTAGCTCGTCGATAAAGGCGTT

GATGGCCTCGATAATGGCATCATTGATAGCCAATAAAATAAAATCATCGTCAGTACCTTTAGAAGATTCT

AAAGCATTGATATATGCTTGGTTGACGAGTTCCCAAGCCTTTTTAAAATAAGGAGCTTCATCATCAGGAC

AAATATCCCGCACGCCTTCAAAGATACGTTTGGCATAATCTAACACCCATTGTACAGGCATGTTTTGAGA

ACGTTCGTTAAACTCTTTAAAGTCCTTAGATTCAAAAAGCTCTTCAGGATAATTATTTCTATTACAAAAA

GCTTTACTAAAGTTACGTTTCATAATGTTTTCCTCATTTGTATAGGCTCATAATATCTCAATCATSAGCC

TATGTAAACTTATTTCATATTATTGAAATATTCTTCTGCGATTTCGTCGTTATCATGGTAAACTTTAGAA

GACAGTTTAACATAACTTTCAGCAGTGAACATGTTAATCACAACCTTTACAGTATACCACTGACCGTCTT

CATTACCCATTACTGCGTAAGTTTCAAACATCGGATGGTCAGGACCGATAACTTTAATATCATTCACCGT

ACGACCGAAATCTTCTGAAACACATTTCATAAAGAAGTTGAAAAGTTCACCGTAATTATCCATTTTATTC

TCCAAGTTATTTTCTGTATCAGTAGTTGATAGTTGTATAGTACCATGGAAGAACAAGGATGTAAACAGTT

TTGTGAAAAAATTTTTAAAAAGTTTTAGGGAATTCTAGGGCGGAGAGGGGCAATTAAAAGATAGGATAAT

ATATTATAAAGGGTATAAACTAAATGATGCCTAGAGAGGTCTGGAAAGGCTTAGATACCAAAAAGCCCCA

ACCTTTCGGTCGGGGCTAACCGTTGCGGCAACCTTGTCGGGGTTCCACCTGCCAAGGCAAGTGTTTGTAC

GAAACGCCGGGATTCGAACCCGGTTATTAAGTAGTTGACGCTACTCAATATTTTTAAAAGGCCATATCTC

AACCATATCCGAACGTTCCGTCAAAAACGCTACTCGGCTTACGGCAAAGATATTTCCTCGAATCGATAAT

TTGGTGCGCCGTTTCTGCTGTGATGTAAGAGGGCATCAATAAACGCAAAGATTATTAACGCAATTCCTTA

CTCAGGGAACCATCAGTCCGACGACTTACCGGTAGCGACCCGGTTTCTCATTTGGTATCCCGCCCTGGGA

TCGAACCAGGACCGCAAACTTAGAAGGATCGTATGCTATCCATTACACCAGCGGGACGTAATTTAAAATT

TCATTTTTCGACCTTTAAACCATCCTTCTGGAATTGGGTCAGTTTTCTTAATACGTTTAGAAACTTTTTC

ATCTAATGAATGAATCCACATCATACCGAATTGGGAATTCTTTTCACCTTTCTGGTGATTATTTTTGGCG

TGAGATTCTTTCATTTTATTAATAGTTTCAGGAGTATGATGCTTATTTAGAAATCTGCTATTATTTAAAA

ATTTTTCCCTGTATTCAGGAGTTGACCACAAACGTTTAAATACATTTGAACCAATTTTACGATATTTTTC

TTGAAGTAAAATATCATTTTCAAAACGTGACTTAAACGATTTAGCTCCTTTTAAGCTAGCATCTTTCTTC

TGGTTTAGCATTCCAGGAATATTTACATGATCCCATCCACCTTCACCGCCAAGTTTTAAATTATACACAT

CTGGTCTATTTAAAAACTCTTCTGTGACAATATTTTTCTCGGCTTCAAGCATAGATTCTTTATCGTCAAA

ATACTCTAATATTTCTTTAGAAAAATTTTCTATACCATATTTATCTTGGGCTCTTTTTAATAATTTACCA
```

-continued

```
GAACCCATATATCCATCATCTAAATTTTCGGTAGAATGCACACCAATATAAATTTTATTATTAATTTTAT

TTGTTATTTTATAAGTGTAATAGAACATAAATATCTCCTATTTCTAAGAGTATTTATGTTCTCAAAATAT

GACCCAGACCAGATTTGAACTGGTAACCTTTCCCTTATGAGGGGACTGCTGCTAACCATTGAGCTACAGG

GCCTTGGTGCTGATTGACGGAATCGAACCGCCGACATCCTCATTACAAGTGAGGTGCTCTACCTACTGAG

CTAAATCAGCAAAATTACGGAGGCGATAGGATTTGAACCTATGAGTCGCCGGAGCGACTGCCGGTTTTCA

AGACCGGTGCATTAAACCACTCTGCCACGCCTCCAGTCTCCATACAAGGATTTGAACCTTGGACCTCCTG

ATCCCAAATCAGGCGCTCTACCAAACTGAGCTACACGGAGTAAATTAAATTGGAGCGGATAATGAGAATC

GAACTCACATCATCAGATTGGAAGTCTGAGGTAATACCATTATACGATATCCGCAAATTTGGTGCGAGAA

GTGGGACTCGAACCCACAAGGAAATCATTCCGCAGCATTTTAAGTGCTGTGCCTTTACCAATTTGACCAT

TCTCGCGCTGGGAATAAAGGACTCGAACCTTTGCATCTAGCAGTCAAAGTGCTATGCCTTACCAACTTGG

CTAATTCCCAATTATTAACAAAGGCTCTCTAACAAGAACCCTTGATGATAGAGGGTATTAATCAGTGCGG

TATGAGTTAATAATAACAAATAATTCTTAAAGCATATTTACCATTTATGATGATACGTATTTACGATACA

TTCAAGACCCAAAGGATTCTTGAAAATATCATATTCAAGAGGACCTTTTTCTGTTTCAATAAAGAAATCA

AAATTTACTGTATTAAATTTACGGTCTTCCTTTACTAATTTAACTTGAGAAGATGAACGATCAATGTAAA

CCTTTTCAACTTCAAAACACGTTAAAATGCCATAATCATCAATCAAGGCTTTAGCTGCTTCTTGATCATA

TTTATATCCATTTTCAACGGATGATACTTTCGCATAAAGAATCATCATCAACCTCTATCAACAATAGCAT

GAGTATGGGCATTTACGATTTGCCACCAGTCGAAACGATTGGAACCATAATCTGGTTTATTTTCATTTTC

TTTAATGATATCACGCAGTTTATCTTCTGTTTCAGCATACGCAATTAAATCATCATATCCACCACAAGGA

TAATAATTATCACCTGCGAATAAAAGAAAATTTACCTTAGATGGATTTACGTAATAATGGTCTTTAGGAT

ATTTAGTTCCTCTCCAATCAGTTACTTCAACATAACGGTAAGAAAATCCATTTTTACTTTCAATCCAACT

CCACGCTTCAAAAGGAGTATTAAAAACTTTATCAGGTATTAAATTACCTTCAAAATGAGAAGGATTTGCA

TAATCCCCGGCATAAACATAATATTCGTTAATACTCATTTATTCACCTTTAGAAATTTTATCCATAACGA

TAGCAATTAAACCAATTAAAAATGCTACTACAAGTGAAAACACATTTTCTGCTGTAGTTAATAATCCGCA

TATAAATCCAACAAACATTGAAAAACTAAAGCAGAAGCAGAAATTGCAATAGCAACATTTCGAATTAAT

TCACAGCGTTTCATTTTATTCTCCTCAGTAGTTGATAGGGTAATAGTATCACAGCTAAAACCCTATGTAA

ACAACTTTGTGAAATATTTATTACAAAAGATTTTTAGCAATAATCTTGAGATGTGCCGCAGAAATGTGTT

TAGCTTTAAACAACGCAGTTTCTTCAGCAGGAGAGATAACGATTGTAGCACCATCCTTTTTAGCAGACCA

CCCATCACCTAGGTAAACAGTACCTTTGATTTCTTCGCCATCAACCAGACTAATCATTGGTTTACCTTCT

CGTCCTTTATTTGCTTTAATAACTTCAGAAGTAAGAGTAGCTTCGGTAATGGTAGAAACCGGGGTAGTTG

TAGAAGTAAATTCTTTAAATGTTTTCATTTTTATTTTCCTAATTAATTTTGATGAGGTAATAGTATCACT

ACCTCATCAGTATGTAAACAACTTTGTGAAATTATTTTAAATCATCTGCCCAATCGAGTTTAAGAGGCTC

TTTGTATTCACGATCTAATACGACCGGAATTTGTACATCACCGCTAAATGATAAGGGCCCAACATTATAA

GACAATGTTATATGCGGTGTGTAATCATCAAAATCATGTGTAGCACCTAGTGCCCGCGCATACATGTGTC

GACAGCGCAGATATTCAGAATCTAGCACAAGTACAAGAGTCGATCCATCTTGTGTTTTCCATACTTCTAA

ATGTCCAGAAGAAGCTACTTCAAAACTTCCACTCGATGGAACATATGGAACATTTACTCTTGAATAACAT

ATAGTCGAATGAATTTTTTCTCTAGGAACTGGATTAGGAACACGTAAAGAGCGCTGAAGTTCTTCCAGCG

CATCAAGTGTTAATTCTGAAAACTTAGCTGCTACATAAAGACCCGTTGAAAAGTCTTTAAATTCCATCAT

TCTTCATCTTTTGCTTCATCTGCAGATTCAGCAGTAAGATTTTTGACAGCTTCAACGATTTCTTCAACTT

TGATAGTATCGCCAGTGATACCTACTGCACGAGCAATTTCAGCCAAAGTTCCTTGCAGAATTTTGGATTC

TTCCATCAGACGAGCAGCTTGATCCTGCGTATCAAGAATGCGAGATTTCAGAGTTACGATTTCAGCAGAC
```

-continued

```
AGTTTTTGTTCAACAGTTTGTTCAGACATTATAGTACCTTTAGTGTATTTTAATTTTAGAAAAAAGTTC

TTCAAGAGAACCATCGTTTGTAATTACTAAATCGCCATCACGAATTGGCAATCCAGCTTCTGTAATATGT

GTATCATTGGATTTTTGACCAGGACGAACTACATGAATTACTGTAGCACCCATCGCCCTAGCCGCATCCA

TTTCATGATCTTGACGGGTATCAGGAACGATATAATAATCATAACCTGAGTTAAATTTATCAAGATAATC

TAAAGCAAATAATTTTACCCAGTACATGCGGTCGAAGTTATTAACAATCAAATCCGTACCTAGGGCTTGC

ATCAGACGACGGACTGACCATTGATCTTCAATATTATTTATAACGTCAGTAATCTTATTAAATGCTACGA

AATTAACTGATTCTTTTCCTTCGTCATCAAAAACAAACACACCTTTAATTGGGCTTTTACCATTAAGATA

ACAAATGCTTGTTCCATAATCGTGATTACTTCTAATTTAGTCAGATTTAAATTAGTCTCACGATCATAG

TCAATTCCTTCAAACTCTTTACGAGTTAAGCAAGGATAGTCAGTGTTTGCTGCAAATACTCCCCATGCAT

AAGCCAATGCATCCTTAATAGGACCAGCAAGTTGGTATTTAACTGCAGAATAATTGCTCATGATAAAATC

AGCAGTAGTATCTTTTCCACTACGCTTTACACCGCTTAAAAAGATTAGTTTCATGTGTTTCTCCTCAAAT

TTAATTAAGATTATAACACACAAAACTGAAGCATTAAACTTCTGCTATAATTTTACCATCTTTTTCTACT

TGAAAATAGGTGTAAGGAATTGTTGCAGTACATACTAAAGCCGGGTCTGAATCTTCCGTGTAGCTAAATT

CTACTTCAGATAGGTCAGAAACCCAAGGCTTATAAAAATTTATTGACATCACGATTTCAGTTTTGCTATT

ATCTAAGATGTAAAGCGTAATGTACTCAGGACCTGTTTTTTGGGCAGTATTTTCACCTGTAAGATAGTTG

CTAGTTCCTAGCATCCATTCATACATTCCTATCCACGACTTAAGTTCTTCATCAACTATAAATCTCACAA

TGAGTGGATCATACTCAAATGTAACACCTGGACGTTGTGCTCGGCCCAGTCCAAACGGCCCAGTCACGGT

ATCAGTAACAGGTATTCTAATTCCTGGAATAGGAACTGACTGAGCATTTAAAGTAAAAGCAGATGTAGTA

TTACTATGTGGTATTGATACTACAAAGTTAGTTGTATTTGCTTGGTTAAAAATTTGTTGCAGAGCTTGCG

ACATATATTCCTCATAATGCTTTATAACTGTTGGTGGTATAATGGGTCTAAGTCCCTTCCATTCAATTCC

ATTTAGAACAAACAACAGAAAAGAATGGAAGATAATAGAATTAGATATTTGACCAGACTTTGTTTGCAGA

GAAACGTTTTCCTTTTGAAACGAACTGCTGAAGTGGCATCAACACAACGTTCGCCCAGTCTTTCGGGGCG

ATTTCAACAAGGCTACCCATAATATTACCAGGTATATATGCCTTAATCATTTGGTCTGCACCCCTAAATC

CTTTCACTTGACTCCAATCAATTTTTAATTTCGTTTTATTAGTAATAGTAGGTGTATTTGCATATTGCTT

TAAAAGCTCTTCTAGGAATTGCTGACGAGCTTTAGGTGGAATATAGTGCAAGTTTAATCCGTACATTAAA

TTATGCTTACCTAAACCAAGGTAAATTATCAAAGGAAATTTATCCCAGTAAGGAAGAGTTTCCTTGTGTT

TAGCATCATAAGCAAAAGCATATATTCGTCCCGGCTGCGGGCGAACAACTTTATGTCCTTTTACTTGCTT

AATAGTTTCAGCAAACCACTTTCTGGTTTTATTATTAATTGCTGCGCCTTCATTACGAATTTTATCACGC

AATGTTTGTCTGAATGAATTTATCATAAGCAGTTGTCTTTCTTGCTTATTGAGTTTATTCATTGGTTTTG

ATTCAAGTTTTTGAATCTTTTCAGCCGTTTTAATTCCTGAAGCATATTTTGACATTGCTGAAGTAAACGT

AGAGTATTTGATTCCTCTTTCTTCAGCAAATTGCTTTCCTGTCATTCCTTTTGCTTTGGCCTTTTTATAT

TCAAGACCTATCTGAATCCATTTCTTTTCGTTTAATGATTGCTTAACCTTTGGAACTTGGGGAGTGCTTT

CATTAATTATTTGAAAAATAGCCATTATGCCCCCTTAAAGCCAAGAGCTCGTAATCCATCTTCTGTTAGA

ATTCTAAATTTTATTCCACGCTTTTCAGCTAAAGATTGTGCTGCTTTCCATTTGTCAGTGTTCACAGACC

AGGTATAAATTTCATTCATAAATCTTTTCTTCGCTGCGGTCGTTAGATGTGCTGGTTTAACTGGTGGTTG

TGTTTCTTTTTTAGGTTTTATTTCAATAAAAAATTCTTGTCCAGAAGAATCTTTCATCCAAATATCCATG

AAGTATCTACGTTTTTTCCCTTCTGCATTACAAAATAAGGAATTACTGCTGTTTCACTACCCCATGCAA

TAATTTCTGGATTTTTATCTAACCATTCAAAAAAGAATTTTTCCCAATTTGATCTATACGTAATTTTTTT

AGGGTCACCTCTATACTTTGATATATTTTAGGAACCCATTTTCCAGAATATGCCATTGGATTCTCCTTA

TAAATAGATAATATATTTATAAACAGGAGGGCCCATGCTCTTTACATTTTTTGATCCGATTGAATATGCG

GCCAAAACGGTGAATAAAAACGCGCCGACTATTCCTATGACAGATATTTTTAGAAACTATAAAGACTATT
```

-continued

```
TTAAACGCGCTCTTGCGGGATACCGCTTACGTACTTATTATATTAAAGGTTCACCACGCCCGGAAGAATT

AGCAAATGCTATATATGGAAATCCACAGCTGTATTGGGTTTTATTGATGTGTAATGATAATTATGACCCG

TATTATGGATGGATTACTTCGCAAGAAGCTGCTTATCAAGCATCTATACAAAAATACAAAAACGTAGGTG

GAGACCAAATAGTATATCATGTGAATGAGAACGGTGAAAAATTTTATAATTTAATATCATACGATGATAA

TCCATATGTTTGGTATGATAAAGGCGATAAAGCTAGAAAATATCCTCAATATGAAGGAGCGCTTGCTGCG

GTCGATACGTATGAAGCTGCTGTTCTTGAAAATGAAAAACTTCGTCAAATAAAAATAATAGCAAATCAG

ACATCAATTCATTTATGAACGACCTTATACGTATAATGGAGAAATCTTATGGAAATGATAAGTAATAACC

TTAATTGGTTTGTCGGTGTTGTTGAAGATAGAATGGACCCATTAAAATTAGGTCGTGTTCGTGTTCGTGT

GGTTGGTCTGCATCCACCTCAAAGAGCACAAGGTGATGTAATGGGTATTCCAACTGAAAAATTACCATGG

ATGTCAGTTATTCAACCTATAACTTCTGCAGCAATGTCTGGAATTGGAGGTTCTGTTACTGGACCAGTAG

AAGGAACTAGAGTTTATGGTCATTTTTTAGACAAATGGAAAACTAATGGAATTGTCCTTGGCACGTATGG

TGGAATAGTTCGCGAAAAACCGAATAGACTTGAAGGATTTTCTGACCCAACTGGGCAGTATCCTAGACGT

TTAGGAAATGATACTAACGTACTAAACCAAGGTGGAGAAGTAGGATATGATTCGTCTTCTAACGTTATCC

AAGATAGTAACTTAGACACCGCAATAAATCCCGATGATAGACCGCTATCAGAGATTCCGACCGATGATAA

TCCAAATATGTCAATGGCTGAAATGCTTCGCCGTGATGAAGGATTAAGATTAAAAGTTTATTGGGATACC

GAAGGATATCCGACAATTGGTATTGGTCATCTTATCATGAAGCAGCCAGTTCGTGATATGGCTCAAATTA

ATAAAGTTTTATCAAAACAAGTTGGTCGTGAAATTACAGGAAATCCAGGTTCTATTACAATGGAAGAGGC

GACGACTTTATTTGAGCGTGATTTGGCTGATATGCAACGGGACATTAAATCACATTCTAAAGTAGGACCA

GTCTGGCAAGCTGTCAACCGTTCTCGTCAAATGGCGTTAGAAAATATGGCATTTCAGATGGGTGTTGGTG

GTGTAGCTAAATTTAACACAATGTTAACTGCTATGTTAGCAGGAGATTGGGAAAAAGCGTATAAAGCCGG

TCGTGATTCATTGTGGTATCAACAAACAAAAGGCCGTGCATCCCGTGTTACCATGATTATTCTTACGGGG

AATTTGGAATCATATGGTGTTGAAGTGAAAACCCCAGCTAGGTCTCTATCAGCAATGGCTGCTACTGTAG

CTAAATCTTCTGACCCTGCTGACCCTCCTATTCCAAATGACTCGAGAATTTTATTCAAAGAACCAGTTTC

TTCATATAAAGGTGAATATCCTTATGTGCATACAATGGAAACTGAAAGCGGACATATTCAGGAATTTGAT

GATACCCCTGGGCAAGAACGATATAGATTAGTTCATCCAACTGGAACTTATGAAGAAGTATCACCATCAG

GAAGAAGAACAAGAAAAACTGTTGATAATTTGTATGATATAACCAATGCTGATGGTAATTTTTTGGTAGC

CGGTGATAAAAAGACTAACGTCGGTGGTTCAGAAATTTATTATAACATGGATAATCGTTTACATCAAATC

GATGGAAGCAATACAATATTTGTACGTGGAGACGAAACGAAAACTGTTGAAGGTAATGGAACTATCCTAG

TTAAAGGTAATGTTACTATTATAGTTGAAGGTAATGCTGACATTACAGTTAAAGGAGATGCTACCACTTT

AGTTGAAGGAAATCAAACTAACACAGTAAATGGAAATCTTTCTTGGAAAGTTGCCGGGACAGTTGATTGG

GATGTCGGTGGTGATTGGACAGAAAAAATGGCATCTATGAGTTCTATTTCATCTGGTCAATACACAATTG

ATGGATCGAGGATTGACATTGGCTAATATACTTCCAATGAGCGCTGATTTAGGAGAATCCATGGAAGGTT

CTTCTATCGACGTCACCTTTACCGCTCAATTAGAAACAGGTGAAACGTTAGTATCTATAAATATAACTAG

TTACGAAGAAACTCCTGGGGTTTTAGTAGAAGAAATCGCTTATATGGAACATATGAATCTGTATTTGGT

TTCGGAAATGACGCGTTGAAATATCGTTTAGGCGATGAATTTAAAACTGCTGCTTCATGGGAAGAACTTC

CTACTGATTCTGATACTCAGTTGTATTTGTGGAAAGCTCCTCAAAACCTCCAGAAGACATTCACTTACGA

AGTAACATTAATATATGACTACCAAGAACAAAGTGAATCTGGGGGTTCTGGCAGTAATTCTAGGTCATCT

TCTGATACTACTGAACCGACAGATCCTCCTGCTCCAGTAAGAAAAACTCTAGTTAAAAATTATACTAAAA

CTATAGTTGGAAATTGGAGTCGTTGGGCTAATAAACTGAGAAAAATATGCCTATGCAAGACCATAAATATT

TTTATTTGTATTCAATAACTAATAAAACAACAGAAAAAATTTATGTAGGCGTCCACAAAACTTCAAATTT
```

-continued

```
GGATGATGGGTATATGGGTTCTGGCGTTGCCATTAAAAATGCCATTAAAAAATATGGCATAGATAATTTT
TATAAGCATATTATAAAATTCTTTGAATCTGAAAAAGCTATGTATGACGCAGAGGCAGAAATAGTCACAG
AGGAATTTGTTAAATCTAAGAAAACTTATAATATGAAACTAGGCGGTATCGGTGGCTTCCCAAAACATAA
CACAGCGGGTGCTAAAAATGGATTTTACGGTAAATCTCATTCGCGTGAAACTAGATTGAAAATTAGCATT
AAATCGTCTAGAAAAAGAGGGCCTAGAGGGCTAGAGGTAAAACTCTGAAGATGTGTGGCGCCAATAACCC
AAGGTATGGCAAAATAGCCCCTAATGCTAAATCTGTTATTATCAACGGCGTTTTATATAAAAGTATTAAA
ATCGCAGCTAAAGCTCTTAATATAAATTATAGTACCTTAAAGGGGCGAGTTAAAGCGGGGTATTATAAAT
GTCAGGATTAAGTTATGATAAGTGTGTTACTGCTGGCCATGAAGCGTGGCCTCCAACAGTTGTGAATGCT
ACACAAAGTAAAGTATTCACTGGAGGAATTGCTGTTCTCGTAGCAGGCGATCCAATTACAGAACATACAG
AAATTAAAAAGCCGTATGAAACACATGGCGGAGTGACACAACCTAGAACTTCTAAGGTATATGTCACTGG
AAAGAAAGCTGTTCAAATGGCTGATCCAATATCATGCGGTGATACTGTGGCTCAGGCATCATCTAAAGTA
TTCATTAAATAGGATTTAAAATGGCAAATACCCCTGTAAATTATCAATTAACAAGAACAGCAAATGCTAT
TCCCGAGATATTCGTCGGGGGTACATTTGCTGAAATAAAACAAAACCTCATTGAATGGCTTAATGGCCAA
AATGAATTTTTGGATTATGATTTTGAAGGCTCAAGATTAAACGTTCTGTGTGACCTTTTAGCTTATAATA
CATTATACATTCAGCAGTTTGGTAATGCTGCTGTGTATGAAAGCTTTATGCGTACTGCTAACTTACGAAG
TTCAGTTGTTCAAGCTGCACAAGATAACGGATATTTACCTACTTCAAAATCCGCTGCGCAGACCGAAATT
ATGTTAACATGCACTGACGCATTGAATAGGAATTACATTACTATTCCTCGCGGAACTCGCTTTTTAGCAT
ATGCAAAAGATACTTCTGTTAATCCATATAACTTCGTTTCTAGGGAAGACGTTATTGCTATTCGTGATAA
AAATAACCAATATTTTCCGCGTTTAAAATTGGCCCAGGGACGTATAGTAAGAACTGAAATCATTTATGAT
AAATTAACACCTATTATCATTTATGATAAAAATATTGATAGAAACCAGGTTAAATTATACGTTGATGGAG
CGGAATGGATTAACTGGACGAGAAAGTCAATGGTTCATGCTGGTTCAACATCAACGATTTACTATATGCG
TGAAACTATTGATGGAAACACTGAATTCTATTTTGGTGAAGGTGAAATTTCTGTTAATGCTTCTGAAGGA
GCTTTGACCGCTAATTATATCGGAGGTCTTAAACCTACTCAGAACTCTACGATTGTTATTGAGTACATTA
GTACTAATGGTGCTGACGCGAACGGAGCAGTCGGATTTTCATACGCAGATACATTAACAAATATAACTGT
CATCAATATTAATGAAAATCCAAACGATGATCCAGATTTTGTTGGGGCAGATGGAGGCGGTGATCCAGAA
GATATTGAGCGTATTCGCGAATTGGGTACTATTAAACGCGAAACCCAACAACGATGCGTAACTGCGACTG
ACTATGATACATTCGTTTCAGAGAGATTTGGTTCTATTATTCAAGCTGTTCAGACTTTCACTGATTCTAC
TAAACCTGGGTATGCATTTATTGCTGCTAAACCTAAATCAGGATTGTATTTAACTACCGTACAGCGTGAA
GATATTAAAAATTATCTCAAAGACTATAATTTAGCTCCTATTACGCCATCAATTATTTCTCCTAATTATC
TTTTTATTAAGACTAATTTAAAAGTCACATATGCTTTAAATAAACTGCAAGAATCCGAACAGTGGCTTGA
AGGTCAAATAATTGATAAAATAGATCGCTATTATACCGAAGATGTAGAAATTTTTAACTCGTCTTTCGCT
AAATCTAAGATGTTGACATATGTAGATGATGCAGATCATTCTGTCATTGGTTCATCAGCGACTATTCAAA
TGGTTCGTGAAGTACAAAACTTCTATAAAACGCCTGAAGCGGGTATTAAATACAATAATCAAATAAAAGA
TCGTTCTATGGAATCTAATACGTTTTCATTTAATTCTGGACGAAAGGTTGTAAATCCTGATACTGGTTTA
GAAGAAGATGTATTATATGACGTTCGTATAGTATCAACAGACCGAGATTCTAAAGGAATTGGTAAAGTTA
TTATTGGTCCATTTGCTTCTGGCGATGTTACAGAAAATGAAAACATTCAGCCGTATACAGGCAACGATTT
TAACAAATTAGCAAATTCTGATGGACGCGACAAATACTATGTTATCGGTGAAATAAATTATCCAGCTGAT
GTGATTTATTGGAATATCGCTAAAATTAATTTAACATCTGAAAAATTTGAAGTTCAGACCATTGAATTAT
ATTCTGACCCAACCGATGATGTTATCTTTACTCGCGATGGTTCACTGATTGTATTTGAAAATGACTTACG
TCCACAATACTTAACTATCGATTTGGAGCCTATATCACAATGACAGTAAAAGCACCTTCAGTCACTAGTC
TCAGAATTTCCAAGTTATCCGCAAATCAGGTGCAAGTACGCTGGGATGACGTTGGTGCTAATTTCTACTA
```

-continued

```
TTTTGTAGAAATCGCTGAGACAAAAACAAACTCGGGGGAAAATCTCCCGAGTAATCAATATCGTTGGATT

AATTTAGGATATACAGCAAATAATAGTTTCTTTTTTGATGATGCTGATCCATTAACAACATACATTATTA

GAGTAGCCACAGCTGCGCAAGATTTTGAGCAGTCTGATTGGATTTATACCGAAGAGTTTGAAACTTTTGC

TACAAATGCTTATACATTTCAAAACATGATTGAAATGCAATTAGCCAATAAATTCATTCAGGAAAAATTT

ACTCTTAATAATTCTGATTATGTTAATTTTAATAATGATACTATAATGGCTGCATTGATGAATGAATCAT

TCCAATTCAGCCCATCGTATGTTGATGTTTCATCAATAAGTAATTTTATTATTGGTGAAAATGAGTATCA

TGAAATACAAGGTTCTATTCAGCAAGTATGTAAGGATATTAACCGAGTTTATTTGATGGAATCAGAAGGA

ATTCTATATCTTTTTGAGCGCTATCAACCTGTAGTTAAAGTATCCAATGATAAAGGACAAACCTGGAAAG

CTGTAAAGCTCTTCAATGACCGTGTAGGATATCCTTTATCTAAGACAGTATATTACCAATCTGCGAACAC

AACATACGTTCTAGGATACGACAAGATTTTCTATGGCCGCAAATCTACTGATGTTAGATGGTCAGCCGAT

GATGTCAGATTTAGTTCTCAGGATATAACATTTGCTAAACTTGGCGACCAATTACATCTAGGATTTGATG

TAGAAATTTTTGCCACTTACGCGACTTTACCAGCGAATGTATACCGCATTGCAGAAGCTATTACTTGCAC

CGATGATTACATTTACGTTGTCGCCAGAGACAAAGTTAGATACATAAAAACGAGTAATGCACTTATAGAT

TTTGATCCATTATCTCCAACATATTCGGAAAGACTTTTTGAACCTGATACCATGACTATAACCGGAAATC

CTAAAGCAGTATGCTATAAAATGGATTCTATCTGTGATAAAGTTTTTGCTCTTATTATTGGTGAAGTTGA

AACATTAAATGCTAATCCTAGAACATCAAAAATAATTGATTCCGCTGATAAAGGAATATATGTTTTAAAT

CATGACGAAAAAACATGGAAAAGAGTTTTTGGTAATACCGAAGAAGAAAGAAGACGTATTCAACCCGGAT

ATGCGAATATGTCAACTGACGGTAAATTAGTTTCTCTGTCTTCGAGTAATTTTAAATTTTTAAGTGATAA

TGTTGTTAATGACCCTGAAACTGCAGCAAAATATCAGTTAATTGGCGCTGTTAAATATGAATTTCCTCGT

GAATGGTTAGCTGATAAGCATTATCATATGATGGCATTTATAGCGGATGAAACATCTGATTGGGAGACTT

TTACTCCTCAACCAATGAAATACTACGCAGAACCATTCTTTAACTGGTCTAAAAAATCTAACACACGTTG

TTGGATAAACAACTCTGATAGAGCTGTGGTAGTTTATGCTGATTTAAAATACACTAAAGTTATAGAAAAT

ATTCCGGAAACATCACCAGATAGATTAGTTCATGAATACTGGGATGATGGTGATTGCACTATAGTAATGC

CAAATGTCAAATTCACTGGATTTAAAAAATACGCATCAGGAATGCTTTTCTATAAAGCCTCCGGTGAAAT

AATTTCTTACTATGATTTTAACTATCGTGTGAGAGATACAGTAGAAATTATTTGGAAGCCAACTGAAGTA

TTTTTAAAAGCATTTTTACAAAACCAAGAGCATGAGACTCCTTGGTCACCAGAAGAAGAGCGTGGATTAG

CTGACCCTGATTTAAGACCATTAATTGGCACAATGATGCCTGATTCTTATTTGTTACAGGATTCGAATTT

TGAGGCATTTTGCGAAGCATATATTCAGTATCTTTCTGATGGATATGGAACTCAATACAATAATTTACGA

AATTTAATTCGTAACCAATATCCACGAGAAGAGCACGCATGGGAATATTTGTGGTCAGAGATATATAAAA

GAAACATTTATTTAAATGCTGATAAACGCGATGCTGTTGCGAGATTCTTTGAATCACGTAGCTATGATTT

TTATTCTACTAAAGGAATTGAAGCATCATACAAGTTTCTTTTTAAAGTTCTTTATAATGAAGAAGTTGAA

ATTGAAATTGAATCTGGGGCTGGTACTGAATATGATATAATCGTTCAATCTGATTCTTTGACTGAAGATT

TAGTAGGACAAACGATTTATACGGCAACAGGAAGATGTAATGTTACTTATATAGAAAGAAGCTATTCTAA

TGGTAAATTGCAATGGACCGTAACTATTCATAATCTTTTGGGACGATTAATTGCTGGTCAAGAAGTTAAA

GCAGAAAGACTCCCTAGTTTTGAAGGCGAAATTATTCGTGGGGTTAAAGGAAAGGATTTGCTTCAAAACA

ATATAGACTATATTAATAGAAGTAGATCATACTATGTAATGAAAATTAAATCCAATTTACCTTCTTCCCG

CTGGAAATCTGACGTTATTCGTTTTGTTCATCCAGTAGGATTTGGATTTATAGCAATTACCCTTTTAACA

ATGTTTATTAATGTTGGTTTAACTCTTAAACATACAGAGACTATAATTAATAAATACAAAAACTATAAAT

GGGATTCTGGATTGCCTACTGAATATGCCGACAGAATAGCTAAATTAACTCCAACCGGTGAAATTGAGCA

TGATTCAGTAACAGGCGAAGCAATTTATGAGCCTGGCCCAATGGCTGGTGTAAAATATCCTCTTCCTGAT
```

-continued

```
GACTATAATGCTGAAAATAATAATTCAATATTTCAAGGTCAATTGCCGTCTGAACGACGTAAATTAATGA
GTCCTTTATTTGATGCATCTGGAACAACATTTGCGCAATTTAGAGATTTAGTTAATAAACGTCTAAAAGA
TAATATAGGAAATCCAAGAGACCCTGAAAATCCAACACAGGTTAAAATAGATGAATGATTCAAGTGTTAT
CTATCGTGCGATAGTTACTTCAAAATTTAGAACAGAAAAAATGTTGAATTTTTATAATTCAATTGGAAGT
GGTCCGGATAAAAACACTATCTTTATCACATTTGGAAGATCAGAACCGTGGTCATCAAATGAAAATGAGG
TGGGCTTTGCCCCACCTTATCCAACCGATTCTGTATTAGGCGTAACTGACATGTGGACGCATATGATGGG
AACAGTAAAAGTTCTTCCATCAATGCTTGATGCTGTTATTCCTCGCAGAGATTGGGGAGATACTAGATAT
CCGGATCCATACACATTTAGAATTAACGATATTGTAGTGTGTAACTCAGCTCCTTACAACGCTACTGAAT
CAGGCGCTGGTTGGTTAGTGTATCGTTGTTTAGATGTTCCTGATACCGGAATGTGTTCAATAGCATCTTT
AACTGATAAAGATGAATGCCTTAAGTTAGGTGGAAAATGGACTCCTTCTGCTAGGTCAATGACTCCGCCT
GAAGGTCGAGGAGATGCTGAAGGAACAATTGAACCCGGAGACGGGTATGTGTGGGAATATCTATTTGAGA
TTCCGCCTGATGTATCTATAAATAGATGCACGAATGAATATATCGTGGTTCCTTGGCCTGAGGAATTAAA
AGAAGACCCGACTAGATGGGGATATGAAGATAATCTCACTTGGCAACAAGATGATTTTGGATTAATTTAC
CGTGTTAAGGCAAATACTATCCGTTTTAAAGCATATTTAGATTCAGTTTATTTTCCTGAAGCTGCATTAC
CAGGAAATAAAGGATTTAGACAAATATCAATAATCACGAATCCTCTTGAAGCTAAAGCTCATCCAAATGA
CCCAAACGTTAAAGCTGAAAAGGATTATTATGACCCAGAAGATTTAATGAGGCATTCGGGTGAAATGATT
TATATGGAAAATAGGCCACCTATTATTATGGCAATGGATCAAACAGAAGAAATCAATATTCTGTTTACAT
TTTAAATTAAGGGAGCCCATGGGCTCCCTTTTTCTTTATAAATACTATAAACTCATAAGGAAACCGCTAT
GTTCATTCAAGAACCAAAGAAATTGATTGATACCGGCGAAATTGGTAACGCTTCTACTGGTGATATCTTA
TTCGACGGTGGTAATAAAATTAATAGTGATTTTAACGCAATTTATAATGCGTTTGGCGATCAGCGTAAAA
TGGCAGTAGCAAATGGCACTGGAGCAGATGGTCAAATTATCCATGCTACTGGATATTATCAAAAACACTC
TATTACAGAGTACGCAACTCCAGTGAAAGTTGGCACTAGACATGATATTGATACCTCTACTGTAGGTGTT
AAAGTTATCATTGAAAGAGGCGAACTCGGCGATTGTGTTGAATTCATTAACTCTAATGGATCAATATCAG
TTACTAATCCTTTGACAATTCAAGCTATTGATTCAATTAAAGGTGTTTCAGGTAATTTAGTAGTAACTAG
CCCATATAGTAAAGTTACTTTACGCTGTATTTCATCTGATAATTCTACGTCGGTTTGGAATTATTCTATT
GAAAGTATGTTTGGACAAAAGGAATCACCAGCTGAAGGTACATGGAATATTTCTACATCTGGATCAGTTG
ACATTCCATTATTTCATCGTACTGAATACAATATGGCTAAATTGCTAGTTACGTGCCAATCGGTAGATGG
AAGAAAAATTAAAACAGCAGAAATAAATATTCTTGTGGATACTGTTAATTCAGAGGTAATTTCTTCTGAA
TATGCTGTCATGCGAGTTGGGAATGAAACCGAAGAAGACGAAATCGCTAATATTGCATTTAGTATTAAAG
AAAATTATGTAACGGCGACTATAAGTTCTTCAACTGTCGGTATGAGAGCAGCAGTTAAAGTTATCGCTAC
GCAGAAAATCGGGGTGGCTCAATAATGAAACAAAATATTAATATCGGTAATGTTGTAGATGATGGTACCG
GTGACTACCTGCGTAAAGGTGGTATAAAAATAAATGAAAACTTTGATGAGCTTTATTATGAACTCGGTGA
TGGTGATGTTCCATATTCAGCCGGTGCCTGGAAAACTTATAATGCTTCATCAGGACAAACATTAACAGCA
GAATGGGAAAATCATACGCTATTAATACATCTTCTGGAAGAGTGACTATAAATCTTCCAAAGGGTACAG
TTAATGATTACAACAAGGTAATTAGAGCTAGAGACGTATTTGCTACATGGAACGTCAACCCAGTTACACT
AGTAGCTGCTTCCGGCGATACGATTAAAGGGTCTGCAGTACCAGTTGAAATTAATGTTCGATTCAGCGAT
TTAGAACTAGTGTATTGTGCCCCAGGACGTTGGGAATATGTCAAAAATAAACAATTGACAAAATTACCA
GTTCAGACATTAGTAATGTAGCTCGCAAAGAATTTTTAGTTGAAGTTCAAGGACAAACAGACTTTTTAGA
TGTTTTCCGTGGAACTAGTTATAATGTAAATAACATCAGAGTAAAACATCGTGGTAACGAATTGTATTAC
GGCGATGTGTTTAGCGAAAACAGCGATTTTGGCTCTCCAGGCGAAATGAAGGAGAACTGGTTCCTCTTG
ATGGATTTAACATTCGATTAAGACAGCCTTGTAATATTGGTGACACTGTTCAAATTGAAACATTTATGGA
```

-continued

```
TGGTGTATCACAGTGGAGAAGTTCATATACAAGACGTCAAATTAGATTGTTAGATTCAAAATTAACGTCA
AAAACTTCTTTAGAAGGAAGCATTTACGTTACTGATTTATCAACAATGAAATCAATTCCATTTTCTGCTT
TTGGATTAATTCCAGGAGAACCTATTAATCCTAACTCTCTTGAGGTTCGTTTTAACGGGATTTTACAGGA
ATTGGCTGGCACAGTTGGAATGCCATTATTTCATTGTGTTGGTGCCGATTCAGACGATGAAGTAGAATGC
TCTGTTTTAGGTGGAACTTGGGAACAATCTCATACCGATTATTCAGTTGAAACTGATGAAAACGGCATAC
CAGAAATTTTACATTTCGATAGCGTATTTGAGCATGGTGACATTATCAATATCACCTGGTTTAATAATGA
TTTGGGTACATTATTAACAAAAGATGAGATTATTGATGAAACTGATAATCTCTATGTATCGCAAGGACCT
GGAGTAGATATTTCTGGTGATGTAAATTTAACAGACTTCGATAAAATTGGTTGGCCAAATGTAGAAGCAG
TTCAATCTTATCAACGCGCATTTAATGCTGTTTCAAATATCTTTGATACGATTTATCCTATTGGAACTAT
ATATGAAAACGCTGTTAATCCAAATAACCCTGTTACATATATGGGATTCGGCTCATGGAAATTATTTGGG
CAAGGAAAAGTTTTAGTTGGATGGAATGAAGATATTTCGGACCCTAACTTTGCTCTAAATAACAACGATT
TAGATTCGGTGGAAATCCTTCACATACCGCAGGTGGAACAGGTGGTTCTACTTCTGTTACATTGGAAAA
TGCTAATCTTCCTGCAACTGAAACAGATGAAGAAGTTCTAATAGTTGATGAAAATGGATCAGTCATTGTT
GGTGGGTGTCAATACGATCCAGATGAATCCGGTCCAATTTACACTAAATACCGTGAAGCTAAAGCATCTA
CTAACTCTACTCACACTCCGCCAACATCAATAACTAACATTCAACCATATATTACAGTTTATCGTTGGAT
AAGGATTGCATAATGAGTTTACTTAATAATAAAGCGGGAGTTATTTCCCGCTTAGCCGATTTTCTTGGTT
TTAGACCTAAAACTGGCGACATTGATGTAATGAATCGTCAATCAGTCGGGTCAGTGACAATATCTCAATT
AGCGAAAGGATTTTATGAACCAAACATAGAATCAGCTATTAATGACGTTCATAATTTTTCTATAAAAGAC
GTTGGCACAATTATTACTAATAAAACTGGTGTTTCTCCTGAGGGTGTTTCTCAAACTGATTATTGGGCAT
TTTCTGGAACTGTAACAGACGATTCTCTTCCTCCGGGTTCTCCTATTACGGTATTAGTATTTGGTCTTCC
AGTTTCAGCAACAACTGGAATGACGGCAATTGAGTTTGTTGCAAAAGTTCGCGTTGCACTACAAGAAGCT
ATTGCGTCATTTACTGCTATCAATTCATATAAAGACCATCCAACTGATGGTAGTAAATTAGAAGTTACTT
ATTTAGATAATCAAAAACATGTATTAAGCACATATTCTACATATGGAATAACTATTTCCCAAGAAATTAT
ATCTGAGTCTAAGCCTGGCTATGGTACATGGAATTTATTGGGCGCACAAACTGTAACTTTAGATAATCAG
CAGACTCCTACAGTATTTTATCATTTTGAGAGAACAGCATGAGTAATAATACATATCAACACGTTTCTAA
TGAATCTCGTTATGTAAAATTTGATCCTACCGATACGAATTTTCCACCGGAGATTACTGATGTTCACGCT
GCTATAGCAGCCATTTCTCCTGCTGGAGTAAATGGAGTTCCTGATGCATCGTCAACAACAAAGGGAATTC
TATTTATTCCCACTGAACAGGAAGTTATAGATGGAACTAATAATACCAAAGCAGTTACACCAGCAACGTT
GGCAACAAGATTATCTTATCCAAATGCAACTGAAACTGTTTACGGATTAACAAGATATTCAACCAATGAT
GAAGCCATTGCCGGAGTTAATAATGAATCTTCTATAACTCCAGCTAAATTTACTGTCGCCCTTAATAATG
CGTTTGAAACGCGAGTTTCAACTGAATCCTCAAATGGTGTTATTAAAATTTCATCTCTACCGCAAGCATT
AGCTGGTGCAGATGATACTACTGCAATGACTCCATTAAAAACACAGCAGTTAGCTATTAAATTAATTGCG
CAAATTGCTCCTTCTGAAACCACAGCTACCGAATCGGACCAAGGTGTTGTTCAATTAGCAACAGTAGCGC
AGGTTCGTCAGGGAACTTTAAGAGAAGGCTATGCAATTTCTCCTTATACGTTTATGAATTCATCTTCTAC
TGAAGAATATAAAGGCGTAATTAAATTAGGAACACAATCAGAAGTTAACTCGAATAATGCTTCTGTTGCG
GTTACTGGCGCAACTCTTAATGGTCGTGGTTCTACGACGTCAATGAGAGGCGTAGTTAAATTAACTACAA
CCGCCGGTTCACAGAGTGGAGGCGATGCTTCATCAGCCTTAGCTTGGAATGCTGACGTTATCCAGCAAAG
AGGTGGTCAAATTATCTATGGAACACTCCGCATTGAAGACACATTTACAATAGCTAATGGTGGAGCAAAT
ATTACGGGTACCGTCAGAATGACTGGCGGTTATATTCAAGGTAACCGCATCGTAACACAAAATGAAATTG
ATAGAACTATTCCTGTCGGAGCTATTATGATGTGGGCCGCTGATAGTCTTCCTAGTGATGCTTGGCGCTT
```

-continued

CTGCCATGGTGGAACTGTTTCAGCGTCAGATTGTCCATTATATGCTTCTAGAATTGGAACAAGATATGGC

GGAAACCCATCAAATCCTGGATTGCCTGACATGCGTGGTCTTTTTGTTCGTGGTTCTGGTCGTGGTTCTC

ACTTAACAAATCCAAATGTTAATGGTAATGACCAATTTGGTAAACCTAGATTAGGTGTAGGTTGTACCGG

TGGATATGTTGGTGAAGTACAGATACAACAGATGTCTTATCATAAACATGCTGGTGGATTTGGTGAGCAT

GATGATCTGGGGGCATTCGGTAATACCCGTAGATCAAATTTTGTTGGTACACGTAAAGGACTTGACTGGG

ATAACCGTTCATACTTCACCAATGACGGATATGAAATTGACCCAGAATCACAACGAAATTCCAAATATAC

ATTAAATCGTCCTGAATTAATTGGAAATGAAACACGTCCATGGAACATTTCTTTAAACTACATAATTAAG

GTAAAAGAATGACAGATATTGTACTGAATGACTTACCATTCGTTGACGGCCCTCCTGCAGAGGGCCAGAG

CCGCATTTCCTGGATTAAAAACGGCGAAGAAATATTAGGAGCTGACACACAGTATGGAAGTGAAGGCTCA

ATGAATAGACCTACGGTTTCTGTACTAAGAAATGTTGAAGTTCTTGATAAAAACATTGGAATACTTAAAA

CATCTTTAGAAACCGCAAATAGTGATATTAAAACAATTCAGGGCATCTTAGATGTATCTGGTGATATTGA

AGCTTTGGCCCAAATAGGTATCAATAAAAAGGATATTTCTGACCTCAAAACGCTAACCAGTGAACACACA

GAAATATTAAATGGAACTAATAATACGGTTGACAGTATTCTTGCCGATATTGGTCCATTTAACGCCGAGG

CCAACTCTGTATACAGAACGATCAGAAATGATTTACTGTGGATAAAGCGTGAACTTGGACAATACACTGG

TCAAGATATTAATGGTCTTCCTGTTGTAGGAAATCCTAGTAGTGGAATGAAGCATCGCATTATTAATAAT

ACTGATGTCATCACTTCGCAGGGAATACGTTTAAGCGAATTAGAAACAAAATTTATTGAATCTGATGTAG

GTTCTTTGACCATTGAAGTTGGTAATCTTCGTGAAGAGCTTGGACCGAAACCACCATCATTTTCACAGAA

CGTTTATAGTCGTTTAAATGAAATTGACACTAAACAGACAACAGTTGAGTCTGACATTAGTGCTATTAAG

ACCTCAATAGGATATCCAGGAAATAATTCGATTATCACGAGTGTTAATACAAACACTGATAATATTGCAT

CTATTAATTTAGAGCTAAATCAAAGTGGAGGTATTAAACAGCGTTTAACCGTTATTGAAACTTCCATTGG

TTCAGATGATATTCCTTCGAGTATTAAAGGTCAAATCAAAGATAATACAACTTCAATCGAATCTCTAAAT

GGAATCGTCGGTGAAAACACTTCATCTGGCTTAAGAGCGAATGTTTCATGGTTAAACCAAATTGTTGGAA

CTGATTCTAGCGGTGGACAACCTTCTCCTCCTGGGTCTCTTTTAAACCGAGTTTCTACAATTGAAACTTC

TGTTTCAGGCTTGAATAACGCTGTTCAAAACCTACAAGTAGAGATTGGTAATAACAGCGCAGGAATTAAA

GGGCAAGTTGTAGCGTTAAATACTTTAGTAAATGGAACTAATCCAAACGGTTCAACTGTTGAAGAGCGCG

GATTAACCAATTCAATAAAAGCTAACGAAACTAACATTGCATCAGTTACACAAGAAGTGAATACAGCTAA

AGGCAATATATCTTCTTTACAAGGTGATGTTCAAGCTCTCCAAGAAGCCGGTTATATTCCTGAAGCTCCA

AGAGATGGGCAAGCTTACGTTCGTAAAGATGGCGAATGGGTATTCCTTTCTACCTTTTTATCACCAGCAT

AACATGGGGCCGCAAGGCCCCAAAGGATTTTAAATGTCAGGATATAATCCTCAGAATCCAAAGGAACTCA

AAGATGTCATTCTAAGACGTTTAGGGGCTCCAATTATTAATGTTGAGTTAACACCCGATCAAATTTACGA

TTGTATCCAGCGTGCCCTAGAATTATACGGTAATACCATTTTGATGGACTCAATAAAGGTTTTCATGTT

TTTTATGTAGGGGATGATGAAGAAAGGTACAAGACCGGAGTCTTCGATTTAAGAGGTTCTAACGTATTTG

CAGTAACCCGCATTTTACGCACAAATATTGGGTCAATAACATCTATGGATGGAAACGCTACATATCCGTG

GTTTACTGACTTTCTTTTAGGAATGGCTGGTATTAATGGCGGAATGGGAACGTCTTGTAATAGATTTTAT

GGACCAAATGCCTTTGGAGCTGATTTAGGATATTTTACCCAGCTTACCAGTTATATGGGAATGATGCAAG

ATATGCTCTCTCCTATTCCAGACTTTTGGTTTAATTCAGCAAATGAACAGCTCAAAGTCATGGGAAACTT

CCAAAAATATGATTTAATTATCGTAGAAAGCTGGACTAAATCATACATTGATACAAACAAAATGGTTGGA

AATACAGTAGGATATGGAACAGTCGGTCCACAAGATAGCTGGTCATTATCTGAACGATATAATAACCCAG

ACCACAATTTAGTAGGTCGTGTTGTCGGCCAAGATCCGAATGTTAAACAGGGTGCTTATAATAATCGTTG

GGTGAAAGACTATGCAACAGCTTTAGCTAAAGAATTGAACGGTCAAATTTTAGCACGCCACCAAGGTATG

ATGCTTCCGGGCGGTGTTACAATTGATGGGCAGCGCTTAATAGAAGAAGCCAGATTAGAAAAAGAAGCAC

-continued

```
TGCGCGAAGAATTATACTTACTTGATCCTCCATTTGGAATTTTGGTAGGTTAATATGGCTACTTATGATA

AAAATCTTTTTGCTAAATTGGAAAACCGCACAGGTTATTCTCAGACCAATGAAACTGAAATATTAAATCC

TTATGTAAATTTCAATCATTATAAAAACAGCCAAATATTAGCTGATGTATTAGTAGCTGAAAGCATTCAA

ATGCGAGGTGTAGAATGCTATTATGTTCCAAGAGAGTATGTTTCCCCTGATTTGATATTCGGCGAAGACT

TAAAAAATAAATTTACTAAAGCTTGGAAATTTGCTGCATATTTAAATTCATTTGAAGGATATGAAGGAGC

TAAATCGTTCTTTAGTAACTTTGGTATGCAAGTACAAGACGAAGTGACTTTATCTATTAACCCAAATTTA

TTTAAGCATCAAGTTAACGGAAAAGAACCCAAGGAAGGTGATTTGATATATTTTCCTATGGATAACAGCT

TATTTGAAATTAACTGGGTTGAACCATATGATCCATTTTATCAATTAGGCCAAAACGCTATTCGTAAAAT

TACGGCAGGTAAATTCATTTATTCTGGAGAAGAAATTAATCCAGTTCTACAGAAAAATGAAGGAATTAAC

ATTCCAGAATTTAGTGAATTAGAATTAAATGCTGTTCGCAATCTTAACGGTATTCATGACATTAATATTG

ATCAGTATGCTGAAGTAGATCAAATTAATTCTGAAGCTAAAGAATACGTTGAACCTTATGTTGTTGTCAA

TAACAGAGGCAAATCTTTCGAATCTAGCCCATTTGACAATGATTTCATGGATTAATAAATATTATAAACT

AATTAAAGCCCGGATTAGGAGAAGTCATGTTTGGTTATTTTTATAATTCGTCTTTTAGACGATATGCTAC

CTTGATGGGCGATTTGTTTTCAAATATCCAAATCAAACGTCAGTTAGAATCTGGTGATAAGTTTATACGT

GTTCCTATTACGTATGCATCAAAGGAACACTTTATGATGAAATTGAATAAATGGACATCAATAAATTCAC

AAGAAGATGTAGCTAAAGTTGAAACTATTCTACCTCGTATAAATTTACATTTAGTTGATTTTAGCTATAA

TGCTCCATTTAAAACAAACATTTTAAATCAGAATTTACTGCAAAAAGGTGCAACTTCTGTAGTATCGCAG

TATAATCCATCTCCTATTAAAATGATTTATGAATTGAGTATCTTTACTCGCTATGAAGATGATATGTTTC

AAATAGTTGAACAGATTCTTCCATATTTTCAACCTCATTTTAATACAACTATGTACGAGCAGTTTGGAAA

TGATATTCCATTTAAAAGGGATATTAAAATTGTACTGATGTCTGCTGCTATAGACGAAGCTATAGATGGG

GATAATTTATCTCGTCGTAGAATTGAATGGTCATTAACATTTGAAGTAAATGGATGGATGTATCCTCCAG

TAGATGATGCAGAAGGATTAATTCGTACTACTTATACAGATTTTCACGCCAATACAAGAGATTTGCCTGA

CGGCGAAGGTGTTTTTGAATCTGTCGATAGCGAAGTTGTTCCTCGAGATATTGACCCAGAAGACTGGGAT

GGAACAGTAAAACAAACTTTTCACTAGTAATGTAAATAGACCAACACCGCCAGAACCTCCTGGCCCAAGAA

CATAGAGGTTATTATGGAAGGTCTTGATATAAACAAACTTTTAGATATTTCTGACCTCCCCGGAATTGAC

GGGGAGGAAATCAAAGTGTATGAACCTCTGCAATTAGTAGAAGTTAAAAGCAATCCACAAAACCGTACTC

CAGACTTAGAAGATGATTATGGAGTAGTTCGTCGAAATATGCATTTTCAGCAACAAATGCTAATGGACGC

TGCCAAGATTTTTCTTGAGACAGCAAAGAATGCTGATTCTCCTCGTCACATGGAAGTATTTGCAACTCTT

ATGGGGCAAATGACTACGACGAACAGAGAAATACTGAAGCTTCATAAAGATATGAAAGACATTACATCTG

AGCAGGTTGGCACCAAAGGCGCTGTTCCTACAGGTCAAATGAATATTCAGAATGCGACAGTATTCATGGG

TTCACCAACAGAATTAATGGACGAAATTGGTGATGCTTACGAGGCTCAAGAAGCTCGTGAGAAGGTGATA

AATGGAACAACCGATTAATGTATTAAATGATTTCCATCCGTTAAATGAAGCTGGAAAAATTTTAATAAAA

CACCCAAGCTTAGCGGAAAGAAAAGATGAAGATGGAATTCATTGGATAAAATCTCAGTGGGATGAAAAT

GGTATCCTGAAAAATTCAGTGATTACCTTCGTCTACACAAAATAGTAAAAATTCCAAACAACTCTGATAA

GCCTGAATTATTTCAAACTTATAAAGATAAGAATAATAAAAGATCTCGGTATATGGGTCTTCCTAACTTG

AAACGAGCTAATATTAAAACACAATGGACTCGTGAAATGGTTGAGGAATGGAAAAAATGCCGAGATGATA

TTGTTTATTTTGCAGAAACATACTGTGCCATTACTCATATTGACTATGGTGTCATAAAGGTTCAATTACG

TGACTATCAGCGTGATATGCTCAAAATAATGTCATCTAAACGTATGACTGTTTGTAATCTATCGCGCCAG

CTCGGTAAAACCACCGTAGTAGCTATTTTCCTTGCACACTTTGTATGTTTTAACAAAGATAAAGCTGTAG

GTATTCTTGCACACAAAGGCTCAATGTCTGCGGAAGTTTTAGACCGTACTAAGCAAGCAATTGAACTGCT
```

-continued

```
TCCTGACTTTTTACAACCAGGAATTGTTGAATGGAATAAGGGTTCAATTGAACTAGATAATGGTTCTTCA
ATTGGCGCTTATGCTTCCTCTCCTGACGCAGTTCGTGGTAACTCGTTCGCAATGATTTACATTGACGAAT
GTGCGTTTATTCCAAACTTCCATGATTCCTGGCTTGCTATTCAACCAGTAATTTCATCTGGTCGTCGTTC
GAAAATTATTATTACTACGACTCCTAATGGATTAAATCATTTTTATGATATTTGGACTGCTGCTGTCGAA
GGTAAATCTGGATTTGAACCATATACTGCTATTTGGAATTCAGTTAAAGAACGTCTTTATAACGATGAAG
ATATTTTTGACGATGGATGGCAATGGAGCATACAAACCATTAATGGTTCTTCATTAGCTCAATTCCGTCA
AGAACATACTGCAGCGTTTGAAGGGACTTCTGGTACATTAATTTCAGGAATGAAATTAGCTGTTATGGAT
TTTATTGAAGTAACACCAGATGATCATGGTTTTCACCAATTTAAAAAACCTGAACCAGATAGAAAATATA
TTGCAACTCTAGATTGCTCAGAAGGTCGTGGGCAAGATTACCACGCTTTGCATATTATTGATGTTACTGA
TGATGTGTGGGAACAGGTTGGTGTTTTGCATTCAAACACTATTTCTCATTTAATTCTACCTGACATCGTT
ATGCGTTATTTAGTAGAATACAATGAATGCCCAGTTTATATTGAATTAAATAGTACTGGTGTGTCAGTTG
CAAAATCGCTTTATATGGATTTAGAATACGAAGGTGTTATCTGCGATTCATATACTGATTTAGGAATGAA
ACAAACTAAACGCACGAAAGCAGTAGGATGTTCCACGCTAAAAGACCTTATTGAAAAAGATAAGCTTATT
ATTCATCACCGAGCGACTATTCAAGAATTTAGAACGTTTAGTGAAAAAGGCGTGTCTTGGGCGGCTGAAG
AAGGTTATCATGACGATTTAGTAATGTCTTTAGTGATTTTTGGATGGTTATCAACGCAGTCAAAATTTAT
TGATTATGCGGATAAAGATGACATGCGATTAGCATCTGAAGTATTTTCAAAAGAGCTTCAGGATATGAGC
GACGACTACGCGCCAGTTATATTTGTGGATTCGGTTCATTCTGCTGAGTATGTTCCAGTATCTCATGGTA
TGTCAATGGTATAAATATATTAAAGCATATTAAAGAGGATTAAAAATGACTTTATTATCTCCGGGCATTG
AGCTCAAAGAAACTACGGTTCAAAGCACCGTAGTTAATAACTCTACTGGTACAGCAGCTTTGGCCGGTAA
ATTCCAGTGGGGTCCTGCTTTTCAGATTAAACAGGTTACAAATGAAGTAGATTTAGTTAATACTTTTGGT
CAACCAACCGCTGAAACTGCTGACTATTTTATGTCTGCGATGAATTTCTTGCAGTACGGAAATGACTTAC
GAGTAGTTCGTGCTGTTGATAGAGATACCGCTAAAAACTCATCGCCAATTGCTGGTAATATTGATTACAC
AATTTCTACCCCAGGTAGTAACTATGCGGTTGGAGATAAAATCACGGTCAAATATGTTTCAGATGATATT
GAAACTGAAGGTAAAATTACTGAAGTAGACGCAGATGGAAAAATTAAGAAAATTAATATTCCTACTGGCA
AAAATTACGCTAAAGCGAAAGAAGTCGGTGAATATCCAACACTAGGTTCTAACTGGACTGCGGAAATTTC
TTCATCTTCCTCTGGTTTAGCTGCAGTAATAACTCTTGGAAAAATTATTACTGATTCTGGTATTTTATTA
GCTGAAATTGAAATGCTGAAGCTGCTATGACAGCGGTTGACTTTCAAGCAAATCTTAAAAAATATGGAA
TTCCAGGAGTAGTAGCGCTTTATCCAGGCGAATTAGGCGATAAAATTGAAATTGAAATCGTATCTAAAGC
TGACTATGCAAAAGGAGCTTCTGCATTACTCCCAATTTATCCAGGTGGTGGTACTCGTGCATCTACTGCT
AAAGCAGTGTTTGGATATGGACCGCAAACTGATTCACAGTACGCTATTATAGTTCGTCGTAATGATGCTA
TTGTTCAAAGCGTTGTTCTTTCAACTAAGCGTGGTGAAAAAGATATTTACGATAGTAACATCTATATCGA
TGACTTTTTCGCAAAAGGTGGTTCAGAATATATTTTTGCAACTGCACAAAACTGGCCAGAAGGCTTCTCT
GGAATTTTAACTCTGTCTGGTGGATTATCATCAAATGCTGAAGTAACAGCAGGAGATTTGATGGAAGCTT
GGGACTTCTTTGCTGACCGTGAATCTGTTGACGTTCAACTGTTTATTGCAGGTTCTTGTGCCGGTGAATC
TTTAGAAACAGCATCTACTGTCCAAAAACACGTCGTTTCAATTGGGGATGCTCGCCAAGATTGCTTAGTA
TTGTGCTCTCCTCCGCGTGAAACTGTAGTTGGAATTCCTGTAACCCGTGCTGTTGATAACCTAGTCAATT
GGAGAACTGCGGCAGGTTCATACACTGATAATAACTTTAATATCAGTTCAACCTATGCAGCAATTGATGG
TAACCATAAGTATCAGTATGACAAATATAATGATGTGAATCGTTGGGTTCCATTAGCAGCTGATATTGCT
GGTTTATGCGCAAGAACTGATAACGTATCTCAGACTTGGATGTCTCCAGCTGGTTATAATCGTGGTCAGA
TTCTTAACGTTATTAAACTTGCTATTGAAACTCGCCAGGCTCAGCGCGACCGTTTATACCAAGAAGCTAT
CAACCCGGTAACCGGTACAGGTGGTGATGGTTACGTATTGTATGGTGATAAAACAGCTACTTCTGTTCCT
```

-continued

```
TCTCCATTTGATCGTATTAACGTTCGTCGTCTGTTTAATATGTTGAAAACGAATATCGGACGTAGTTCAA

AATATCGTTTGTTCGAATTAAACAACGCGTTTACTCGTTCATCATTCCGCACAGAAACTGCCCAGTACTT

ACAAGGGAATAAAGCTCTCGGTGGAATTTATGAATATCGTGTAGTTTGCGATACAACAAATAACACTCCG

TCAGTAATTGATAGAAATGAGTTTGTTGCAACATTCTACATCCAACCGGCTAGAAGCATTAACTACATTA

CCTTAAACTTCGTAGCAACTGCTACTGGTGCAGATTTCGATGAGTTAACTGGTCTTGCTGGTTAATACGG

TGCATTCTAAAGGCCTGTTTCGGCAGGCCATATAAATACACTATATCCTTAATTCTTTAATTCTATATGC

CCTAGGTTAAACATAGGGATATAAATACTACAGAGGCTAATATGTTTGTAGATGATGTAACACGAGCGTT

TGAATCTGGTGATTTTGCTCGACCTAACTTATTCCAAGTAGAAATTTCTTATCTTGGACAAAATTTTACG

TTCCAATGTAAAGCTACTGCTCTACCAGCTGGTATTGTAGAAAAAATTCCAGTCGGATTTATGAACCGTA

AAATTAACGTAGCAGGCGATCGTACATTCGATGACTGGACTGTTACAGTAATGAACGATGAAGCTCATGA

TGCTCGTCAGAAGTTCGTTGATTGGCAAAGCATTGCTGCGGGCAAGGAAACGAAATTACTGGTGGAAAA

CCTGCAGAGTATAAAAAGAGCGCTATCGTTCGTCAATATGCTCGTGACGCTAAAACAGTAACAAAAGAAA

TTGAAATTAAAGGTCTGTGGCCTACTAACGTGGGTGAACTTCAATTAGATTGGGATTCAAACAATGAAAT

CCAAACTTTTGAAGTAACTCTTGCTCTCGATTATTGGGAATAAAATGAATGGGGAGAAATCCCCATCCTG

CTTAAAGCAGAGAAGTCCATTATAAATATAACTATAATTCCCATTTGGAGAATACAATGAAATTTAATGT

ATTAAGTTTGTTTGCTCCATGGGCTAAAATGGACGAACGAAATTTTAAAGACCAAGAAAAAGAAGATCTT

GTTTCCATTACAGCCCCAAAGCTTGATGATGGAGCAAGAGAATTTGAAGTAAGCTCGAATGAAGCTGCTT

CTCCTTATAATGCTGCATTCCAAACAATTTTTGGTTCATATGAACCAGGAATGAAAACTACTCGTGAGCT

TATTGATACATATCGTAATCTCATGAATAACTATGAAGTAGATAATGCAGTTTCAGAAATCGTTTCAGAT

GCTATCGTCTATGAAGATGATACTGAAGTCGTAGCGTTAAATTTGGATAAATCTAAATTTAGCCCAAAAA

TTAAAAATATGATGTTAGATGAATTTAGTGATGTATTAAATCATCTATCGTTTCAACGAAAAGGTTCTGA

TCATTTTAGACGTTGGTATGTTGATTCAAGAATTTTCTTTCATAAAATCATTGATCCAAAACGTCCAAAA

GAAGGCATAAAAGAATTACGTAGATTAGACCCTCGCCAAGTTCAGTATGTTCGTGAAATTATAACAGAAA

CTGAAGCTGGCACAAAAATAGTTAAAGGTTACAAAGAATATTTTATATATGATACTGCCCATGAGTCATA

TGCATGTGATGGTAGAATGTATGAAGCTGGCACAAAAATAAAAATTCCTAAAGCTGCCGTCGTTTATGCC

CATTCTGGATTAGTCGATTGTTGCGGTAAAAATATCATCGGGTATTTGCATCGTGCTGTTAAACCTGCTA

ACCAATTAAAATTATTAGAAGATGCTGTAGTCATTTATCGCATTACTCGTGCTCCTGACCGTCGTGTTTG

GTATGTAGACACAGGTAATATGCCTGCTCGTAAAGCTGCTGAGCACATGCAACATGTTATGAACACGATG

AAAAACCGTGTAGTATATGATGCATCAACAGGTAAAATAAAAAATCAACAGCATAATATGTCTATGACCG

AAGACTATTGGTTGCAGCGCCGTGATGGTAAAGCTGTGACAGAAGTTGATACTCTTCCTGGTGCTGATAA

TACTGGCAATATGGAAGATATTCGTTGGTTTAGACAAGCTCTTTATATGGCATTACGTGTTCCTCTTTCA

CGCATTCCGCAAGACCAACAAGGCGGTGTGATGTTTGATTCTGGAACTAGCATTACACGTGATGAATTAA

CGTTTGCTAAATTTATTCGTGAGTTACAGCACAAGTTTGAAGAAGTTTTCCTAGATCCGCTTAAAACAAA

TCTTTTGCTTAAAGGTATAATCACAGAAGATGAGTGGAATGATGAAATAAATAATATTAAGATAGAATTT

CATCGGGATAGCTACTTTGCTGAGCTCAAAGAAGCAGAAATTTTGGAACGAAGAATTAATATGCTAACCA

TGGCAGAACCATTTATTGGTAAATATATTTCTCACAGAACTGCTATGAAAGACATTTTGCAGATGACTGA

TGAAGAAATAGAACAAGAAGCCAAGCAAATTGAAGAAGAGTCTAAAGAGGCTCGTTTCCAAGACCCCGAC

CAAGAACAAGAGGATTTTTAATGGAAGGTTTAATTGAAGCTATTAAATCAAACGACCTCGTAGCCGCTCG

TAAATTATTTGCTGAAGCCATGGCTGCAAGAACGATTGATTTAATTAAAGAAGAAAAAATCGCTATCGCT

CGCAATTTCTTAATCGAAGGTGAAGAACCTGAAGACGAGGATGAAGATGAAGATGACGAAGATAGTGATG
```

-continued

```
ATAAAGACGACAAAAAAGACGAAGACTCTGACGAAGACGAGGATGATGAATAATGCTTCTGATCCCTGAA

ACTCATGAATTAGTTCTCGAGAATGTCGAAGCACTTATTCCTGAAGCACAGGGTCGCTTTGACGAATTGT

CTTCTGCTTTAAATAAAGACGATATAAATACAATTGTCGAGAATATGCTTGATGATGAAACTGATTTAGC

GGTTGCATTAGCTTCTATTAATGAAAATATGCCGTTAAATGAATTCATCGTTAAACATGTTTCTGCCCGT

GGTGAAATTACTCGCACTAAAGACCGCAAAACGCGTGAACGAAATGCATTTCAAACCACTGGGCTGTCTA

AAGCAAAACGTAGACAAATTGCTCGTAAAGCTACCAAAACGAAGATTGCCAATCCAGCAGGTCAATCTCG

TGCTCAGCGTAAGCGTAAAAAAGCTCTTAAACGCCGTAAAGCATTAGGATTAAGCTAATGAATGAACCCC

AATTACTAATTGAAACTTGGGGTCAACCTGGCGAAATTATTGATGGCGTACCAATGCTTGAATCTCATGA

TGGAAAAGACTTAGGTTTAAAACCGGGTTTATACATCGAAGGAATATTCATGCAAGCGGAAGTCGTCAAT

AGAAATAAACGTCTTTATCCAAAACGTATATTAGAAAAAGCGGTAAAAGACTATATTAATGAGCAAGTTT

TAACTAAACAAGCTCTCGGAGAATTAAATCATCCTCCACGCGCTAATGTTGACCCGATGCAAGCCGCTAT

CATTATAGAAGATATGTGGTGGAAAGGAAATGACGTATACGGACGAGCTCGTGTTATTGAAGGTGACCAT

GGTCCTGGAGATAAATTAGCAGCTAATATTCGTGCCGGATGGATTCCAGGAGTTTCTTCTCGTGGATTAG

GTTCATTGACTGACACAAATGAAGGTTATCGTATCGTAAACGAAGGATTCAAATTAACTGTAGGTGTTGA

TGCAGTATGGGGTCCAAGTGCTCCAGATGCATGGGTAACTCCTAAGGAAATTACCGAATCACAGACGGCG

GAAGCCGATACAAGTGCCGATGACGCCTATATGGCTCTCGCAGAGGCCATGAAAAAAGCGTTATAAATAT

TATTATCTAAACAACAGGACTACAAAATGCTTAAAGAACAACTGATTGCCGAAGCGCAGAAAATTGATGC

TTCCGTTGCTCTTGATAGTATTTTCGAATCAGTTAATATTTCTCCGGAAGCAAAAGAAACTTTCGGCACT

GTATTCGAAGCTACCGTCAAGCAGCACGCCGTTAAATTAGCTGAATCTCATATCGCTAAAATTGCTGAAA

AAGCAGAAGAAGAAGTAGAAAAAAATAAAGAAGAAGCCGAAGAAAAAGCTGAGAAGAAAATCGCTGAGCA

AGCTTCTAAATTCATTGACCATCTTGCAAAAGAATGGCTCGCTGAAAATAAATTAGCAGTTGATAAAGGC

ATCAAAGCCGAACTGTTTGAATCCATGCTTGGTGGATTAAAAGAGCTCTTTGTTGAACACAACGTTGTTG

TTCCAGAAGAATCAGTTGATGTTGTAGCTGAAATGGAAGAAGAGCTGCAAGAACATAAAGAAGAATCGCC

TCGTCTGTTCGAAGAACTGAATATGCGCGACGCATATATCAATTATGTGCAGCGTGAAGTGGCATTGAGC

GAAAGTACTAAAGATCTGACTGAGTCTCAAAAAGAAAAGTCTCTGCTCTGGTCGAAGGTATGGATTATT

CAGATGCATTCTCAAGTAAATTGAGTGCAATCGTAGAAATGGTGAAGAAATCTAATAAAGATGAAAGCAC

TATTACTGAGAGTATAAATACTCCTGATACTGAAGCAGCCGGACTGAATTTCGTCACTGAAGCTGTAGAA

GATAAAGCTGCACAGGGTGCAGAAGATATTGTAAGTGTATATGCGAAAGTCGCATCTCGTTTCTAATTTT

AAAGGTTAACACAAATGACTATCAAAACTAAAGCTGAACTTTTGAACAAATGGAAGCCATTACTGGAAGG

TGAAGGTTTACCGGAAATTGCTAATAGCAAACAAGCGATTATCGCTAAAATCTTTGAAAACCAGGAAAAA

GATTTCCAGACAGCTCCGGAATATAAAGACGAAAAAATTGCTCAGGCATTCGGTTCTTTCTTAACAGAAG

CTGAAATCGGTGGTGACCACGGTTACAATGCTACCAACATCGCTGCAGGTCAGACTTCTGGCGCAGTAAC

TCAGATTGGCCCAGCTGTTATGGGTATGGTACGTCGTGCTATTCCTAACCTGATTGCTTTCGATATTTGT

GGTGTTCAGCCGATGAACAGCCCGACTGGCCAGGTATTCGCACTGCGCGCAGTATATGGTAAAGACCCAG

TGGCTGCCGGTGCTAAAGAAGCATTCCACCCAATGTATGGTCCAGATGCAATGTTCTCTGGTCAGGGTGC

TGCTAAGAAATTCCCAGCTCTGGCTGCTAGCACACAAACCACAGTAGGTGATATCTATACTCACTTCTTC

CAGGGAAACTGGTACTGTATATCTGCAAGCTTCTGTTCAAGTAACAATCGATGCTGGTGCGACTGATGCTG

CTAAATTAGATGCTGAAATTAAGAAACAAATGGAAGCTGGTGCACTGGTAGAAATCGCTGAAGGTATGGC

TACTTCTATCGCTGAACTCCAGGAAGGTTTCAATGGTTCTACCGATAACCCATGGAATGAAATGGGCTTC

CGTATCGATAAGCAAGTTATCGAAGCTAAATCTCGTCAGCTGAAAGCTGCTTACTCTATTGAATTAGCAC

AAGACCTCCGCGCTGTTCACGGTATGGATGCTGATGCTGAACTGTCTGGTATTCTGGCTACAGAAATTAT
```

-continued

```
GCTGGAAATCAACCGTGAAGTTGTTGATTGGATTAACTACTCAGCTCAGGTTGGTAAATCTGGTATGACC

CTGACTCCGGGTTCTAAAGCTGGTGTATTTGACTTCCAGGACCCAATTGATATTCGTGGTGCTCGCTGGG

CGGGTGAATCCTTTAAAGCTCTGTTGTTCCAGATTGACAAAGAAGCAGTTGAAATTGCTCGTCAGACCGG

TCGTGGTGAAGGTAACTTCATTATCGCTTCCCGTAACGTAGTTAACGTTTTGGCTTCAGTTGATACCGGC

ATTTCTTATGCTGCACAGGGTCTGGCTACCGGCTTTAGCACTGATACTACCAAGTCAGTATTTGCTGGTG

TTCTGGGTGGTAAATACCGCGTATATCGACCAGTATGCTAAACAGGATTATTTCACTGTAGGTTATAA

AGGTCCGAACGAAATGGATGCTGGTATTTACTATGCTCCATATGTAGCTCTGACTCCGCTGCGTGGTTCC

GATCCGAAGAACTTCCAACCGGTAATGGGATTCAAAACTCGTTACGGTATCGGTATCAACCCATTTGCAG

AATCCGCTGCTCAGGCTCCGGCTTCTCGCATCCAGAGCGGTATGCCTTCTATTCTGAATAGCCTTGGTAA

AAACGCTTACTTTAGACGTGTATATGTTAAAGGTATCTAATCTCTAACGATAGAAACACAATTTTAGGGA

ACCTTCGGGTTCCCTTTTTTCTATTTTATACGATAGCAATCAGGCATATCATCCGCATTTATCCAATTGC

GAATAGTTTTAGGACTAACTTTAAAATGCTCCGCTGCGTAATCAGGATTATCAAATTTAACGCCCTTTAT

ACATATTGGAATAAATTTTTTAATACCACCAAGTTTTTCAGAAATAGCTTTACGATGTGAAATCGATATA

GGTTTGTTTTTTCGTGGATGAACATGTGTTTTATAATATTCATTGCGCCCTTTAACTCGCTTCGCAATAG

TTTCATCAGATTGCTTAACGCCTGTTTTTGCCTTTGATATTTTTCGTTTAGCTTCCACAGTCATTCCTTC

TTTTGTTCGTATTGATAACATATTACGATATGAAGGATCTTGCAAATGAACTATAACTGGATTTCCTCTG

CCACCAATAGCAGCATTATAGGTATCAGTTCTCATAACGAATTCCTCATTAACTAGTAAAGCTTCCATTT

TATACATCTCCTCAGATGAGGAGAAAGAATAAAGAATTTCTTTTTTAAAGTTATGAATACCATATTTTTT

GATGGATTTTTTGATGTTTACGCCAGAACCCATATAACCATCGTTTTCGTCAAGAGTAGCATGAGCTCCG

ATGTAAATTTTTCCATTGATGATATTAGTAATTTGATATATTAAATATTTCATTTTAAACATCACTCCGT

TTGTATATGATTATAATATCATATTACTTTGGTCTTGTAAATAACTTTATAAATAGTATTATATTTCAAC

AAGGAAAATACAATGGCTAAAATCAACGAACTTCTGCGCGAATCAACCACAACGAATAGCAACTCAATCG

GTCGCCCAAATCTCGTTGCTTTGACTCGCGCTACCACTAAATTAATATATTCTGACATTGTAGCAACGCA

AAGAACTAATCAACCTGTTGCTGCTTTTTATGGTATCAAATACCTTAACCCAGACAACGAATTTACATTT

AAAACTGGTGCTACTTACGCTGGCGAAGCTGGATATGTAGACCGAGAACAAATCACAGAATTAACAGAAG

AGTCTAAATTAACTCTCAATAAAGGCGATTTATTCAAATATAATAATATCGTTTATAAAGTATTAGAAGA

TACTCCATTTGCTACTATCGAAGAAAGTGATTTAGAATTAGCTCTTCAGATTGCAATCGTTCTTTTAAAG

GTTCGTCTATTTTCTGACGCAGCGTCAACAAGCAAATTTGAAAGCTCTGATAGTGAAATTGCGGATGCTA

GATTCCAGATTAATAAATGGCAAACTGCAGTTAAATCTCGTAAACTTAAAACTGGCATCACAGTTGAATT

AGCGCAAGATTTAGAAGCAAATGGATTCGATGCTCCTAATTTCTTGGAAGATTTGCTTGCAACTGAAATG

GCAGATGAAATCAATAAAGACATTCTGCAGTCTTTGATTACAGTGTCAAAACGCTATAAAGTTACAGGAA

TTACTGATAGTGGATTCATCGATTTGAGTTATGCATCTGCTCCTGAAGCTGGTCGTTCATTATACCGAAT

GGTATGTGAAATGGTTTCGCATATCCAAAAAGAATCAACTTATACAGCAACGTTCTGTGTTGCTTCAGCT

CGTGCCGCTGCGATTCTTGCTGCATCAGGCTGGTTAAAACATAAACCAGAAGATGACAAATATCTTTCAC

AAAATGCCTACGGGTTCTTAGCTAATGGTTTACCGCTTTATTGCGATACTAACAGCCCATTAGATTATGT

AATCGTTGGCGTAGTAGAAAATATCGGTGAAAAGAAATTGTTGGATCAATTTTCTATGCTCCGTATACA

GAAGGTCTCGACTTAGATGACCCTGAACATGTAGGTGCATTTAAAGTTGTTGATCCAGAAAGCTTAC

AACCATCTATCGGTTTATTAGTTAGATATGCTTTATCAGCAAATCCTTATACTGTAGCAAAAGATGAAAA

AGAAGCAAGAATAATTGACGGTGGAGACATGGATAAAATGGCAGGTCGTTCAGATTTGTCTGTTTTATTA

GGTGTTAAGCTACCAAAAATTATCATTGATGAATAAAACAAAGGGACCTTTCGGTCCCTTTTTATTTAAC
```

-continued

```
TTACCAACTCAATCCAAGCTGGACGAAGTACATCTTGTACCATTTTAACTAATTCCTTTTTAATCAAAGA
AGGATTATCTGCTTGAGTTAGAGTAATACCTTCACGAGAAGTTTCTTCCAAAATATCTTGAACAGTTAGC
CCCATCACCTTTCCAAAATCCTTTGGACCAATTTCGCCAATTTTAGAAATAACGTTATTTACGCGGTTCA
GTGTAACGTAACAAGCTAAAATTCCCACCAATTTGTTATCAGCTTCTGATAGCTCAACTTTAGCTTTAAT
AGGCTTATCAGACTTTTTCTTTTCACTAAATTTAGAGTTCTTGCATTTAATCGCTACACGATTTCCATTA
CGAAGCCAAGAAGGATAACAAGGTTTCAATACATATCCTTCAGCAGTAAATACTTCGCCTTTTGCTTCGG
CATTCCAAACGCATTTATTTGCATCAACTAATCCAGCATGGTCTACTGTAAAATTATAATCTTGGACGAC
AGAATCTAAATCATTTGGCAATTTAATAAGCTCTTCAAATTTACCGCGACCTAAAAGTGGAGCCATTTTA
AATTTAAATGTATTACAGAATGATTCCATCATATAATCATCTACATAAGTCACATCACCGCTTTCTGTAG
TAACAATAATGTCAAATACATAAAAATCTTTATCACAATAATCAACATTCTTCTGAATGCCAGGTCCAGC
GAATTCGCCAAAGACTTGATAAGATACAACCGCTGAGGTTTCCATAATATCTTGTACAGCTTTAATGGAA
TCAGCATAATTCTTCAAAATAATTTCATACCCAAAGAAATCTTCAGCAGGAAGAATCGGTCCAGTGCGTT
TAGCGCAAGTCACTTTATCACGCTCAATAATCAATGAGAAATTTGTGCCGTGAATCTTTTCACGAGCTAC
CCACTCCCCACCAGTCAATCCCAAGCTATAAAGTTTTTCAATAAATTTAGAGTTGTAATGATTTTCAAGA
CTGCTATACTTTTTAAACATAATTAATCCTCAAAATGTAATTTCTAACCAATCACCATCACGCTGATCAC
TATTGACTTTAAAGCTGAATCCTTCTTTTCTCAGCCAATCACCAATTTCTTCTGTAATCAATTTATCACG
AGCAATACAATAATAATTAAAATGTGTTTTACCTTGTTCAGCTGCTTTATTAGCAAGTTCTGAAAAATCT
TTAATAAAACACTCTAGCTTAAACTGTTTACTTTTTAATGCTTTTTCGCGTAATTGATTAGCAAAAGATT
CATTTTCATAAAGATCATACTGTTCCATTTTTCACCTTTTTATTGATATGTCTTTTTCTATAGACAACTT
TTTCTCGAGCCCATAATACAGCCACTTCTTTTGCCTGTAAGTTTAATTCACGAGCAATTTCAATGAATGA
CTTTCCAGACTCATGAAGAGTAAACACCACAACCTCAGTTCTCATAATCAATCTCATGTTATCGAGTTGG
TGCCATTATATACATCATTTTCTGATTGTGTTTTGTGTGCTTTCAAAATGAAGAAAGGGGCCGAAGCCCC
TTATGATTATGGATAGGTATAGATGATACCAGTTTCTAAAGCAGTTTTATGAATGATGTATCCATTACGC
GATTCTTGGACATCAACTTCTGGATAGTCTTTCATCATCTTCTGGAGAGTGTAACGATGCAGGTAATATT
TACTATCTGGGTCGTCAGTTTTCCAATCTTTACCTTCTTCGGTCATTTTTTGGATTTCATCCATAACCCA
CCAACCGCACCAGATGTAAGCTGAGCTACGGTGTGGAAGAGGATGAACATAAGGTAATTCACCTTCTGGT
TCTGGAGCAACTTTAGCCGTGACTGTTACATTACCAGTTTTGGTAACGGTTACAGGGTTATAATCTGCAG
CAGTAACAGTTGCAGTAACTTCAATAGTTTGACTTCCAACAGATGAGGTATCGACAGTATATACGTTAGT
TGACCCTTCTACAGGAGAAGAATCTTTCTTCCATGAGTAAGTAATTTGTGCTTCTTCTGGAGCACCCGTA
ACATTAGCCGTAAATGTAGCCGAAGCATCTTGCTGAACATTAATAGAAGGAGGAGTCAATGTAACCTGTG
GATTCATTGTCTTCTTATTAACCGTTAATGATACTTCATTAGAAGTAACGCTTAGTGCATCATAATCTGT
CGCGGTTACTTGGGCTACGCATTTAATTCTTTTTACTCCACTTGTAGTTGGAGTATAGCTAAATGTAGAG
TTAGTTTCTCCACCAACTTGTGAATCATCTACATACCACTGATACGTAGCAGATGCTCCATCAGGTTGAG
AAGCTAAGGCAGCAGTAAATTGAACTGGGGTTCCAATCACTCCAGCCGCAGGACTAGCAGGAGTTACGGC
TAAGGTAGTCGTCTGTGTCTTATTTTAACTGTGATAGTTGTTGTCGCTTCAGCCGTTTCCGGGCCTCCT
TCAGAAAGTGTATTTGTTGCAACTACTTTAATAGTCTTTTGACCGGCAGGTCCTTTTAGTACATAACTAA
AAGTTGCTTCAGCTCCATCTTGTGGAACATTATCTACGCTCCAAGCATATGTAATAGTTCCGCCTCCAGT
TTGACCACTGGGTGTAGCAGTAAACTGCTTAGTTTCATCAATAACCCCTGTAGGTGTTTTAGGAGTTATA
TCAACTGTAAAAGTCATAAGTTATCCTTATTTTAATGTTACGAAAGAAGAGTTGCGTGTTTCACGAATTA
AAACTGATCCATCGCGATTAATGTAATAAATTAAGCTAAATAAAGTTTGGTGTGCTGACGCATGTTCAAA
ACTAGTTGGGTGAGATTTCCAATCAGGAGTTTCAGCAATCCATTGATAAATCCACCAAGGAACAGTACAG
```

```
AATCCTAGATTTTTTCCAATCAGTTGAAGATTCGGACTAAAGTTTTCCGGAAGAGTAAATACAGACGGCT

TTTCAGATTCAATAATCTCAGCTACAGCCTGTTCGAATTTTCTTCAACAAAAGGAGTATCTTCAATCAA

AACATCGGTATTTTCAGGAATTTTATCCGTTTCTACTACTTCAATTTTAATGTCAGATTTAATCGGAGAA

TCAATCAGAAGTGCTGCTTCTGGATTGACTTCTTCATCGTCATATTTTAATCCCTCTGCGGCATCAGCAG

CATCAATTAAGTCTTTAATAGATAACCCATCAGTCTCTGGCATAGGTTCACTAGCGAGCTTCTGGAGGGC

TTCTTCAATATCAACAACGATATTATCAAAAGATTTATTCTTTTTGACCTTTATACCAAACTGTTCAGCA

TATTCAGCTAATTTAGCTTTAGCTTCTTTGTTATCATCAAGAGCCTTCAGCTCTGCAATATAATCTTTAT

CTATCATAATATTTCCTCAGTATAAATATAGATATATTTATTACTCGGAAAATAGTATGTACCACTTTGT

ATATGAAACAACAAATCTAATAAATGGTAAAAGTATATAGGAAAGCACTCTACTGATGACTTGAATGAT

GGTTACCTTGGTTCCGGTAAGGCAATTCAGCAGGCTATAAAGAAATATGGTGAAAACAATTTCTCTAGAA

CAATACTAAAAGAGTTTAAAACTTCCGAAGAAGCGTACATGTATGAAGAAGAAATTATAACTCCTGAACT

AATAAAAAGCAAAAATTATTATAATATGAAACCTGGTGGAATTGGTGGAATTGTTATGACTACAGATGTT

ATAGCAAAGATGAAAGAATCTTCCGCTAAAAGATTTGAAAACTCACCGGGCACGGTATTAGGTAAAACTT

GTTATACTAATGGAACTAAAAATATTTTTATTAAACCTGGAGAACTTGTTCCAGAAGGATTTGTAAAAGG

GATGGTTCATCCTAATAGAAAGTCCAGAAAAGGATGTAAAGTCAAACCGACTACCACAGGAACTTTTTGG

GTCAATAATGGCGCAATAAATAAATTAATACAACCAGACGGTATTATTCCCGACGGATTTATTAAAGGTC

GTCTCATGAAAAGAGATTCTAAAGGCAAATTTAGTAAGGCATAATTATGGATATTAAAGTACATTTTCAC

GACTTCAGTCATGTACGCATCGATTGTGAAGAGAGCACGTTCCACGAATTAAGAGATTTCTTTTCGTTTG

AGGCCGATGGATATAGATTTAATCCTCGCTTCAGATATGGCAACTGGGATGGACGAATCCGTCTTTTAGA

TTATAATCGTCTTCTTCCATTCGGCTTAGTCGGGCAAATTAAAAAAATTCGTGATAATTTTGGCTATAAA

GCCTGGATTGACCCACAAATTAACGAAAAAGAAGAATTATCAAGAAAAGATTTTGATGAATGGCTTTCTA

AATTAGAAATCTATTCAGGAAATAAAAGAATTGAACCGCACTGGTATCAAAAAGATGCAGTGTTCGAAGG

ATTAGTTAATCGTCGTAGAATTCTTAATCTTCCAACATCTGCAGGTAAATCTTTAATTCAAGCTTTGCTT

GCGCGATATTATTTGGAAAATTATGAAGGTAAAATTCTTATCATTGTTCCAACAACTGCTCTGACAACTC

AGATGGCTGATGACTTCGTCGACTATCGTTTATTCAGCCATGCAATGATAAAGAAAATTGGTGGCGGAGC

ATCAAAAGATGATAAATATAAAAATGATGCACCAGTCGTTGTTGGTACATGGCAAACTGTAGTAAAACAA

CCGAAAGAATGGTTCTCACAGTTTGGAATGATGATGAATGATGAATGCCATCTTGCTACAGGAAAAAGTA

TTTCATCTATCATATCAGGTTTAAATAACTGCATGTTCAAATTCGGTTTGTCTGGTTCATTACGTGATGG

CAAAGCCAATATCATGCAGTATGTTGGAATGTTTGGTGAAATATTTAAACCAGTAACGACTTCTAAATTA

ATGGAAGATGGACAAGTAACTGAGCTAAAAATTAATAGTATTTTTCTTCGCTATCCCGATGAGTTCACTA

CTAAATTAAAGGGAAAAACTTACCAAGAAGAAATAAAAATTATTACTGGGCTTAGTAAAAGAAATAAATG

GATCGCTAAATTAGCTATTAAGCTTGCGCAAAAAGATGAAAACGCTTTTGTCATGTTTAAACATGTATCG

CATGGTAAAGCTATTTTCGATTTAATTAAAAATGAATACGATAAAGTTTATTACGTATCAGGGGAAGTTG

ATACCGAAACCCGCAATATAATGAAAACCTTAGCTGAAAATGGTAAAGGAATAATTATAGTAGCTAGTTA

TGGTGTATTTTCTACTGGTATTTCAGTTAAAAATCTGCATCACGTTGTTTTAGCGCACGGTGTTAAATCA

AAAATCATTGTATTACAAACAATCGGTCGTGTATTACGTAAGCATGGTTCTAAGACAATAGCAACAGTCT

GGGACCTCATAGATAGCGCAGGCGTCAAGCCAAAATCTGCTAATACGAAAAAGAAATATGTTCATTTGAA

CTATCTTTTAAAACACGGCATTGATCGTATTCAGCGCTACGCAGATGAAAAATTTAATTACGTAATGAAA

ACAGTTAATTTAATAAGCTTCGGCCCTTTGGAGAAAAAGATGTTACTAGAATTTAAACAATTTCTTTATG

AAGCTTCTATTGATGAATTTATGGGTAAAATTGCCTCTTGTCAAACATTAGAAGGTTTAGAAGAACTTGA
```

-continued

```
AGCTTATTATAAGAAAAGAGTCAAAGAAACTGAATTAAAAGATACTGATGACATCTCTGTGAGAGATGCT

TTGGCAGGAAAAAGAGCTGAATTAGAAGATTCAGACGATGAAGTAGAAGAAAGCTTTTAAATTAAAAAG

GCCCAACCAAAAAGGAAGGGCCAAAACTATAGACTAAAGGTCACACTATAGCAAAAGTTGTGTTTCATTT

AATTGTTCTTCCGAACTTTCTGAAACTGGTAGTTCTTTAATGTAATTATAGCAAGGCCCAGGATGTACAG

GACCTTTGTCTGTTTCAACAACCAATGCAGAATCGATTGGAGTTTTACAGACAACACAAATCTTATCTGA

CATGATTGTCTCCTCTGAATTATATCTATTTATACAACTCTCATATGCATATCAATGCCCATATCTTTAG

AATAAAAATATTCATCAAGATATCCGGCAAATTTTCCTTTAATATAAAGGACATCTTCACCACACGGGTG

GTCGGCCAGGATACGAATATCCTGACGCTTAAGATTATGCTTTTTCATTAAGAATTGAATTTCCGTTTCA

AATTCTTCTTCATAATTAAAAGCATCATCAATGCTATATCTCATTATTTTCCAGCCTCAAATGCTCGCAT

GTCTTGAATATGCTTAATAGCAAATCCACGTGATTTAATAGCATCAAGAGCTCCGCTACAGAAATCTAAT

AAAATCCCCCAATACTGCAACGAGGTATCAACCTTTAAAACATCCTTATCCGCTGATAGAACTGTCTTCA

TTTCTGATTTCTCGTAACGATCCATACTAAATTCATCACCATCTCCTCGTCCCGAGTAGTAGTCTAATCT

AGCTTTAAGAGCAACTTTTTTCTGTGCTTCAATTCTAAGCATTTCCTTTTTAATACTTGAATGCTTATTA

AGCCATTTACTATATAACATCACATTATTAGCTGCTTCATACTGTAATTTAGTCGAATCTATAAACACAT

CTTTCTTCAATTCTTCTTGAAGATCTTCTAATCTCATATTGTTCTCTATTCAATTGTTATTGGTTGTTAT

TGGATGGACTTAGATTCATTATACCACGTTTTAACGTGAAGCATTATACTCTATTACTGGAAGCCAGCTG

CAGTTTTATCTGCTCAATATCATCAGGATTATCGATGACCGAAAAGCGTATTTCTACTATCAGAGTATAA

TCGTCATAAACGGGTATCACATTAACTGCTAATTTATCAATACGTGGCTCATAGTTTCTTACTGCGCTTT

CGATATTGCGTTCAACCGTGTCAGCAGTAAGAGGAGTCATATTTTCAAAAAGCTGGTCTGATAAATCACA

TCCAAATTCAGGGTCAAACGGTCTTGAACCTTTTCTTGTTGTAATAATTCCCAAAAGACTGTTTTTAATT

GACCTTAATCCAAGCGATCTGGAAACGTCTTTGTTCCAATCCATTTTCATTTCCGGGTCAATATCAGAAT

AAAGCTTATTAATATTTGCCATTATAGTAACTCAAAGAACTCTTTGAGGCCTCTTATTACGTGAGCATGG

GTTTTTCCACACTCTGGACACTTAATTGGAACAGCCAAATAAACGGTAGGCTTTAAAAGCATATCTTTTA

TAGCTACAATATCTGACTCTGTGATGATAGAATATAAATCTTCTAGTTCCTTTTCATTTAAGTCTTCAAC

TGGAATGCTTTCCCCGTTAGCATGAATCGTTTCTATACATGATACTATCATGTGGGCTATATTTTTATCA

TCAAAAATTTTAGGGTATCGGAATTTAATTTTAATGTCACCTAGTGTATACCAGAGGTCTTCTGGTGCAT

CTATTTGTGTATGTAATAGATTTATATGGGTTGGTATTTCAGTTCCACAGGTGCACTTCCAGGAGTTTTC

GTGATTAACTTCACCGAGAGAATGTGCCCATAAATGAATCAACAATAGTTCTGATTCTTGGCGGTTTAAA

TCTTTTGCATTTGTGCAGTCTTTGATTAGCTTTTTAACAATTACTTCTACGGAACCATTATTTTTGGCAG

TAATAAGTTCTAGATATTCTTTAAGCGTGAATGCGCGACAATTGATTATTTTAGAACCAACTCTCACATC

AAATTTGTATTCATACATATTTAGCTCCTTTATTTATCATATTTATAAATAGAATAAAAGGAGCATCTAT

GGCAAACATTATTCGTTGTAAATTACCAGATGGTGTTCATCGTTTTAAACCATTTACGGTAGAAGATTAT

CGAGATTTTTTGTTAGTTCGAAACGATATAGAACATCGGTCACCACAAGAACAAAAGCAAATAATTACTG

ATTTAATTGATGATTATTTTGGAGACTATCCGAAGACTTGGCAACCATTTATATTTTTGCAGGTATTTGT

AGGGTCAATAGGTAAAACTAAAAGTACGGTCACATTTATATGTCCAAAATGTAAAAAAGAAAAGACAGTT

CCATTTGAAATATATCAAAAAGAATTAAAGGACCTTGTTTTTGATGTAGCTAATGTTAAAATTAAATTAA

AGTTTCCTTCTGAGTTTTATGAAAATAAAGCAAAGATGATTACTGAAAATATTCATTCTGTTCAAGTAGA

TGAAATATGGTATGATTGGAAGGAAATTAGCGAGTCCAGTCAAATAGAACTAGTTGACGCCATCGAGATA

GAAACATTAGAAAAAATTCTCGATGCAATGAATCCTATTAATTTAACTCTACACATGTCATGCTGTAATA

AGTACATTAAAAAATACACTGATATAGTAGACGTGTTTAAGCTATTAGTTAACCCAGATGAGATATTTAC

TTTTTATCAAATTAATCACACACTCGTAAAAAGTAATTATAGCTTAAATTCAATAAGTAAAATGATTCCT
```

-continued

```
GCCGAGCGCGGATTCGTATTAAAACTGATTGAGAAGGATAAACAATAATGAGTATGTTGCAACGCCCCGG
ATATCCAAATCTCAGCGTTAAATTATTTGATAGCTACGACGCTTGGAGTAATAATAGATTTGTTGAATTA
GCTGCTACTATTACCACATTAACTATGCGGGATTCTCTTTATGGCCGAAATGAAGGAATGCTGCAGTTTT
ATGATTCTAAAAACATCCATACAAAAATGGATGGAAATGAAATAATTCAGATTTCTGTAGCTAATGCAAA
TGATATTAATAATGTTAAAACACGAATTTATGGATGTAAGCATTTTTCCGTGTCAGTAGATTCAAAAGGT
GATAACATCATTGCTATTGAATTGGGAACTATTCATTCTATAGAAAATCTTAAATTTGGTAGACCATTTT
TCCCTGATGCAGGTGAATCTATAAAAGAAATGCTTGGTGTCATTTATCAGGATCGCACATTATTAACTCC
AGCAATAAATGCTATAAATGCTTATGTTCCTGATATTCCATGGACTAGCACATTTGAAAACTATTTGTCA
TATGTAAGAGAAGTTGCTCTAGCTGTAGGAAGCGACAAATTTGTATTTGTATGGCAAGACATCATGGGCG
TTAACATGATGGACTATGATATGATGATAAATCAAGAACCATATCCAATGATTGTCGGTGAGCCATCTTT
AATAGGTCAATTCATCCAAGAATTAAAATATCCATTAGCATATGATTTCGTTTGGTTGACTAAATCGAAT
CCTCACAAACGTGACCCAATGAAAAACGCTACTATCTATGCGCATTCATTTTTAGATTCTTCAATACCAA
TGATTACTACAGGAAAGGGTGAAAACTCTATTGTGGTGTCAAGGTCAGGTGCTTATTCTGAAATGACTTA
TAGGAATGGATATGAAGAAGCTATTCGTCTTCAAACTATGGCACAATATGACGGCTATGCTAAATGTTCT
ACTATCGGTAATTTTAACTTGACTCCTGGTGTTAAAATTATTTTTAATGATAGTAAAAACCAATTTAAAA
CAGAATTTTACGTTGATGAAGTTATCCATGAATTATCCAATAATAATTCAGTAACTCATCTATATATGTT
CACTAATGCAACGAAACTGGAAACAATAGACCCAGTTAAGGTTAAAAATGAATTTAAATCTGATACTACC
ACTGAAGAAAGTAGTTCTTCCAATAAGCAATAAAGAAGTTTCTATTCCTAAAATGGGTCTTAAACATTAT
AACATTTTAAAAGATGTTAAAGGTCCTGATGAAAATTTAAAACTTCTCATTGATTCTATTTGTCCGAATT
TATCACCGGCAGAAGTTGATTTCGTTTCTATTCATTTATTGGAATTTAATGGAAAGATTAAATCTCGTAA
AGAAATAGATGGTTATACTTATGACATTAATGATGTTTATGTATGCCAAAGATTGGAATTTCAATACCAA
GGAAATACATTTTATTTTAGACCTCCTGGAAAATTTGAACAATTTTTAACGGTGAGCGATATGTTATCTA
AATGCTTACTTAGGGTCAACGATGAAGTTAAAGAAATTAATTTTCTTGAGATGCCAGCATTCGTTTTAAA
ATGGGCAAATGATATTTTTACAACTTTAGCAATTCCTGGCCCTAATGGTCCAATAACTGGAATTGGCAAT
ATTATTGGATTATTTGAATGAAAAAGCCACAAGAAATGCAAACGATGCGTAGAAAAGTTATTTCAGATAA
TAAACCAACACAGGAAGCGGCTAAATCCGCTTCTAATACTTTATCTGGGCTTAATGACATATCTACGAAA
TTGGATGATGCTCAAGCTGCTTCTGAATTAATAGCTCAAACTGTCGAAGAAAATCGAATGAATAATTG
GAGCAATTGACAATGTAGAAAGCGCAGTGAGTGATACATCTGCCGGTTCTGAGTTAATTGCTGAAACTGT
CGAAATTGGCAACAATATTAATAAAGAAATCGGTGAATCGCTCGGAAGCAAATTAGATAAATTAACAAGT
TTACTAGAGCAAAAAATCCAGACAGCTGGAATTCAACAGACTGGAACTAGTTTAGCTACGGTTGAAAGCG
CTATTCCTGTTAAAGTCGTTGAGGATGATACTGCTGAATCTGTGGGTCCTTTATTACCAGCTCCTGAAGC
AGTTAATAATGATCCTGACGCTGATTTTTTCCCTACCCCTCAGCCAGTTGAGCCAAAGCAAGAATCACCA
GAAGAAAACAGAAAAAGAAGCATTTAACTTAAAATTATCTCAAGCTTTAGATAAATTAACGAAGACTG
TTGATTTTGGATTTAAAAAATCCATTTCAATTACTGATAAAATATCAAGCATGCTATTTAAGTACACCGT
CAGTGCTGCTATTGAAGCTGCTAAAATGACTGCAATGATATTGGCTGTTGTTGTTGGAATAGACCTTTTG
ATGATTCACTTTAAATACTGGTCAGATAAATTTTCAAAAGCCTGGGATTTGTTTAGTACAGACTTTACCA
AATTCTCTAGCGAAACCGGAACTTGGGGTCCTTTATTACAGAGCATCTTTGATTCTATTGATAAAATTAA
ACAACTTTGGGAAGCGGGAGATTGGGGTGGATTGACAGTAGCTATTGTTGAAGGGCTTGGAAAGGTTCTT
TTTAATTTAGGTGAACTTATTCAATTAGGTATGGCTAAATTATCTGCAGCAATTCTTCGAGTCATTCCTG
GTATGAAGGATACTGCTGATGAAGTAGAAGGAAGAGCATTAGAAAATTTCCAAAATTCTACTGGAGCATC
```

-continued

```
TCTCAATAAAGAAGACCAAGAAAAAGTAGCAAATTATCAAGATAAACGAATGAATGGAGACCTTGGCCCA
ATAGCAGAAGGACTAGACAAAATCTCTAACTGGAAAACTCGTGCATCTAACTGGATTCGTGGTGTAGATA
ATAAAGAAGCGCTGACTACCGACGAAGAGCGTGCGGCAGAAGAAGAAAAATTAAAGCAACTTTCACCGGA
AGAAAGAAAAAATGCTTTAATGAAGGCTAATGAAGCTCGTGCTGCGATGATTCGTTTTGAAAAATATGCC
GATTCAGCTGATATGAGTAAAGACTCAACGGTTAAATCAGTTGAAGCTGCCTATGAAGACCTTAAAAAAC
GGATGGATGACCCGGATTTAAATAATTCACCGGCAGTTAAAAAAGAACTTGCTGCTAGATTTTCTAAAAT
TGATGCTACTTATCAAGAGCTCAAGAAAAATCAGCCTAATGCCAAACCTGAAACTTCTGCTAAATCACCA
GAAGCGAAACAAGTCCAGGTGATTGAAAAGAACAAAGCACAGCAAGCTCCTGTTCAACAAGCATCTCCTT
CGATCAATAATACTAATAATGTTATTAAGAAAAATACTGTCGTTCATAATATGACACCTGTAACGAGCAC
GACTGCTCCTGGTGTATTTGATGCGACTGGAGTTAATTAAGGAATAATATGGCAATTGTTAAAGAAATAA
CTGCTGATTTAATTAAAAAGTCCGGTGAGAAAATTTCAGCCGGACAGAGTACTAAATCAGAAGTAGGAAC
TAAAACATACACAGCCCAGTTTCCAACTGGGCGTGCTAGTGGTAATGACACTACAGAGGACTTCCAGGTA
ACAGATCTATATAAGAATGGATTATTATTTACTGCATACAATATGTCATCTAGGGATTCTGGAAGTCTTA
GATCGATGAGATCTAACTACTCTTCTTCATCTTCGAGTATTTTACGTACAGCTAGAAACACTATTAGTAG
TACAGTATCAAAACTATCAAATGGATTAATATCAAATAATAATTCAGGAACAATAAGTAAATCTCCTATC
GCAAACATTCTTTTACCGAGATCTAAATCTGATGTTGATACATCATCACATAGATTTAATGATGTTCAAG
AAAGCCTTATCAGTAGAGGCGGAGGTACTGCTACTGGTGTGCTAAGTAATATTGCTTCAACCGCAGTATT
TGGGGCACTGGAAAGTATAACACAAGGTATAATGGCTGATAATAATGAACAGATTTATACGACAGCCAGA
AGTATGTATGGTGGTGCTGAAAATAGAACTAAAGTGTTTACATGGGATTTGACTCCACGTTCAACAGAAG
ATTTAATGGCTATTATTAATATCTATCAATATTTTAACTATTTTTCTTATGGTGAAACGGGTAAATCTCA
ATATGCTGCTGAAATAAAGGGGTATTTAGATGATTGGTATCGTTCTACGTTAATTGAACCTTTATCTCCG
GAAGACGCAGCTAAAAATAAAACACTATTTGAGAAAATGACATCGAGTTTAACTAACGTTCTAGTAGTTT
CAAACCCGACAGTTTGGATGGTGAAAAACTTTGGCGCAACATCTAAGTTTGATGGAAAAACGGAAATATT
TGGTCCATGTCAAATACAGAGCATTAGATTTGATAAAACACCTAATGGTAACTTTAACGGATTAGCTATT
GCTCCAAACCTCCCTAGTACATTTACTCTCGAGATTACTATGAGAGAAATTATCACGTTAAACCGTGCTT
CTTTATATGCGGGGACTTTTTAATGTATTCTTTAGAGGAATTTAATAATCAAGCAATAAACGCAGATTTC
CAACGTAATAATATGTTTAGCTGCGTTTTTGCGACAACTCCATCAACTAAAAGCTCTTCGTTGATAAGTT
CAATTAGCAACTTTTCTTATAATAACTTGGGCCTAAATTCAGATTGGTTAGGATTAACTCAAGGTGATAT
TAATCAGGGAATTACCACGCTAATTACAGCTGGCACACAAAAACTGATAAGAAAATCAGGAGTCAGTAAA
TATCTTATTGGTGCCATGAGTCAACGTACAGTTCAAAGTTTATTAGGCTCATTTACAGTTGGTACATATT
TAATTGACTTCTTTAACATGGCATATAACTCATCTGGATTGATGATATACTCTGTAAAAATGCCAGAGAA
TAGATTATCCTATGAAACTGACTGGAACTATAATTCTCCTAATATTCGTATAACCGGAAGAGAATTAGAC
CCTTTGGTTATTTCATTTAGAATGGATTCAGAAGCTTGTAACTATCGTGCAATGCAAGACTGGGTTAACT
CCGTTCAAGACCCAGTAACTGGACTGCGTGCTTTGCCACAAGATGTCGAGGCAGATATTCAGGTTAATCT
TCATTCTCGCAATGGATTACCTCATACTGCGGTGATGTTCACGATGCATTCAATATCAGTGAGCGCTCCT
GAGTTATCATATGATGGAGATAACCAAATAACTACATTTGATGTTACTTTTGCGTACAGAGTGATGCAGG
CTGGAGCAGTTGATAGGCAACGTGCGCTTGAATGGCTTGAATCTGCTGCTATAAATGGTATTCAAAGCGT
TCTCGGAAATAGTGGAGGTGTTACTGGACTATCTAATTCGCTTTCACGACTTAGTAGATTAGGGGGAACT
GCAGGAAGCATTTCAAACATTAATACTATGACAGGAATTGTCAATTCGCAGAGTAAAATATTAGGAGCAA
TATAACAATGGGACCGAAAGGTCCATATTTTTATTTACGGAATGAAATGAAAGCAGCAACTGAAGCAAC
TAAACTGTCTTCAATATAAACTTCAATTTTTACAGGAGCTTCTGACTCAAATTTACCTGTTACTACACCC
```

-continued

```
TGAAAAATACTTTCAGTCTGTTCTGGCTTTGAAAAATTTTCAGAAGGAAAAATTCCGAACTTTTTATCTG

TTCCAAAAATTTTGATAAATTCATCGTAAACCGCTTCGTTAAAAGCATTATCAGCAGGAATAACGCCTTC

AACTACAAGTTCTTGACCTAAAAAGCGTAAAGAAGATTTCATTTTGTGTTCCTCATGTTATGTTAGTAAG

ACTACTATAACACAACACGAGGGACTTGTAAACTACATTTTGAACTTTTTAGTACGCGTAATAGGCATGC

GTCGATTTTATACTGTTTCATTGTTTGAAGAGCAGTATCAAAAACAGCATTAATGACACCAATTGGATTT

CCACCCAAGTTTTTAAGCTTAACTAATGATAGTTTCTCATTAACACCTATCATTACGATATGCATCATTT

TATCGCCTGGTTTAACGTTTTATTTGTATCACCGCCAGAGGTGTATGTACAAAATCTAAATCCAGGAAGT

ACACTTTCTTCACCGGCTTGAATAGCAAAAATTTGTGGTATTTTATGCTTAGGATTTAATGTAACAACCG

GCGCCGAAGCGCCGTCAAATAATTCTGTAATAAGTTCCATGATTTATCCTTGAACGAACTTGTAAGGCAT

GTTTGCAATATCTATGCAAGACGCAATAATTCCAAGAGATGATTCTACTTTCTGTTTAACATTTGATGAA

ACAAATGATGCAAAGTCAACTCTATCTTCTATATCACCTGTCATTGTAACCAATTCACCAGTTTCCATTA

AATGGTCTCCGTCATAGATTACCGATTCGGTGAGTTCTTCTGTGGTCATAACTTCAGCTTGAATAAGCTT

GTTGTTAGTTTTAACTGTTCCATCATTGTAAGATGCATCGGTTATTTTATTAACTTTGACCATTAATCCA

CGTGGCAAAATGACTTCCATTTCATTTGAAGGCGCTAAACTTCCACCGGGTAAAACAACATTGACCTTAT

CAGCCCCAGTAATAACCCATCCAATTCCAACTAAATTATCGCTAGAATTTACAAGTCCTTCATCAGTTTT

ATCAATAGAAACGCTTAAACGCTTTTCGTCTGGTAAAACACCTATAGATGAATCAGTCATCCAAGTACCA

AAAATATTTGGATATAATGATGTTGACACAAAGTTTCTAAAATAAAAAACTCGATTTTTTACCATTGCTT

CGTATATTGAAGGTAACATTCGTTGTGAACGATACAAAGTAATACCTTTTGGTAATCGTTCACCATTTTT

AAAGGCTGAATCTAAATTATCAATAGCTTTTTCTATGTCAGATGCTGTCAAAATACTTGTACGCTCATCT

GGATTATATAATCCCAAAAGAGCATTATTTATGTCTACATATCCTGAACCTACGTATTCACGAATTCCGC

GTTTTTGCGCTGGTGTGTATTTAGATGAATCTTTATTTTCGACTATAGGATGTAATGACCATCCAGCGGT

AAGAGCATATCCACGTAATTCTCTTCGAATAATCTTTGTTTTTATTGCATTCCAAGAATTTTGTACTAAC

TCATTTGCAGCATCTTGGTTTAAATGCGAATGTTTGTTAATATTTCTTTCAAACCAAGCACCCTTATATT

TTTCTAAAGTATCATCGACGATAGAAGCAATAGTTTCTAAGGTTTTTATTGAAGTAATAGATTCTTTTCG

TAATCTTTCTAAAGCTTTATTTTTTATTTCTGCGTTAATAATGGATTCTTTATCTTCAGGAATTATAGAA

GCTTCTCTGAATGCCATCCCAGCTGTAACACTGCTAAGAGCATTCTCTAGTGCAAATCCTGAAGTAGAAA

TTACCGTTAATTCATTAGAATCAGAAATTAAAGGCGCGTCCGCTGGTTTATTTAATTCGGCCGCTGAAGC

CTCAAATTTTTGAAACATTGGTGTTTCAAATCTAGAAGATTCCAATGACTGACTTTGCGCAATTGCTCTA

CGGGAAATTTTAACTTTAACGATTACAGCTTGGTCAGAACGTTTATCATTTTCTTGCGCAATAGATGCTG

CAATTGCCTCATTTTTAGTTACTTGAGCCCCAGTATCTTTATTGATATAAACATCACCGACCTTCGATTC

AACTTTAGTAAAGAGCTCGGTACTAATTTCCGGAACTCCTGGAATGTCTTCTAGTGATACATTTTTGCGA

TGTATAAGAATATATGCATACTTTTTATCGTAATCCCAGAGTTCCTTAAGAAGGACGTATCTACCACCTG

AACGACTACGGATAAGTCTATCAGCAATAACTTGAATTTGTCGAGCTTGGCCAGCAGTTTTAGACTTAAG

AATACGGAGCATACAGGCATCAATTTTATACTGGCGCATTGTTTGCATTGCAACAGTAAAAACTGAATTG

ATATAATTAATTGGGCTTGGACCAAGACCTTTTAATTTAGCAATTGAACCTTTAGCAGTTAATGTAAAAG

GAACAATATGCATCATTTTATCGCCCATCTTTAAATCACGATTAGTATCACCTCCAGATGTATAGGTACA

TAAACGAAAGCCTGGTTGTTCAATTGCATCATCAACATGAACTGAAAAAATTTGCGGTATTTTCTTCTTT

GGATATAAGTTTGTAATTGGAAGAGTAGTATCTTCGTCAAATAATTCTGTAATAAGTTCCATCATATCCT

CTCTAGTGTTTATTCTATTCTATTTATAAAATTAAAGGCCCGAAGGCCTTTAATAATCTATTGGTAAGAG

AGTACGATATATTTCAAACTTTGGACCTTTTTCATAAGCATCAAATGTTTCTGTGAATTTATTATAAGCA
```

-continued

```
TATGCATCTATAAATTCAATCATGATTTGTGATACAGAAGTAGAAACATCTCCACCTTCTTTTTGAGCCA
CGACAATTGTTTCTAAGTAAGCTTTCATAGACCAGTTACCTCATGAAAATCACCAAATACATCTTCGAAT
GTATTAGCTTTAGTTTTATCTTCACGTAAACGAATCGCAATCGGAAGAAATAATTTAACGTAATCAGTGC
GGCCATCAGATTTTAACCAACCGTTGCATTCGCACTCTAGAATTTTTCCAATATAATAATTTTGGTTTTC
CATAATGCGAGTACGGTCAAGTTCATGCGATTTTACACCGGCTTTATCTTTTAAGCCTGAACCAGCATTT
ACCTTAATTTTTCCACACTCTGACTCAAGAATAAATCCACCCGCTTTAGTAGGGTCTTTACGGTGAGGAT
AAATTCCTACAATTTTTAAATCAACATCAATTACTTCTTTAAATTTATAAAGATTTTTTGAACGAGCATT
TTCCCATAATCCATCGATATTTTTGAGAATAATACCTTCAAGACCTTGGTCAATATACTTTTTATAAATT
ACCTTAGCTTCATCTAGGTTATTTACTACCTGGTTTTCAATTAAAATTACTTTATCATATCCAGATGTCA
TTTGTTCTAGTTTAGAAAAACGTACATCATATTTCAAACGAAATGCAGGAAGACTGTATATTTCTACCAA
CGGGACATAATCCCAGACCTGAAACTTCATGCATTGTGCTTCTTTTTCAGAAATGGTTCCCTTTAAAGAT
TTATTGGCGATTCCATTAGAAGCAGTACGTGATTCAGCTACTTCGGCGAATTCTTTAGCTTTACTGTTTT
CAGGATAAGCATCAAAAAGAAAATCTAGGCCTTCTGGCTCCTTTTTAACTTGCTCATGGTATACCAATTC
GCCATCAATCAACACACCTTCTGGATGAATCTGGCGGGCTTCAGCGGTCATTTTAATTAACTCTTCCTTA
AGAAGATCTAATCCTAGATATTCATTACCAGCTCGTGATAAAAGACGAACATCATCTAATTCATCACCTC
TAACTTCAGCAAAACACCGAGCTCCATCAGCTTTTAACTGAGCAAAGGCTGGAAATTTGATATTCTTATT
AATGCCTTTTTCATCATAAGAACTTGCGAGCATTTGAGGTTGTTCAGGAATTAAACCTGGCCAAACTTTG
TTTGCAATAGATACTGAAGCACCACATTCAAGGTCTCGCATCATCACTCGACGCAAAACTTCAACATCAT
CTTTTTTACCATCGGTGATATATCCAGTTAATTCCTCAATTGCTGCATTTCCAGTCAATTTCCGAGTAGC
TAATGTGAATTCAATGAAGTCAAGCATATCGGTAAGAGTCAACATTCCAAAACTCTGGGTAGCAATACCA
GGTTTAGGCCATTTCTTGATATAATACTGTAACCCACGAGAATAAGTCAGACGATATACTCGTTTAAGCA
ATTCATTATCTTTATTCTTTTCAAGAATTGCTTGCTTCTGTTTAGTTGAACCAATAGATGCTATTTCGTT
CAGAATTTTAAGAATCATTGTTCATCCTTTAGAGTTTGGTTTACAGCTCTATTATAAATCAATTCATCAT
TAAGCTCAGTCAAAGACCTGTGGTACGTGGTTCTAACTTTATTTCCTTGCATCCAGTGCTTGATATAAAT
GAAACCTTGCTCTACACATTTTTTAAAAATTCGTTCGTCTTTTTGAGCTCGGAATTCTGGATTGCATCTA
AAAAATTGATTTACGTGACCGTAATCACGTGTAGTATTACCTTCATTTTCATAAATAGTGTGAACAACAA
ACATTAGAATGCTCCTTGGAAAATATTATCACCACAAGTAGGTCTATTATACAAATACTCTATACCGCCG
GGCTTAATATAGTTCCATGTCTGAAACGGATGCGTCTGATATGGATGATATGGATTATAAGGATTAAATC
CAGGAGTTCTCCAGGTAGTGTTCCAAGGAAAAGAATCGTTTTTAATCATCTTTTCAATTACATCTTTTAT
AGCTTTTTCACTATCAAAACTTTCTTTATTTTCCTTTGGTGAAAAAAGCTTATTCTCTACATCGTTCCAT
GTATAAACTCGCTGAGCAGTTTTTGGAATATTGTCACGCTCTCCTCGAGCCATCCAATACACAGGAACAC
GTAATATTTCACTCGCGTGATCGCAGTGGTGAGCGAGATCGTCAATATAACAAATTACGTTATATTTCTC
TTTTGCTTTTTGAACAACTCTTCTTTTGAAGAATCATGACTACACATCAGTACTTCTGAGAAAGCACCA
GGAAAAAGAGCATTCAAATTAAATTGACGATTTAATAGAGCGTCAATAGAATCACCCAATGCTGTAACAG
CAACAAAATTATAATCTTCTTTTAATTTGTTAATTACACACAGAGCATCTTTATATGGAGACAAGTAACG
AATAAAATCCGAACGATTGTATTTTTCAATTAACTTGACGCCAAGTTCTTCATCACAGTTAAAGAGTTTA
CCAGGAGAAATAAATTTCTCATCTTGGATCATTTTTAAAATATGTTCTAACGGAAGATTATATTTCTGAG
CAAAATAAGGAAGGCCTGATTGCCAGCTTAAACATACTCCATCAATATCAGTTAAAATAGTAGGCTTCAT
AGAGAGTCTCTTAATAGGTTTAACACATCAATAAATTCAGCTTCGGTTAGTATTGTATCATCTTTTGTTA
GACCACTAGCAATGCTGTGCTTCAAAACTTTTCCTTTCGAGGCTTGTAATGCATCACGAAAGCCCTTGTT
TTGAATCGCTGCTTCAAAATATGCATTTGTGTATAATTCTTTCCACGCCGGGGAGTATCTTGAAAACGGA
```

-continued

```
ACTCCAAGCCAAAAGAGGGTCCCACGGTCCTGAGCTCTAGCATAAGACCTTCCAGCTTGTTGGGCGGCAA

GCCCGGATAACCCAAATATACGACGTTGTTGTTCAACATTTTTCACCTTACACCCTTGGAGGAATCCTTC

AAGACCTCCAAATTGAATACCATCCATAACGAAAGGCCATTGGGCGAAATTACTTAATGCACATGATGGC

CACCTAAAATTGCTTCTAATCTCTAACTCAGACATTTTCAATGCTTATAATTTCAACATCAGCCCAATGA

CCATAGCAAGGAAGACGAAATTCAACTGGCCAGTTAGGGTCCCTTTCTAATATAATAGACTCAACTTGTG

GTTCTTCGTGTTCATCAGTATACGGATTTTTATCTGTTACTTTATATGTGACCTTAATGTACTGAATTCC

AAAAATCTTATTAATTATATTCATACTAATTCCTTTAATCCGTAGATAGGAGATAATTCATCACCCATAC

GAAGGTCTTCATTTCCATCTACCCAGGAAACAATATAAGCCTCTTTTATTTGAATACCACTCCATTTAAA

TGGAGGTAGAACCTTAGAAATTAATCCAGGTATACCAACTCCCTTTAATTCAACAGTTTGACCTAAAAG

AATTTCATTAGAACCTCATCTGAAAACCGTGCGATTTAACATTACCGCCGCCAATATCAGAAATGTTAAT

TTCACGCGCAATTGAAGGGTCAATGTCAATTTCACGATTGAGTTTAGTGATAGCTAAAGTATCACGCCCA

TTTACAGTACGGAACTCTAAAGGACAAACCACATCAACGTAGTTTTTAATCGATTCGCTAGTAAGTTGCA

AATGTGCAGGAAGGTCTTTAGGTGCCTTTGAGAAAACCACTTCACAGAAATTTTTGCGGGTATCAAAATA

AGTAGTCATAAACATAATATTTTCCTCAGTAAGGGGCTGAAGCCCCTCATTTTATTTTAAATATCAAATT

CATTAAGAACTACATCAAAGATTGCTTCAAGATGCTCAGGTTTAGCTCTGTTACTCAGAATATGACGAAT

CCAAGTTTTAACTAAGAGTTTACGATTAGCACCATTCCAGCAAGGATGAGTCCCTAAATCGCGTTGGCGG

AAATCATCATCCAGAGCGATTTTGAAGTTGGAACCTTTCATCGTGATTGAAACCGTGATACCGTTTTCAA

ATCGCATATAAACGTAGTTAGGAGTCATATACTGTTCAATTTCGCATACTGATCCATTTTGATGTTTCCA

GAGGCAAATAGTATCAATAGAACCTGCAATACCATTAGAAACATATTTACGTTCAAAGTTAATGTAGTTC

ATTTTTATTCTCCGAGATGTTTAATTGCGGTACAGGTATATAATATCATATCCTGTACCAAAGTAAACAA

TTATTTTACTACTTTCCAATGCTGCATGTCAAGTTTACCAACTTTTTTCATCTTCTCAATTAAGCGTTCT

GCACGTTGGCGAGCTGTAACATAATGCCATTCGCCTAATTCATTTTGTTCAATTTTTCCAACGATTACTG

TATTCAATTCATAAATCCAACCAGTAAAGAAATTATGAACTTGAATTGTAAAGGTGAAATCTGTTCCCAT

ACCTTCTGTTGTTTCTACTTCAATAATATCACCTTCAACTGCCATTAAGAACCACATAGTTTCATCATAT

TTACCATTGAAGCATTTAGTTTTAACTGCAGCGTTCAGATTAATCGTTTTCATTTTATTCTCCTTTGTTT

GTGTAAGATAATACTATCACAAAGGAACTATACTGTAAACAACTTTGTGCAATCTTTGGAAAATAAAAA

GGACTCCCGAAGGAGTCCTCAACTTATGCTTTCTGCTTACCAAAACGAGAAGCATCATCTCGAAGAACCG

CACGTGCTCGGCGCATGATCTTCTCAACAGTTTGATTGATACGAGAGTTCGACCCACGCTTGTAGCCAGC

GCGTTTAGAATCACCAACTTTCTTTTCAACTGCTTTCTTTGCTTTAGCTTGTTTTGCCATTATAAATTCT

CTTTTAAATGAAAATGCAGGACTTATTGGCATTGCCTGCGCAAGCCCTCAAGGGGAACATAGGTTTTTGG

ATATTTAACGACCAGGATAACCATAAACCCGTCATCATTCACATTCAAGAGGTACACCGTAAAACTGTCG

GGGTCTTAAAACTATAATGATTCGCAAATCATTAATCAGACAGTTCGACGGCTCCTCGATTTAGCTCACA

CTAAGGCAGTGAATCTCCAATAAATTACTTCAGTGTTACCACAAAGTGACGAACTGCTTTTCGTGCAGCA

GAAGCCAGAGGCTTAGCATATTTAAGTTCATCTTTTTCCTGAAGCTCAGCAGCTAATGCAGTTTGAGCAG

GATTCAGATGTTTGAAATAACGCAGGATTTCAAGAGCTTCGGCTTCAACATCAATAGATGCGCCATAGTT

TTCGTGACCATTATTCCATGCGTTTCGTTGCAGTTCAAGAGCGTGTTGTAATTGTTTAATCATTTAAAAA

TTCTCGTTAGAGATTAAAACTCGGTAGTCACGTTCTTCTGAATTTCATCTTCTTTCGACAGATCTCTCAG

TTGTAGACTACCACATAGAATTGTTCGGTTAACTTATTATTCCGACACCCAATTCATATTATTATTTATA

TCACTTATAAAGACACGGAATAGCTTTATAGTGACAGGTAACGAATTTTGTTTAATTTCTTTTGGCTGC

TTAAGACCCAGAGCTACAAAAGGATGCGGAACATTTCGAATTTGACCAACTGGAAGAGAAGTCAAATCAC
```

-continued

```
CAACTTCGCAGAAACCTTCAGGAACATCAGGACCGACAGAGTGAACTACACAGTTCAGGAACTTCACC

TTGAACACGTTTACCGATAATAAGTCCTGATTCTGTAACTTCTTCATCACCGGCTTGTGCAGGTTCAGAA

ACTAAAATAACATATTCACCGACAGCACGAATTGGTAGCTGTTGTACTTCAGACATCGTTTTTCCTTTTT

GTTAACAGATGAATTAATAATAACAAATAGTTCTTAAAGCATTTATTTACCAATAAATTGAAGCAAATGC

TCAACTTTCATACCATTAACGGAAATCAATTTGTCAATAGAAAAACCTCGCCACGCACCAAGCTCAACAT

CAAATACTGGAATCATGTCAGTAGATTCTTTCCGAGTAGATTCAGTCAATTTGCCAGTTTGCATGGTTGG

CATAAAGTCTGCATCACGAGTACCTTTCATAGTACGAATAGTACCATCAGACTTTTCAAAAACTACGTTT

GAAACACCCATGGACAATTTAGTTTTCAAAATTTCACGAATTGCTACTTTCTGCTCAGTTGTCAGTTTCA

TTTATTTACCTATTACAGTTTTAATATGAGTTGTTCCACGTTCTTTAAGGGTGGAAAGTAATTTTTGGCA

TTTTTCTAAATCAGATTTCCAACTATATGGTCTATCAATACAAACCCAATTTGTCTTATAATACTGTTTC

CATTTAGAGAAAAAATATTTCTTATACTCTACAGCAAATGAGATGTTCTCGTTAGAATAAGAACTAATTG

CTGTGAGTTTTACCAAACGAAATTTCATTATTCACCACAGAATTCGTTGATATTTTCCCAGTTTAACTTA

TTCAAGTTTTTCTTAGGAACATTAAACACTTCAATACCTGCATTTCGCAGAATATCATCCCAACCGGGTT

TATTTTTGTCGTATGTTTCACAATAAACCAGCTTTTTAATACCAGATTGAGCTATCGCTTTTGCGCAATC

TGGACAAGGAGAAAGTGTTACATACATAGTAGCACCTTCAATAGAAGAACCATTTCGTGCAGCAAACAAA

ATTGCATTTAGTTCAGCATGAATTTCATTTTTAGATGACCATTCCGAGTGAGCACTACGATGTTCTTTCG

CCAAAACAAAACGATCAGTTGAACCAAATGATACGCATTCAGGCTTATGACCTTGAATGATAGCATGTTT

AGGCTTATTCAACAACCATCCTTGCTCAGCAGCATAATCACAACAGTTCACACCCCCTGCGGGTGAACCA

TTATACCCAGTAGAAATAATACGTCCATTCTTTTCAATTACTGCTCCTACCTTCCAGGAGCAACATTTTG

ATTCCTGCGATACTAAATATGCAATTTGAAGTACTGTACTCGCTTTCATTTCATAATCACCAGATAAGCA

GATTTAGCAGTTTCAACACGATAAATTTCGTGACGAAGTTTAGTTATACTTTTAATAACAGAACTAATTA

TATTCTGCCCATCTTTAAAGCGGTTTTTCTTATCAATAAAAACTGCGCCAGTCATCTTTTTGTGAAGCTC

AACTGGATACTTCGTCACAATAATAGCATCATACACAGAAGGATGAATACTATTCACCAGAGTATCATTC

ATTAAAGTTATTCTAATGAACTGTGCTGTTTCAGAATCAAGCGCTCTATGATCGCCAGTATCATTTTCAA

GACAATTATCAATTATATCAGTTAAATTCATCATAGTACGCCATACACCCTTTGTGCTTCAACTAATCCA

TCAAAATCCAGTTTAAGATGCGATATTTGATCGCCATCACCTGGATTCACAATTACTAATACTGAACGAG

GAGTTTCGGTAATAACACGAACCGATGTTTCAGGAAATCGTTCAGAAACCTTATTTACTAATTCCTGCGC

AAATAGTTTAACTTTTTCTTGGAATTCCTTTAACAGTAATCGGTTTTTCACTTAGCAACATTTTGTTTTC

CTCATTTGTTTTGGTAGAGCTATAATATCACAACTCTACCGTAAAGTAAACCATTAAATCGCTTTGAATT

CCGCAGTTTGAGATTCAAAGCGAATATCGCCTTTGATAACAAGCTCAGCATCAAGACCAAATACGACAAT

GATATGCGCGGAACCTGGATACAGTGTAATGGCAATAGAATCCACCTGGTCTGGAAGCAAAGTGTTCAAT

ACATGAGTCACTTGAGCATGGATTCGAAGCTCAGCTGCGTTATCAAGTTTTTCAAACATATTATTAGCGA

TAATTTGGCTAAACACTACTTCTACGATTTTAGAGTAAGTCGGAAACATATTTACCTCACATAATTTTCT

TCAAGCCAATCAATAACATCCAACGCATTATCAAAAGTTGAACCATCTACTCTGTCTTCTGTTTCATAAT

CAAGAACATCTAGGCCTACTCTTCCGTCAACAATAGGCCATAGACAAAATAGATATTTCTTTTCTTTTTC

AATTTTATCACAAAGACGATAAATCTTTTCTAGGTTATTCATAAGTTTTCCATGGTAAAGGCAGTTTAGT

TTTCTTTACTACTAGTTCAACATCGGGATTCTTTTCTCTTAATTTAAGACATTCCTCCCATGCTCTATTT

TCACTAGTAAATACACAAAATTGCCCATTACTAGTACCAACTAAACCGCTATTTACAATAACAATAGCCC

AAGTTTCATGGTGCCAAGCCATTAAAAATCTCCCGAAGCGACTTGCCAGCATTCAACACCGATACGACGC

CACATTTCAACTACTTGAGTTCGGTCATCAATAGCTAATTTCACGTCAAAATGCGGTGCAATGTGTTTCC

AGAAAATTTCTTCTTTAACTACATCGTCTTTACGGGTATCGCCTTGTTCGCGCTGACATTGCATAACTAA
```

-continued

```
TGGAACGCCAGCAATGTCCTCAACCCATTTACGGGTCATACGATAATATTTCGTTGGGTCTTCTTTAGTT
CCACTTTCACGACCTGAAACGACTACGATTTGATAACCCATAAGAGCATACATCTTAGACAGTTCAACAA
CCATAGGATTGATAACATCGGTATCGCATTTTTCAAGGTCATAAGGACCACGACCATTCATTTTAGCTAG
TGTACCATCAACATCAAAAATAACTGCTTTTGGTTTACCAGGAGTCCCATTATATACTGGAAGACCGAGA
TACTCTCGCATGCTTTTATACATTGAACGTAAAACATCAATTGGTACTGCTTTAGTTCCGCGTTTTGAGT
TACGTTTAACCAATTCAGTCCAAGGAACATCAAACACTTTATGTTCAACTTTCCAGCCGTATTCTTTGGC
AAAAGTTTCCCATGCTAGGCGACGTTCAGGATTCAGGTTAGTATCTGAAATGATTACTCCCTTAACAGAA
TCGCCACCGTACAGAATACTTTTAGCTGTATCAAACTGCATACCAGTTACGATACCTTCTTTCTTTTTGG
TATACTTGTACTCATCGCGTTCTTCATGCGCCATAATAGATTGGCGATAGTCATCACGATTGATATTATA
AAACCCGGGATTCTTAGCAATAAATTCACGAGCCCAAGTACTCTTACCAGAACCAGGACAGCCAATAGTC
AAAATAATCTTTTTCATTTATTTTTCTCAACTAATGATTGAATATAATCATGTAGGTCTTTAGATGCTT
TACCCCACTTATTTTGATATTCATTTTTGAGATTAGCACGTGATTGAGCTAATAAAACATCATTAGTTGG
AGGTAAAGATTCTAACCGCTGAATCTGGCGTCCATAAATCATTGCAGCCATCTCGGATTCATAAATCAAT
CCTTTGAGATGTTCAAATTGATGCCATGAAATCATTTACATTTATCCTCTTTTAGCTCTTGACGATAATA
ACATATCATAGTTTTCTGGTCATGTACATATCGTTTTACATCATTAAGCCAAATACGAAATTCCTGAGAA
TCTTCAAATGGCATACCGACCCAGGCTTTACCATCAATAACTTTAACTTGCCAAGATAGTTTAGCTTCAT
CATATGACTTTATTTGCACAGGCCAATTAGGATGAACTGTTTCTTTCTTTACTTCTAGAGGCTTTGTCGA
ACAACCAACTAGAAGACCAATAGATAATATTACTGCTGATAGTTTAATCATTTAGAAAGGTCCTGGATGT
CTTCTGCGAACTTGTTGAAGGAGTTGTTGATTTGTTTTTCAACCAATCCTGGCTTATGAGCCACCACATC
CGCCTTCTTTGCATCTTTGCGCAGTTTTTCATTTTCACGCTCAATAGCAGCAATTGCCTCACGATTTTTA
TTATTCATCGCATCAATATAATTATACTGAATTCGCAAATTATTTAATGCTAAGGCGTTTTCATTGGCCG
TTTTTGTAATTTCAGTAACTGATGTTTCTAATCTTTCTACCTTATGTTTAAAATAATAGATGTTCCGCC
AAATGCTATTACAAGTAATAGCAATCCAGCTGTAAAATTACTTACATGCATAAAGTTTTAATAACCTCTA
CAATATCGTCTTGAGAAAGACCGTTAATTAAAATATGATGTTCAGCTGGAGATTTAGAAATTTTAAAGCA
TGCCTCAACATCTTCTGCCATATCCGATGCACTACGATTTGGATTACTAATACCAAGGCGATGTTTTCCC
GTCAAAGGATTAACGATGATATAGCATTTGCAGCTATTGATATGAACATTGGGTTGAGTCTGATTAATGA
ACACTTCACAATCATACTTAGCAAGTTGATTTTCTAAAAAGACTTTCATCTCTTCAACCGCATCAGGAAG
CATATCACGGGCTTGCTCAAGACGACGATTTCGATATTCTTTAATGGTCGTTTTCCGCTTGACTTGCTTA
GCTAAATCTTTCTTAAGACCAGTGATATATCCAACTCGACGATTTCCTTTGAATACAGAAATCCCATCTG
TAGTATCACCGTATGCTTCAACGACCATTTCAGTAGTAATAAGTTGTAAATCCATCATAAAGTCCTCATG
TTATGTCAGTAAGACTACTATAACACAACACGAGGGACTTGTAAACAACTTAGTATCCTTCTGGGATAAA
TTTTTTATAATTTTTCAAAAAATTCTGTTCGATTTCACACATGACCTTTTCTTGACTATCGTACCCCTGG
TATAAGCTCATGATGATACCGAACAGGTGATCCATTCCAGCACCTTTAGCAACACCTTGTGCTTCCATTG
CATAAGTCTTTCTATCCTTACCGCAATGCTTATTATGACAGTCAAGAACTAAAAACAGAGCTCGGTCTAA
GTACTTCAGATAAGTCGTTTCAAATGCTTCAATTTTTCTGTATGAATATTCATCGTCAGCATACATTGCT
TTAAGATCATCTGATGCACCATCAATAATAGTCTTAAACAATTTTTCTGGATTATCTAATGAACTTTTTG
TACTATGAAGAGACACGTACCAGTCAGACTTAATTTTAAAATGAGAACCATCTTTCATCACAGCAACATA
GCCTTCGATGTTTTCTGCATTTTTAGCTTCTTCTATCCATTTAGGGCTATCGATTTCGTATCGTTCAACT
AGATACGGACGAAGAGTAGCATCTTTATAAATATCATCGTATGAAATGTATTCACCCGTTTCGTTTTCAC
GAACATTCAGTAAAATAATTTTCATCTCTTGATAAGCAAGAACGATTCTATTCGTCGGGGCAACGAATTC
```

-continued
```
GAAGTTAGCAGTAAATCCATCTTCAGCTAATTCTTTAAGTCTATCACGCAACCGATGGTGATTAATATTC
ATCAAAATTCCATTAGCCATTAAAGCCTGCTCAGATTTGATTGAACCCTTTGATTTGAACAGAATTTCAT
CACCGTCTAAATAAGTTGATACCAAAGACCCGTCTTCTTTTGTTAGAATATAATCAACATCGTTTAAATC
GATATTCATCGTGAACGGATTTTCATTCAAGTTAAAAAACTTTTCCATAGGACGAGAAGCAATTCTTACT
GGTTTTTCTCCATCCATTTCAAACATAATTCCACGACATTCTAGTGCATCTGGAAGTAACCAATCAGAAT
AAGATGCATAATTATATGAGAAAATTCTGTAAGTTCTTCCAGATGCACTTACATCATCTGAGTAAAAAAA
CTTACGCTGCGAATCCTTACATAGTTCCATTAAATTGTTAAAAAGTTCTTGCATTGTGTATCCTCTTTTG
TGTTTTGAATATAGTACCACACTCCATGTGGAAGCATCATTTTTTCTTGTGTTGAATATTCCAAGGCGGG
TTAAACAGTTTAATGAATAGAGGCTCCTCTAAGTCAATCGTTGCGATTGTCATTGTACCTAACTCATTTG
TCATAGAAAGATTAAAACATTGGCGGGCGTAAAATTCAACTTTGCTTCCTTCCTTTAGCGCAGAATGAAT
TAATGCAGATTTAGTAGAATCAGACGTTTTGTCTTTGCGGTTAATAGCAGTTCTATAATAGTTTATTCTT
TTACGTAAATTTTTAGTTTTTCCAATATAAACAAGCTCATCATTTATAGCAATAGCATAAATTACGTTAT
ACTTGTTTGGAATAGATAATTGTTTTATACTTCCATTGTCGTCTAATTCTAGCTCAGTATATTTAATAAA
TGAATATTCTGTTGCAATTTCTTTCATAATAAAATGGGCCTTGCGGCCCACTCCTTAAAAGTATTTTTTA
AAACTCATCATAACTTTATCATCAACATCATTATCAATCTGTGCAACAAGGTAAGATGACAGTTCTACTT
CTTGCGGCGCGGATTGAACATTATCAGAATTAAGATATTCACGAATCCAAGGATATGGATGTTTAACCGG
AGCATCGGTAATTGGGCATGGAAGACCGCACTGTTTCATACGAGATACAGTTAAGTAATCAATAAAGCTC
CACATGCTATTTGTATTTAATCCAGGAACATCACCATCTTTAAATAAATGAACTGCCCAGTCTTTTCCT
GGCGGTTAACTTCCATGAAAATATCAACTGCTTCTTGTTCACACTCTTGGGCAATTTTAACCCATTCATC
ACCATCAGTACCGGATTGAAGTTGACGAATAATATATTGGGTGCCTTTAAGGTGAAGCTGTTCATCACGT
GCAATGAACTTCATAATCTTGGCATTACCTTCCATGATTTCCATGTTCTTATGGAAGTTAAAGGTACCGT
ATGTTCGATTGAGCTCGCTAATTCTCAACCCGTTCTCTTATGAACTGCTGCATGTTACCATGCAGTCCAG
ACTATATCACAATCCCGGAGGGATTCTCCCCATTTCGAGTCGCTTGACCCTACGTCCGAAGACTAGTCGT
TGAACCTTGTTTTGCAATTGTCGCCGTGCCATCGTTTATATGTTGATGGTGATAAATCTTTCTTATCACA
ATATGGACAATTCAATTGAATTCTATTTGGATTTAATTTACATCTGTCATTATGTTTTAGATAAAATCCA
GGACCTTTACCAATGTGACCACAGAAATCACATGTGATTTCTTTTTGTGCAGGATGGGTCCCGTTCTTAA
CCATTTCTAATGTTTTTGCTGATGTTCTTTTCTTATGTTCTTCCATCAGAATCTTTAGGTATAGGTCCGT
TAGCATCTATCCAAATTTTTCTATAGTTCAATTGTGCATCCTCTTAAAAGTATAATCATATTTATATTAT
ACTAATTAAAGGTGCAAGCAAAACCTTGGCTGCTAGTTTTCCATAAAGGACTTTCCAGCAATTAAAGGAG
TTTTCGATAAACGTTACCGTTTAAAGGCGCATTTTACGCAAAAGATACATAAAAACGAATAGCTTCTAAG
GCATTAATAACGTGCAAACAGAGGTAAAGAGATTTCATCAGATCTCGTTTAGCTCTTTGCTCAACGTCTT
TATCAGCTAGAATTAGACCTTGGTCTTTATAATATTCAACCATGTCTTTAGCATTTTCCCATTCACGGGT
TTTAACCAAGACATCATCGTAATATCGCCCAATGGACTCAGCACGTTTCATAATAGCTTCATCTAATACA
ATCTCATCAAACACCTTCGATGGATCAGTATAAAGATTTCGCATGATATGAGTATATGAACGACTGTGAA
TAGTTTCACTAAAAGTCCATGTAGCAACCCATGTATCAAGGCTTGGGTCTGAAATTAATGACATAAGTAC
AGCAGATGGCGCACGACCCTGAATGCTATCCAAAAGTGATTGATACTTCAGGTTGTTAGTAAAAATATTT
TGCTGATACTGAGGAAGCTTATTAAATTGCGCAGCATCCATCATTAAGTTTACTTCTTCAGGACGCCAAA
AAAAACTGATCTGCCGCTCAATGAGTTCTTCAAATACTCGATGTCGTTGAATATCATATCGAGCTAAACC
TAATCCAGAACCAAAGAACATCGGTTCATTCAAAACATCAACTGGATTTGTATTAAAAACTGTACTCATT
TAGAATCCTTAAATTTACATTTATCATAATGCCATCTTAAAGCATTGCCTTTATTAACTTTCTTACCACA
GTGCGGGCAAGGTGGATACTCTGCTCCTTGTTTAGTTCTCAAAGAAATCAAATCACGGGTTTCTTTAGTA
```

```
TGAGGAACATCTCTTGTCGGAGAAATTGTACCATACATCGGATTAAGCACGCCGACTTTAGCAGCAGCTA

TATTCTTTTTAGCTTCTTCAGTTTTAGGCTTTCTCATCTTTTTCTTAGGTTTCTTCGCTTTTAGCCCTTC

CTTTGGTTGCCGCCGATATTTTGTGTTTGGTTTCTTCTGTTAAACGCAGACCTGTTTTCGCTTTTTGACA

TTTTCAGTCTCGTTTCTTCAGAAATGACCGTACCTTTGCGAAATTGCGAATTTAACTTCTTTGCATGGGC

ATATATTTTAGAATGAACTTTATAATGACGTTTCTTAGTTCCTTTCATATTGCACATCATGAAAAATGCG

AATATAACAGATTTTACCGGATAAATCTTTGATAAAATAGCATGCGCTATAAAATGCTCTCTAGCTGTTA

ATTCAACTAAATTTTCTTTATCATCAGAACCTCCCATGCATCTAGGGATTATATGATGTGTCTCTTTATA

TTCGGATAAAGGTTCCCGAGCCTGAGCTCGGGAAATTAGGTCGTTATAGATTTTTTGATAATTCATTACA

ATTTACACGCTGCACAATCATCGGCTTTAGGAGTTTCTATTTCATAATCATCAGTACCAGAACCATCACG

GGTATTATGATAATAGAAATTTTTAATGCCATAATACCATCCGTATAGCATGTCATCAATCATTATTGAC

ATTGGAACCTTTCCTTTTGGAAAAATCTGCGGGTCATAATATGTATTCGCTGAAGCTGATTGACATACCC

ATTTCAGCATAATAGCTACCTGCGTAAGATAAGGTTTATTACCTTTCTTAGCTAATTTCCATGTATAATC

ATAGAGGTCTATGTTATGCTCAATATTGGGCACGACTTGATTAAAGGAACCCTCTTTTGATTCTTTAACA

CTTACCGGTCCACGTGGAGGCTCGTAGCCGTTTGTACTGTTAGAAACTTGGGAAGATGACTCACATGGCA

TAAGTGCTGATAATGTGCTATTACGGATGCCAAATAGCTTAAGGTCTTCCCGCAGCGCCGACCAGTCACA

AACGTATTTTGGAGCTGCGATTTGGTCAATCTTTTTATTGTACCAGTCGATAGGTAATTCGCCTCGAGAC

CAACGAGTGTCTGAATAATATTCCGAAGGTCCTTTTTCTTTGGCGAGCTTAATGGATGCTTTAATGAGTC

CATACTGTAATCTCTCAAATAGTTCATGTGTTAAATCGTTAGCATCTTCATAAGAAGCAAAGTTACTTGC

CAGCCAAGCTGCATAGTTGGTAACACCTACACCGAGGTTACGACGCTTTTTAGCTTTTTCTGCTTCAGGA

ACCGGATATCCTTGGTAATCCAACAGATTATCAAGAGCACGAACTTGAACTTCTGCCAATTCATTAATTT

TATCTTGGTCTTGCCAGTCAAAATTATCTAATACGAATGCAGAGAGAGTACACAATCCAATTTCAGCATC

AGGGCTATTCACATCATTTGTTGGAATAGCAATTTCACAGCACAAGTTACTCTGACGAATAGGTGCCTTT

TCACGAATAAACGGAGTATAGTTATTCGTATTATCAATGAACTGCACATAAATCCTTGCTGTTCCTGAAC

GTTCAGTCATGAGCAATTCAAATAGTTCACGGGCTTTAATACGCTTTTTACGAATATTAGGGTCTTTTTC

TGCTGCTTCGTATAATTCACGGAAACGGTCTTGGTCTTTAAAATAAGAATAATAAAGCTCGCCACCCATT

TCATGCGGACTGAACAAAGTAATGTAATCGTTTTTTCCAAAACGTTCCATCATCAAATCATTCAGTTGAA

CACCATAATCCATATGACGAATGCGGTTTTCTTCTACGCCTTTGTTATTTTTCAAAACGAGAAGATTTTC

AACTTCCAAATGCCAAATAGGATAATAAGCAGTAGCAGCGCCGCCACGAATTCCACCCTGTGAACATGAT

TTAACTGCAGTCTGAAAATGTTTCCAAAAAGGAATAACACCAGTATGGCGTACTTCACCCATGCCAATCT

TAGAACCTTCGGCACGAATCATACCAACGTTAATACCAATTCCAGCGCGTTTAGAGATATATTCAACAAT

TGAAGCAGAAGCCTTATTGATAGACTTCAATGAATCTCCTGCCTCAATAACAACACATGAACTAAACTGT

CGAGTCGGAGTACGACAACCAGCCATAATAGGAGTTGGCAATGAAATCTGTCGAGTTGATACTGCTTCAT

AAAAACGGATAACATGTTTTAATCTATCAACAGGTTCATCTTGATGCAGTGCCATTCCAATAGTCATAAA

TGCAAACTGTGGAGTTTCATAAATTTGACCAGTGGTTTTATCTTTAACTAGATATTTTCTTTTAATTGC

ATTGCCCCGGAATAAGTAAATTCCATATCCCGTTCGTGCTTAATTTTTGATTCTAAAAATGTAATTTCTT

CTGCTGAATATTTTGACAATAATTCAGGGTCGTATTTACCTGCATTTACACAATAAGAAATATGGTCAAT

AAATGAACGTGGTTCATACTGCCCATAAACATGCTTACGAAGAGCAAACATTAAACAGCGTGCAGCTACA

TATTGATAATCAGGTTCTTCAACCGAAATAGAATTCGCAGCAGCCTTAATGACAATAGTCTGAATATCAT

CAGTTGTCATTCCATCACGGAGATAAGATTTAATATTTTCATATAATTCATAAGGATCTACTGATGTTCC

TTCAGCTGCCCAAGATAAAACTTTAATAATTTTTTGTGGGTCAAAGCTCTGAGAAACACCACTACTTTTG
```

-continued

```
ATAACATTAATTAATTGCATAAGTCCTCAACTTGAAAATCGTCTTTAAACAATCGGTTAACTATATGAGC

TATTATATCACCATGACACGGCTTTGGTTTACATGTGCATCCTAGCCTCATTCCACGTAAAGGCTCTAAA

TGTGCTTTAGTTATTTCTCCGGATTTAATTCGACGTATAAAATCTTTTTTGAATAATTCAATGGCAGCCT

CCCGGCTGCCAGCATCTTTACCGACGTAATTTCCCCAAAATGTACCGCGGTGAATATTAACATCAAAGTC

GGATTTATATTTATTCACTACCCGGCATAGACGGCCCACGCTGGAATAATTCGTCATATTGTTTTTCCGT

TAAAACAGTAATATCGTAGTAACAGTCAGAAGAAGTTTTAACTGTGGAAATTTTATTATCAAATACTCA

CGAGTCATTTTATGAGTATAGTATTTTTTACCATAAATGGTAATAGGCTGTTCTGGTCCTGGAACTTCTA

ACTCGCTTGGGTTAGGAAGTGTAAAAAGAACTACACCAGAAGTATCTTTAAATCGTAAAATCATATATCC

TCGCAATAATAAAATTACACCGCCATCTTTCCTTTAATAGGAGGGTGTGATACATAGTTGTTAAGAACGA

AATCTTTAGGCCTAAGTTTAAGAACATATTTTAATTGTTCTTTAGTAGAAAGATATCGGAATTTATAAGG

TAGACCACTTATTACCAGCTCACAAAGCTCTTTAGGTTCACGCCTCAAAATTTCTTTACATTGTTCTACG

TGATTCATATAGATATGAGTATTACCACCAGAAAATATCAAATCCCCTGGAATAAGATTACACATCTTAG

CTACAATATGAACTAACGTAGCATATGACGCAATATTAAACGGTAGCATTATGTTCAGATAAGGTCGTTA

ATCTTACCCCGGAATTATATCCAGCTGCATGTCACCATGCAGAGCAGACTATATCTCCAACTTGTTAAAG

CAAGTTGTCTATCGTTTCGAGTCACTTGACCCTACTCCCCAAAGGGATAGTCGTTAGGCATTTATGTAGA

ACCAATTCCATTTATCAGATTTTACACGATAAGTAACTAATCCAGACGAAATTTTAAAATGTCTAGCTGC

ATCTGCTGCACAATCAAAAATAACCCCATCACATGAAATCTTTTTAATATTACTAGGCTTTTTACCTTTC

ATCTTTTCTGATATTTTAGATTTAGTTATGTCTGAATGCTTATGATTAAAGAATGAATTATTTTCACCTG

AACGATTTCTGCATTTACTACAAGTATAAGCAGAAGTTTGTATGCGAACACCGCACTTACAAAACTTATG

GGTTTCTGGATTCCAACGCCCGTTTTTACTTCCGGGTTTACTGTAAAGAGCTTTCCGACCATCAGGTCCA

AGTTTAAGCATCTTAGCTTTAACAGTTTCAGAACGTTTCTTAATAATTTCTTCTTTTAATGGATGCGTAG

AACATGTATCACCAAACGTTGCATCAGCAATATTGTATCCATTAATTTTAGAATTAAGCTCTTTAATCCA

AAAATTTTCTCGTTCAATAATCAAATCTTTCTCATATGGAATTTCTTCCAAAATAGAACATTCAAACACA

TTACCATGTTTGTTAAAAGACCTCTGAAGTTTTATAGAAGAATGGCATCCTTTTTCTAAATCTTTAAAAT

GCCTCTTCCATCTCTTTTCAAAATCTTTAGCACTTCCTACATATACTTTATTGTTTAAAGTATTTTTAAT

CTGATAAATTCCGCTTTTCATAAATACCTCTTTAAATATAGAAGTATTTATTAAAGGGCAAGTCCTACAA

TTTAGCACGGGATTGTCTACTAGAGAGGTTCCCCGTTTAGATAGATTACAAGTATAAGTCACCTTATACT

CAGGCCTCAATTAACCCAAGAAAACATCTACTGAGCGTTGATACCACTGCAAATCCAAATAGCCATTACG

CACATTAAACTGATAGAACATATGACAAGGCGGTAATGCCATATATTTAAGTTCAGCTGGATTCCATGCA

GAAACAATTTGACGCCTATCATTTGGCAGTTTTTTAATACGATCAATAACTTCTATAATTTGGTCTACAC

CACCAAAATCACGCCACTGTTTTCCATAAATTGGACCAAGTTCACCGCTATGGTATCCTAAATCTTTTGC

TTGATTTTCGTAATTTTCATCCCAGACTGTTTTGCCTTGGATTAACGAATCGTGTTGAATTAATCGTAAA

TCATTGACATTTGTGCTTCCTGATAAAAACCATATTAGCTCAGCAATGCAAGCTTTCCAGGCGAGCTTCT

TAGTTGTTACCGCAGGAAAACCTTTAGTTAAATCCCAGCGTAATTTAGATCCGAACAGAGCAATTGTTCC

TGTGCCTGTACGATCATCGGTTTCATAACCATTTTCAAAAATGTCTTTAATTAAATCTTGGTATTGTTTC

ATTTATATACTGATTCCGTAAGGGTTGTTACTTCATCTATTTTATACCAATGCGTTTCAACCATTTCACG

CTTGCTTATATCATCAAGAAAACTTGCGTCTAATTGAACTGTTGAATTAACACGATGCCTTTTAACGATG

CGAGAAACAACTACTTCATCTGCATAAGGTAATGCAGCATATAACAGAGCAGGCCCGCCAATTACACTTA

CTTTAGAATTCTGATCAAGCATAGTTTCGAATGGTGCATTAGGGCTTGACACTTGAATTTCGCCGCCAGA

AATGTAAGTTATATATTGCTCCCAAGTAATATAGAAATGCTAAATCGCCGTCTTTAGTTACAGGATAA

TCACGCGCAAGGTCACACACCACAATATGGCTACGACCAGGAAGTAATGTAGGCAATGACTGGAACGTTT
```

-continued

```
TAGCACCCATAATCATAATTGTGCCTTCAGTACGAGCTTTAAAATTCTGGAGGTCCTTTTTAACTCGTCC

CCATGGTAAACCATCACCTAAACCGAATGCTAATTCATTAAAGCCGTCGACCGTTTTAGTTGGAGAATAA

CGGAATACCAATTTAATCATTACGTAAATCCTATTTTAATTGAAAACGAATGCTTACTTGGATAATTTCA

ATGACATACATAATATTTTCCTCAAACAGACTTTTTCACAATTTTCCAATCAGCTTTAAACTGCTCGACG

TCAGAATGGTAAATCCAAAATCCTGCGCTTTCTCCGTCTTCATAAAGAGGACATCCATCGCATTCATCTT

CCCATCCCATATCACGTAAAAGATGTTCAGCTTTTTCAACAAGTTCAGAATCTTTACCGATGATATTAAA

ATACCATTTACCTCTAACTTCTGAATCTTTGATGCTCTGGCGTTGTAATCTCATTTTATTCTCCTTAGCA

AGCTTTAATCAAAGATATAAACAGACCAACATAACTGCTGCCATAATATAAGGTGCGAACATTTTCTTT

TCTCCATTAGTTTTGATAGGGTAATAGTATCACACTACTACCCTGATGTAAACTACTTTTTGAAAGTTTT

TCGCAAAAGTTCAATGATTTCATCTACATTGTTTTCGTCAACAATGCAGTGAATTTTTGTTACGCCAGAA

ACCTTGTCTTTGACTTCATCTTCTTCAGAAGTCGGTTCTTTATATTCGCGGAAACAATAAAACTCTTCTT

CACTAAGTTCAAAATAATCATCACCCATACCATCATCATTATAGATTTCACCATTAGCACAAATGATTTC

GGTTACATAATCAAAGCCATCTAAACTTGATATTGATTTAACTTCAAACCAACCGCCATTTTCTTGAATG

ATGCCGACCATACTAGCATTTGATGAACTAATATCAATGAAAGATTTAATACGATGTGGATTTAACTCGT

ATTTTTTGCCGATTTCCATTTTGATTTTCCTCATTTTAATAGGGGCTTGATAGCCCCTTGATAATTATTG

TTCAATCAGTCCCATGTAAAATTCTGCGTCTTCAGAATCCATGCCATCACAATATTCATTAGCCATAAAG

CGGGTGAGGTCTTCAAGAGGACCTTCAATAACGATTTGAATACTCCAAAACTTAGAATCTTGCACGCTTG

TGATACTAAGTTCAGGATAACGATTACGAATAATCTCTTCAATATATTCAAAATCAACGATGTCAATATC

AACTTTAGCCATATTATTTTCCTCTTTAATTATTAGCAGTATTGCCGATAGTTGTATAGTACCATAAAGC

TTTATGCTTGTAAACCGTTTTGTGAAAAAATTTTTAAAATAAAAAAGGGGACCTCTAGGGTCCCCAATTA

ATTAGTAATATAATCTATTAAAGGTCATTCAAAAGGTCATCCAGGTCCGTGTCATCAGCACTAGATGAAC

TACCAGAGCTTGAGCTCATAAAATCATCTTCAGTTTTTGTATTGAAGTCATCAACATTGAATGCATCCAA

ATCATCAGCCACTTTATCAGCTTTCTTAGCAGCAGTTGCAGCAGCACCGCCCATCACAGCAGTTCCCATA

ACTTGACCGAATTTAGTATTAAGTTCTTCAAACGATTTGAATTTATCTTTAGAAGTCATTTCAGAAAGGT

CAACCATTTGTTCGAACAGTTCTTTCTGGAAAGATTCATCGTCAATGTTTGGAATCGCAGATTGATTCAG

GAATTTAGATTCATCGTAGTTACTAAATCCAGAAACTTGTTTAACTTTCAGTACAAAGTTAGCACCTTCC

CACGGACAAGTTACATCAACTGGAGTTTCACCCATTTCAACATCAACCGCAATCATTGCATTGATTTTAT

CCCAGATTTTCTTACCAAAGCGGTATTTAAATACTTTACCTTCGTTTTCTGGAGCAGCTGGGTCTTTTAC

TACAAGAATGTTAGCCCAGTAAGAAGTTTTACGTTTAACAAGACTGTACTCTTTATTGTCAGTGTTGTAT

AGATCATTTTTACTGATGTATTGACATACTGGGCAAGAATCGTAATCACCATGGGTAGATGAACATGTTT

CAATATACCATTTACCATTTTTCTTGAAACCGTGATTTACAAGAATTGCGAATGGTGCTTGTTCATCATT

TTTAGACGGAAGAAAACGAATTACTGCTTGACCGTTACCCGCATTATCGAGTTTCAGTTTCCACTCGCCT

TTATCTTCAGAAGAAAAACCTTTATTGCCATTCAGTTTAGCCATTTGTGCAGCGAGTTCAGCAGTAGATT

TACGTTTAAACATTTTTATTTCCTTTTTAATTTAATTTAATTAACAGTTGGTGCTATGACACTTTACCTC

ATAGCTGGCATAATTCGCAATACTCTGGGTCTTCGAGAGGTATCCAACCTGAGTTGAAATACTTTACCAT

CGATTTAGCAGTTGTATCAGTTATATTTATATTACCTTTAACTCTTCGCCATCCAGGAGTTTTACCGTAC

AGATTAGAGGATAATAATAACACATAATTCTCGTAAGCAATATGAGATAATTTCCAAGACTCTATATTAG

CTCGTGATGTTTTCCAAGGTCTAAAATCGTCACGGTTCATATAATTAGCCAATCTCATATGCTCTCTAAC

TTCCGGGTCTTTGGCTGGATGAGTTTCACCACTCACACCAAATCCACCACCAGCATATACCAGATTAAAA

TAGTCTGGATTATCTCTGGCATTTACTTCAAGTTGGTATTTTCGTTCTGCTTCAATAACATCCAAGTCAT
```

-continued

```
CATCAATTTGAATTATTTTAACGCTCGGTTTTTGAAGCATTAGCGCATTCAAAAATCTTTTTTGTTTACA
TGAGCTCCAGTATTCCTTTCCGGAAGAGTCATATATTATTCCGTTCTCAAATGAGCAATTTAATTTACTA
CCGATATAGTAGTATGGCGGAGTCTTATTTTTGACACGGTCTTCAAATGTAAACCAATATACTATATTCA
TATCAATACTTGCAAGATTTCACAGTTTCAATGAAAACATTTTTAGCTTTCTGTGAATCAATATTTAAAA
TTTTTCTATAAGCCTTTAACTTTATAGAATAATTATTCCAGACTAAATTATCAGTCTGTTCATCATGTTT
ATCAATTATATTTAAAAACGAATCAAGCAAGATAAACGTCTCAAACGAAATTATGTTCGATTGCAGAAGT
TTAAAAATATAACTTGATTGAACTTTTGGATTATACTCAAAAATTTCTTTAAAAGCAGAAACTTCAACTT
TTTTACTAAAATAATAAATGTTGCGAATATCTTCTTCAAACTTAAATTTAATTTGCTTTAAGCGTCCGAT
ATATTCACGATAAAACACAAGTGCATCAGCGTCAGAGATGTCACCAATCCAAGCATCTTGGTTAGCAACC
AAATTGCTTATAAAGATTAAAGCAAGTTCCTTTAATTTATATTTTTCTGATAACTTCTGGAAAAAATACT
TATCCCTTCGCTTTTGATAAGCGGCATCAGACACCCGCATGCACCAATTATACTTAATTACATCATACTT
TCCATTCATATGTTGTTTTATCATTAAGTATAATTTATAAACTGATTTACCATCAATGTATCTTTCACCA
CCAGCAGGCATGCGGAGTTTAATCATAGTAGAAAATCTAATGTATTAGTTTTTTCACAACGAACAACAGA
AGGACGTAAAAGATTTTCGTCAATAGCTTCTGACTGAATTTTTTCAATTATACCCGAAGGAATAAATTTA
GCAAATTGAGTTTCAGGAATAGAATTTCTTCTAAGAATGCTGTTGTAGCTTCAAGATAACTCATTCCAA
ACTCTTCTACCATTTTTTCAATAATAAATCCATTTTCTTGGCGGTCAAGAAGCTTTGCTATTTCATCCTT
TTCTTTCTTAATTGAAAGTTCTTTTTCTGAAAGACCGGTCTCATCGACCGGACGAATATCATTTAGAGAA
AACTGTGTCATAAAGTTCAACTACCTCTTCAGTTTCAGCTTCAAACACATCACGGTTATCTTTATGATAC
AAAGCTAATAGACGATTAAACATCTTACCATCAACGCCAAGTTCATCTTTAGCACGAATTCGAATATCTT
TAATCAGTTCATTATAACCGGAAATTTTCAGTTTATGATCAGATGCTTCTTTAATAAATTTAGCCAAGTC
TTCGCCATGGATAGCTTCATCAAATTCAACCATTTCTTTTTTAGCCATTATTCACCTCAAAATTCATTAA
TGCTATTAGTTAATTTAGAAAGACCCGCTTTTACAAAATATGAATAAATTTTGCCACGCGGTGGTAATTT
ATATGAATTATAGTAATTCACAATGTTTGAAGCAATATTATCAGGAATATAATCAAAATCAATTAGAACT
AAATTTTCTTTATAACGATTATATTCAGATTCAGTGAGAAGCACCTTAGCTTGCTCACGGTCATTAGCAA
TAGCTTCAACGATTGAAGTTTTCATTGAAGGAGTTCGTTCACCTTCAACTCTGGTAAACCAAAAGTCAGA
TCGTACTTTAACTGAAGCAACGTTATCCTTTTTGTCGCCTTTAAGGATTTTAGTCATACAGTCAATTTCA
GCAGAACCGCTTTTAATTTTAACCCATTTCTTATGCATCGGAGACCATTGCTTAACATTTGGATATTTGT
GAAGCTGAGTAAAGTCACCATCTGACGAAATGATTAAAATCTTATGTCCTTCTAAAGAGAACTTTTTAAC
AAGAACAGCAATGTGGTCATCTGCTTCATACTTATCAATATCCATAACAATGTATGGCATATAAGCTTTC
AATTCATCTATAACTTTATGGCTGGATTCAAAATAACCTTCCCAGTCCCAAGTAGATTCTTCTCGTGCTT
TTCCACGGTTTTTCTTATAATAATAAGCGAAATCACGACGCCAATATCCAGATTTCGCGTTATCAATACA
CAGTACAATTTTAGTGTATCCAAGCGTTTTTGCTTTTTTGACATTAAACTTAATTGAGTTCAATATCAAA
TGACGAACCATTGATAAATTAATTTTTTCTTTATCTGGGAAGTTTACCAAAGCAGTTGAAAGCGCAATTT
GACTAAAGTCAATTAAGCAGATTCCTTCTTTGTAATCTTCATCCAACATCATTTCTAAATCCATATGAAC
CTCGTTCAATTAGTGAGATTTCTATTATATACCATCCAAATCTTAAAGTAAACAAGTATAAATACTTATT
ATTGAAAACACAATAGGAGCCCGGGAGAATGGCCGAGATTAAAAGAGAATTCAGAGCAGAAGATGGTCTG
GACGCAGGTGGTGATAAAATAATCAACGTAGCTTAGCTGATCGTACCGTAGGAACTGACGGTGTTAACG
TTGATTACTTAATTCAAGAAAACACAGTTCAACAGTATGATCCAACTCGTGGATATTTAAAAGATTTTGT
AATCATTTATGATAACCGCTTTTGGGCTGCTATAAATGATATTCCAAAACCAGCAGGAGCTTTTAATAGC
GGACGCTGGAGAGCATTACGTACCGATGCTAACTGGATTACGGTTTCATCTGGTTCATATCAATTAAAAT
CTGGTGAAGCAATTTCGGTTAACACCGCAGCTGGAAATGACATCACGTTTACTTTACCATCTTCTCCAAT
```

-continued

```
TGATGGTGATACTATCGTTCTCCAAGATATTGGAGGAAAACCTGGAGTTAACCAAGTTTTAATTGTAGCT
CCAGTACAAAGTATTGTAAACTTTAGAGGTGAACAGGTACGTTCAGTACTAATGACTCATCCAAAGTCAC
AGCTAGTTTTAATTTTTAGTAATCGTCTGTGGCAAATGTATGTTGCTGATTATAGTAGAGAAGCTATAGT
TGTAACACCAGCGAATACTTATCAAGCGCAATCCAACGATTTTATCGTACGTAGATTTACTTCTGCTGCA
CCAATTAATGTCAAACTTCCAAGATTTGCTAATCATGGCGATATTATTAATTTCGTCGATTTAGATAAAC
TAAATCCGCTTTATCATACAATTGTTACTACATACGATGAAACGACTTCAGTACAAGAAGTTGGAACTCA
TTCCATTGAAGGCCGTACATCGATTGACGGTTTCTTGATGTTTGATGATAATGAGAAATTATGGAGACTG
TTTGACGGGGATAGTAAAGCGCGTTTACGTATCATAACGACTAATTCAAACATTCGTCCAAATGAAGAAG
TTATGGTATTTGGTGCGAATAACGGAACAACTCAAACAATTGAGCTTAAGCTTCCAACTAATATTTCTGT
TGGTGATACTGTTAAAATTTCCATGAATTACATGAGAAAAGGACAAACAGTTAAAATCAAAGCTGCTGAT
GAAGATAAAATTGCTTCTTCAGTTCAATTGCTGCAATTCCCAAAACGCTCAGAATATCCACCTGAAGCTG
AATGGGTTACAGTTCAAGAATTAGTTTTTAACGATGAAACTAATTATGTTCCAGTTTTGGAGCTTGCTTA
CATAGAAGATTCTGATGGAAAATATTGGGTTGTACAGCAAAACGTTCCAACTGTAGAAAGAGTAGATTCT
TTAAATGATTCTACTAGAGCAAGATTAGGCGTAATTGCTTTAGCTACACAAGCTCAAGCTAATGTCGATT
TAGAAAATTCTCCACAAAAAGAATTAGCAATTACTCCAGAAACGTTAGCTAATCGTACTGCTACAGAAAC
TCGCAGAGGTATTGCAAGAATAGCAACTACTGCTCAAGTGAATCAGAACACCACATTCTCTTTTGCTGAT
GATATTATCATCACTCCTAAAAAGCTGAATGAAAGAACTGCTACAGAAACTCGTAGAGGTGTCGCAGAAA
TTGCTACGCAGCAAGAAACTAATGCAGGAACCGATGATACTACAATCATCACTCCTAAAAAGCTTCAAGC
TCGTCAAGGTTCTGAATCATTATCTGGTATTGTAACCTTTGTATCTACTGCAGGTGCTACTCCAGCTTCT
AGCCGTGAATTAAATGGTACGAATGTTTATAATAAAAACACTGATAATTTAGTTGTTTCACCTAAAGCTT
TGGATCAGTATAAAGCTACTCCAACACAGCAAGGTGCAGTAATTTTAGCAGTTGAAAGTGAAGTAATTGC
TGGACAAAGTCAGCAAGGATGGGCAAATGCTGTTGTAACGCCAGAAACGTTACATAAAAAGACATCAACT
GATGGAAGAATTGGTTTAATTGAAATTGCTACGCAAAGTGAAGTTAATACAGGAACTGATTATACTCGTG
CAGTCACTCCTAAAACTTTAAATGACCGTAGAGCAACTGAAAGTTTAAGTGGTATAGCTGAAATTGCTAC
ACAAGTTGAATTCGACGCAGGCGTCGACGATACTCGTATCTCTACACCATTAAAAATTAAAACCAGATTT
AATAGTACTGATCGTACTTCTGTTGTTGCTCTATCTGGATTAGTTGAATCAGGAACTCTCTGGGACCATT
ATACACTTAATATTCTTGAAGCAAATGAGACACAACGTGGTACACTTCGTGTAGCTACGCAGGTCGAAGC
TGCTGCGGGAACATTAGATAATGTTTTAATAACTCCTAAAAAGCTTTTAGGTACTAAATCTACTGAAGCG
CAAGAGGGTGTTATTAAAGTTGCAACTCAGTCTGAAACTGTGACTGGAACGTCAGCAAATACTGCTGTAT
CTCCAAAAAATTTAAAATGGATTGCGCAGAGTGAACCTACTTGGGCAGCTACTACTGCAATAAGAGGTTT
TGTTAAAACTTCATCTGGTTCAATTACATTCGTTGGTAATGATACAGTCGGTTCTACCCAAGATTTAGAA
CTGTATGAGAAAAATAGCTATGCGGTATCACCATATGAATTAAACCGTGTATTAGCAAATTATTTGCCAC
TAAAAGCAAAGCTGCTGATACAAATTTATTGGATGGTCTAGATTCATCTCAGTTCATTCGTAGGGATAT
TGCACAGACGGTTAATGGTTCACTAACCTTAACCCAACAAACGAATCTGAGTGCCCCTCTTGTATCATCT
AGTACTGGTGAATTTGGTGGTTCATTGGCCGCTAATAGAACATTTACCATCCGTAATACAGGAGCCCCGA
CTAGTATCGTTTTCGAAAAAGGTCCTGCATCCGGGGCAAATCCTGCACAGTCAATGAGTATTCGTGTATG
GGGTAACCAATTTGGCGGCGGTAGTGATACGACCCGTTCGACAGTGTTTGAAGTTGGCGATGACACATCT
CATCACTTTTATTCTCAACGTAATAAAGACGGTAATATAGCGTTTAACATTAATGGTACTGTAATGCCAA
TAAACATTAATGCTTCCGGTTTGATGAATGTGAATGGCACTGCAACATTCGGTCGTTCAGTTACAGCCAA
TGGTGAATTCATCAGCAAGTCTGCAAATGCTTTTAGAGCAATAAACGGTGATTACGGATTCTTTATTCGT
```

-continued

```
AATGATGCCTCTAATACCTATTTTTTGCTCACTGCAGCCGGTGATCAGACTGGTGGTTTTAATGGATTAC
GCCCATTATTAATTAATAATCAATCCGGTCAGATTACAATTGGTGAAGGCTTAATCATTGCCAAAGGTGT
TACTATAAATTCAGGCGGTTTAACTGTTAACTCGAGAATTCGTTCTCAGGGTACTAAAACATCTGATTTA
TATACCCGTGCGCCAACATCTGATACTGTAGGATTCTGGTCAATCGATATTAATGATTCAGCCACTTATA
ACCAGTTCCCGGGTTATTTTAAAATGGTTGAAAAAACTAATGAAGTGACTGGGCTTCCATACTTAGAACG
TGGCGAAGAAGTTAAATCTCCTGGTACACTGACTCAGTTTGGTAACACACTTGATTCGCTTTACCAAGAT
TGGATTACTTATCCAACGACGCCAGAAGCGCGTACCACTCGCTGGACACGTACATGGCAGAAAACCAAAA
ACTCTTGGTCAAGTTTTGTTCAGGTATTTGACGGAGGTAACCCTCCTCAACCATCTGATATCGGTGCTTT
ACCATCTGATAATGCTACAATGGGGAATCTTACTATTCGTGATTTCTTGCGAATTGGTAATGTTCGCATT
GTTCCTGACCCAGTGAATAAAACGGTTAAATTTGAATGGGTTGAATAAGAGGTATTATGGAAAAATTTAT
GGCCGAGTTTGGACAAGGATATGTCCAAACGCCATTTTTATCGGAAAGTAATTCAGTAAGATATAAAATA
AGTATAGCGGGTTCTTGCCCGCTTTCTACAGCAGGACCATCATATGTTAAATTTCAGGATAATCCTGTAG
GAAGTCAAACATTTAGCGCAGGCCTCCATTTAAGAGTTTTTGACCCTTCCACCGGAGCATTAGTTGATAG
TAAGTCATATGCCTTTTCGACTTCAAATGATACTACATCAGCTGCTTTTGTTAGTTTCATGAATTCTTTG
ACGAATAATCGAATTGTTGCTATATTAACTAGTGGAAAGGTTAATTTTCCTCCTGAAGTAGTATCTTGGT
TAAGAACCGCCGGAACGTCTGCCTTTCCATCTGATTCTATATTGTCAAGATTTGACGTATCATATGCTGC
TTTTTATACTTCTTCTAAAAGAGCTATCGCATTAGAGCATGTTAAACTGAGTAATAGAAAAAGCACAGAT
GATTATCAAACTATTTTAGATGTTGTATTTGACAGTTTAGAAGATGTAGGGGCTACCGGGTTTCCAAGAG
GAACGTATGAAAGTGTTGAGCAATTCATGTCGGCAGTTGGTGGAACTAATGACGAAATTGCGAGATTGCC
AACTTCAGCTGCTATAAGTAAATTATCTGATTATAATTTAATTCCTGGAGATGTTCTTTATCTTAAAGCT
CAGTTATATGCTGATGCTGATTTACTTGCTCTTGGAACTACAAATATATCTATCCGTTTTTATAATGCAT
CTAACGGATATATTTCTTCAACACAAGCTGAATTTACTGGGCAAGCTGGGTCATGGGAATTAAAGGAAGA
TTATGTAGTTGTTCCAGAAAACGCAGTAGGATTTACGATATACGCACAGAGAACTGCACAAGCTGGCCAA
GGTGGCATGAGAAATTTAAGCTTTTCTGAAGTATCAAGAAATGGCGGCATTTCGAAACCTGCTGAATTTG
GCGTCAATGGTATTCGTGTTAATTATATCTGCGAATCCGCTTCACCCCCGGATATAATGGTACTTCCTAC
GCAAGCATCGTCTAAAACTGGTAAAGTGTTTGGGCAAGAATTTAGAGAAGTTTAAATTGAGGGACCCTTC
GGGTTCCCTTTTTCTTTATAAATACTATTCAAATAAAGGGGCATACAATGGCTGATTTAAAAGTAGGTTC
AACAACTGGAGGCTCTGTCATTTGGCATCAAGGAAATTTTCCATTGAATCCAGCCGGTGACGATGTACTC
TATAAATCATTTAAAATATATTCAGAATATAACAAACCACAAGCTGCTGATAACGATTTCGTTTCTAAAG
CTAATGGTGGTACTTATGCATCAAAGGTAACATTTAACGCTGGCATTCAAGTCCCATATGCTCCAAACAT
CATGAGCCCATGCGGGATTTATGGGGGTAACGGTGATGGTGCTACTTTTGATAAAGCAAATATCGATATT
GTTTCATGGTATGGCGTAGGATTTAAATCGTCATTTGGTTCAACAGGCCGAACTGTTGTAATTAATACAC
GCAATGGTGATATTAACACAAAAGGTGTTGTGTCGGCAGCTGGTCAAGTAAGAAGTGGTGCGGCTGCTCC
TATAGCAGCGAATGACCTTACTAGAAAGGACTATGTTGATGGAGCAATAAATACTGTTACTGCAAATGCA
AACTCTAGGGTGCTACGGTCTGGTGACACCATGACAGGTAATTTAACAGCGCCAAACTTTTTCTCGCAGA
ATCCTGCATCTCAACCCTCACACGTTCCACGATTTGACCAAATCGTAATTAAGGATTCTGTTCAAGATTT
CGGCTATTATTAAGAGGACTTATGGCTACTTTAAAACAAATACAATTTAAAAGAAGCAAAATCGCAGGAA
CACGTCCTGCTGCTTCAGTATTAGCCGAAGGTGAATTGGCTATAAACTTAAAAGATAGAACAATTTTTAC
TAAAGATGATTCAGGAAATATCATCGATCTAGGTTTTGCTAAAGGCGGGCAAGTTGATGGCAACGTTACT
ATTAACGGACTTTTGAGATTAAATGGCGATTATGTACAAACAGGTGGAATGACTGTAAACGGACCCATTG
GTTCTACTGATGGCGTCACTGGAAAAATTTTCAGATCTACACAGGGGTTCATTTTATGCAAGAGCAACAAA
```

-continued

```
CGATACTTCAAATGCCCATTTATGGTTTGAAAATGCCGATGGCACTGAACGTGGCGTTATATATGCTCGC

CCTCAAACTACAACTGACGGTGAAATACGCCTTAGGGTTAGACAAGGAACAGGAAGCACTGCCAACAGTG

AATTCTATTTCCGCTCTATAAATGGAGGCGAATTTCAGGCTAACCGTATTTTAGCATCAGATTCGTTAGT

AACAAAACGCATTGCGGTTGATACCGTTATTCATGATGCCAAAGCATTTGGACAATATGATTCTCACTCT

TTGGTTAATTATGTTTATCCTGGAACCGGTGAAACAAATGGTGTAAACTATCTTCGTAAAGTTCGCGCTA

AGTCCGGTGGTACAATTTATCATGAAATTGTTACTGCACAAACAGGCCTGGCTGATGAAGTTTCTTGGTG

GTCTGGTGATACACCAGTATTTAAACTATACGGTATTCGTGACGATGGCAGAATGATTATCCGTAATAGC

CTTGCATTAGGTACATTCACTACAAATTTCCCGTCTAGTGATTATGGCAACGTCGGTGTAATGGGCGATA

AGTATCTTGTTCTCGGCGACACTGTAACTGGCTTGTCATACAAAAAACTGGTGTATTTGATCTAGTTGG

CGGTGGATATTCTGTTGCTTCTATTACTCCTGACAGTTTCCGTAGTACTCGTAAAGGTATATTTGGTCGT

TCTGAGGACCAAGGCGCAACTTGGATAATGCCTGGTACAAATGCTGCTCTCTTGTCTGTTCAAACACAAG

CTGATAATAACAATGCTGGAGACGGACAAACCCATATCGGGTACAATGCTGGCGGTAAAATGAACCACTA

TTTCCGTGGTACAGGTCAGATGAATATCAATACCCAACAAGGTATGGAAATTAACCCGGGTATTTTGAAA

TTGGTAACTGGCTCTAATAATGTACAATTTTACGCTGACGGAACTATTTCTTCCATTCAACCTATTAAAT

TAGATAACGAGATATTTTTAACTAAATCTAATAATACTGCGGGTCTTAAATTTGGAGCTCCTAGCCAAGT

TGATGGCACAAGGACTATCCAATGGAACGGTGGTACTCGCGAAGGACAGAATAAAAACTATGTGATTATT

AAAGCATGGGGTAACTCATTTAATGCCACTGGTGATAGATCTCGCGAAACGGTTTTCCAAGTATCAGATA

GTCAAGGATATTATTTTTATGCTCATCGTAAAGCTCCAACCGGCGACGAAACTATTGGACGTATTGAAGC

TCAATTTGCTGGGGATGTTTATGCTAAAGGTATTATTGCCAACGGAAATTTTAGAGTTGTTGGGTCAAGC

GCTTTAGCCGGCAATGTTACTATGTCTAACGGTTTGTTTGTCCAAGGTGGTTCTTCTATTACTGGACAAG

TTAAAATTGGCGGAACAGCAAACGCACTGAGAATTTGGAACGCTGAATATGGTGCTATTTTCCGTCGTTC

GGAAAGTAACTTTTATATTATTCCAACCAATCAAAATGAAGGAGAAAGTGGAGACATTCACAGCTCTTTG

AGACCTGTGAGAATAGGATTAAACGATGGCATGGTTGGGTTAGGAAGAGATTCTTTTATAGTAGATCAAA

ATAATGCTTTAACTACGATAAACAGTAACTCTCGCATTAATGCCAACTTTAGAATGCAATTGGGGCAGTC

GGCATACATTGATGCAGAATGTACTGATGCTGTTCGCCCGGCGGGTGCAGGTTCATTTGCTTCCCAGAAT

AATGAAGACGTCCGTGCGCCGTTCTATATGAATATTGATAGAACTGATGCTAGTGCATATGTTCCTATTT

TGAAACAACGTTATGTTCAAGGCAATGGCTGCTATTCATTAGGGACTTTAATTAATAATGGTAATTTCCG

AGTTCATTACCATGGCGGCGGAGATAACGGTTCTACAGGTCCACAGACTGCTGATTTTGGATGGGAATTT

ATTAAAAACGGTGATTTTATTTCACCTCGCGATTTAATAGCAGGCAAAGTCAGATTTGATAGAACTGGTA

ATATCACTGGTGGTTCTGGTAATTTTGCTAACTTAAACAGTACAATTGAATCACTTAAAACTGATATCAT

GTCGAGTTACCCAATTGGTGCTCCGATTCCTTGGCCGAGTGATTCAGTTCCTGCTGGATTTGCTTTGATG

GAAGGTCAGACCTTTGATAAGTCCGCATATCCAAAGTTAGCTGTTGCATATCCTAGCGGTGTTATTCCAG

ATATGCGCGGGCAAACTATCAAGGGTAAACCAAGTGGTCGTGCTGTTTTGAGCGCTGAGGCAGATGGTGT

TAAGGCTCATAGCCATAGTGCATCGGCTTCAAGTACTGACTTAGGTACTAAAACCACATCAAGCTTTGAC

TATGGTACGAAGGGAACTAACAGTACGGGTGGACACACTCACTCTGGTAGTGGTTCTACTAGCACAAATG

GTGAGCACAGCCACTACATCGAGGCATGGAATGGTACTGGTGTAGGTGGTAATAAGATGTCATCATATGC

CATATCATACAGGGCGGGTGGGAGTAACACTAATGCAGCAGGGAACCACAGTCACACTTTCTCTTTTGGG

ACTAGCAGTGCTGGCGACCATTCCCACTCTGTAGGTATTGGTGCTCATACCCACACGGTAGCAATTGGAT

CACATGGTCATACTATCACTGTAAATAGTACAGGTAATACAGAAAACACGGTTAAAAACATTGCTTTTAA

CTATATCGTTCGTTTAGCATAAGGAGAGGGGCTTCGGCCCTTCTAAATATGAAAATATATCATTATTATT
```

-continued

TTGACACTAAAGAATTTTACAAAGAAGAAAATTACAAACCGGTTAAAGGCCTCGGTCTTCCTGCTCATTC

AACAATTAAAAAACCTTTAGAACCTAAAGAAGGATACGCGGTTGTATTTGATGAACGTACTCAGGATTGG

ATTTATGAAGAAGACCATCGCGGAAAACGCGCATGGACTTTTAATAAAGAAGAAATTTTATAAGTGACA

TTGGAAGCCCGGTTGGTATAACTTTCGATGAGCCCGGCGAATTTGATATATGGACTGATGACGGTTGGAA

AGAAGACGAAACATATAAGCGAGTTTTAATTCGTAATAGAAAAATTGAAGAATTATATAAAGAGTTCCAA

GTTTTAAATAATATGATTGAAGCTTCTGTCGCCAATAAAAAGGAAAAATTCTATTATAAAAACCTTAAGC

GGTTCTTTGCTCTTTTAGAAAAGCATGAGCATTTAGGTGGTGAATTCCCTTCATGGCCTGAAAAGAACA

GAAGCCTTGGTATAAGCGTTTATTCAAGCATTACGTATAAATATCTTAAAAGGAGGGTCTATGGCAGCAC

CTAGAATATCATTTTCGCCCTCTGATATTCTATTTGGTGTTCTAGATCGCTTGTTCAAAGATAACGCTAC

CGGGAAGGTTCTTGCTTCCCGGGTAGCTGTCGTAATTCTTTTGTTTATAATGGCGATTGTTTGGTATAGG

GGAGATAGTTTCTTTGAGTACTATAAGCAATCAAAGTATGAAACATACAGTGAAATTATTGAAAAGGAAA

GAACTGCACGCTTTGAATCTGTCGCCCTGGAACAACTCCAGATAGTTCATATATCATCTGAGGCAGACTT

TAGTGCGGTGTATTCTTTCCGCCCTAAAAACTTAAACTATTTTGTTGATATTATAGCATACGAAGGAAAA

TTACCTTCAACAATAAGTGAAAAATCACTTGGAGGATATCCTGTTGATAAAACTATGGATGAATATACAG

TTCATTTAAATGGACGTCATTATTATTCCAACTCAAAATTTGCTTTTTTACCAACTAAAAAGCCTACTCC

CGAAATAAACTACATGTACAGTTGTCCATATTTTAATTTGGATAATATCTATGCTGGAACGATAACCATG

TACTGGTATAGAAATGATCATATAAGTAATGACCGCCTTGAATCAATATGTGCTCAGGCGGCCAGAATAT

TAGGAAGGGCTAAATAATTATTTGTTCGTATACATCTCTAGATATCGATATACACCCTCAAAACCCTCGT

TGAATTCGTCGATGAGGGTTTTCTTATCTTCTTGAGTTAATTCAGAAACAATTTTACGGAATGAATTTTG

ATTTAACTTTCTACCTTCATGCGTTACTCCAATCTCATTTAGAAATGCAATAAAATTAGCACGATTCTCA

ACAATATCTTCTCTGGAAAATTTAATCAAATAGATGCAACAGTAATAATTTCACGAACTGTATCAATGT

TTTTATTCATTAACTATACCACTCAATTAGTTGACTTTGTTATAATATCATCAGACGCTTGATTTGTAAA

CTGGTCTGTGTAATTTTCTTCAAAAATTTTTTCTACGAATTCCTTGAACGATTCACGTTCCTGAGCTACA

TTATGCTCGATTACCTTTTCAAGATTATGACTCATTCGAAATAATCTTCAATTTCATAATCATGGACATA

AATCATTATAGTTTTTAATACATCATCAATATTTTTTCCTGGAGCTGGAATTACGTAAAAATACCCTGCT

TTTGAGAGGTCTTTATAAGTTCCAATCAAGAAATCATTATTCTCAAGATGTAACTCTTCAACTAATTCAT

TGACAATTGAATGGTATAGGTTTGGCAGAAACTTATATAGCTTTTCTAGAATATCAATTTTGAATGTATA

TTGAACCACGGACTGAGAATCAATAATCATAGACCTTCCCCTTATGTTTCTGTTTGCGATTAGATTCTTT

AAACGCTTTCTTCTTATCCTTATGAACAGAAGCTTTATTAAAATTATGCTTTGCGACTAAATTGTTCATA

GTGCTGAATTACCTCTCTTAAACATTTGCATGTGAATGAAAACTTTTTAGCTACACCACATTCAAATATA

TGTTCTCTTAAATCGCGTGTATCGGTATATCCCATCTCAACAATAAAATGCCGTATTAGATTTTTATCTT

TATCGTTTAGAGAATTAAAATAATCAGATTTTGAATTAATTTCCCTGGCCAAATTGAATCACCTTCAGTT

GACGTTTTAACTCTTTTATCATCTCTTCGTTCATCGCAATATAAAGATCGCGTAGAGCAGGTTTTAGCAT

TCCATTTACTGGAGAACTAAATGGACATACATAATCTTTTCCTACGAGCTTTTTAGTGAATTCCATATCA

CAGAACTGAAATCCCGGCTCATTGGTATAAATTCCCCAATTAGTTGACATCATTTTATTGGCATATTCCA

GTGCCTGGATTTGATTCATAATTCCATCAATTTGAAACTTTTAATATTCATTAGTAAAGGTCCTCAGAG

TAAAGTTCTTTTTCACTACCACGTTCAATACTTACTTGTCCAGCGTAAGTTGCAATAATCATTGCTTCTT

CACGTGTCCAATAATTACTATATTGGTCAATAAACCCTTGGTCATCATCACAAACTTGCTGAGTAACTAA

TTGAGGTTTAACTACATCTAAAACTTCTGCCATATCTTTAGAATAATGACGAGCACCTGGAATAATAAGA

GTTCGTCCATCTTTTAATTTAAAACGGTTGGCTGCGCAAACAATTCGTCGTTGATACTTTTGGTTTTCAT

CCCAGTACGCAGTCTGCCAACAGATTTCAGGAACTTCTTTCAGAATATCTTCTTCTGTGCATTTATAACC

-continued

```
ATGCGCTTTAAATTTTTCAACAAGACTTTCTGGAGTTTCACGAGATAAAGGAACATTCAGCATTTTTAAA
CGATTGATAAATGGGTTCATTTAAACCATCCTTTAATACGCTGCCACAAAGTTTTCTGTTGAGCTTTGTT
GACGCCAATTGAGCGAATAACCGGTTGAGATTCCTGGAATTCTTTATAATCAGCAAGGTAAATTTCGTAA
GCTGCATCCGTAAATGAACTTATCGCTGCCATAAAATTATTGCGAATACCTACTGGAGCATCTTTACTTT
CACGAATGATCATGTATTTACCAGTCTTAATCTTTACGATAGTTCCAAGATAAGCTCCATGGTACCAAAT
ATCCCAACCCTCTTGAGTAGGTTCTGCGCAACGACGAAGTTCATTGACAATTTCTAACTTGTTTATTATT
TATTCCTCACAGTTCAGATGCTACAGTGATTACAGCTTCAATGTTTTCTGCCGAGCGTTTAATGTCAAGA
TACACATTACCGTTTTTAGCGATTTTACATGACATTCCGATGTCAGTAAATTTCTGAATATGATGTTCCA
TCATTTTGTATCCAAAAATTCGCATATTTCCATTGTTATTAATTTCAAAATTACGAATTCCGTTAGTGCG
TTTTTCTAAAATAGCAAGATAATTACTACGATAAATTTCAACCTTTTTAAGAACAAATCCATTTTTATCT
AAAAGTTTTAACATGAGGTCTTTATCTTCTTCCATATCGGAAGTAATCTCGCGAGCTTTACGAGTTGCTC
GTTTTTTCAGCAGTTCCGGAGCATTTTCCTGTGCATATAAAGTTGCTGCATTTGAAATAATATCCTGAGC
TTCACCAGTAATGATTAATCCATCACCAGATTTCTCCACCAGGCCTTTTTTAATCAATACCCCAATATTA
CTATTAACTACTGCGTTACCTAAATCTGGATGCACCTCACGAACTTCTGCAGCTGTAATGAAATCTTTCT
TAGCAATGGTAATTAAAATCGTAGCAGTTTTTTCATTCAGAACATCGTTAGAAGCTTTGATGATGTAAGT
TACTTTAGACATTTTCTAATCTCCGTAATTCTGTATCAGTAGTTGATAGTTGTATAGTACCACAGTATGC
TTTGGTTGTAAACCGTTTTGTGAAAAAATTTTAAAATAAAAAGGGAGAGCCTCGGCTCTCCCTAAAAT
TACTGCATGACTGTGATAACTGTCATGATAACACGTTGAATTCCGAACGCAAGAAGACCTCCTGCTACGG
CTGGAACAACGCCTAAACCCGCCAGTAAAATGCTACCAGATACTAATGCAGCGCTTGTAATACCAATGAA
TGGACTCATTTGATTTCCTCTAAATCTTTGGTGTATTCAGTAACTACATCAGTAGTTTTCCAATATTCGT
TTTCTTCTTTTTTAGCTTTAGCTTCTTCAGCAAGTTTCTTTGCTTCATCGGAAGTCATATGAAAAATATT
CATTCCAACTAGTTTATCAACATAAGAAGAATACATATCGATTTTCGAAAGTTCTTCGGTCAGTTCTTTA
CGAGTTTTACCCTGTACAACAATTTCACCTGAAATTACTTTCTTAATGAAATGTGCTTTGGCAAAGGCTA
AACGAAAAGCTGACTCAGTTTCTTTAATTTTGTTATCAATTCGTTTTTGGACATAAGTTTTACGAACTTC
AACAAAGTCTTTAATTAAATCAACTACGTTATCGTAAACTTGCAGCTTTCCTTTCTCATTAATAACCGTA
ATATTCTGGGAACGACGCTCAATCAGTCCGAAGTCTTTCATAATTTTTGCATGGCGTTCTTCTTCGTTAT
CGCTCAAAGAATATTCTTTGCGGAATTTAACTTTGAAGCCAAAACCATGCTCACCACAAGCATCATCCCA
TGTAATGAAGCCTTTATTTTCAAGTGGGTCTAAGATTTTACTCACATAAGTTTCACGATCATACTTATAC
GGAATCTCAGTGATATGCATTTGAGTTCGTGAAGTAAACTTATATGTTCCACGAATTTCATATTGCCCAT
CAATTTCAACGACTTCACCACGAAATTCTGGGAATTCTACTTTCGGTTTAGTTACTTTCTTTCCTTGAAG
AGCTTGCAGTACAGCTTTCTTGACAGAAGAAACACTATGAGGAAGAATGTAAGTTGCATAACCAGTTGCA
ATACCGGAAACGCCATTAAGAAGAACAGTAGGAATAATAGGCAAATAGAAAGCAGGCGGAATGTGTTCTT
TATCTTGATGTACCGGAGCATATTCAGTATCTTTATATACGTTATAGAAATTTTTACTTACACGAGCAAA
AATATAACGACTTGCCGCTGCCTTTTGGACAGTACGAGAACCAAAGTTTCCTTGACCATCTAACAGAGGA
AAGTTATTATTCCAAGTATTAGCCATCAAAGCACCTGCGTCTTGTGCAGAGTTTTCACCATGATGATATC
CAAGGTCCGCTACACCACCTGCAATAGAAGCGAGTTTGTGAAACTTATCTTTATTTCCTCGTGCCAAATC
AAGAGCTCGAGCAATAACAAATCGTTGAACTGGCTTAAATCCATCAATCATATTTGGGATAGCACGATTT
TCAACCGTGTACATAGCATAAGCCAATGCTTCATTATCAATGATACTTTTTAAATCGCGATTATTCAGTT
GCATAAATTTACCATACTAGTGAATGTAGTGCCATAATAACATCAGAAATGAAAAGCACGACTTGAATTA
ATCCGAACATTACTCCGTAATATAGTGCTACCAATAAAGCAGCAAGGGCTAATGAATAGCCCAAGATTTT
```

-continued

```
CTTAATCATTAGATAACAACACAAATGTTAAATATGCACACATACCCTGGGCTAAAGCTTGTGAAAACAC

ACTGCTAGCATCGATACAGATAGTTAAAACACATGCTACTATCCAACAAATAAATGAAATAACTCCTAAT

AATTTTGCAATATTCATATTTTCCTCACTGGCGTCCGAAGACGCCTTTAGTTTTAAGATTGTTACGATAG

AACTGCATCACGTGTTCGTTATGGAAATTACTCATTAATATGCCTGTAAAACAAATTTAAAGTTATCAGC

CAACATACGGTTCATTTCTTCGAGTGTTTGATACTCAGAATGATGATTACGAGTAAACGCCAAAGCTAGC

TGACCTTTTCCAAATCCCGTCGTTAGAGGTTTCATCTTAGAAGCAGGCAGATAAAACACTGTGTATGGAA

CATTGTTATTTGCAATAGTACGCGCAAGTTGAGACCGGCGTTGACGAATATGACTTAAAACCGCACTGAA

TCCTTGCTTAGAACGCTGATTACCTACATAAAATCGTGCAGATACGCATGGATTACTAAATGGACCACCG

AGTTTACTCACTAAAAAGTAAAATCCAGGTTTAGATAAAATATCTTTATGCGGAGTTCCTAAAAACCATT

CACCACCCTTGATTGTACCAATAACAGTAGCGCCTGCATCATTCAGATCAGTAACAGTCATATATTTCAT

ATTAATTTCCTCTAAATTATTTTCTACTCCAAGGCCGCATGAATACACACGGCCATTAAATTACTCGTCG

CAGTCGACGCTCAATTCCCAAAACTCTTCTACAGTATAAGTTTCAGTATCATTTTCAATACAGAAACGTT

CATTACTATTATTTGCTAAAGTAGCATTAACTGTCATTTTTTCGCTAGTGCTCTTAAGAGGTGAAATACG

AATTAACTGATCACCGTTATCTAAACAAAAAATTTCACCAACTTTTACATCTTTAAAACTTTTCATAATT

CACCTCAAGGAGTATAAAATCCAAATGCAGTTGTTGACCATCCCATCCAATATGGAAAATTTACACCAAT

GTAAAACATAAGAATATAAAACCAACCGCTCAGCAAATTCATCATTTTACACCATTCCAAATTGTTTCAA

CCACGGATTTTAAACCATTTTGATGAATATCCATTCCTACTACCGCCATCAAATAAATTCCAACTACAAC

TGAACCTAAGGCAAAAATCAGCATGAAAATGAATAAAGCCGGAAAAATATTATCGAAAAACCATTCAATA

AATGTAAAAGCACTGCGTTTACGTTCATATTTTCCTCACATAAATCCAAAGTAAACGTTTAATACATCAA

TCATTAAAACGATTGGGAATATACTCAAAACTATTAGTATTATAACTACATTCCATATAGCTTTAATAAT

CTTTTTCATTTTCTGTTCCTCCATAGTTGATAGGGTAATAGTACCACGGAAGAACAGTCTTGTAAACAAC

TTTTTTAAAAATATTCGTAATAAATGTGAATACCAACTACTACCGCTGAAACCTGTGCAACCCACCACGC

ACAAGCAATAAGTACAGAATTCAAAATTTTCATAATAACCTCATTACAAAAGTAAATGTTAAACAAATTA

CTGGAATACTAATTAACCAAACAAAACACCACCATAATGAACTCATAGTTCAATCTCAGCGATTTTCATT

TTATTCTCCAAATCCGTATCAGTAGTTGATAGTTGTATAGTACCACGGTCCTTGTGGTATGTAAACTGTT

TTGTGAAATTTTTTAAATGGAAAGATACCATCCGTTGTAGTTGCTTTTTCTTACAACTTTACGAAGGTCT

TCTCTGTCACCGATGAACTTCGGAGTGTACTGGATGACACCTGGATGAATTTCTTTAGTGTTGAATATAA

TTATACAGTCAGCGACTTGATGATTTAGAATGGGCCCTAGATTTATTCCAGAACCATATGGATACTCTCC

GCTGCATCCCGTTGTTACCGAAATCCAACGTGAGTCAGTTTGATGTGTCTTAACTTCTACACGAAGCCCG

CAGTATTTTGGATGAGCCAATACATCCCATGCATATGTGTACGGATCATCGACATCCTCTTGGCCTTTAT

TGACATATCCACTCAACCAATCTGCCACAAAAAACTCTGCGTACACAGCGATACGGCATCTTTCGATAAC

TTCTGCCTTATCTTGATTTGGGTTTTGTTTTAAAGAGTATCTTGCAGTATCAGCAATTTTGACCTTCATT

TCACAGGTCAAGTCACTGTTCGATAGGGTAAATGTCGGAATCTGAAATAGTCTCTGTAACCCAGGATTCG

TTTTCTGCATTTAAACTTTCCTTTATGTCGGAATCACCGATATTCATATAAATCATAATTTCTCTTAAAA

CAAAAGGCCGAAGCCCTTTATTTTACTTGAATTGTGCAATTCTTTTCTAGACATTCAGCATAAGATTT

CATTGAGATGAACTGCGAAAGTAGCAGTTCTTGCTCAACTGCGCTAACTGTTAGAAACTTTGCGCTTTCT

AAAAATTTGCTCAGTGCATTAATTTTGAGCATTAATTGATCGTATTCTTCTTTTACTCGTGCTTGATAAG

CTAACATAATTTTCCTTAGTTAAGGGCCGAAGCCTTATTTAAATTGTTCAGTAACGTCTTCAACTACTTC

ATATTGGCAGGTACGCATTTTAGCATCGTTGTAATCAATCGGAATTGATACTACATCGCGAGGATGAACT

TTAACTTTTACAACTCGGCTGGTTGAACTACCAAAGTGACGAATATAAGATTTAGAACACACATGCAAAC

CACGAGAACAAGTTTGTGTATCATCGTCATTCACACGAGTACGTGGCATTTTAACTACTTTACCCGGACT
```

-continued

```
GTTATCAAAGGTGTTTGAGTGACAGTCAAAGTAATTGCTGCGAACTACTTTCCAAGCATAGAAGTAACCA

TCTTCTGTAATTTCAATATCGTTTGCTACCAAGAAATCAAAGAGTCGAGATACCGCTTTTTGGCTTGGGT

TTTCCAACAGATTTTCCAAGAACGGAAAATAAAATTCAAAGTTTTCGCCTTTTTCCATCGAGTCAAGAAT

ACGATCAACCAAACCAGACCGCAATTCAATATTTTGATAGAACAAGCTTCCACCTTCAATTCGAACATCG

CCGGAAATATATTTTTCAACAGCACGACGAACATTAATTTTTTGTGCCGCTTCTTCCAACTTATCCGCTA

CAAGCAGATTAAGAATTTCCTGGAAGTTTGAATGAGTATTAGGAGTTGCGTTATAAGTTACGCCATCAAC

AGTAATTGAAATGAATTTTTTAGATGCATTCCAAATAATGTCAGATTTAGCAACTGGAGCAATAACTGCA

TCGCTATTAACTTTAACTGTAATATCACCGCTAATAGTAACTTTAGGGCGTTTAGCTTCTTCAGCATTTT

TCAAAACACGACGGATTGTGTCAACCGATACACCTTGCCAATCAGCCAATTCCTGTTGGGTGTAATTACC

ACTTGAATACAGTTTAACAATTTCAGCTTGTTCGTTTTGGTCAGGCATTTAATATTGTACAT
```

Spacer targeting E coli fimH (SEQ ID NO: 6)

CGAATGACCAGGCATTTACCGACCAGCCCATC

Spacer targeting E coli bolA (SEQ ID NO: 7)

AGTGGGAAGGGTTGCAGGACACCGTCTTTGCC

Spacer targeting E coli rpoH (SEQ ID NO: 8)

CCGATGTTACCTTCCTGAATCAAATCCGCCTG

Spacer targeting E coli lptA (SEQ ID NO: 9)

TGATTGACGGCTACGGTAAACCGGCAACGTTC

Spacer targeting E coli murA (SEQ ID NO: 10)

GCTGTTAACGTACGTACCGCGCCGCATCCGGC

---

The invention claimed is:

1. A method for treating or preventing an infection by *Escherichia coli* (*E. coli*) cells in a human or animal subject, wherein the method comprises administering a plurality of transduction particles to the subject, wherein
(a) each transduction particle comprises a nucleic acid encoding a Cas nuclease and a nucleic acid encoding a crRNA or guide RNA that is operable with the Cas nuclease for targeting the genomes of *E. coli* cells, wherein (i) each transduction particle is a phage and the nucleic acid encoding the Cas nuclease is integrated into the genome of the phage, or (ii) each transduction particle is a phage capsid and the nucleic acid encoding the Cas nuclease is a phagemid contained in the phage capsid,
wherein the administered transduction particles contact the cells and introduce therein the nucleic acid, wherein the Cas nuclease is expressed in the cells and cuts genomic DNA of the cells, thereby killing the cells or reducing growth or proliferation of the cells in the subject;
(b) the *E. coli* cells are cells of *E. coli* phylogroup B2; and (c) wherein the plurality of transduction particles comprises a first type of transduction particle and a second type of transduction particle, wherein the first type of transduction particle comprises a first adhesion moiety that is capable of recognizing and binding to LPS displayed on the surface of phylogroup B2 *E. coli* cells, and the second type of transduction particle comprises a second adhesion moiety that is capable of recognizing and binding to Tsx displayed on the surface of phylogroup B2 *E. coli* cells.

2. The method of claim 1, wherein the *E. coli* cells comprise an *E. coli* strain selected from the group consisting of ST131 and ST1193.

3. The method of claim 1, wherein the *E. coli* cells comprise a plurality of different phylogroup B2 strains of *E. coli*.

4. The method of claim 1, wherein the subject is a transplant patient, urinary tract infection (UTI) patient, or cancer patient.

5. The method of claim 4, wherein the method is carried out prior to the subject receiving a transplant.

6. The method of claim 1, wherein the subject is a human subject and the B2 *E. coli* cells comprise a strain of *E. coli* that causes sepsis, septicaemia or diarrhoea in humans.

7. The method of claim 1, wherein the method prevents haemolytic uremic syndrome (HUS), a UTI infection, sepsis, septicaemia or diarrhoea in the subject.

8. The method of claim 1, wherein each particle comprises a phage capsid containing the nucleic acid.

9. A method for treating or preventing an infection by *Escherichia coli* (*E. coli*) cells in a human or animal subject, wherein the method comprises administering a plurality of transduction particles to the subject, wherein (a) each transduction particle comprises a nucleotide sequence (N1) encoding a Cas nuclease for targeting the genomes of *E. coli* cells and a nucleic acid encoding a crRNA or guide RNA that is operable with the Cas nuclease for targeting the genomes of *E. coli* cells, wherein the administered transduction particles contact the cells and introduce therein the nucleic acid, wherein the Cas nuclease is expressed in the cells and cuts genomic DNA of the cells, thereby killing the cells or reducing growth or proliferation of the cells in the subject;

(b) the *E. coli* cells are cells of *E. coli* phylogroup B2; and
each transduction particle comprises an adhesion moiety recognizing and binding to a cognate moiety selected from the group consisting of a LPS, LamB and Tsx displayed on the surface of phylogroup B2 *E. coli* cells, wherein each transduction particle is a synthetic T-even phage comprising an insertion of N1 into the genome of the phage, wherein the insertion is between a pin (protease inhibitor) gene and an iPII (internal protein) gene.

10. The method of claim 1, wherein the nuclease is a Type I, II, III, IV, V or VI Cas nuclease.

11. The method of claim 1, wherein at least $1 \times 10^7$ PFU of the transduction particles are administered to the subject.

12. The method of claim 1, wherein the transduction particles are administered to the subject at an MOI (multiplicity of infection) of at least 0.01.

13. The method of claim 1, wherein the *E. coli* cells comprise a strain or at least one strain that is an antibiotic-resistant or MDR (multidrug resistant) strain; and/or wherein the *E. coli* cells comprise a strain or at least one strain that is a B2-I strain.

14. The method of claim 13, wherein the antibiotic-resistant strain is resistant to fluoroquinolone, carbapenem or vancomycin; and/or wherein the *E. coli* are a beta-lactamase (ESBL)-producing *E. coli*.

15. A method for treating or preventing an infection by *E. coli* cells in a human or animal subject, the method comprising administering to the subject a plurality of transduction particles, wherein (a) each transduction particle comprises a nucleic acid encoding a crRNA or guide RNA that is operable with a Cas nuclease for chromosomal targeting in the cells, wherein (i) each transduction particle is a phage and the nucleic acid encoding the crRNA or guide RNA is integrated into the genome of the phage, or (ii) each transduction particle is a phage capsid and the nucleic acid encoding the crRNA or guide RNA is a phagemid contained in the phage capsid, wherein the administered transduction particles contact the cells and introduce therein the nucleic acid, wherein the crRNA or guide RNA is expressed and guides the Cas nuclease, wherein the nuclease cuts the chromosomes of the cells, thereby killing the cells or reducing growth or proliferation of the cells in the subject;

(b) the *E. coli* cells are cells of *E. coli* phylogroup B2; and
(c) wherein the plurality of transduction particles comprises a first type of transduction particle and a second type of transduction particle, wherein the first type of transduction particle comprises a first adhesion moiety that is capable of recognizing and binding to LPS displayed on the surface of B2 *E. coli* cells, and the second type of transduction particle comprises a second adhesion moiety that is capable of recognizing and binding to Tsx displayed on the surface of phylogroup B2 *E. coli* cells.

16. The method of claim 15, wherein the nuclease is an endogenous nuclease of the cells and is not encoded by the nucleic acid comprised by the transduction particles.

17. The method of claim 1, wherein the method prevents translocation of B2 phylogroup *E. coli* from the gastrointestinal or urinary tract to the blood stream of the subject, thereby preventing or reducing bacteremia in the patient.

18. The method of claim 1, wherein each transduction particle is a lytic phage.

19. The method of claim 3, wherein the plurality of different phylogroup B2 strains of *E. coli* comprises *E. coli* ST131 and ST1193 cells.

20. The method of claim 1, wherein the subject is suffering from or at risk of a urinary tract infection (UTI).

21. The method of claim 4, wherein the transplant is a solid organ or stem cell transplant or wherein the transplant is a transplant of a medical device.

22. The method of claim 8, wherein the phage capsid comprises capsid proteins of a T-even or lambda phage.

23. The method of claim 1, wherein the crRNA or guide RNA is operable with the Cas nuclease for targeting the genome of an *E. coli* strain selected from the group consisting of ST131 and ST1193.

24. The method of claim 1, wherein the plurality of transduction particles comprises a third type of transduction particle, wherein the third type of transduction particle comprises a third adhesion moiety that is capable of recognizing and binding to LamB.

25. The method of claim 1, wherein each transduction particle is a synthetic T-even phage.

26. The method of claim 1, wherein the Cas nuclease is a Type I Cas nuclease.

27. The method of claim 15, wherein the plurality of transduction particles comprises a third type of transduction particle, wherein the third type of transduction particle comprises a third adhesion moiety that is capable of recognizing and binding to LamB.

28. The method of claim 9, wherein each transduction particle comprises a nucleic acid encoding a crRNA or guide RNA that is operable with the Cas nuclease for targeting the genomes of *E. coli* cells.

29. The method of claim 9, wherein the plurality of transduction particles comprises a first type of transduction particle and a second type of transduction particle, wherein the first type of transduction particle comprises a first adhesion moiety that is capable of recognizing and binding to LPS displayed on the B2 *E. coli* cells, and the second type of transduction particle comprises a second adhesion moiety that is capable of recognizing and binding to Tsx.

30. The method of claim 9, wherein the nuclease is a Type I Cas nuclease.

31. The method of claim 29, wherein the plurality of transduction particles comprises a third type of transduction particle, wherein the third type of transduction particle comprises a third adhesion moiety that is capable of recognizing and binding to LamB.

* * * * *